US012559463B2

(12) United States Patent
Huang et al.

(10) Patent No.: US 12,559,463 B2
(45) Date of Patent: Feb. 24, 2026

(54) CRYSTALLINE FORMS OF A JAK2 INHIBITOR

(71) Applicant: Impact Biomedicines, Inc., Summit, NJ (US)

(72) Inventors: Lianfeng Huang, Basking Ridge, NJ (US); Nancy Tsou, Edison, NJ (US); Wenju Wu, Warren, NJ (US); Daozhong Zou, Raritan, NJ (US)

(73) Assignee: IMPACT BIOMEDICINES INC., Princeton, NJ (US)

( * ) Notice: Subject to any disclaimer, the term of this patent is extended or adjusted under 35 U.S.C. 154(b) by 1084 days.

(21) Appl. No.: 17/430,188

(22) PCT Filed: Feb. 11, 2020

(86) PCT No.: PCT/US2020/017765
§ 371 (c)(1),
(2) Date: Aug. 11, 2021

(87) PCT Pub. No.: WO2020/167845
PCT Pub. Date: Aug. 20, 2020

(65) Prior Publication Data

US 2023/0250068 A1 Aug. 10, 2023

Related U.S. Application Data

(60) Provisional application No. 62/804,332, filed on Feb. 12, 2019.

(51) Int. Cl.
*C07D 239/48* (2006.01)

(52) U.S. Cl.
CPC ........ *C07D 239/48* (2013.01); *C07B 2200/13* (2013.01)

(58) Field of Classification Search
CPC .................................................... C07D 239/48
See application file for complete search history.

(56) References Cited

U.S. PATENT DOCUMENTS

| | | | |
|---|---|---|---|
| 7,528,143 B2 | 5/2009 | Noronha et al. | |
| 7,825,246 B2 | 11/2010 | Noronha et al. | |
| 8,133,900 B2 | 3/2012 | Hood et al. | |
| 8,138,199 B2 | 3/2012 | Noronha et al. | |
| 8,604,042 B2 | 12/2013 | Noronha et al. | |
| 10,040,804 B2 | 8/2018 | Chan et al. | |
| 10,391,094 B2 | 8/2019 | Jayan et al. | |
| 11,306,062 B2 * | 4/2022 | Yao | C07D 239/48 |
| 2013/0243853 A1 * | 9/2013 | Jayan | A61P 35/00 424/452 |
| 2015/0361050 A1 | 12/2015 | Brown et al. | |
| 2016/0332993 A1 | 11/2016 | Bradner et al. | |
| 2018/0078561 A1 | 3/2018 | Beckett et al. | |
| 2019/0381041 A1 | 12/2019 | Jayan et al. | |
| 2021/0244735 A1 | 8/2021 | Jayan et al. | |
| 2022/0332706 A1 * | 10/2022 | Robert | A61K 31/506 |

FOREIGN PATENT DOCUMENTS

| | | |
|---|---|---|
| WO | WO-2007/053452 A1 | 5/2007 |
| WO | WO-2012/060847 A1 | 5/2012 |
| WO | WO-2012/061833 A1 | 5/2012 |
| WO | WO-2013/013195 A1 | 1/2013 |
| WO | WO-2016/138458 A1 | 9/2016 |
| WO | WO-2020/068754 A1 | 4/2020 |
| WO | WO-2020/068755 A1 | 4/2020 |
| WO | WO-2020/167844 A1 | 8/2020 |
| WO | WO-2020/167845 A1 | 8/2020 |

OTHER PUBLICATIONS

Chadha et al., "Solvated Crystalline Forms of Nevirapine: Thermoanalytical and Spectroscopic Studies", PharmSciTech, Sep. 2010 (Year: 2010).*
David Aycock, "Solvent Applications of 2-Methyltetrahydrofuran in Organometallic and Biphasic Reactions", Organic Process Research and Development, Dec. 6, 2006 (Year: 2006).*
"Lattice Structures in Crystalline Solids", Lumen Learning, Dec. 21, 2016 (Year: 2016).*
Haskell Adler, "Novel BRD4/JAK2 Dual inhibitor Cancer Therapeutics", Moffitt, Sep. 8, 2018 (Year: 2018).*
U.S. Appl. No. 16/549,043.
U.S. Appl. No. 17/220,073.
Caira, M.R., Crystalline Polymorphism of Organic Compounds, Topics in Current Chemistry, 198:163-208 (1998).
Cumaraswamy, A. et al., Inhibitors of Stat5 protein signalling, Med. Chem. Commun., 3(22):22-27 (2012).
Hazell, A. S. et al., Treatment of Rats With The JAK-2 Inhibitor Fedratinib Does Not Lead to Experimental Wernicke's Encephalopathy, Neurosci. Lett., 21 pages (2017).
International Search Report for PCT/US2020/017764, 2 pages (mailed Jun. 5, 2020).
International Search Report for PCT/US2020/017765, 3 pages (mailed Apr. 14, 2020).
Lasho, T. L. et al., TG101348, a JAK2-selective antagonist, inhibits primary hematopoietic cells derived from myeloproliferative disorder patients with JAK2V617F, MPLW515K or JAK2 exon 12 mutations as well as mutation negative patients, Leukemia, 22:1790-1792 (2008).
Pardanani et al., Safety and Efficacy of TG101348, a Selective JAK2 Inhibitor, in Myelofibrosis, Journal of Clinical Oncology, 29(7):789-796 (2011).
Pardanani, A. D. et al., A Phase I Evaluation of TG101348, a Selective JAK2 Inhibitor, in Myelofibrosis: Clinical Response is Accompanied by Significant Reduction in JAK2V617F Allele Burden, BLOOD (Ash Annual Meeting Abstract), 114(22):755, 3 pages (2009).

(Continued)

*Primary Examiner* — Andrew D Kosar
*Assistant Examiner* — Gillian A Hutter
(74) *Attorney, Agent, or Firm* — Henry Hadad

(57) ABSTRACT

The present disclosure provides crystalline forms of a JAK2 inhibitor, compositions thereof and methods of treating a JAK2-mediated disorder.

22 Claims, 126 Drawing Sheets

(56) References Cited

OTHER PUBLICATIONS

PubChem: CID16722836, 27 pages, Create Date Sep. 3, 2007.
Verstovsek, S., Therapeutic potential of JAK2 inhibitors, Hema. Am. Soc. Educ. Prog., 636-642 (2009).
Wernig, G. et al., Efficacy of TG101348, a Selective JAK2 Inhibitor, in Treatment of a Murine Model of JAK2V617F-Induced in Polycythemia Vera, Cancer Cell, 13:311-320 (2008).
Written Opinion for PCT/US2020/017764, 7 pages (mailed Jun. 5, 2020).
Written Opinion for PCT/US2020/017765, 20 pages (mailed Apr. 14, 2020).
Zhang, Q. et al., The Janus Kinase 2 Inhibitor Fedratinib Inhibits Thiamine Uptake: A Putative Mechanism, for the Onset of Wernicke's Encephalopathy, Drug Meta. Dispo., 42:1656-1662 (2014).

* cited by examiner

CRYSTALLINE FORMS OF A JAK2 INHIBITOR

CROSS-REFERENCE TO RELATED APPLICATIONS

The present application is a 371 national phase application of PCT App. No. PCT/US20/17765, filed Feb. 11, 2020, which claims priority to U.S. provisional application No. 62/804,332, filed Feb. 12, 2019, each of which is hereby incorporated by reference in its entirety.

FIELD OF THE INVENTION

The present invention provides compounds, and compositions thereof, useful as inhibitors of protein kinases.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there remains a need to find protein kinase inhibitors useful as therapeutic agents.

SUMMARY OF THE INVENTION

In some embodiments, the present disclosure provides one or more crystalline forms of Compound 1:

1

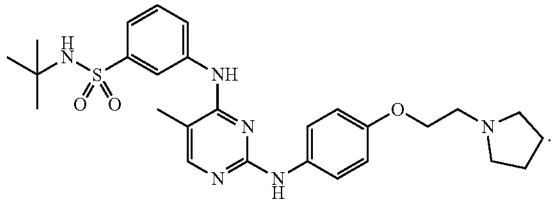

In some embodiments, the present disclosure provides one or more complex forms comprising Compound 1 and a co-former X, wherein:

X is selected from the group consisting of hydrobromic acid, sulfuric acid, toluenesulfonic acid, methanesulfonic acid, 2-naphthalenesulfonic acid, phosphoric acid, DL-tartaric acid, succinic acid, gentisic acid, hippuric acid, adipic acid, galactaric acid, naphthalene-1,5-disulfonic acid, (S)-camphor-10-sulfonic acid, ethane-1,2-disulfonic acid, ethanesulfonic acid, benzenesulfonic acid, oxalic acid, maleic acid, pamoic acid, 1-hydroxy-2-naphthoic acid, malonic acid, L-tartaric acid, fumaric acid, citric acid, L-lactic acid, acetic acid, propionic acid, DL-lactic acid, D-gluconic acid, DL-malic acid, glutaric acid, camphoric acid, DL-mandelic acid, glutamic acid, glycolic acid, L-mandelic acid, L-malic acid, L-aspartic acid, benzoic acid, saccharin, nicotinic acid, ascorbic acid, gallic acid, salicylic acid, orotic acid, acetylsalicylic acid, choline, potassium hydroxide, and sodium hydroxide.

In some embodiments, Compound 1, or a crystalline form or complex thereof, is useful in treating a myeloproliferative disorder. In some embodiments, a myeloproliferative disorder is selected from myelofibrosis, polycythemia vera and essential thrombocythemia. In some embodiments, myelofibrosis is selected from primary myelofibrosis or secondary myelofibrosis. In some embodiments, secondary myelofibrosis is selected from post-polycythemia vera and post-essential thrombocythemia.

In some embodiments, the present disclosure provides a method of inhibiting activity of a JAK2 kinase, or a mutant thereof, in a biological sample comprising the step of contacting said biological sample with Compound 1, or a crystalline form or complex thereof, or a composition thereof.

According to another embodiment, the present disclosure relates to a method of inhibiting activity of a JAK2 kinase, or a mutant thereof, in a patient comprising the step of administering to said patient Compound 1, or a crystalline form or complex thereof, or a composition thereof. In other embodiments, the present disclosure provides a method for treating a JAK2-mediated disease or disorder, in a patient in need thereof, comprising the step of administering to said patient Compound 1, or a crystalline form or complex thereof, or a composition thereof.

BRIEF DESCRIPTION OF THE DRAWINGS

FIG. 119 depicts the TGA pattern of Form A oxalate salt of Compound 1 (119A), and the DSC pattern of Form A oxalate salt of Compound 1 (119B).

FIG. 120 depicts the TGA pattern of Form B oxalate salt of Compound 1 (120A), and the DSC pattern of Form B oxalate salt of Compound 1 (120B).

FIG. 121 depicts the XRPD pattern of Form A maleate salt of Compound 1.

FIG. 122 depicts the TGA pattern of Form A maleate salt of Compound 1 (122A), and the DSC pattern of Form A maleate salt of Compound 1 (122B).

FIG. 123 depicts the XRPD pattern of Form A pamoate salt of Compound 1.

FIG. 124 depicts the TGA pattern of Form A pamoate salt of Compound 1 (124A), and the DSC pattern of Form A pamoate salt of Compound 1 (124B).

FIG. 125 depicts the XRPD pattern of Form A 1-hydroxy-2-naphthoate salt of Compound 1.

FIG. 126 depicts the DSC pattern of Form A 1-hydroxy-2-naphthoate salt of Compound 1.

FIG. 127 depicts the XRPD pattern of Form A malonate salt of Compound 1.

FIG. 128 depicts the TGA pattern of Form A malonate salt of Compound 1 (128A), and the DSC pattern of Form A malonate salt of Compound 1 (128B).

FIG. 129 depicts the XRPD pattern of Form B malonate salt of Compound 1.

FIG. 130 depicts the TGA pattern of Form B malonate salt of Compound 1 (130A), and the DSC pattern of Form B malonate salt of Compound 1 (130B).

Figure 131:
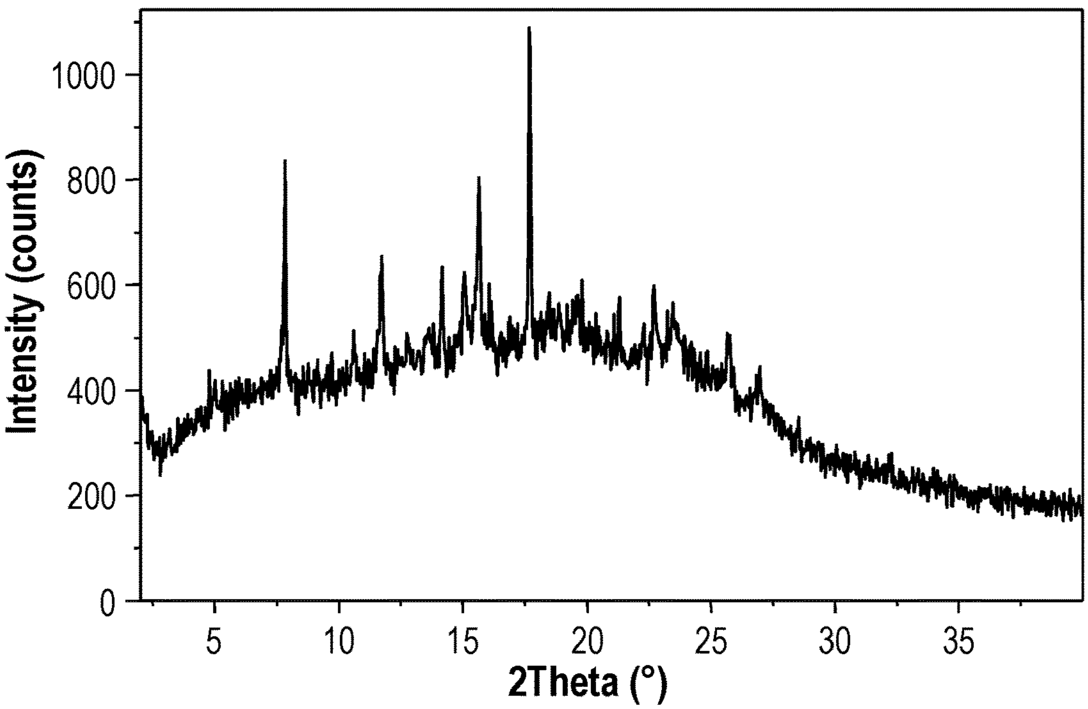

FIG. 131 depicts the XRPD pattern of Form C malonate salt of Compound 1.

Figure 132:
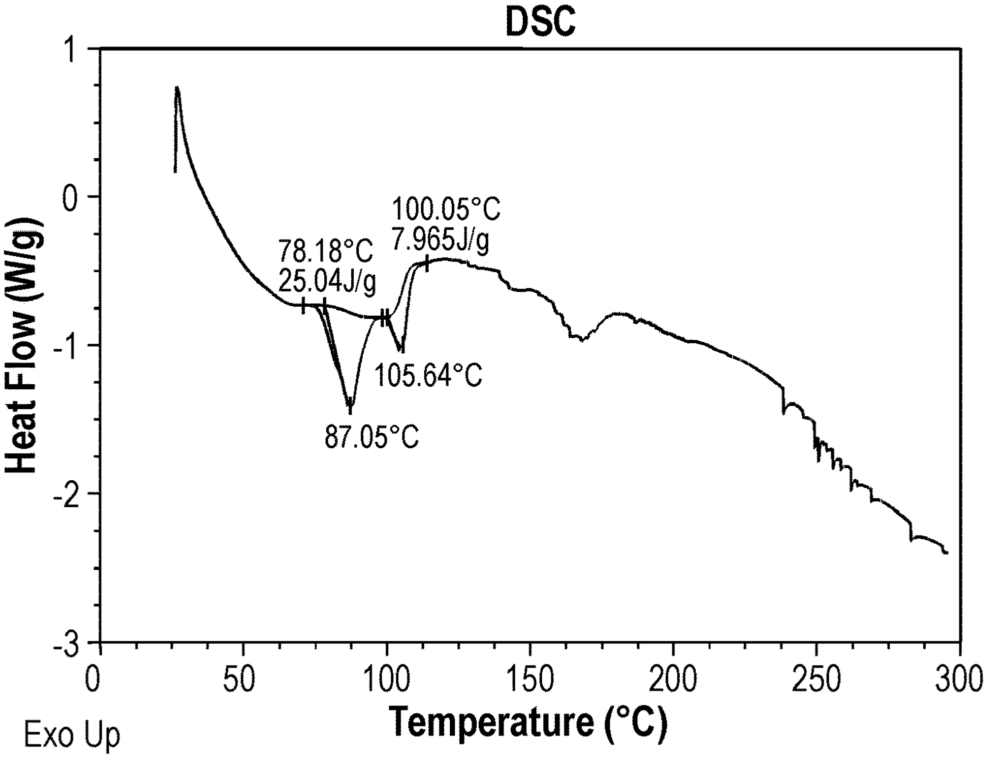

FIG. 132 depicts the DSC pattern of Form C malonate salt of Compound 1.

Figure 133:
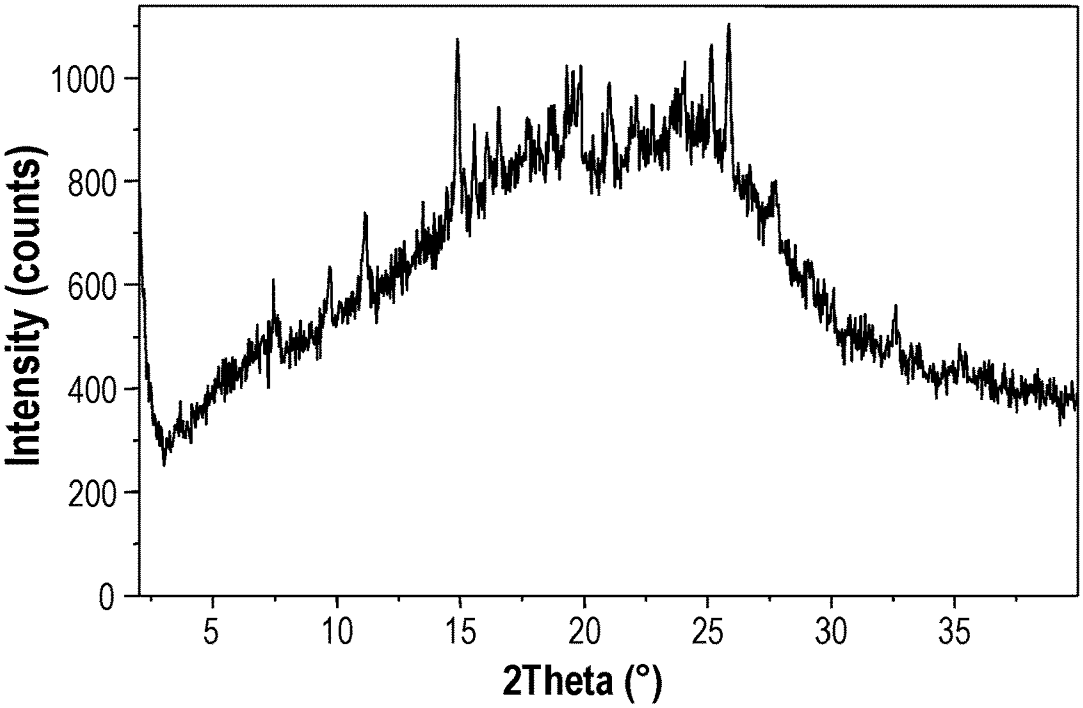

FIG. 133 depicts the XRPD pattern of Form A L-tartrate salt of Compound 1.

Figure 134:
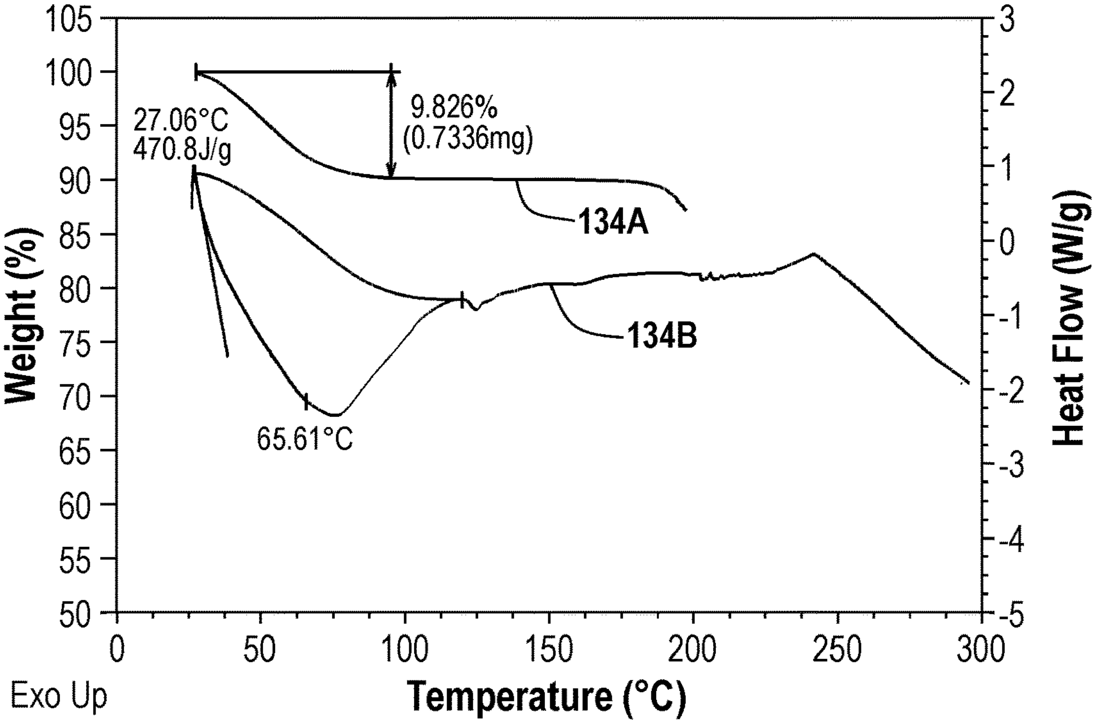

FIG. 134 depicts the TGA pattern of Form A L-tartrate salt of Compound 1 (134A), and the DSC pattern of Form A L-tartrate salt of Compound 1 (134B).

Figure 135:
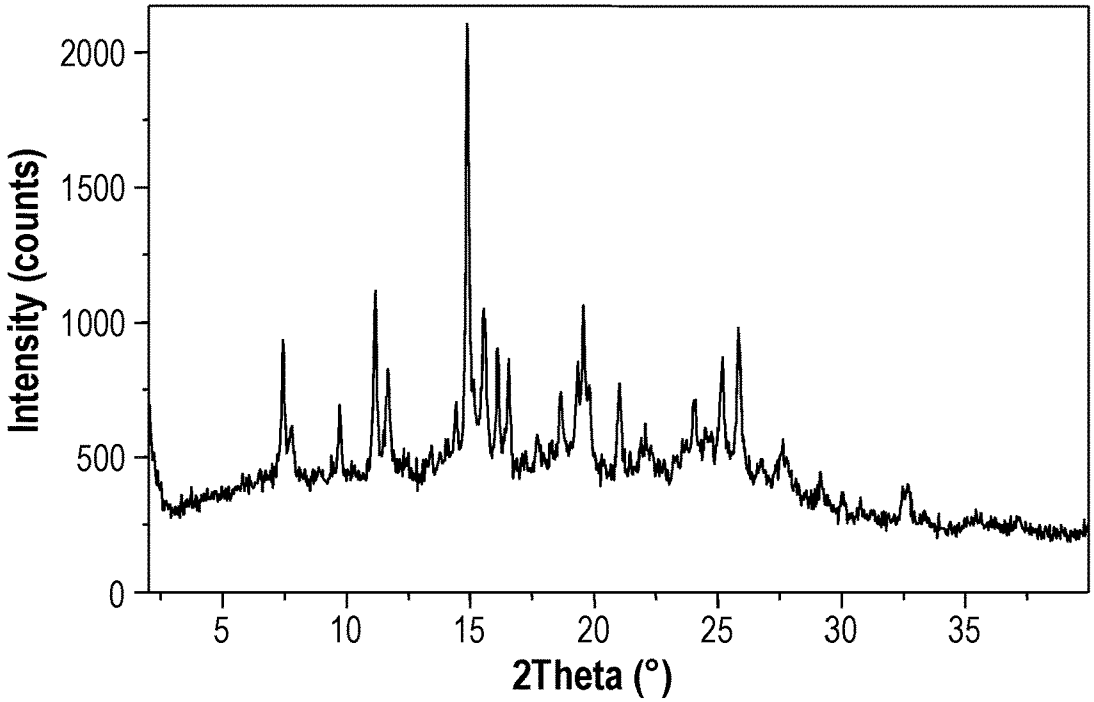

FIG. 135 depicts the XRPD pattern of Form B L-tartrate salt of Compound 1.

Figure 136:
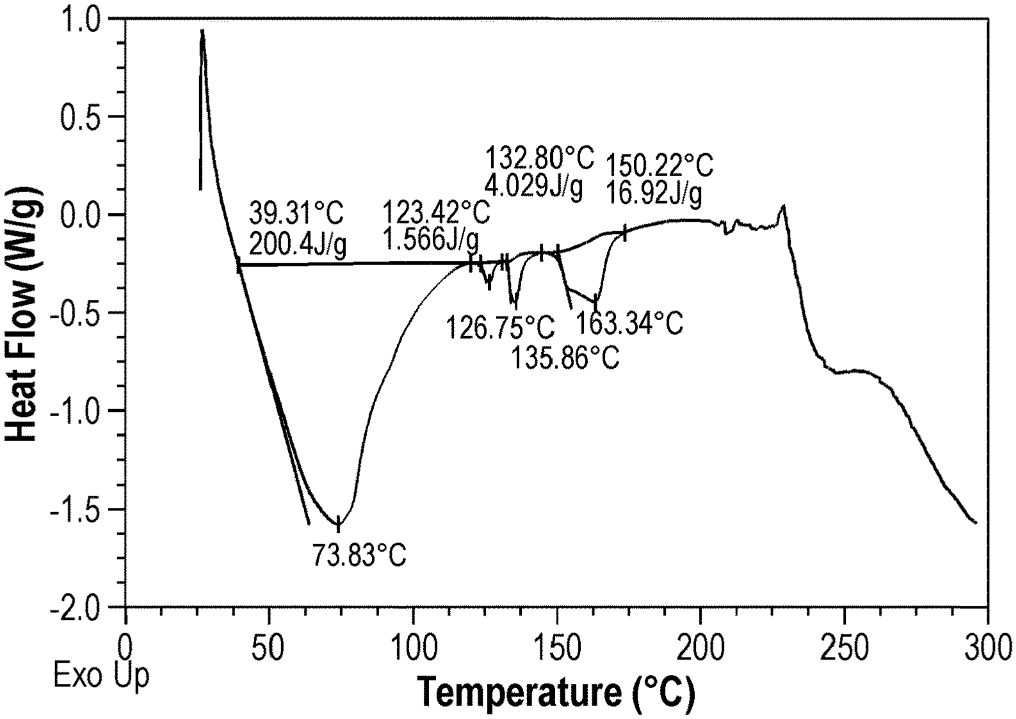

FIG. 136 depicts the DSC pattern of Form B L-tartrate salt of Compound 1.

Figure 137:
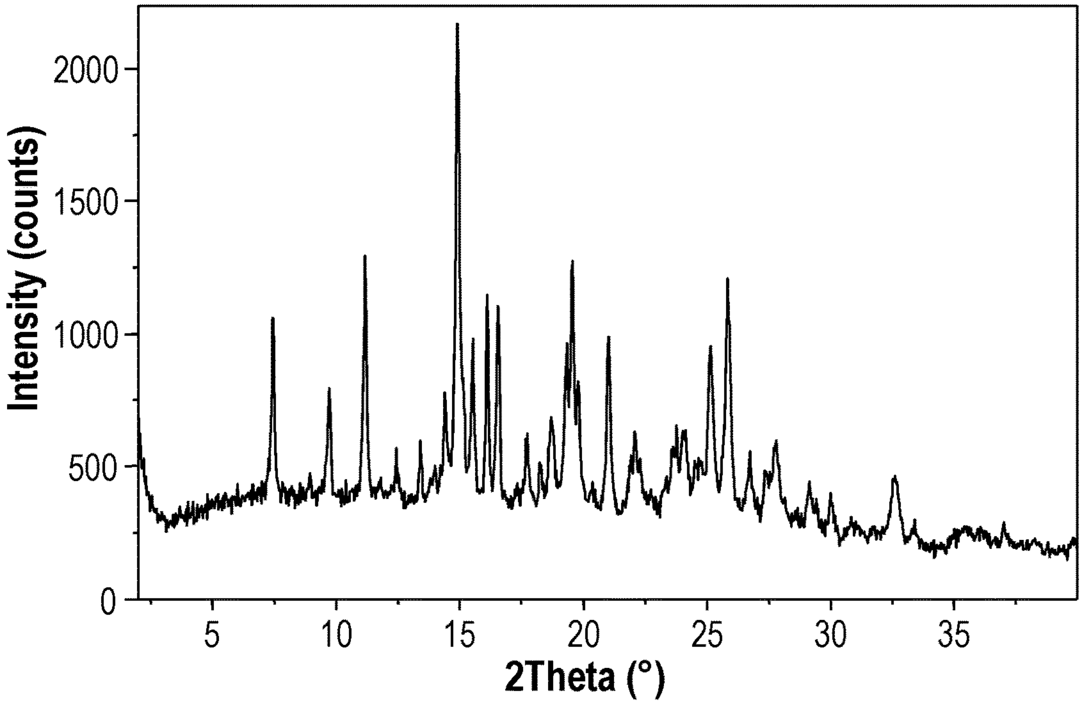

FIG. 137 depicts the XRPD pattern of Form C L-tartrate salt of Compound 1.

Figure 138:
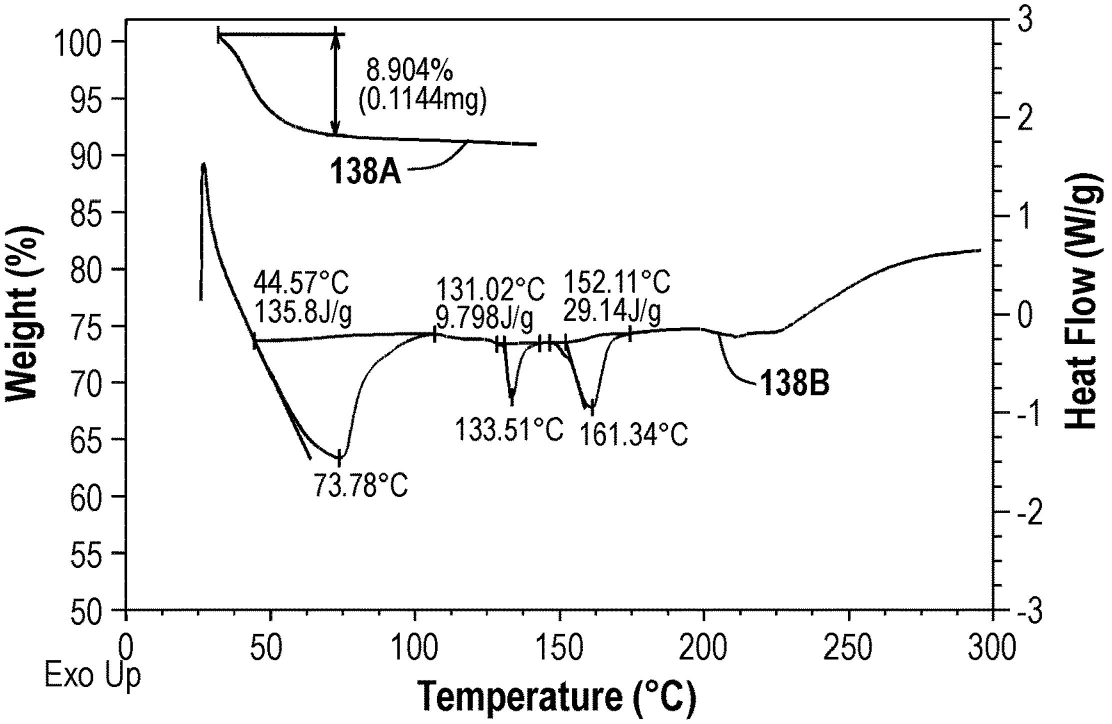

FIG. 138 depicts the TGA pattern of Form C L-tartrate salt of Compound 1 (138A), and the DSC pattern of Form C L-tartrate salt of Compound 1 (138B).

Figure 139:
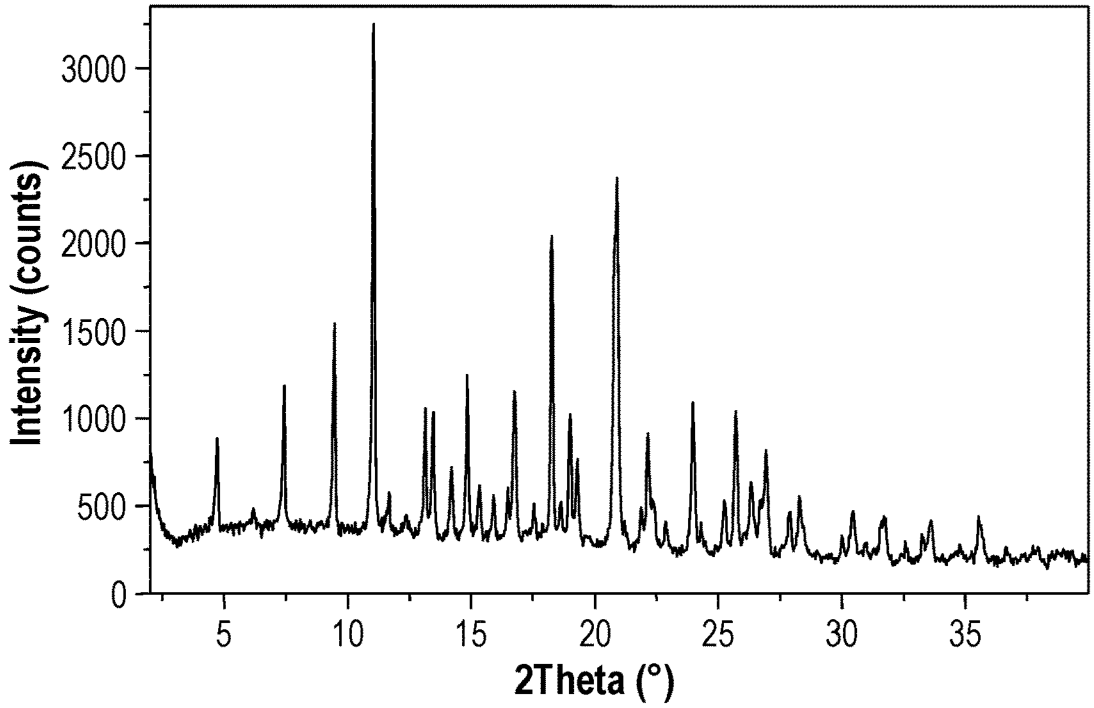

FIG. 139 depicts the XRPD pattern of Form D L-tartrate salt of Compound 1.

Figure 140:
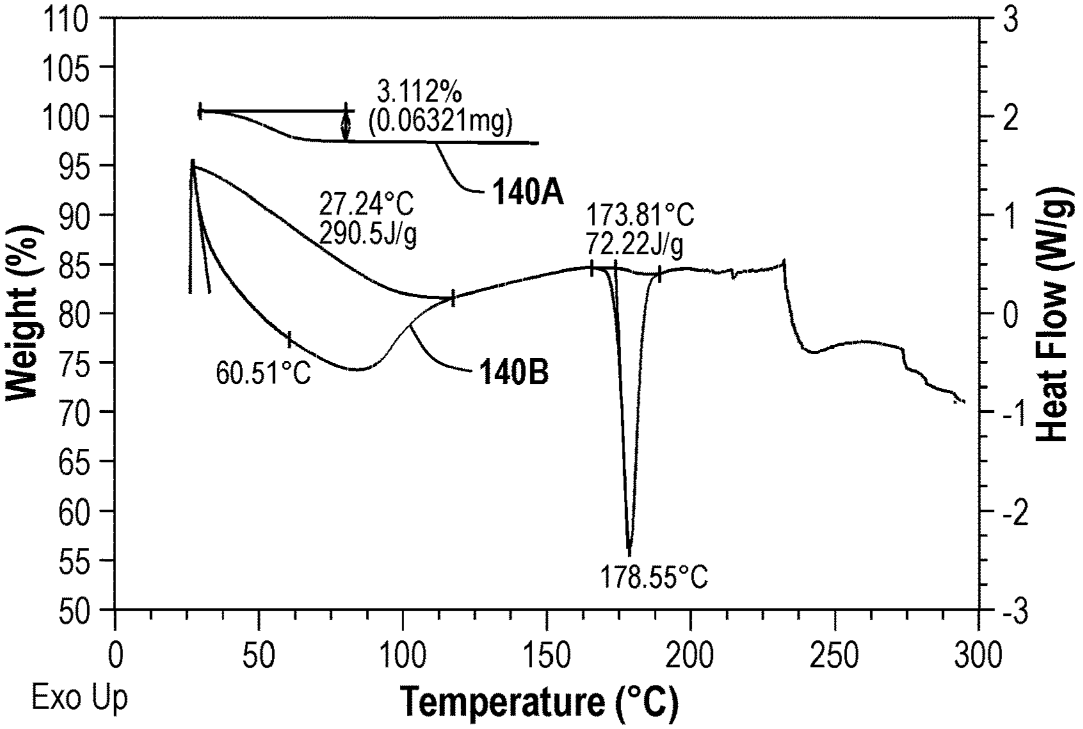

FIG. 140 depicts the TGA pattern of Form D L-tartrate salt of Compound 1 (140A), and the DSC pattern of Form D L-tartrate salt of Compound 1 (140B).

Figure 141:
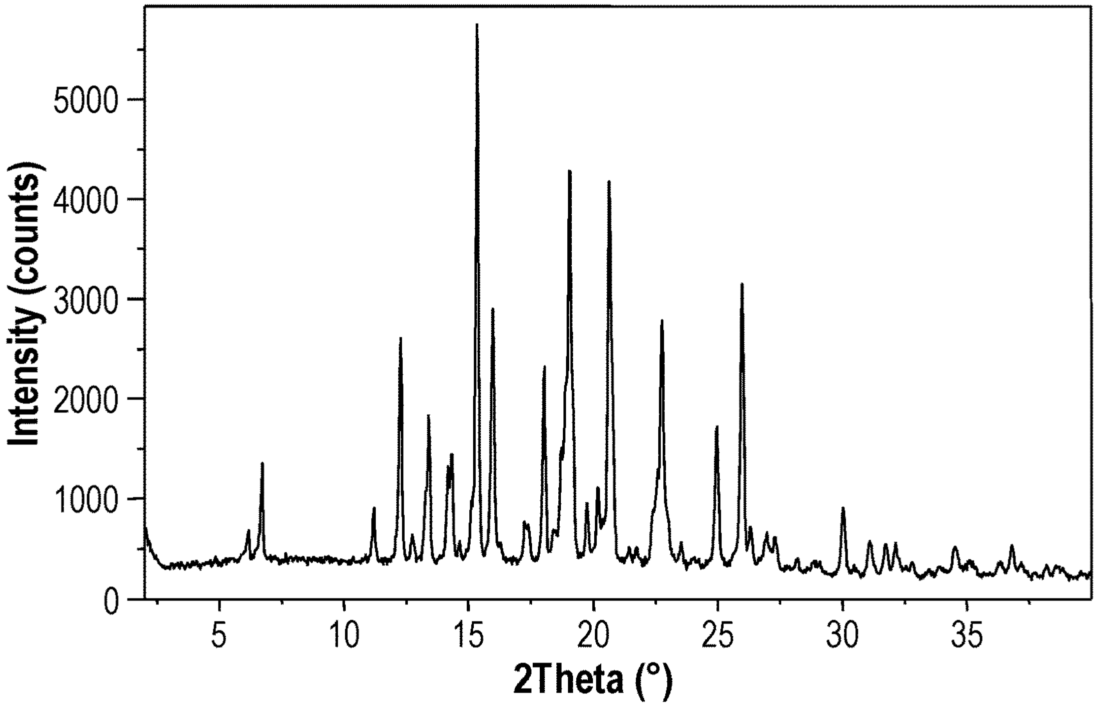

FIG. 141 depicts the XRPD pattern of Form A fumarate salt of Compound 1.

Figure 142:
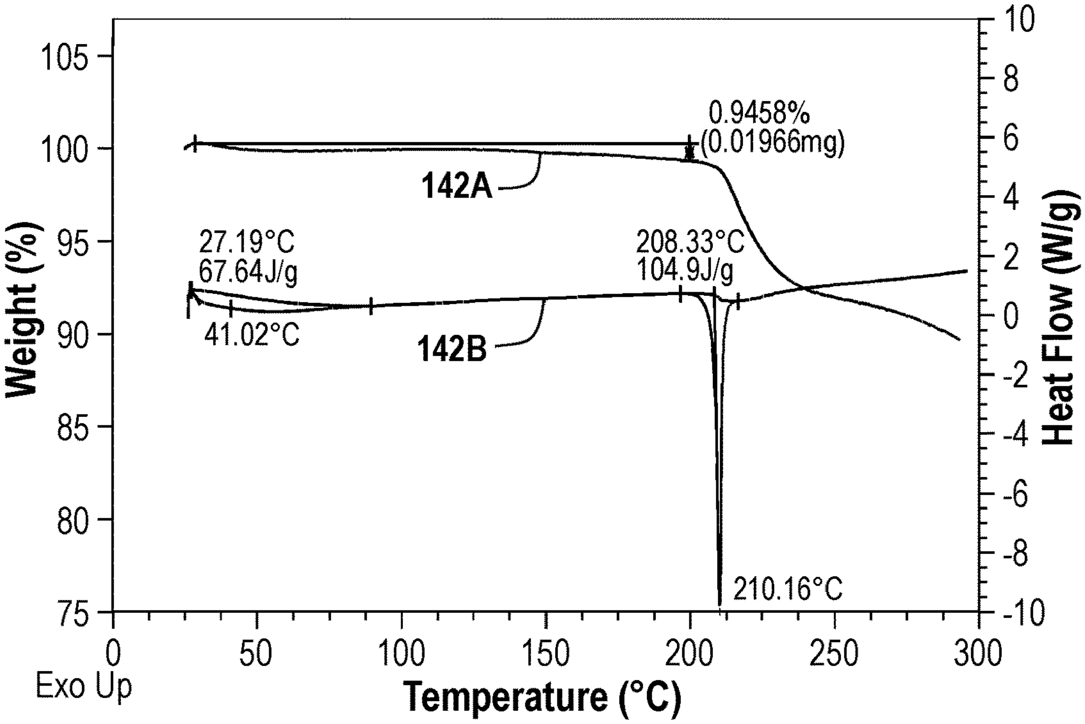

FIG. 142 depicts the TGA pattern of Form A fumarate salt of Compound 1 (142A), and the DSC pattern of Form A fumarate salt of Compound 1 (142B).

Figure 143:
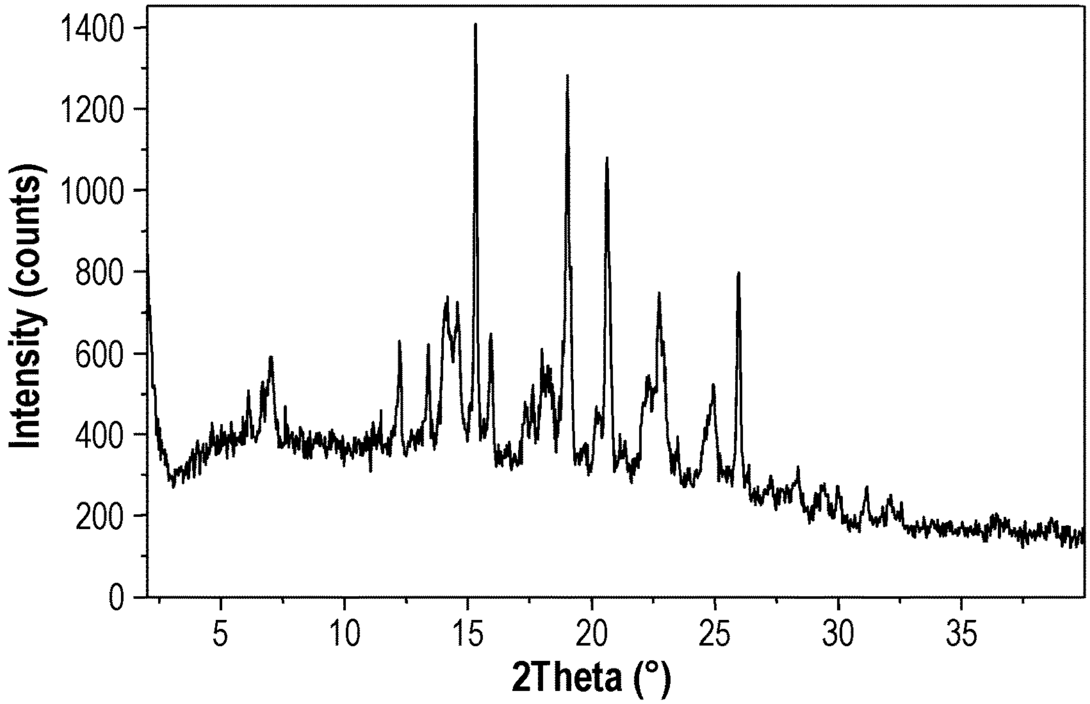

FIG. 143 depicts the XRPD pattern of Form B fumarate salt of Compound 1.

Figure 144:
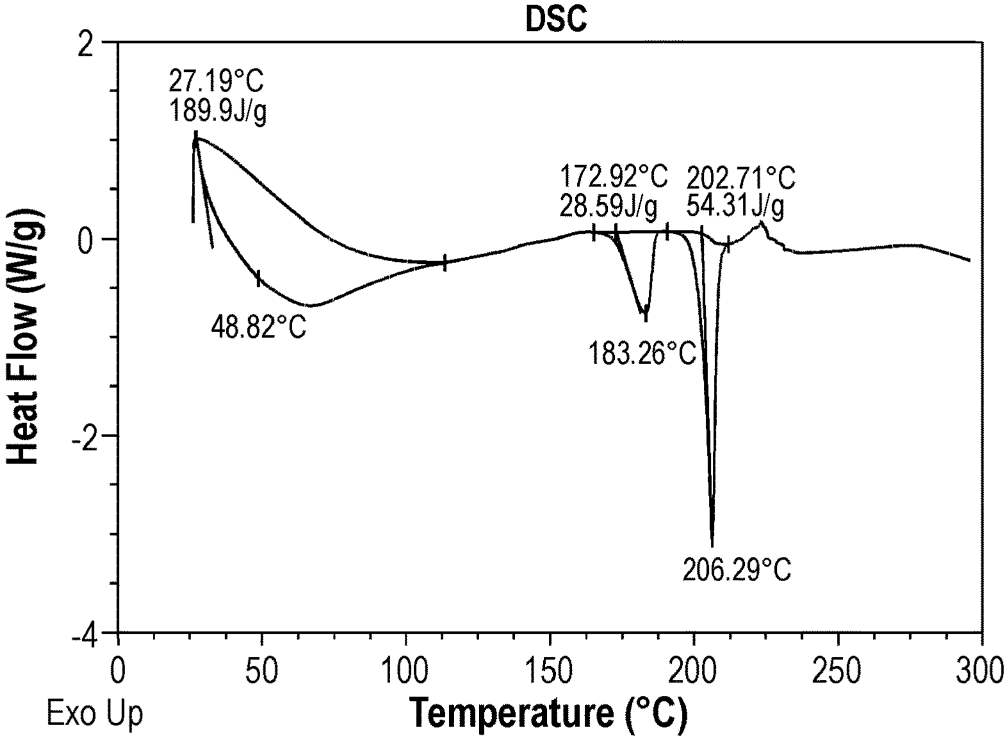

FIG. 144 depicts the DSC pattern of Form B fumarate salt of Compound 1.

Figure 145:
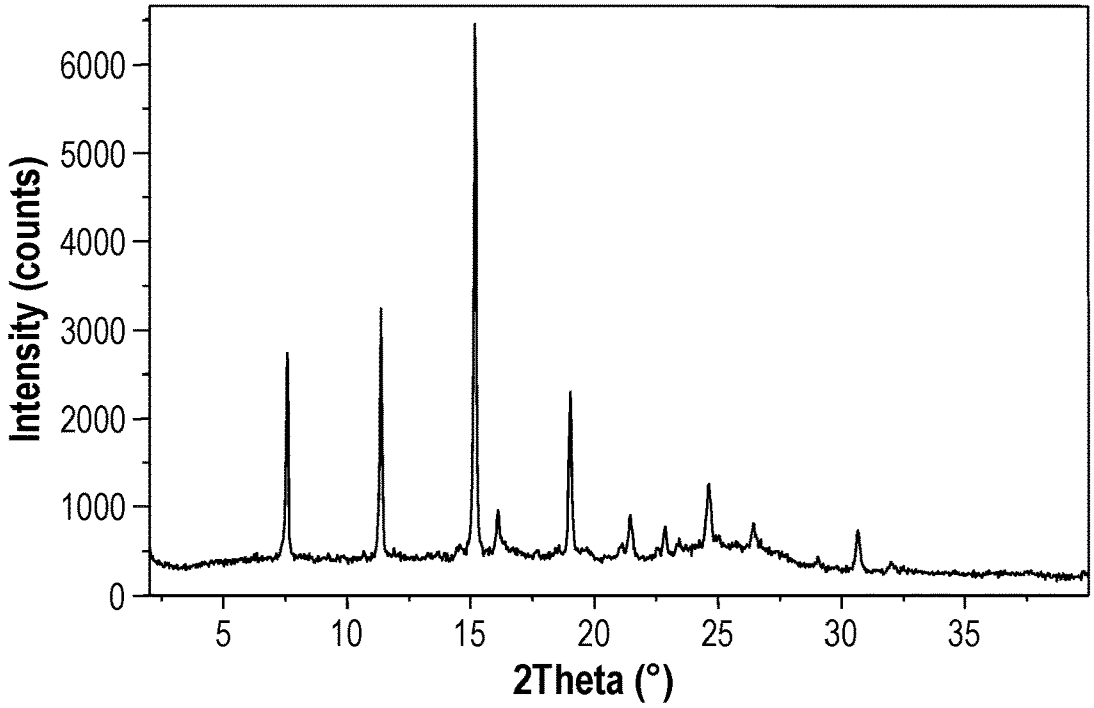

FIG. 145 depicts the XRPD pattern of Form C fumarate salt of Compound 1.

Figure 146:
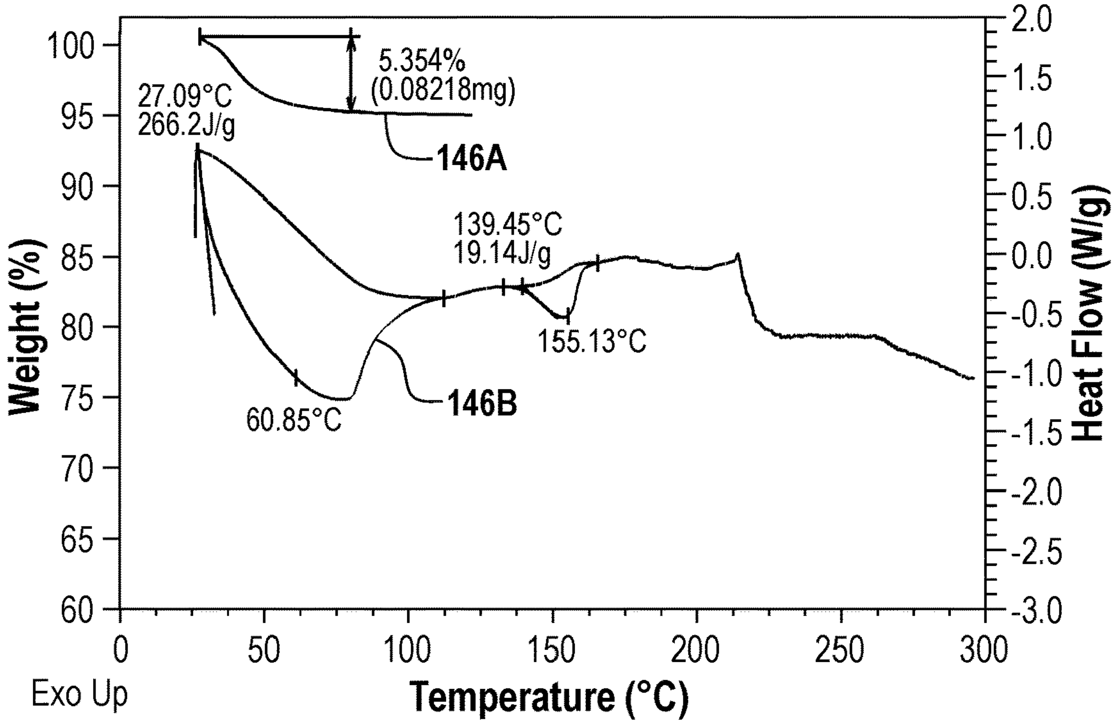

FIG. 146 depicts the TGA pattern of Form C fumarate salt of Compound 1 (146A), and the DSC pattern of Form C fumarate salt of Compound 1 (146B).

Figure 147:
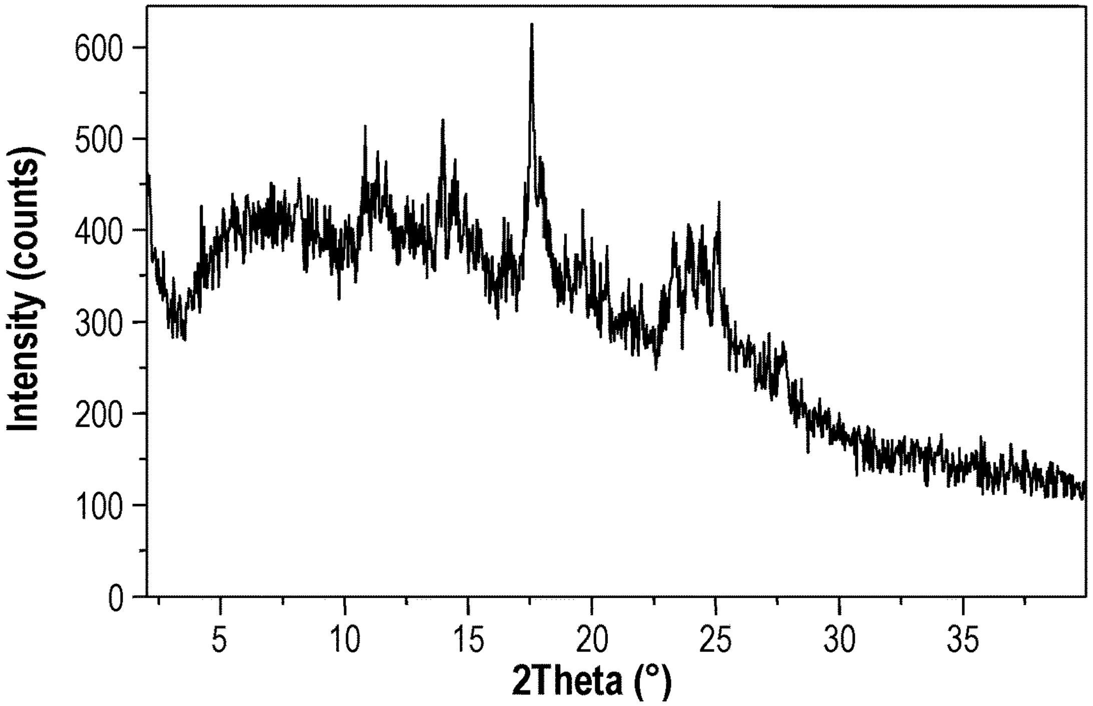

FIG. 147 depicts the XRPD pattern of Form D fumarate salt of Compound 1.

Figure 148:
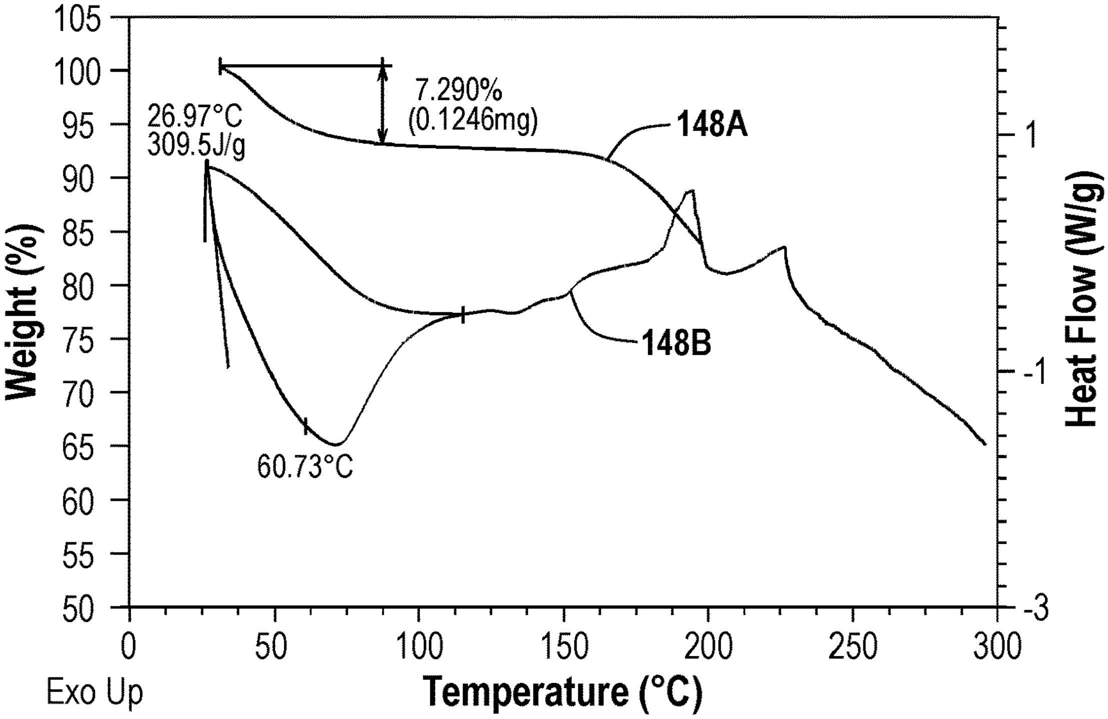

FIG. 148 depicts the TGA pattern of Form D fumarate salt of Compound 1 (148A), and the DSC pattern of Form D fumarate salt of Compound 1 (148B).

Figure 149:
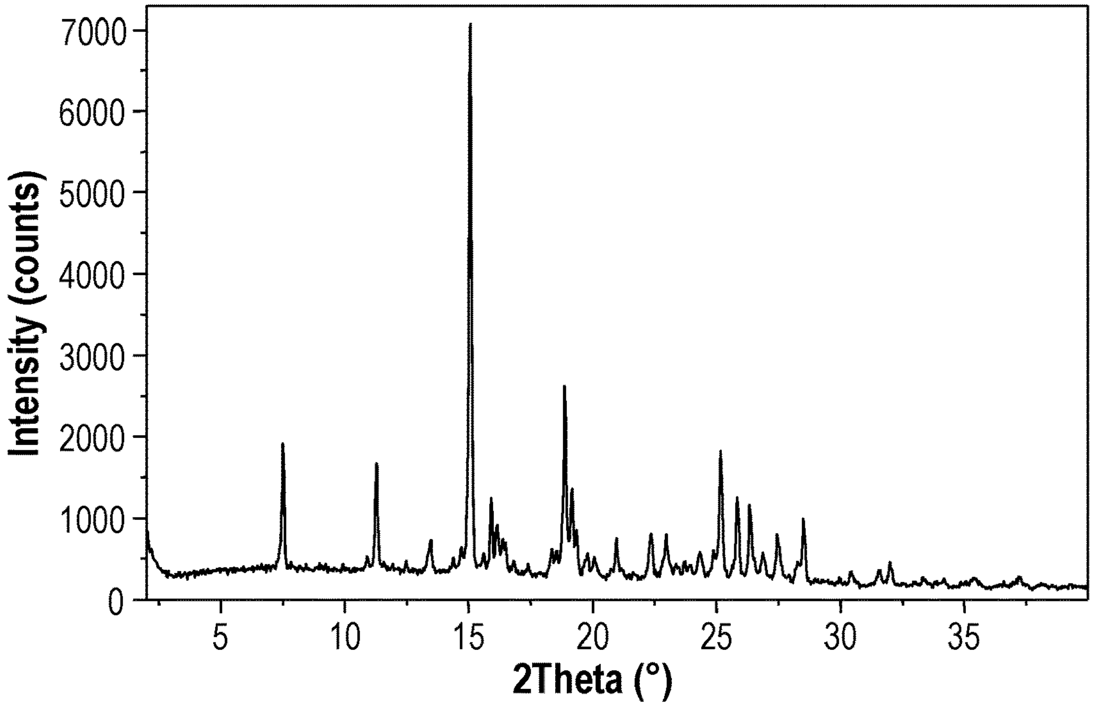

FIG. 149 depicts the XRPD pattern of Form A citrate salt of Compound 1.

Figure 150:
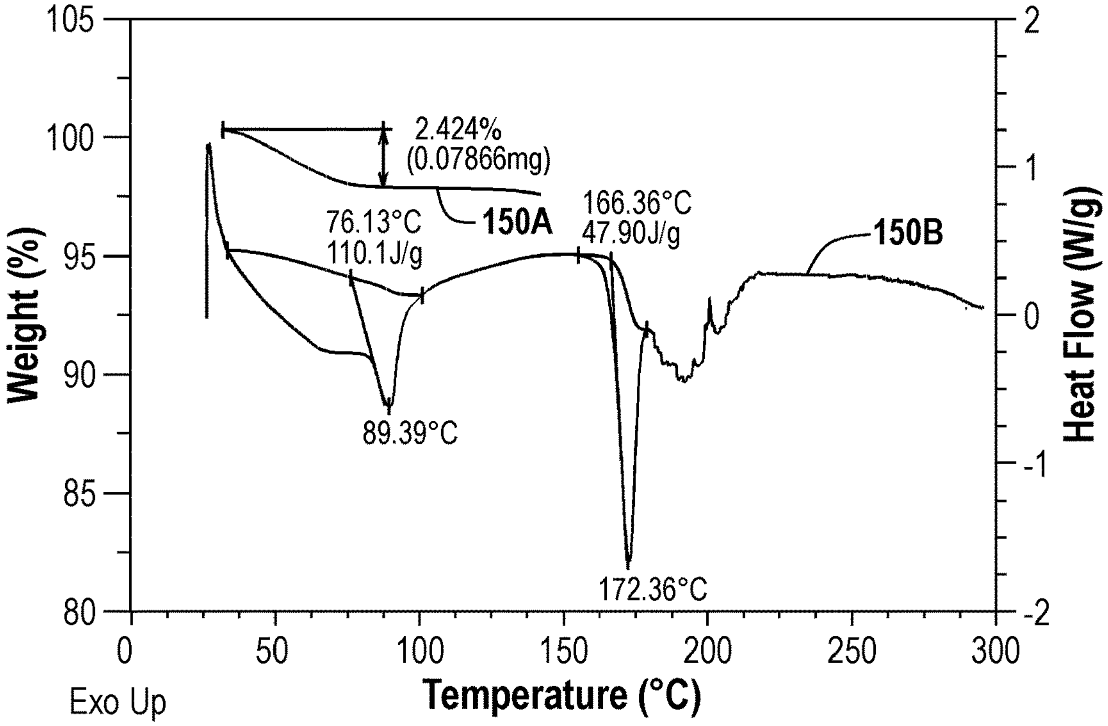

FIG. 150 depicts the TGA pattern of Form A citrate salt of Compound 1 (150A), and the DSC pattern of Form A citrate salt of Compound 1 (150B).

Figure 151:
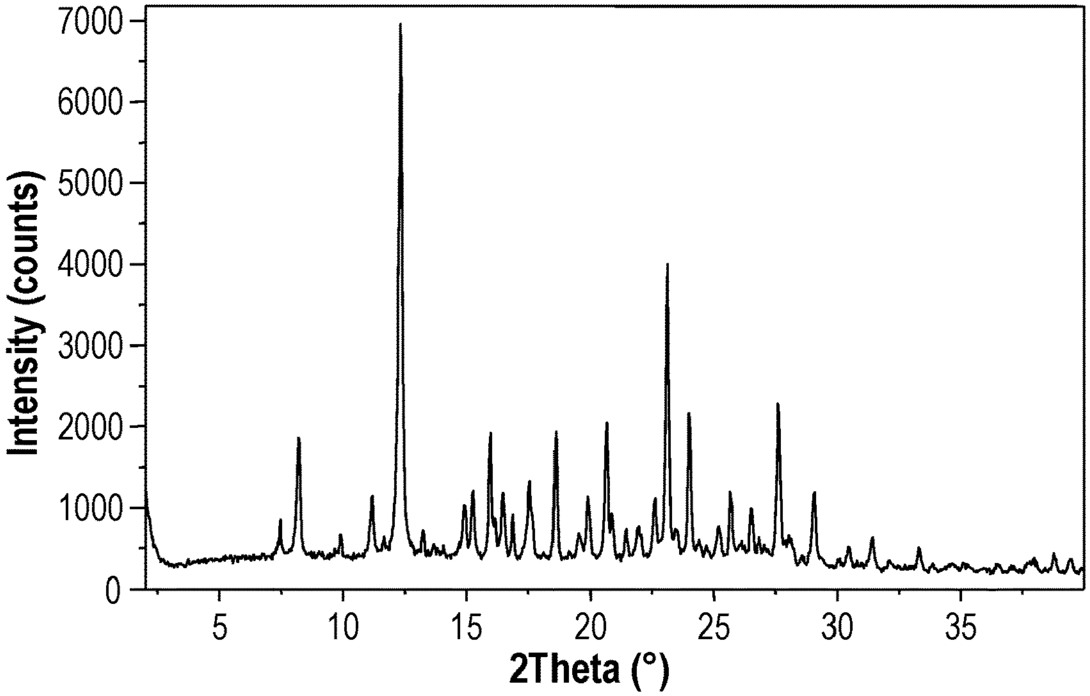

FIG. 151 depicts the XRPD pattern of Form A L-lactate salt of Compound 1.

Figure 152:
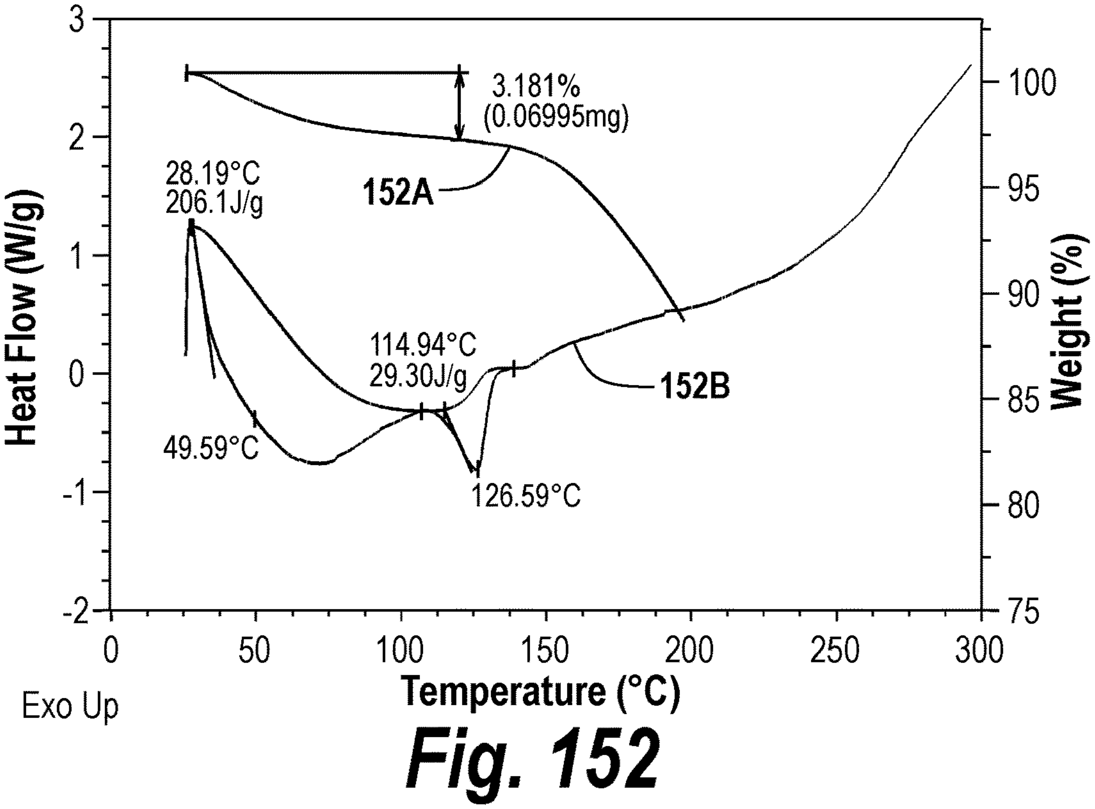

FIG. 152 depicts the TGA pattern of Form A L-lactate salt of Compound 1 (152A), and the DSC pattern of Form A L-lactate salt of Compound 1 (152B).

Figure 153:
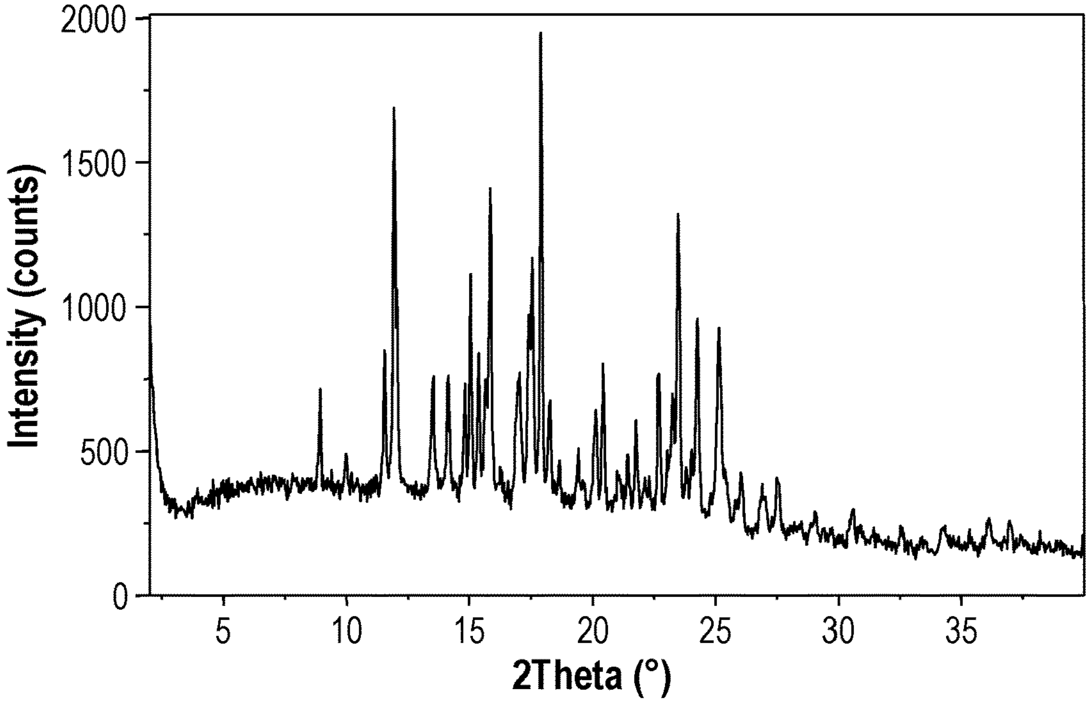

FIG. 153 depicts the XRPD pattern of Form A acetate salt of Compound 1.

Figure 154:
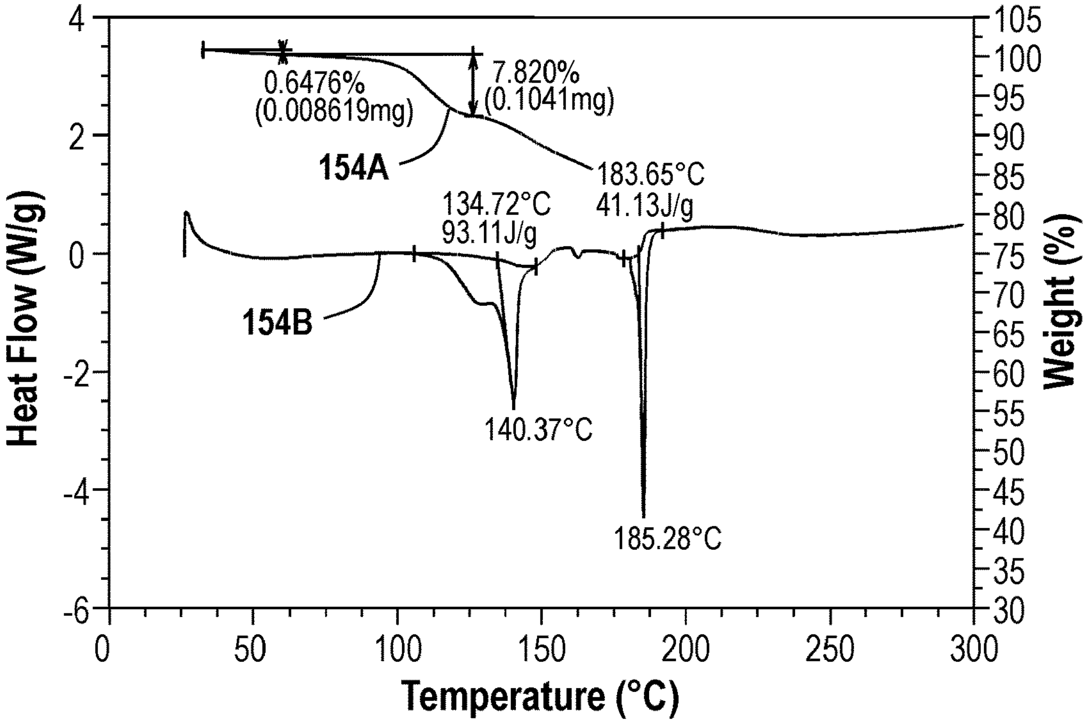

FIG. 154 depicts the TGA pattern of Form A acetate salt of Compound 1 (154A), and the DSC pattern of Form A acetate salt of Compound 1 (154B).

Figure 155:
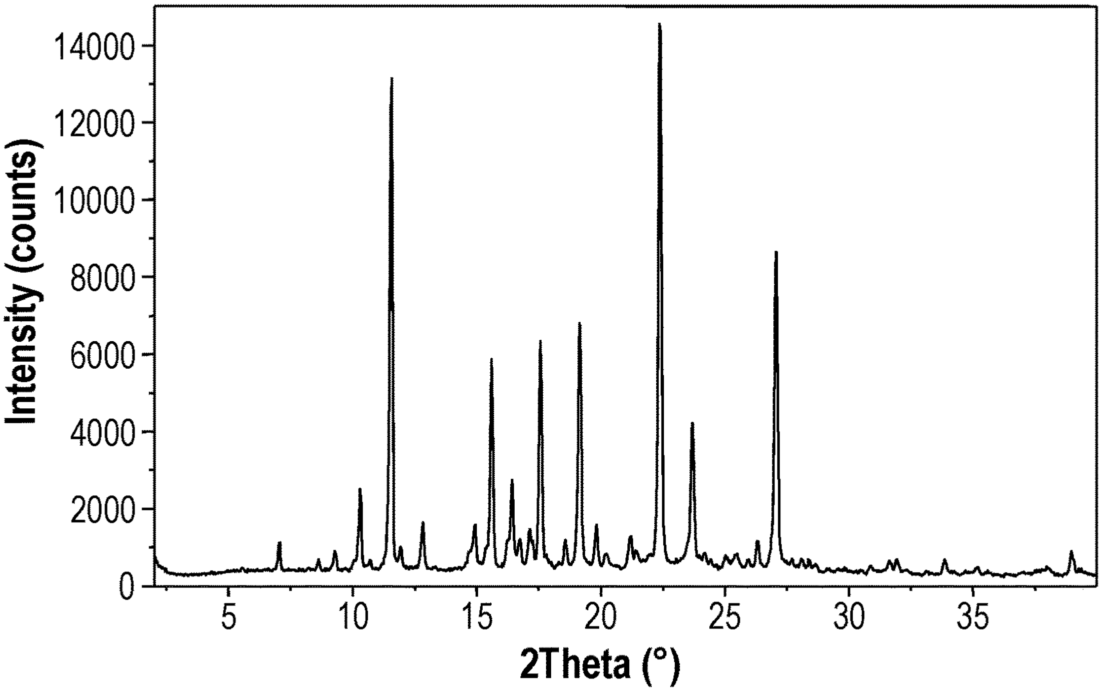

FIG. 155 depicts the XRPD pattern of Form B acetate salt of Compound 1.

Figure 156:
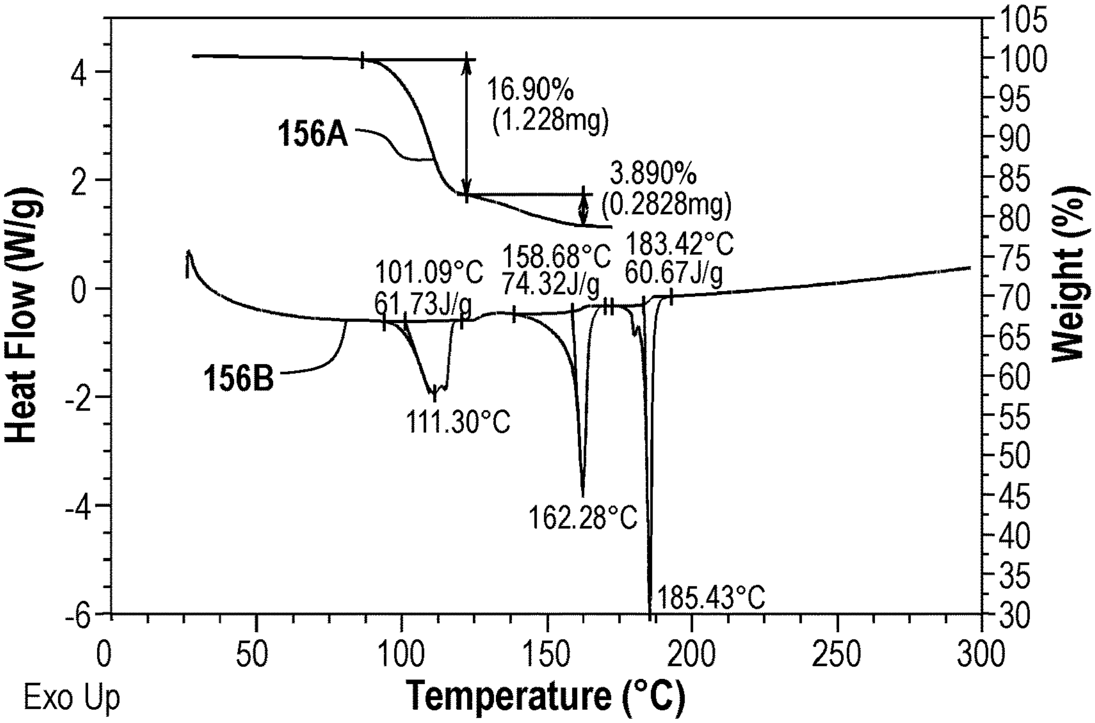

FIG. 156 depicts the TGA pattern of Form B acetate salt of Compound 1 (156A), and the DSC pattern of Form B acetate salt of Compound 1 (156B).

Figure 157:
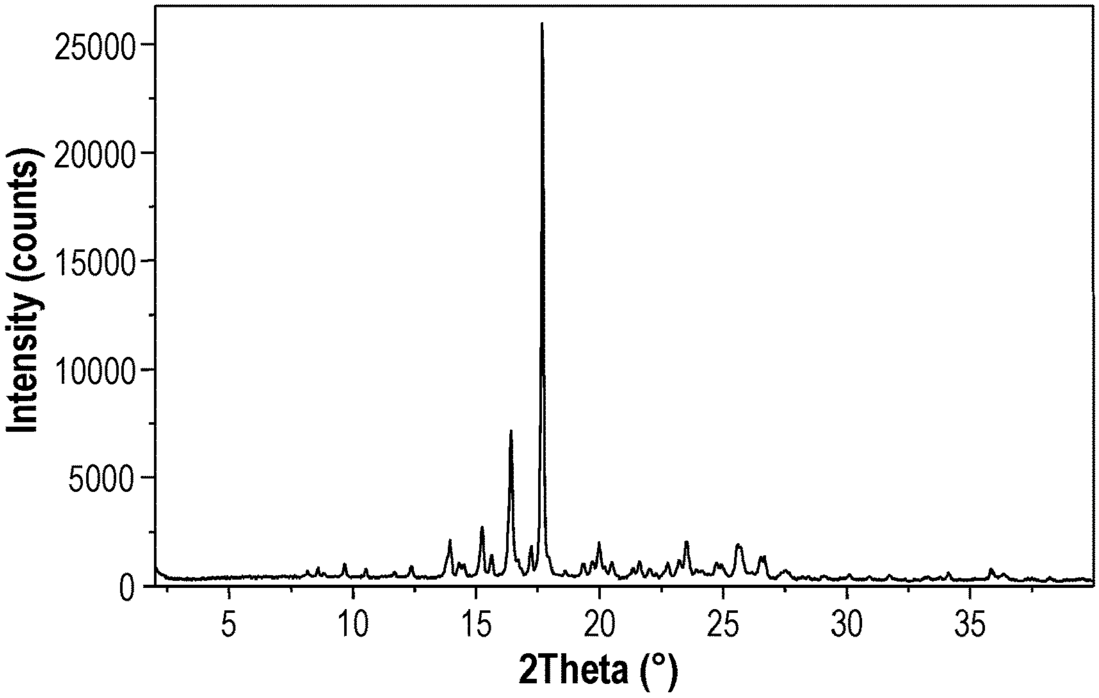

FIG. 157 depicts the XRPD pattern of Form A propionate salt of Compound 1.

Figure 158:
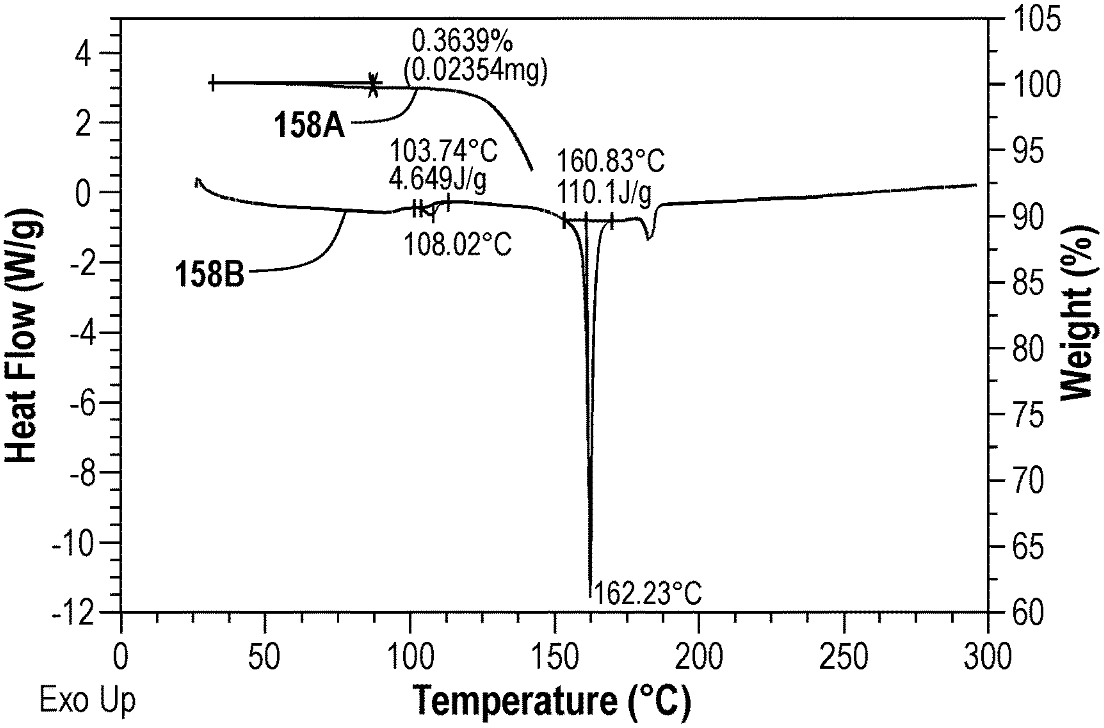

FIG. 158 depicts the TGA pattern of Form A propionate salt of Compound 1 (158A), and the DSC pattern of Form A propionate salt of Compound 1 (158B).

Figure 159:
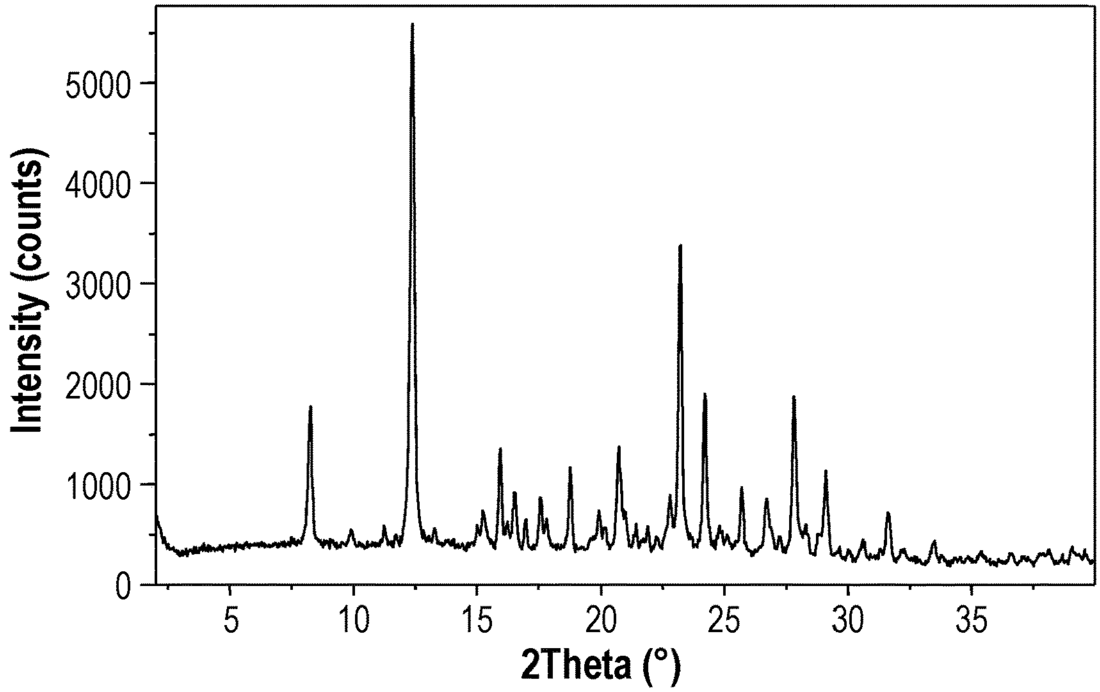

FIG. 159 depicts the XRPD pattern of Form A DL-lactate salt of Compound 1.

Figure 160:
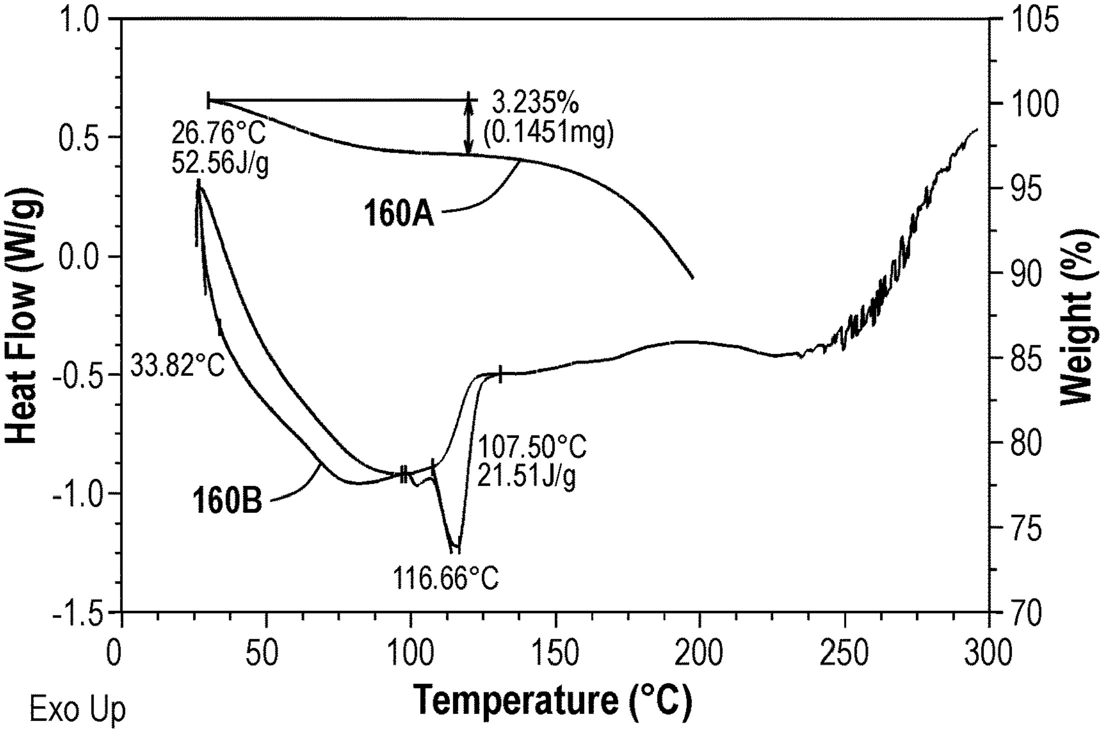

FIG. 160 depicts the TGA pattern of Form A DL-lactate salt of Compound 1 (160A), and the DSC pattern of Form A DL-lactate salt of Compound 1 (160B).

Figure 161:
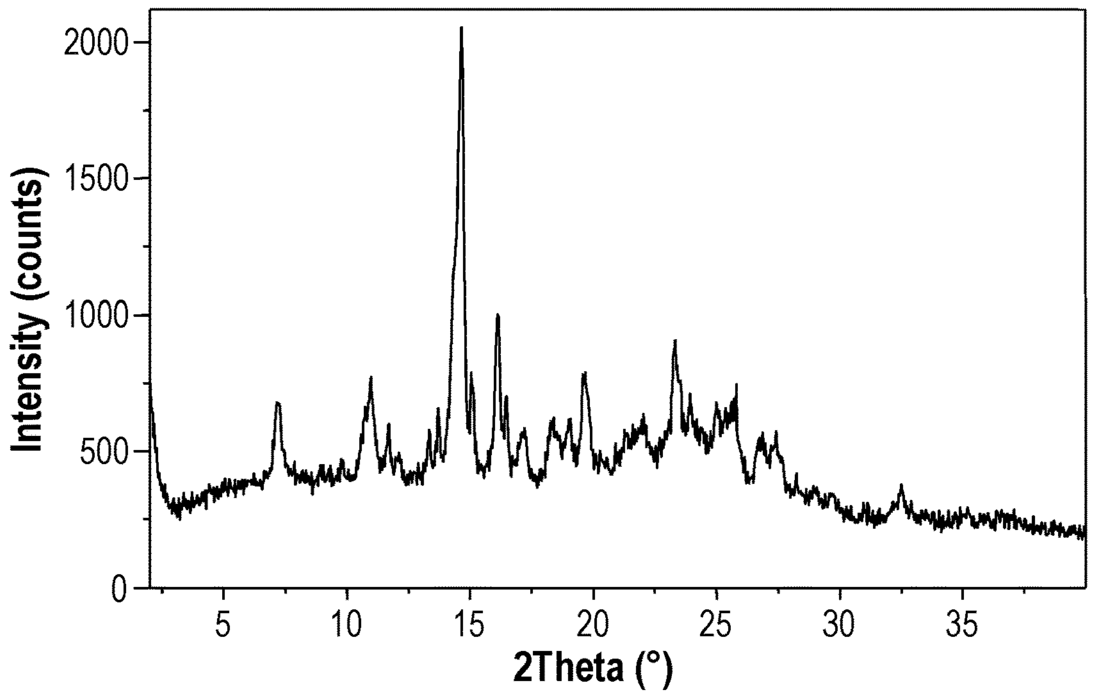

FIG. 161 depicts the XRPD pattern of Form A D-gluconate salt of Compound 1.

Figure 162:
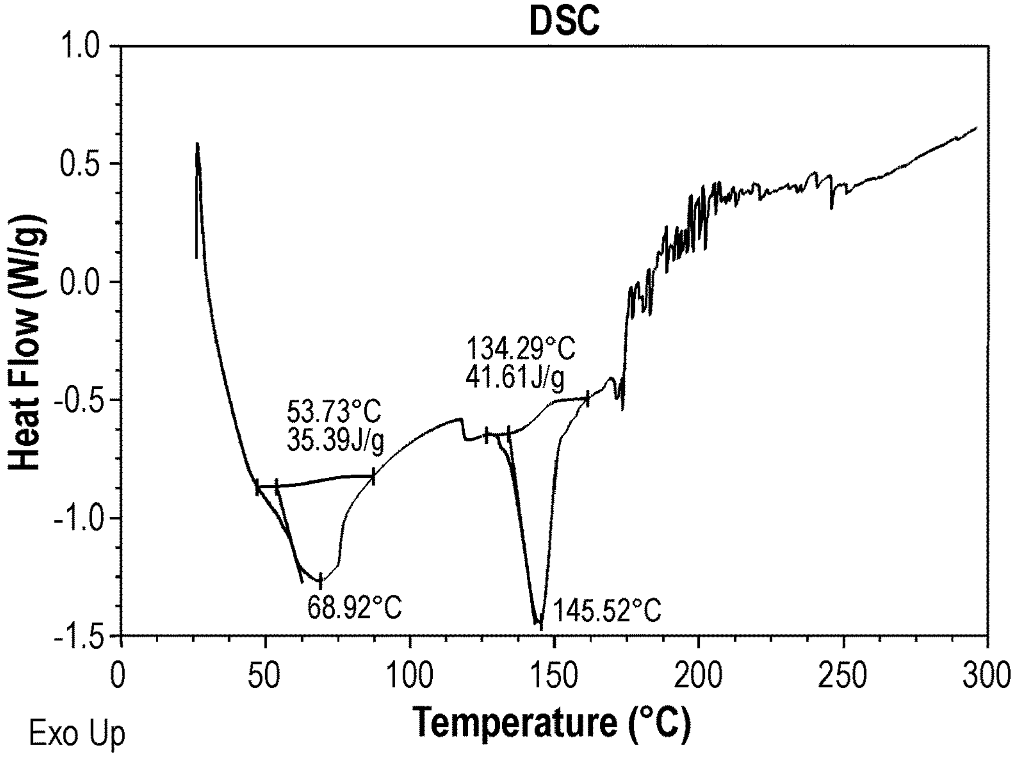

FIG. 162 depicts the DSC pattern of Form A D-gluconate salt of Compound 1.

Figure 163:
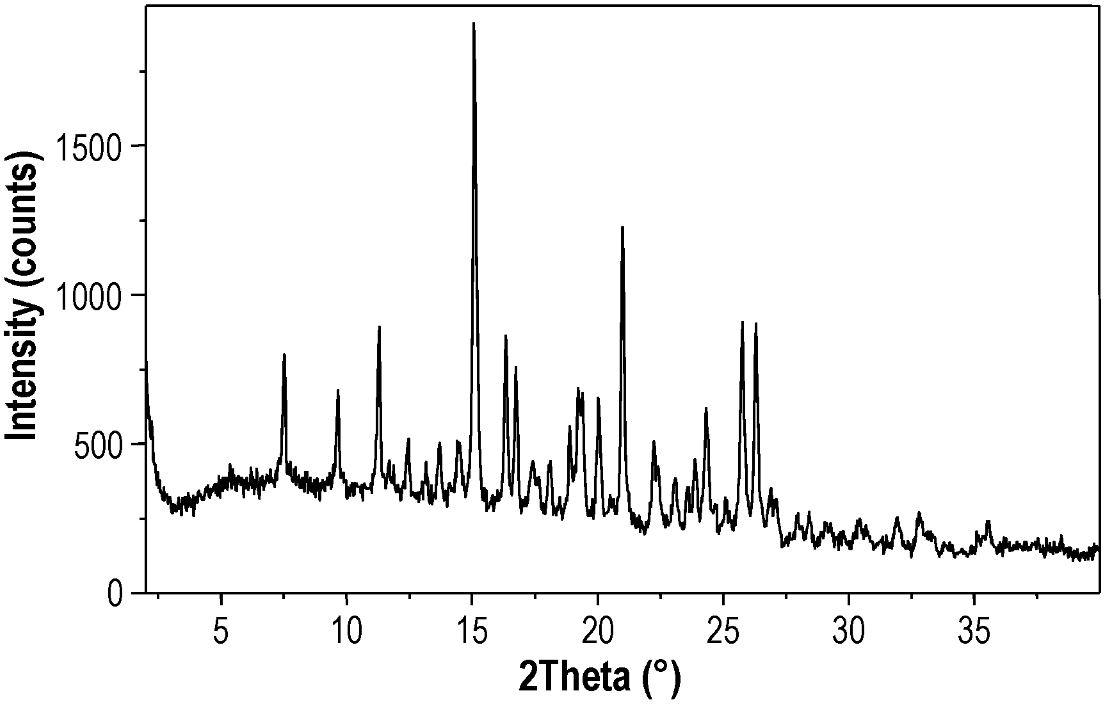

FIG. 163 depicts the XRPD pattern of Form A DL-malate salt of Compound 1.

Figure 164:
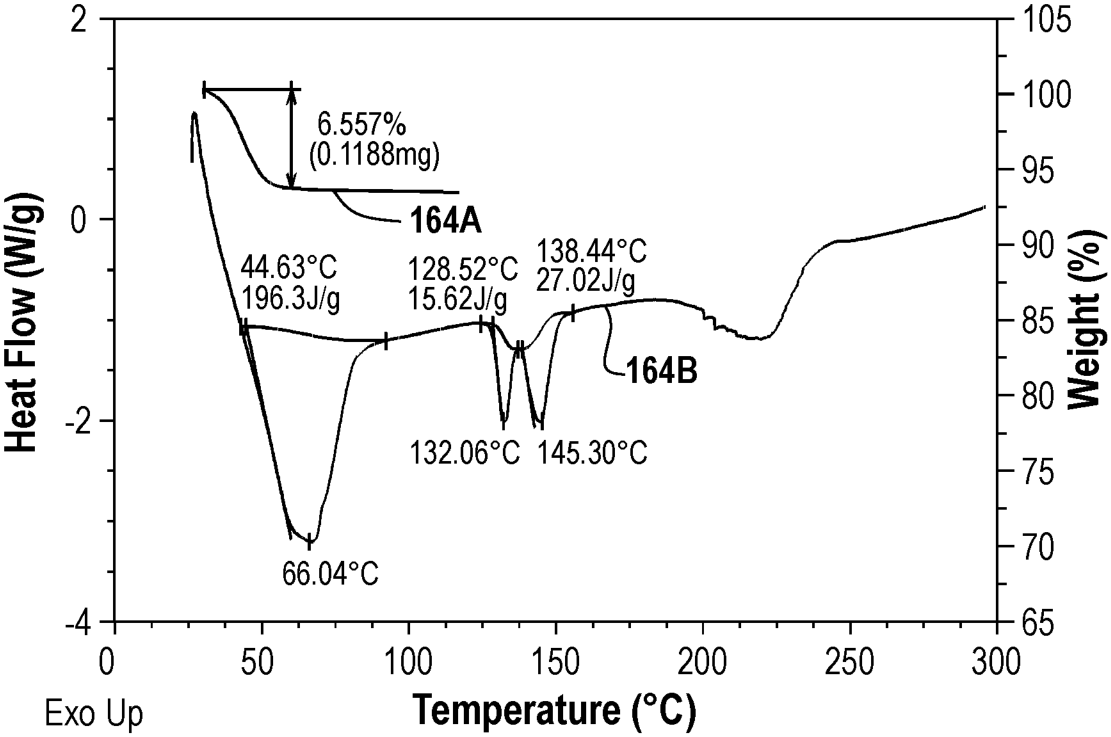

FIG. 164 depicts the TGA pattern of Form A DL-malate salt of Compound 1 (164A), and the DSC pattern of Form A DL-malate salt of Compound 1 (164B).

Figure 165:
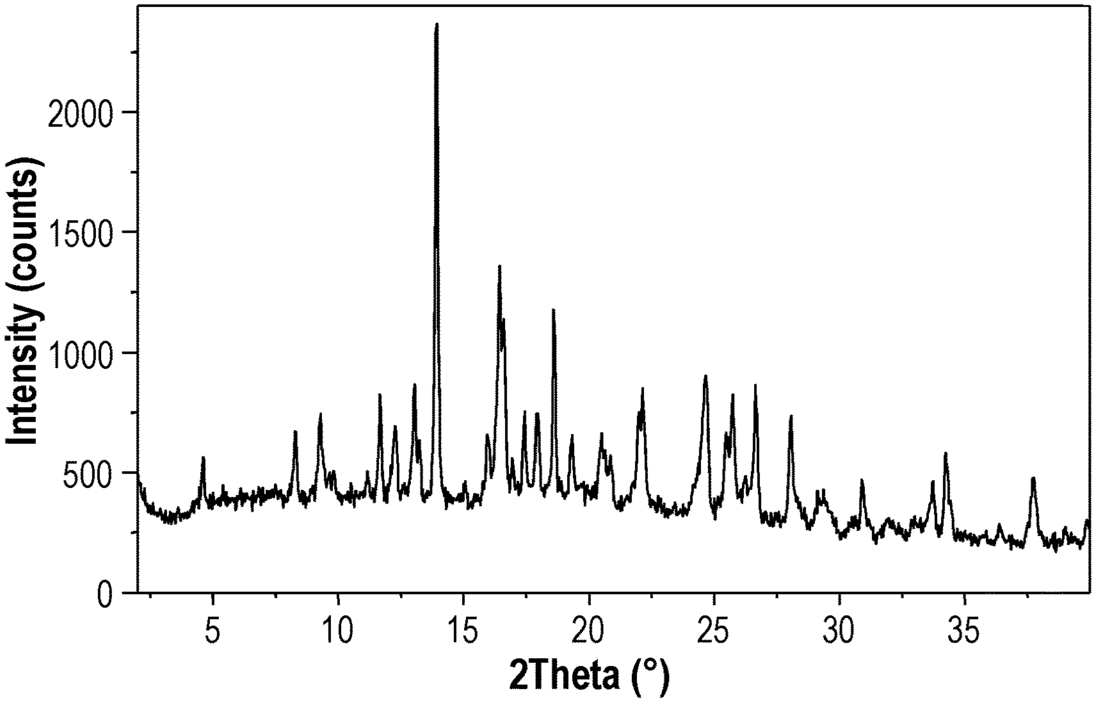

FIG. 165 depicts the XRPD pattern of Form B DL-malate salt of Compound 1.

Figure 166:
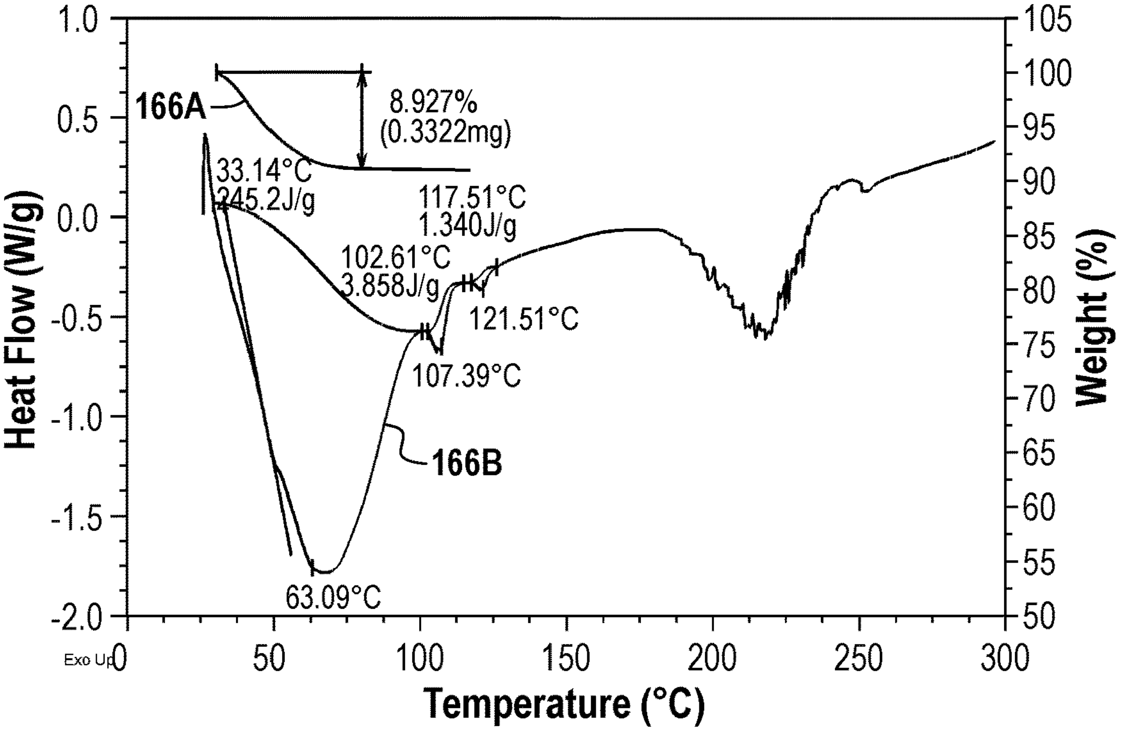

FIG. 166 depicts the TGA pattern of Form B DL-malate salt of Compound 1 (166A), and the DSC pattern of Form B DL-malate salt of Compound 1 (166B).

Figure 167:
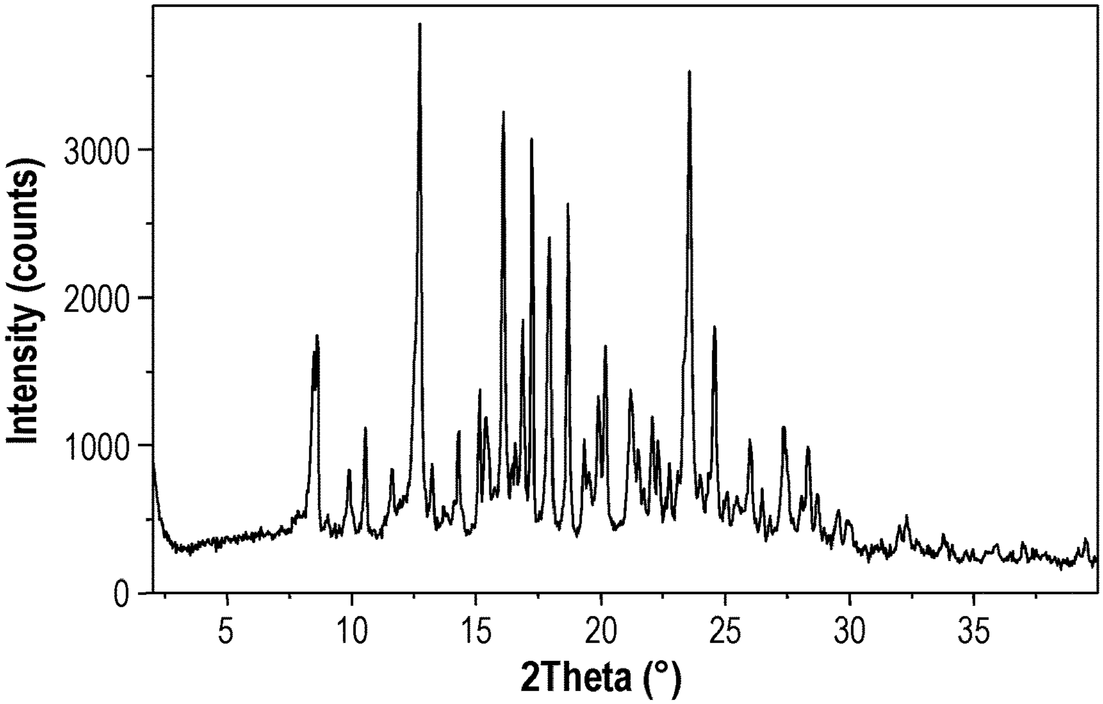

FIG. 167 depicts the XRPD pattern of Form A glycolate salt of Compound 1.

Figure 168:
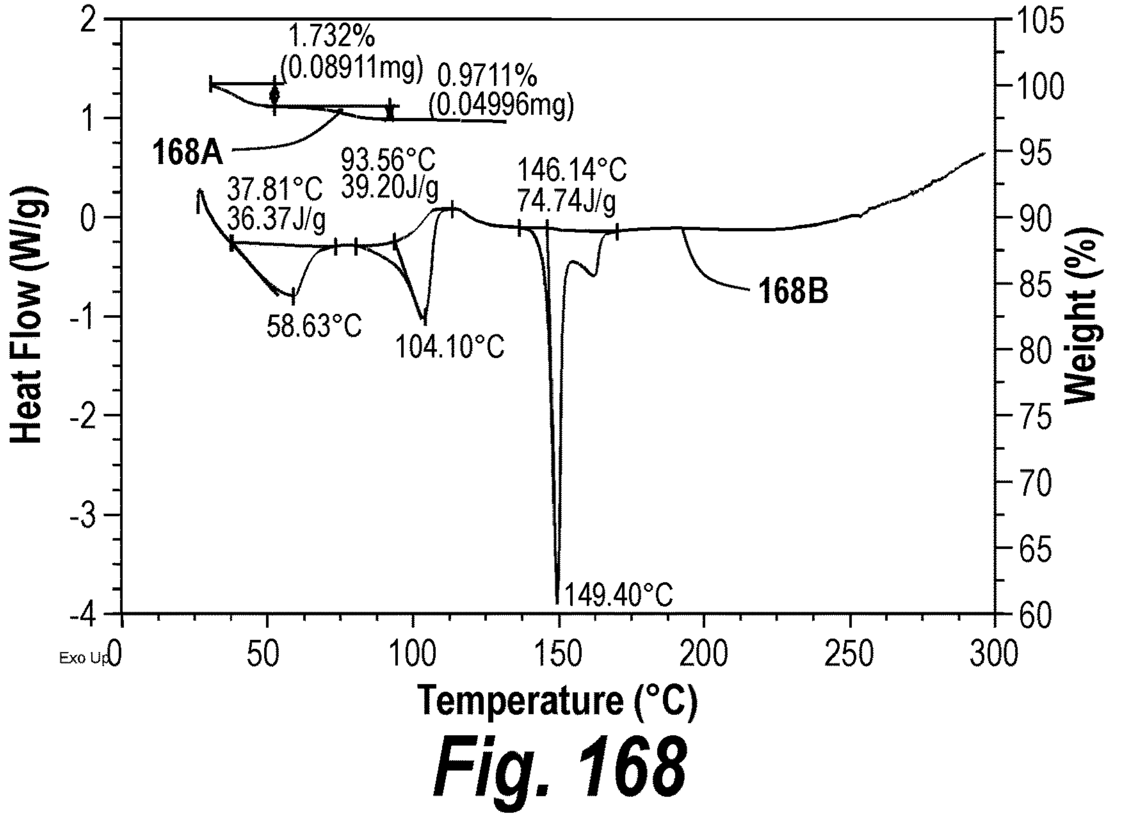

FIG. 168 depicts the TGA pattern of Form A glycolate salt of Compound 1 (168A), and the DSC pattern of Form A glycolate salt of Compound 1 (168B).

Figure 169:
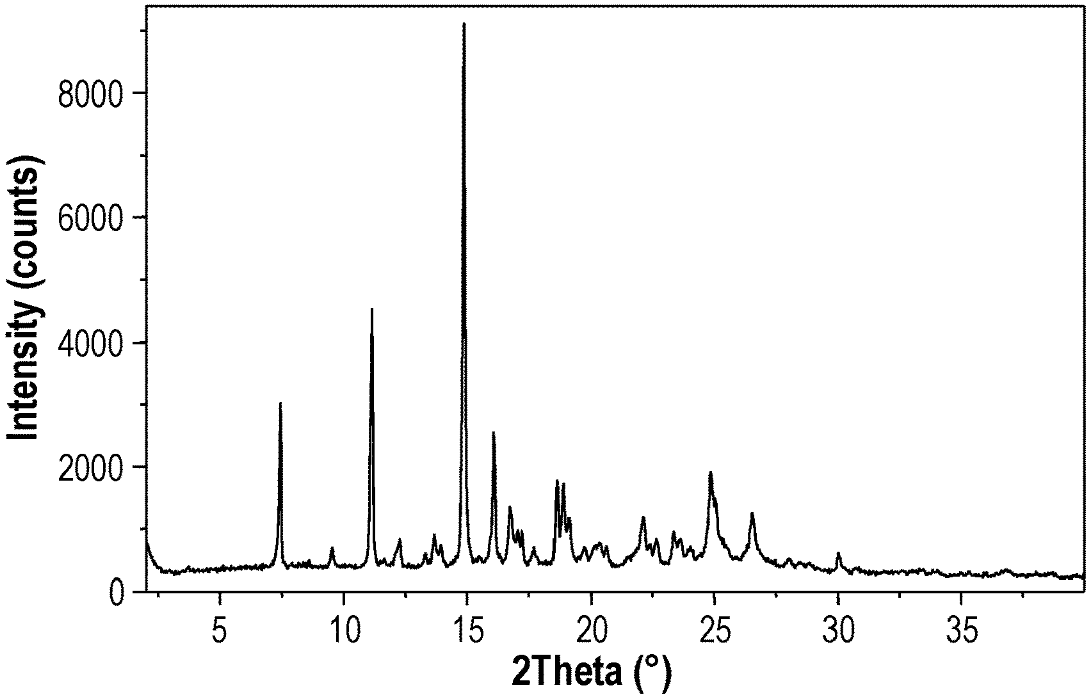

FIG. 169 depicts the XRPD pattern of Form A glutarate salt of Compound 1.

Figure 170:
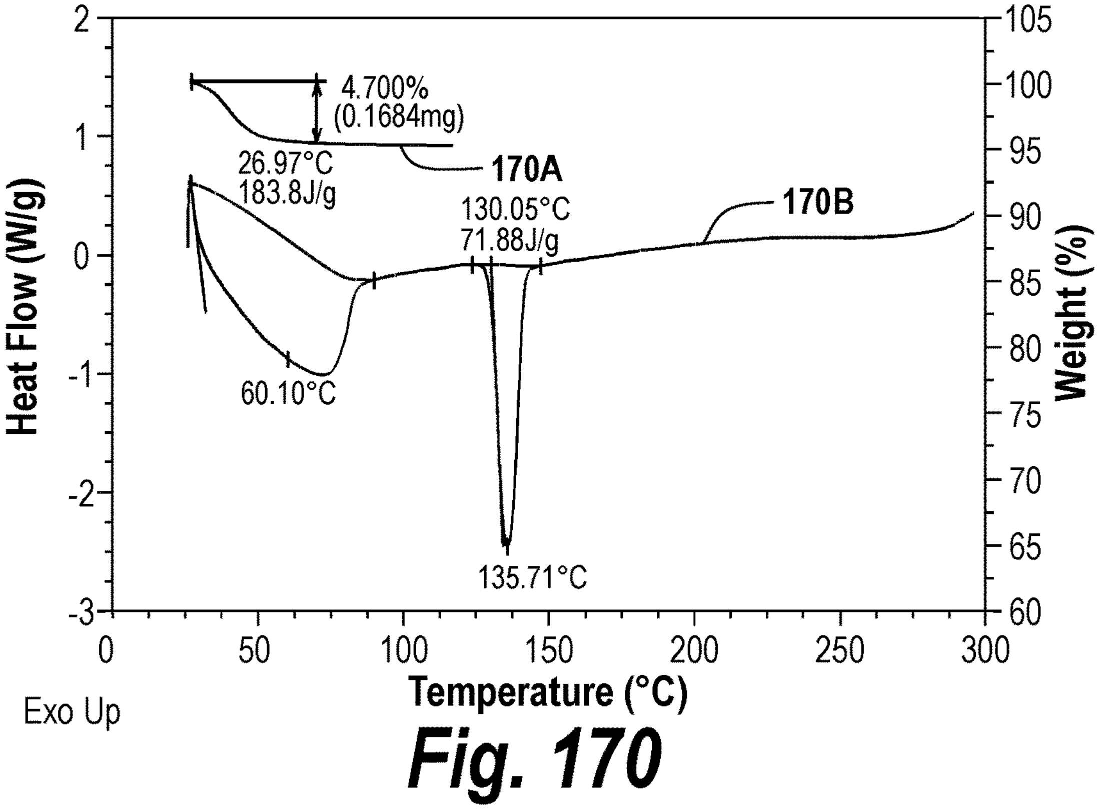

FIG. 170 depicts the TGA pattern of Form A glutarate salt of Compound 1 (170A), and the DSC pattern of Form A glutarate salt of Compound 1 (170B).

Figure 171:
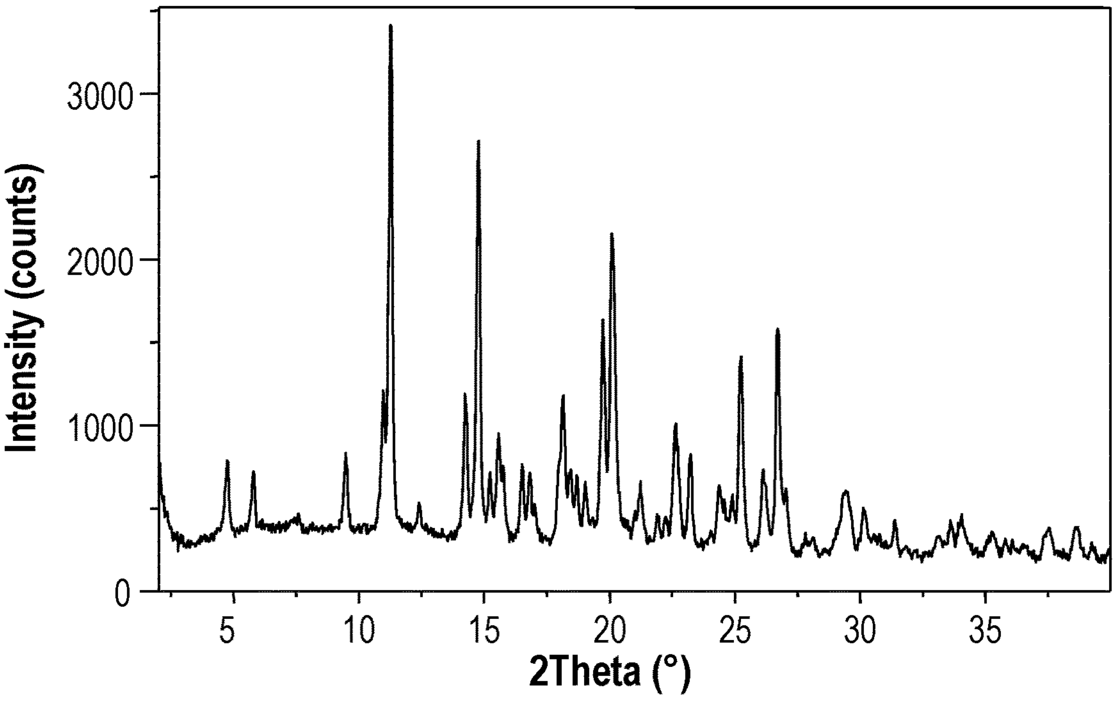

FIG. 171 depicts the XRPD pattern of Form B glutarate salt of Compound 1.

Figure 172:
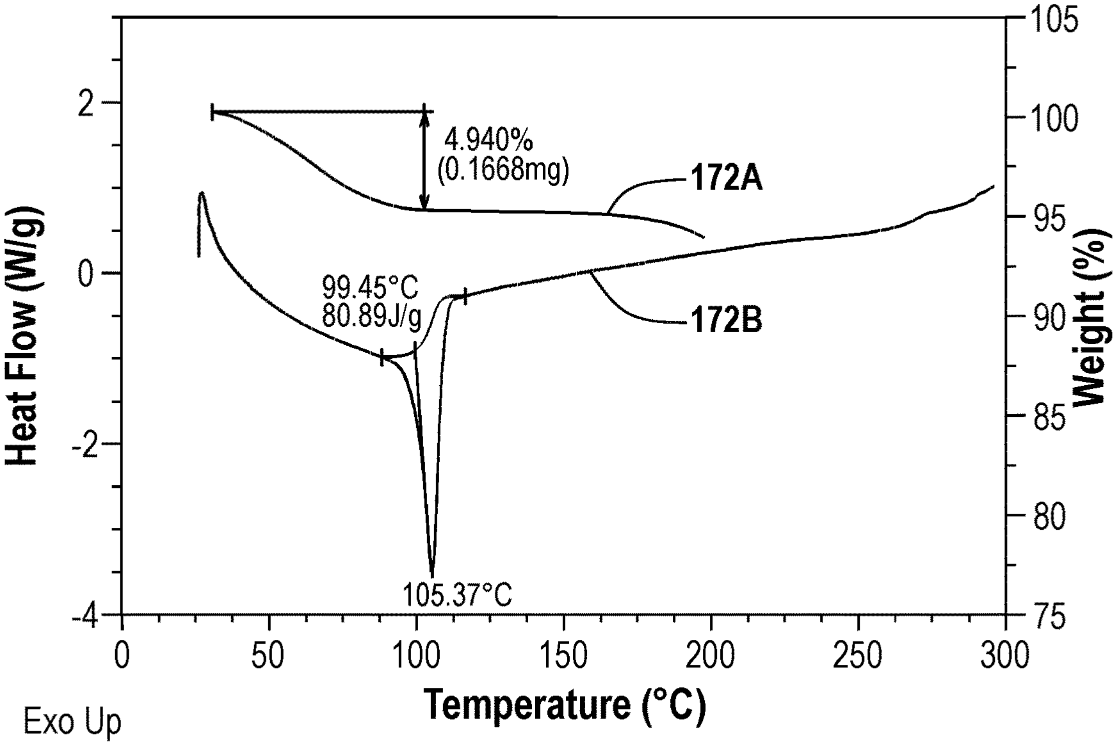

FIG. 172 depicts the TGA pattern of Form B glutarate salt of Compound 1 (172A), and the DSC pattern of Form B glutarate salt of Compound 1 (172B).

Figure 173:
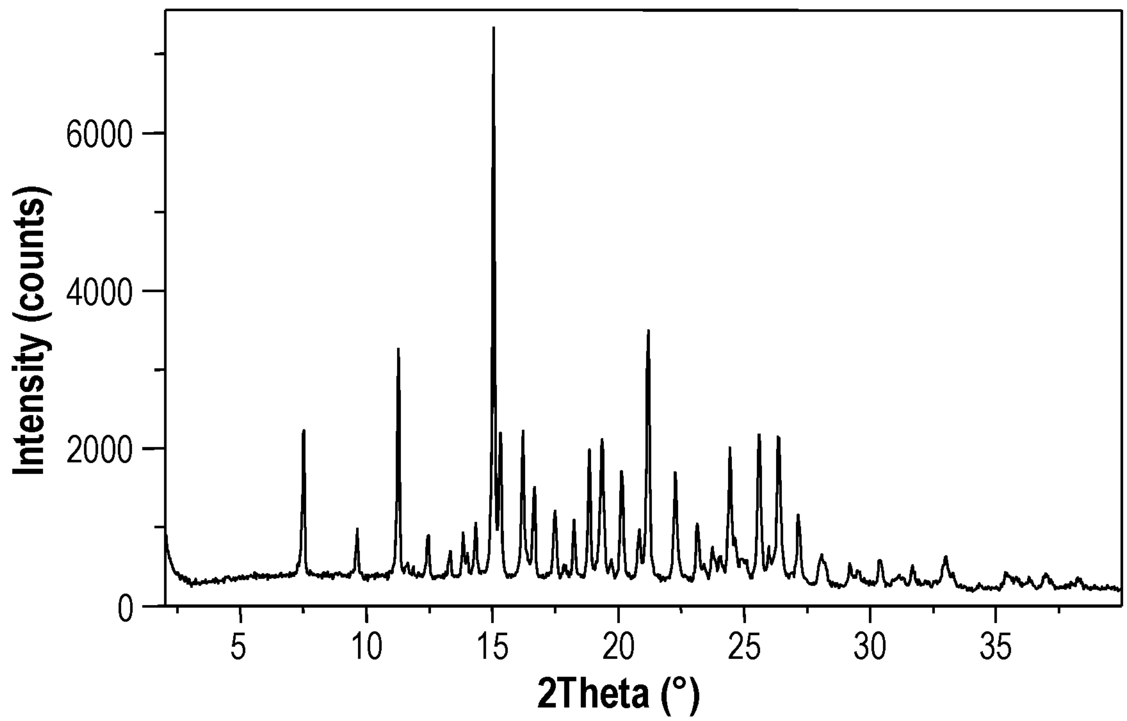

FIG. 173 depicts the XRPD pattern of Form A L-malate salt of Compound 1.

Figure 174:
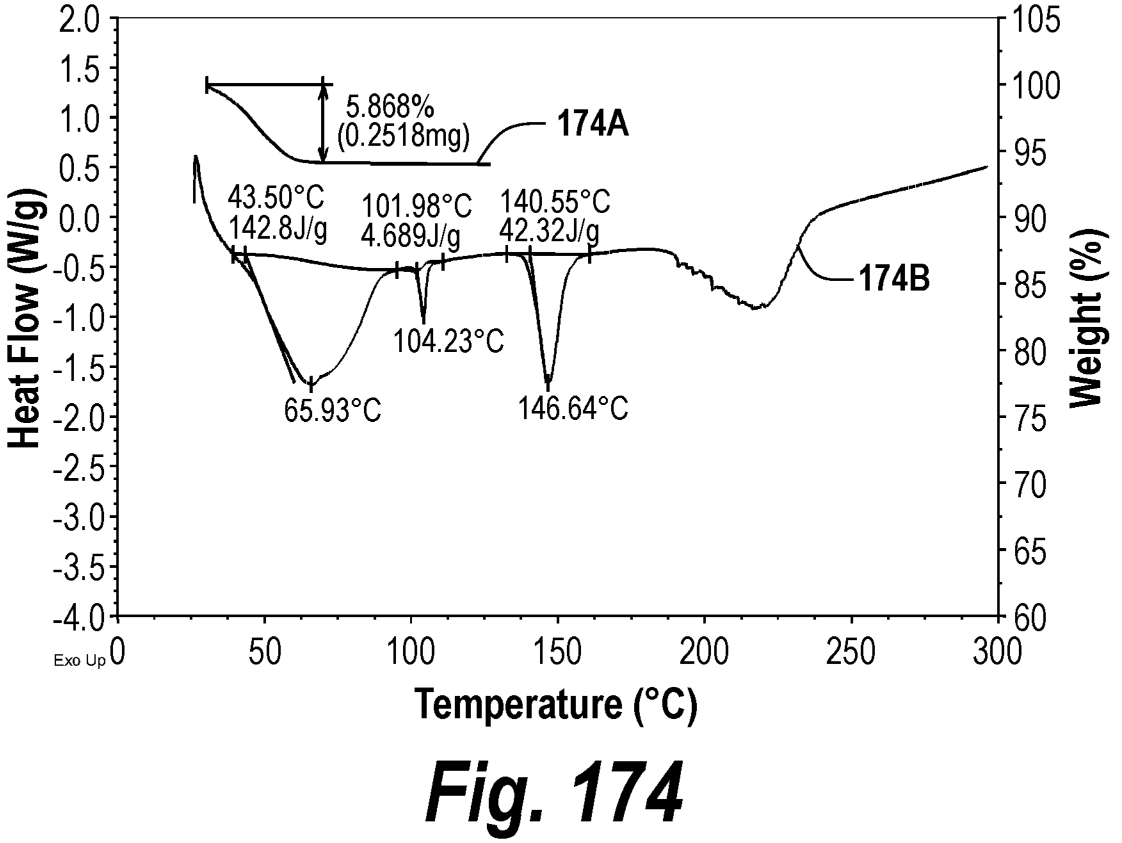

FIG. 174 depicts the TGA pattern of Form A L-malate salt of Compound 1 (174A), and the DSC pattern of Form A L-malate salt of Compound 1 (174B).

Figure 175:
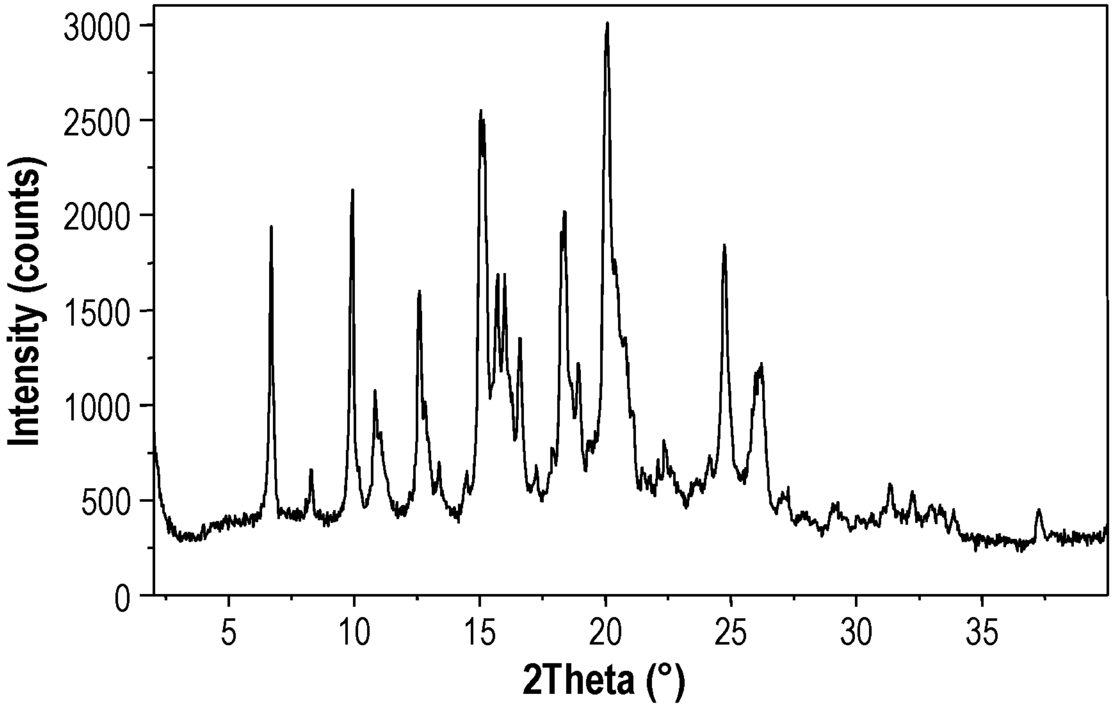

FIG. 175 depicts the XRPD pattern of Form A camphorate salt of Compound 1.

Figure 176:
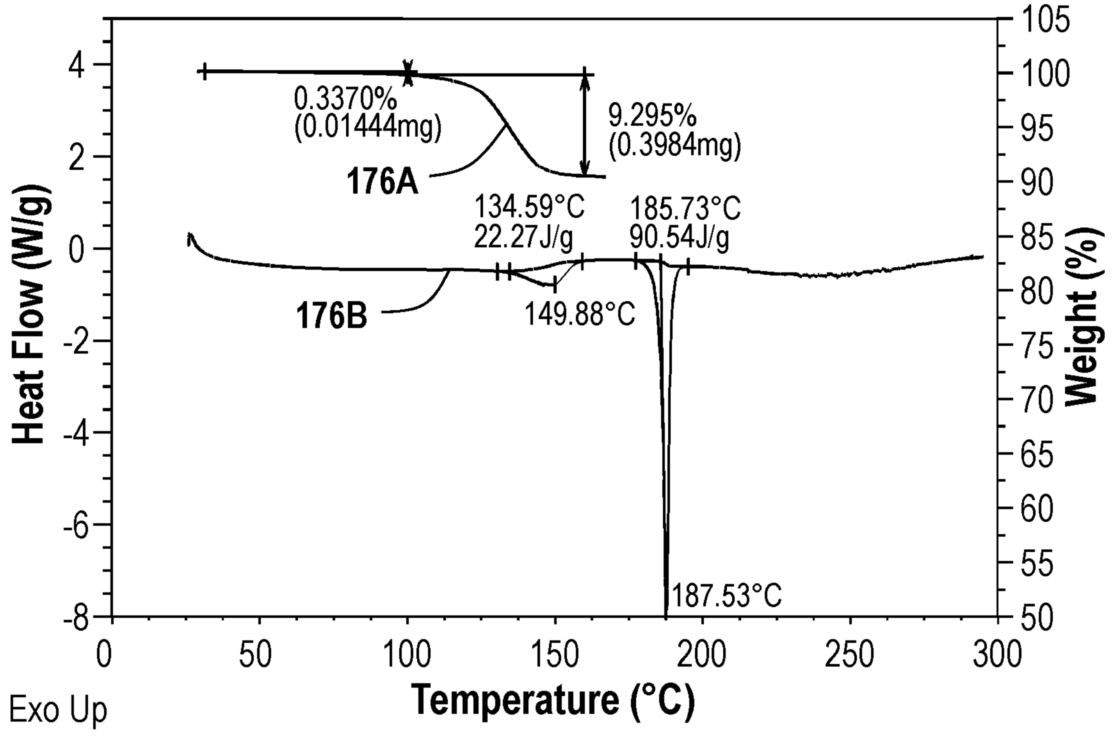

FIG. 176 depicts the TGA pattern of Form A camphorate salt of Compound 1 (176A), and the DSC pattern of Form A camphorate salt of Compound 1 (176B).

Figure 177:
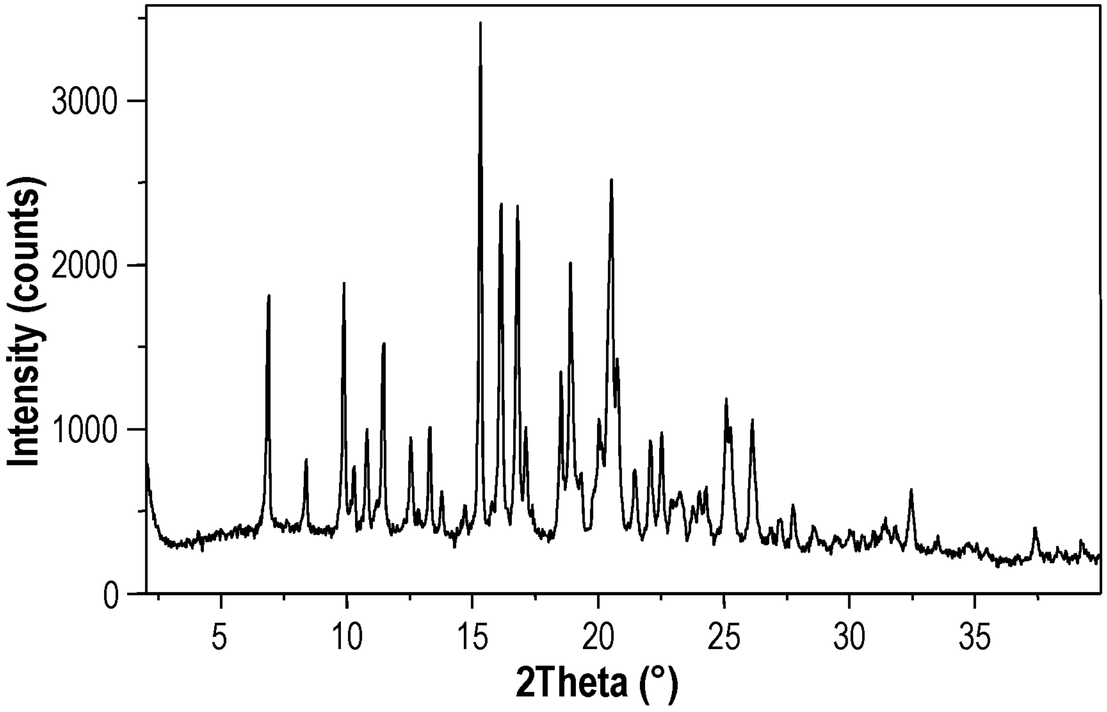

FIG. 177 depicts the XRPD pattern of Form B camphorate salt of Compound 1.

Figure 178:
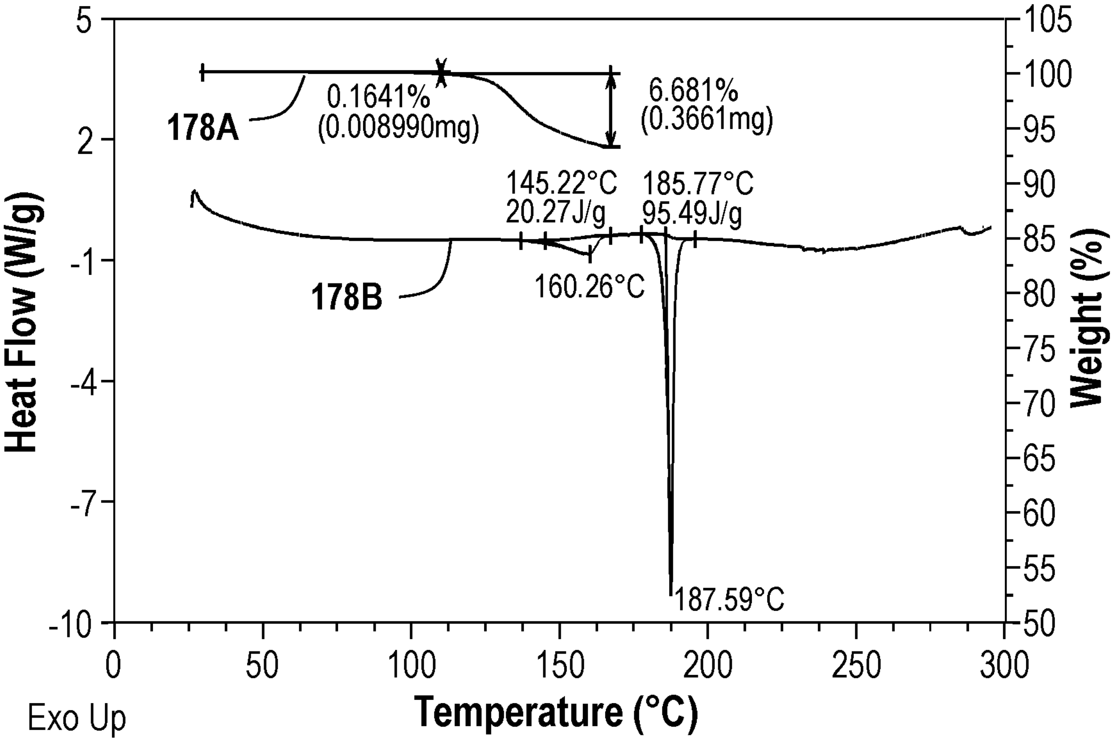

FIG. 178 depicts the TGA pattern of Form B camphorate salt of Compound 1 (178A), and the DSC pattern of Form B camphorate salt of Compound 1 (178B).

Figure 179:
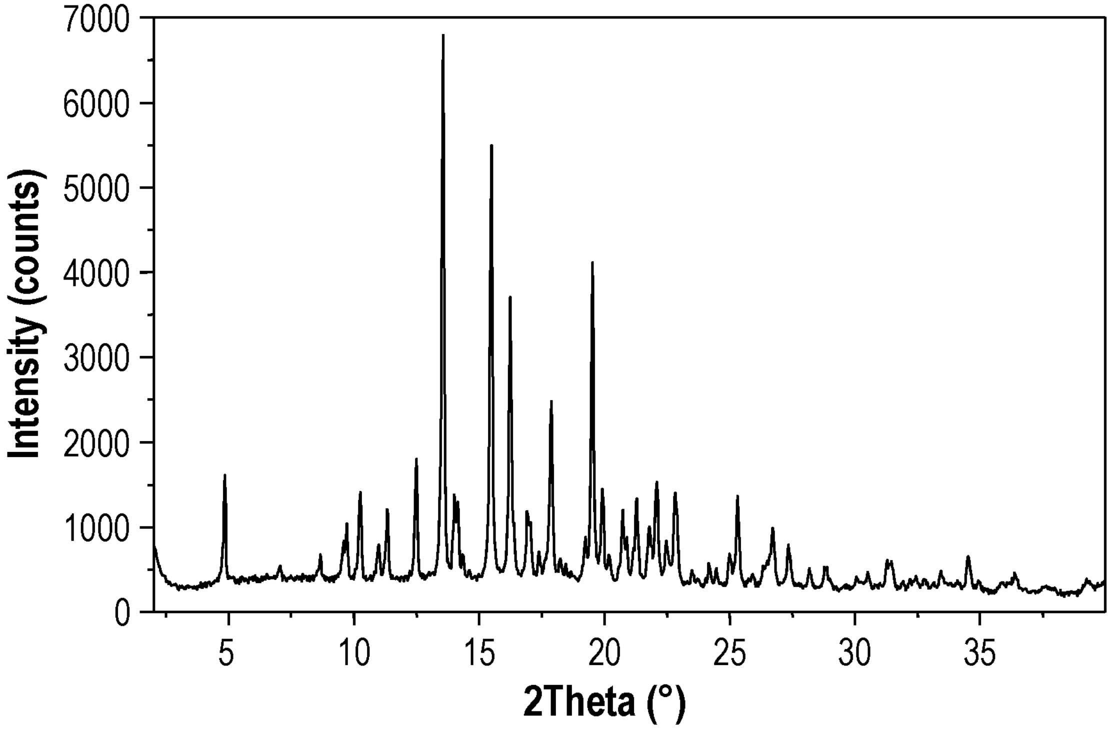

FIG. 179 depicts the XRPD pattern of Form C camphorate salt of Compound 1.

Figure 180:
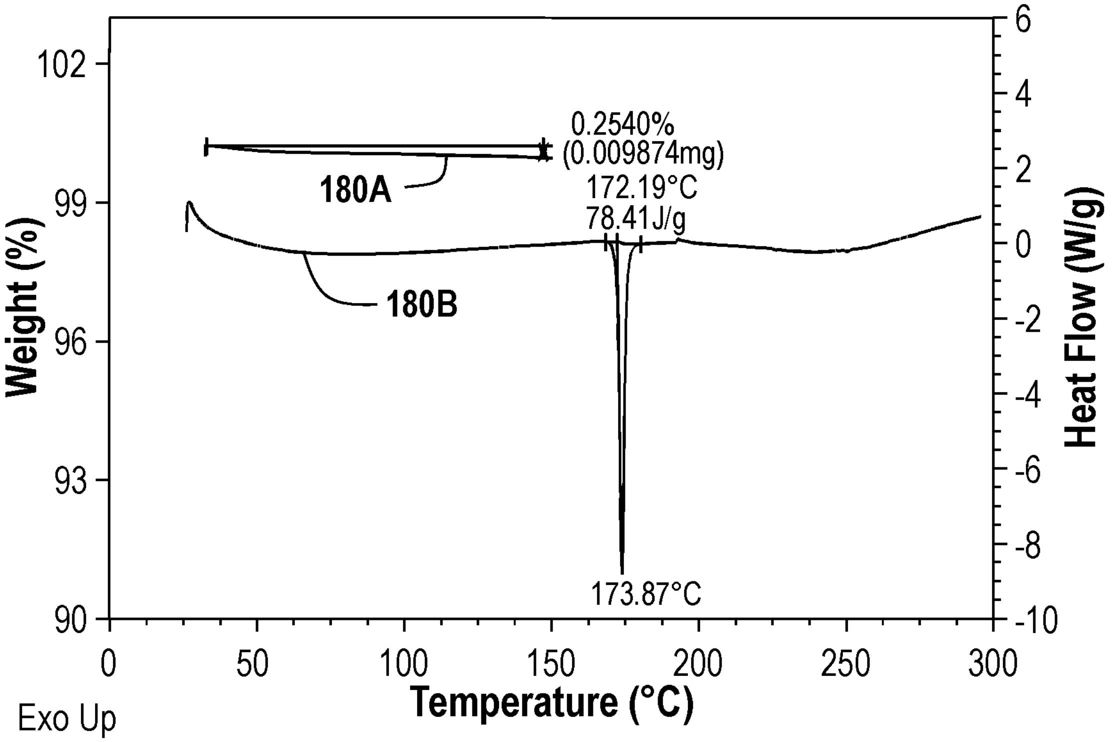

FIG. 180 depicts the TGA pattern of Form C camphorate salt of Compound 1 (180A), and the DSC pattern of Form C camphorate salt of Compound 1 (180B).

Figure 181:
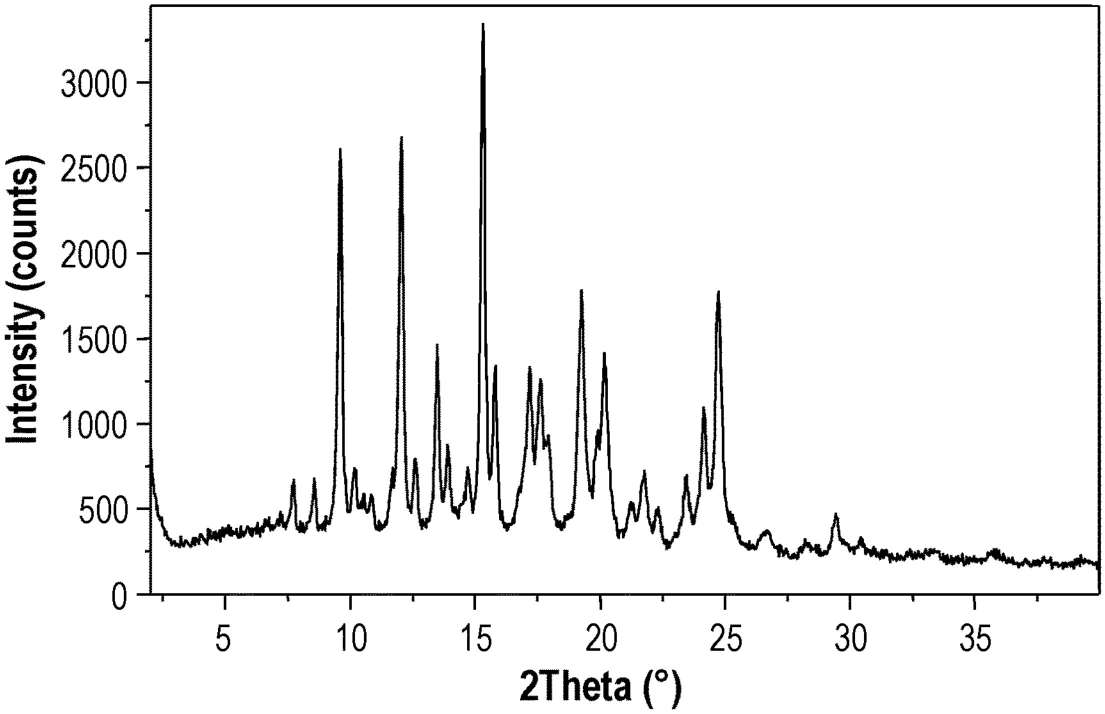

FIG. 181 depicts the XRPD pattern of Form D camphorate salt of Compound 1.

Figure 182:
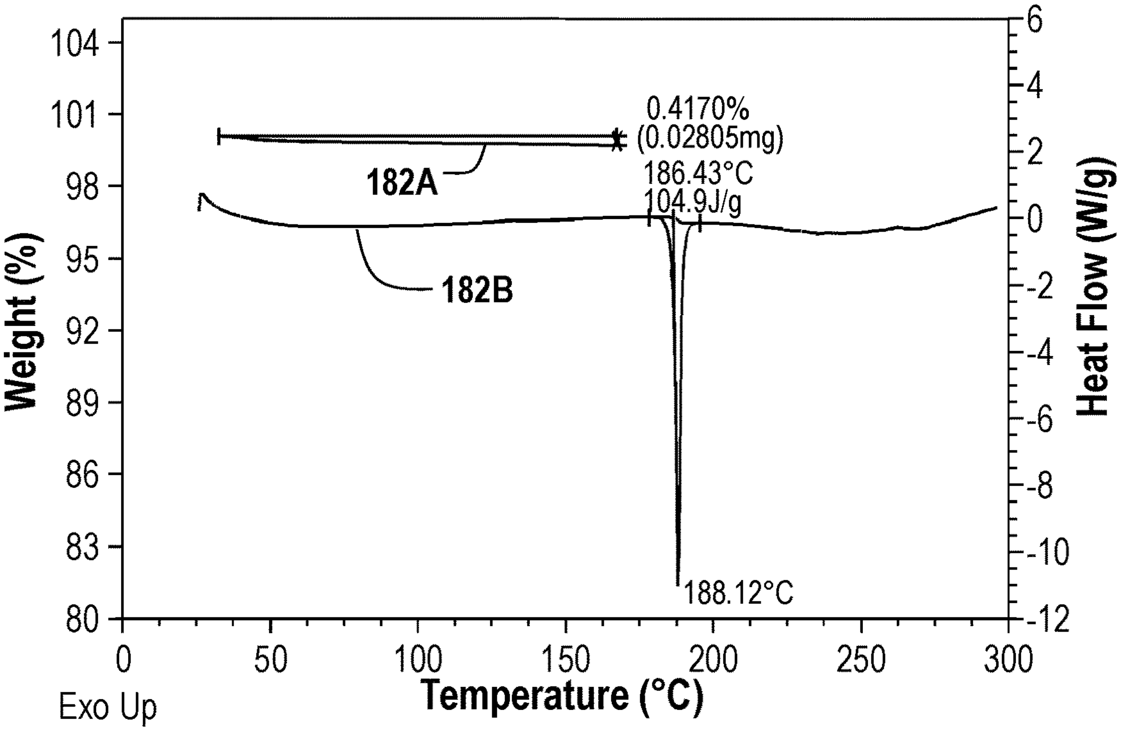

FIG. 182 depicts the TGA pattern of Form D camphorate salt of Compound 1 (182A), and the DSC pattern of Form D camphorate salt of Compound 1 (182B).

Figure 183:
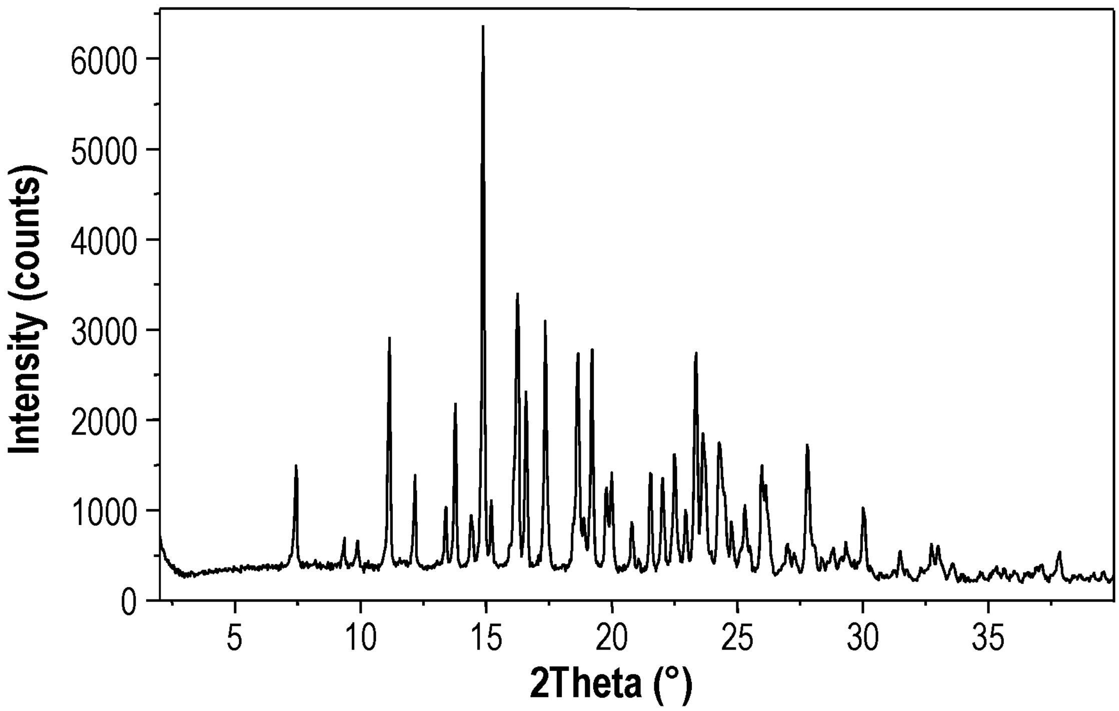

FIG. 183 depicts the XRPD pattern of Form A DL-mandelate salt of Compound 1.

Figure 184:
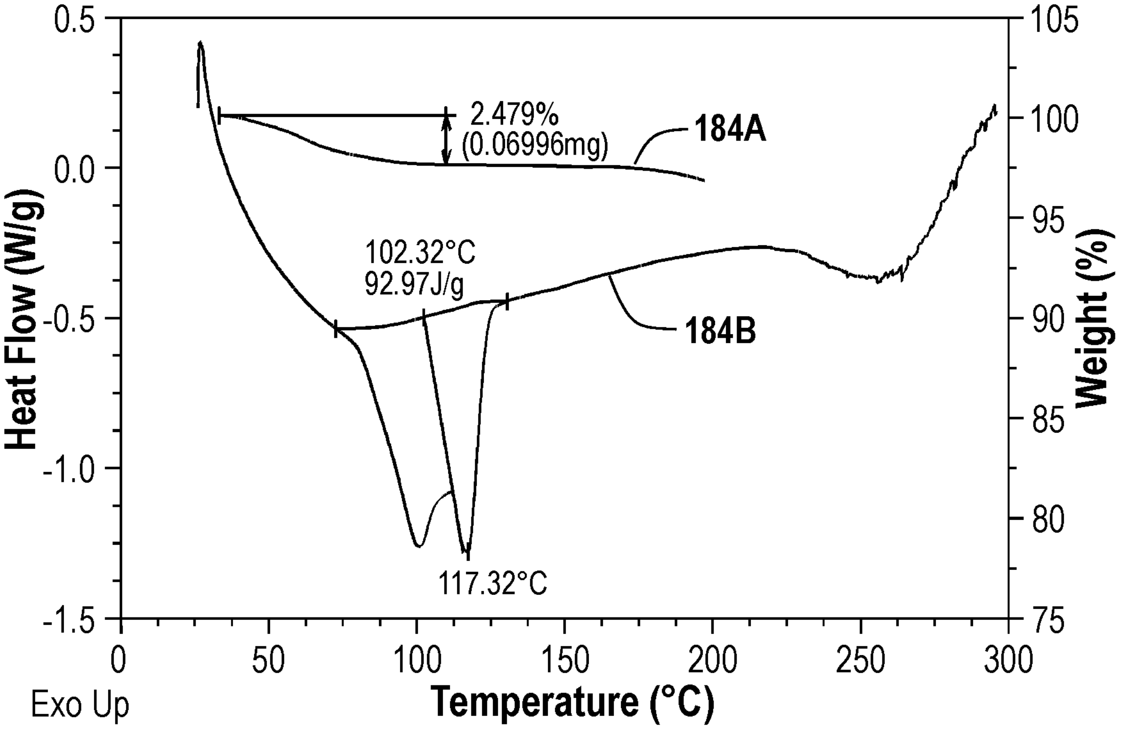

FIG. 184 depicts the TGA pattern of Form A DL-mandelate salt of Compound 1 (184A), and the DSC pattern of Form A DL-mandelate salt of Compound 1 (184B).

Figure 185:
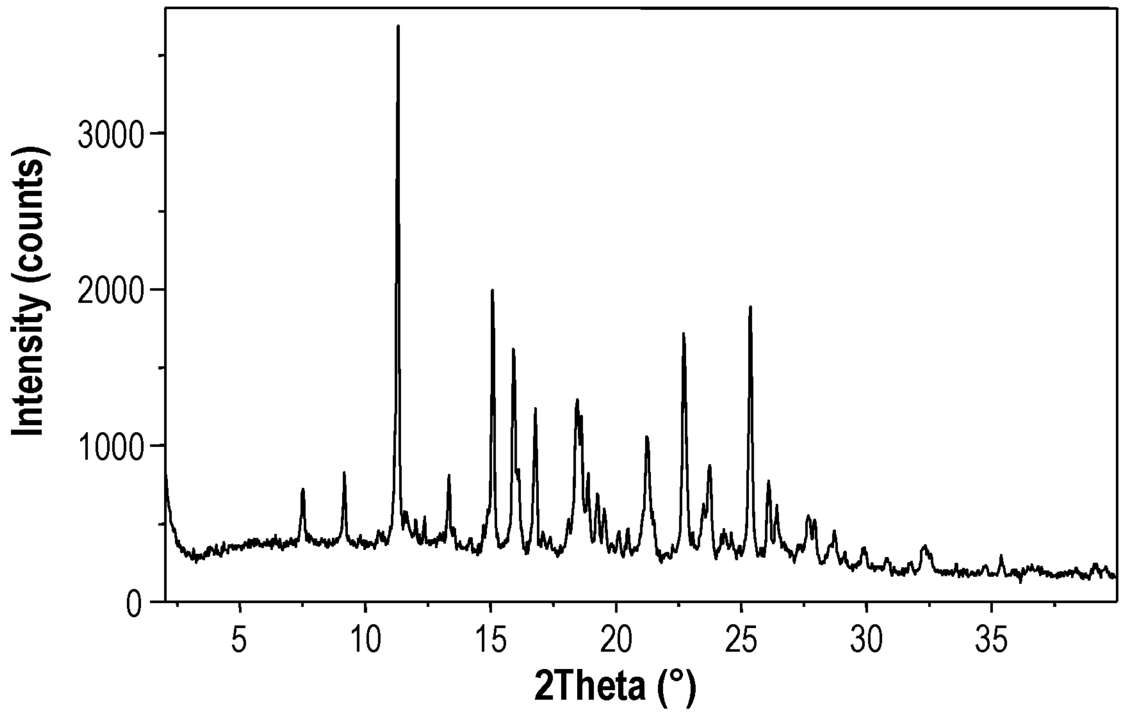

FIG. 185 depicts the XRPD pattern of Form B DL-mandelate salt of Compound 1.

Figure 186:
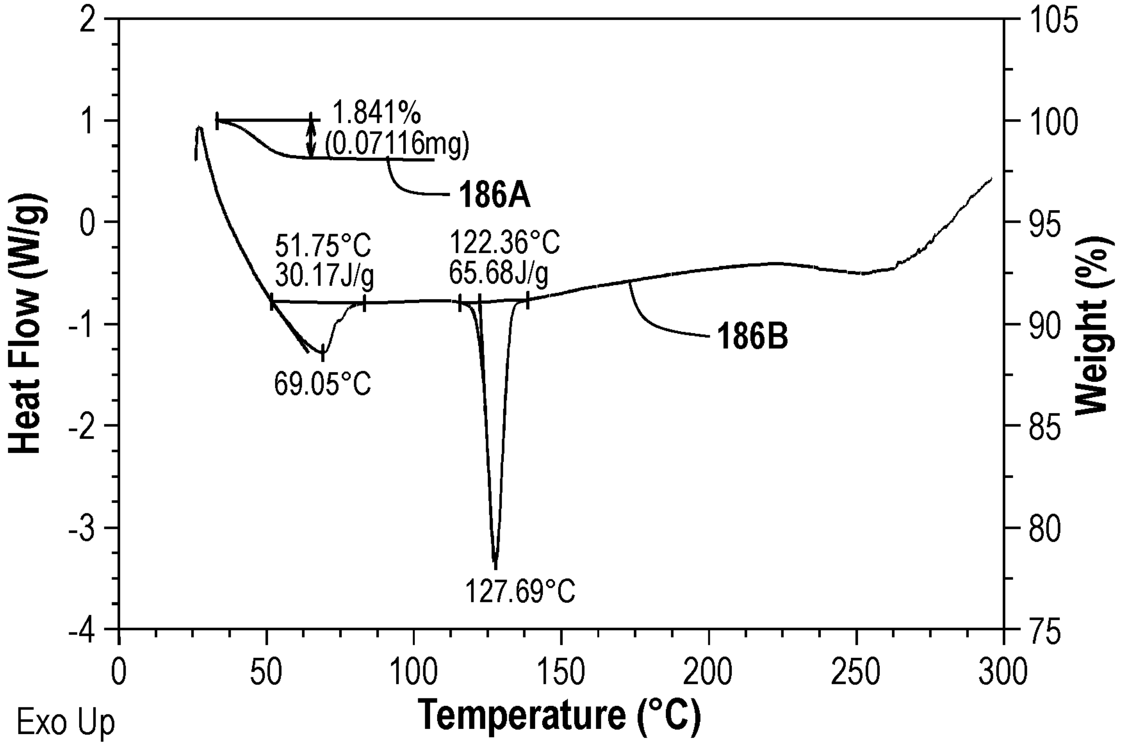

FIG. 186 depicts the TGA pattern of Form B DL-mandelate salt of Compound 1 (186A), and the DSC pattern of Form B DL-mandelate salt of Compound 1 (186B).

Figure 187:
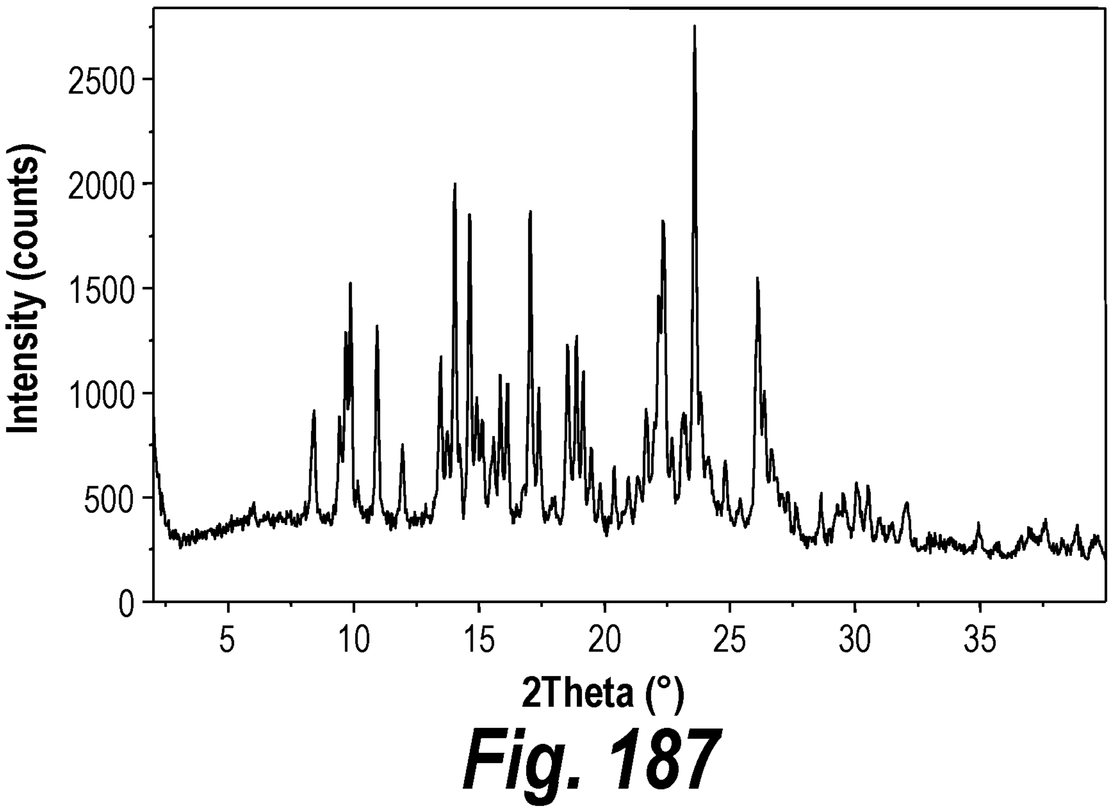

FIG. 187 depicts the XRPD pattern of Form C DL-mandelate salt of Compound 1.

Figure 188:
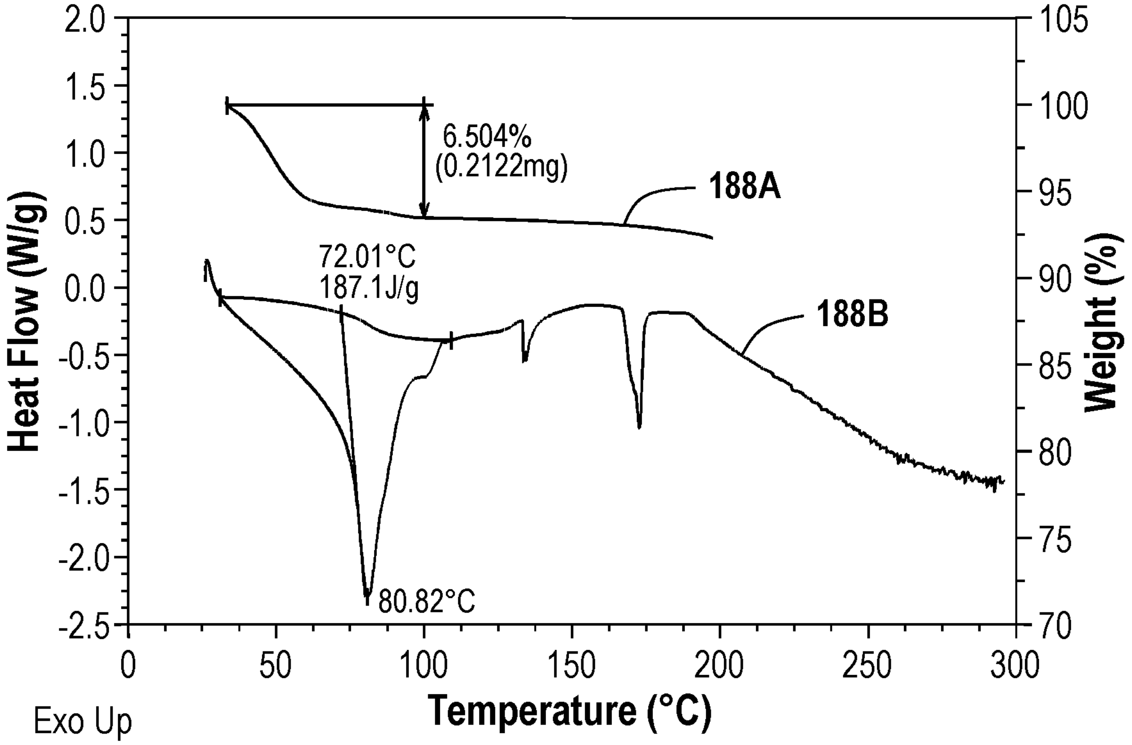

FIG. 188 depicts the TGA pattern of Form C DL-mandelate salt of Compound 1 (188A), and the DSC pattern of Form C DL-mandelate salt of Compound 1 (188B).

Figure 189:
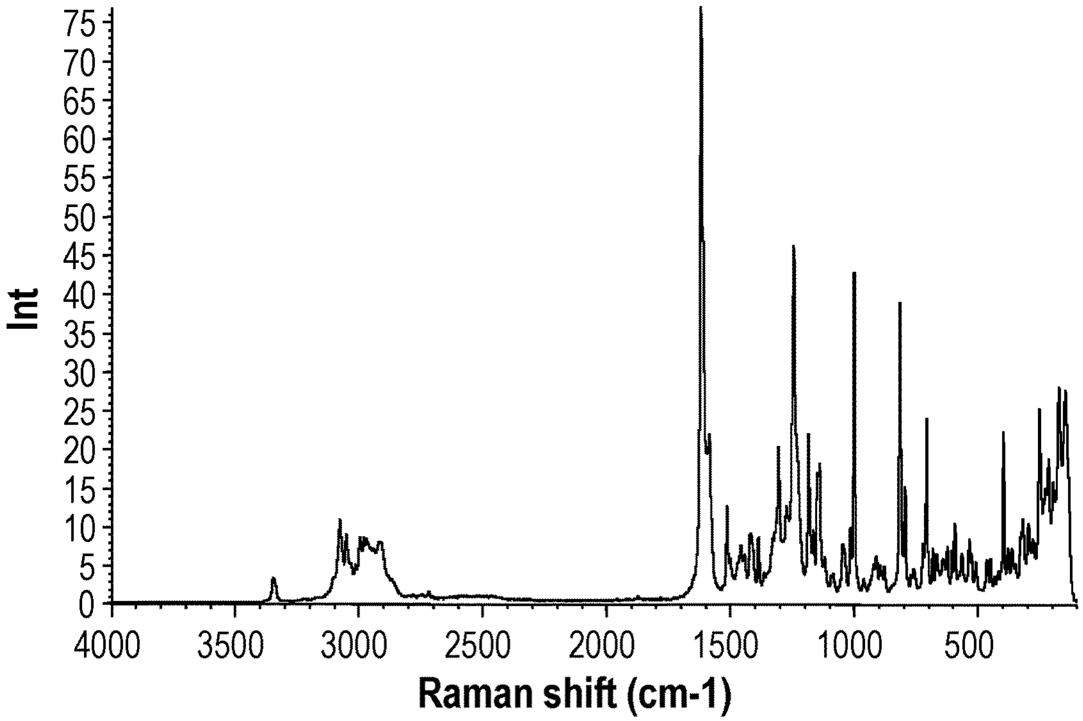

FIG. 189 depicts the FT-Raman spectrum of Form A saccharin co-crystal of Compound 1.

Figure 190:
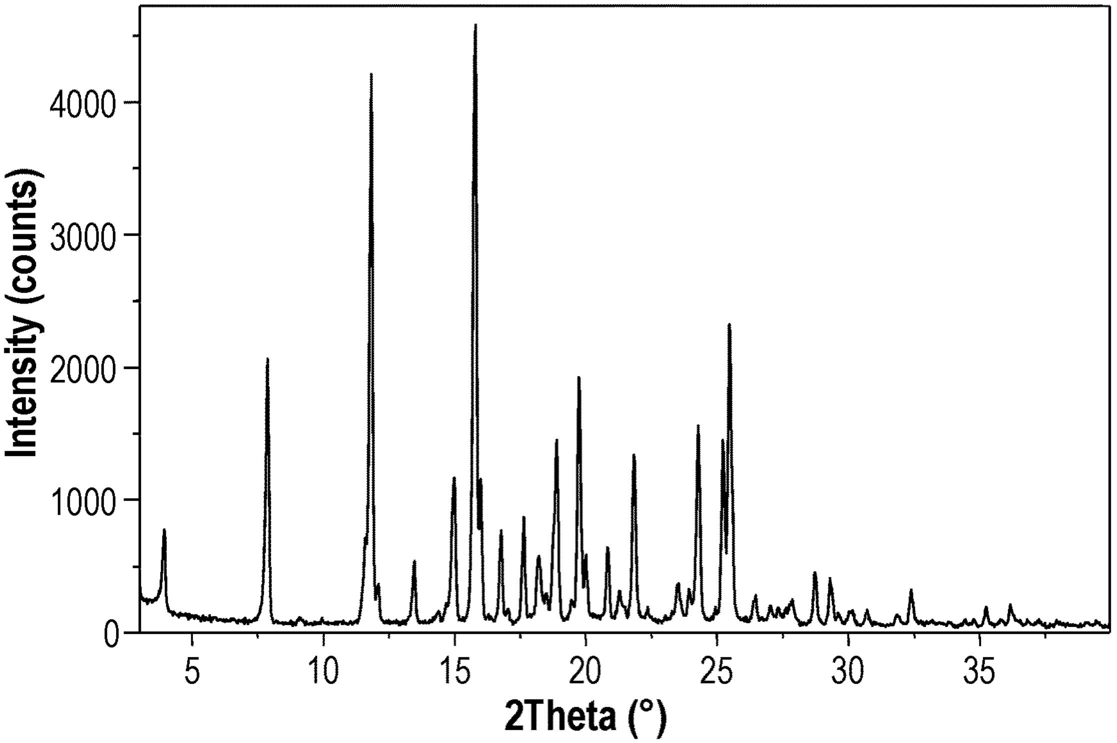

FIG. 190 depicts the XRPD pattern of Form A saccharin co-crystal of Compound 1.

Figure 191:
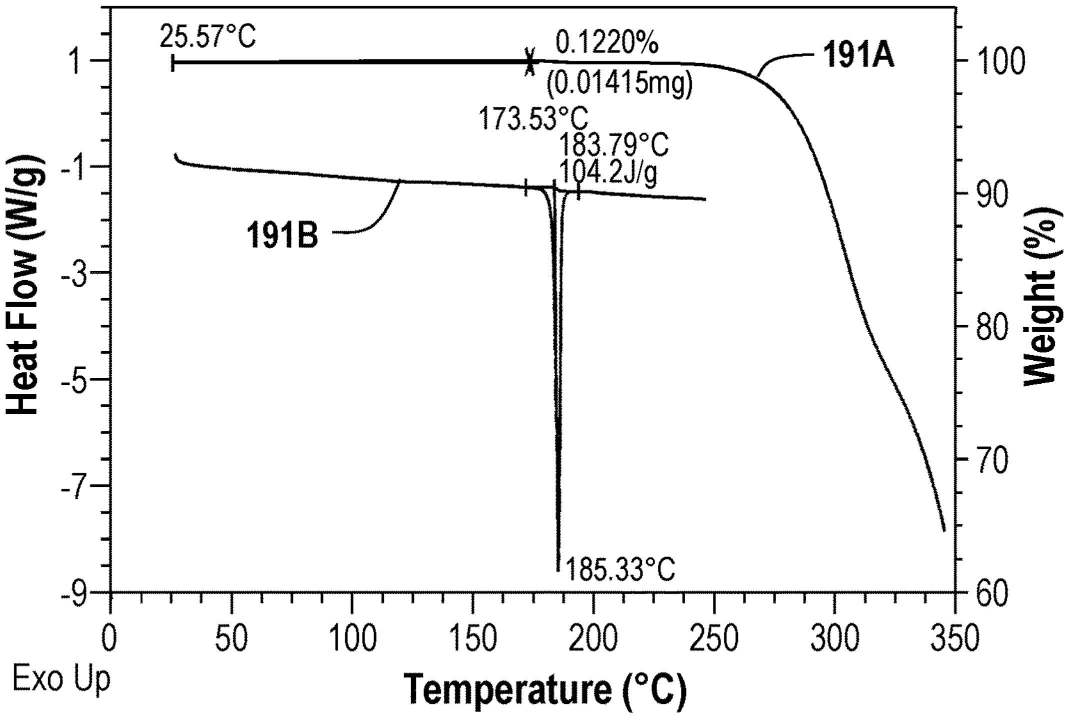

FIG. 191 depicts the TGA pattern of Form A saccharin co-crystal of Compound 1 (191A), and the DSC pattern of Form A saccharin co-crystal of Compound 1 (191B).

Figure 192:
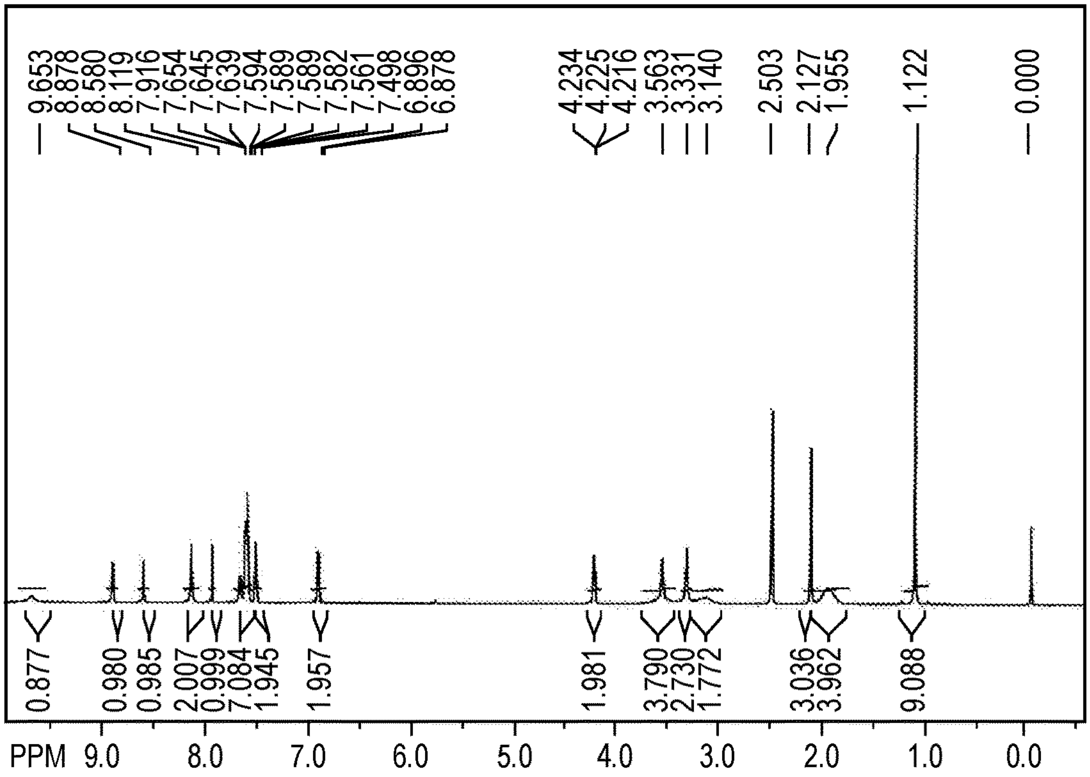

FIG. 192 depicts the $^1$H-NMR spectrum of Form A saccharin co-crystal of Compound 1.

Figure 193:
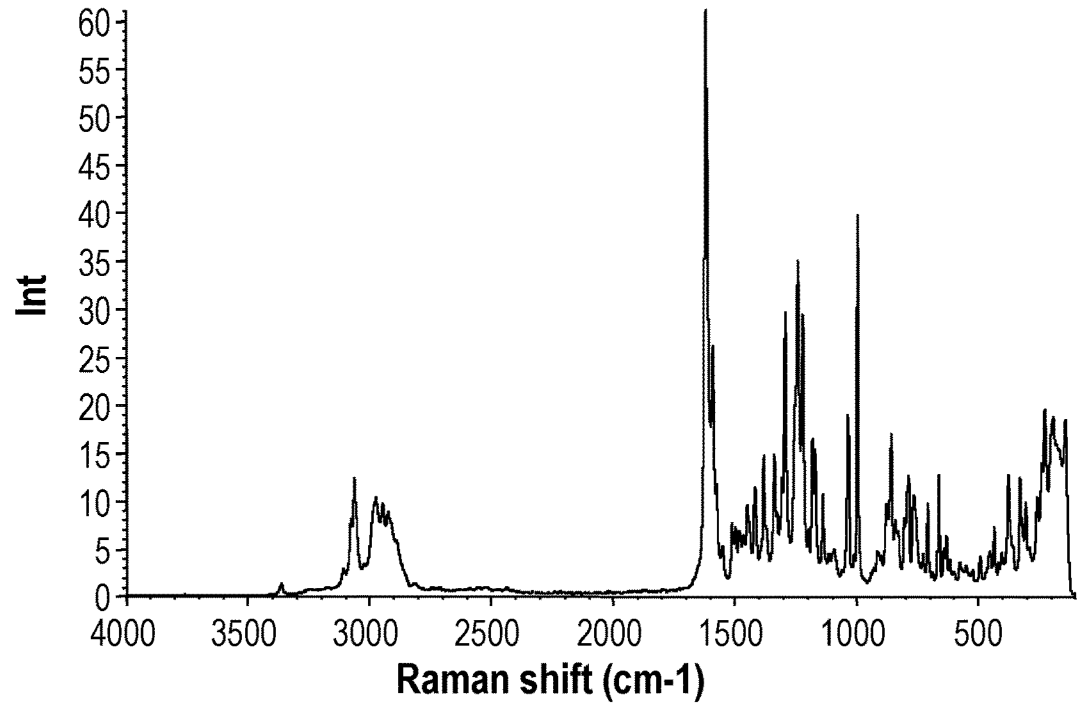

FIG. 193 depicts the FT-Raman spectrum of Form A nicotinic acid salt of Compound 1.

Figure 194:
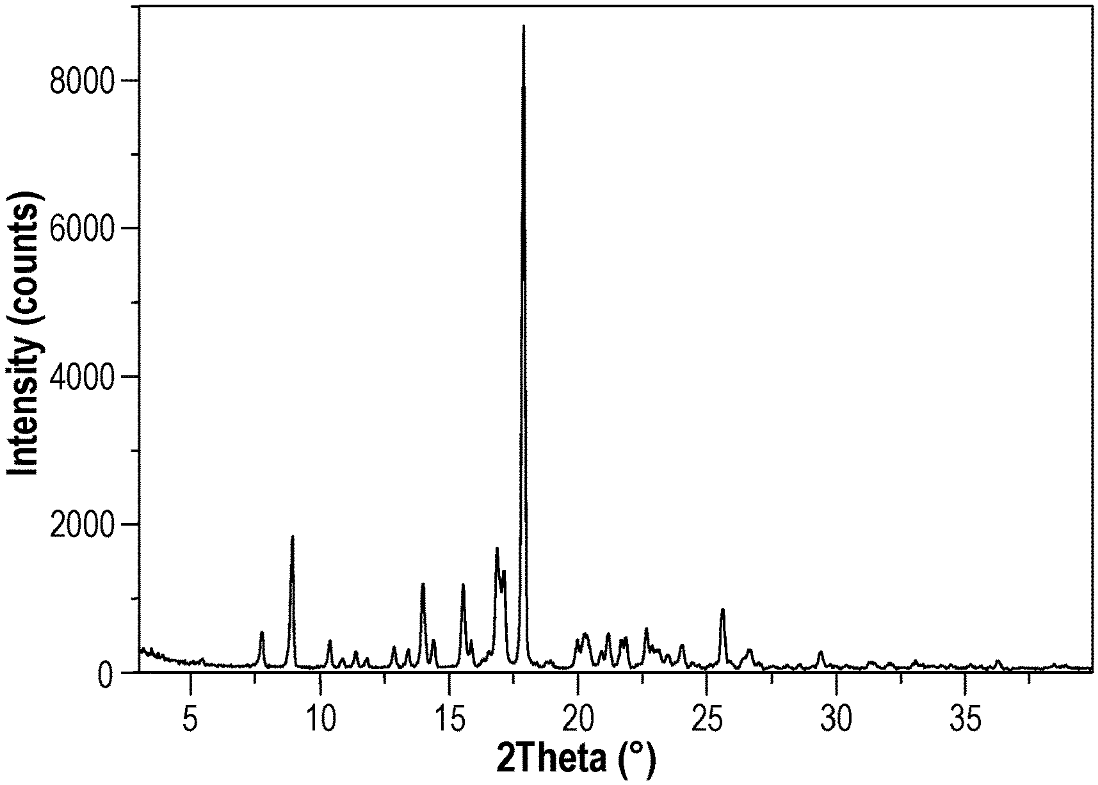

FIG. 194 depicts the XRPD pattern of Form A nicotinic acid salt of Compound 1.

Figure 195:
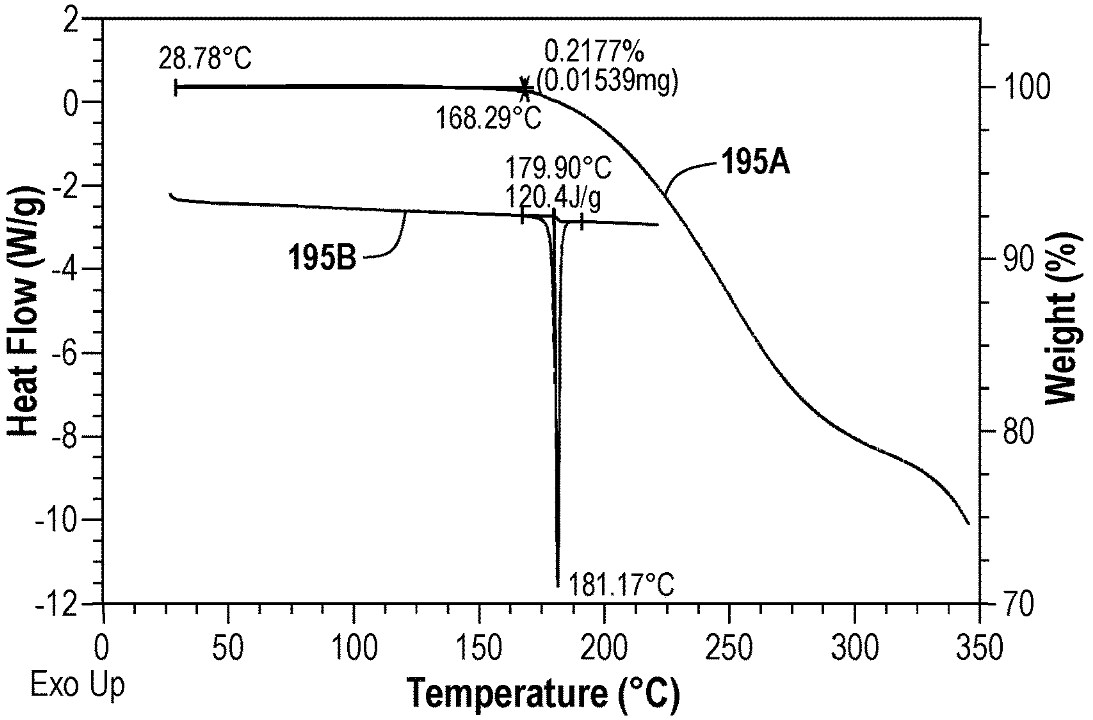

FIG. 195 depicts the TGA pattern of Form A nicotinic acid salt of Compound 1 (195A), and the DSC pattern of Form A nicotinic acid salt of Compound 1 (195B).

Figure 196:
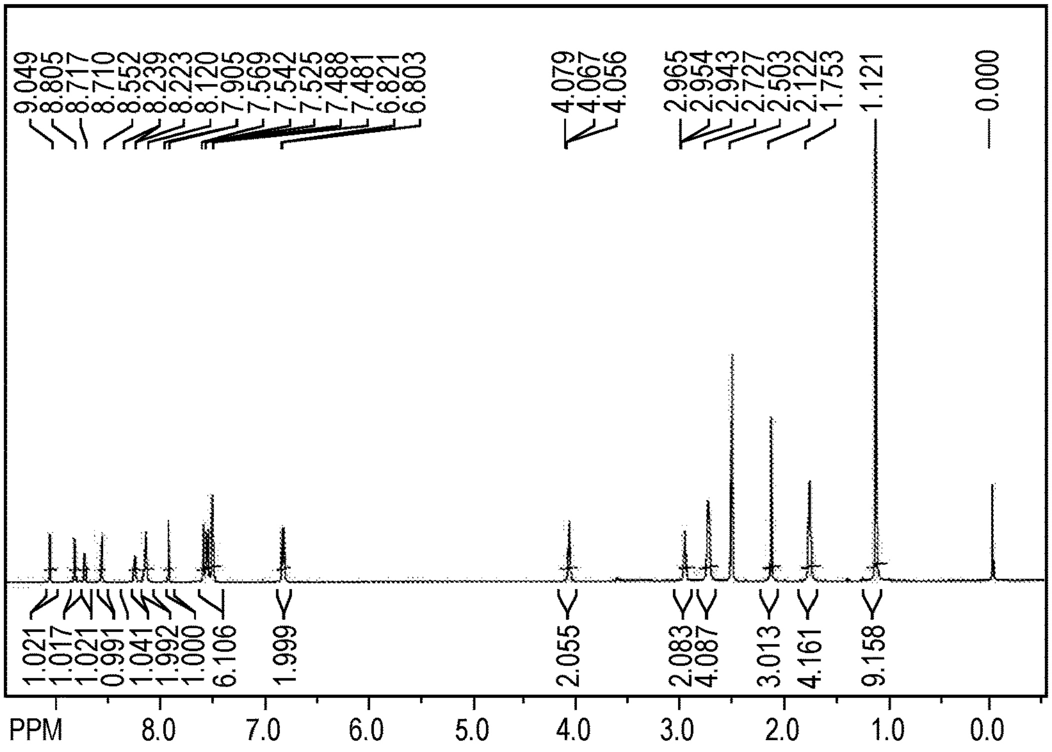

FIG. 196 depicts the $^1$H-NMR spectrum of Form A nicotinic acid salt of Compound 1.

Figure 197:
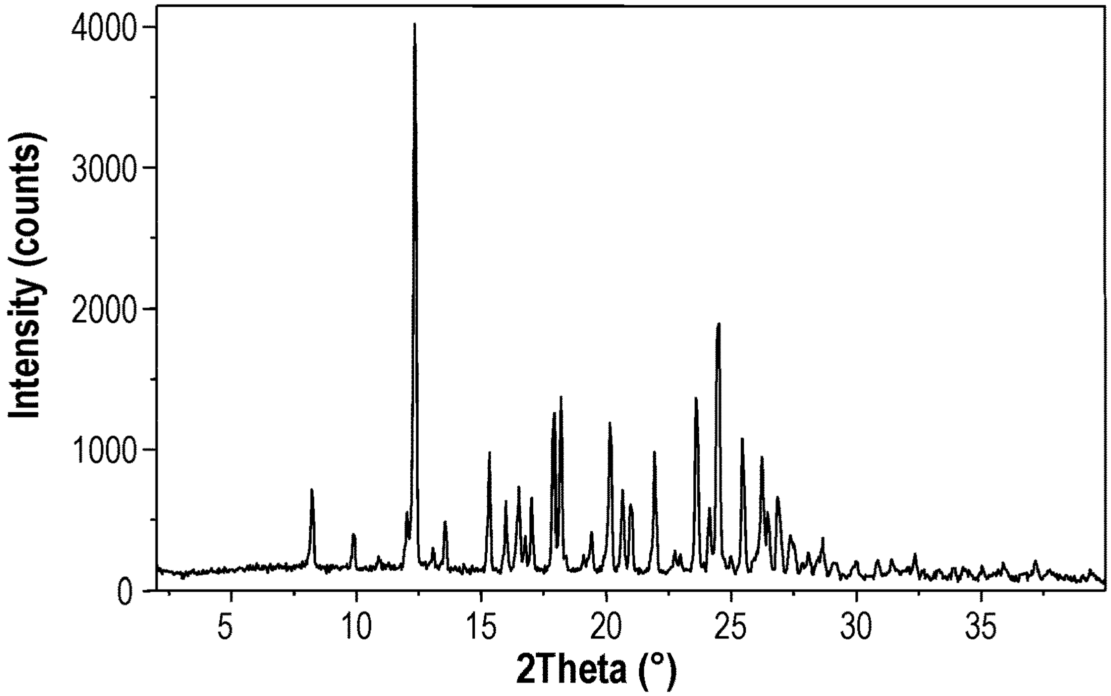

FIG. 197 depicts the XRPD pattern of Form B nicotinic acid salt of Compound 1.

Figure 198:
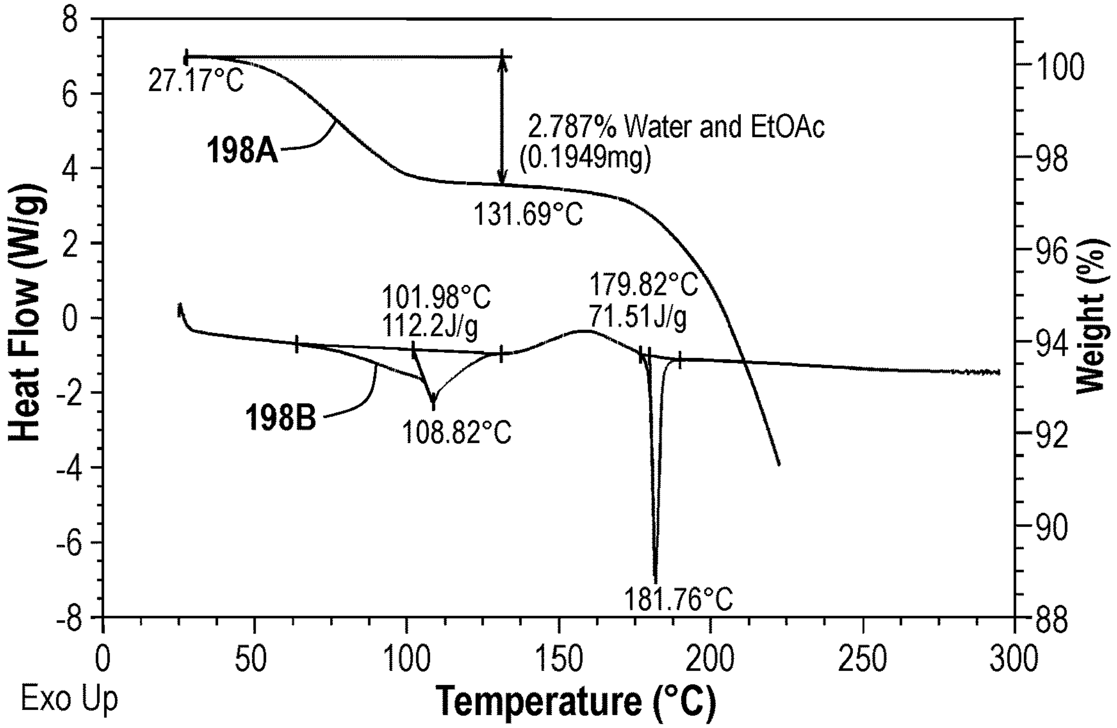

FIG. 198 depicts the TGA pattern of Form B nicotinic acid salt of Compound 1.

FIG. 198B depicts the DSC pattern of Form B nicotinic acid salt of Compound 1.

Figure 199:
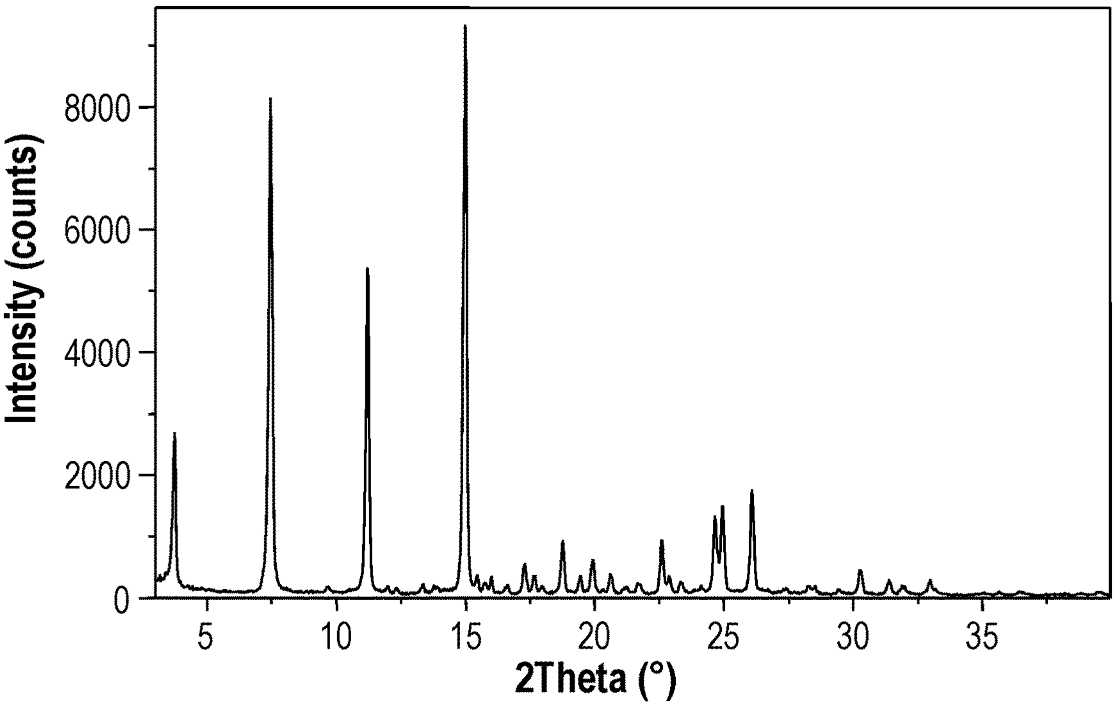

FIG. 199 depicts the XRPD pattern of Form C nicotinic acid salt of Compound 1.

Figure 200:
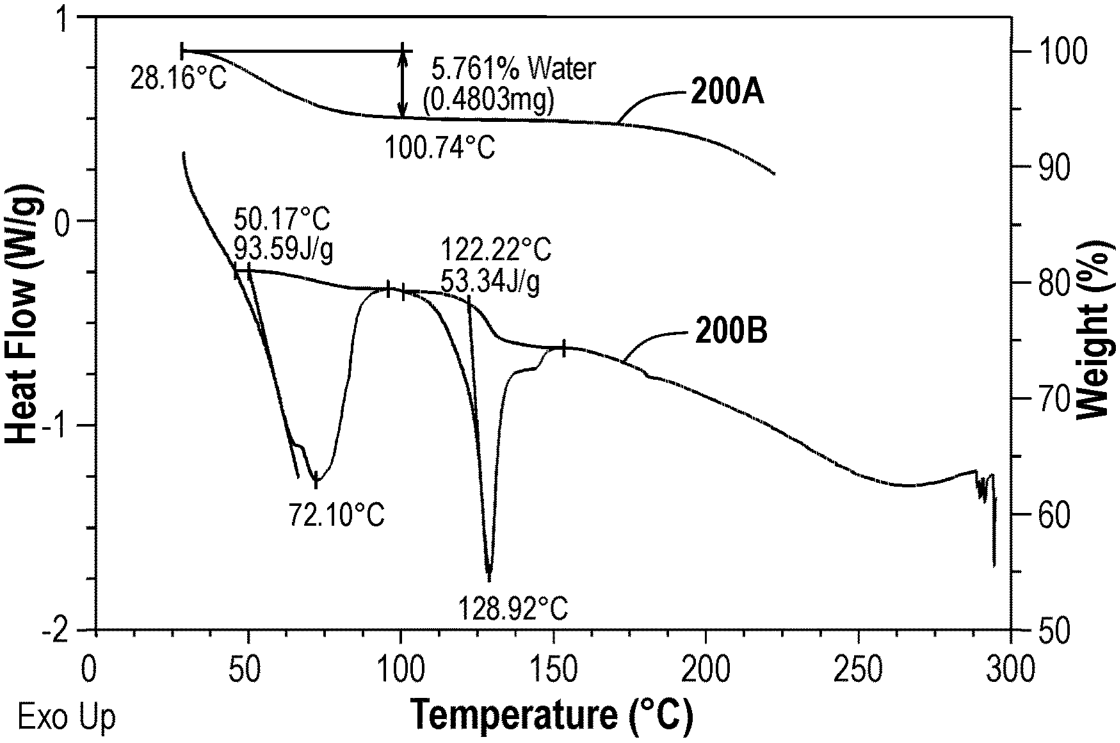

FIG. 200 depicts the TGA pattern of Form C nicotinic acid salt of Compound 1 (200A), and the DSC pattern of Form C nicotinic acid salt of Compound 1 (200B).

Figure 201:
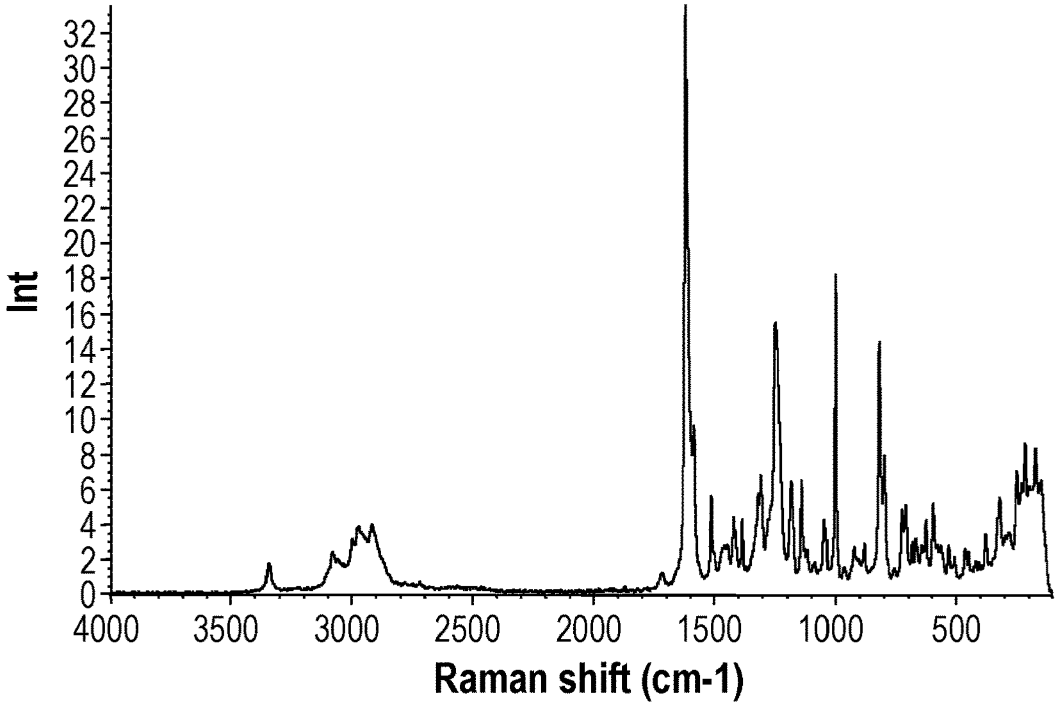

FIG. 201 depicts the FT-Raman spectrum of Form A ascorbic acid salt of Compound 1.

Figure 202:
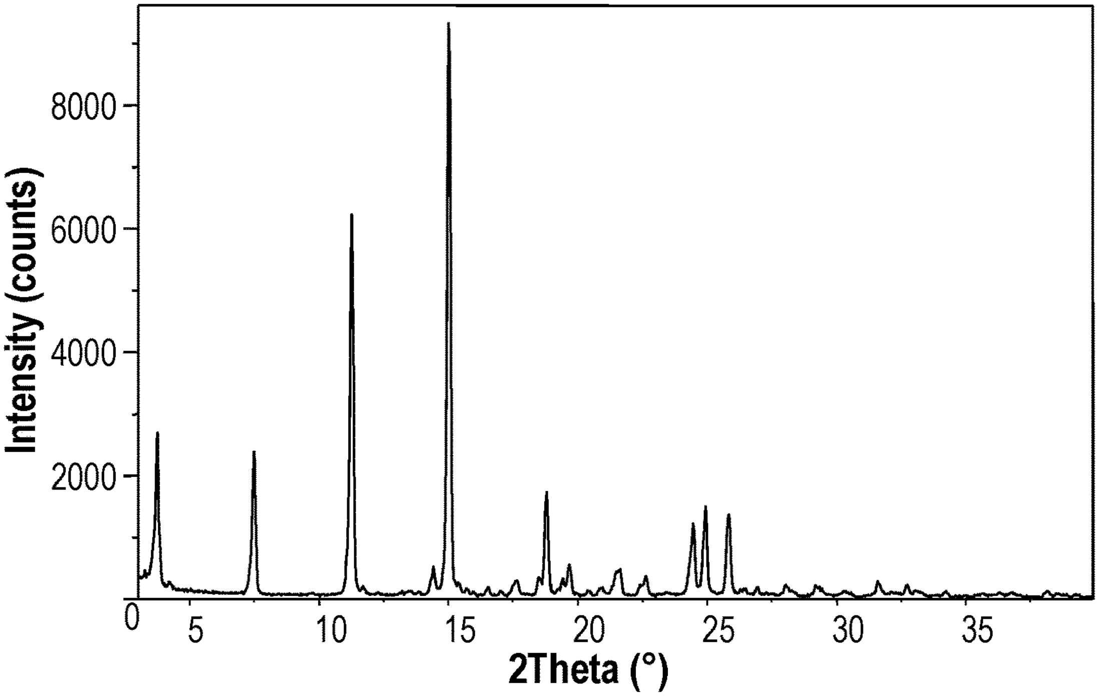

FIG. 202 depicts the XRPD pattern of Form A ascorbic acid salt of Compound 1.

Figure 203:
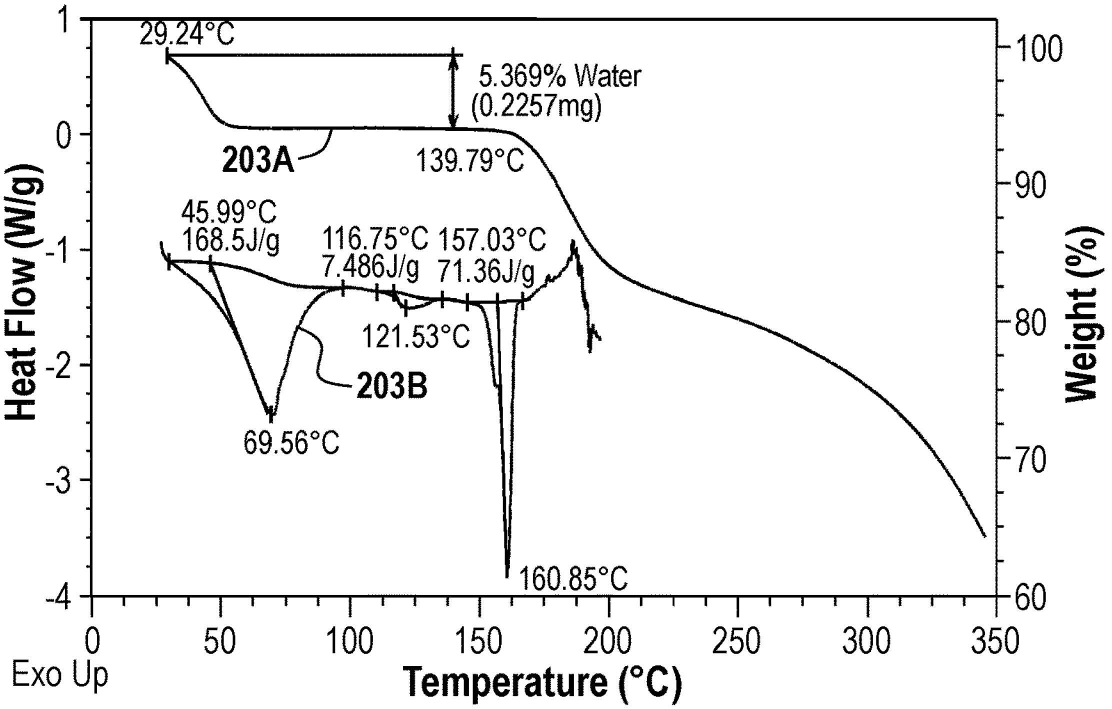

FIG. 203 depicts the TGA pattern of Form A ascorbic acid salt of Compound 1 (203A), and the DSC pattern of Form A ascorbic acid salt of Compound 1 (203B).

Figure 204:
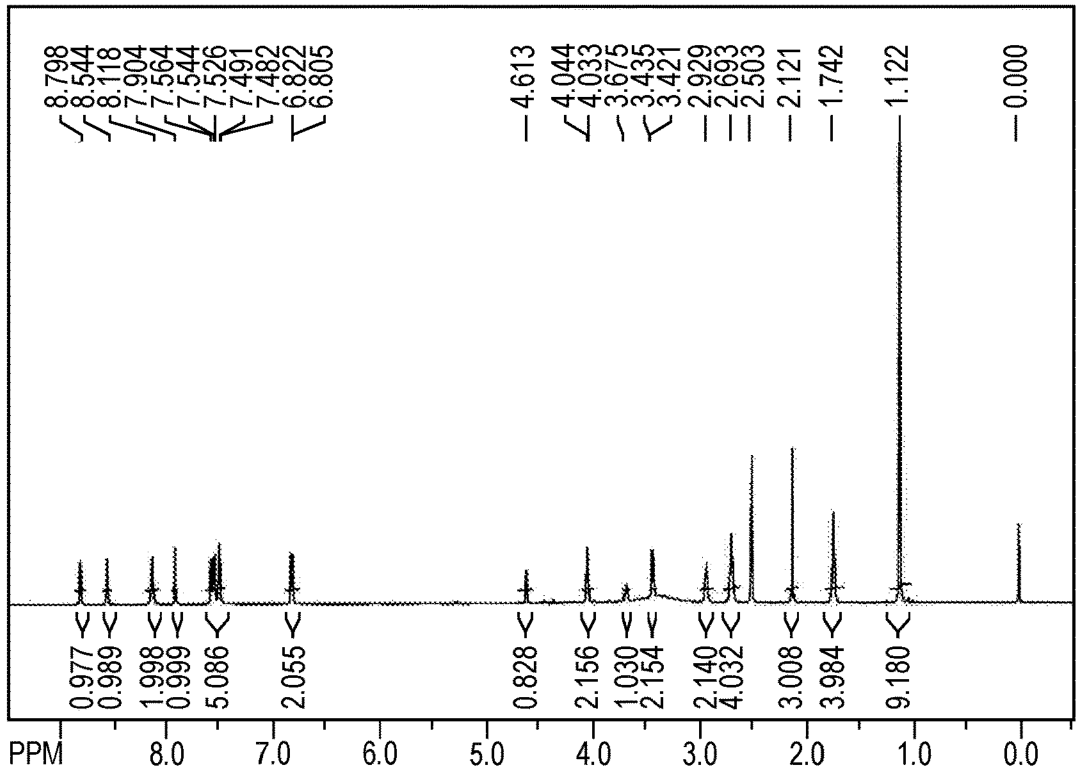

FIG. 204 depicts the $^1$H-NMR spectrum of Form A ascorbic acid salt of Compound 1.

Figure 205:
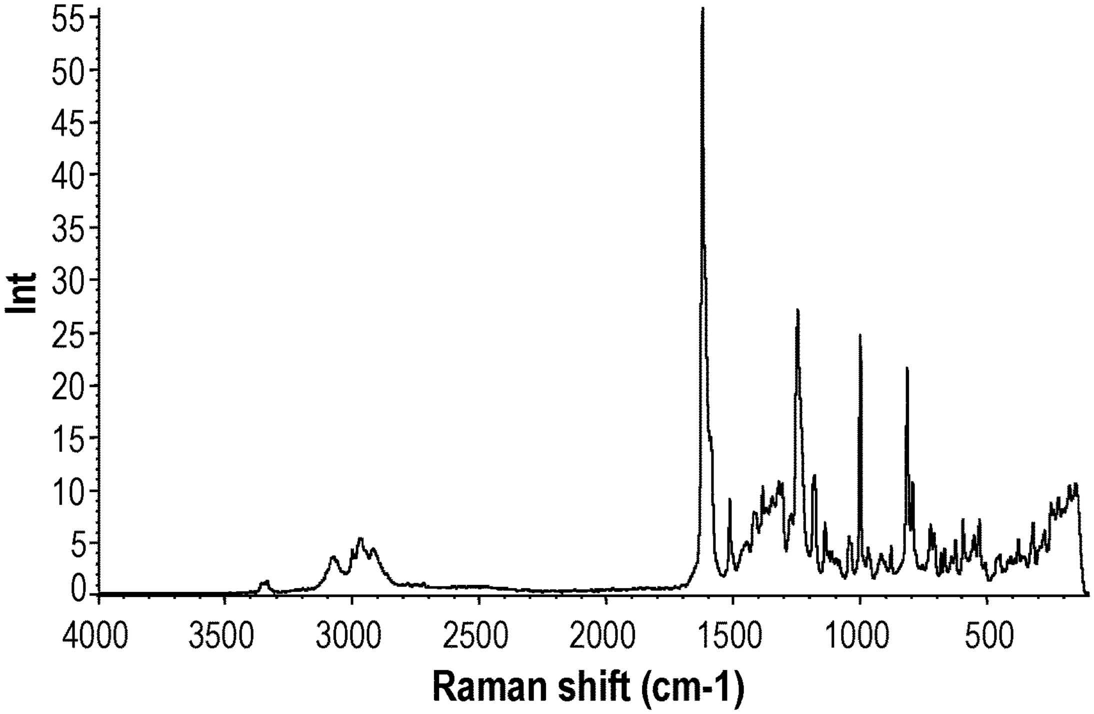

FIG. 205 depicts the FT-Raman spectrum of Form A gallic acid salt of Compound 1.

Figure 206:
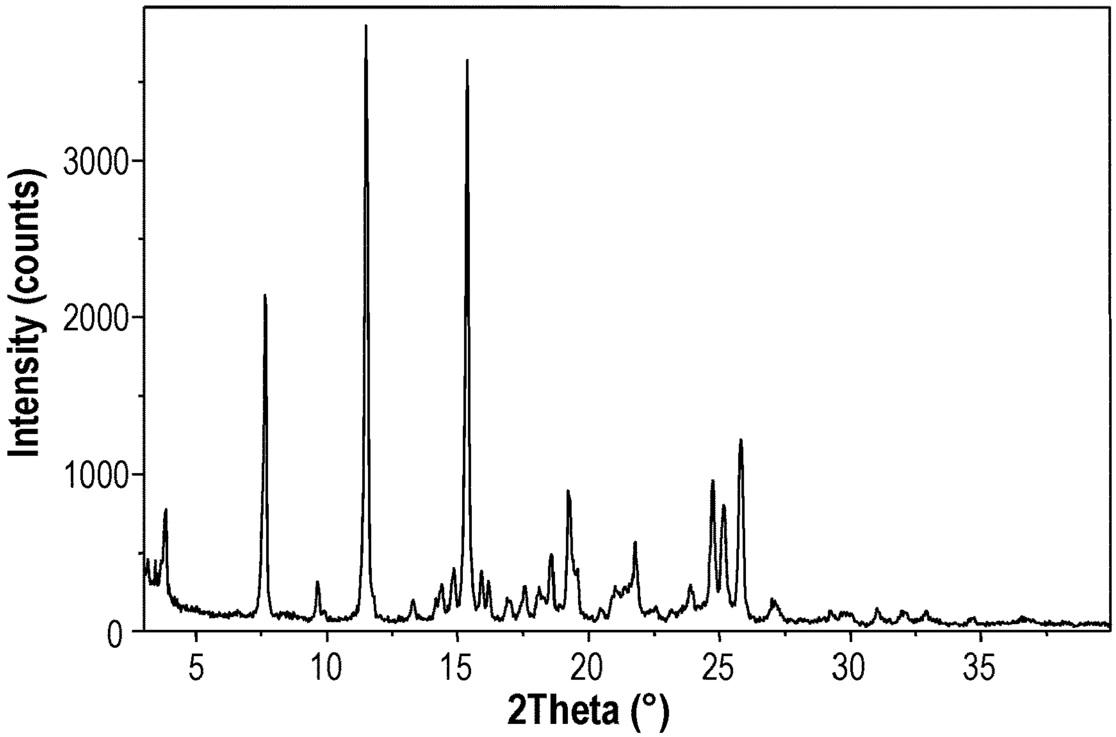

FIG. 206 depicts the XRPD pattern of Form A gallic acid salt of Compound 1.

Figure 207:
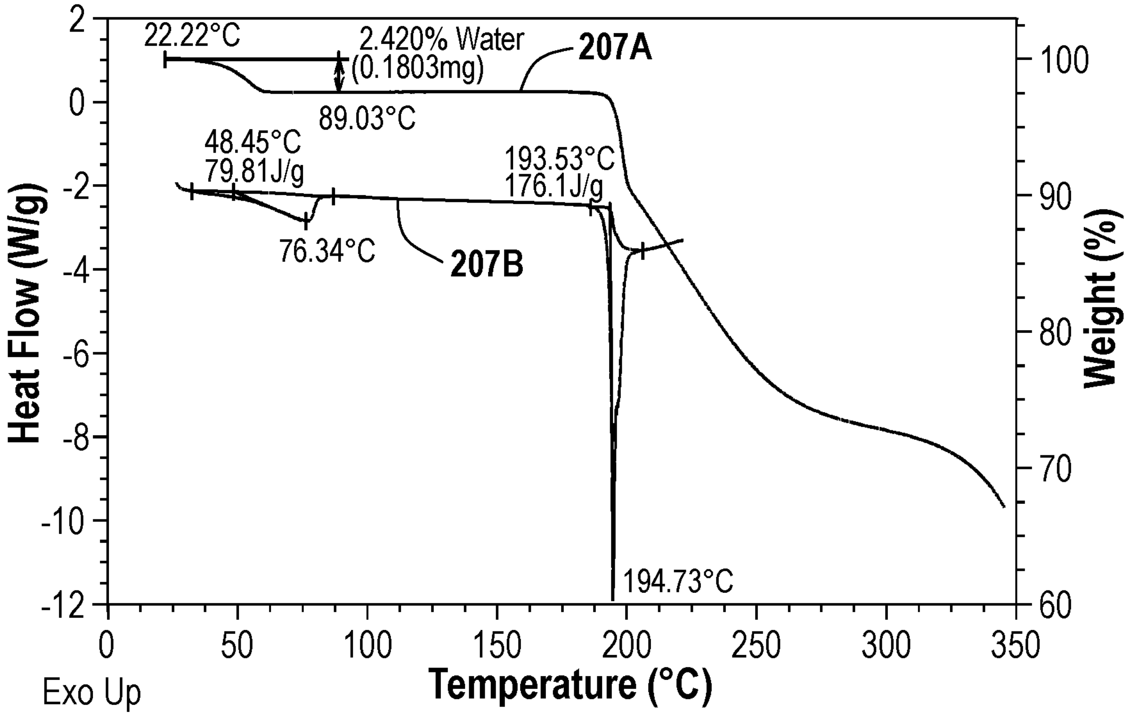

FIG. 207 depicts the TGA pattern of Form A gallic acid salt of Compound 1 (207A), and the DSC pattern of Form A gallic acid salt of Compound 1 (207B).

Figure 208:
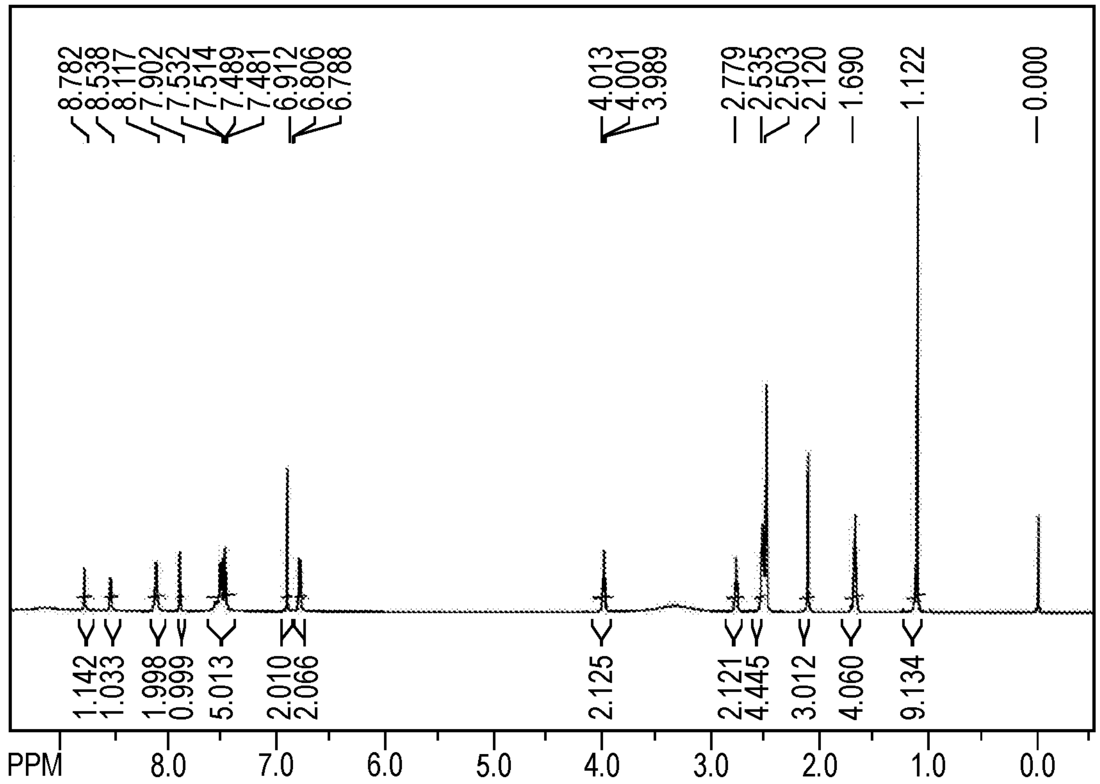

FIG. 208 depicts the $^1$H-NMR spectrum of Form A gallic acid salt of Compound 1.

Figure 209:
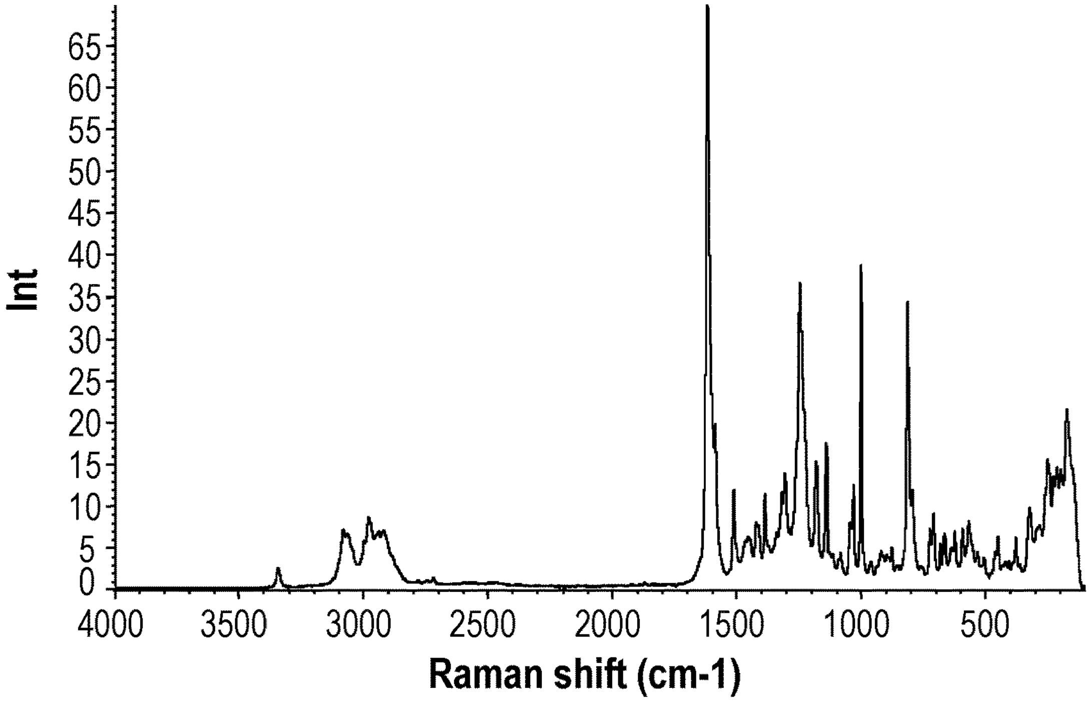

FIG. 209 depicts the FT-Raman spectrum of Form A salicylic acid salt of Compound 1.

Figure 210:
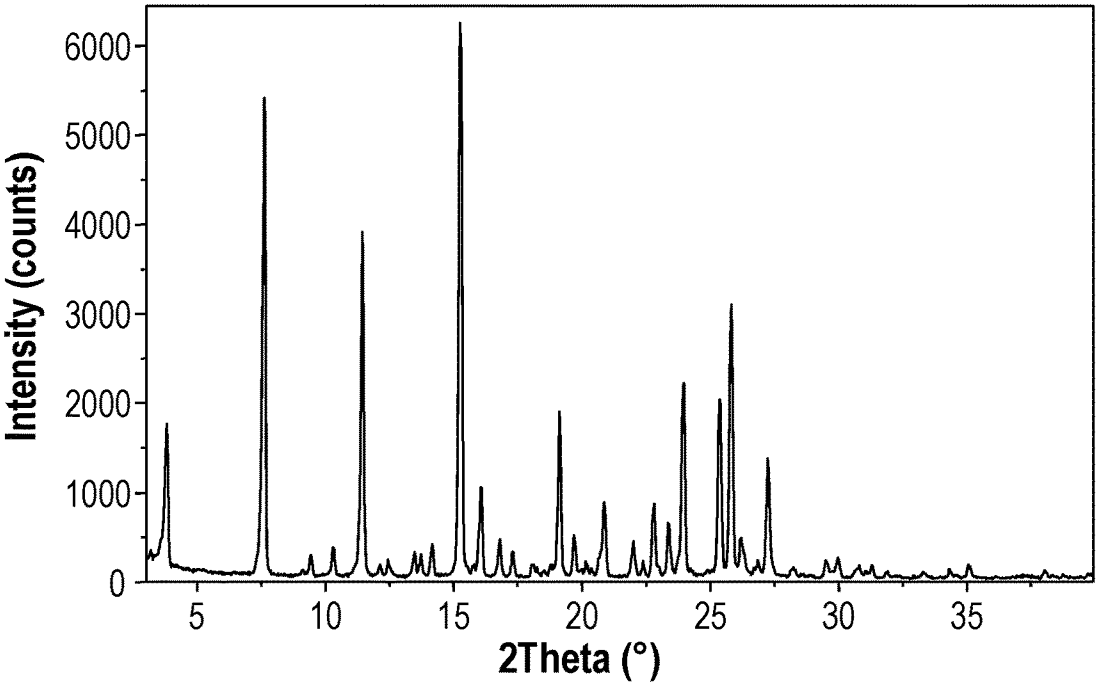

FIG. 210 depicts the XRPD pattern of Form A salicylic acid salt of Compound 1.

Figure 211:
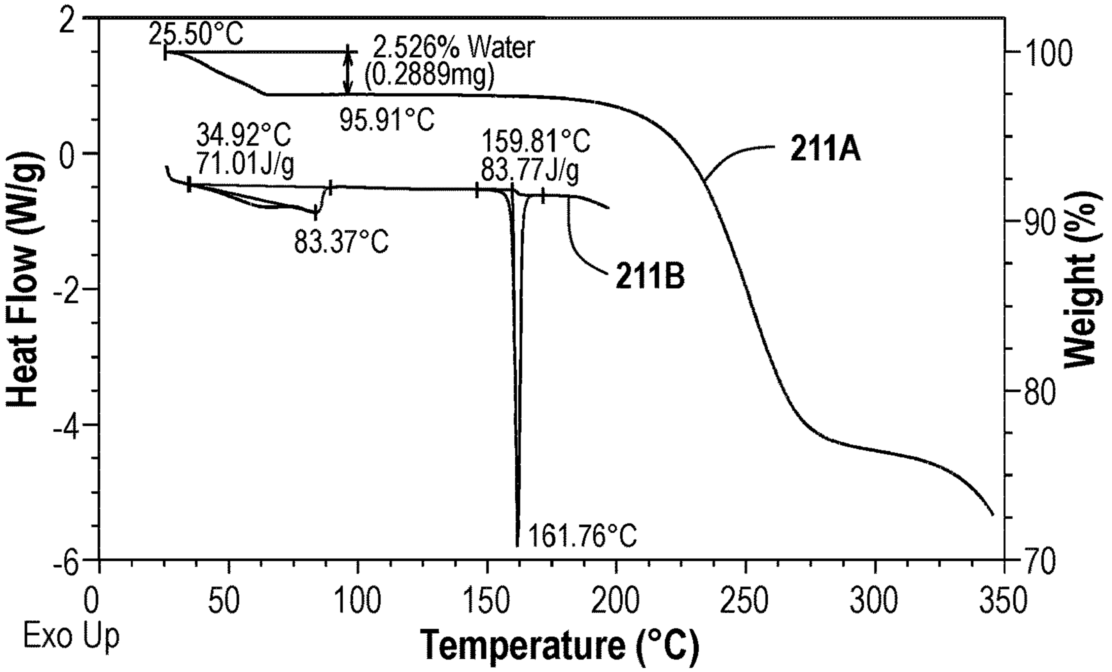

FIG. 211 depicts the TGA pattern of Form A salicylic acid salt of Compound 1 (211A), and the DSC pattern of Form A salicylic acid salt of Compound 1 (211B).

Figure 212:
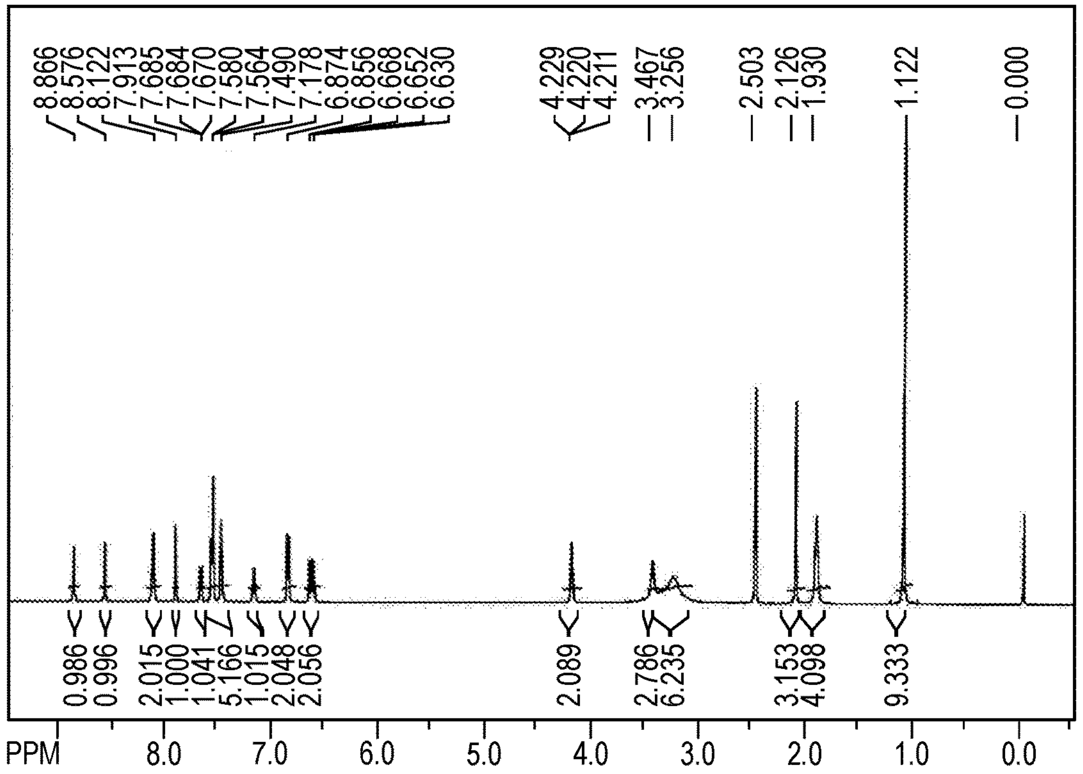

FIG. 212 depicts the $^1$H-NMR spectrum of Form A salicylic acid salt of Compound 1.

Figure 213:
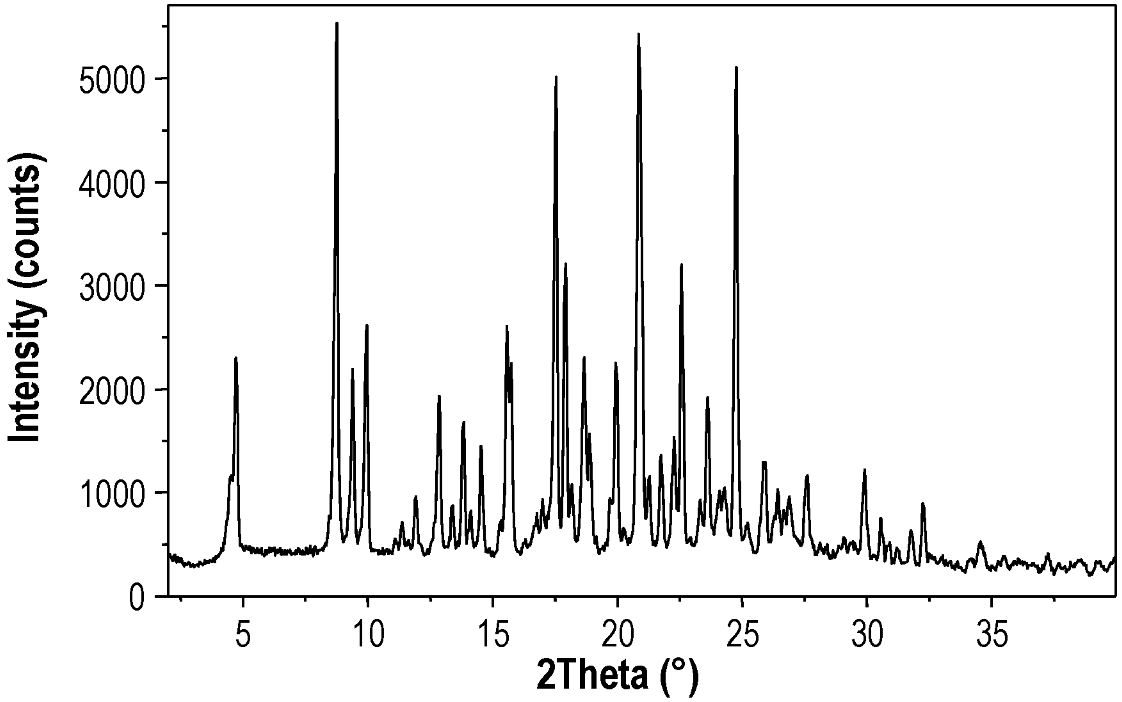

FIG. 213 depicts the XRPD pattern of Form A orotic acid salt of Compound 1.

Figure 214:
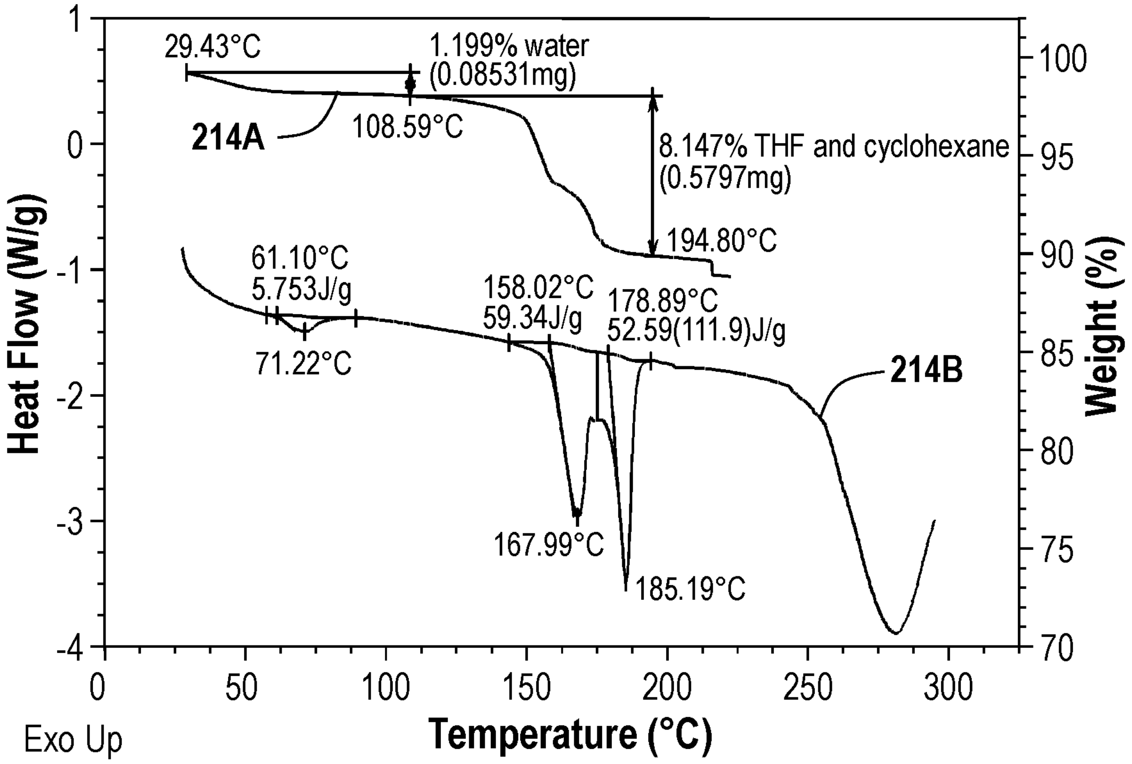

FIG. 214 depicts the TGA pattern of Form A orotic acid salt of Compound 1 (214A), and the DSC pattern of Form A orotic acid salt of Compound 1 (214B).

Figure 215:
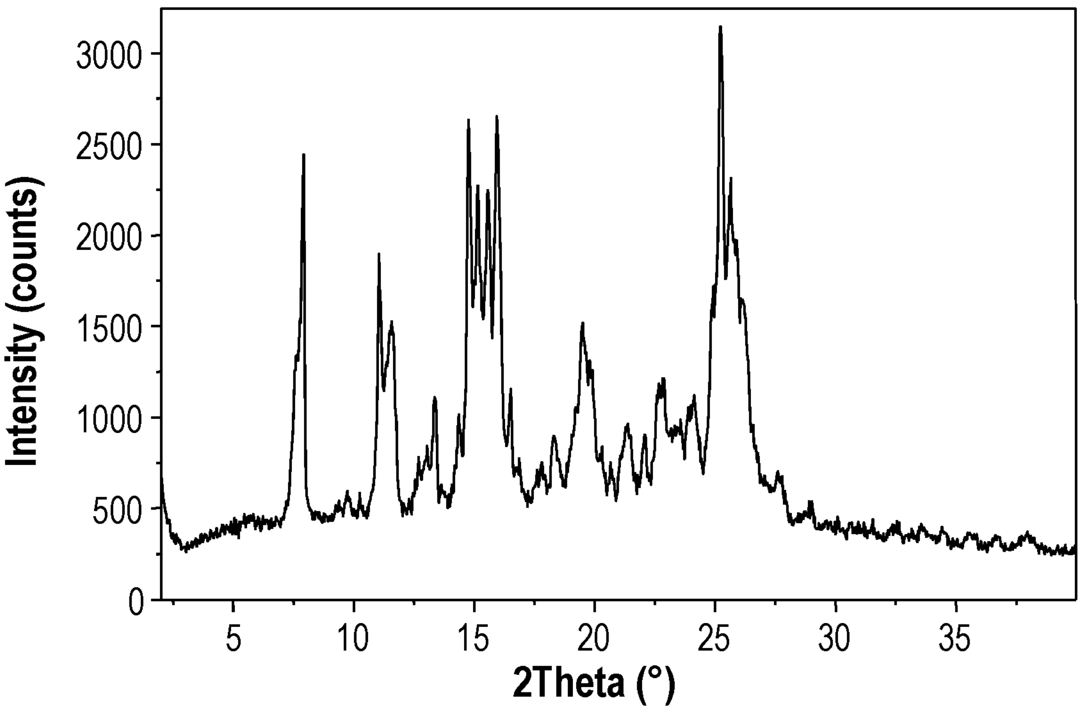

FIG. 215 depicts the XRPD pattern of a mixture of Form B and Form E orotic acid salts of Compound 1.

Figure 216:
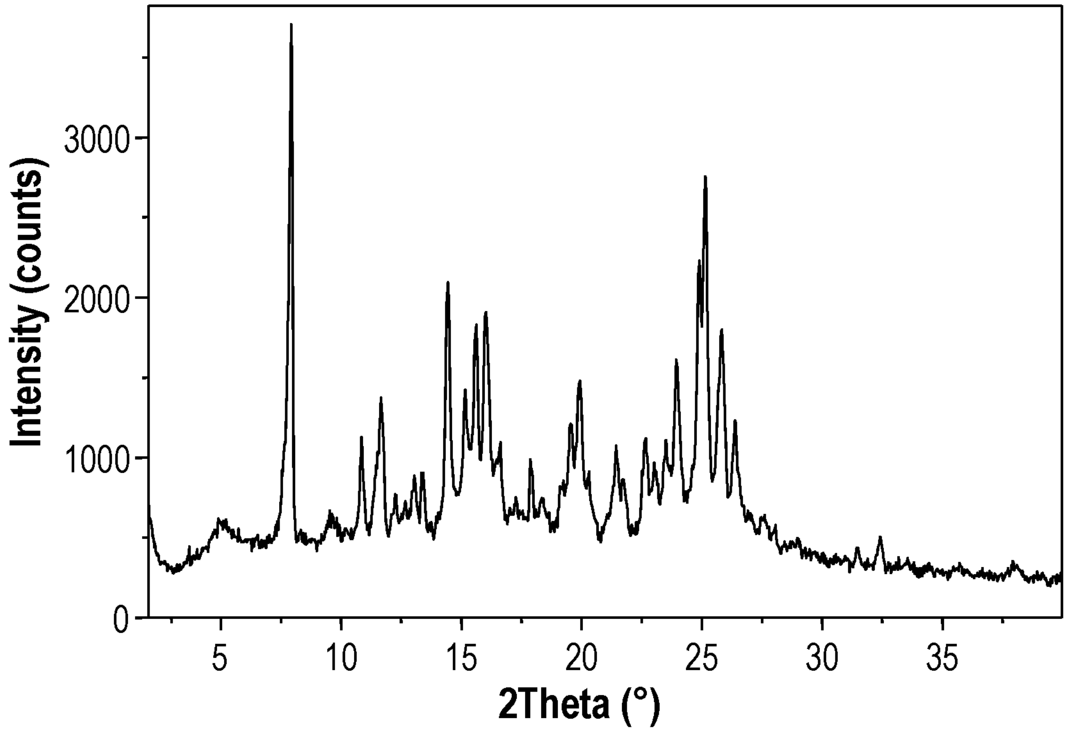

FIG. 216 depicts the XRPD pattern of a mixture of Form C and Form E orotic acid salts of Compound 1.

Figure 217:
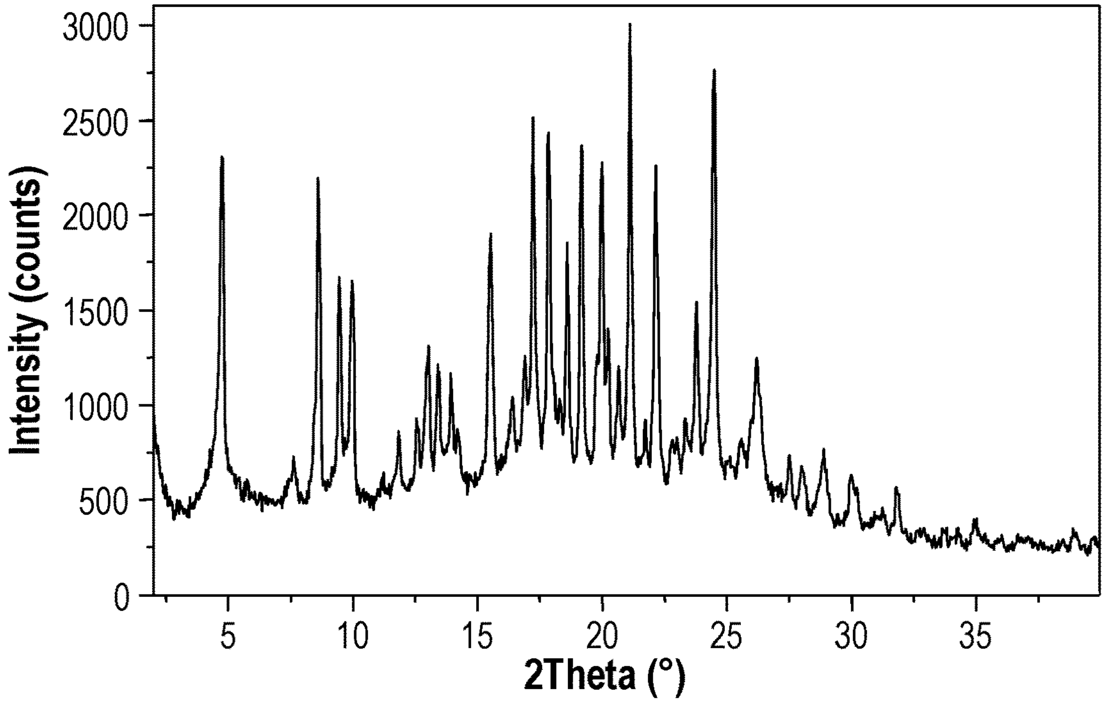

FIG. 217 depicts the XRPD pattern of Form D orotic acid salt of Compound 1.

Figure 218:
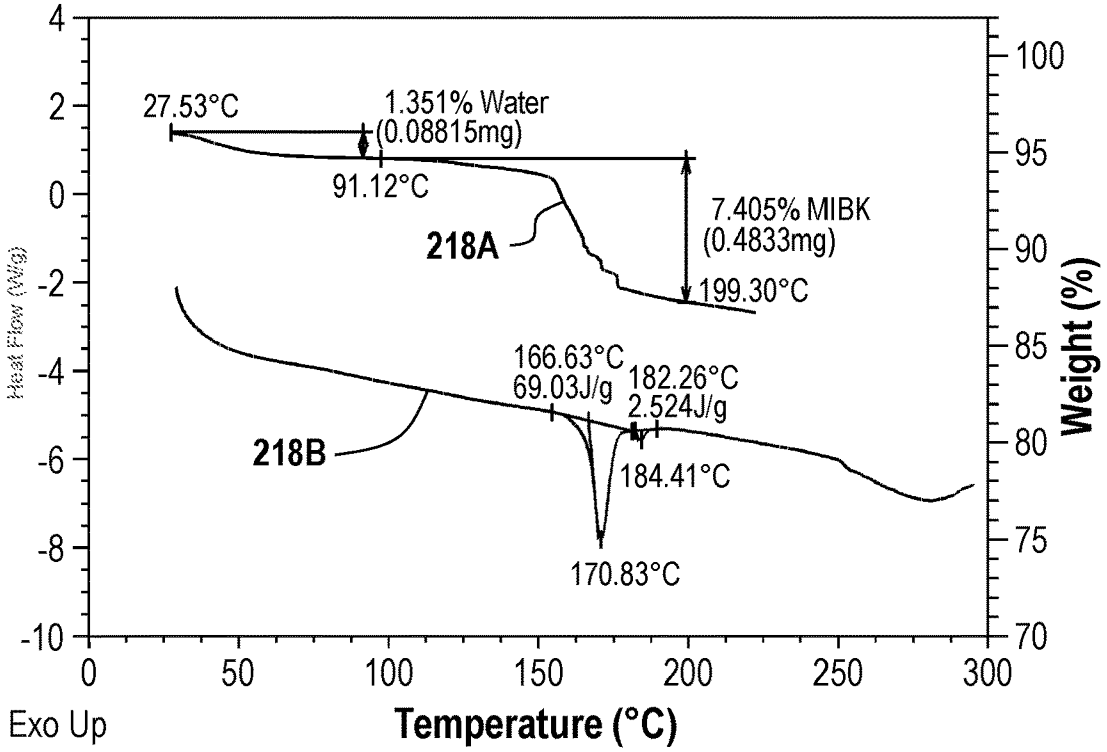

FIG. 218 depicts the TGA pattern of Form D orotic acid salt of Compound 1 (218A), and the DSC pattern of Form D orotic acid salt of Compound 1 (218B).

Figure 219:
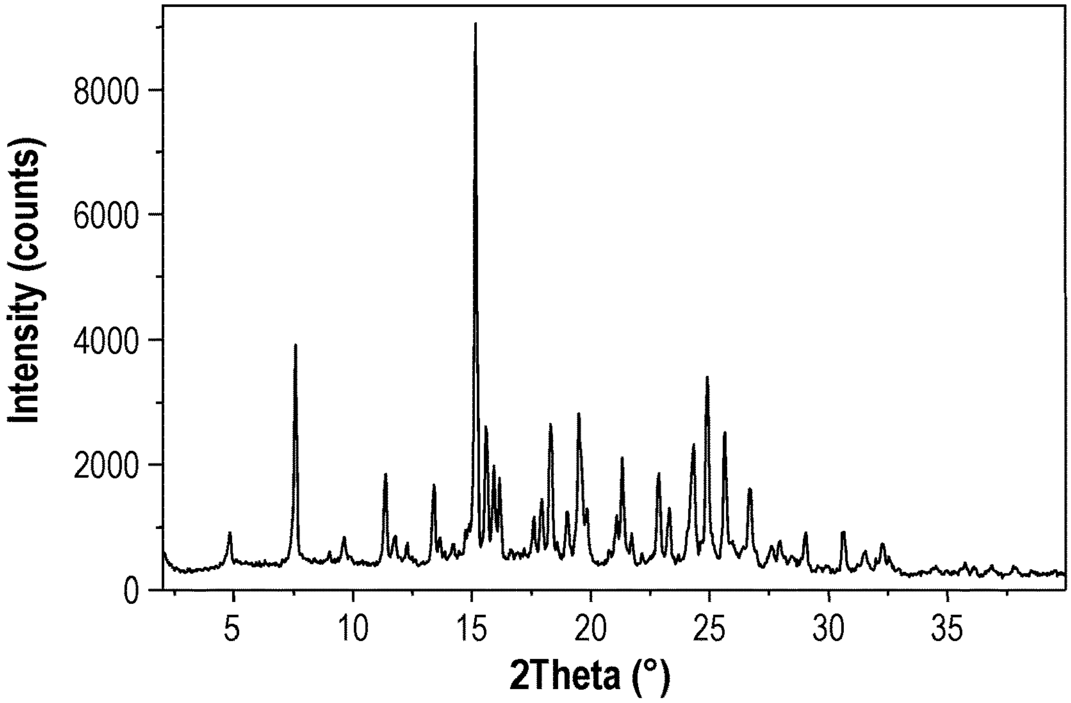

FIG. 219 depicts the XRPD pattern of Form E orotic acid salt of Compound 1.

Figure 220:
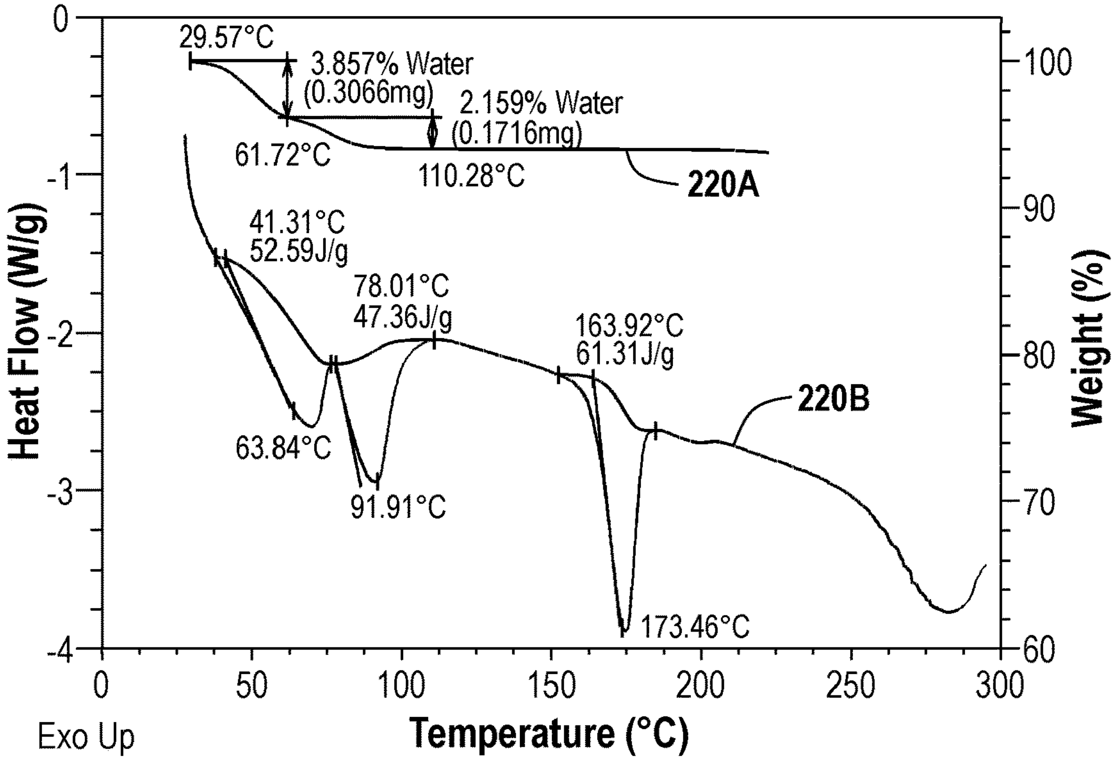

FIG. 220 depicts the TGA pattern of Form E orotic acid salt of Compound 1 (220A), and the DSC pattern of Form E orotic acid salt of Compound 1 (220B).

Figure 221:
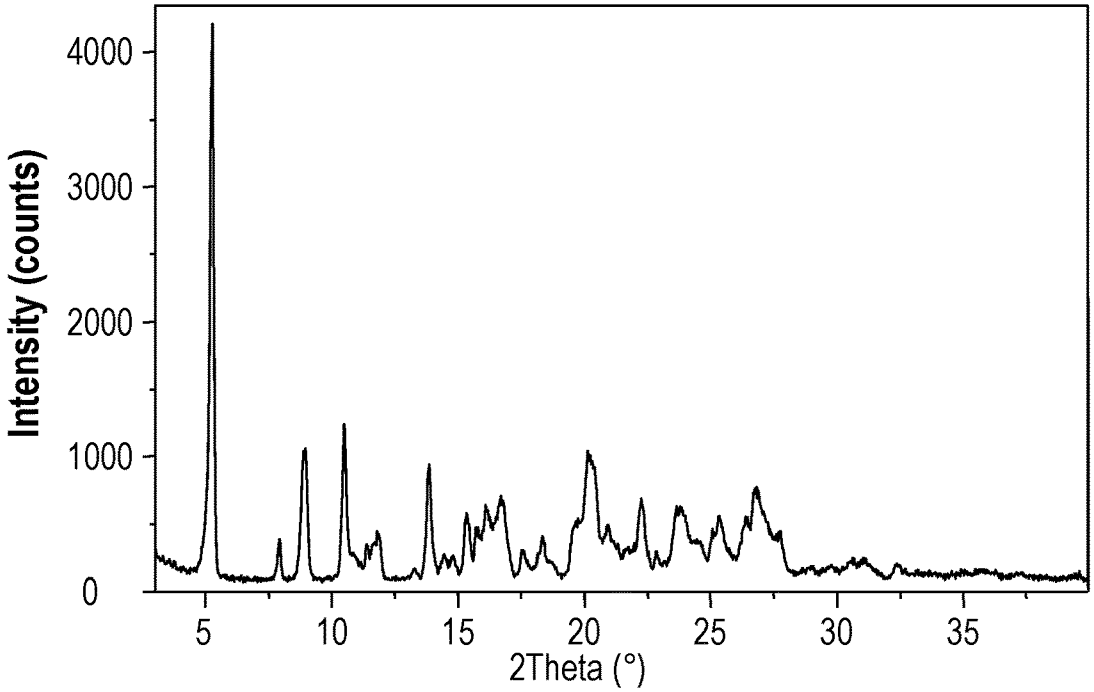

FIG. 221 depicts the XRPD pattern of Form G orotic acid salt of Compound 1.

Figure 222:
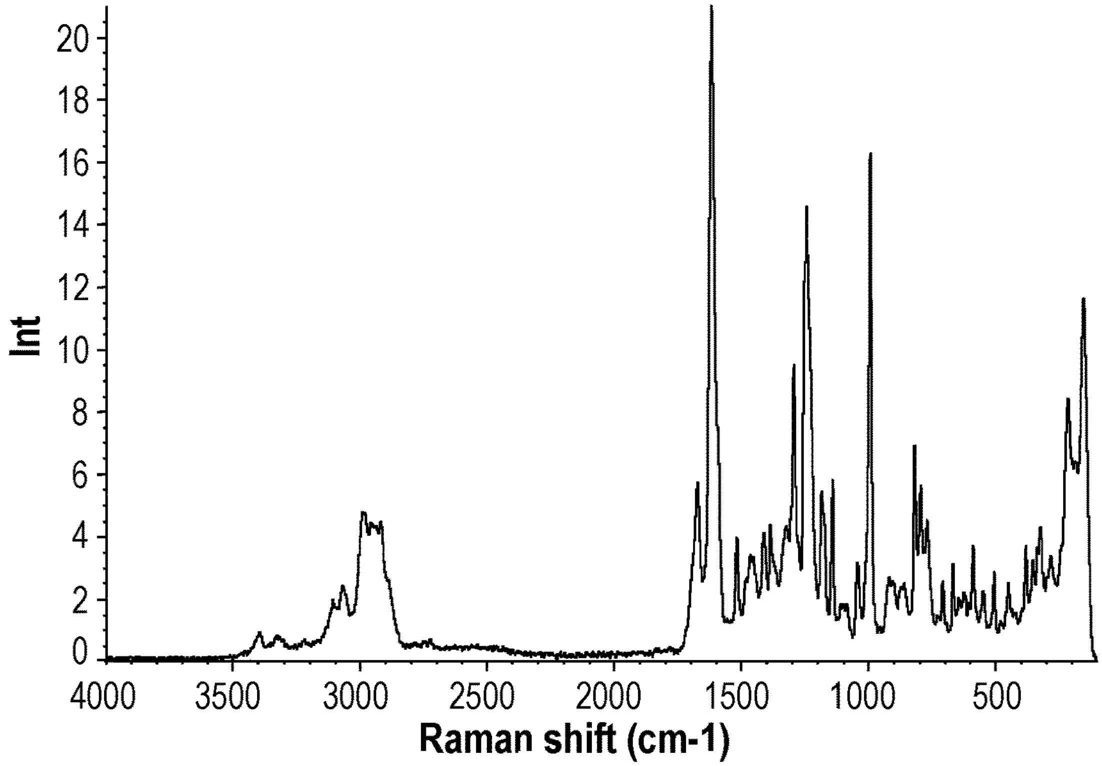

FIG. 222 depicts the FT-Raman spectrum of Form F orotic acid salt of Compound 1.

Figure 223:
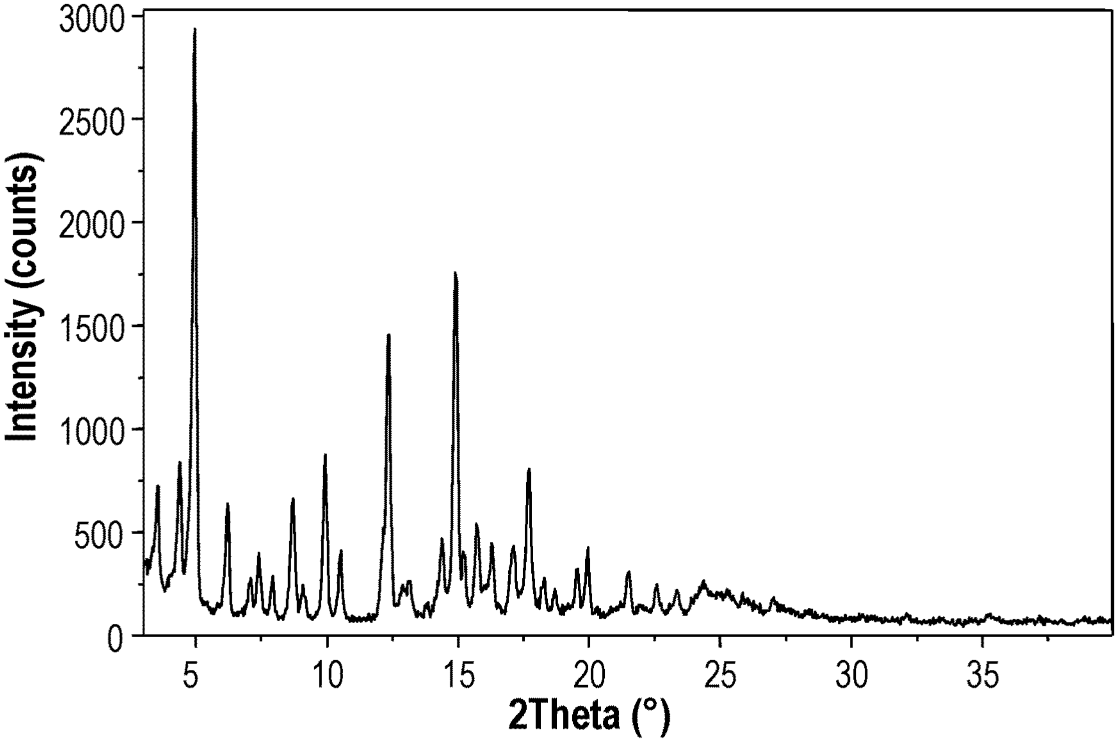

FIG. 223 depicts the XRPD pattern of Form F orotic acid salt of Compound 1.

Figure 224:
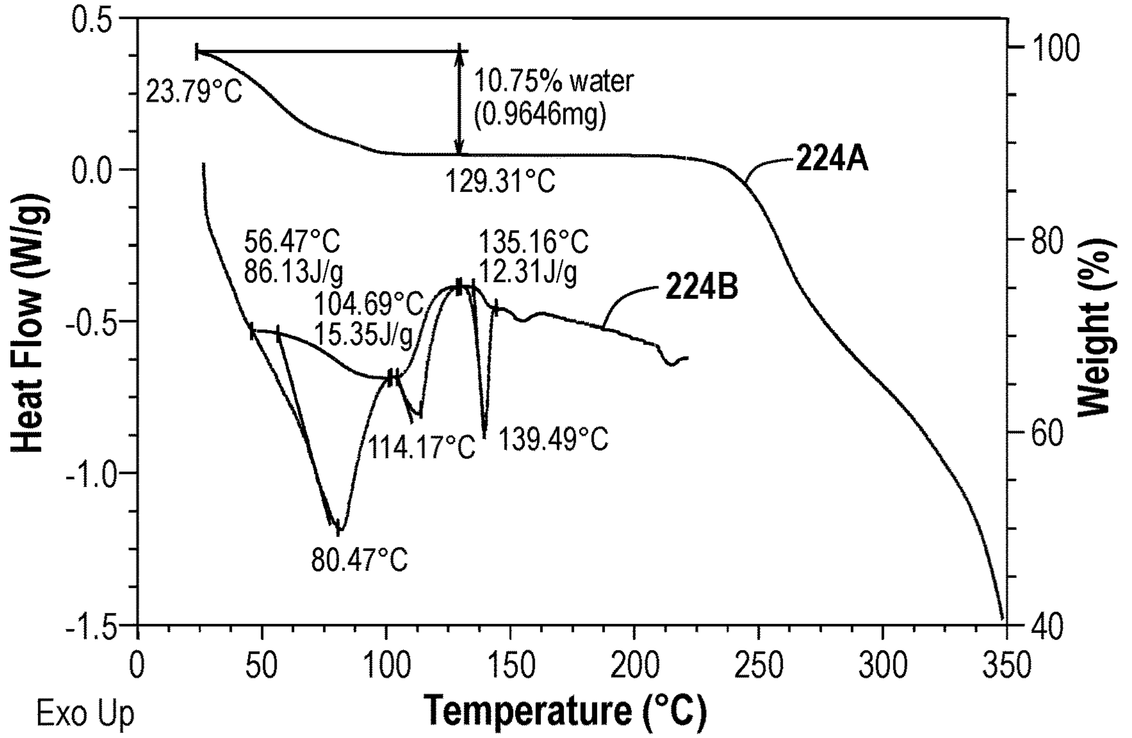

FIG. 224 depicts the TGA pattern of Form F orotic acid salt of Compound 1 (224A), and the DSC pattern of Form F orotic acid salt of Compound 1 (224B).

Figure 225:
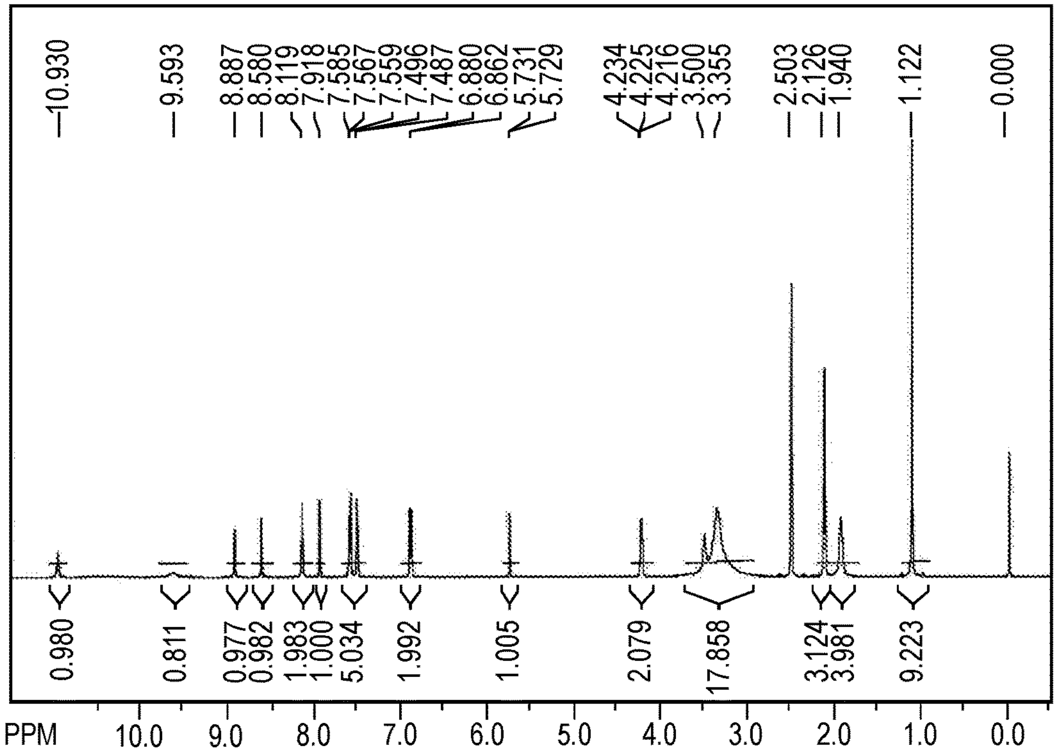

FIG. 225 depicts the $^{1}$H-NMR spectrum of Form F orotic acid salt of Compound 1.

Figure 226:
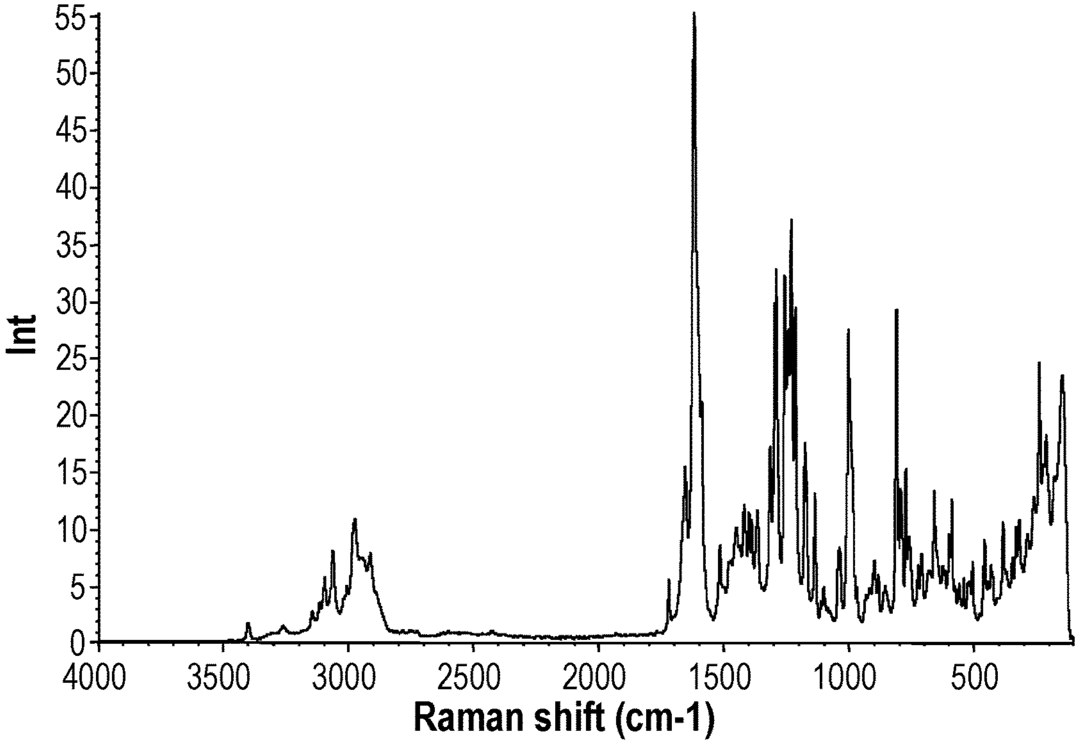

FIG. 226 depicts the FT-Raman spectrum of Form H orotic acid salt of Compound 1.

Figure 227:
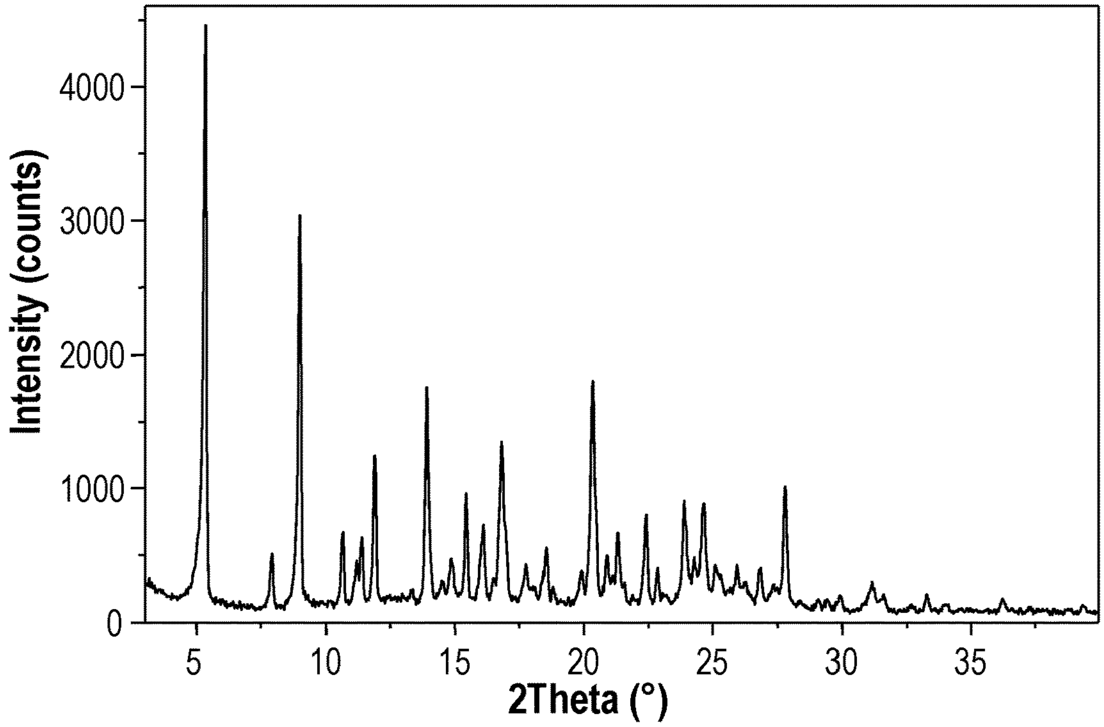

FIG. 227 depicts the XRPD pattern of Form H orotic acid salt of Compound 1.

Figure 228:
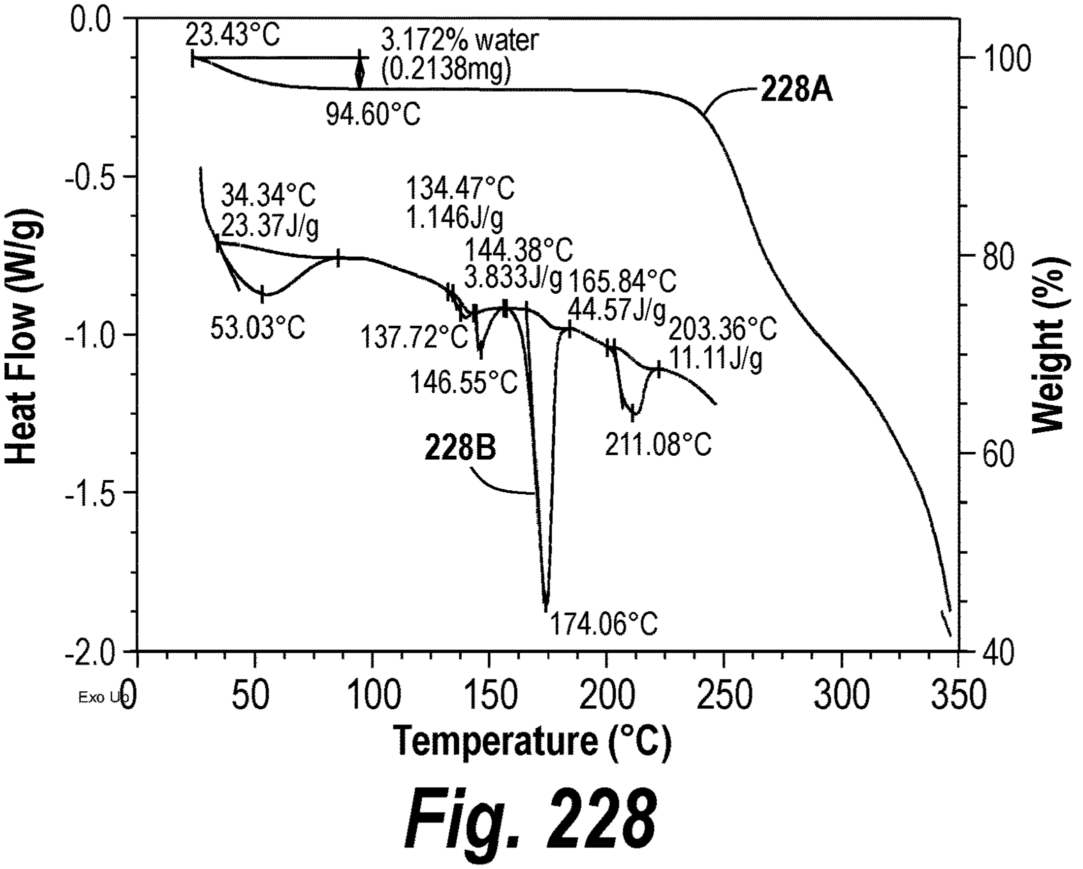

FIG. 228 depicts the TGA pattern of Form H orotic acid salt of Compound 1 (228A), and the DSC pattern of Form H orotic acid salt of Compound 1 (228B).

Figure 229:
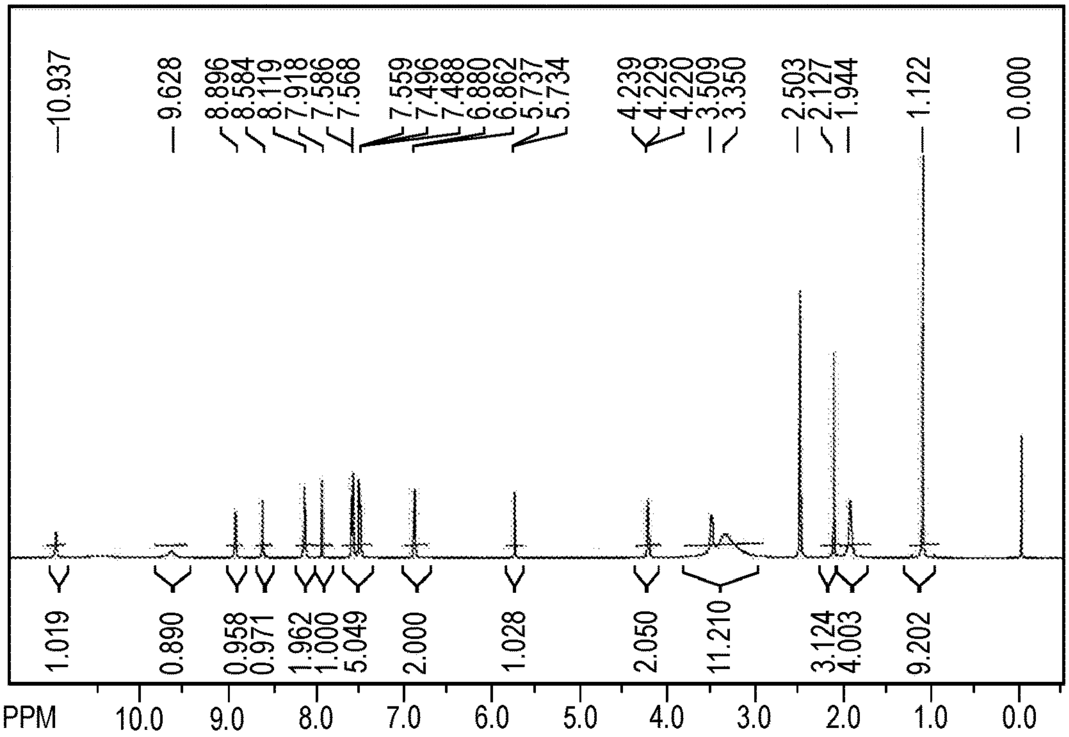

FIG. 229 depicts the $^{1}$H-NMR spectrum of Form H orotic acid salt of Compound 1.

Figure 230:
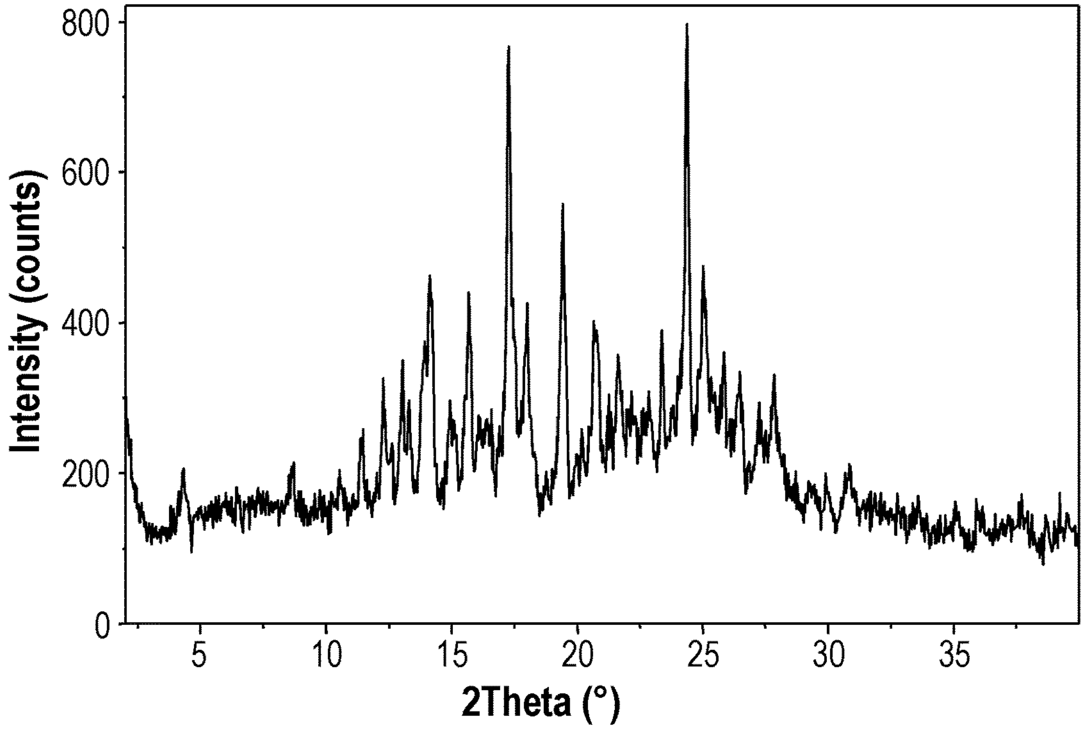

FIG. 230 depicts the XRPD pattern of a mixture of Form A of Compound 1, Form A isonicotinamide co-crystal of Compound 1 and isonicotinamide co-former.

Figure 231:
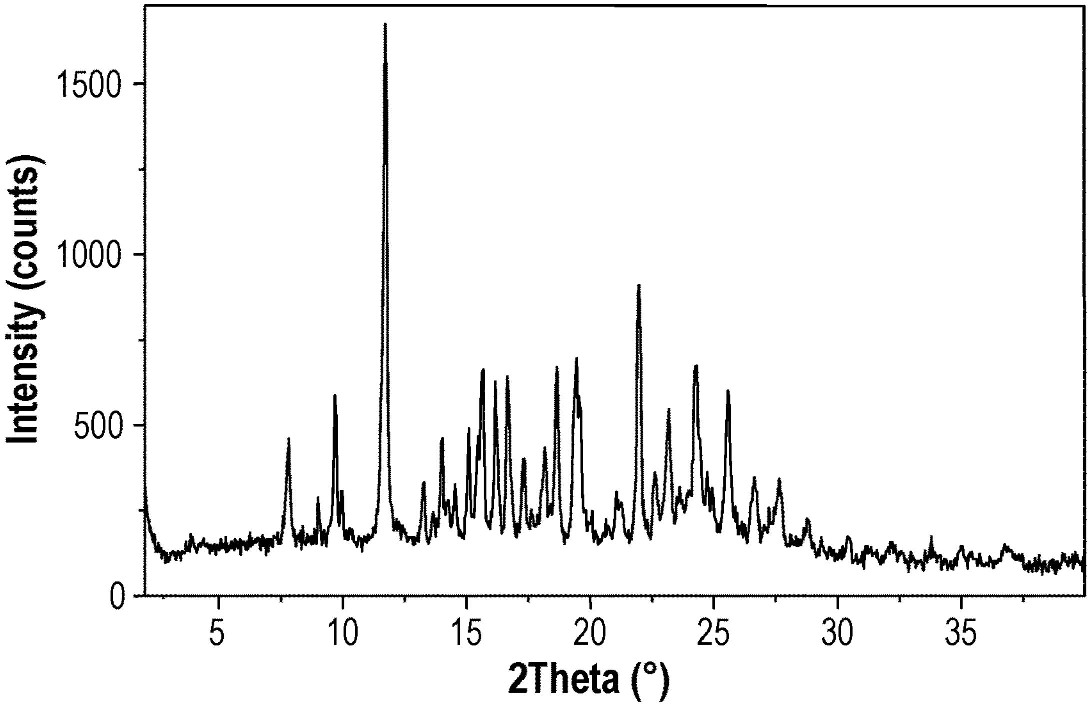

FIG. 231 depicts the XRPD pattern of Form A pyrogallol co-crystal of Compound 1 likely mixed with one or more forms of Compound 1 free base.

Figure 232:
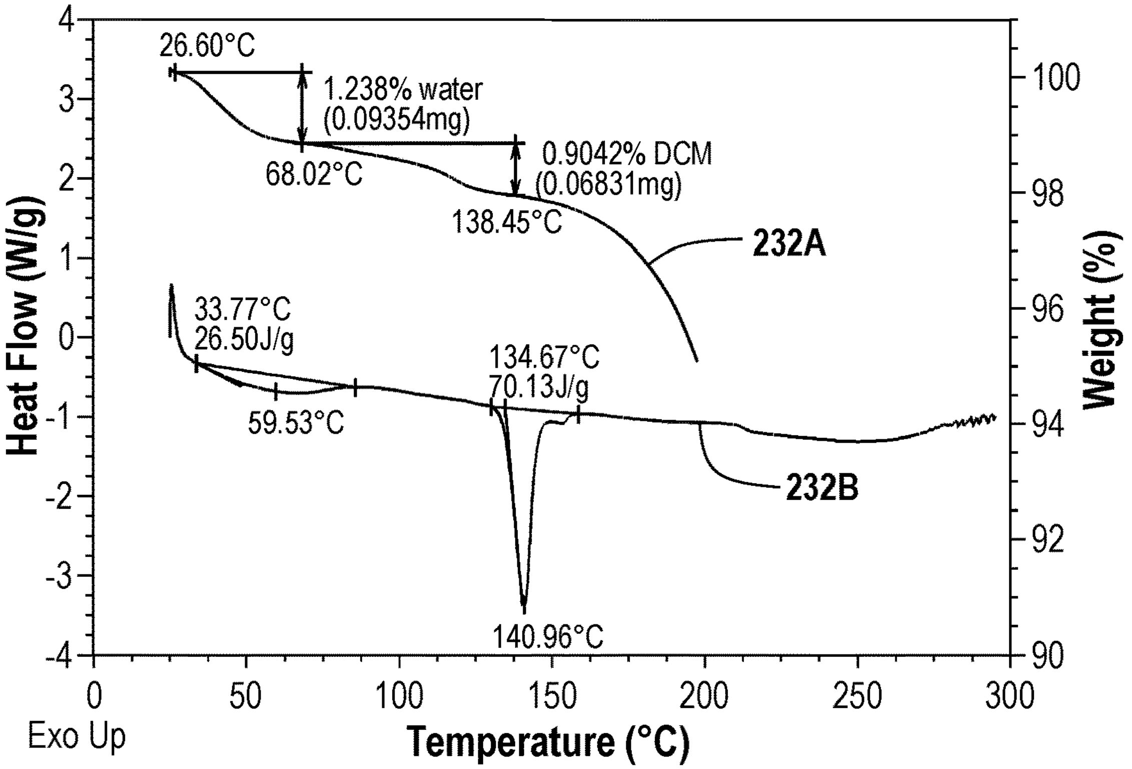

FIG. 232 depicts the TGA pattern of Form A pyrogallol co-crystal of Compound 1 likely mixed with one or more forms of Compound 1 free base (232A), and the DSC pattern of a mixture of Form A pyrogallol co-crystal of Compound 1 likely mixed with one or more forms of Compound 1 free base (232B).

Figure 233:
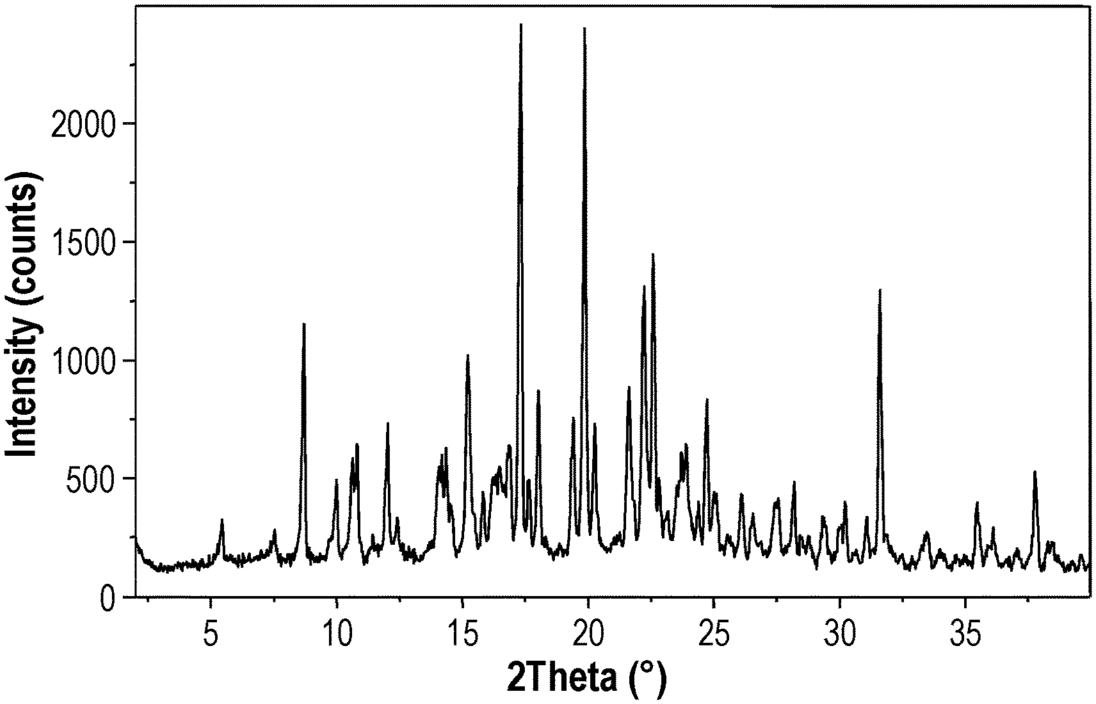

FIG. 233 depicts the XRPD pattern of Form A xylitol co-crystal of Compound 1 likely mixed with one or more forms of Compound 1 free base, and xylitol co-former.

Figure 234:
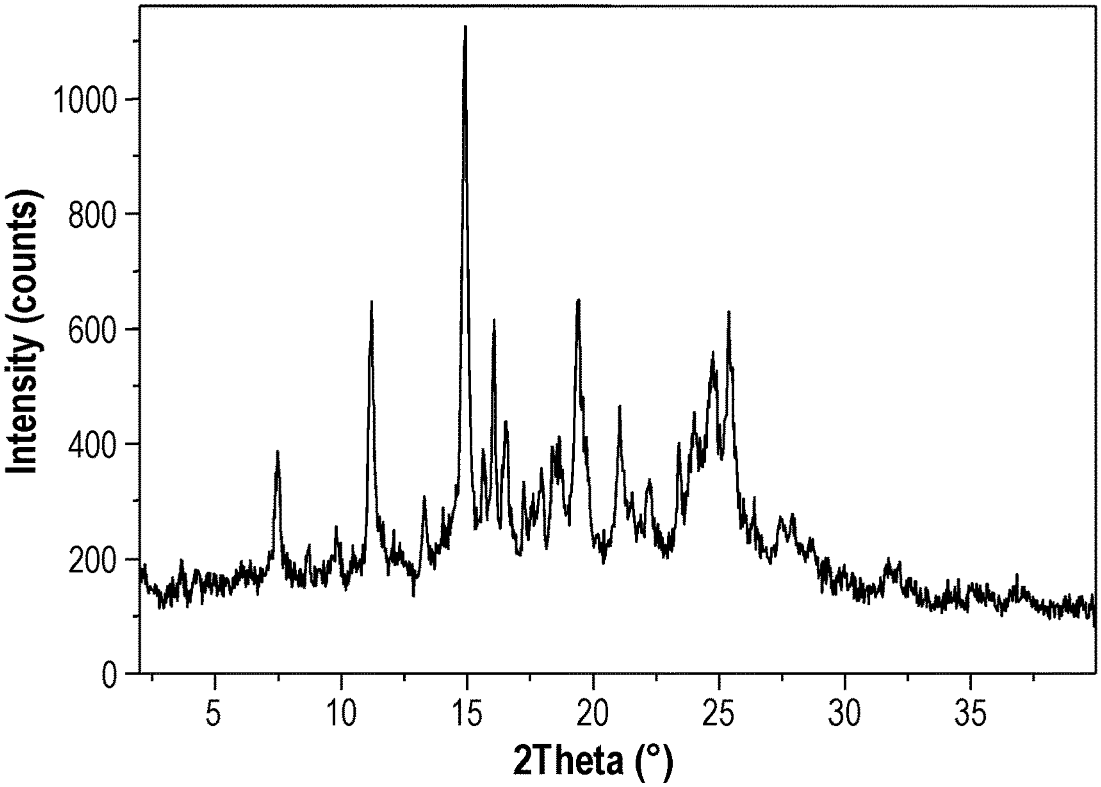

FIG. 234 depicts the XRPD pattern of Form B ascorbic acid salt of Compound 1.

Figure 235:
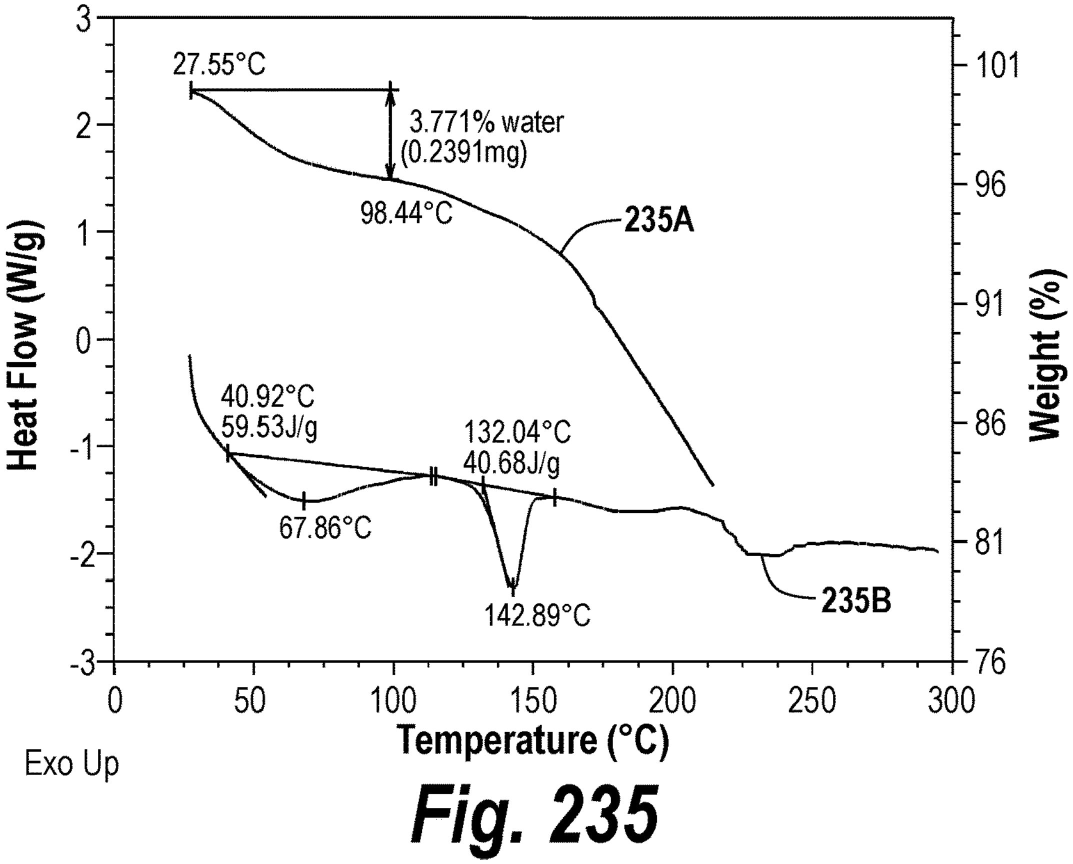

FIG. 235 depicts the TGA pattern of Form B ascorbic acid salt of Compound 1 (235A), and the DSC pattern of Form B ascorbic acid salt of Compound 1 (235B).

Figure 236:
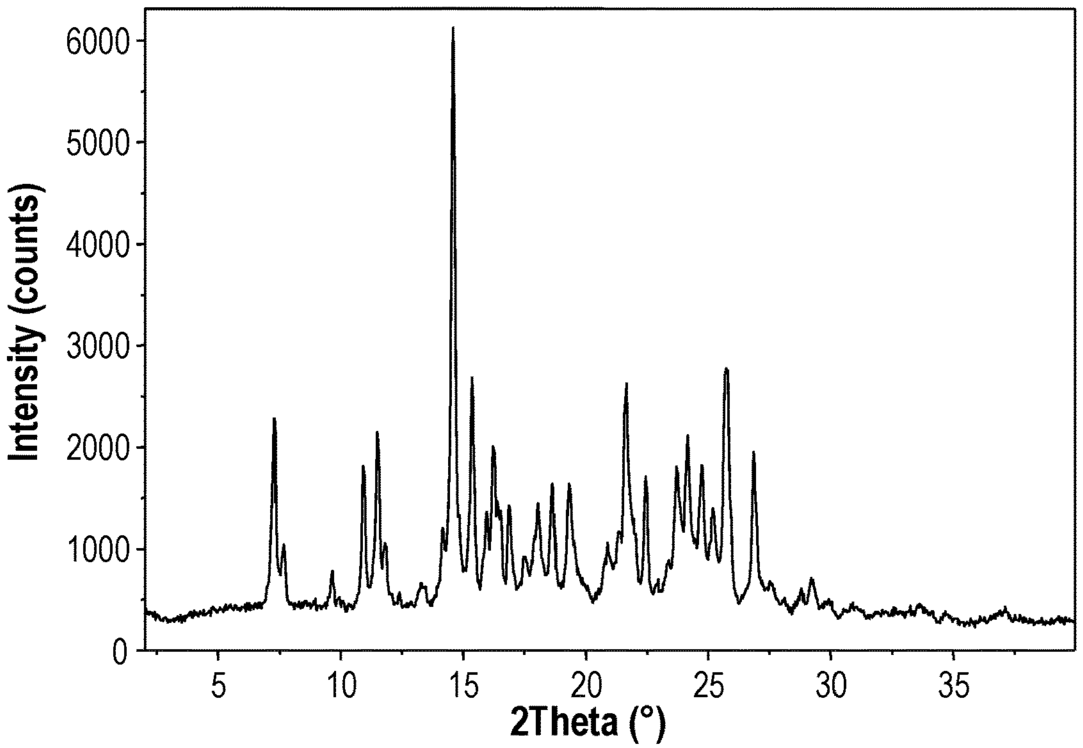

FIG. 236 depicts the XRPD pattern of mixture of Form A gallic acid salt of Compound 1 and Form B gallic acid salt of Compound 1.

Figure 237:
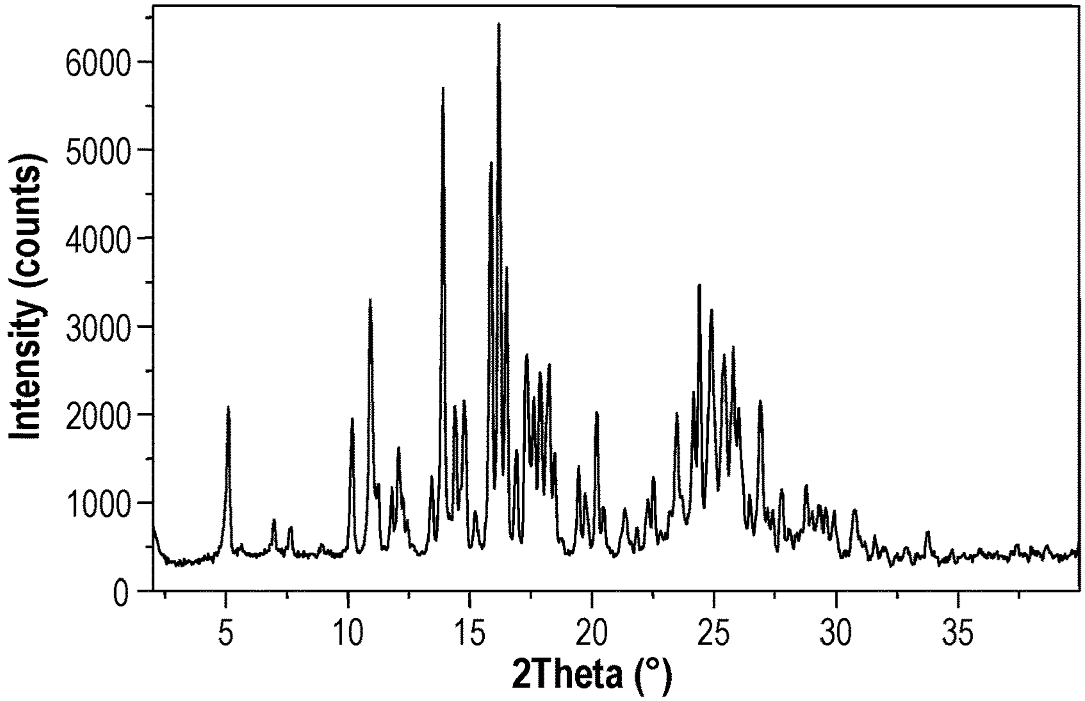

FIG. 237 depicts the XRPD pattern of Form B salicylic acid salt of Compound 1.

Figure 238:
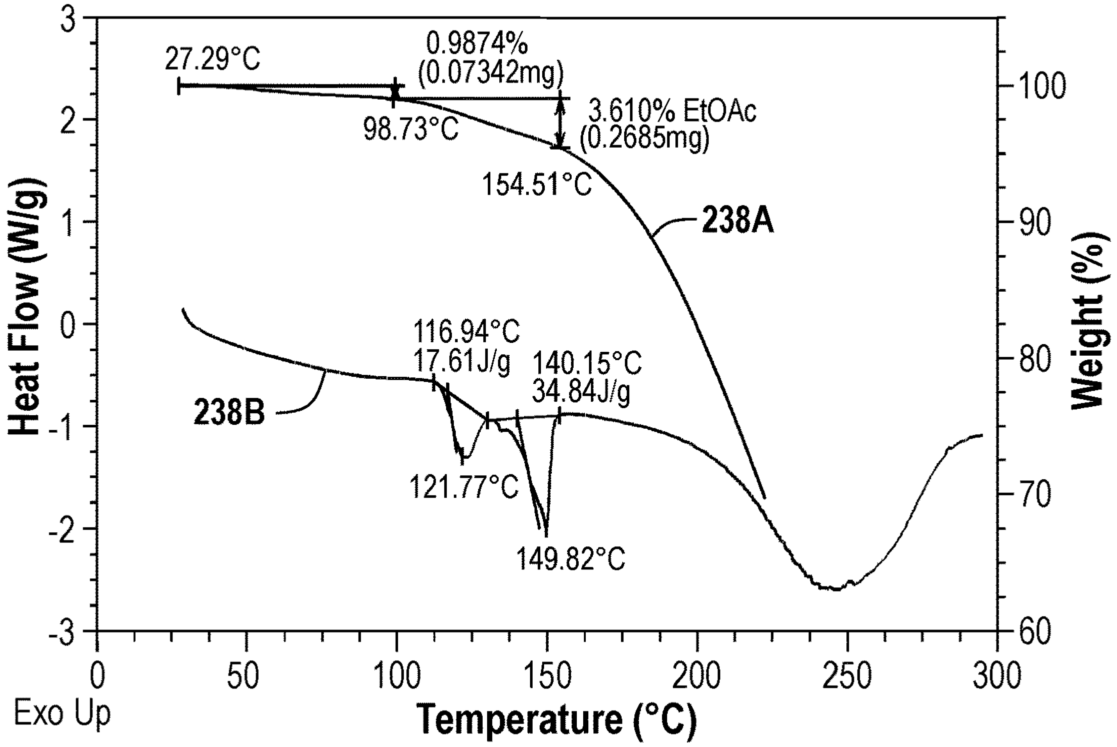

FIG. 238 depicts the TGA pattern of Form B salicylic acid salt of Compound 1, (238A), and the DSC pattern of Form B salicylic acid salt of Compound 1 (238B).

Figure 239:
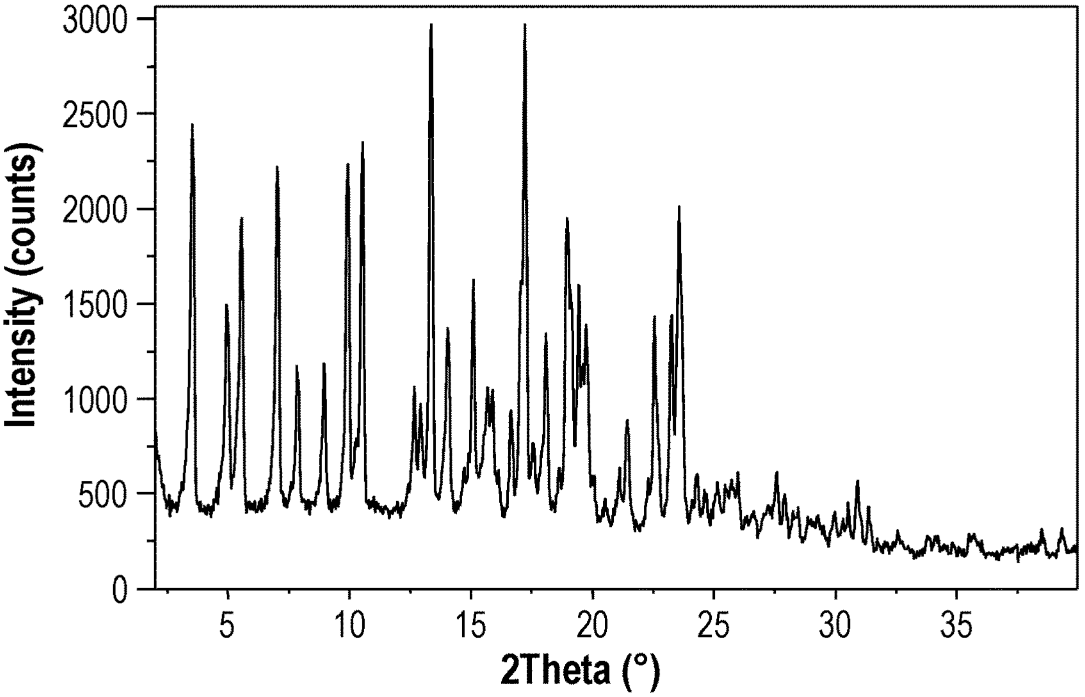

FIG. 239 depicts the XRPD pattern of Form B acetylsalicylic acid salt of Compound 1.

Figure 240:
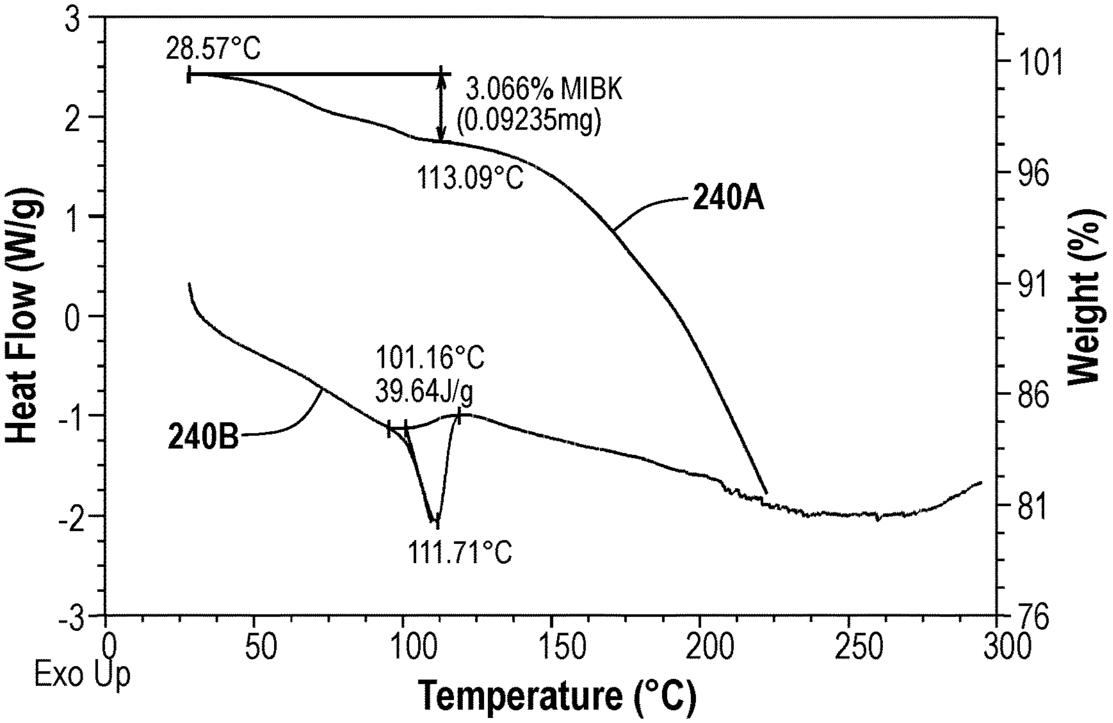

FIG. 240 depicts the TGA pattern of Form B acetylsalicylic acid salt of Compound 1 (240A), and the DSC pattern of Form B acetylsalicylic acid salt of Compound 1 (240B).

DETAILED DESCRIPTION OF THE INVENTION

General Description of Certain Aspects of the Invention

U.S. Pat. No. 7,528,143, issued May 5, 2009 ("the '143 patent"), the entirety of which is hereby incorporated herein by reference, describes certain 2,4-disubstituted pyrimidine compounds that are useful in treating myeloproliferative disorders, including polycythemia vera, essential thrombocythemia and myelofibrosis (e.g., primary myelofibrosis and secondary myelofibrosis such as post-polycythemia vera myelofibrosis and post-essential thrombocythemia myelofibrosis). Such compounds include Compound 1:

1

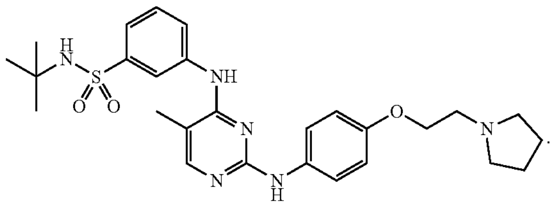

Compound 1, N-tert-butyl-3-[(5-methyl-2-{[4-(2-pyrrolidin-1-ylethoxy)phenyl]amino}pyrimidin-4-yl)amino]benzenesulfonamide, is designated as compound number LVII and the synthesis of Compound 1 is described in detail at Example 90 of the '143 patent.

Compound 1 is active in a variety of assays and therapeutic models demonstrating inhibition of Janus kinase 2 (JAK2). Accordingly, Compound 1, or a crystalline form or complex thereof, is useful for treating one or more disorders associated with activity of JAK2.

Crystalline Forms of Compound 1

In some embodiments, the present disclosure provides a crystalline form of Compound 1. It will be appreciated that a crystalline form of Compound 1 can exist in a neat or unsolvated form, a hydrated form, and/or a solvated form. In some embodiments, a crystalline form of Compound 1 is a neat or unsolvated crystal form and thus does not have any water or solvent incorporated into the crystal structure. In some embodiments, a crystalline form of Compound 1 is a hydrated or solvated form. In some embodiments, a crystalline form of Compound 1 is a hydrate/solvate form (also referred to herein as a "heterosolvate").

Accordingly, in some embodiments, the present disclosure provides one or more crystalline anhydrous forms of Compound 1:

1

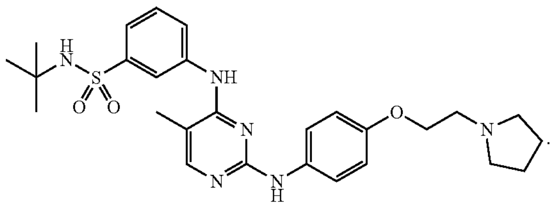

In some embodiments, the present disclosure provides one or more crystalline hydrate forms of Compound 1:

1

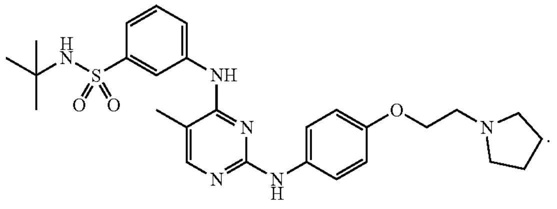

In some embodiments, the present disclosure provides one or more crystalline solvate forms of Compound 1:

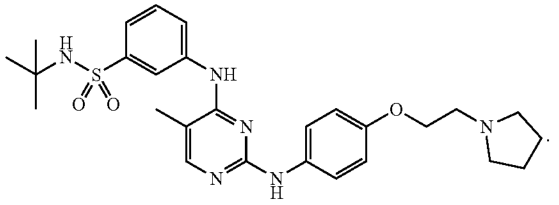

In some embodiments, the present disclosure provides a sample comprising a crystalline form of Compound 1, wherein the sample is substantially free of impurities. As used herein, the term "substantially free of impurities" means that the sample contains no significant amount of extraneous matter. In some embodiments, a sample comprising a crystalline form of Compound 1 is substantially free of amorphous Compound 1. In certain embodiments, the sample comprises at least about 90% by weight of a crystalline form of Compound 1. In certain embodiments, the sample comprises at least about 95% by weight of a crystalline form of Compound 1. In still other embodiments, the sample comprises at least about 99% by weight of a crystalline form of Compound 1.

According to some embodiments, the sample comprises at least about 95, 97, 97.5, 98.0, 98.5, 99, 99.5, 99.8 weight percent (wt %) of a crystalline form of Compound 1, where the percentages are based on the total weight of the sample. According to some embodiments, a sample comprising a crystalline form of Compound 1 comprises no more than about 5.0 percent of total organic impurities. In some embodiments, a sample comprising a crystalline form of Compound 1 comprises no more than about 3.0 percent of total organic impurities. In some embodiments, a sample comprising a crystalline form of Compound 1 comprises no more than about 1.5 percent of total organic impurities. In some embodiments, a sample comprising a crystalline form of Compound 1 comprises no more than about 1.0 percent of total organic impurities. In some embodiments, a sample comprising a crystalline form of Compound 1 comprises no more than about 0.6 percent of total organic impurities. In some embodiments, a sample comprising a crystalline form of Compound 1 comprises no more than about 0.5 percent of total organic impurities. In some embodiments, the percent of total organic impurities is measured by HPLC.

It has been found that Compound 1 can exist in at least four distinct crystal forms, or polymorphs.

In some embodiments, the present disclosure provides an anhydrous form of Compound 1. In some embodiments, an anhydrous form of Compound 1 is a crystalline anhydrous form of Compound 1. In some embodiments, a crystalline anhydrous form of Compound 1 is characterized by one or more peaks in its X-ray powder diffraction pattern selected from 9.7, 14.6, 19.5, 24.3, and 25.6±0.2 degrees 2θ. In some such embodiments, a crystalline anhydrous form of Compound 1 is Form A.

In some embodiments, Form A of Compound 1 is characterized by the following peaks in its X-ray powder diffraction pattern:

-continued

| Position ° 2θ ± 0.2 degrees | d-spacing [Å] | Height [cts] |
|---|---|---|
| 8.8 | 10.102 | 1414 |
| 9.7 | 9.120 | 88376 |
| 10.5 | 8.463 | 2192 |
| 13.6 | 6.516 | 1881 |
| 14.6 | 6.082 | 50409 |
| 16.0 | 5.543 | 3640 |
| 16.4 | 5.413 | 2620 |
| 17.7 | 5.014 | 3311 |
| 18.5 | 4.797 | 5807 |
| 19.1 | 4.637 | 1316 |
| 19.5 | 4.563 | 6885 |
| 19.8 | 4.492 | 1686 |
| 20.1 | 4.415 | 1686 |
| 20.4 | 4.360 | 4156 |
| 21.0 | 4.229 | 4358 |
| 22.7 | 3.914 | 1551 |
| 23.0 | 3.874 | 2648 |
| 23.5 | 3.781 | 1611 |
| 23.9 | 3.730 | 9006 |
| 24.3 | 3.660 | 13329 |
| 24.6 | 3.614 | 1849 |
| 25.6 | 3.479 | 7883 |
| 28.0 | 3.192 | 1510 |
| 28.6 | 3.119 | 1592 |
| 29.4 | 3.043 | 2105 |

Figure 1:
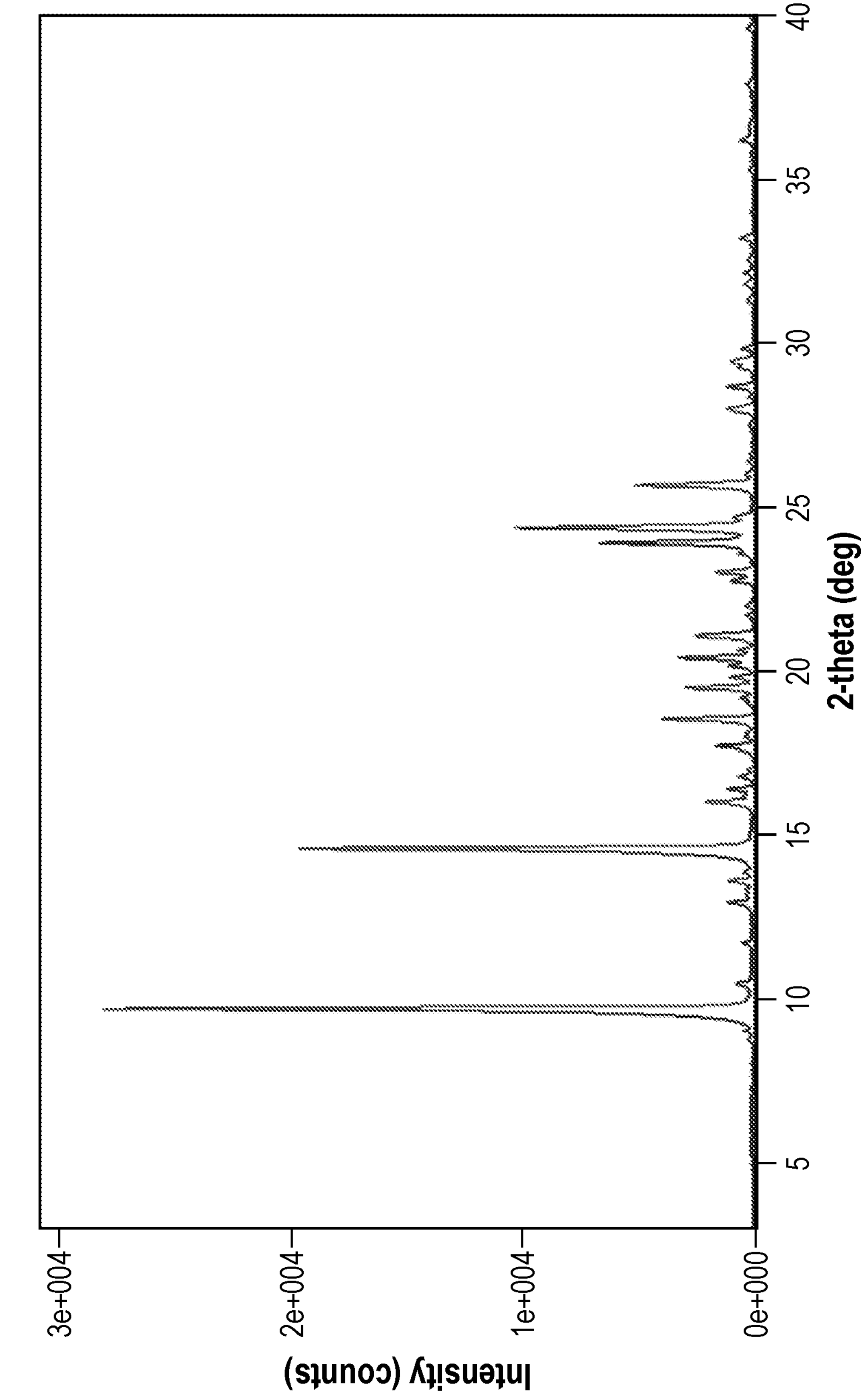
FIG. 1 depicts the X-ray powder diffraction (XRPD) pattern of Form A of Compound 1.

In some embodiments, Form A of Compound 1 is characterized by the x-ray powder diffraction (XRPD) pattern depicted in FIG. 1.

Figure 2A:
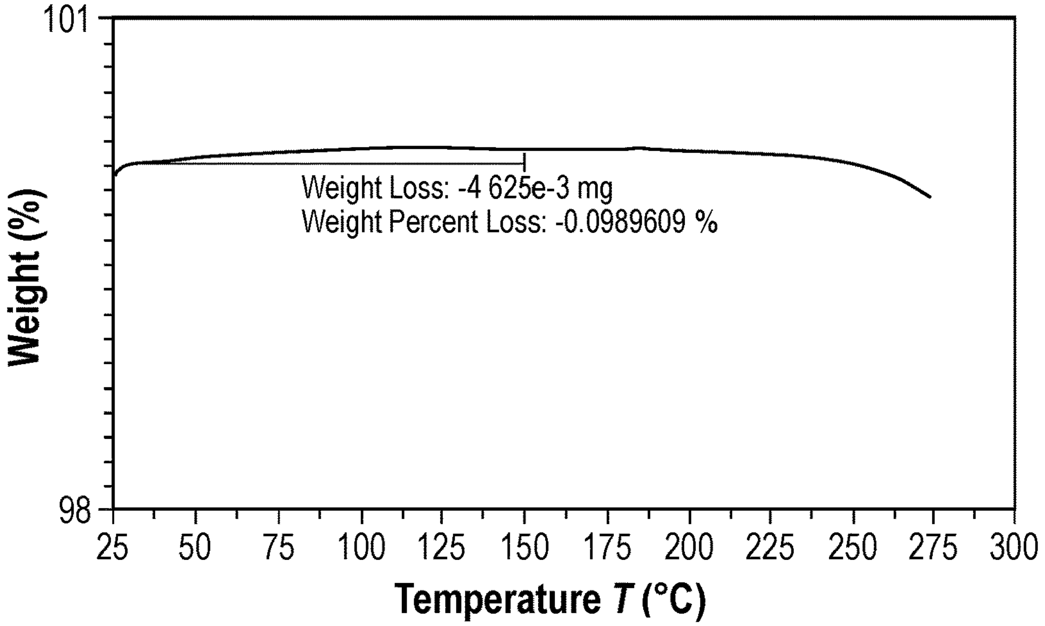
FIG. 2A depicts the thermogravimetric analysis (TGA) pattern of Form A of Compound 1.

In some embodiments, Form A of Compound 1 is characterized by the thermogravimetric analysis (TGA) pattern depicted in FIG. 2A.

Figure 2B:
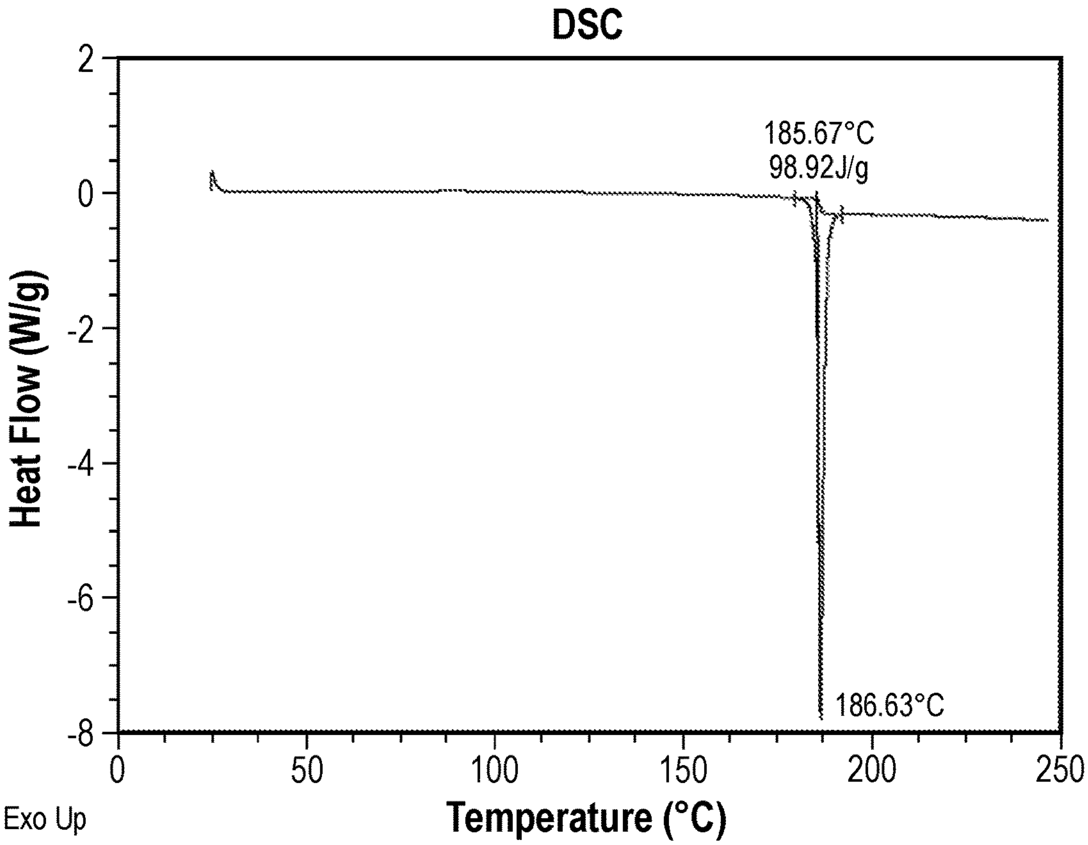
FIG. 2B depicts the differential scanning calorimetry (DSC) pattern of Form A of Compound 1.

In some embodiments, Form A of Compound 1 is characterized by the differential scanning calorimetry (DSC) pattern depicted in FIG. 2B.

Figure 2C:
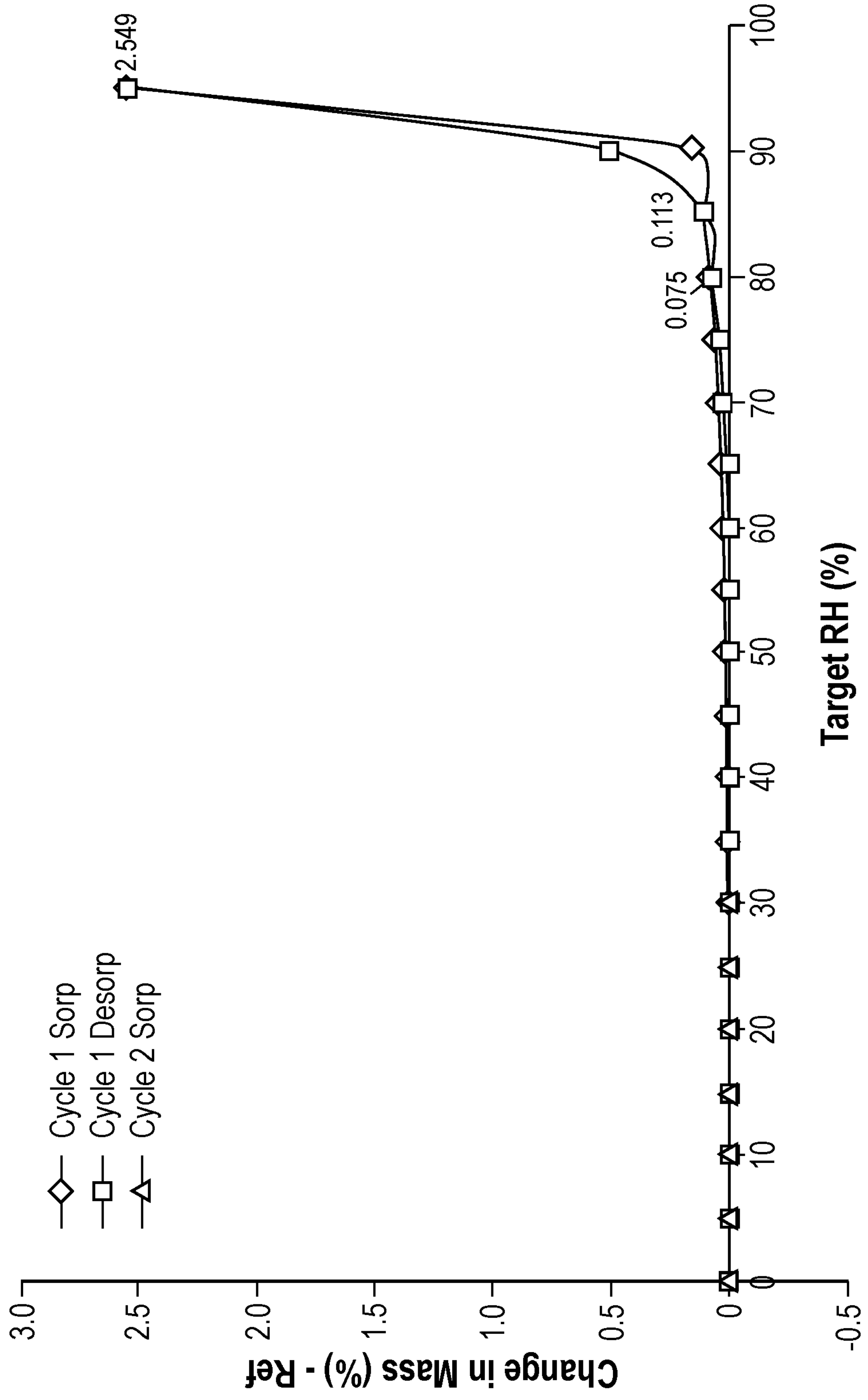
FIG. 2C depicts the dynamic vapor sorption (DVS) isotherm of Form A of Compound 1.

In some embodiments, Form A of Compound 1 is characterized by the dynamic vapor sorption (DVS) isotherm depicted in FIG. 2C.

In some embodiments, the present disclosure provides a solvate form of Compound 1. In some such embodiments, a solvate form of Compound 1 is a 2-methyl-tetrahydrofuran solvate. In some embodiments, a 2-methyl-tetrahydrofuran solvate form of Compound 1 is a crystalline 2-methyl-tetrahydrofuran solvate form of Compound 1. In some embodiments, a crystalline 2-methyl-tetrahydrofuran solvate form of Compound 1 is characterized by one or more peaks in its X-ray powder diffraction pattern selected from 12.5, 18.3, 18.9, 20.1, and 23.8±0.2 degrees 2θ. In some such embodiments, a crystalline 2-methyl-tetrahydrofuran solvate form of Compound 1 is Form B.

In some embodiments, Form B of Compound 1 is characterized by the following peaks in its X-ray powder diffraction pattern:

| Position ° 2θ ± 0.2 degrees | d-spacing [Å] | Height [cts] |
|---|---|---|
| 7.6 | 11.633 | 715 |
| 10.2 | 8.690 | 521 |
| 11.9 | 7.430 | 2468 |
| 12.5 | 7.096 | 3531 |
| 12.7 | 6.963 | 2843 |
| 14.1 | 6.265 | 2984 |
| 14.5 | 6.096 | 1620 |
| 16.1 | 5.494 | 2249 |
| 18.3 | 4.836 | 6390 |

-continued

| Position ° 2θ ± 0.2 degrees | d-spacing [Å] | Height [cts] |
|---|---|---|
| 18.9 | 4.699 | 5752 |
| 20.1 | 4.411 | 6304 |
| 21.4 | 4.147 | 1605 |
| 23.1 | 3.853 | 1981 |
| 23.8 | 3.734 | 25579 |
| 25.5 | 3.498 | 1600 |
| 26.0 | 3.433 | 1425 |
| 27.6 | 3.231 | 1295 |
| 28.3 | 3.149 | 1147 |
| 28.9 | 3.090 | 556 |
| 30.4 | 2.937 | 356 |
| 31.7 | 2.824 | 477 |
| 34.2 | 2.620 | 224 |
| 35.5 | 2.530 | 569 |
| 36.0 | 2.497 | 405 |
| 36.9 | 2.434 | 141 |

Figure 3:
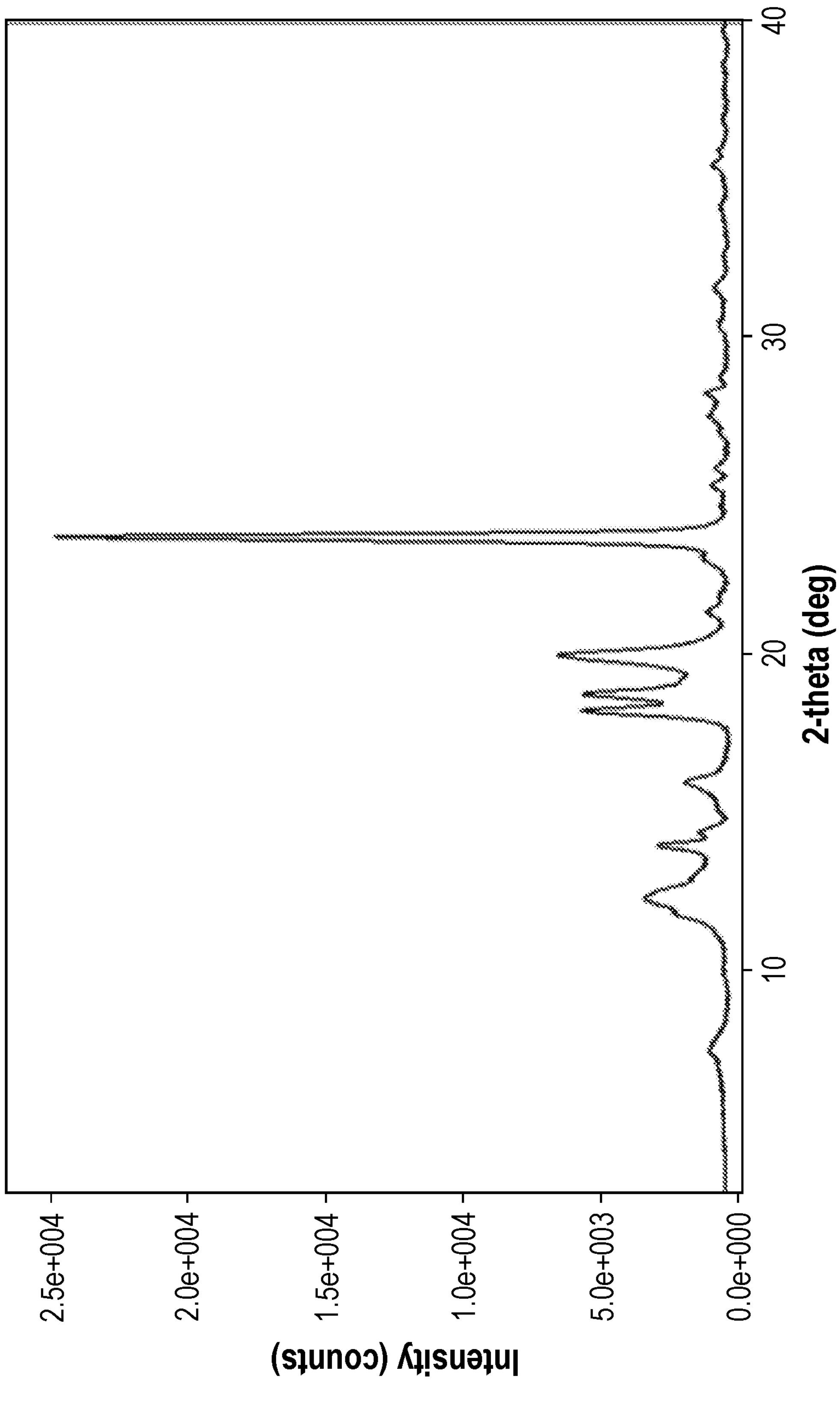
FIG. 3 depicts the XRPD pattern of Form B of Compound 1.

In some embodiments, Form B of Compound 1 is characterized by the x-ray powder diffraction (XRPD) pattern depicted in FIG. 3.

Figure 4A:
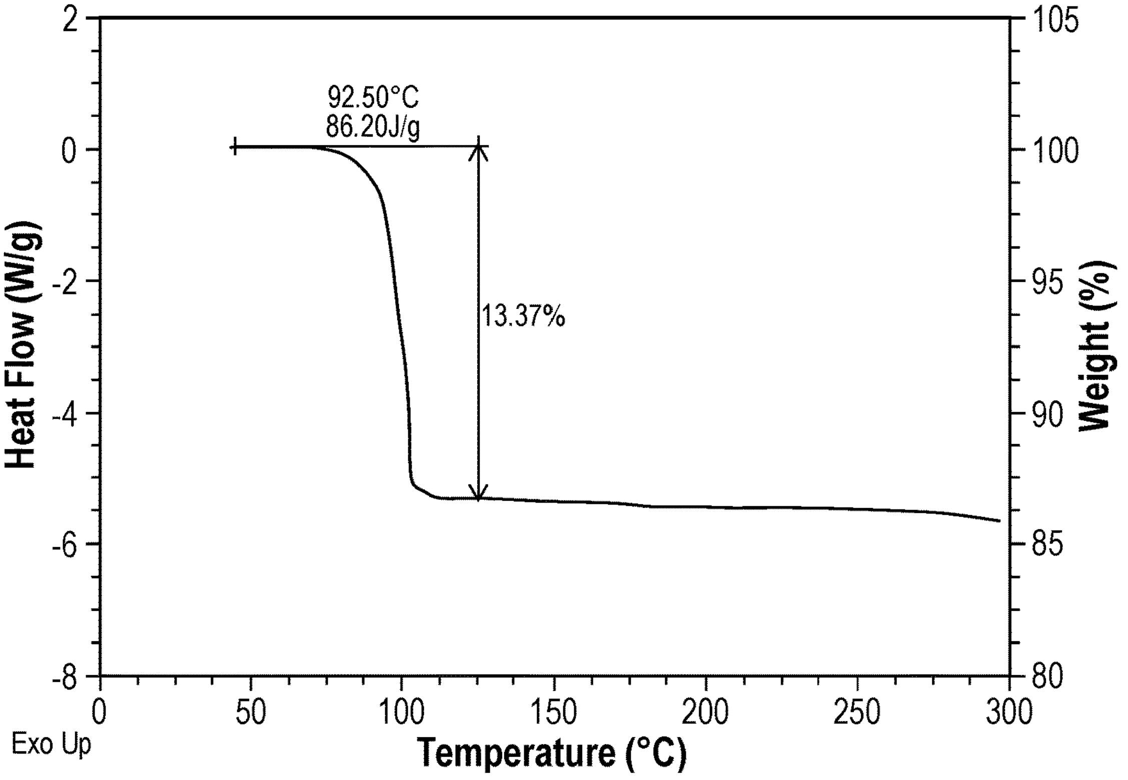
FIG. 4A depicts the TGA pattern of Form B of Compound 1.

In some embodiments, Form B of Compound 1 is characterized by the thermogravimetric analysis (TGA) pattern depicted in FIG. 4A.

Figure 4B:
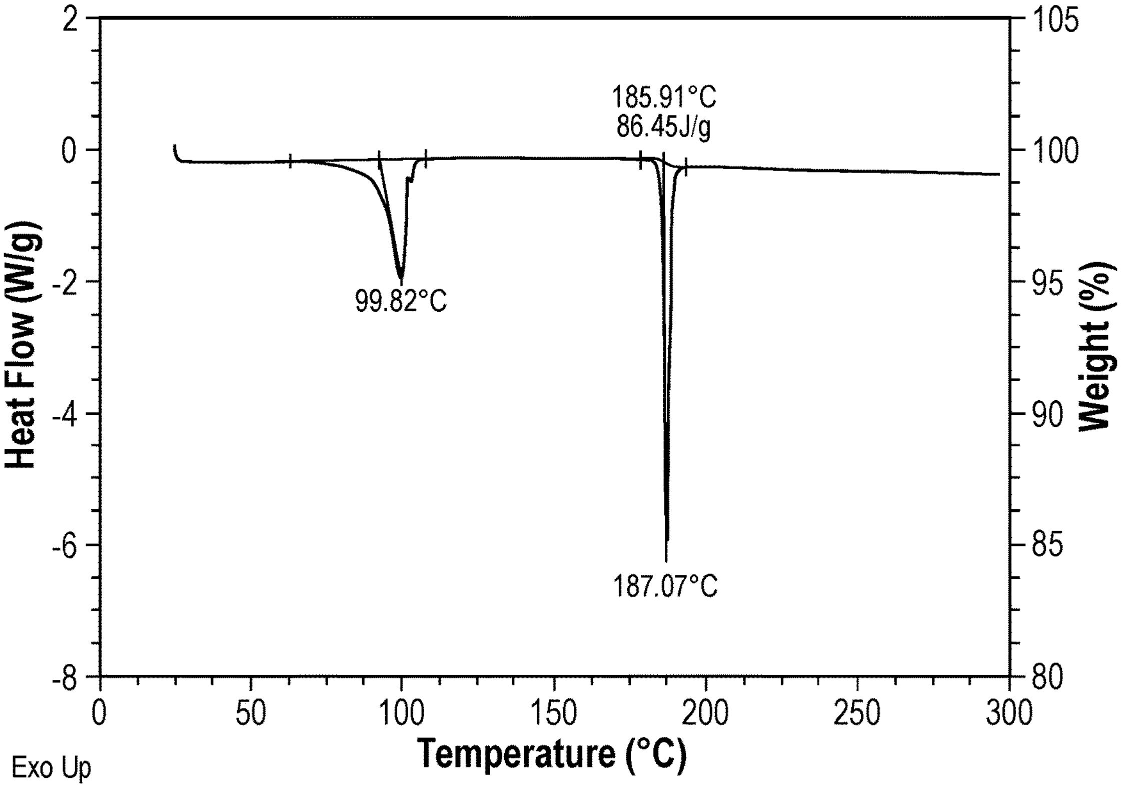
FIG. 4B depicts the DSC pattern of Form B of Compound 1.

In some embodiments, Form B of Compound 1 is characterized by the differential scanning calorimetry (DSC) pattern depicted in FIG. 4B.

In some embodiments, the present disclosure provides a hydrate form of Compound 1. In some embodiments, a hydrate form of Compound 1 is a crystalline hydrate form of Compound 1. In some embodiments, a crystalline hydrate form of Compound 1 is a monohydrate. In some embodiments, a crystalline monohydrate form of Compound 1 is characterized by one or more peaks in its X-ray powder diffraction pattern selected from 8.7, 15.2, 17.3, 18.0, and 19.4±0.2 degrees 2θ. In some such embodiments, a crystalline monohydrate form of Compound 1 is Form C.

In some embodiments, Form C of Compound 1 is characterized by the following peaks in its X-ray powder diffraction pattern:

| Position ° 2θ ± 0.2 degrees | d-spacing [Å] | Height [cts] |
|---|---|---|
| 8.7 | 10.184 | 23473 |
| 10.6 | 8.332 | 6912 |
| 14.4 | 6.172 | 8862 |
| 15.2 | 5.825 | 11716 |
| 15.5 | 5.719 | 3493 |
| 16.3 | 5.439 | 5672 |
| 16.6 | 5.329 | 5294 |
| 16.9 | 5.244 | 7167 |
| 17.3 | 5.120 | 51890 |
| 18.0 | 4.917 | 15095 |
| 19.4 | 4.578 | 10908 |
| 20.2 | 4.388 | 8419 |
| 21.8 | 4.078 | 5043 |
| 22.1 | 4.017 | 7400 |
| 22.4 | 3.974 | 6455 |
| 22.8 | 3.894 | 6416 |
| 23.2 | 3.841 | 3537 |
| 23.5 | 3.783 | 7215 |
| 24.4 | 3.647 | 4592 |
| 25.0 | 3.559 | 4787 |

-continued

| Position ° 2θ ± 0.2 degrees | d-spacing [Å] | Height [cts] |
|---|---|---|
| 25.2 | 3.540 | 4028 |
| 26.1 | 3.414 | 4525 |
| 26.6 | 3.356 | 4349 |
| 27.4 | 3.255 | 5512 |
| 27.6 | 3.231 | 4683 |

Figure 5:
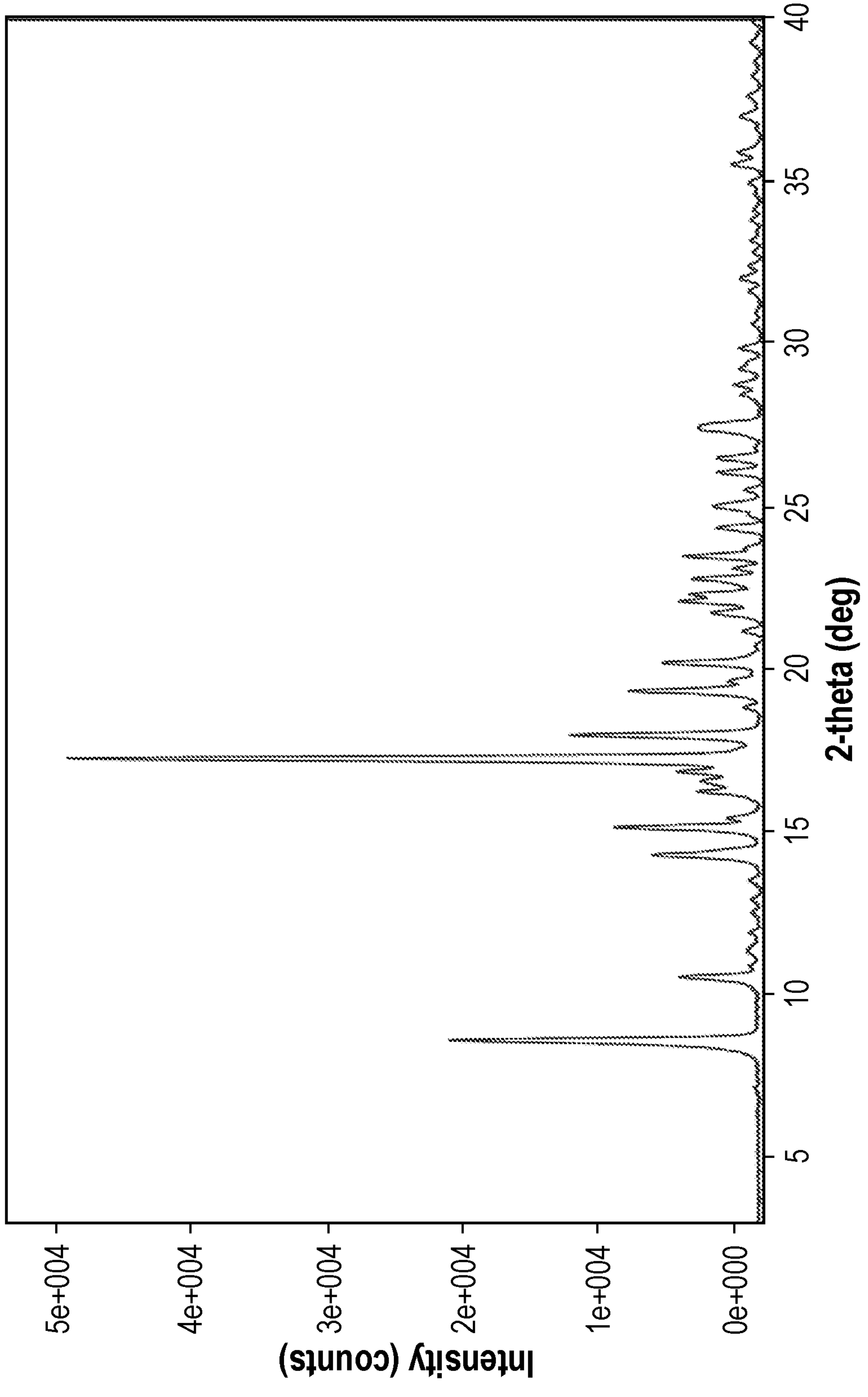
FIG. 5 depicts the XRPD pattern of Form C of Compound 1.

In some embodiments, Form C of Compound 1 is characterized by the x-ray powder diffraction (XRPD) pattern depicted in FIG. 5.

Figure 6A:
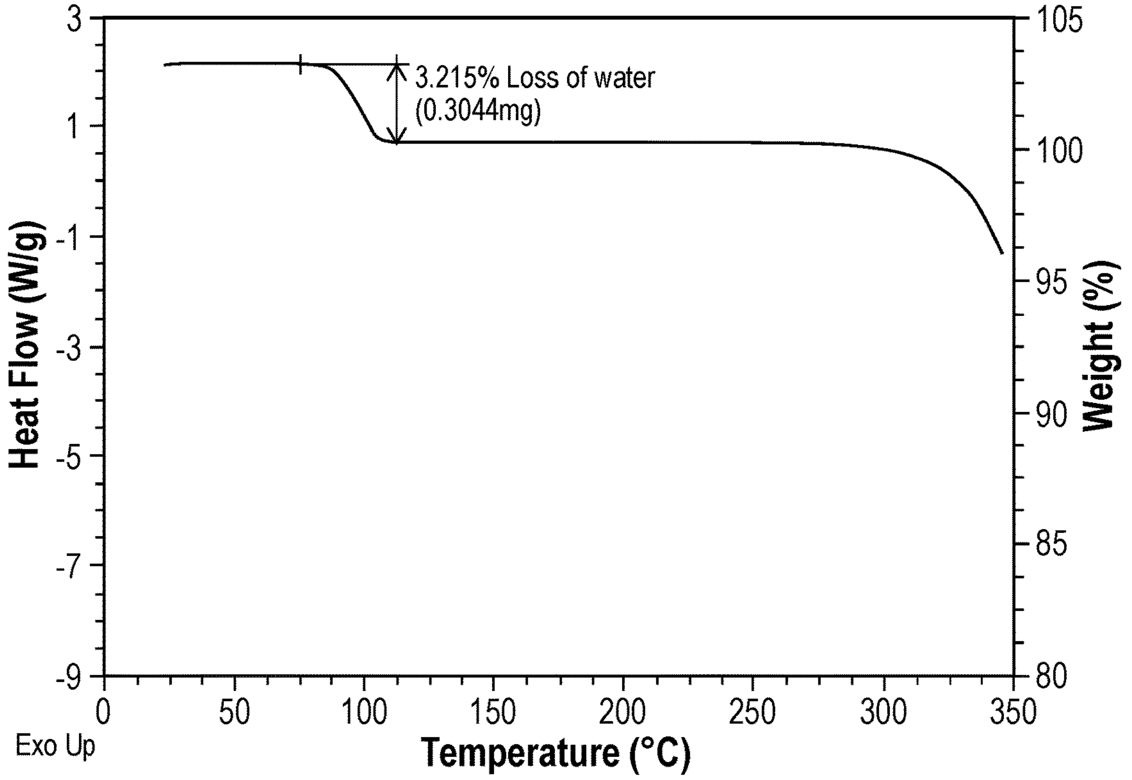
FIG. 6A depicts the TGA pattern of Form C of Compound 1.

In some embodiments, Form C of Compound 1 is characterized by the thermogravimetric analysis (TGA) pattern depicted in FIG. 6A.

Figure 6B:
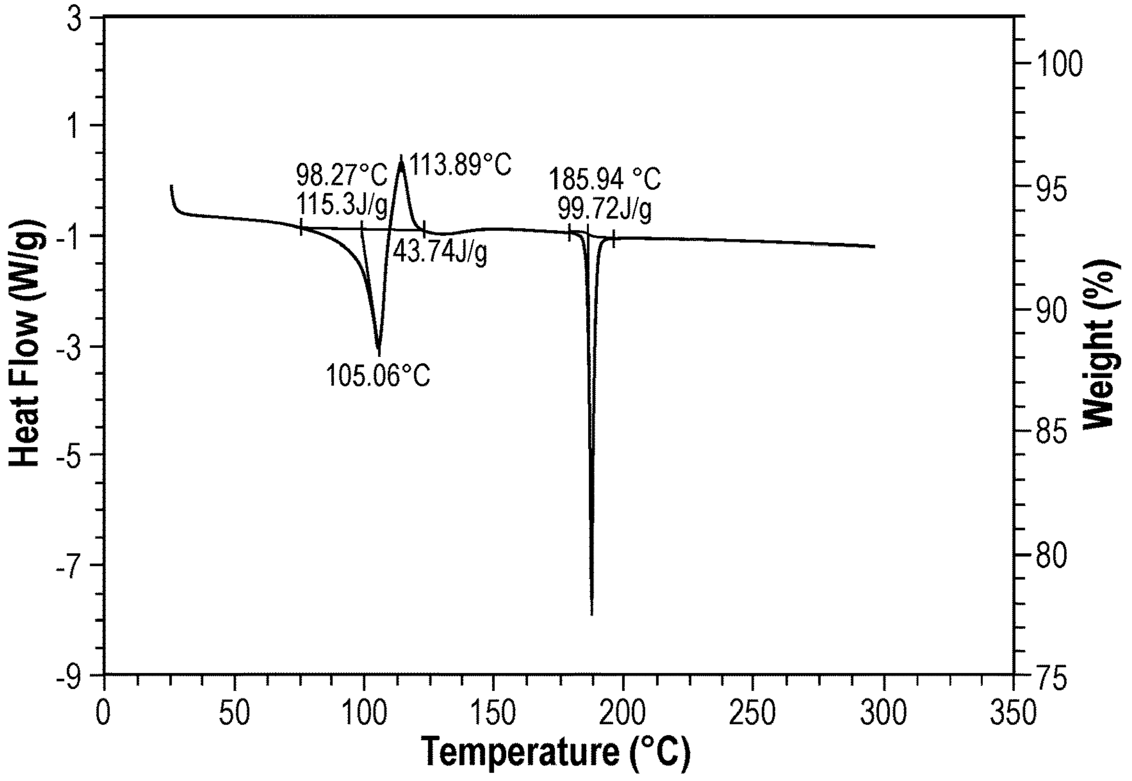
FIG. 6B depicts the DSC pattern of Form C of Compound 1.

In some embodiments, Form C of Compound 1 is characterized by the differential scanning calorimetry (DSC) pattern depicted in FIG. 6B.

Figure 7:
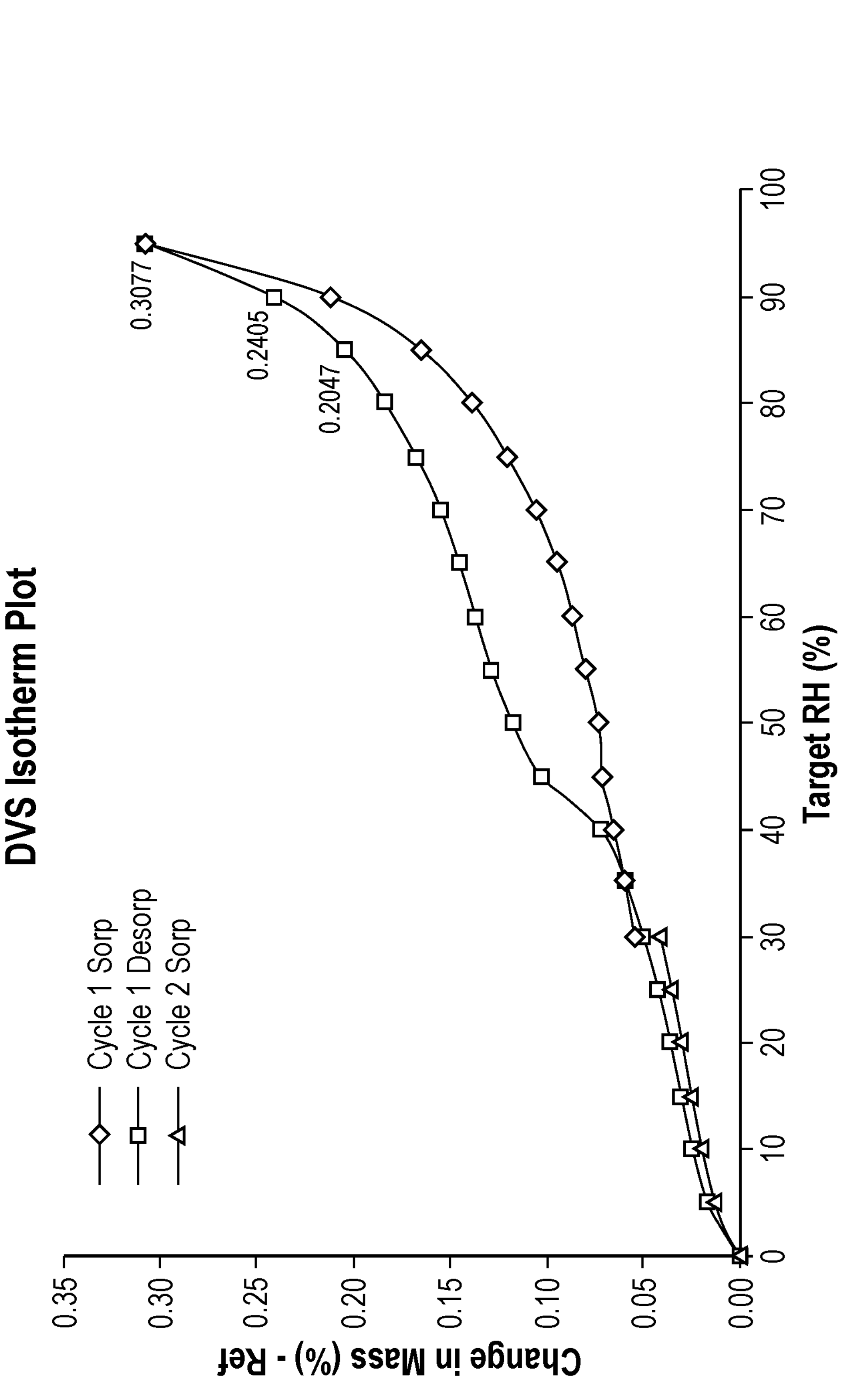
FIG. 7 depicts the DVS isotherm of Form C of Compound 1.

In some embodiments, Form C of Compound 1 is characterized by the dynamic vapor sorption (DVS) isotherm depicted in FIG. 7.

In some embodiments, a crystalline hydrate form of Compound 1 is a tetrahydrate. In some embodiments, a crystalline tetrahydrate form of Compound 1 is characterized by one or more peaks in its X-ray powder diffraction pattern selected from 12.4, 18.5, 19.3, 20.3, and 23.6±0.2 degrees 2θ. In some such embodiments, a crystalline tetrahydrate form of Compound 1 is Form D.

In some embodiments, Form D of Compound 1 is characterized by the following peaks in its X-ray powder diffraction pattern:

| Position ° 2θ ± 0.2 degrees | d-spacing [Å] | Height [cts] |
|---|---|---|
| 7.7 | 11.475 | 1223 |
| 11.8 | 7.529 | 1943 |
| 12.0 | 7.372 | 2255 |
| 12.4 | 7.142 | 4460 |
| 12.9 | 6.874 | 1805 |
| 13.4 | 6.619 | 1735 |
| 14.1 | 6.282 | 2143 |
| 14.5 | 6.122 | 1529 |
| 15.4 | 5.772 | 1552 |
| 16.4 | 5.397 | 3326 |
| 18.5 | 4.800 | 7100 |
| 19.3 | 4.591 | 4008 |
| 19.7 | 4.497 | 2119 |
| 20.0 | 4.435 | 3039 |
| 20.3 | 4.380 | 4906 |
| 20.8 | 4.267 | 1987 |
| 21.3 | 4.163 | 1495 |
| 21.9 | 4.066 | 999 |
| 22.7 | 3.925 | 836 |
| 23.6 | 3.770 | 22852 |
| 24.8 | 3.585 | 1474 |
| 25.8 | 3.453 | 907 |
| 26.2 | 3.405 | 1278 |
| 27.0 | 3.306 | 1347 |
| 28.5 | 3.133 | 823 |

Figure 8:
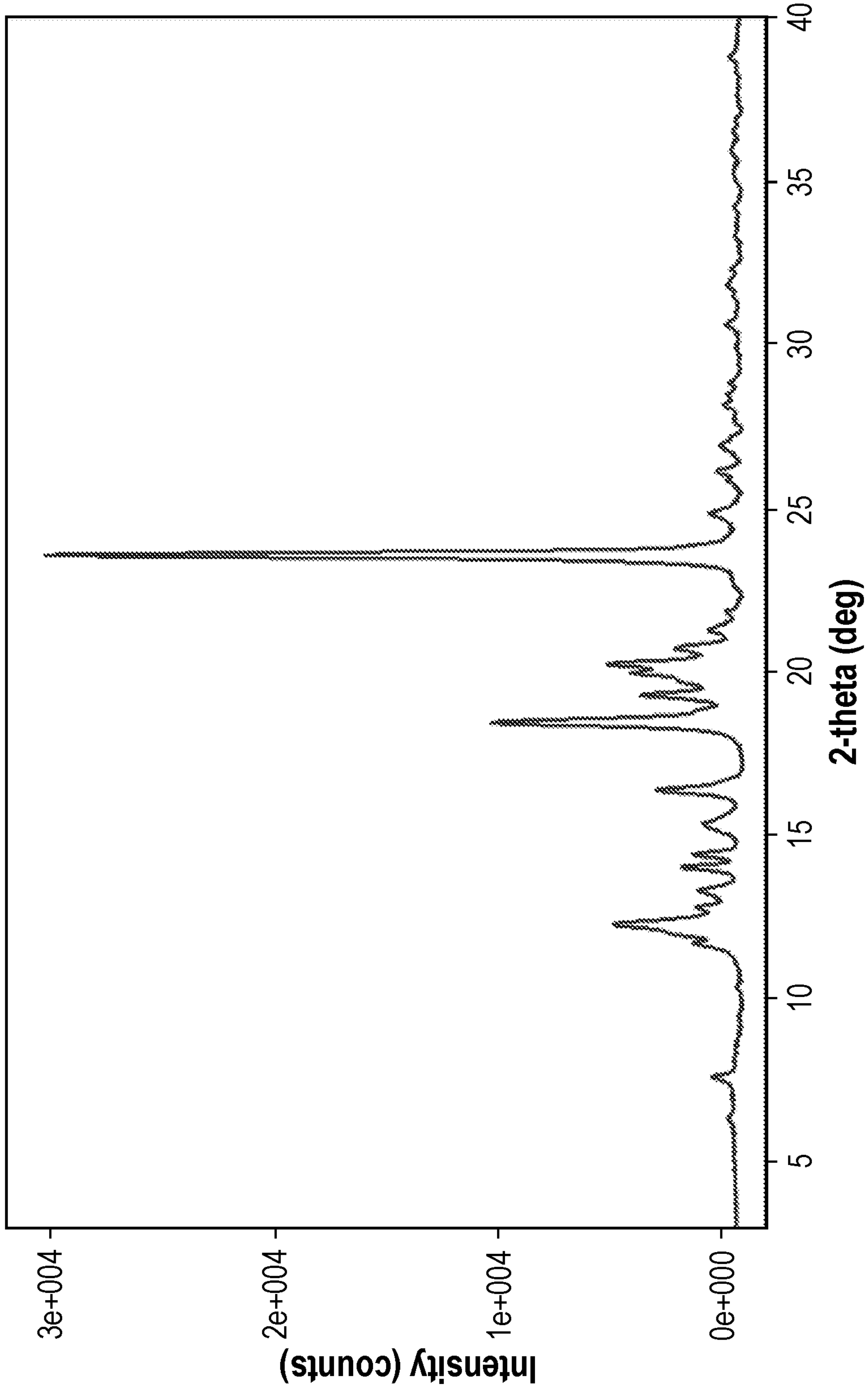
FIG. 8 depicts the XRPD pattern of Form D of Compound 1.

In some embodiments, Form D of Compound 1 is characterized by the x-ray powder diffraction (XRPD) pattern depicted in FIG. 8.

Figure 9A:
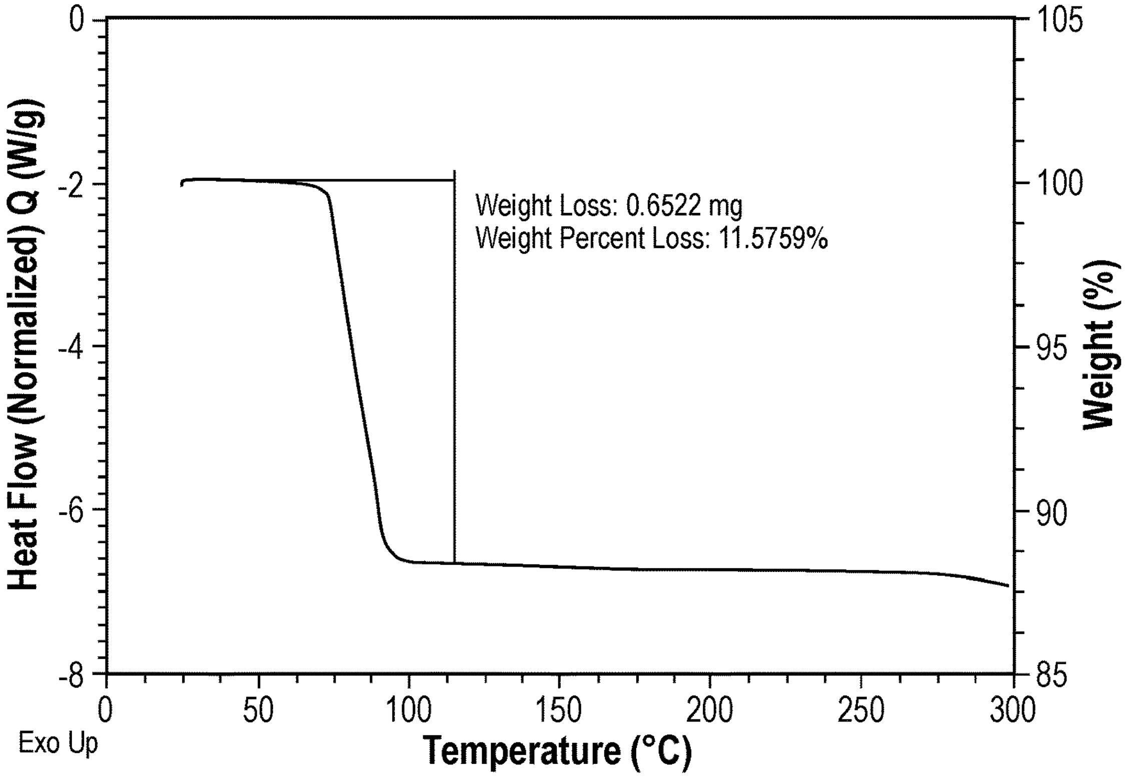
FIG. 9A depicts the TGA pattern of Form D of Compound 1.

In some embodiments, Form D of Compound 1 is characterized by the thermogravimetric analysis (TGA) pattern depicted in FIG. 9A.

Figure 9B:
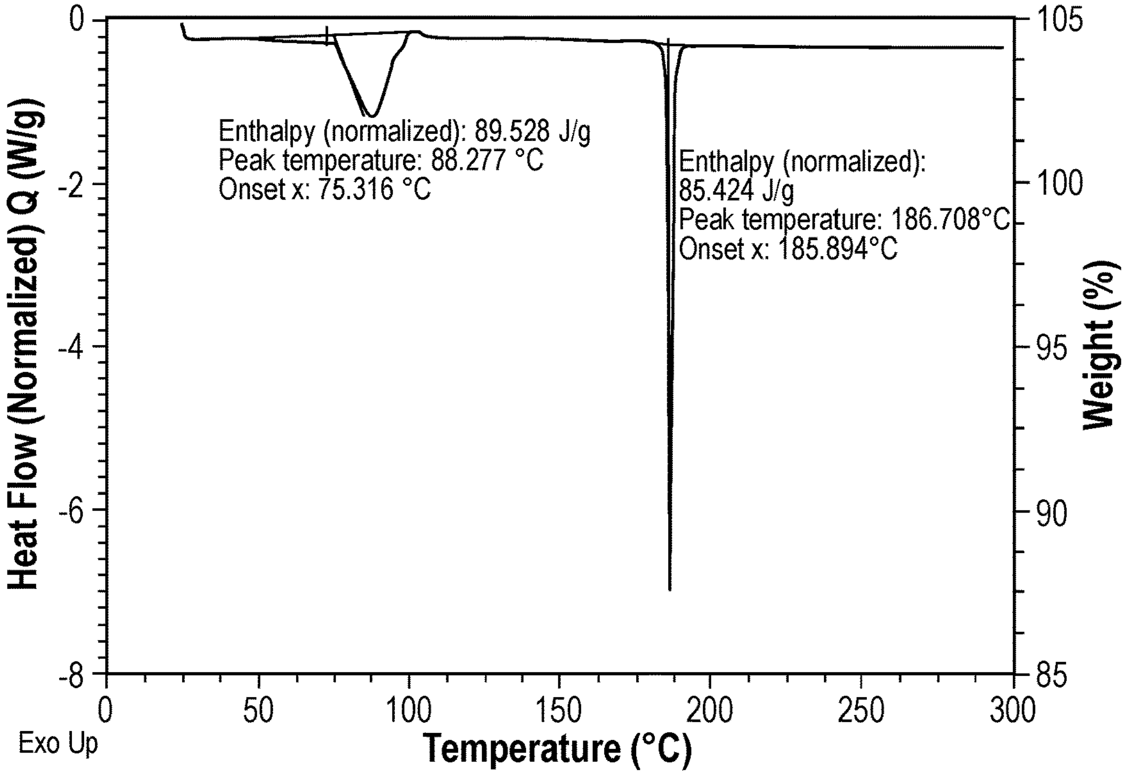
FIG. 9B depicts the DSC pattern of Form D of Compound 1.

In some embodiments, Form D of Compound 1 is characterized by the differential scanning calorimetry (DSC) pattern depicted in FIG. 9B.

In some embodiments, it would be desirable to provide a form of Compound 1 that, as compared to Compound 1, imparts characteristics such as improved aqueous solubility, stability and ease of formulation. Accordingly, the present invention provides complexes of Compound 1.

Complex Forms of Compound 1

In some embodiments, the present disclosure provides a complex comprising Compound 1:

1

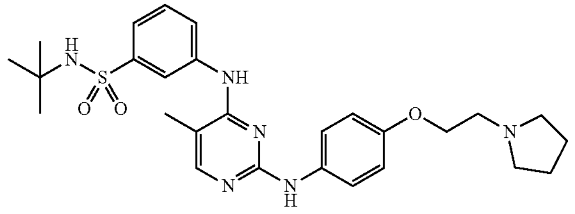

and a co-former X;

wherein:

X is selected from the group consisting of hydrobromic acid, sulfuric acid, toluenesulfonic acid, methanesulfonic acid, 2-naphthalenesulfonic acid, phosphoric acid, DL-tartaric acid, succinic acid, gentisic acid, hippuric acid, adipic acid, galactaric acid, naphthalene-1,5-disulfonic acid, (S)-camphor-10-sulfonic acid, ethane-1, 2-disulfonic acid, ethanesulfonic acid, benzenesulfonic acid, oxalic acid, maleic acid, pamoic acid, 1-hydroxy-2-naphthoic acid, malonic acid, L-tartaric acid, fumaric acid, citric acid, L-lactic acid, acetic acid, propionic acid, DL-lactic acid, D-gluconic acid, DL-malic acid, glutaric acid, camphoric acid, DL-mandelic acid, glutamic acid, glycolic acid, L-mandelic acid, L-malic acid, L-aspartic acid, benzoic acid, saccharin, nicotinic acid, ascorbic acid, gallic acid, salicylic acid, orotic acid, acetylsalicylic acid, choline, potassium hydroxide, and sodium hydroxide.

It will be appreciated that a complex comprising Compound 1 and a co-former X can exist in a neat or unsolvated form, a hydrated form, a solvated form, and/or a heterosolvated form. In some embodiments, a complex comprising Compound 1 and a co-former X is a neat or unsolvated crystal form and thus does not have any water or solvent incorporated into the crystal structure. In some embodiments, a complex comprising Compound 1 and a co-former X is a hydrated or solvated form. In some embodiments, a complex comprising Compound 1 and a co-former X is a hydrate/solvate form (also referred to herein as a "heterosolvate"). In some embodiments, the present disclosure provides an anhydrous form of a complex comprising Compound 1:

1

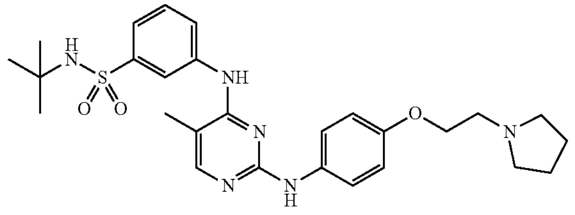

and a co-former X;

wherein:

X is selected from the group consisting of hydrobromic acid, sulfuric acid, toluenesulfonic acid, methanesulfonic acid, 2-naphthalenesulfonic acid, phosphoric acid, DL-tartaric acid, succinic acid, gentisic acid, hippuric acid, adipic acid, galactaric acid, naphthalene-1,5-disulfonic acid, (S)-camphor-10-sulfonic acid, ethane-1, 2-disulfonic acid, ethanesulfonic acid, benzenesulfonic acid, oxalic acid, maleic acid, pamoic acid, 1-hydroxy-2-naphthoic acid, malonic acid, L-tartaric acid, fumaric acid, citric acid, L-lactic acid, acetic acid, propionic acid, DL-lactic acid, D-gluconic acid, DL-malic acid, glutaric acid, camphoric acid, DL-mandelic acid, glutamic acid, glycolic acid, L-mandelic acid, L-malic acid, L-aspartic acid, benzoic acid, saccharin, nicotinic acid, ascorbic acid, gallic acid, salicylic acid, orotic acid, acetylsalicylic acid, choline, potassium hydroxide, and sodium hydroxide.

In some embodiments, the present disclosure provides a hydrate form of a complex comprising Compound 1:

1

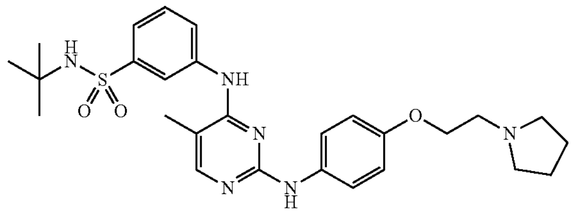

and a co-former X;

wherein:

X is selected from the group consisting of hydrobromic acid, sulfuric acid, toluenesulfonic acid, methanesulfonic acid, 2-naphthalenesulfonic acid, phosphoric acid, DL-tartaric acid, succinic acid, gentisic acid, hippuric acid, adipic acid, galactaric acid, naphthalene-1,5-disulfonic acid, (S)-camphor-10-sulfonic acid, ethane-1, 2-disulfonic acid, ethanesulfonic acid, benzenesulfonic acid, oxalic acid, maleic acid, pamoic acid, 1-hydroxy-2-naphthoic acid, malonic acid, L-tartaric acid, fumaric acid, citric acid, L-lactic acid, acetic acid, propionic acid, DL-lactic acid, D-gluconic acid, DL-malic acid, glutaric acid, camphoric acid, DL-mandelic acid, glutamic acid, glycolic acid, L-mandelic acid, L-malic acid, L-aspartic acid, benzoic acid, saccharin, nicotinic acid, ascorbic acid, gallic acid, salicylic acid, orotic acid, acetylsalicylic acid, choline, potassium hydroxide, and sodium hydroxide.

In some embodiments, the present disclosure provides a solvate form of a complex comprising Compound 1:

1

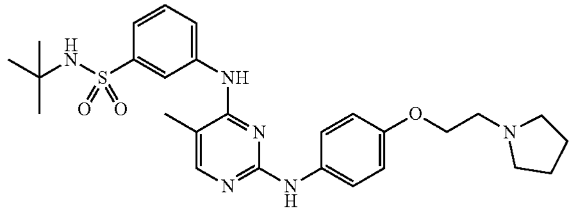

and a co-former X;

wherein:

X is selected from the group consisting of hydrobromic acid, sulfuric acid, toluenesulfonic acid, methanesulfonic acid, 2-naphthalenesulfonic acid, phosphoric acid, DL-tartaric acid, succinic acid, gentisic acid, hippuric acid, adipic acid, galactaric acid, naphthalene-1,5-disulfonic acid, (S)-camphor-10-sulfonic acid, ethane-1, 2-disulfonic acid, ethanesulfonic acid, benzenesulfonic acid, oxalic acid, maleic acid, pamoic acid, 1-hydroxy-2-naphthoic acid, malonic acid, L-tartaric acid, fumaric acid, citric acid, L-lactic acid, acetic acid, propionic acid, DL-lactic acid, D-gluconic acid, DL-malic acid, glutaric acid, camphoric acid, DL-mandelic acid, glutamic acid, glycolic acid, L-mandelic acid, L-malic acid, L-aspartic acid, benzoic acid, saccharin, nicotinic acid, ascorbic acid, gallic acid, salicylic acid, orotic acid, acetylsalicylic acid, choline, potassium hydroxide, and sodium hydroxide.

In some embodiments, the present disclosure provides a heterosolvate form of a complex comprising Compound 1:

1

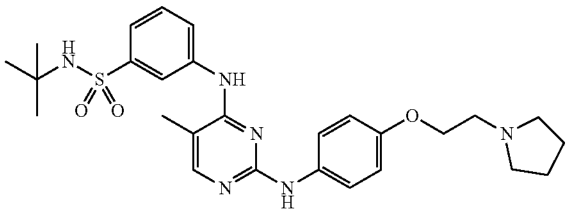

and a co-former X;

wherein:

X is selected from the group consisting of hydrobromic acid, sulfuric acid, toluenesulfonic acid, methanesulfonic acid, 2-naphthalenesulfonic acid, phosphoric acid, DL-tartaric acid, succinic acid, gentisic acid, hippuric acid, adipic acid, galactaric acid, naphthalene-1,5-disulfonic acid, (S)-camphor-10-sulfonic acid, ethane-1, 2-disulfonic acid, ethanesulfonic acid, benzenesulfonic acid, oxalic acid, maleic acid, pamoic acid, 1-hydroxy-2-naphthoic acid, malonic acid, L-tartaric acid, fumaric acid, citric acid, L-lactic acid, acetic acid, propionic acid, DL-lactic acid, D-gluconic acid, DL-malic acid, glutaric acid, camphoric acid, DL-mandelic acid, glutamic acid, glycolic acid, L-mandelic acid, L-malic acid, L-aspartic acid, benzoic acid, saccharin, nicotinic acid, ascorbic acid, gallic acid, salicylic acid, orotic acid, acetylsalicylic acid, choline, potassium hydroxide, and sodium hydroxide.

In some embodiments, the term "complex" is used herein to refer to a form comprising Compound 1 non-covalently associated with a co-former. Such non-covalent associations include, by way of example, ionic interactions, dipole-dipole interactions, π-stacking interactions, hydrogen bond interactions, etc.

It will be appreciated that the term "complex" encompasses salt forms resulting from an ionic interaction between Compound 1 and an acid or base, as well as non-ionic associations between Compound 1 and a neutral species.

In some embodiments, the term "complex" is used herein to refer to a form comprising Compound 1 ionically associated with a co-former. Accordingly, in some such embodiments, the term "complex" is used herein to refer to a salt comprising Compound 1 and an acid or a base.

In some embodiments, a "complex" is an inclusion complex, a salt form, a co-crystal, a clathrate, or hydrates and/or solvates thereof, etc. In some embodiments, the term "complex" is used to refer to a 1:1 (i.e., stoichiometric) ratio of Compound 1 and co-former. In some embodiments, the term "complex" does not necessarily indicate any particular ratio of Compound 1 to co-former. In some embodiments, a complex is a salt form, or a hydrate or solvate thereof. In some embodiments, a complex is a co-crystal form, or a hydrate or solvate thereof. In some embodiments, a complex is an inclusion complex, or a hydrate or solvate thereof. In some embodiments, a complex is a clathrate, or a hydrate or solvate thereof.

In some embodiments, co-former X and Compound 1 are ionically associated. In some embodiments, Compound 1 is non-covalently associated with co-former X.

A complex form of Compound 1 can exist in a variety of physical forms. For example, a complex form of Compound 1 can be in solution, suspension, or in solid form. In some embodiments, a complex form of Compound 1 is in solution form. In certain embodiments, a complex form of Compound 1 is in solid form. When a complex of Compound 1 is in solid form, said compound may be amorphous, crystalline, or a mixture thereof. In some embodiments, a complex form of Compound 1 is an amorphous solid. In some embodiments, a complex form of Compound 1 is a crystalline solid. Exemplary complex forms of Compound 1 are described in more detail below.

It will be appreciated that a complex comprising Compound 1 and a co-former X can comprise one equivalent of X. Accordingly, in some embodiments, complexes described herein comprise Compound 1 and one equivalent of X. In some embodiments, complexes described herein comprise Compound 1 and two equivalents of X. In some embodiments, complexes described herein comprise Compound 1 and three equivalents of X. In some embodiments, complexes described herein comprise Compound 1 and 0.5-2.5 equivalents of X (e.g., 0.5, 0.9, 1.2, 1.5, etc., equivalents of X).

In some embodiments, the present invention provides a sample comprising a complex form of Compound 1, wherein the sample is substantially free of impurities. In some embodiments, a sample comprising a complex form of Compound 1 is substantially free of any of excess co-former X, excess Compound 1, residual solvents, or any other impurities that may result from the preparation of, and/or isolation of, a complex form of Compound 1. In certain embodiments, the sample comprises at least about 90% by weight of a complex form of Compound 1. In certain embodiments, the sample comprises at least about 95% by weight of a complex form of Compound 1. In still other embodiments, the sample comprises at least about 99% by weight of a complex form of Compound 1.

According to some embodiments, the sample comprises at least about 95, 97, 97.5, 98.0, 98.5, 99, 99.5, 99.8 weight percent (wt %) of a complex form of Compound 1, where the percentages are based on the total weight of the sample. According to some embodiments, a sample comprising a complex form of Compound 1 comprises no more than about 5.0 percent of total organic impurities. In some embodiments, a sample comprising a complex form of Compound 1 comprises no more than about 3.0 percent of total organic impurities. In some embodiments, a sample comprising a complex form of Compound 1 comprises no more than about 1.5 percent of total organic impurities. In some embodiments, a sample comprising a complex form of Compound 1 comprises no more than about 1.0 percent of total organic impurities. In some embodiments, a sample comprising a complex form of Compound 1 comprises no more than about 0.6 percent of total organic impurities. In some embodiments, a sample comprising a complex form of Compound 1 comprises no more than about 0.5 percent of total organic impurities. In some embodiments, the percent of total organic impurities is measured by HPLC.

The structure depicted for a complex form of Compound 1 includes compounds that differ only in the presence of one or more isotopically enriched atoms. For example, compounds having the present structure except for the replacement of hydrogen by deuterium or tritium, or the replacement of a carbon by a $^{13}C$- or $^{14}C$-enriched carbon are within the scope of this invention.

In some embodiments, a complex form of Compound 1 is crystalline, wherein X is selected from the group consisting of hydrobromic acid, sulfuric acid, toluenesulfonic acid, methanesulfonic acid, 2-naphthalenesulfonic acid, phosphoric acid, DL-tartaric acid, succinic acid, gentisic acid, hippuric acid, adipic acid, galactaric acid, naphthalene-1,5-disulfonic acid, (S)-camphor-10-sulfonic acid, ethane-1,2-disulfonic acid, ethanesulfonic acid, benzenesulfonic acid, oxalic acid, maleic acid, pamoic acid, 1-hydroxy-2-naphthoic acid, malonic acid, L-tartaric acid, fumaric acid, citric acid, L-lactic acid, acetic acid, propionic acid, DL-lactic acid, D-gluconic acid, DL-malic acid, glutaric acid, camphoric acid, glycolic acid, L-malic acid, saccharin, nicotinic acid, ascorbic acid, gallic acid, salicylic acid, orotic acid, and acetylsalicylic acid.

In some embodiments, X is selected from the group consisting of 2-naphthalenesulfonic acid, succinic acid, gentisic acid, hippuric acid, adipic acid, galactaric acid, naphthalene-1,5-disulfonic acid, (S)-camphor-10-sulfonic acid, ethane-1,2-disulfonic acid, ethanesulfonic acid, benzenesulfonic acid, maleic acid, pamoic acid, 1-hydroxy-2-naphthoic acid, malonic acid, fumaric acid, L-lactic acid, propionic acid, DL-lactic acid, D-gluconic acid, DL-malic acid, glutaric acid, camphoric acid, glutamic acid, glycolic acid, L-malic acid, L-aspartic acid, benzoic acid, saccharin, nicotinic acid, ascorbic acid, gallic acid, salicylic acid, orotic acid, acetylsalicylic acid, and choline.

In some embodiments, X is selected from the group consisting of 2-naphthalenesulfonic acid, succinic acid, gentisic acid, hippuric acid, adipic acid, galactaric acid, naphthalene-1,5-disulfonic acid, (S)-camphor-10-sulfonic acid, ethane-1,2-disulfonic acid, ethanesulfonic acid, benzenesulfonic acid, maleic acid, pamoic acid, 1-hydroxy-2-naphthoic acid, malonic acid, fumaric acid, L-lactic acid, propionic acid, DL-lactic acid, D-gluconic acid, DL-malic acid, glutaric acid, camphoric acid, glycolic acid, L-malic acid, saccharin, nicotinic acid, ascorbic acid, gallic acid, salicylic acid, orotic acid, and acetylsalicylic acid.

In some embodiments of a complex form of Compound 1, X is hydrobromic acid. In some such embodiments, a complex form of Compound 1 is a hydrobromide salt. In some embodiments, a complex form of Compound 1 comprises one equivalent of hydrobromic acid. In some embodiments, a hydrobromide salt of Compound 1 is a crystalline hydrobromide salt. In some embodiments, a crystalline hydrobromide salt of Compound 1 is characterized by one or more peaks in its X-ray powder diffraction pattern selected from 9.3, 13.9, 16.6, 19.0 and 20.0±0.2 degrees 2θ. In some such embodiments, a complex form of Compound 1 is Form A hydrobromide salt.

In some embodiments, Form A hydrobromide salt is characterized by the following peaks in its X-ray powder diffraction pattern:

| Position ° 2θ ± 0.2 degrees | d-spacing [Å] | Height [cts] |
|---|---|---|
| 9.3 | 9.553 | 1045 |
| 12.6 | 7.052 | 604 |
| 13.9 | 6.371 | 11592 |
| 16.2 | 5.460 | 1922 |
| 16.6 | 5.354 | 1052 |
| 16.9 | 5.248 | 1422 |
| 17.4 | 5.088 | 848 |
| 17.8 | 4.990 | 1208 |
| 18.6 | 4.780 | 1929 |
| 19.0 | 4.664 | 3197 |
| 19.6 | 4.521 | 1183 |
| 20.0 | 4.431 | 1797 |
| 20.3 | 4.381 | 1077 |
| 20.9 | 4.253 | 2885 |
| 21.5 | 4.130 | 707 |
| 21.9 | 4.065 | 1369 |
| 23.5 | 3.779 | 1077 |
| 24.2 | 3.683 | 1832 |
| 24.6 | 3.623 | 636 |
| 25.4 | 3.500 | 4118 |
| 26.0 | 3.432 | 2147 |
| 26.3 | 3.393 | 732 |
| 26.8 | 3.331 | 748 |
| 27.2 | 3.273 | 7515 |
| 27.9 | 3.198 | 2238 |
| 29.0 | 3.083 | 1330 |
| 29.9 | 2.986 | 601 |
| 31.4 | 2.845 | 809 |

Figure 10:
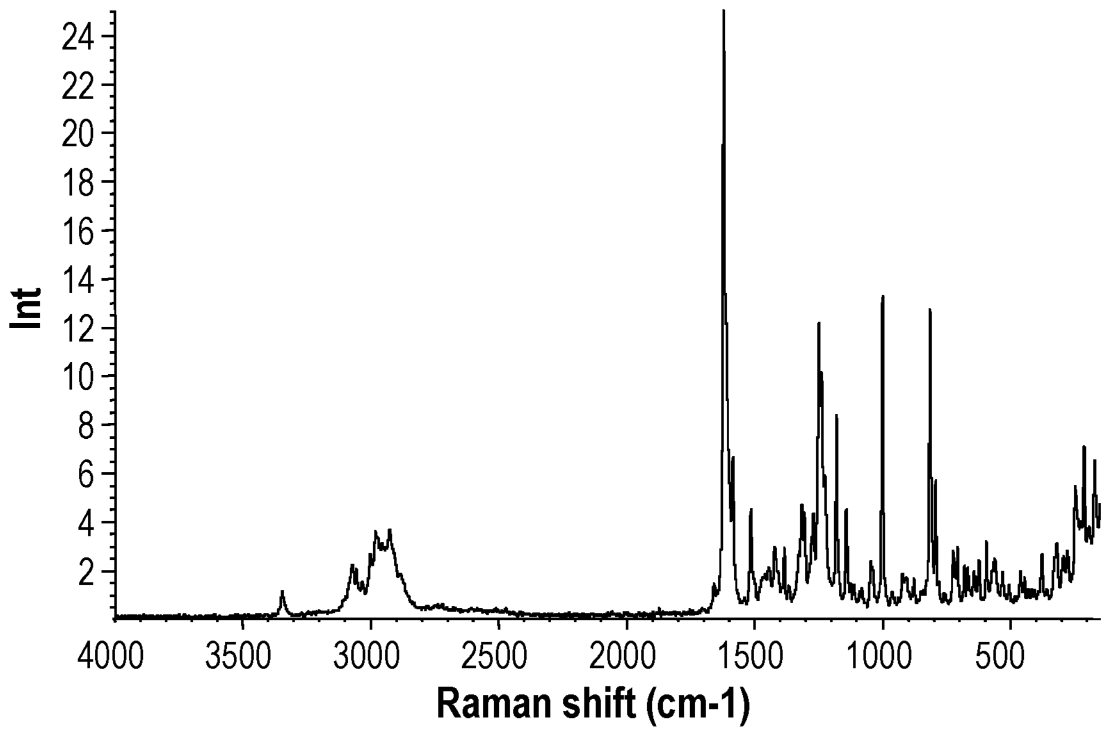
FIG. 10 depicts the FT-Raman spectrum of Form A hydrobromide salt of Compound 1.

In some embodiments, Form A hydrobromide salt is characterized by the FT-Raman spectrum depicted in FIG. 10.

Figure 11:
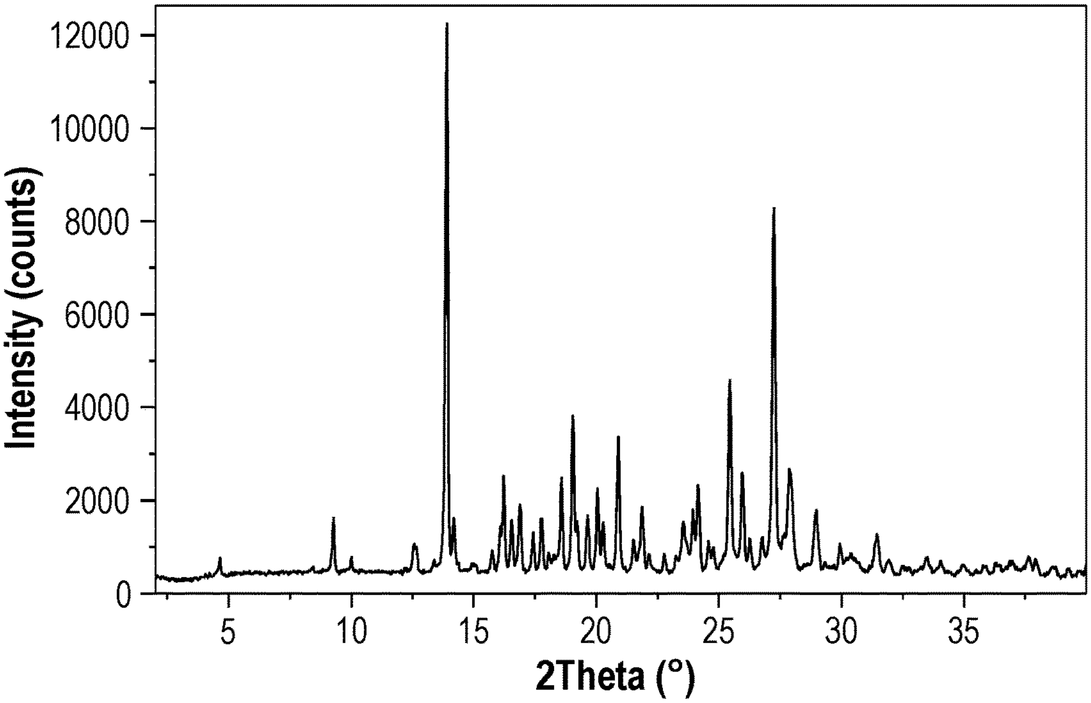
FIG. 11 depicts the XRPD pattern of Form A hydrobromide salt of Compound 1.

In some embodiments, Form A hydrobromide salt is characterized by the x-ray powder diffraction (XRPD) pattern depicted in FIG. 11.

Figure 12:
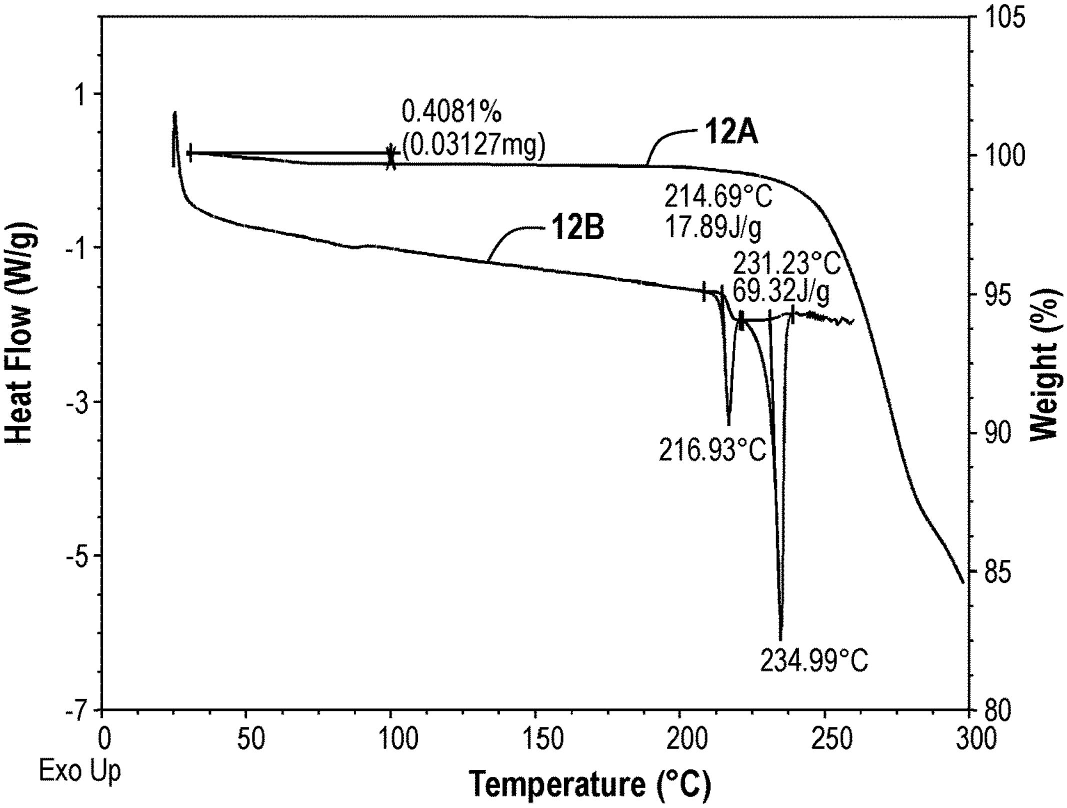
FIG. 12 depicts the TGA pattern of Form A hydrobromide salt of Compound 1 (12A), and the DSC pattern of Form A hydrobromide salt of Compound 1 (12B).

In some embodiments, Form A hydrobromide salt is characterized by the thermogravimetric analysis (TGA) pattern depicted in FIG. 12, trace 12A.

In some embodiments, Form A hydrobromide salt is characterized by the differential scanning calorimetry (DSC) pattern depicted in FIG. 12, trace 12B.

In some embodiments, a complex form of Compound 1 comprises two equivalents of hydrobromic acid. In some embodiments, a hydrobromide salt of Compound 1 is a hydrate. In some embodiments, a hydrate form of a hydrobromide salt of Compound 1 is a crystalline hydrate form of a hydrobromide salt. In some embodiments, a crystalline hydrate form of a hydrobromide salt of Compound 1 is characterized by one or more peaks in its X-ray powder diffraction pattern selected from 8.4, 9.8, 18.4, and 25.8±0.2 degrees 2θ. In some such embodiments, a complex form of Compound 1 is Form B hydrobromide salt.

In some embodiments, Form B hydrobromide salt is characterized by the following peaks in its X-ray powder diffraction pattern:

| Position ° 2θ ± 0.2 degrees | d-spacing [Å] | Height [cts] |
|---|---|---|
| 8.4 | 10.485 | 501 |
| 9.8 | 8.990 | 429 |
| 12.2 | 7.229 | 419 |

-continued

| Position ° 2θ ± 0.2 degrees | d-spacing [Å] | Height [cts] |
|---|---|---|
| 13.4 | 6.608 | 1155 |
| 15.8 | 5.616 | 2263 |
| 16.9 | 5.256 | 3329 |
| 17.4 | 5.083 | 4997 |
| 17.8 | 4.985 | 6598 |
| 18.4 | 4.823 | 823 |
| 19.7 | 4.505 | 727 |
| 21.5 | 4.125 | 3852 |
| 22.3 | 3.983 | 459 |
| 23.6 | 3.775 | 1559 |
| 23.9 | 3.725 | 1215 |
| 24.6 | 3.620 | 809 |
| 25.0 | 3.556 | 502 |
| 25.4 | 3.506 | 1351 |
| 25.8 | 3.456 | 1049 |
| 27.2 | 3.282 | 1188 |
| 27.7 | 3.226 | 522 |
| 28.1 | 3.179 | 469 |
| 28.8 | 3.103 | 482 |
| 29.4 | 3.040 | 648 |
| 30.2 | 2.963 | 653 |
| 31.2 | 2.871 | 800 |
| 31.4 | 2.849 | 597 |
| 34.1 | 2.632 | 1253 |
| 34.9 | 2.569 | 653 |
| 35.8 | 2.509 | 944 |
| 38.7 | 2.329 | 763 |

Figure 13:
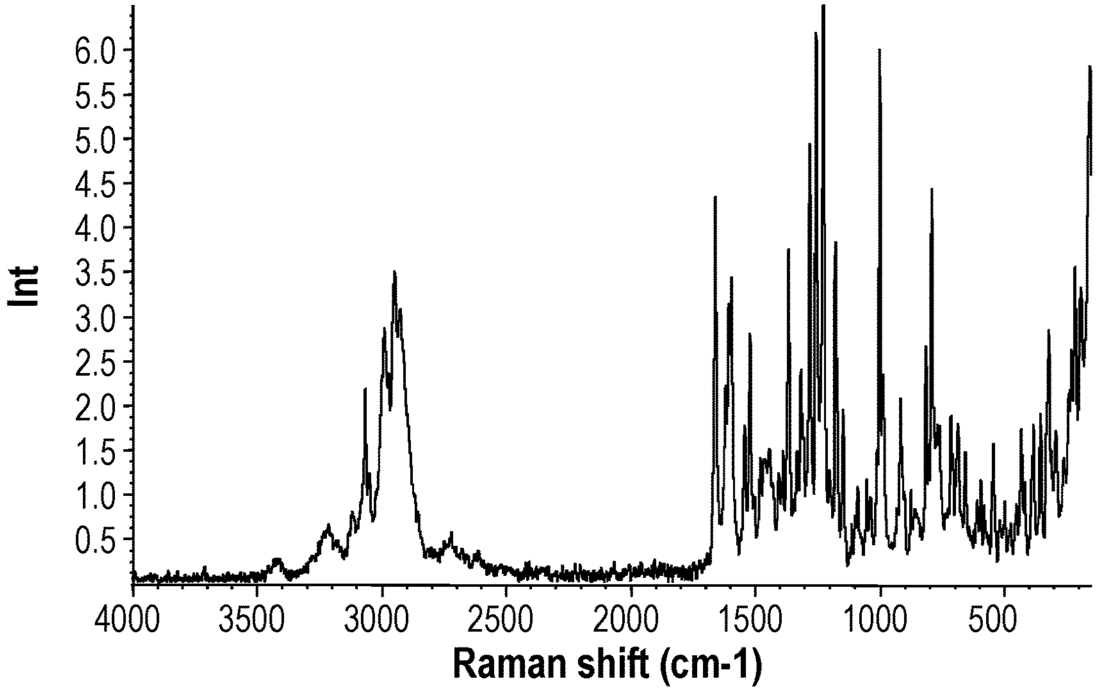
FIG. 13 depicts the FT-Raman spectrum of Form B hydrobromide salt of Compound 1.

In some embodiments, Form B hydrobromide salt is characterized by the FT-Raman spectrum depicted in FIG. 13.

Figure 14:
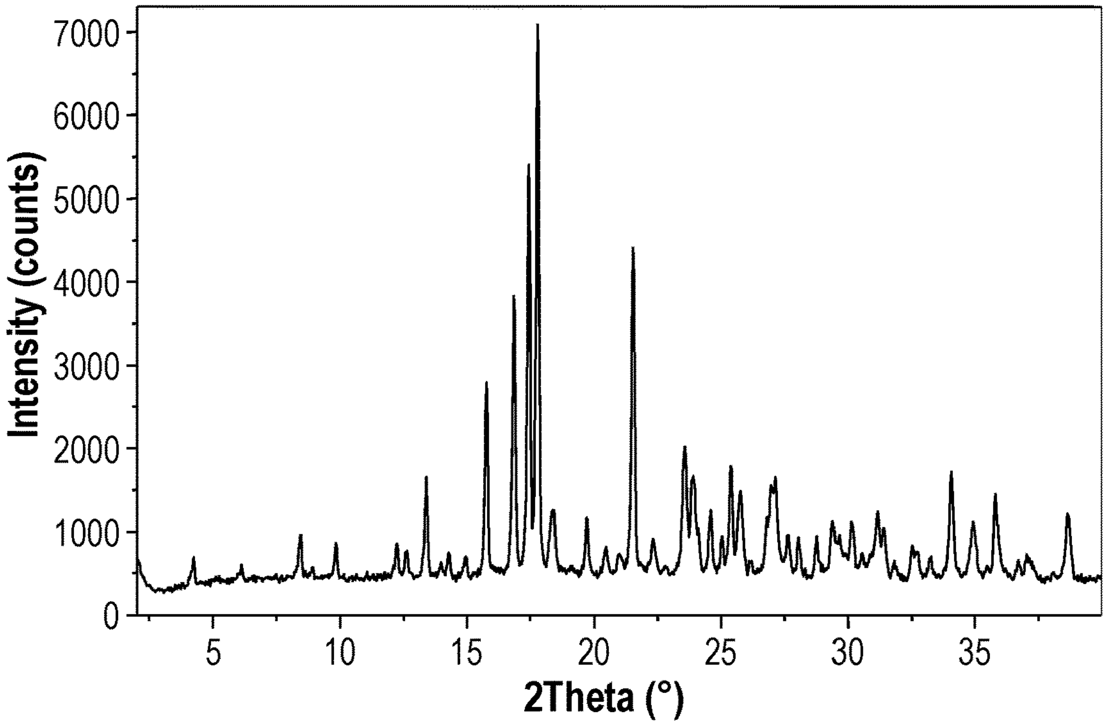
FIG. 14 depicts the XRPD pattern of Form B hydrobromide salt of Compound 1.

In some embodiments, Form B hydrobromide salt is characterized by the x-ray powder diffraction (XRPD) pattern depicted in FIG. 14.

Figure 15:
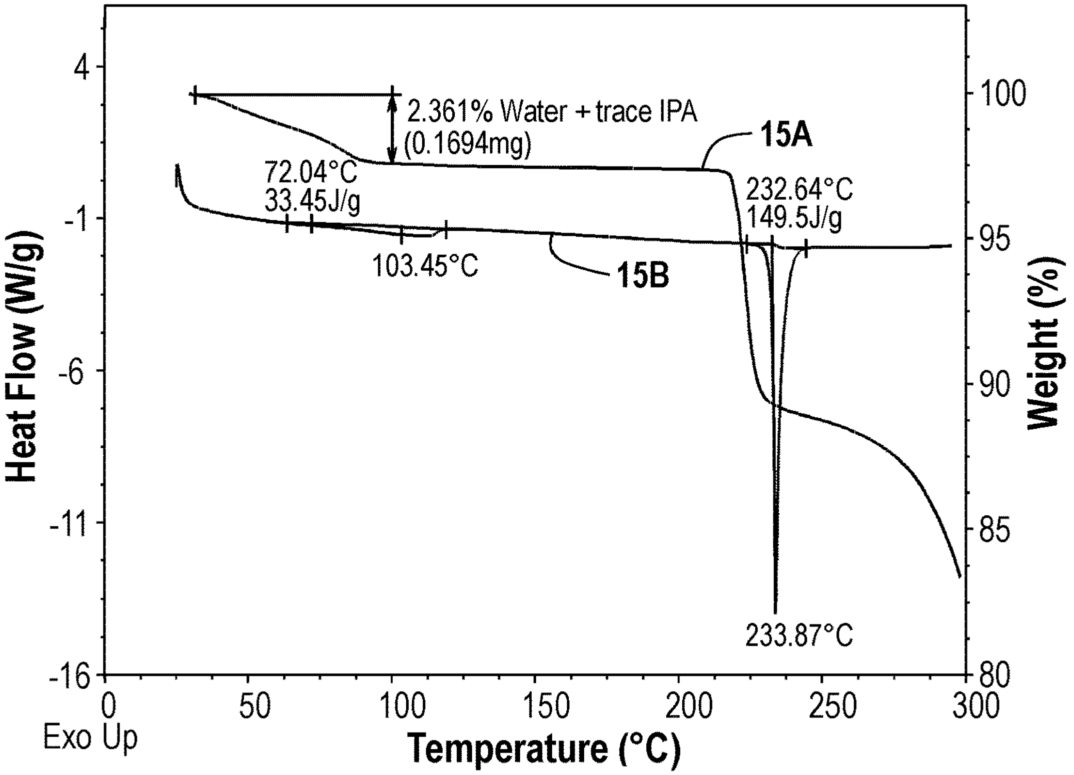
FIG. 15 depicts the TGA pattern of Form B hydrobromide salt of Compound 1 (15A), and the DSC pattern of Form B hydrobromide salt of Compound 1 (15B).

In some embodiments, Form B hydrobromide salt is characterized by the thermogravimetric analysis (TGA) pattern depicted in FIG. 15, trace 15A.

In some embodiments, Form B hydrobromide salt is characterized by the differential scanning calorimetry (DSC) pattern depicted in FIG. 15, trace 15B.

Figure 16:
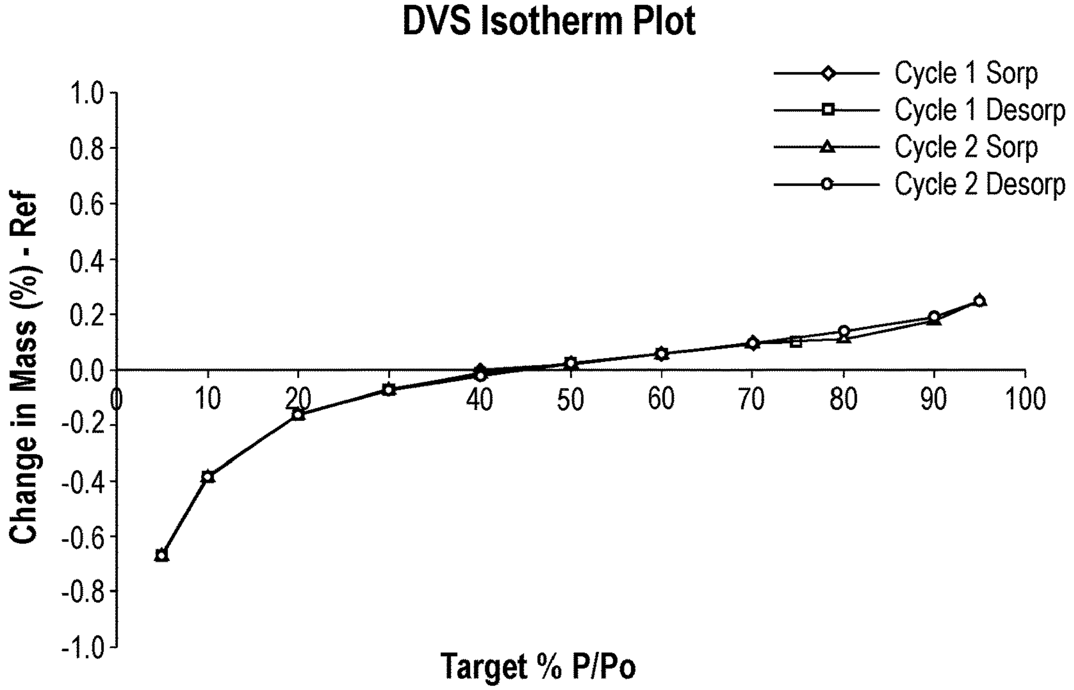
FIG. 16 depicts the dynamic vapor sorption (DVS) isotherm of Form B hydrobromide salt of Compound 1.

In some embodiments, Form B hydrobromide salt is characterized by the dynamic vapor sorption (DVS) isotherm depicted in FIG. 16.

In some embodiments of a complex form of Compound 1, X is sulfuric acid. In some such embodiments, a complex form of Compound 1 is a sulfate salt. In some embodiments, a sulfate salt of Compound 1 is a crystalline sulfate salt.

In some embodiments, a sulfate salt of Compound 1 is a hydrate. In some embodiments, a hydrate form of a sulfate salt of Compound 1 is a crystalline hydrate form of a sulfate salt. In some embodiments, a crystalline hydrate form of a sulfate salt of Compound 1 is characterized by one or more peaks in its X-ray powder diffraction pattern selected from 5.9, 7.4, 10.8, 11.8, 15.7, 17.1, and 17.7±0.2 degrees 2θ. In some such embodiments, a complex form of Compound 1 is Form A sulfate salt.

In some embodiments, Form A sulfate salt is characterized by the following peaks in its X-ray powder diffraction pattern:

| Position ° 2θ ± 0.2 degrees | d-spacing [Å] | Height [cts] |
|---|---|---|
| 5.9 | 14.964 | 521 |
| 7.4 | 11.907 | 303 |
| 8.0 | 10.991 | 390 |
| 10.0 | 8.860 | 559 |
| 10.8 | 8.215 | 471 |
| 11.8 | 7.503 | 2427 |
| 13.9 | 6.366 | 312 |
| 14.3 | 6.174 | 490 |
| 15.2 | 5.837 | 550 |
| 15.7 | 5.642 | 1321 |
| 16.1 | 5.522 | 994 |
| 16.4 | 5.408 | 655 |
| 17.1 | 5.176 | 1280 |
| 17.7 | 5.010 | 1379 |
| 18.4 | 4.833 | 548 |
| 18.9 | 4.699 | 374 |
| 19.6 | 4.540 | 438 |
| 20.3 | 4.380 | 289 |
| 21.2 | 4.188 | 1783 |
| 22.7 | 3.919 | 1034 |
| 23.2 | 3.839 | 809 |
| 23.8 | 3.746 | 416 |
| 24.2 | 3.680 | 443 |
| 24.9 | 3.579 | 646 |
| 25.5 | 3.488 | 707 |
| 26.5 | 3.366 | 263 |
| 29.8 | 3.000 | 279 |
| 31.8 | 2.817 | 296 |

Figure 18:
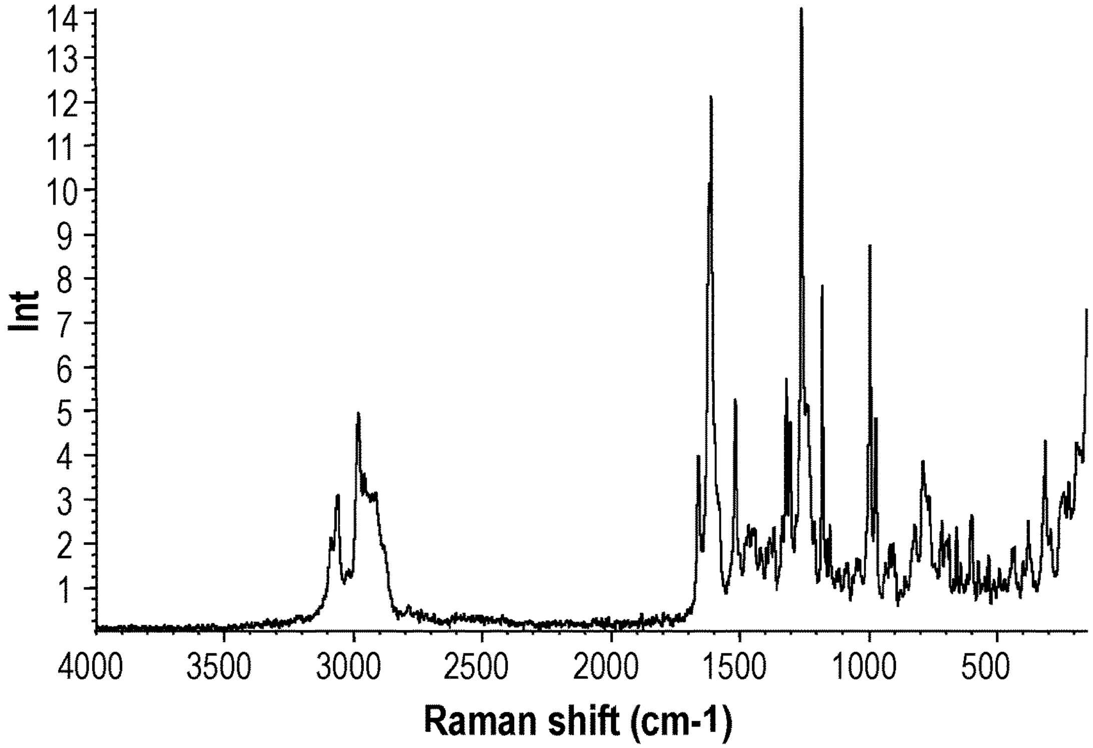
FIG. 18 depicts the FT-Raman spectrum of Form A sulfate salt of Compound 1.

In some embodiments, Form A sulfate salt is characterized by the FT-Raman spectrum depicted in FIG. 18.

Figure 19:
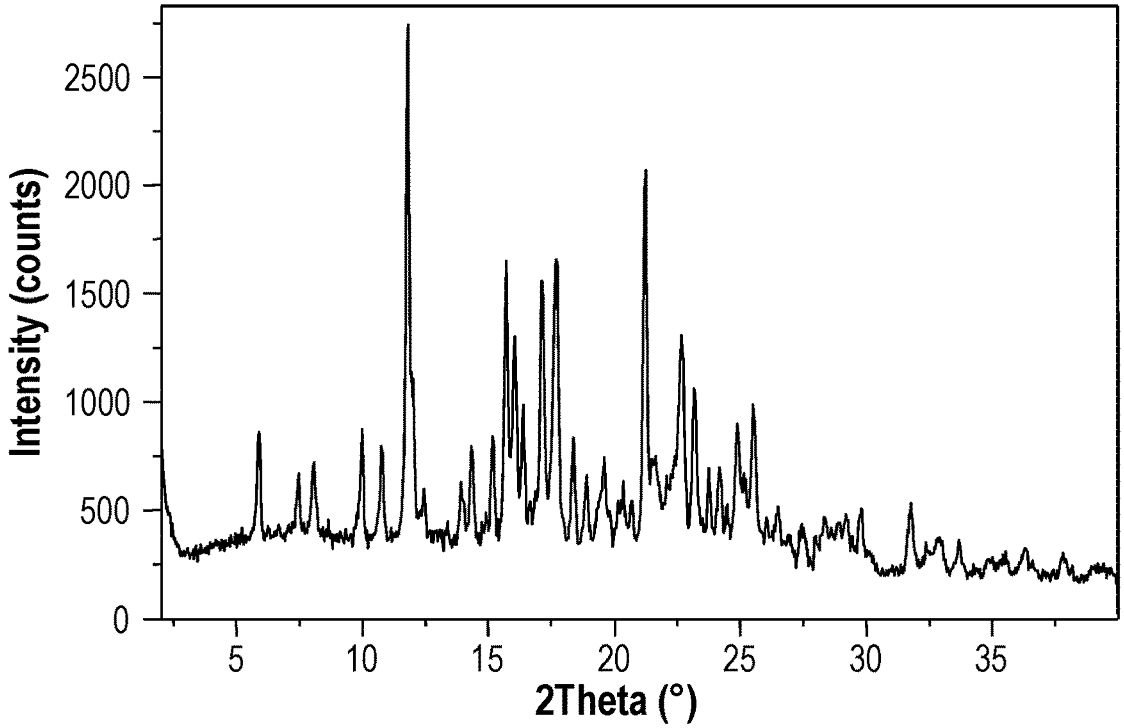
FIG. 19 depicts the XRPD pattern of Form A sulfate salt of Compound 1.

In some embodiments, Form A sulfate salt is characterized by the x-ray powder diffraction (XRPD) pattern depicted in FIG. 19.

Figure 20:
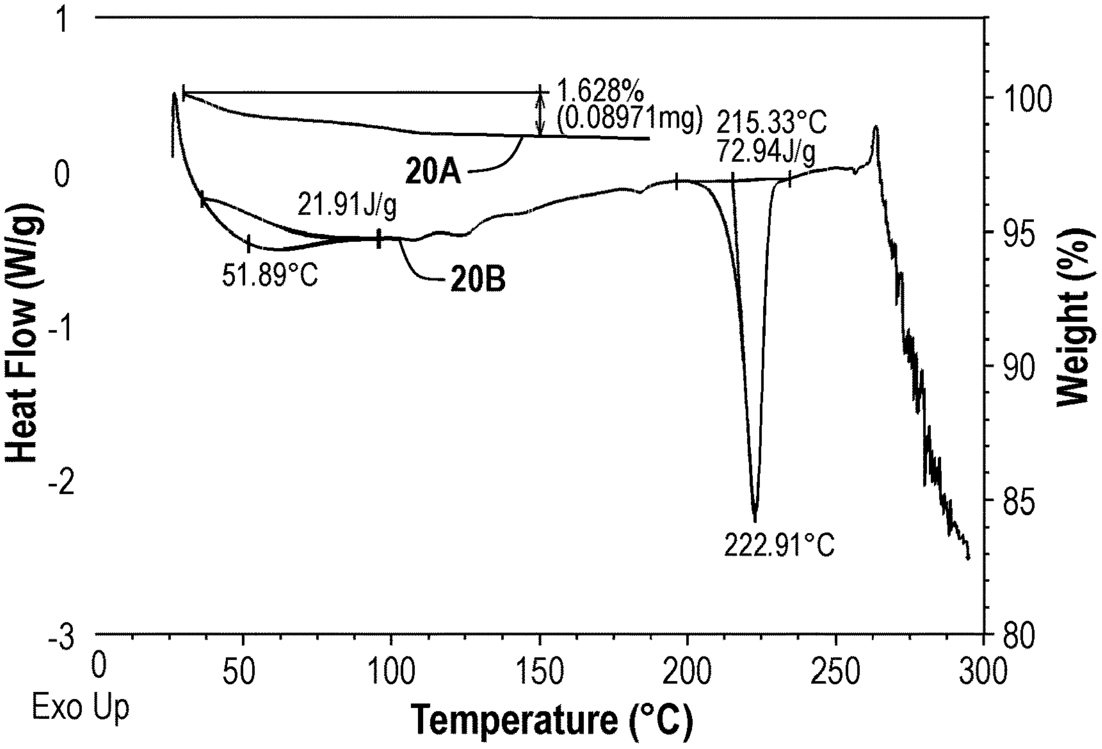
FIG. 20 depicts the TGA pattern of Form A sulfate salt of Compound 1 (20A), and the DSC pattern of Form A sulfate salt of Compound 1 (20B).

In some embodiments, Form A sulfate salt is characterized by the thermogravimetric analysis (TGA) pattern depicted in FIG. 20, trace 20A.

In some embodiments, Form A sulfate salt is characterized by the differential scanning calorimetry (DSC) pattern depicted in FIG. 20, trace 20B.

In some embodiments, a sulfate salt of Compound 1 is a heterosolvate. In some such embodiments, a heterosolvate form of a sulfate salt of Compound 1 is a water:tetrahydrofuran heterosolvate. In some embodiments, a water:tetrahydrofuran heterosolvate form of a sulfate salt of Compound 1 is a crystalline water:tetrahydrofuran heterosolvate form of a sulfate salt. In some embodiments, a crystalline water:tetrahydrofuran heterosolvate form of a sulfate salt of Compound 1 is characterized by one or more peaks in its X-ray powder diffraction pattern selected from 5.3, 6.9, 7.5, 10.5, 18.1, and 18.8±0.2 degrees 2θ. In some such embodiments, a complex form of Compound 1 is Form B sulfate salt.

In some embodiments, Form B sulfate salt is characterized by the following peaks in its X-ray powder diffraction pattern:

| Position ° 2θ ± 0.2 degrees | d-spacing [Å] | Height [cts] |
|---|---|---|
| 5.3 | 16.694 | 1898 |
| 6.9 | 12.877 | 210 |
| 7.5 | 11.754 | 400 |
| 10.0 | 8.834 | 665 |
| 10.5 | 8.408 | 2928 |
| 13.9 | 6.359 | 364 |
| 15.2 | 5.835 | 474 |
| 15.9 | 5.560 | 901 |

-continued

| Position ° 2θ ± 0.2 degrees | d-spacing [Å] | Height [cts] |
|---|---|---|
| 17.3 | 5.132 | 371 |
| 18.1 | 4.900 | 750 |
| 18.8 | 4.732 | 898 |
| 19.1 | 4.649 | 580 |
| 20.4 | 4.344 | 707 |
| 21.1 | 4.210 | 569 |
| 22.0 | 4.043 | 528 |
| 22.4 | 3.967 | 739 |
| 23.7 | 3.762 | 762 |
| 25.5 | 3.496 | 725 |
| 26.3 | 3.391 | 622 |
| 29.0 | 3.077 | 483 |
| 31.2 | 2.865 | 54 |
| 32.9 | 2.722 | 93 |

Figure 21:
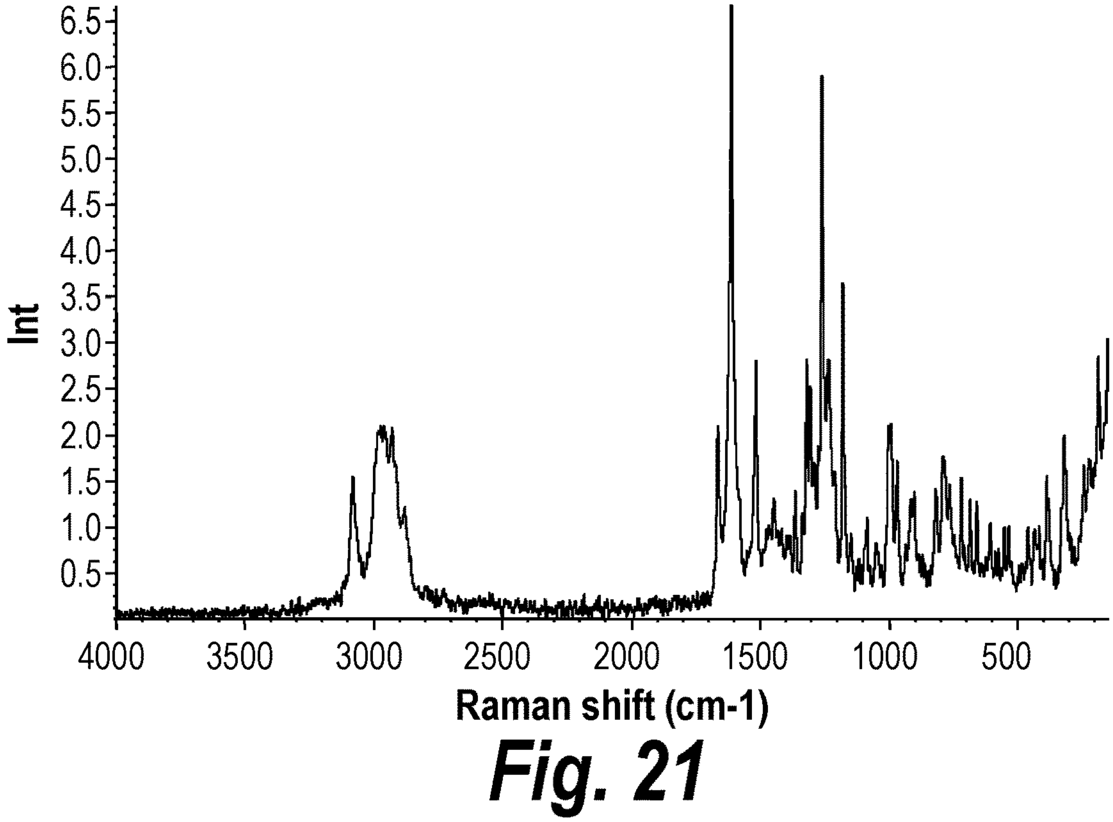
FIG. 21 depicts the FT-Raman spectrum of Form B sulfate salt of Compound 1.

In some embodiments, Form B sulfate salt is characterized by the FT-Raman spectrum depicted in FIG. 21.

Figure 22:
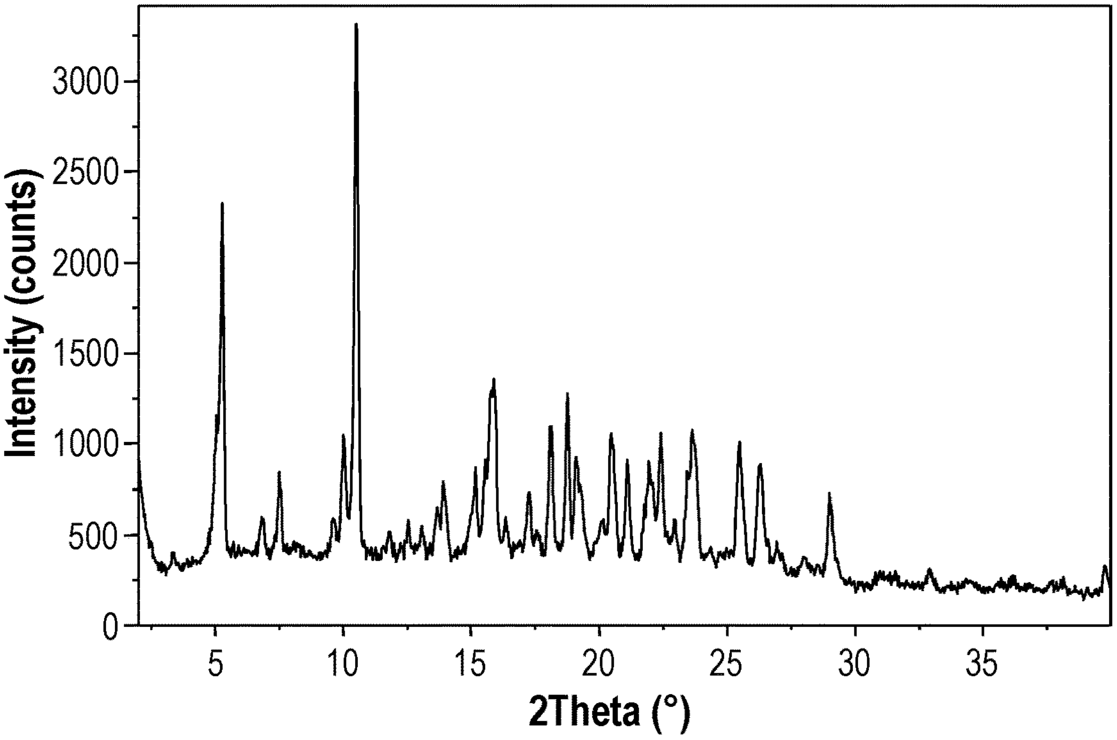
FIG. 22 depicts the XRPD pattern of Form B sulfate salt of Compound 1.

In some embodiments, Form B sulfate salt is characterized by the x-ray powder diffraction (XRPD) pattern depicted in FIG. 22.

Figure 23:
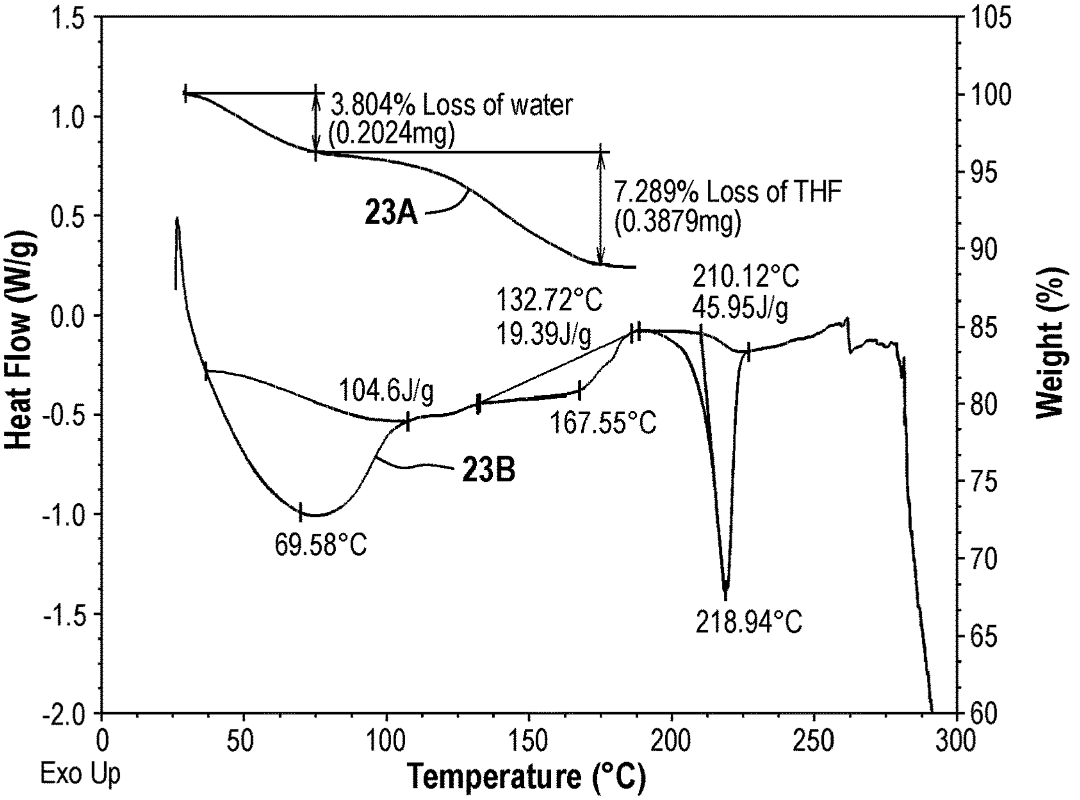
FIG. 23 depicts the TGA pattern of Form B sulfate salt of Compound 1 (23A), and the DSC pattern of Form B sulfate salt of Compound 1 (23B).

In some embodiments, Form B sulfate salt is characterized by the thermogravimetric analysis (TGA) pattern depicted in FIG. 23, trace 23A.

In some embodiments, Form B sulfate salt is characterized by the differential scanning calorimetry (DSC) pattern depicted in FIG. 23, trace 23B.

In some embodiments, a crystalline sulfate salt of Compound 1 is characterized by one or more peaks in its X-ray powder diffraction pattern selected from 6.1, 6.5, and 7.1±0.2 degrees 2θ. In some such embodiments, a complex form of Compound 1 is Form C sulfate salt.

In some embodiments, Form C sulfate salt is characterized by the following peaks in its X-ray powder diffraction pattern:

| Position ° 2θ ± 0.2 degrees | d-spacing [Å] | Height [cts] |
|---|---|---|
| 6.1 | 14.499 | 278 |
| 6.5 | 13.627 | 281 |
| 7.1 | 12.487 | 773 |
| 8.3 | 10.592 | 294 |
| 9.3 | 9.523 | 332 |
| 10.0 | 8.873 | 347 |
| 10.8 | 8.221 | 751 |
| 11.2 | 7.867 | 356 |
| 11.6 | 7.616 | 324 |
| 12.2 | 7.262 | 527 |
| 12.6 | 7.032 | 318 |
| 13.0 | 6.829 | 546 |
| 13.6 | 6.503 | 365 |
| 14.5 | 6.121 | 410 |
| 15.0 | 5.902 | 328 |
| 15.4 | 5.746 | 444 |
| 16.4 | 5.405 | 559 |
| 16.8 | 5.272 | 538 |
| 18.3 | 4.840 | 326 |
| 19.0 | 4.665 | 826 |
| 19.6 | 4.524 | 1387 |
| 20.2 | 4.398 | 470 |
| 20.8 | 4.268 | 626 |
| 21.0 | 4.225 | 645 |
| 21.8 | 4.078 | 641 |
| 22.2 | 3.997 | 614 |
| 23.4 | 3.803 | 1045 |
| 24.0 | 3.707 | 402 |
| 24.7 | 3.599 | 594 |

-continued

| Position ° 2θ ± 0.2 degrees | d-spacing [Å] | Height [cts] |
|---|---|---|
| 25.2 | 3.530 | 580 |
| 25.6 | 3.475 | 486 |
| 26.3 | 3.391 | 591 |
| 27.0 | 3.304 | 621 |

Figure 24:
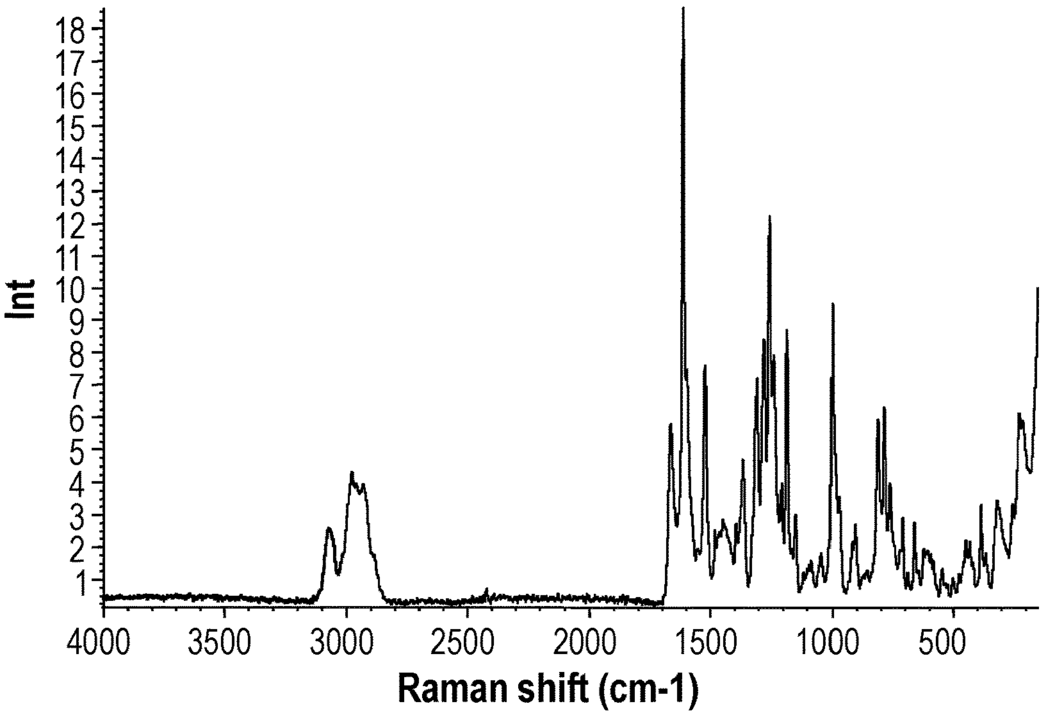
FIG. 24 depicts the FT-Raman spectrum of Form C sulfate salt of Compound 1.

In some embodiments, Form C sulfate salt is characterized by the FT-Raman spectrum depicted in FIG. 24.

Figure 25:
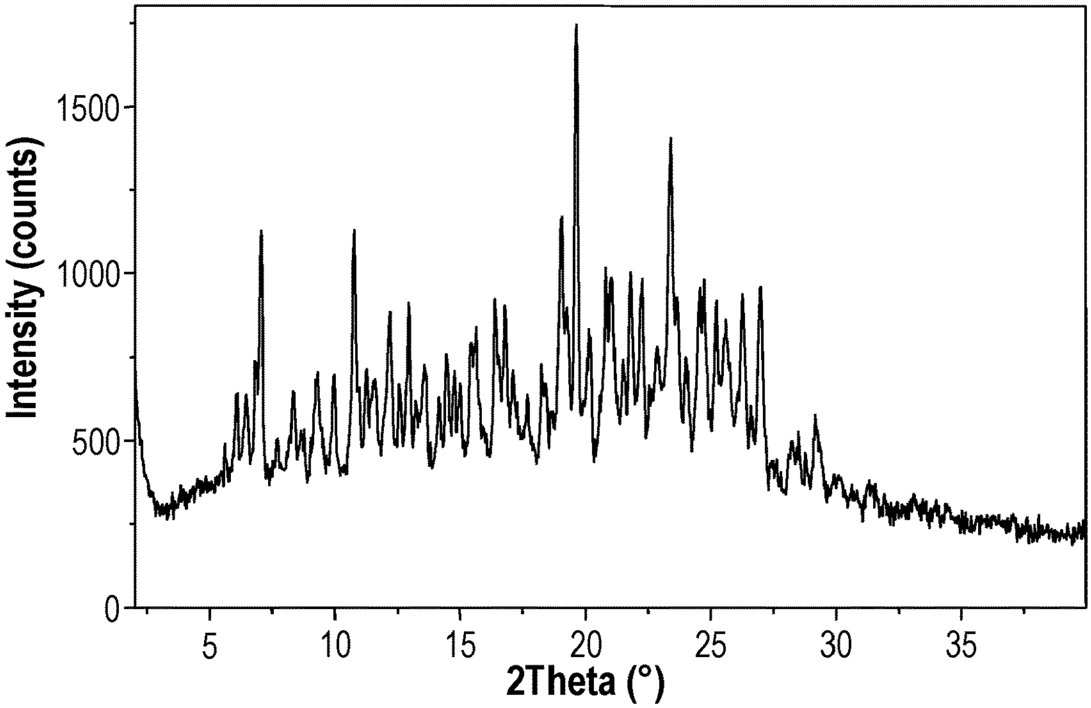
FIG. 25 depicts the XRPD pattern of Form C sulfate salt of Compound 1.

In some embodiments, Form C sulfate salt is characterized by the x-ray powder diffraction (XRPD) pattern depicted in FIG. 25.

Figure 26:
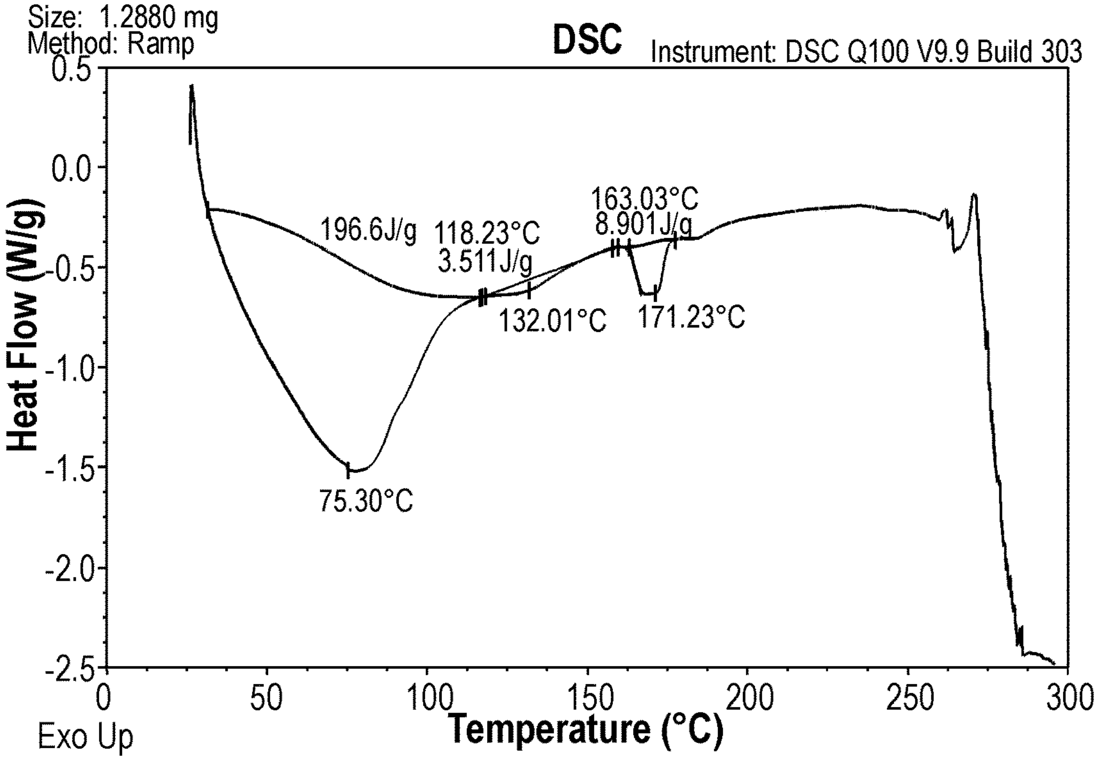
FIG. 26 depicts the DSC pattern of Form C sulfate salt of Compound 1.

In some embodiments, Form C sulfate salt is characterized by the differential scanning calorimetry (DSC) pattern depicted in FIG. 26.

In some embodiments, a complex form of Compound 1 comprises 0.5 equivalents of sulfuric acid. In some embodiments, a sulfate salt of Compound 1 is a solvate. In some embodiments, a solvate form of a sulfate salt of Compound 1 is an acetone solvate. In some such embodiments, a solvate form of a sulfate salt of Compound 1 is a bis-acetone solvate. In some embodiments, a bis-acetone solvate form of a sulfate salt of Compound 1 is a crystalline bis-acetone solvate form of a sulfate salt. In some embodiments, a crystalline bis-acetone solvate form of a sulfate salt of Compound 1 is characterized by one or more peaks in its X-ray powder diffraction pattern selected from 6.9, 11.6, 12.1, 16.4, 16.9, and 18.8±0.2 degrees 2θ. In some such embodiments, a complex form of Compound 1 is Form D sulfate salt.

In some embodiments, Form D sulfate salt is characterized by the following peaks in its X-ray powder diffraction pattern:

| Position ° 2θ ± 0.2 degrees | d-spacing [Å] | Height [cts] |
|---|---|---|
| 6.9 | 12.826 | 478 |
| 8.1 | 10.898 | 3000 |
| 10.0 | 8.835 | 1906 |
| 11.6 | 7.641 | 2009 |
| 12.1 | 7.324 | 2866 |
| 12.7 | 6.979 | 791 |
| 15.1 | 5.871 | 566 |
| 16.0 | 5.542 | 848 |
| 16.4 | 5.391 | 2833 |
| 16.9 | 5.231 | 1708 |
| 18.0 | 4.930 | 1291 |
| 18.8 | 4.719 | 8621 |
| 19.4 | 4.570 | 1096 |
| 19.8 | 4.477 | 1406 |
| 20.6 | 4.306 | 608 |
| 21.5 | 4.125 | 707 |
| 21.9 | 4.063 | 1120 |
| 22.8 | 3.908 | 863 |
| 23.3 | 3.817 | 439 |
| 23.9 | 3.728 | 2467 |
| 24.2 | 3.672 | 1929 |
| 24.8 | 3.596 | 4801 |
| 26.9 | 3.314 | 1273 |
| 28.6 | 3.119 | 262 |
| 31.4 | 2.852 | 132 |
| 32.7 | 2.738 | 295 |

Figure 27:
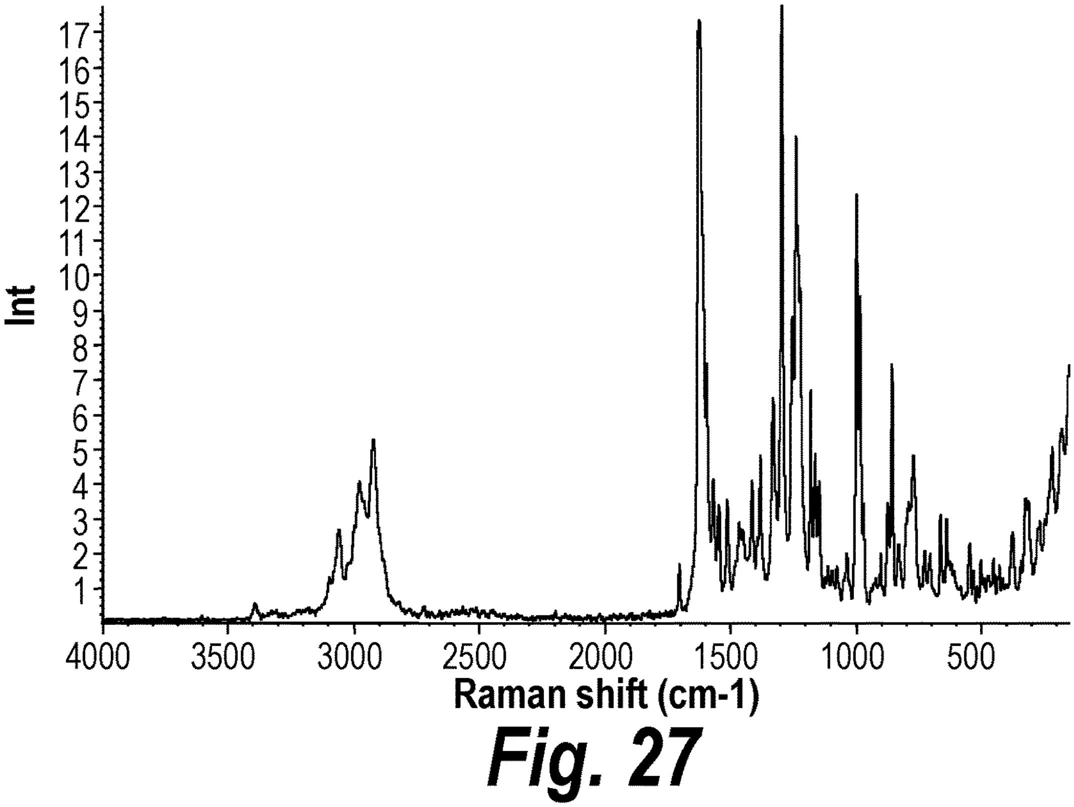
FIG. 27 depicts the FT-Raman spectrum of Form D sulfate salt of Compound 1.

In some embodiments, Form D sulfate salt is characterized by the FT-Raman spectrum depicted in FIG. 27.

Figure 28:
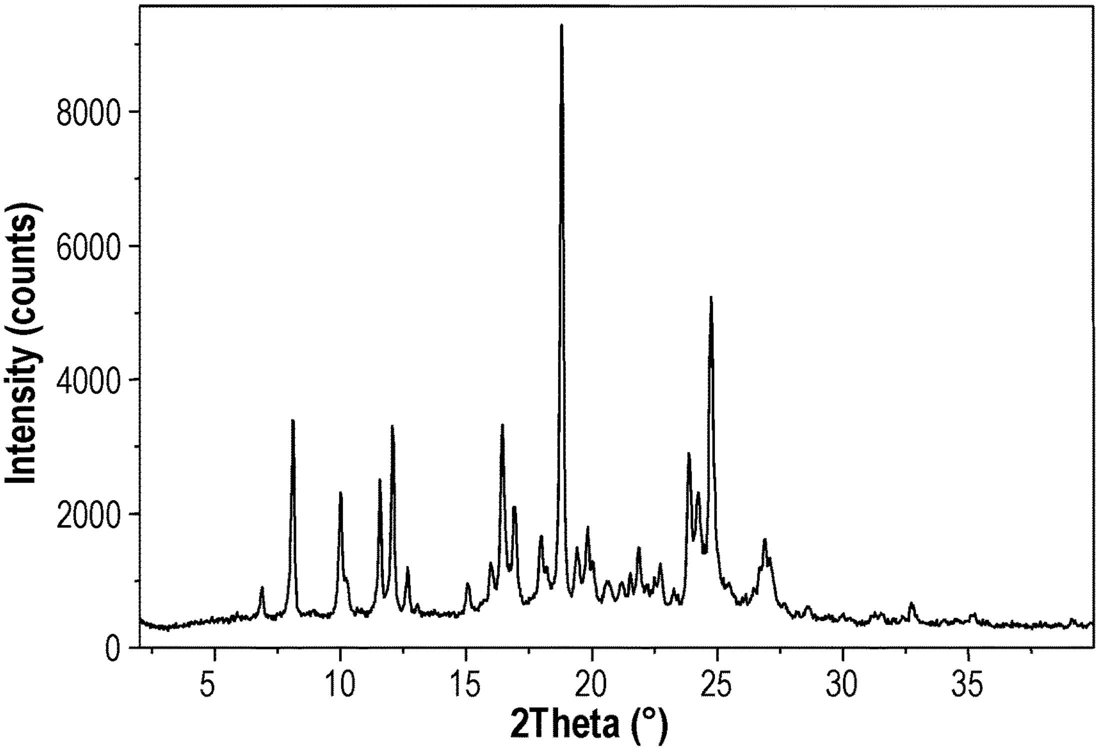
FIG. 28 depicts the XRPD pattern of Form D sulfate salt of Compound 1.

In some embodiments, Form D sulfate salt is characterized by the x-ray powder diffraction (XRPD) pattern depicted in FIG. 28.

Figure 29:
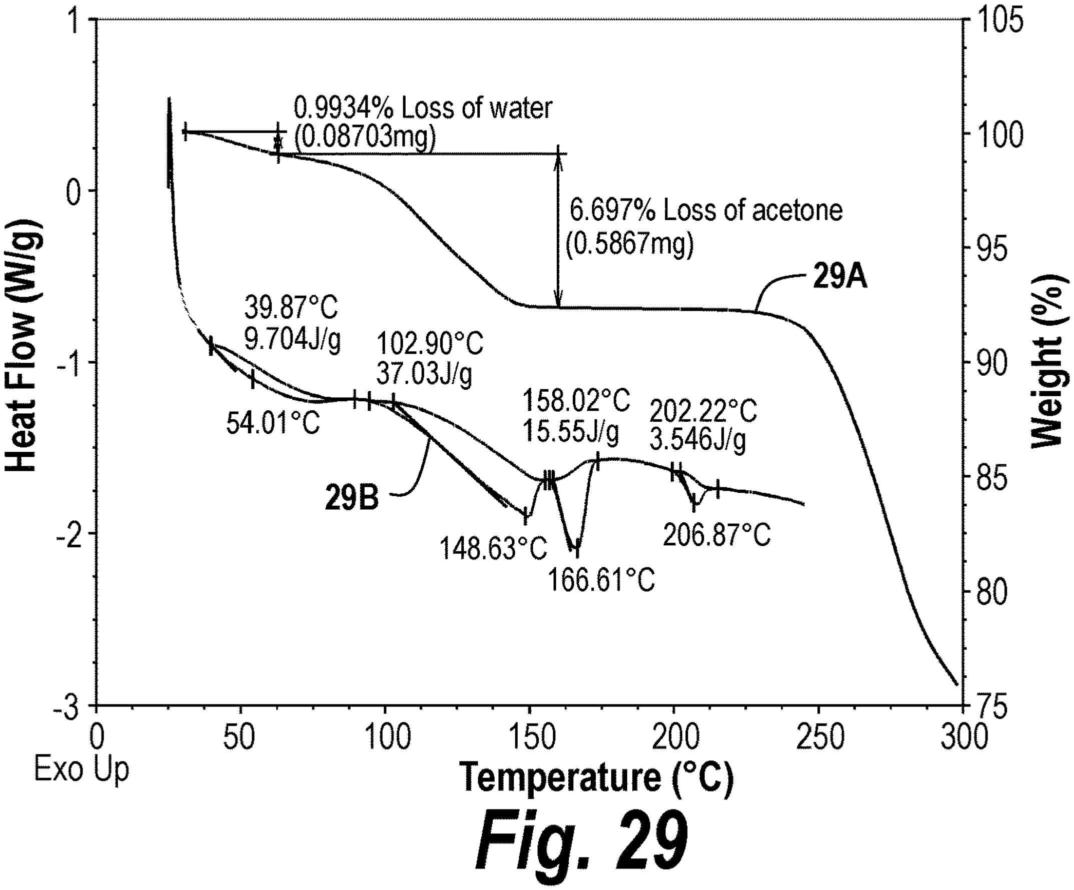
FIG. 29 depicts the TGA pattern of Form D sulfate salt of Compound 1 (29A), and the DSC pattern of Form D sulfate salt of Compound 1 (29B).

In some embodiments, Form D sulfate salt is characterized by the thermogravimetric analysis (TGA) pattern depicted in FIG. 29, trace 29A.

In some embodiments, Form D sulfate salt is characterized by the differential scanning calorimetry (DSC) pattern depicted in FIG. 29, trace 29B.

In some embodiments of a complex form of Compound 1, X is p-toluenesulfonic acid. In some such embodiments, a complex form of Compound 1 is a p-toluenesulfonate salt (also referred to as a "tosylate" salt). In some embodiments, a tosylate salt of Compound 1 is a crystalline tosylate salt.

In some embodiments, a crystalline tosylate salt of Compound 1 is characterized by one or more peaks in its X-ray powder diffraction pattern selected from 4.3, 7.1, 8.6, 9.3, 17.2, and 17.8±0.2 degrees 2θ. In some such embodiments, a complex form of Compound 1 is Form A tosylate salt.

In some embodiments, Form A tosylate salt is characterized by the following peaks in its X-ray powder diffraction pattern:

| Position ° 2θ ± 0.2 degrees | d-spacing [Å] | Height [cts] |
|---|---|---|
| 4.3 | 20.495 | 1088 |
| 7.1 | 12.517 | 1173 |
| 8.6 | 10.301 | 1772 |
| 9.3 | 9.460 | 727 |
| 11.3 | 7.858 | 435 |
| 11.8 | 7.517 | 587 |
| 12.8 | 6.896 | 536 |
| 13.7 | 6.482 | 284 |
| 14.1 | 6.262 | 505 |
| 14.7 | 6.044 | 434 |
| 15.5 | 5.708 | 412 |
| 16.9 | 5.251 | 631 |
| 17.2 | 5.155 | 2517 |
| 17.8 | 4.988 | 2650 |
| 19.9 | 4.463 | 2733 |
| 20.3 | 4.384 | 1692 |
| 21.3 | 4.173 | 299 |
| 21.9 | 4.051 | 467 |
| 22.4 | 3.973 | 588 |
| 22.6 | 3.934 | 582 |
| 23.0 | 3.866 | 404 |
| 23.9 | 3.730 | 616 |
| 25.1 | 3.553 | 832 |
| 26.6 | 3.357 | 319 |
| 27.2 | 3.274 | 189 |
| 28.6 | 3.126 | 101 |
| 30.4 | 2.942 | 168 |
| 32.3 | 2.773 | 99 |

Figure 30:
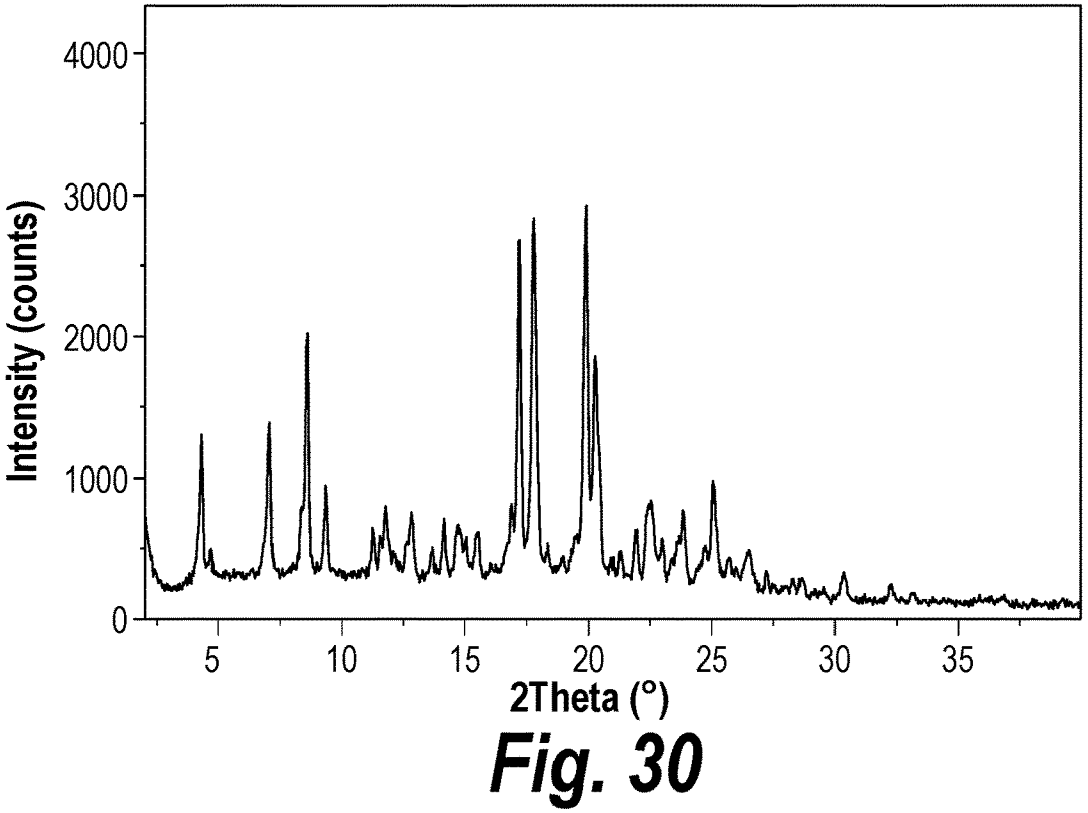
FIG. 30 depicts the XRPD pattern of Form A tosylate salt of Compound 1.

In some embodiments, Form A tosylate salt is characterized by the x-ray powder diffraction (XRPD) pattern depicted in FIG. 30.

Figure 31:
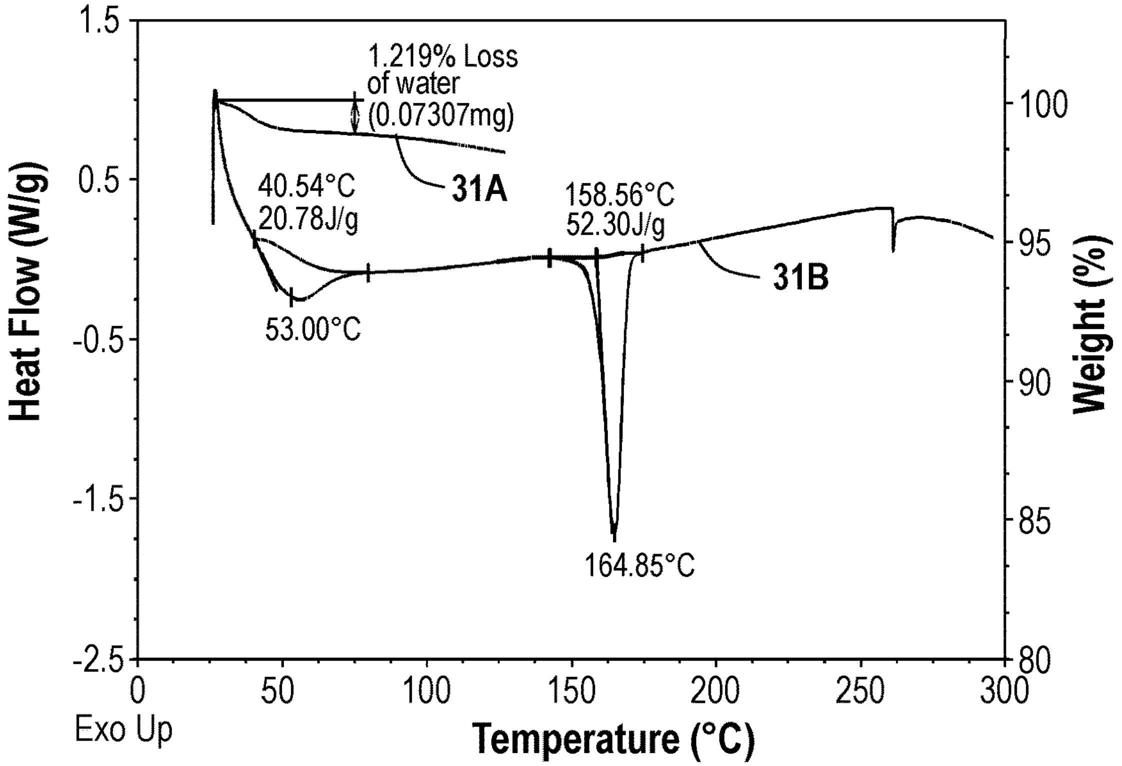
FIG. 31 depicts the TGA pattern of Form A tosylate salt of Compound 1 (31A), and the DSC pattern of Form A tosylate salt of Compound 1 (31B).

In some embodiments, Form A tosylate salt is characterized by the thermogravimetric analysis (TGA) pattern depicted in FIG. 31, trace 31A.

In some embodiments, Form A tosylate salt is characterized by the differential scanning calorimetry (DSC) pattern depicted in FIG. 31, trace 31B.

In some embodiments, a crystalline tosylate salt of Compound 1 is characterized by one or more peaks in its X-ray powder diffraction pattern selected from 5.5, 9.3, 11.0, 15.2, 15.7, and 16.5±0.2 degrees 2θ. In some such embodiments, a complex form of Compound 1 is Form B tosylate salt.

In some embodiments, Form B tosylate salt is characterized by the following peaks in its X-ray powder diffraction pattern:

| Position ° 2θ ± 0.2 degrees | d-spacing [Å] | Height [cts] |
|---|---|---|
| 5.5 | 16.054 | 285 |
| 9.3 | 9.510 | 762 |
| 11.0 | 8.022 | 2884 |
| 13.7 | 6.471 | 369 |
| 15.2 | 5.834 | 705 |
| 15.7 | 5.649 | 242 |
| 16.5 | 5.366 | 419 |
| 18.0 | 4.942 | 981 |
| 18.9 | 4.701 | 904 |
| 19.9 | 4.465 | 881 |
| 20.4 | 4.348 | 600 |
| 21.0 | 4.236 | 498 |
| 21.3 | 4.163 | 692 |
| 22.5 | 3.948 | 342 |
| 23.7 | 3.754 | 1029 |
| 24.9 | 3.582 | 812 |
| 26.5 | 3.370 | 527 |
| 27.8 | 3.212 | 151 |
| 30.1 | 2.972 | 73 |
| 32.1 | 2.790 | 106 |
| 33.2 | 2.695 | 116 |
| 38.6 | 2.335 | 58 |

Figure 32:
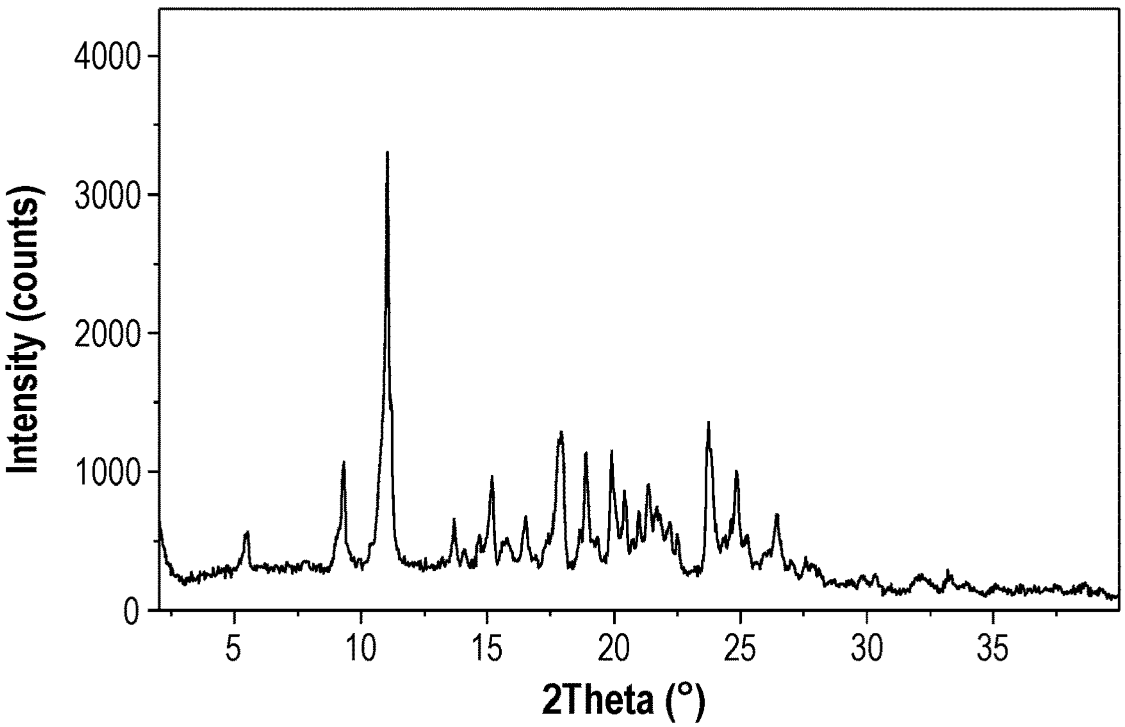
FIG. 32 depicts the XRPD pattern of Form B tosylate salt of Compound 1.

In some embodiments, Form B tosylate salt is characterized by the x-ray powder diffraction (XRPD) pattern depicted in FIG. 32.

Figure 33:
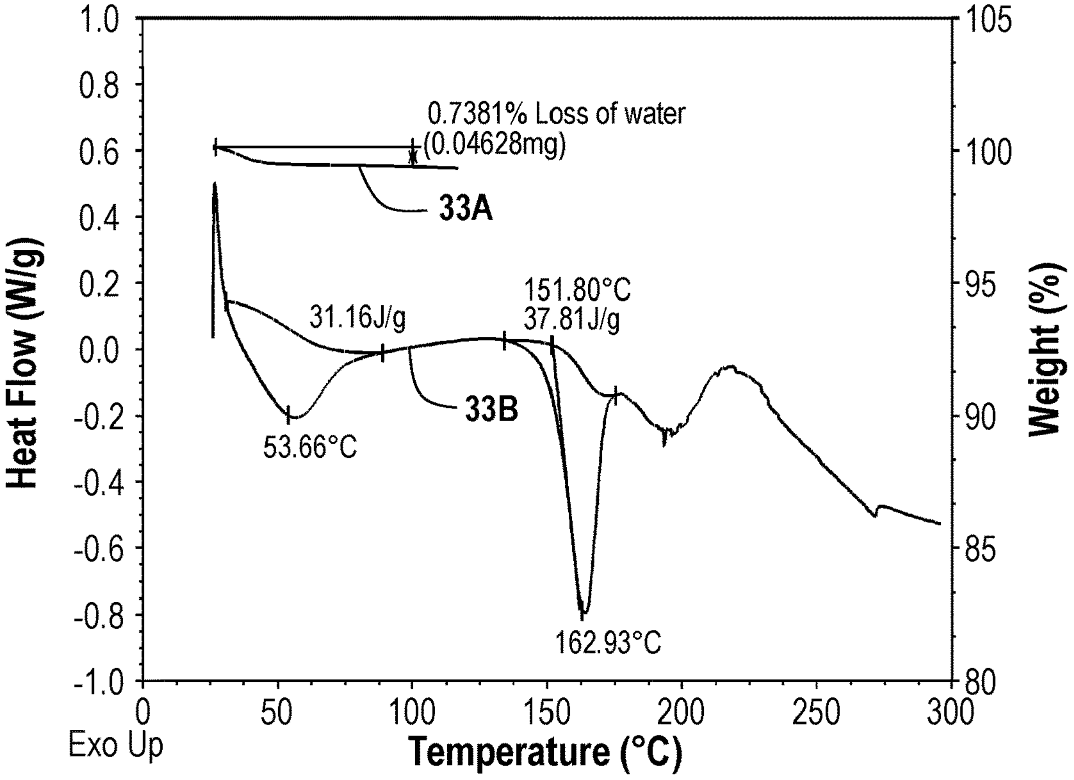
FIG. 33 depicts the TGA pattern of Form B tosylate salt of Compound 1 (33A), and the DSC pattern of Form B tosylate salt of Compound 1 (33B).

In some embodiments, Form B tosylate salt is characterized by the thermogravimetric analysis (TGA) pattern depicted in FIG. 33, trace 33A.

In some embodiments, Form B tosylate salt is characterized by the differential scanning calorimetry (DSC) pattern depicted in FIG. 33, trace 33B.

In some embodiments, a complex form of Compound 1 comprises one equivalent of p-toluenesulfonic acid. In some embodiments, a crystalline tosylate salt of Compound 1 is characterized by one or more peaks in its X-ray powder diffraction pattern selected from 7.6, 12.0, 15.9, 17.9, and 19.8±0.2 degrees 2θ. In some such embodiments, a complex form of Compound 1 is Form C tosylate salt.

In some embodiments, Form C tosylate salt is characterized by the following peaks in its X-ray powder diffraction pattern:

| Position ° 2θ ± 0.2 degrees | d-spacing [Å] | Height [cts] |
|---|---|---|
| 7.3 | 12.067 | 1751 |
| 7.6 | 11.672 | 5992 |
| 8.8 | 10.008 | 1435 |
| 9.3 | 9.464 | 631 |
| 10.0 | 8.807 | 361 |
| 10.9 | 8.132 | 794 |
| 11.4 | 7.773 | 279 |
| 12.0 | 7.405 | 1679 |
| 12.8 | 6.891 | 1481 |
| 13.3 | 6.678 | 1232 |
| 13.6 | 6.499 | 1006 |
| 14.4 | 6.130 | 912 |
| 15.9 | 5.590 | 16694 |
| 16.1 | 5.500 | 1980 |
| 17.2 | 5.143 | 444 |
| 17.9 | 4.955 | 8213 |
| 18.4 | 4.827 | 1508 |
| 19.1 | 4.644 | 381 |
| 19.5 | 4.543 | 1366 |
| 19.8 | 4.479 | 6683 |
| 20.3 | 4.376 | 2996 |
| 21.3 | 4.173 | 560 |
| 21.7 | 4.104 | 748 |

-continued

| Position ° 2θ ± 0.2 degrees | d-spacing [Å] | Height [cts] |
|---|---|---|
| 22.4 | 3.969 | 3743 |
| 23.3 | 3.822 | 21634 |
| 23.8 | 3.742 | 1530 |
| 24.1 | 3.685 | 6012 |
| 24.9 | 3.574 | 1845 |
| 25.5 | 3.498 | 1225 |
| 26.3 | 3.392 | 1838 |
| 26.7 | 3.340 | 1939 |
| 27.4 | 3.260 | 1217 |

Figure 34:
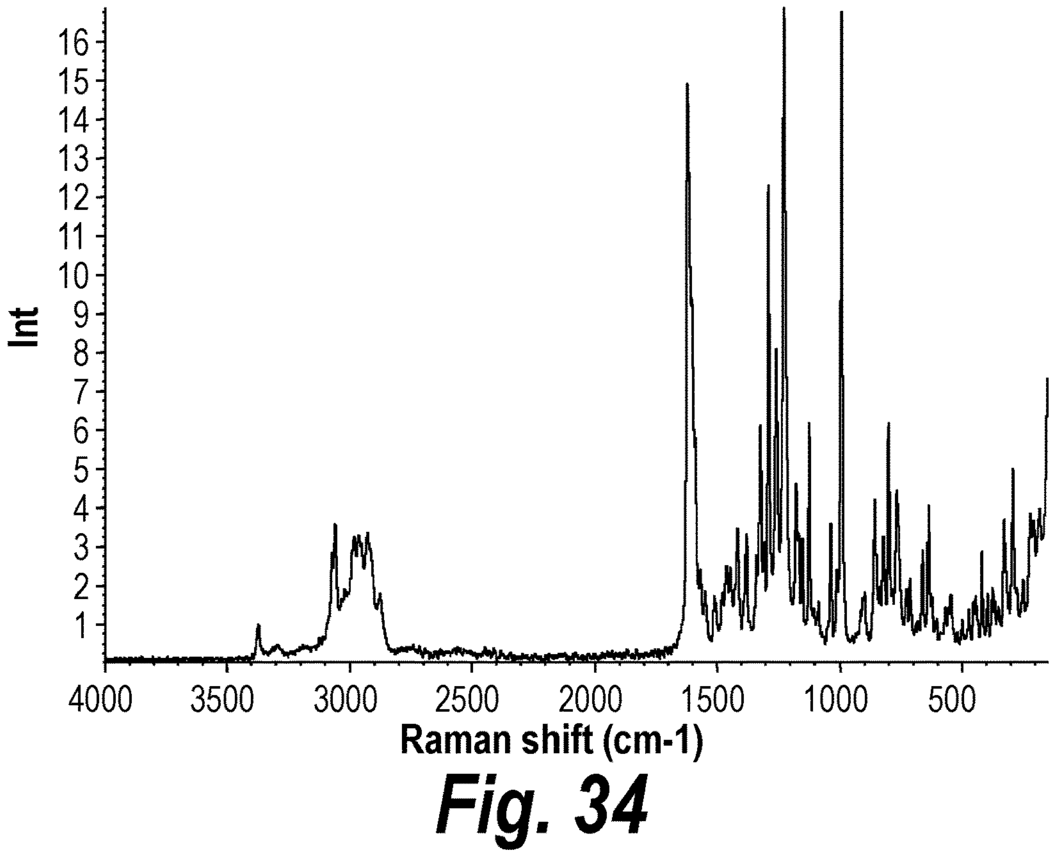
FIG. 34 depicts the FT-Raman spectrum of Form C tosylate salt of Compound 1.

In some embodiments, Form C tosylate salt is characterized by the FT-Raman spectrum depicted in FIG. 34.

Figure 35:
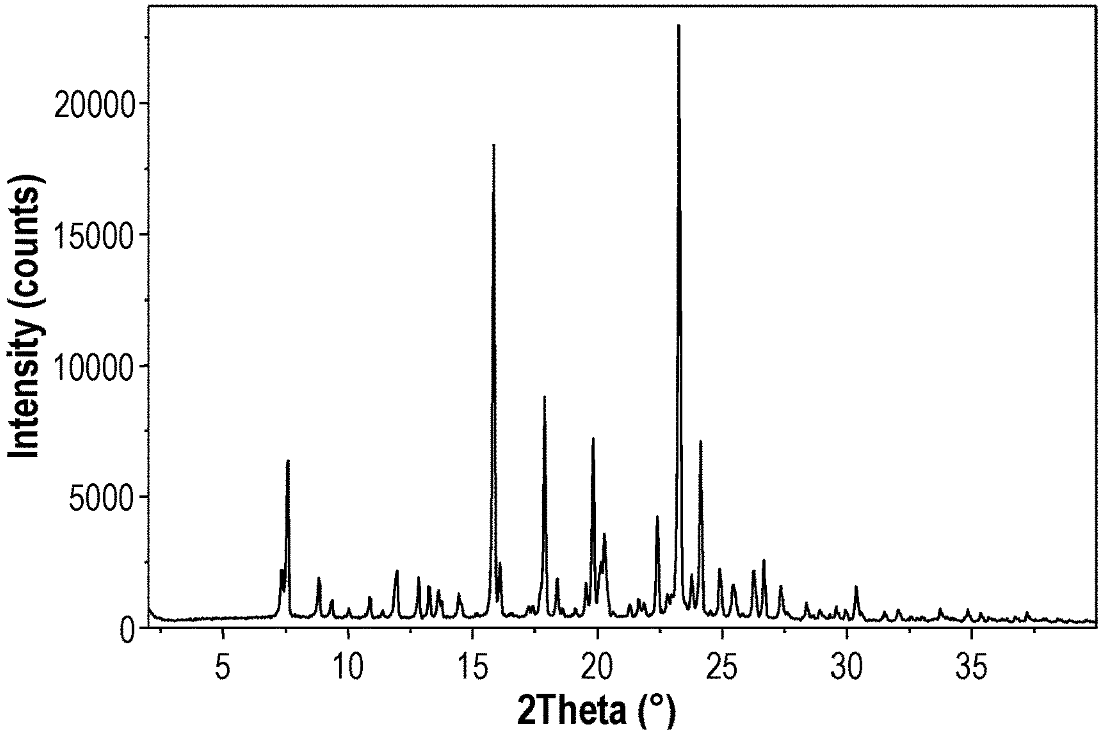
FIG. 35 depicts the XRPD pattern of Form C tosylate salt of Compound 1.

In some embodiments, Form C tosylate salt is characterized by the x-ray powder diffraction (XRPD) pattern depicted in FIG. 35.

Figure 36:
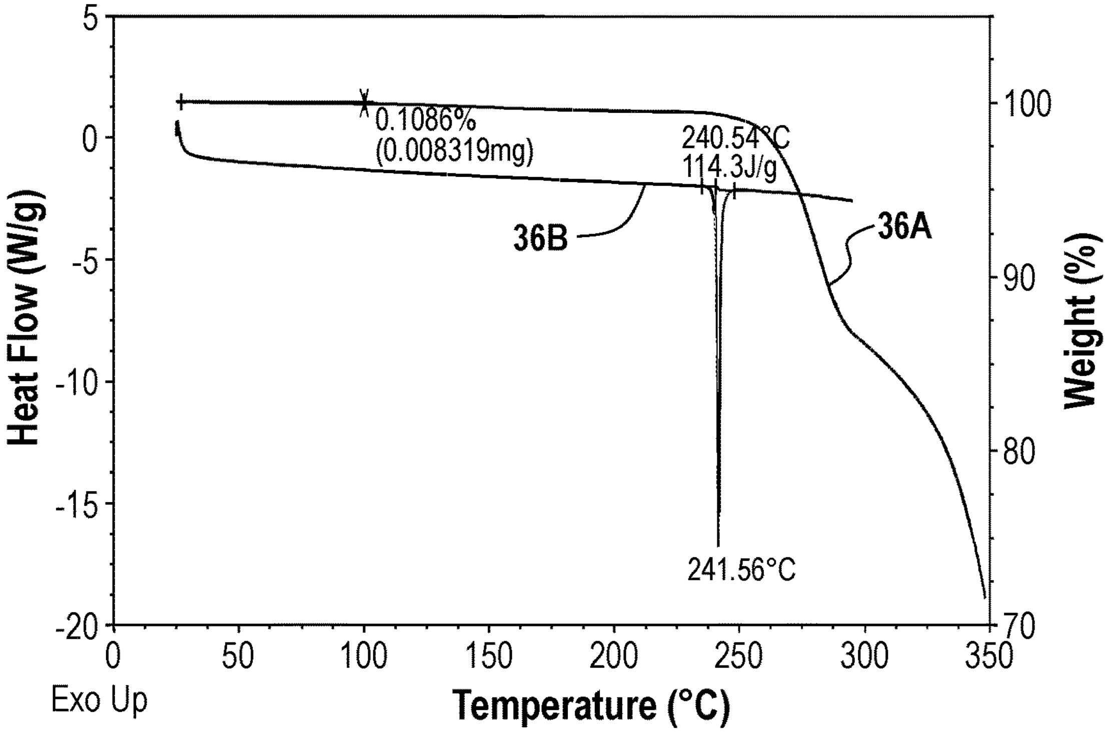
FIG. 36 depicts the TGA pattern of Form C tosylate salt of Compound 1 (36A), and the DSC pattern of Form C tosylate salt of Compound 1 (36B).

In some embodiments, Form C tosylate salt is characterized by the thermogravimetric analysis (TGA) pattern depicted in FIG. 36, trace 36A.

In some embodiments, Form C tosylate salt is characterized by the differential scanning calorimetry (DSC) pattern depicted in FIG. 36, trace 36B.

Figure 37:
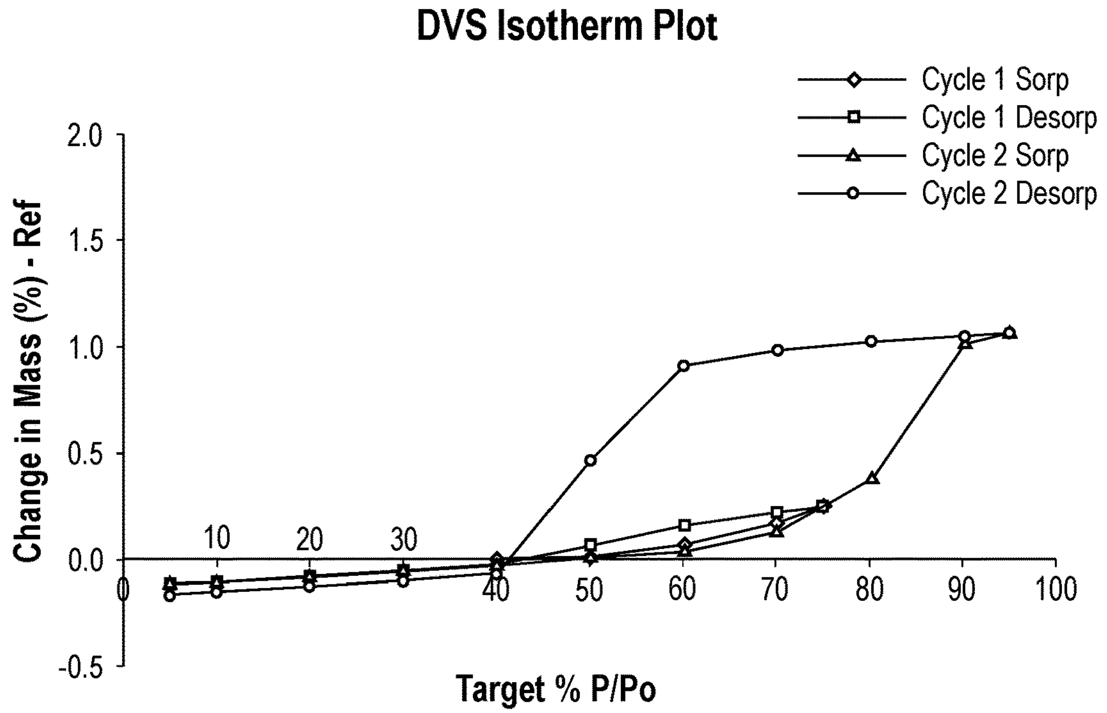
FIG. 37 depicts the DVS isotherm of Form C tosylate salt of Compound 1.

In some embodiments, Form C tosylate salt is characterized by the dynamic vapor sorption (DVS) isotherm depicted in FIG. 37.

Figure 38:
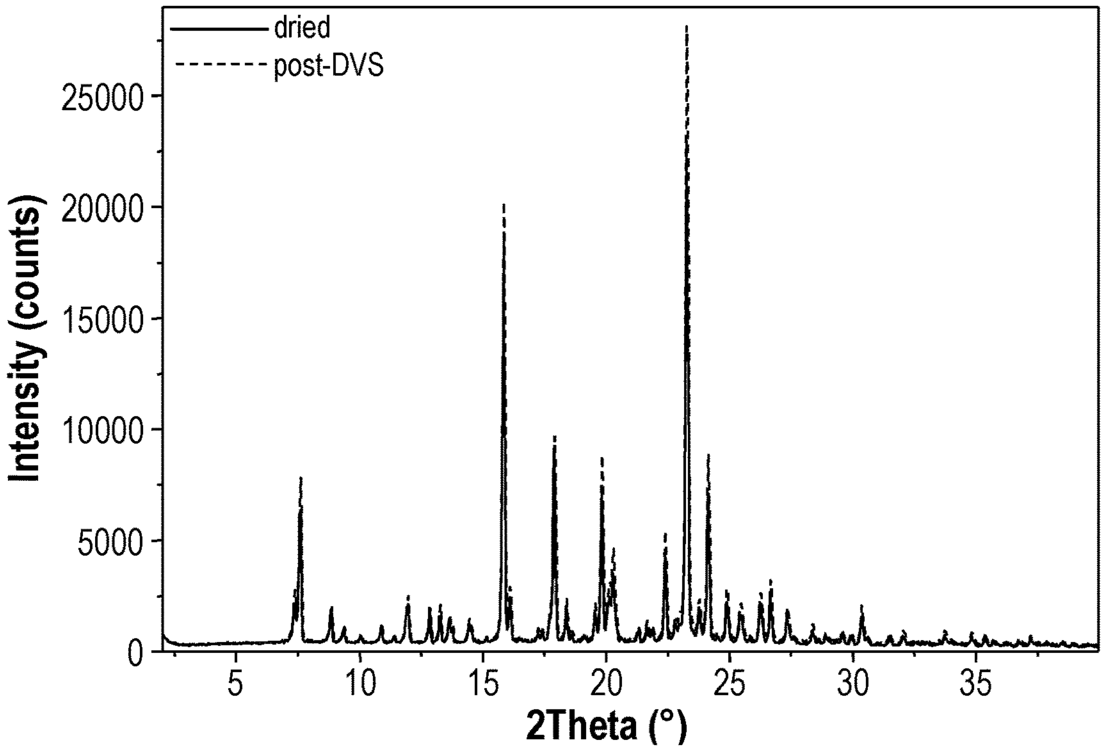
FIG. 38 depicts the XRPD pattern of Form C tosylate salt of Compound 1 post-DVS.

In some embodiments, Form C tosylate salt is characterized by the post-DVS x-ray powder diffraction (XRPD) pattern depicted in FIG. 38.

Figure 39:
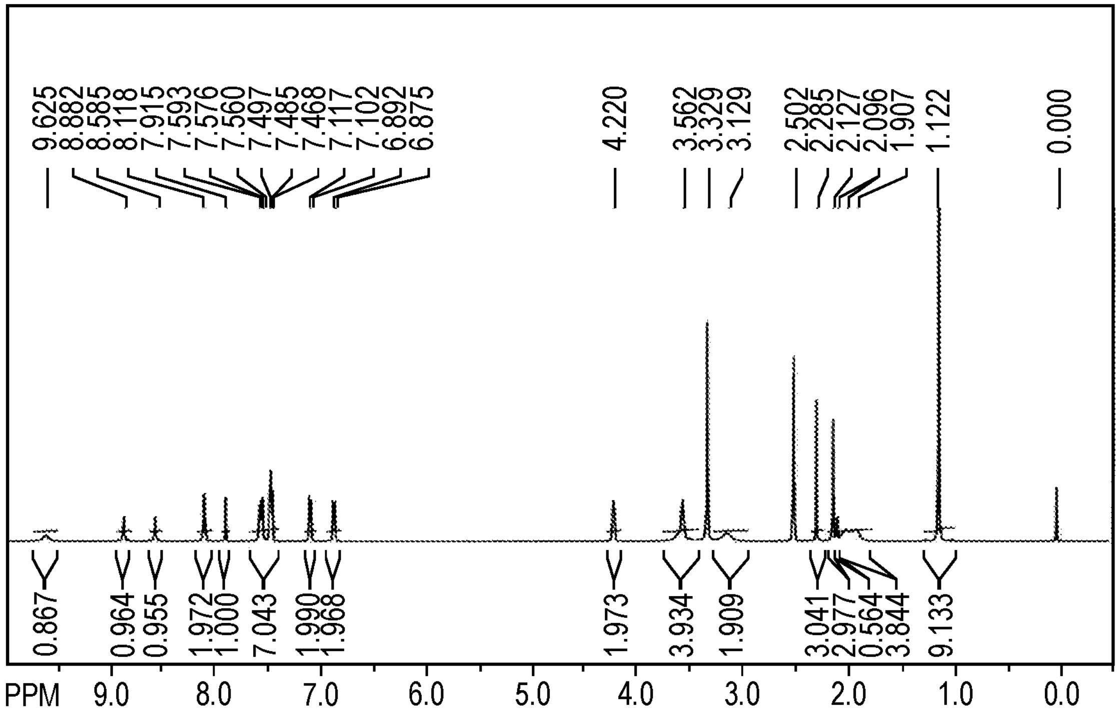
FIG. 39 depicts the $^1$H-NMR spectrum of Form C tosylate salt of Compound 1.

In some embodiments, Form C tosylate salt is characterized by the $^{1}H$ NMR depicted in FIG. 39.

In some embodiments of a complex form of Compound 1, X is methanesulfonic acid. In some such embodiments, a complex form of Compound 1 is a methansulfonate salt (also referred to as a "mesylate" salt). In some embodiments, a complex form of Compound 1 comprises 1.2 equivalents of methanesulfonic acid. In some embodiments, a mesylate salt of Compound 1 is a crystalline mesylate salt.

In some embodiments, a crystalline mesylate salt of Compound 1 is characterized by one or more peaks in its X-ray powder diffraction pattern selected from 12.2, 12.6, 13.2, and 18.9±0.2 degrees 2θ. In some such embodiments, a complex form of Compound 1 is Form A mesylate salt.

In some embodiments, Form A mesylate salt is characterized by the following peaks in its X-ray powder diffraction pattern:

| Position ° 2θ ± 0.2 degrees | d-spacing [Å] | Height [cts] |
|---|---|---|
| 12.2 | 7.260 | 908 |
| 12.6 | 7.051 | 1161 |
| 13.2 | 6.718 | 1024 |
| 14.5 | 6.105 | 1594 |
| 15.0 | 5.917 | 2297 |
| 15.9 | 5.581 | 1351 |
| 16.7 | 5.301 | 2787 |
| 17.3 | 5.139 | 3596 |
| 17.5 | 5.080 | 1088 |
| 18.9 | 4.694 | 8601 |
| 19.8 | 4.492 | 3231 |
| 20.0 | 4.432 | 798 |
| 20.5 | 4.327 | 2042 |
| 20.8 | 4.273 | 1237 |
| 21.6 | 4.114 | 1469 |
| 22.0 | 4.034 | 1283 |

-continued

| Position ° 2θ ± 0.2 degrees | d-spacing [Å] | Height [cts] |
|---|---|---|
| 22.3 | 3.981 | 1353 |
| 22.7 | 3.923 | 883 |
| 22.9 | 3.884 | 1556 |
| 23.3 | 3.825 | 502 |
| 23.6 | 3.773 | 3272 |
| 23.9 | 3.728 | 1633 |
| 24.5 | 3.633 | 1366 |
| 24.8 | 3.596 | 1304 |
| 25.1 | 3.546 | 1222 |
| 25.7 | 3.469 | 496 |
| 26.0 | 3.426 | 946 |
| 26.9 | 3.317 | 1155 |
| 27.6 | 3.235 | 501 |
| 28.4 | 3.138 | 784 |
| 33.0 | 2.713 | 435 |

Figure 40:
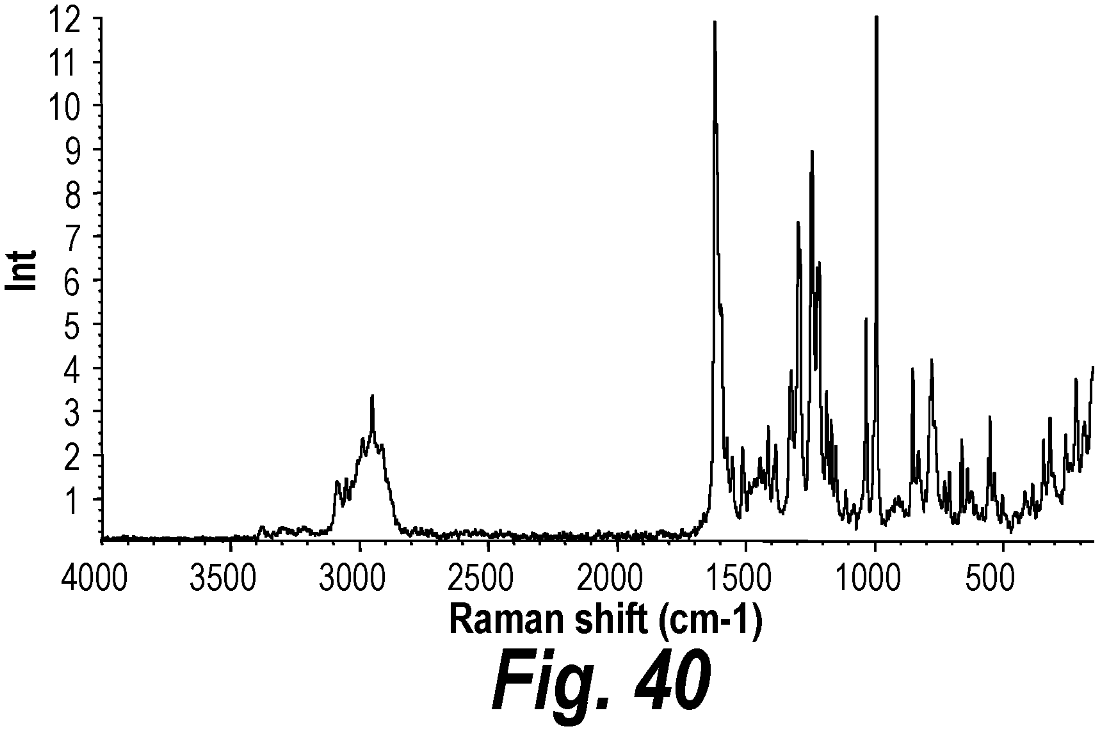
FIG. 40 depicts the FT-Raman spectrum of Form A mesylate salt of Compound 1.

In some embodiments, Form A mesylate salt is characterized by the FT-Raman spectrum depicted in FIG. 40.

Figure 41:
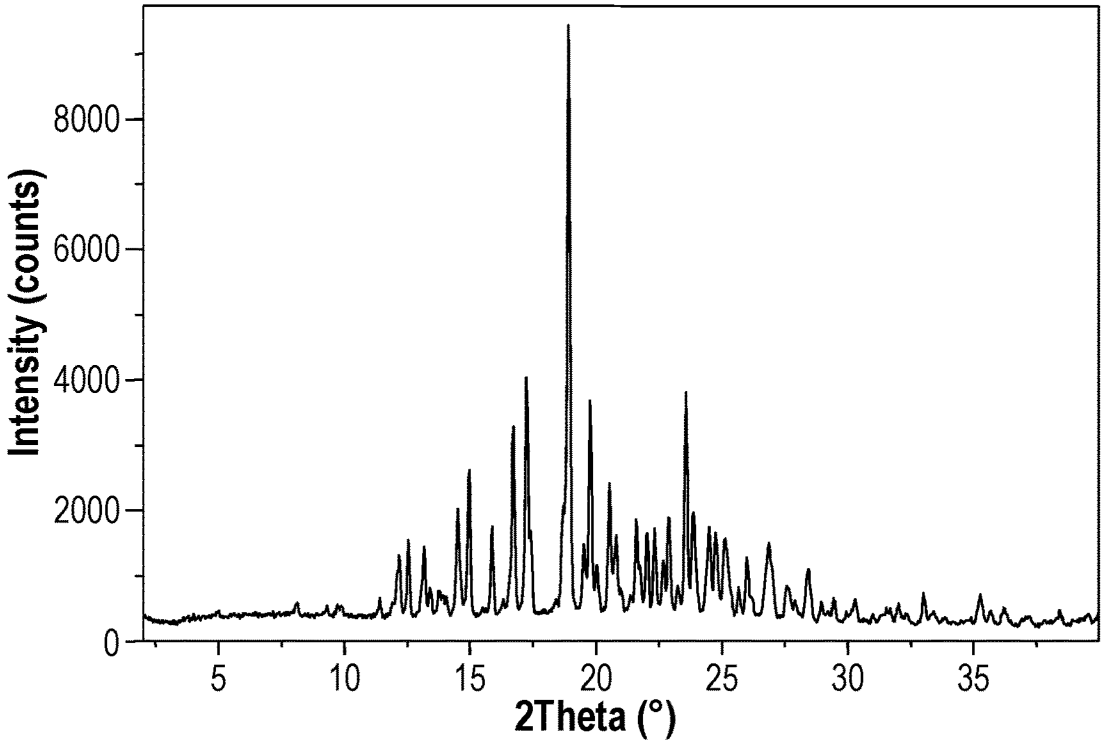
FIG. 41 depicts the XRPD pattern of Form A mesylate salt of Compound 1.

In some embodiments, Form A mesylate salt is characterized by the x-ray powder diffraction (XRPD) pattern depicted in FIG. 41.

Figure 42:
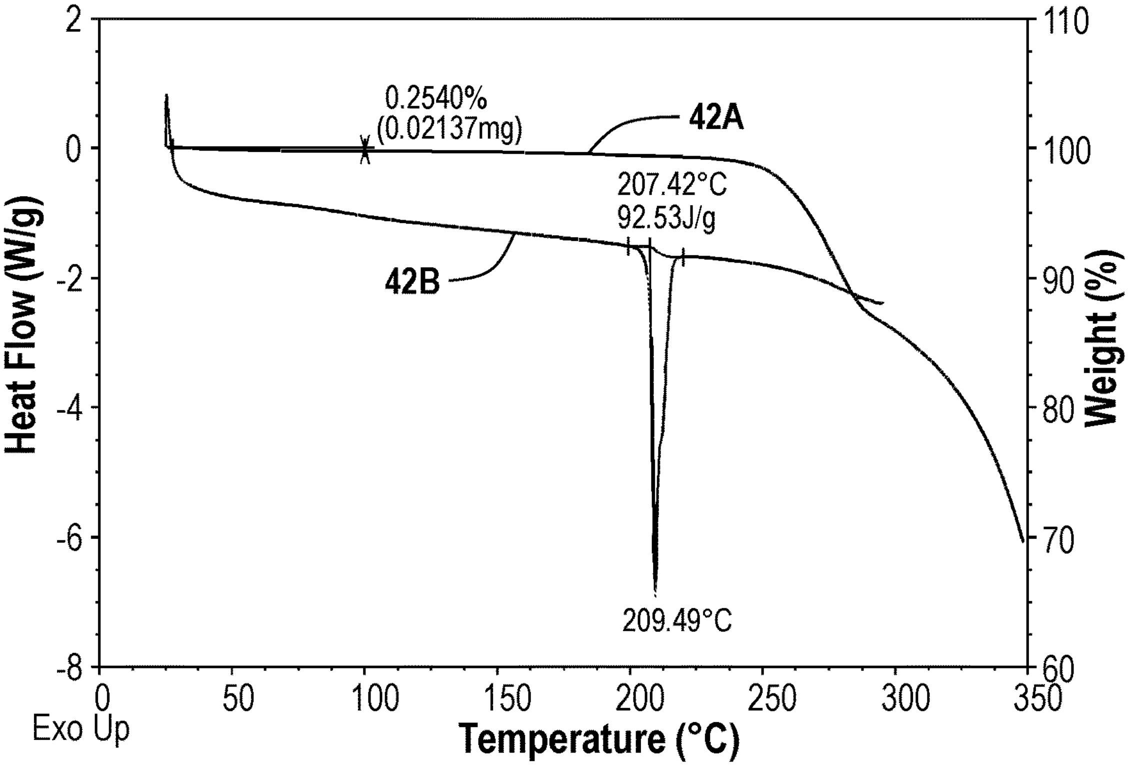
FIG. 42 depicts the TGA pattern of a dried sample of Form A mesylate salt of Compound 1 (42A), and the DSC pattern of a dried sample of Form A mesylate salt of Compound 1 (42B).

In some embodiments, Form A mesylate salt is characterized by the thermogravimetric analysis (TGA) pattern depicted in FIG. 42, trace 42A.

In some embodiments, Form A mesylate salt is characterized by the differential scanning calorimetry (DSC) pattern depicted in FIG. 42, trace 42B.

Figure 43:
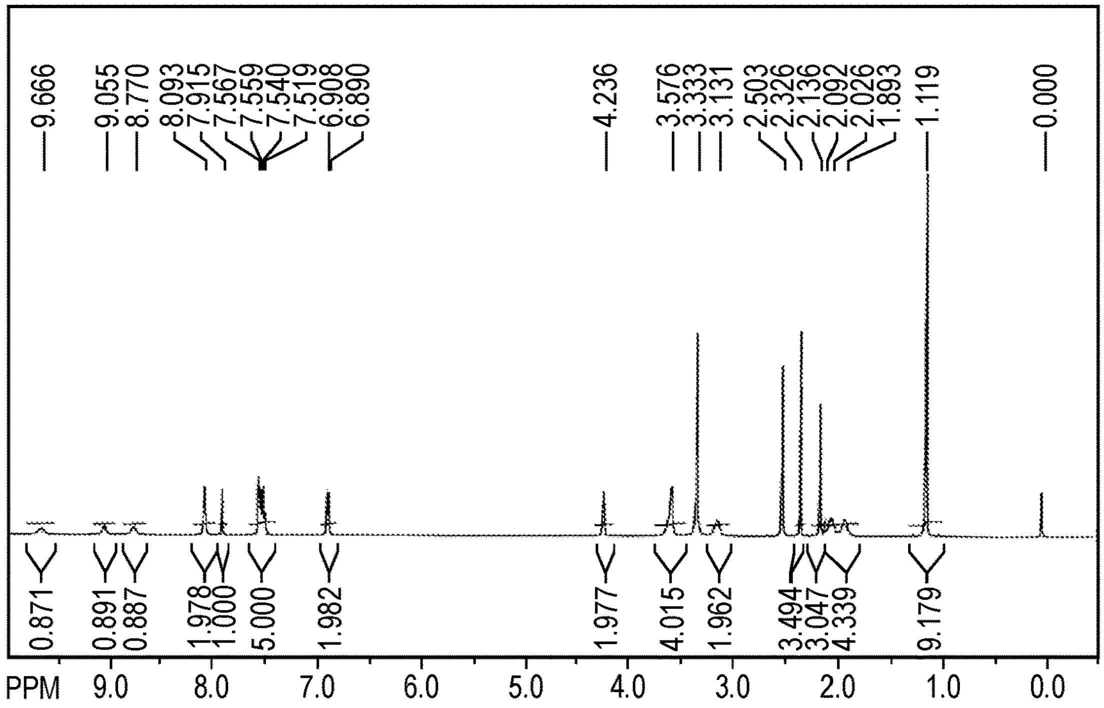
FIG. 43 depicts the $^1$H-NMR spectrum of Form A mesylate salt of Compound 1.

In some embodiments, Form A mesylate salt is characterized by the $^{1}H$ NMR depicted in FIG. 43.

In some embodiments, a crystalline mesylate salt of Compound 1 is characterized by one or more peaks in its X-ray powder diffraction pattern selected from 13.4, 13.6, 14.0, and 18.9±0.2 degrees 2θ. In some such embodiments, a complex form of Compound 1 is Form B mesylate salt.

In some embodiments, Form B mesylate salt is characterized by the following peaks in its X-ray powder diffraction pattern:

| Position ° 2θ ± 0.2 degrees | d-spacing [Å] | Height [cts] |
|---|---|---|
| 13.4 | 6.591 | 2087 |
| 13.6 | 6.491 | 3189 |
| 14.0 | 6.304 | 1065 |
| 15.2 | 5.842 | 2145 |
| 16.0 | 5.546 | 1954 |
| 16.4 | 5.395 | 873 |
| 16.8 | 5.263 | 1348 |
| 18.0 | 4.941 | 2513 |
| 18.2 | 4.884 | 2691 |
| 18.4 | 4.818 | 1636 |
| 18.9 | 4.702 | 8276 |
| 19.2 | 4.631 | 3862 |
| 19.6 | 4.535 | 973 |
| 20.5 | 4.333 | 476 |
| 21.0 | 4.227 | 783 |
| 22.2 | 4.008 | 650 |
| 22.7 | 3.916 | 670 |
| 23.1 | 3.845 | 3754 |
| 23.4 | 3.800 | 1660 |
| 23.7 | 3.761 | 1458 |
| 24.1 | 3.688 | 4055 |
| 24.7 | 3.601 | 478 |
| 25.0 | 3.558 | 982 |
| 25.2 | 3.534 | 839 |
| 26.8 | 3.325 | 758 |
| 29.3 | 3.050 | 1908 |

-continued

| Position ° 2θ ± 0.2 degrees | d-spacing [Å] | Height [cts] |
|---|---|---|
| 32.0 | 2.801 | 679 |
| 35.3 | 2.544 | 416 |

Figure 44:
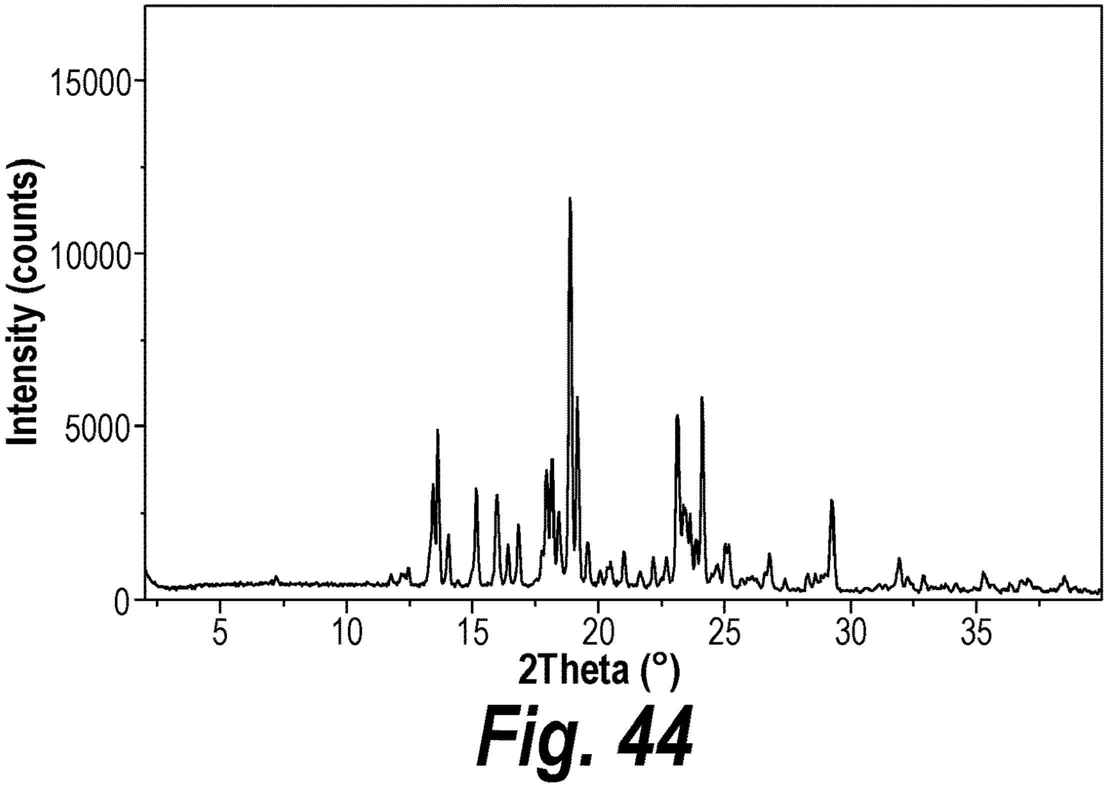
FIG. 44 depicts the XRPD pattern of Form B mesylate salt of Compound 1.

In some embodiments, Form B mesylate salt is characterized by the x-ray powder diffraction (XRPD) pattern depicted in FIG. 44.

Figure 46:
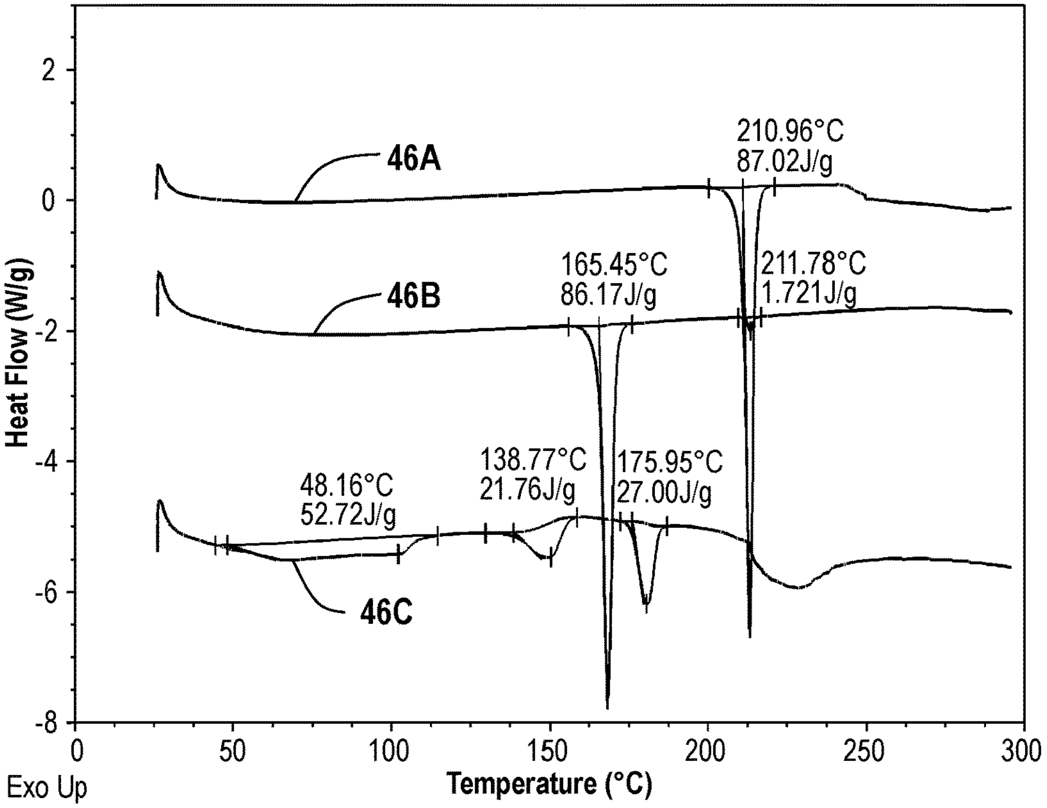
FIG. 46 depicts the DSC pattern of Form A mesylate salt of Compound 1 (46A), the DSC pattern of Form B mesylate salt of Compound 1 (46B), and the DSC pattern of Form C mesylate salt of Compound 1 (46C).

In some embodiments, Form B mesylate salt is characterized by the differential scanning calorimetry (DSC) pattern depicted in FIG. 46, trace 46B.

In some embodiments, a crystalline mesylate salt of Compound 1 is characterized by one or more peaks in its X-ray powder diffraction pattern selected from 4.6, 8.9, 9.1, 13.0, 13.3, 13.6, 17.8, and 18.2±0.2 degrees 2θ. In some such embodiments, a complex form of Compound 1 is Form C mesylate salt.

In some embodiments, Form C mesylate salt is characterized by the following peaks in its X-ray powder diffraction pattern:

| Position ° 2θ ± 0.2 degrees | d-spacing [Å] | Height [cts] |
|---|---|---|
| 4.6 | 19.377 | 1665 |
| 8.9 | 9.972 | 2136 |
| 9.1 | 9.724 | 2497 |
| 10.9 | 8.133 | 1151 |
| 11.3 | 7.842 | 713 |
| 13.0 | 6.830 | 1093 |
| 13.3 | 6.651 | 1156 |
| 13.6 | 6.492 | 1681 |
| 14.6 | 6.058 | 433 |
| 15.6 | 5.664 | 460 |
| 17.1 | 5.175 | 1953 |
| 17.4 | 5.108 | 1706 |
| 17.8 | 4.988 | 9832 |
| 18.2 | 4.869 | 16084 |
| 18.5 | 4.783 | 1180 |
| 18.8 | 4.723 | 508 |
| 19.4 | 4.579 | 1864 |
| 20.1 | 4.418 | 1205 |
| 21.2 | 4.200 | 1765 |
| 21.6 | 4.107 | 1230 |
| 22.6 | 3.940 | 696 |
| 23.3 | 3.825 | 1128 |
| 23.9 | 3.731 | 883 |
| 24.9 | 3.572 | 527 |
| 25.2 | 3.535 | 514 |
| 26.0 | 3.432 | 941 |
| 26.6 | 3.353 | 628 |
| 27.5 | 3.247 | 434 |
| 31.6 | 2.830 | 457 |

Figure 45:
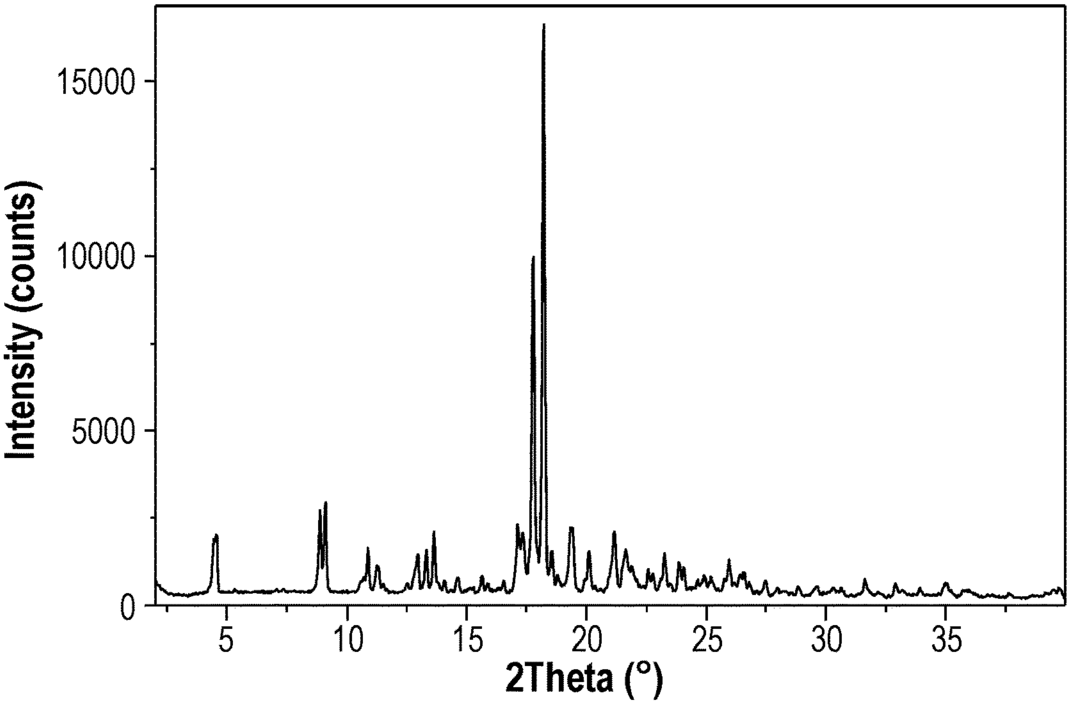
FIG. 45 depicts the XRPD pattern of Form C mesylate salt of Compound 1.

In some embodiments, Form C mesylate salt is characterized by the x-ray powder diffraction (XRPD) pattern depicted in FIG. 45.

In some embodiments, Form C mesylate salt is characterized by the differential scanning calorimetry (DSC) pattern depicted in FIG. 46, trace 46C.

In some embodiments of a complex form of Compound 1, X is 2-naphthalenesulfonic acid. In some such embodiments, a complex form of Compound 1 is a 2-naphthalenesulfonate salt. In some embodiments, a 2-naphthalenesulfonate salt of Compound 1 is a crystalline 2-naphthalenesulfonate salt.

In some embodiments, a complex form of Compound 1 comprises 1.5 equivalents of 2-naphthalenesulfonic acid. In some embodiments, a 2-naphthalenesulfonate salt of Compound 1 is a hemi solvate. In some such embodiments, a hemi solvate form of a 2-naphthalenesulfonate salt of Compound 1 is a hemi acetone solvate. In some embodiments, a hemi acetone solvate form of a 2-naphthalenesulfonate salt of Compound 1 is a crystalline hemi acetone solvate form of a 2-naphthalenesulfonate salt.

In some embodiments, a crystalline hemi acetone solvate form of a 2-naphthalenesulfonate salt of Compound 1 is characterized by one or more peaks in its X-ray powder diffraction pattern selected from 6.6, 10.5, 10.9, 11.1, 12.6, 16.8, and 17.5±0.2 degrees 2θ. In some such embodiments, a complex form of Compound 1 is Form A 2-naphthalenesulfonate salt.

In some embodiments, Form A 2-naphthalenesulfonate salt is characterized by the following peaks in its X-ray powder diffraction pattern:

| Position ° 2θ ± 0.2 degrees | d-spacing [Å] | Height [cts] |
|---|---|---|
| 6.6 | 13.461 | 659 |
| 9.8 | 9.035 | 619 |
| 10.5 | 8.429 | 1275 |
| 10.9 | 8.108 | 891 |
| 11.1 | 7.937 | 923 |
| 11.6 | 7.629 | 689 |
| 12.0 | 7.357 | 503 |
| 12.6 | 7.036 | 1199 |
| 13.1 | 6.751 | 647 |
| 13.6 | 6.528 | 646 |
| 14.3 | 6.198 | 1190 |
| 15.2 | 5.846 | 1568 |
| 15.7 | 5.648 | 1731 |
| 16.5 | 5.380 | 1604 |
| 16.8 | 5.276 | 3793 |
| 17.5 | 5.056 | 3039 |
| 17.8 | 4.987 | 3847 |
| 18.2 | 4.876 | 1556 |
| 18.5 | 4.788 | 1841 |
| 19.4 | 4.566 | 1256 |
| 19.6 | 4.519 | 873 |
| 20.1 | 4.417 | 1669 |
| 20.6 | 4.304 | 2050 |
| 20.9 | 4.252 | 1152 |
| 21.6 | 4.105 | 2381 |
| 22.3 | 3.980 | 609 |
| 22.7 | 3.914 | 1810 |
| 23.1 | 3.847 | 933 |
| 23.4 | 3.808 | 983 |
| 24.0 | 3.711 | 1079 |
| 24.8 | 3.589 | 1591 |
| 25.3 | 3.518 | 1173 |
| 25.7 | 3.473 | 1566 |
| 26.0 | 3.433 | 1078 |
| 26.5 | 3.368 | 493 |
| 27.0 | 3.299 | 836 |
| 28.0 | 3.186 | 415 |
| 28.3 | 3.150 | 520 |

Figure 47:
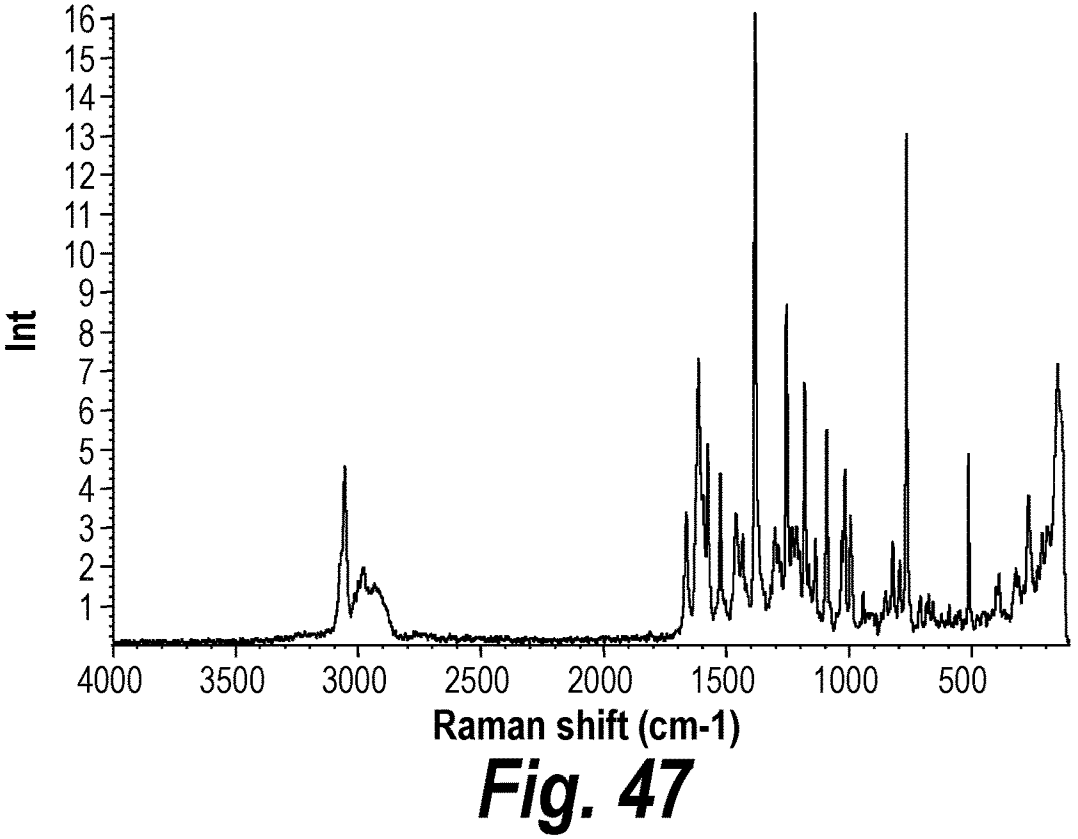
FIG. 47 depicts the FT-Raman spectrum of Form A 2-naphthalenesulfonate salt of Compound 1.

In some embodiments, Form A 2-naphthalenesulfonate salt is characterized by the FT-Raman spectrum depicted in FIG. 47.

Figure 48:
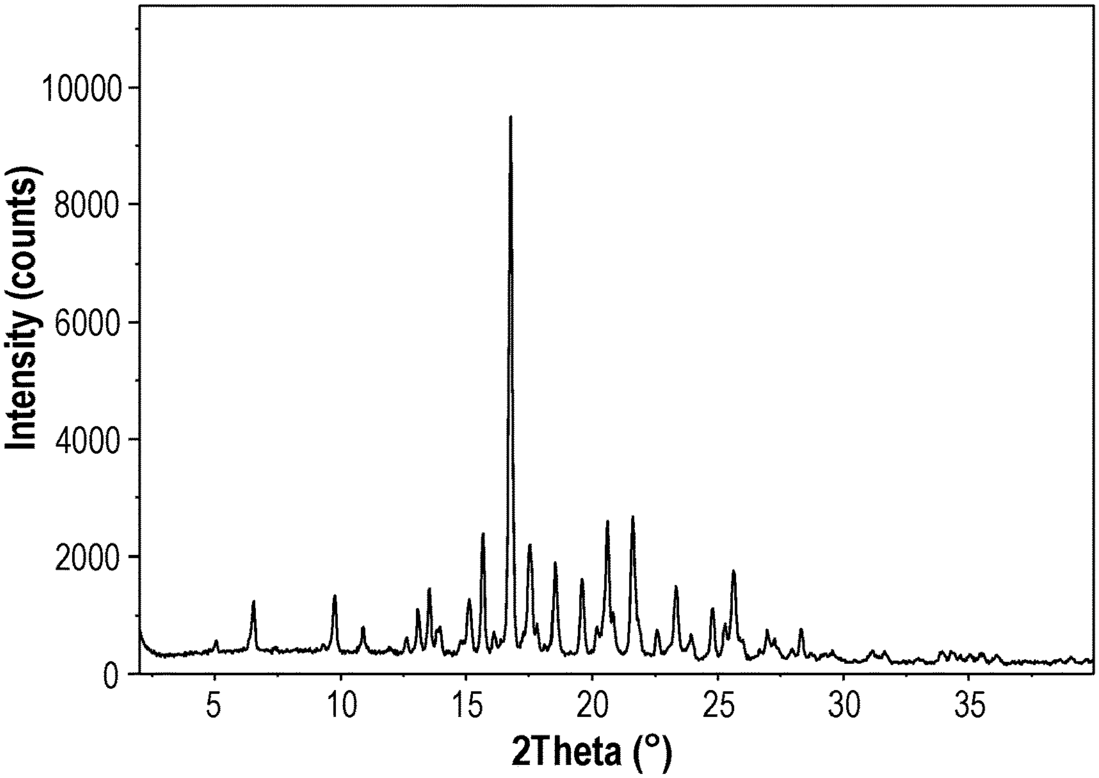
FIG. 48 depicts the XRPD pattern of Form A 2-naphthalenesulfonate salt of Compound 1.

In some embodiments, Form A 2-naphthalenesulfonate salt is characterized by the x-ray powder diffraction (XRPD) pattern depicted in FIG. 48.

Figure 50:
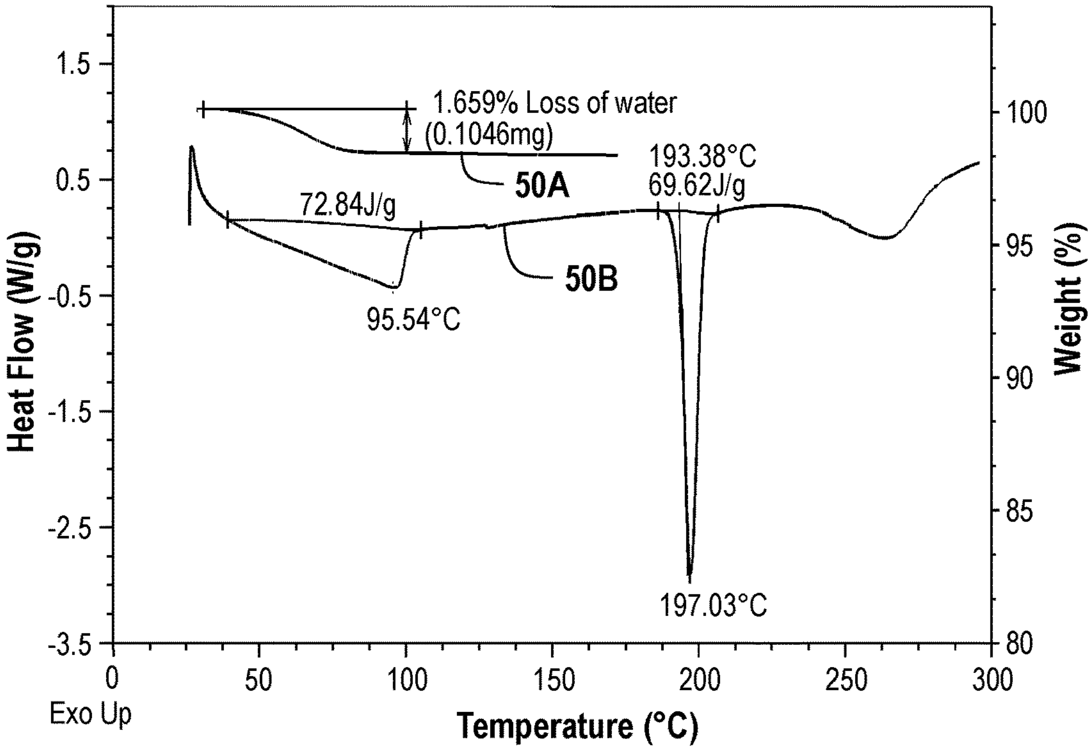
FIG. 50 depicts the TGA pattern of Form A 2-naphthalenesulfonate salt of Compound 1 (50A), and the DSC pattern of Form A 2-naphthalenesulfonate salt of Compound 1 (50B).

In some embodiments, Form A 2-naphthalenesulfonate salt is characterized by the thermogravimetric analysis (TGA) pattern depicted in FIG. 50, trace 50A.

In some embodiments, Form A 2-naphthalenesulfonate salt is characterized by the differential scanning calorimetry (DSC) pattern depicted in FIG. 50, trace 50B.

In some embodiments of a complex form of Compound 1, X is phosphoric acid. In some such embodiments, a complex form of Compound 1 is a phosphate salt. In some embodiments, a phosphate salt of Compound 1 is a crystalline phosphate salt.

In some embodiments, a crystalline phosphate salt of Compound 1 is characterized by one or more peaks in its X-ray powder diffraction pattern selected from 9.2, 10.9, 13.5, 15.0, and 16.7±0.2 degrees 2θ. In some such embodiments, a complex form of Compound 1 is Form A phosphate salt.

In some embodiments, Form A phosphate salt is characterized by the following peaks

| Position ° 2θ ± 0.2 degrees | d-spacing [Å] | Height [cts] |
|---|---|---|
| 9.2 | 9.644 | 145 |
| 10.9 | 8.109 | 293 |
| 12.6 | 7.042 | 311 |
| 13.5 | 6.551 | 362 |
| 15.0 | 5.915 | 464 |
| 15.6 | 5.675 | 556 |
| 16.1 | 5.511 | 578 |
| 16.4 | 5.420 | 361 |
| 16.7 | 5.309 | 1000 |
| 19.8 | 4.492 | 385 |
| 21.8 | 4.077 | 336 |
| 22.9 | 3.881 | 458 |
| 24.0 | 3.711 | 407 |
| 25.5 | 3.499 | 665 |
| 26.1 | 3.417 | 379 |
| 26.7 | 3.343 | 259 |
| 27.8 | 3.214 | 346 |
| 29.7 | 3.005 | 183 |
| 32.0 | 2.796 | 57 |

Figure 52:
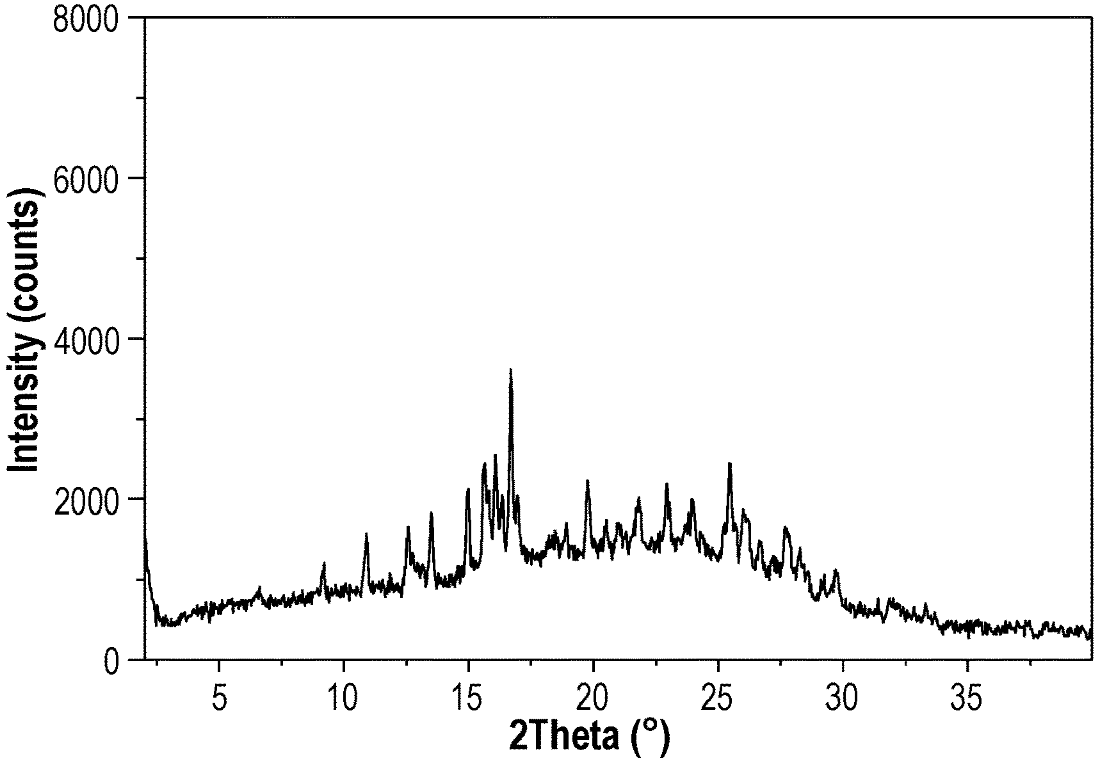
FIG. 52 depicts the XRPD pattern of Form A phosphate salt of Compound 1.

In some embodiments, Form A phosphate salt is characterized by the x-ray powder diffraction (XRPD) pattern depicted in FIG. 52.

Figure 56:
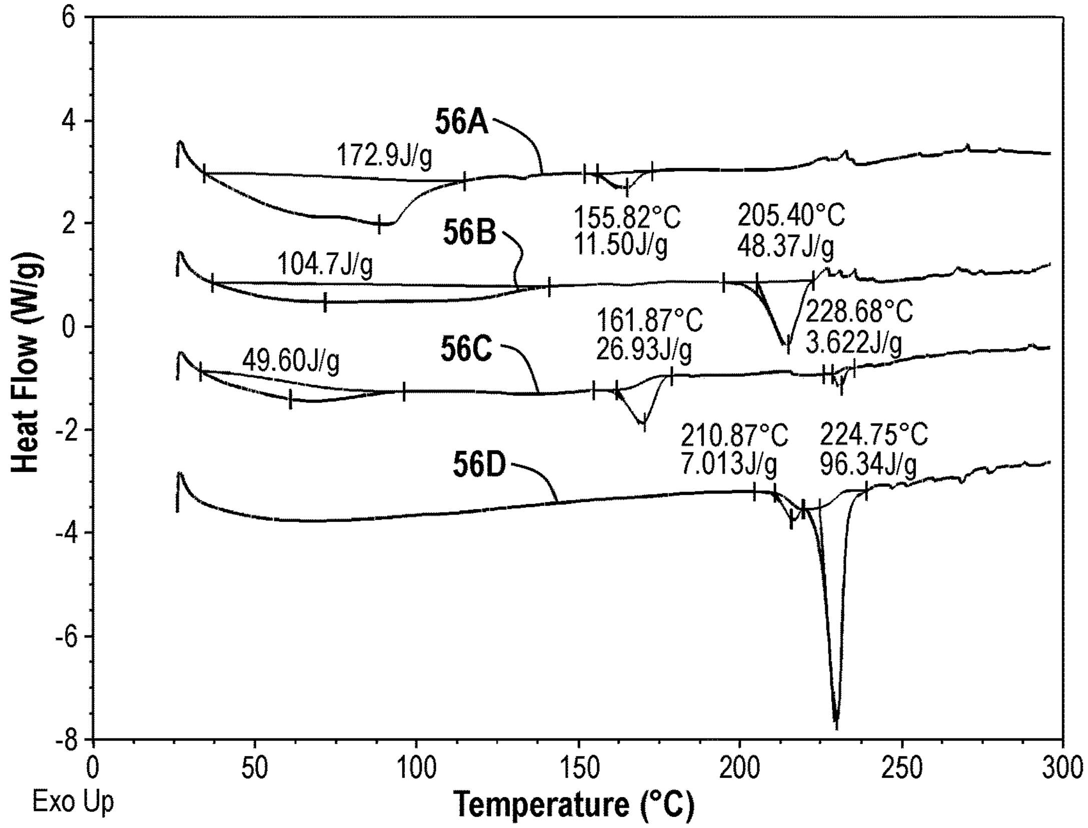
FIG. 56 depicts the DSC pattern of Form A phosphate salt of Compound 1 (56A), the DSC pattern of Form B phosphate salt of Compound 1 (56B), the DSC pattern of Form C phosphate salt of Compound 1 (56C), and the DSC pattern of Form D phosphate salt of Compound 1 (56D).

In some embodiments, Form A phosphate salt is characterized by the differential scanning calorimetry (DSC) pattern depicted in FIG. 56, trace 56A.

In some embodiments, a crystalline phosphate salt of Compound 1 is characterized by one or more peaks in its X-ray powder diffraction pattern selected from 4.9, 8.3, 9.8, 11.0, 17.2, and 19.7±0.2 degrees 2θ. In some such embodiments, a complex form of Compound 1 is Form B phosphate salt.

In some embodiments, Form B phosphate salt is characterized by the following peaks in its X-ray powder diffraction pattern:

| Position ° 2θ ± 0.2 degrees | d-spacing [Å] | Height [cts] |
|---|---|---|
| 4.9 | 18.046 | 300 |
| 8.3 | 10.634 | 368 |
| 9.8 | 9.017 | 1856 |
| 11.0 | 8.078 | 370 |
| 11.7 | 7.532 | 349 |
| 14.0 | 6.308 | 281 |
| 16.2 | 5.484 | 544 |
| 16.5 | 5.357 | 473 |
| 17.2 | 5.166 | 919 |
| 17.7 | 4.999 | 471 |
| 18.6 | 4.763 | 281 |
| 19.7 | 4.512 | 3231 |
| 20.0 | 4.429 | 773 |

-continued

| Position ° 2θ ± 0.2 degrees | d-spacing [Å] | Height [cts] |
|---|---|---|
| 20.7 | 4.285 | 1867 |
| 21.3 | 4.170 | 1312 |
| 22.0 | 4.044 | 1990 |
| 22.5 | 3.957 | 543 |
| 23.5 | 3.783 | 1164 |
| 25.0 | 3.558 | 258 |
| 25.4 | 3.511 | 472 |
| 26.2 | 3.397 | 571 |
| 26.7 | 3.340 | 308 |
| 27.2 | 3.275 | 249 |
| 29.0 | 3.075 | 222 |
| 29.4 | 3.034 | 288 |
| 33.2 | 2.696 | 203 |

Figure 53:
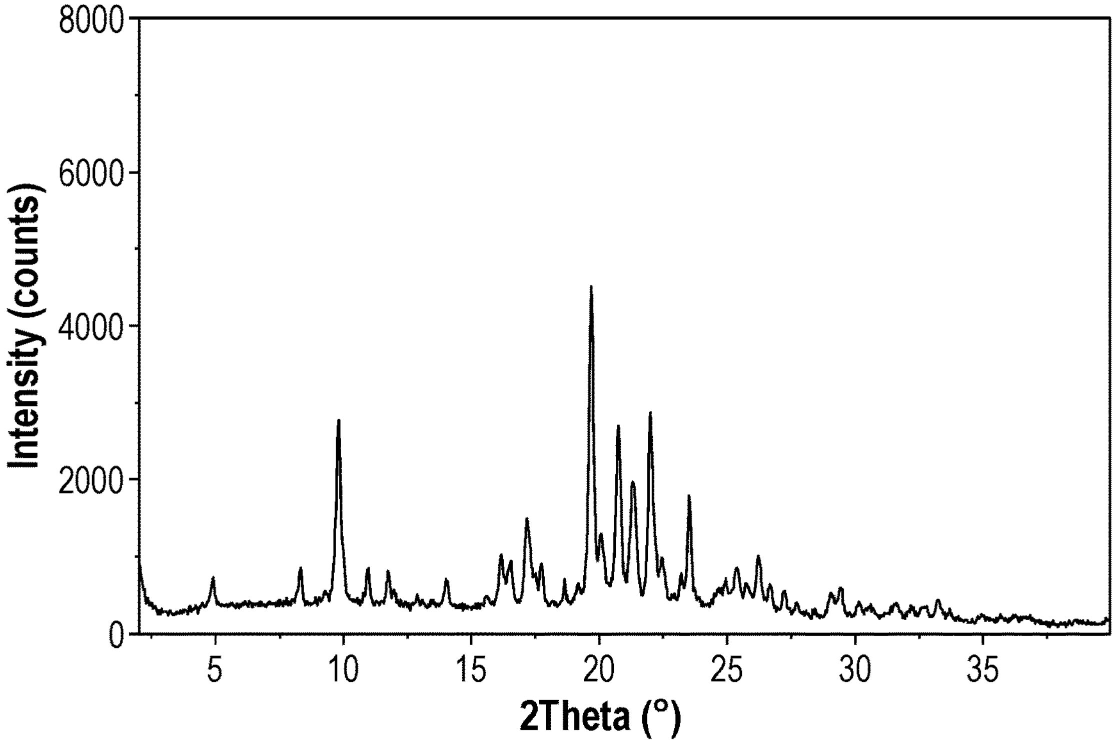
FIG. 53 depicts the XRPD pattern of Form B phosphate salt of Compound 1.

In some embodiments, Form B phosphate salt is characterized by the x-ray powder diffraction (XRPD) pattern depicted in FIG. 53.

In some embodiments, Form B phosphate salt is characterized by the differential scanning calorimetry (DSC) pattern depicted in FIG. 56, trace 56B.

In some embodiments, a crystalline phosphate salt of Compound 1 is characterized by one or more peaks in its X-ray powder diffraction pattern selected from 7.4, 9.9, 10.4, 12.3, and 14.5±0.2 degrees 2θ. In some such embodiments, a complex form of Compound 1 is Form C phosphate salt.

In some embodiments, Form C phosphate salt is characterized by the following peaks in its X-ray powder diffraction pattern:

| Position ° 2θ ± 0.2 degrees | d-spacing [Å] | Height [cts] |
|---|---|---|
| 7.4 | 12.007 | 251 |
| 9.1 | 9.694 | 323 |
| 9.9 | 8.907 | 264 |
| 10.4 | 8.541 | 369 |
| 11.8 | 7.499 | 534 |
| 12.3 | 7.194 | 2459 |
| 14.5 | 6.126 | 1531 |
| 14.7 | 6.022 | 550 |
| 15.5 | 5.704 | 1395 |
| 16.1 | 5.504 | 2200 |
| 16.8 | 5.292 | 1139 |
| 18.4 | 4.813 | 1152 |
| 19.2 | 4.614 | 920 |
| 19.6 | 4.527 | 836 |
| 20.1 | 4.419 | 607 |
| 20.8 | 4.281 | 1134 |
| 21.1 | 4.210 | 2018 |
| 21.7 | 4.091 | 542 |
| 22.1 | 4.020 | 1889 |
| 23.1 | 3.851 | 1152 |
| 23.4 | 3.795 | 1163 |
| 23.7 | 3.755 | 1378 |
| 24.2 | 3.683 | 1529 |
| 24.8 | 3.585 | 1388 |
| 25.2 | 3.538 | 718 |
| 25.9 | 3.443 | 494 |
| 26.7 | 3.338 | 276 |
| 28.3 | 3.151 | 1099 |
| 29.6 | 3.017 | 426 |

Figure 54:
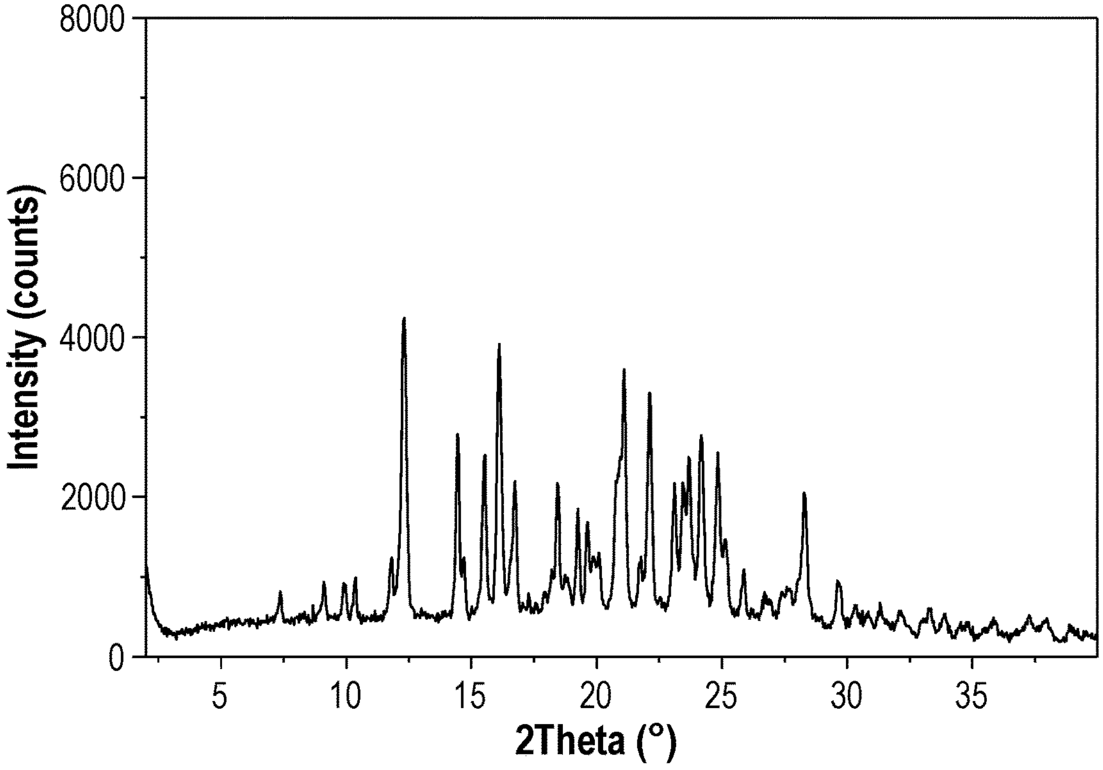
FIG. 54 depicts the XRPD pattern of Form C phosphate salt of Compound 1.

In some embodiments, Form C phosphate salt is characterized by the x-ray powder diffraction (XRPD) pattern depicted in FIG. 54.

In some embodiments, Form C phosphate salt is characterized by the differential scanning calorimetry (DSC) pattern depicted in FIG. 56, trace 56C.

In some embodiments, a crystalline phosphate salt of Compound 1 is characterized by one or more peaks in its X-ray powder diffraction pattern selected from 7.1, 11.1, 14.2, 16.9, and 22.3±0.2 degrees 2θ. In some such embodiments, a complex form of Compound 1 is Form D phosphate salt.

In some embodiments, Form D phosphate salt is characterized by the following peaks in its X-ray powder diffraction pattern:

| Position ° 2θ ± 0.2 degrees | d-spacing [Å] | Height [cts] |
|---|---|---|
| 7.1 | 12.521 | 1469 |
| 7.9 | 11.130 | 605 |
| 9.7 | 9.154 | 824 |
| 11.1 | 7.958 | 5253 |
| 14.2 | 6.241 | 1090 |
| 15.3 | 5.796 | 697 |
| 15.9 | 5.562 | 878 |
| 16.9 | 5.262 | 1827 |
| 17.6 | 5.031 | 674 |
| 18.0 | 4.917 | 871 |
| 18.5 | 4.805 | 1777 |
| 19.7 | 4.497 | 1006 |
| 20.2 | 4.399 | 1507 |
| 20.8 | 4.263 | 587 |
| 21.9 | 4.060 | 1538 |
| 22.3 | 3.982 | 15460 |
| 23.4 | 3.799 | 3528 |
| 23.8 | 3.736 | 2832 |
| 25.0 | 3.555 | 837 |
| 25.7 | 3.470 | 906 |
| 27.3 | 3.263 | 330 |
| 27.9 | 3.200 | 709 |
| 29.1 | 3.071 | 1291 |

Figure 55:
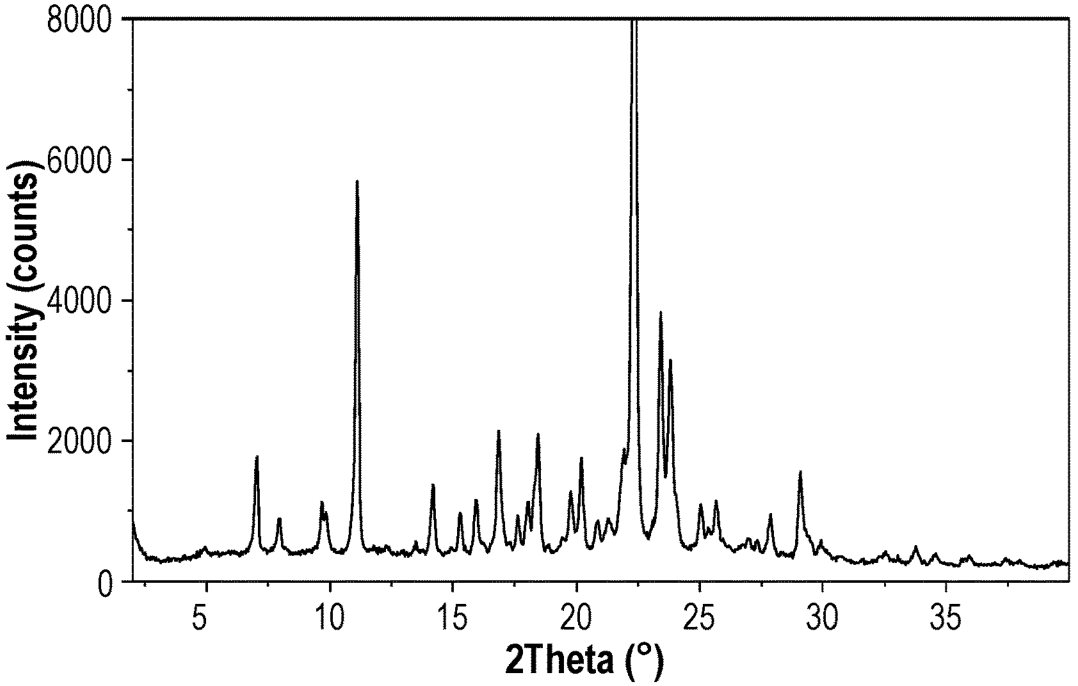
FIG. 55 depicts the XRPD pattern of Form D phosphate salt of Compound 1.

In some embodiments, Form D phosphate salt is characterized by the x-ray powder diffraction (XRPD) pattern depicted in FIG. 55.

In some embodiments, Form D phosphate salt is characterized by the differential scanning calorimetry (DSC) pattern depicted in FIG. 56, trace 56D.

In some embodiments, a complex form of Compound 1 comprises one equivalent of phosphoric acid. In some embodiments, a phosphate salt of Compound 1 is a solvate. In some embodiments, a solvate form of a phosphate salt of Compound 1 is a methanol solvate. In some embodiments, a methanol solvate form of a phosphate salt of Compound 1 is a crystalline methanol solvate. In some embodiments, a crystalline methanol solvate form of a phosphate salt of Compound 1 is characterized by one or more peaks in its X-ray powder diffraction pattern selected from 8.2, 10.1, 10.9, 14.5, 14.8, 18.0, and 19.5±0.2 degrees 2θ. In some such embodiments, a complex form of Compound 1 is Form E phosphate salt.

In some embodiments, Form E phosphate salt is characterized by the following peaks in its X-ray powder diffraction pattern:

| Position ° 2θ ± 0.2 degrees | d-spacing [Å] | Height [cts] |
|---|---|---|
| 8.2 | 10.758 | 1688 |
| 10.1 | 8.790 | 1615 |
| 10.9 | 8.086 | 3754 |
| 13.0 | 6.826 | 717 |
| 14.5 | 6.128 | 1664 |
| 14.8 | 5.990 | 2416 |
| 15.8 | 5.611 | 3163 |
| 16.5 | 5.386 | 3674 |
| 16.8 | 5.289 | 2981 |
| 18.0 | 4.940 | 4748 |
| 19.0 | 4.667 | 778 |
| 19.5 | 4.562 | 6039 |
| 20.2 | 4.401 | 1144 |
| 21.7 | 4.089 | 554 |
| 22.1 | 4.016 | 3380 |
| 22.5 | 3.946 | 698 |
| 22.8 | 3.897 | 1439 |
| 23.2 | 3.840 | 2339 |
| 23.8 | 3.732 | 627 |
| 24.1 | 3.695 | 692 |
| 24.8 | 3.593 | 399 |
| 25.9 | 3.445 | 1952 |
| 26.2 | 3.397 | 2062 |
| 26.5 | 3.366 | 1368 |
| 27.1 | 3.289 | 1303 |
| 27.3 | 3.268 | 1105 |
| 28.5 | 3.130 | 312 |
| 29.8 | 2.997 | 818 |
| 32.1 | 2.787 | 318 |
| 32.9 | 2.719 | 571 |

Figure 57:
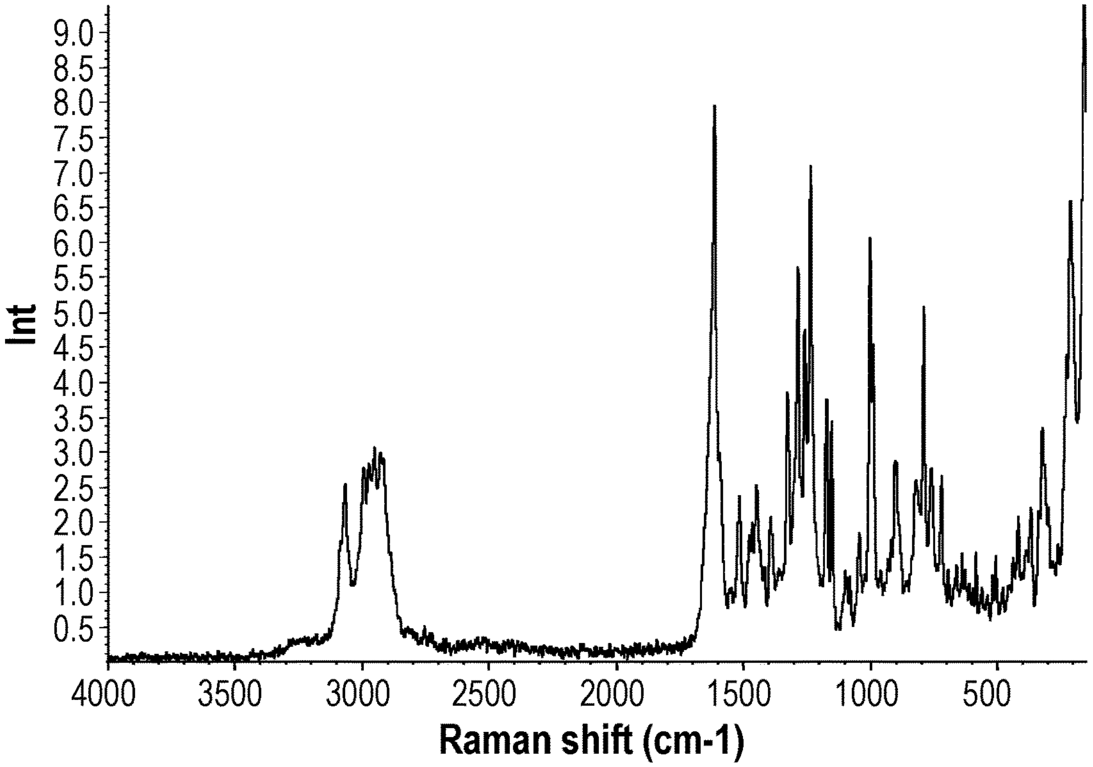
FIG. 57 depicts the FT-Raman spectrum of Form E phosphate salt of Compound 1.

In some embodiments, Form E phosphate salt is characterized by the FT-Raman spectrum depicted in FIG. 57.

Figure 58:
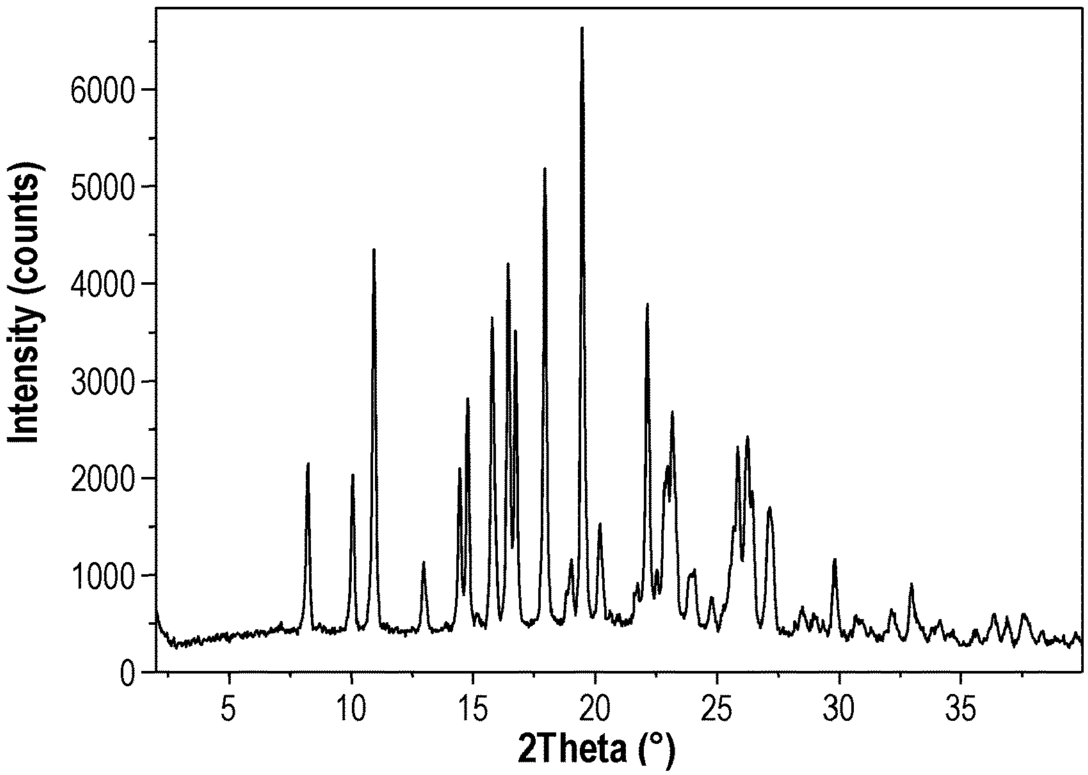
FIG. 58 depicts the XRPD pattern of Form E phosphate salt of Compound 1.

In some embodiments, Form E phosphate salt is characterized by the x-ray powder diffraction (XRPD) pattern depicted in FIG. 58.

Figure 59:
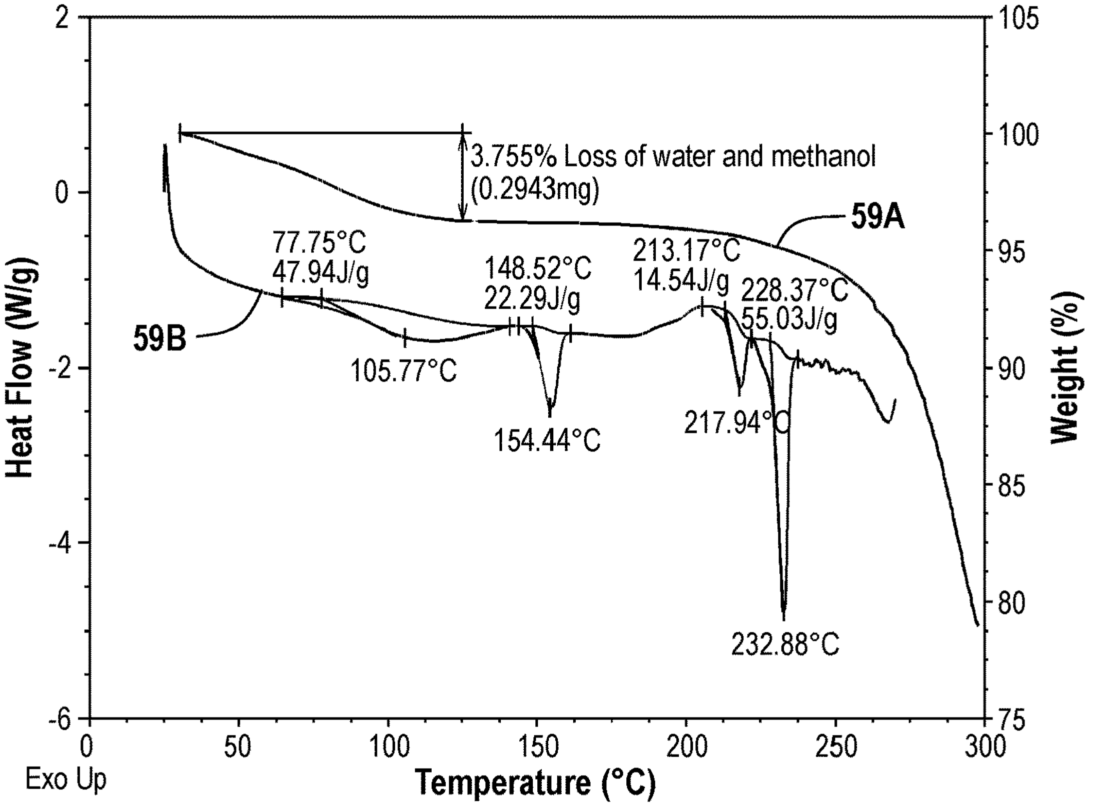
FIG. 59 depicts the TGA pattern of Form E phosphate salt of Compound 1 (59A), and the DSC pattern of Form E phosphate salt of Compound 1 (59B).

In some embodiments, Form E phosphate salt is characterized by the thermogravimetric analysis (TGA) pattern depicted in FIG. 59, trace 59A.

In some embodiments, Form E phosphate salt is characterized by the differential scanning calorimetry (DSC) pattern depicted in FIG. 59, trace 59B.

In some embodiments of a complex form of Compound 1, X is DL-tartaric acid. In some such embodiments, a complex form of Compound 1 is a DL-tartrate salt. In some embodiments, a complex form of Compound 1 comprises one equivalent of DL-tartaric acid. In some embodiments, a DL-tartrate salt of Compound 1 is a crystalline DL-tartrate salt.

In some embodiments, a DL-tartrate salt of Compound 1 is a hydrate. In some embodiments, a hydrate form of a DL-tartrate salt of Compound 1 is a crystalline hydrate form of a DL-tartrate salt. In some embodiments, a crystalline hydrate form of a DL-tartrate salt of Compound 1 is characterized by one or more peaks in its X-ray powder diffraction pattern selected from 4.7, 7.4, 9.3, 11.0, and 13.0±0.2 degrees 2θ. In some such embodiments, a complex form of Compound 1 is Form A DL-tartrate salt.

In some embodiments, Form A DL-tartrate salt is characterized by the following peaks in its X-ray powder diffraction pattern:

| Position ° 2θ ± 0.2 degrees | d-spacing [Å] | Height [cts] |
|---|---|---|
| 4.7 | 18.988 | 6462 |
| 6.2 | 14.286 | 80 |
| 7.4 | 11.921 | 780 |
| 9.3 | 9.502 | 1716 |
| 11.0 | 8.071 | 3146 |
| 11.8 | 7.510 | 69 |

-continued

| Position ° 2θ ± 0.2 degrees | d-spacing [Å] | Height [cts] |
|---|---|---|
| 13.0 | 6.819 | 519 |
| 13.5 | 6.557 | 208 |
| 14.0 | 6.341 | 524 |
| 14.8 | 5.966 | 391 |
| 16.7 | 5.322 | 304 |
| 17.3 | 5.126 | 264 |
| 18.2 | 4.883 | 809 |
| 18.6 | 4.759 | 486 |
| 19.1 | 4.640 | 230 |
| 20.7 | 4.300 | 288 |
| 21.2 | 4.187 | 243 |
| 21.8 | 4.081 | 358 |
| 22.5 | 3.953 | 68 |
| 24.2 | 3.674 | 276 |
| 25.4 | 3.513 | 312 |
| 26.1 | 3.419 | 283 |
| 26.9 | 3.319 | 114 |
| 27.4 | 3.258 | 92 |
| 28.4 | 3.147 | 123 |
| 30.0 | 2.977 | 145 |
| 33.0 | 2.717 | 76 |
| 35.0 | 2.563 | 149 |

Figure 60:
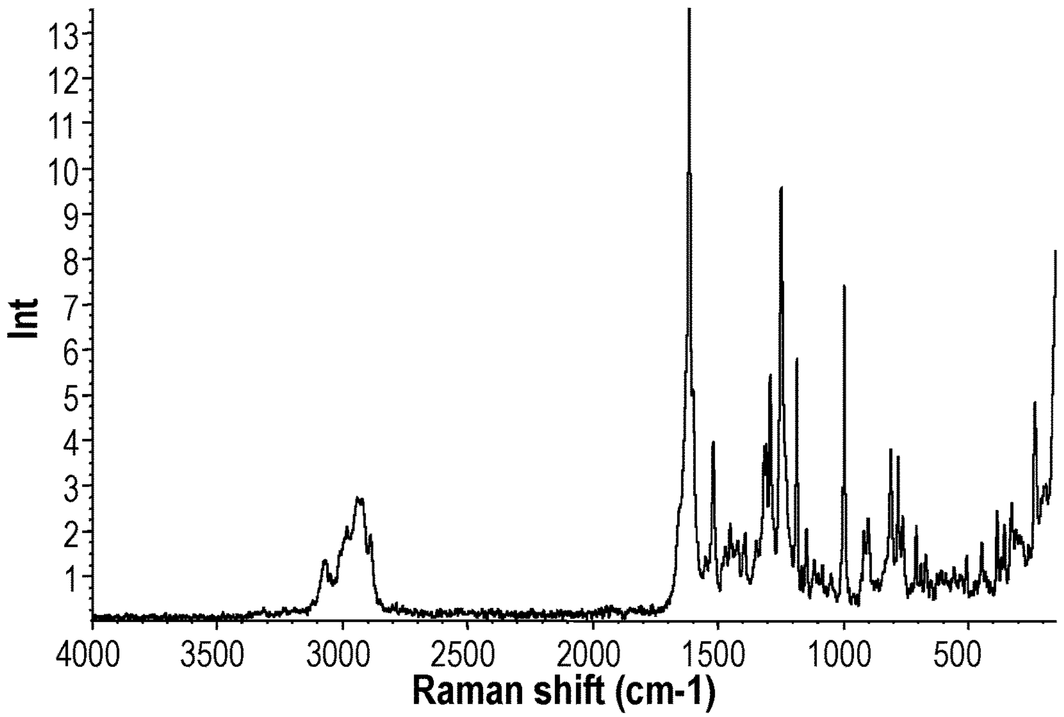
FIG. 60 depicts the FT-Raman spectrum of Form A DL-tartrate salt of Compound 1.

In some embodiments, Form A DL-tartrate salt is characterized by the FT-Raman spectrum depicted in FIG. 60.

Figure 61:
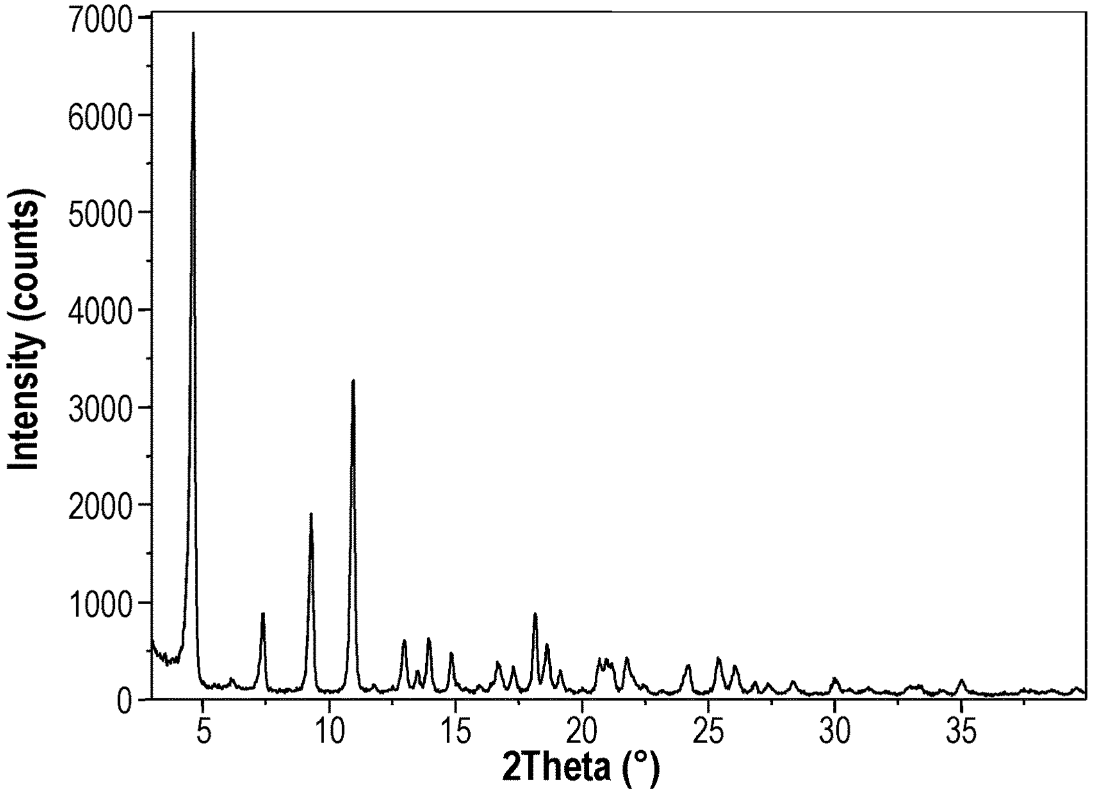
FIG. 61 depicts the XRPD pattern of Form A DL-tartrate salt of Compound 1.

In some embodiments, Form A DL-tartrate salt is characterized by the x-ray powder diffraction (XRPD) pattern depicted in FIG. 61.

Figure 62:
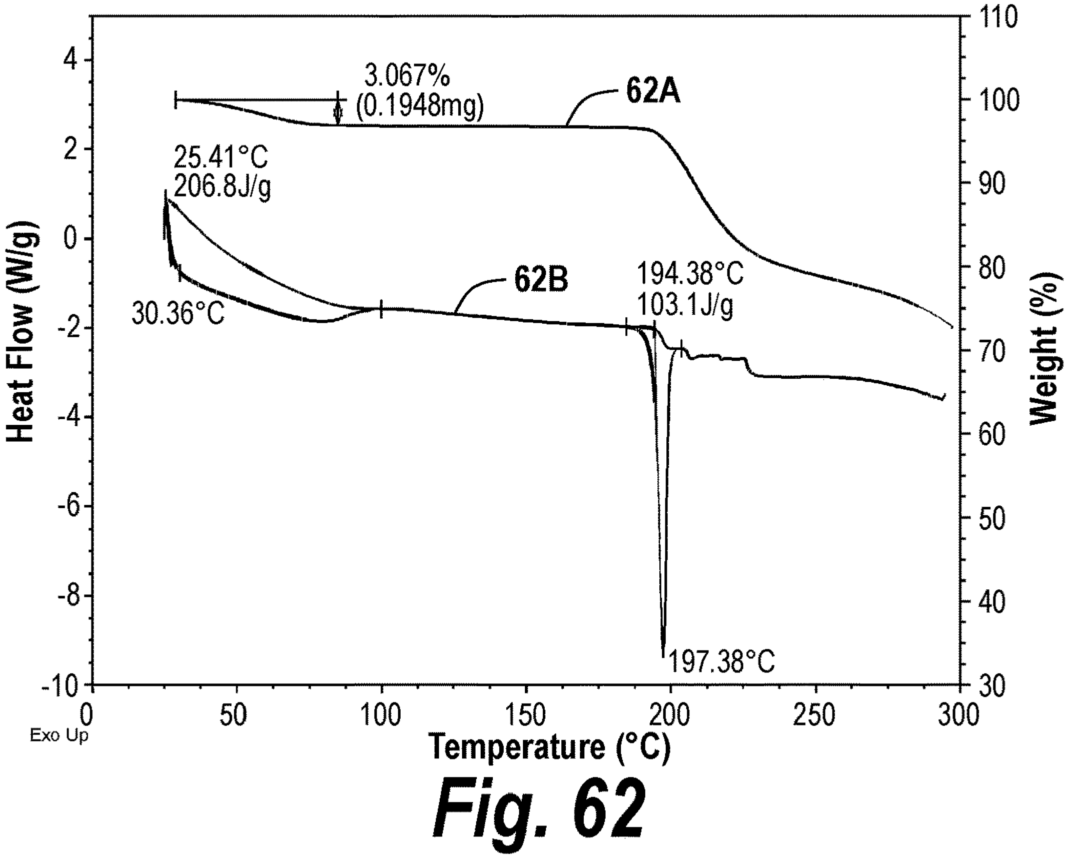
FIG. 62 depicts the TGA pattern of Form A DL-tartrate salt of Compound 1 (62A), and the DSC pattern of Form A DL-tartrate salt of Compound 1 (62B).

In some embodiments, Form A DL-tartrate salt is characterized by the thermogravimetric analysis (TGA) pattern depicted in FIG. 62, trace 62A.

In some embodiments, Form A DL-tartrate salt is characterized by the differential scanning calorimetry (DSC) pattern depicted in FIG. 62, trace 62B.

Figure 63:
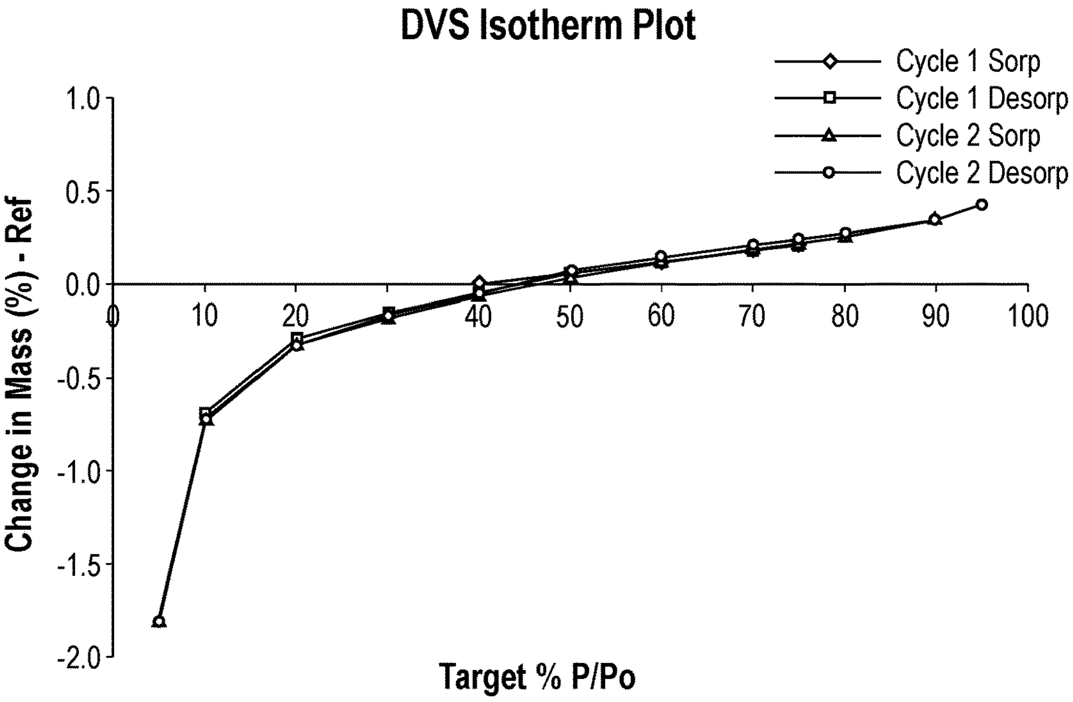
FIG. 63 depicts the DVS isotherm of Form A DL-tartrate salt of Compound 1.

In some embodiments, Form A DL-tartrate salt is characterized by the dynamic vapor sorption (DVS) isotherm pattern depicted in FIG. 63.

Figure 64:
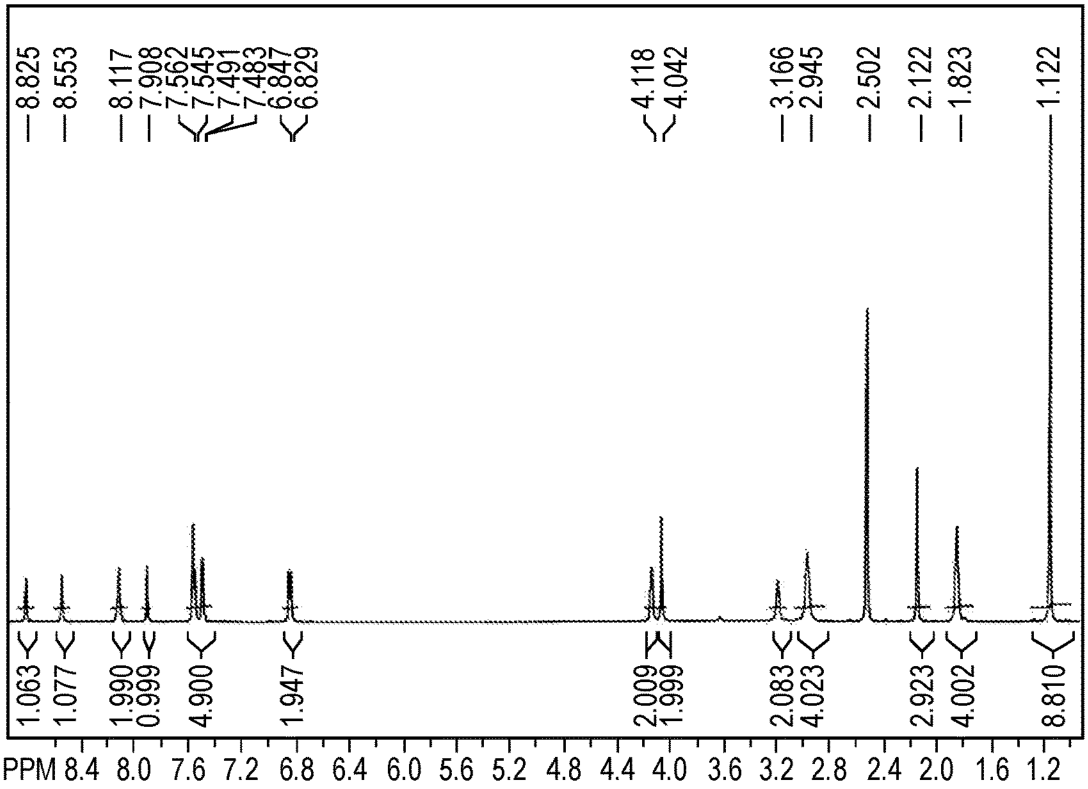
FIG. 64 depicts the $^1$H-NMR spectrum of Form A DL-tartrate salt of Compound 1.

In some embodiments, Form A DL-tartrate salt is characterized by the $^{1}$H NMR depicted in FIG. 64.

In some embodiments, a crystalline DL-tartrate salt of Compound 1 is characterized by one or more peaks in its X-ray powder diffraction pattern selected from 5.9, 9.7, 13.1, 13.4, 16.9, and 17.9±0.2 degrees 2θ. In some such embodiments, a complex form of Compound 1 is Form B DL-tartrate salt.

In some embodiments, Form B DL-tartrate salt is characterized by the following peaks in its X-ray powder diffraction pattern:

| Position ° 2θ ± 0.2 degrees | d-spacing [Å] | Height [cts] |
|---|---|---|
| 5.9 | 14.882 | 1498 |
| 9.7 | 9.106 | 790 |
| 12.4 | 7.137 | 620 |
| 12.6 | 7.015 | 824 |
| 13.1 | 6.736 | 5330 |
| 13.4 | 6.615 | 1566 |
| 14.0 | 6.330 | 1105 |
| 14.6 | 6.076 | 632 |
| 14.8 | 5.992 | 618 |
| 15.5 | 5.708 | 1622 |
| 16.1 | 5.499 | 1159 |
| 16.4 | 5.403 | 1491 |
| 16.6 | 5.325 | 1196 |
| 16.9 | 5.235 | 6795 |

-continued

| Position ° 2θ ± 0.2 degrees | d-spacing [Å] | Height [cts] |
|---|---|---|
| 17.4 | 5.083 | 1109 |
| 17.9 | 4.959 | 5788 |
| 18.4 | 4.812 | 1275 |
| 18.8 | 4.732 | 5043 |
| 21.0 | 4.238 | 502 |
| 21.3 | 4.179 | 1777 |
| 23.5 | 3.782 | 1835 |
| 23.9 | 3.719 | 1302 |
| 24.5 | 3.636 | 3815 |
| 25.4 | 3.507 | 1010 |
| 26.3 | 3.392 | 683 |
| 27.6 | 3.228 | 1013 |
| 28.2 | 3.170 | 1812 |
| 29.4 | 3.041 | 1037 |
| 29.6 | 3.014 | 1780 |
| 30.1 | 2.972 | 496 |
| 34.8 | 2.575 | 544 |
| 18.4 | 4.812 | 1275 |

Figure 65:
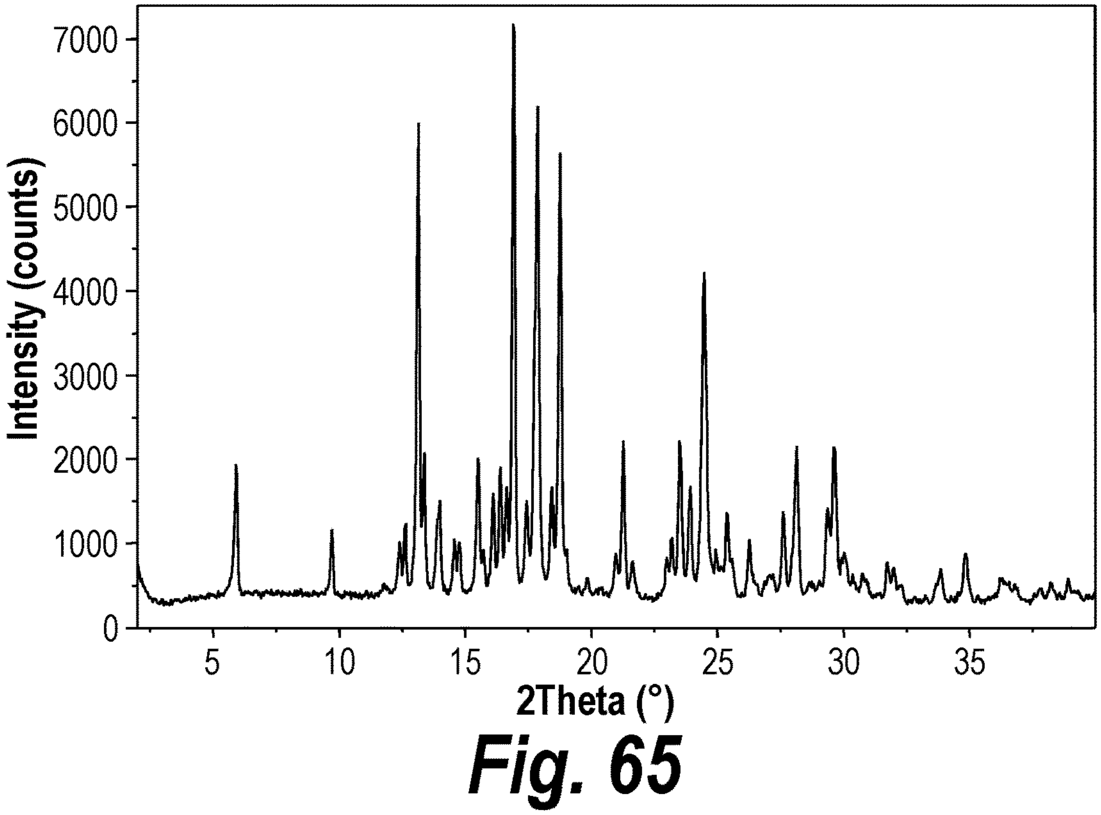
FIG. 65 depicts the XRPD pattern of Form B DL-tartrate salt of Compound 1.

In some embodiments, Form B DL-tartrate salt is characterized by the x-ray powder diffraction (XRPD) pattern depicted in FIG. 65.

Figure 66:
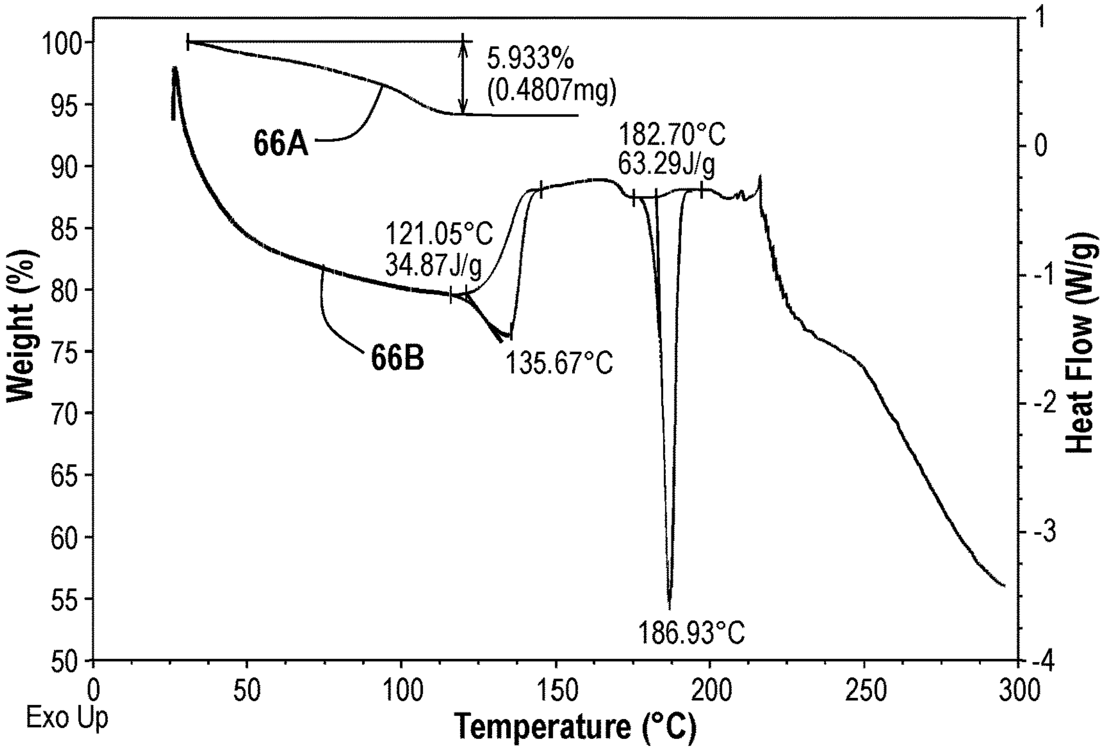
FIG. 66 depicts the TGA pattern of Form B DL-tartrate salt of Compound 1 (66A), and the DSC pattern of Form B DL-tartrate salt of Compound 1 (66B).

In some embodiments, Form B DL-tartrate salt is characterized by the thermogravimetric analysis (TGA) pattern depicted in FIG. 66, trace 66A.

In some embodiments, Form B DL-tartrate salt is characterized by the differential scanning calorimetry (DSC) pattern depicted in FIG. 66, trace 66B.

In some embodiments of a complex form of Compound 1, X is succinic acid. In some such embodiments, a complex form of Compound 1 is a succinate salt. In some embodiments, a succinate salt of Compound 1 is a crystalline succinate salt. In some embodiments, a crystalline succinate salt of Compound 1 is characterized by one or more peaks in its X-ray powder diffraction pattern selected from 5.0, 5.4, 6.0, 6.4, 6.8, and 16.7±0.2 degrees 2θ. In some such embodiments, a complex form of Compound 1 is Form A succinate salt.

In some embodiments, Form A succinate salt is characterized by the following peaks in its X-ray powder diffraction pattern:

| Position ° 2θ ± 0.2 degrees | d-spacing [Å] | Height [cts] |
|---|---|---|
| 5.0 | 17.537 | 1910 |
| 5.4 | 16.421 | 2826 |
| 6.0 | 14.743 | 490 |
| 6.4 | 13.832 | 573 |
| 6.8 | 13.004 | 447 |
| 8.0 | 11.026 | 270 |
| 10.1 | 8.794 | 903 |
| 10.8 | 8.222 | 383 |
| 12.0 | 7.378 | 384 |
| 12.8 | 6.903 | 463 |
| 13.6 | 6.506 | 801 |
| 13.9 | 6.364 | 499 |
| 15.1 | 5.853 | 494 |
| 16.0 | 5.549 | 845 |
| 16.7 | 5.301 | 1287 |
| 17.0 | 5.204 | 791 |
| 17.3 | 5.115 | 683 |
| 18.5 | 4.786 | 672 |
| 19.2 | 4.612 | 626 |
| 20.1 | 4.427 | 541 |
| 20.8 | 4.274 | 393 |
| 22.9 | 3.885 | 365 |

-continued

| Position ° 2θ ± 0.2 degrees | d-spacing [Å] | Height [cts] |
|---|---|---|
| 23.5 | 3.782 | 271 |
| 24.5 | 3.629 | 562 |
| 25.0 | 3.566 | 525 |
| 25.4 | 3.509 | 512 |
| 25.8 | 3.455 | 448 |
| 27.3 | 3.267 | 219 |
| 28.0 | 3.188 | 215 |
| 30.6 | 2.923 | 85 |

Figure 67:
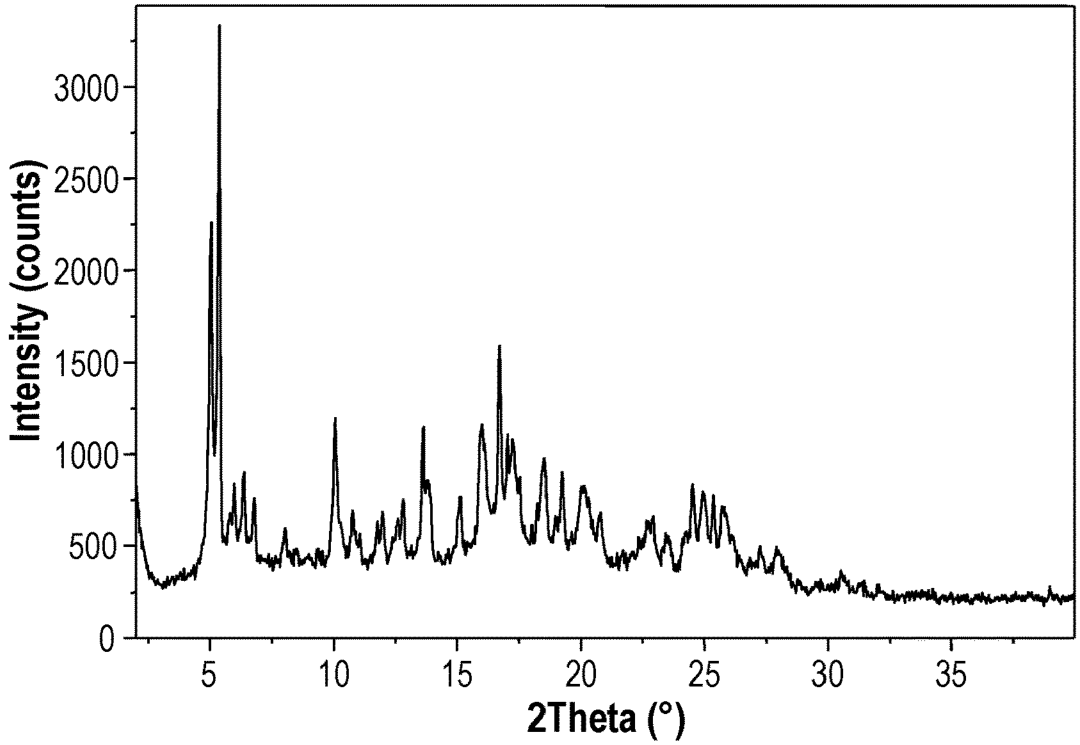
FIG. 67 depicts the XRPD pattern of Form A succinate salt of Compound 1.

In some embodiments, Form A succinate salt is characterized by the x-ray powder diffraction (XRPD) pattern depicted in FIG. 67.

Figure 68:
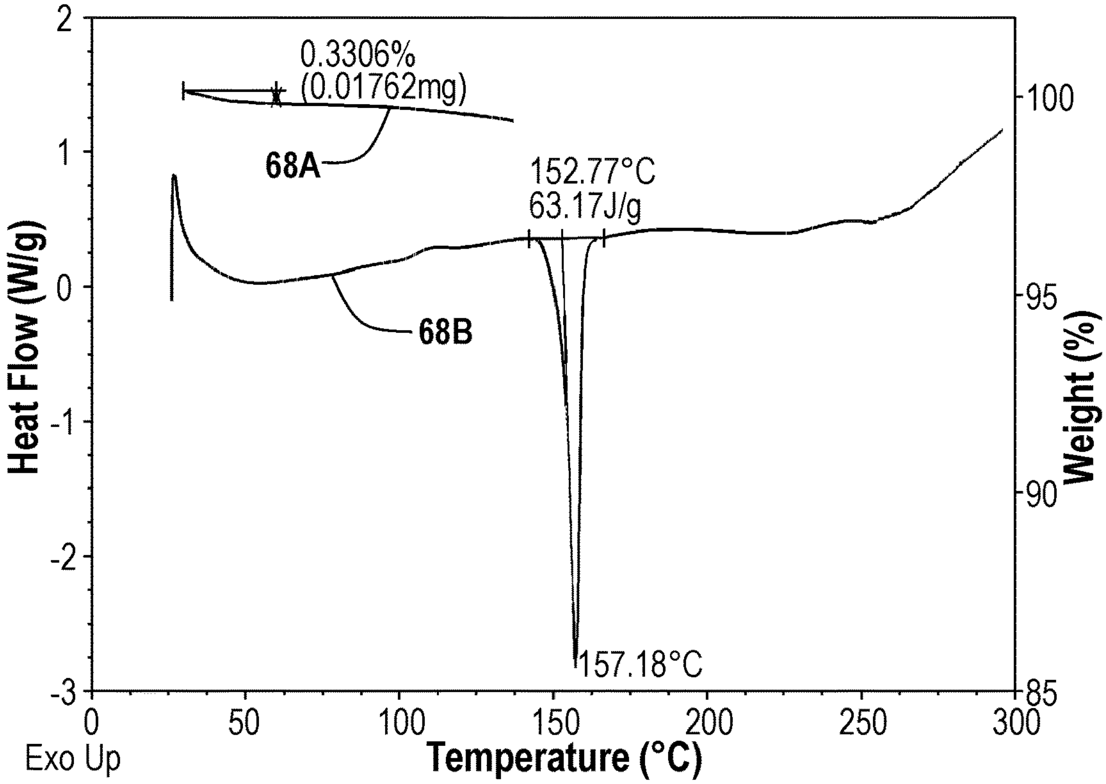
FIG. 68 depicts the TGA pattern of Form A succinate salt of Compound 1 (68A), and the DSC pattern of Form A succinate salt of Compound 1 (68B).

In some embodiments, Form A succinate salt is characterized by the thermogravimetric analysis (TGA) pattern depicted in FIG. 68, trace 68A.

In some embodiments, Form A succinate salt is characterized by the differential scanning calorimetry (DSC) pattern depicted in FIG. 68, trace 68B.

In some embodiments, a complex form of Compound 1 comprises one equivalent of succinic acid. In some embodiments, a crystalline succinate salt of Compound 1 is characterized by one or more peaks in its X-ray powder diffraction pattern selected from 4.7, 5.8, 6.2, 6.7, 9.4, and 10.0±0.2 degrees 2θ. In some such embodiments, a complex form of Compound 1 is Form B succinate salt.

In some embodiments, Form B succinate salt is characterized by the following peaks in its X-ray powder diffraction pattern:

| Position ° 2θ ± 0.2 degrees | d-spacing [Å] | Height [cts] |
|---|---|---|
| 4.7 | 18.855 | 2977 |
| 5.2 | 17.044 | 156 |
| 5.8 | 15.223 | 451 |
| 6.2 | 14.359 | 339 |
| 6.7 | 13.177 | 298 |
| 8.3 | 10.634 | 177 |
| 9.4 | 9.437 | 1595 |
| 10.0 | 8.856 | 632 |
| 11.3 | 7.814 | 125 |
| 11.6 | 7.611 | 139 |
| 12.2 | 7.262 | 468 |
| 13.2 | 6.722 | 225 |
| 13.4 | 6.614 | 289 |
| 14.4 | 6.165 | 168 |
| 15.4 | 5.753 | 1280 |
| 15.7 | 5.652 | 972 |
| 16.0 | 5.551 | 466 |
| 18.1 | 4.895 | 432 |
| 18.7 | 4.757 | 623 |
| 19.0 | 4.667 | 1040 |
| 19.3 | 4.609 | 391 |
| 19.6 | 4.521 | 174 |
| 20.6 | 4.309 | 733 |
| 22.6 | 3.941 | 413 |
| 24.3 | 3.670 | 194 |
| 24.7 | 3.602 | 184 |
| 25.0 | 3.564 | 128 |
| 26.0 | 3.429 | 575 |

Figure 69:
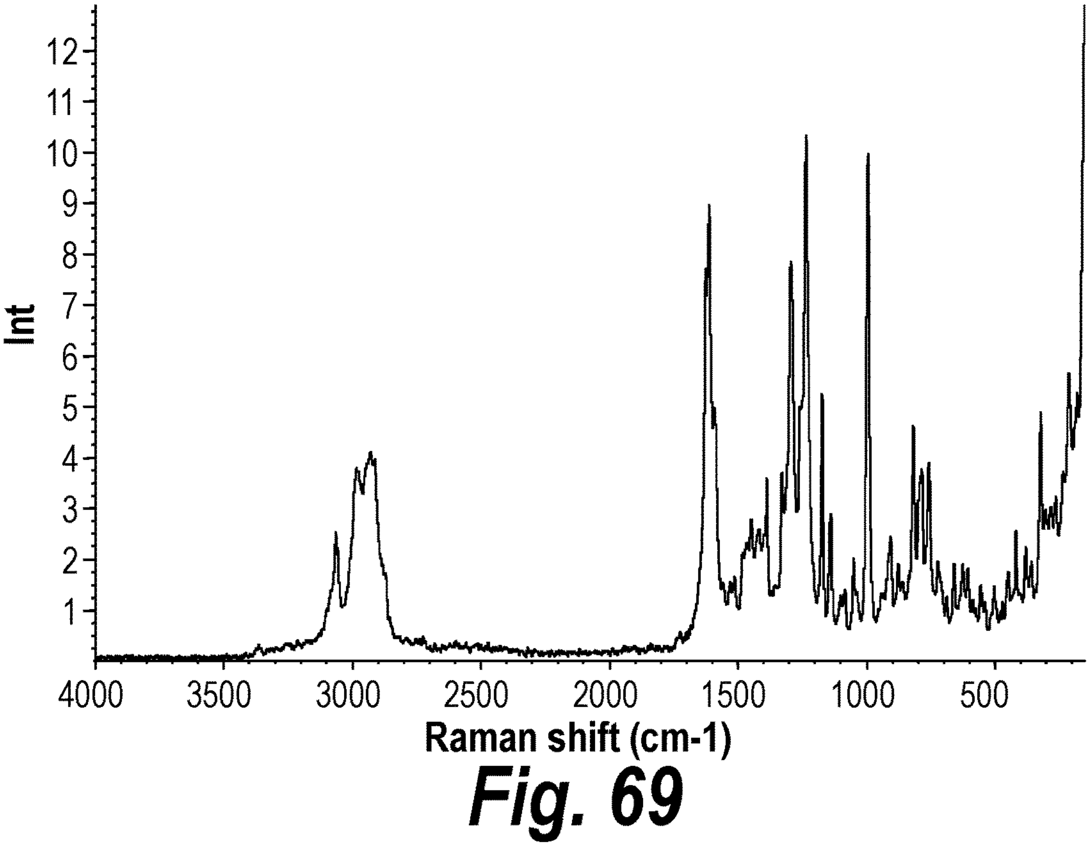
FIG. 69 depicts the FT-Raman spectrum of Form B succinate salt of Compound 1.

In some embodiments, Form B succinate salt is characterized by the FT-Raman spectrum depicted in FIG. 69.

Figure 70:
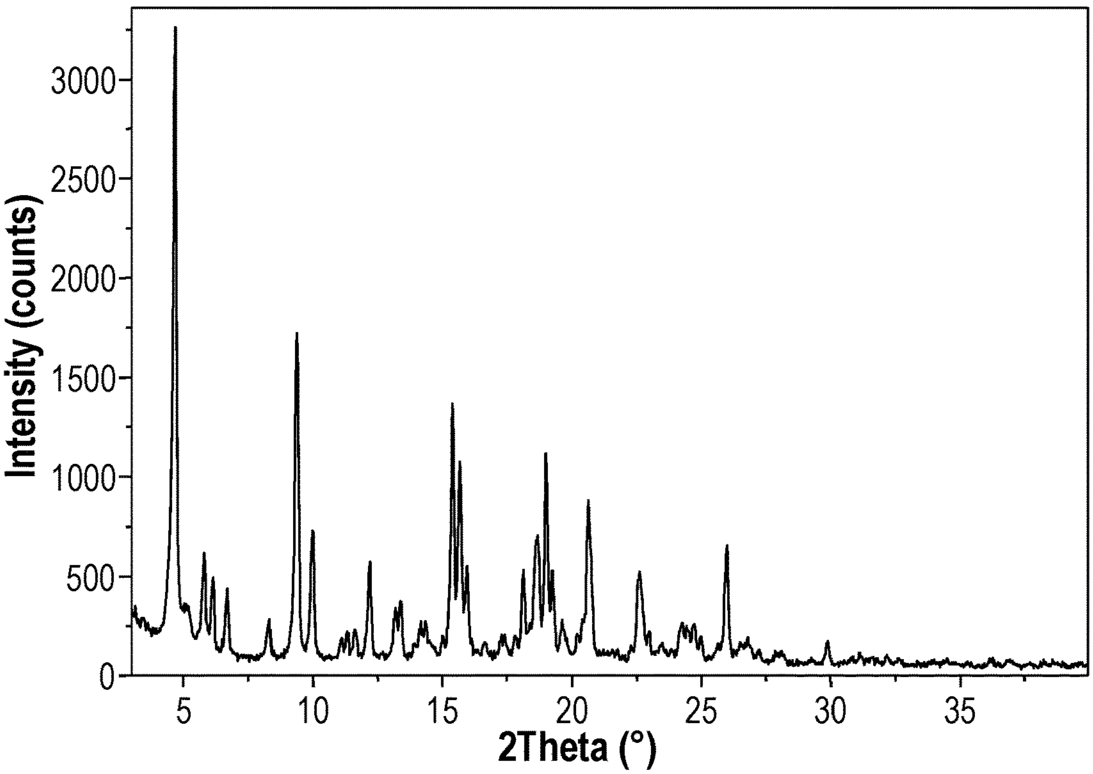
FIG. 70 depicts the XRPD pattern of Form B succinate salt of Compound 1.

In some embodiments, Form B succinate salt is characterized by the x-ray powder diffraction (XRPD) pattern depicted in FIG. 70.

Figure 71:
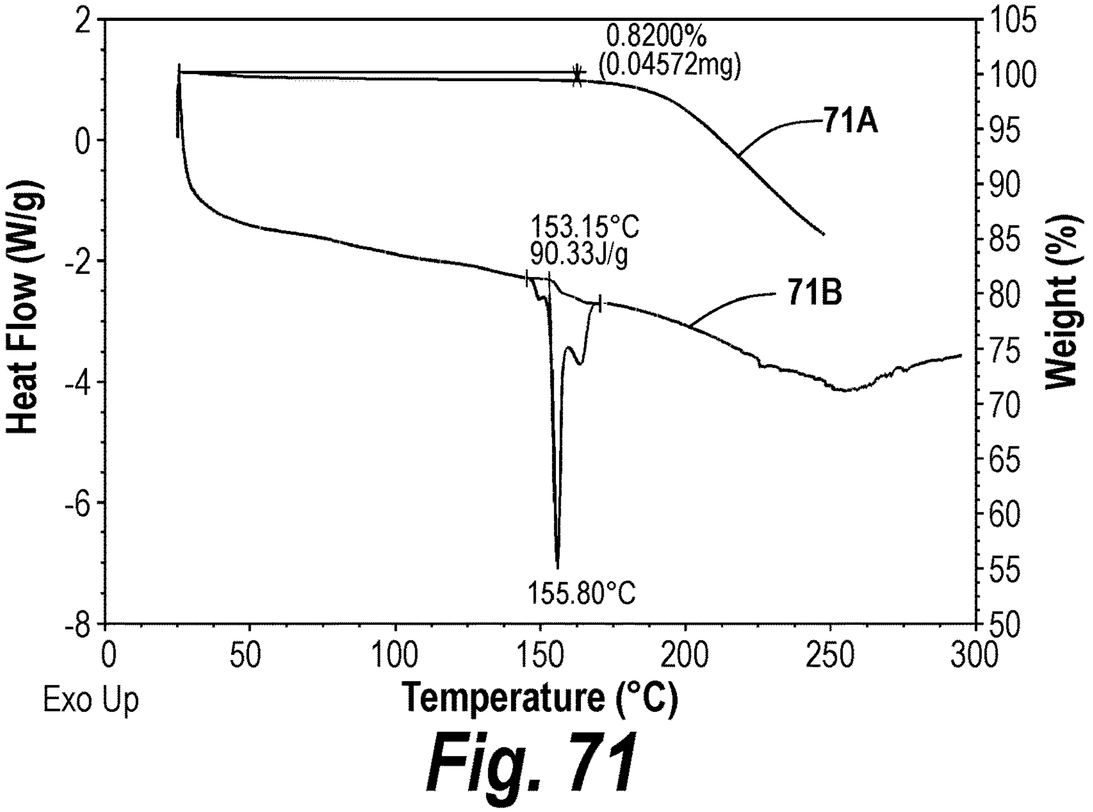
FIG. 71 depicts the TGA pattern of Form B succinate salt of Compound 1 (71A), and the DSC pattern of Form B succinate salt of Compound 1 (71B).

In some embodiments, Form B succinate salt is characterized by the thermogravimetric analysis (TGA) pattern depicted in FIG. 71, trace 71A.

In some embodiments, Form B succinate salt is characterized by the differential scanning calorimetry (DSC) pattern depicted in FIG. 71, trace 71B.

Figure 72:
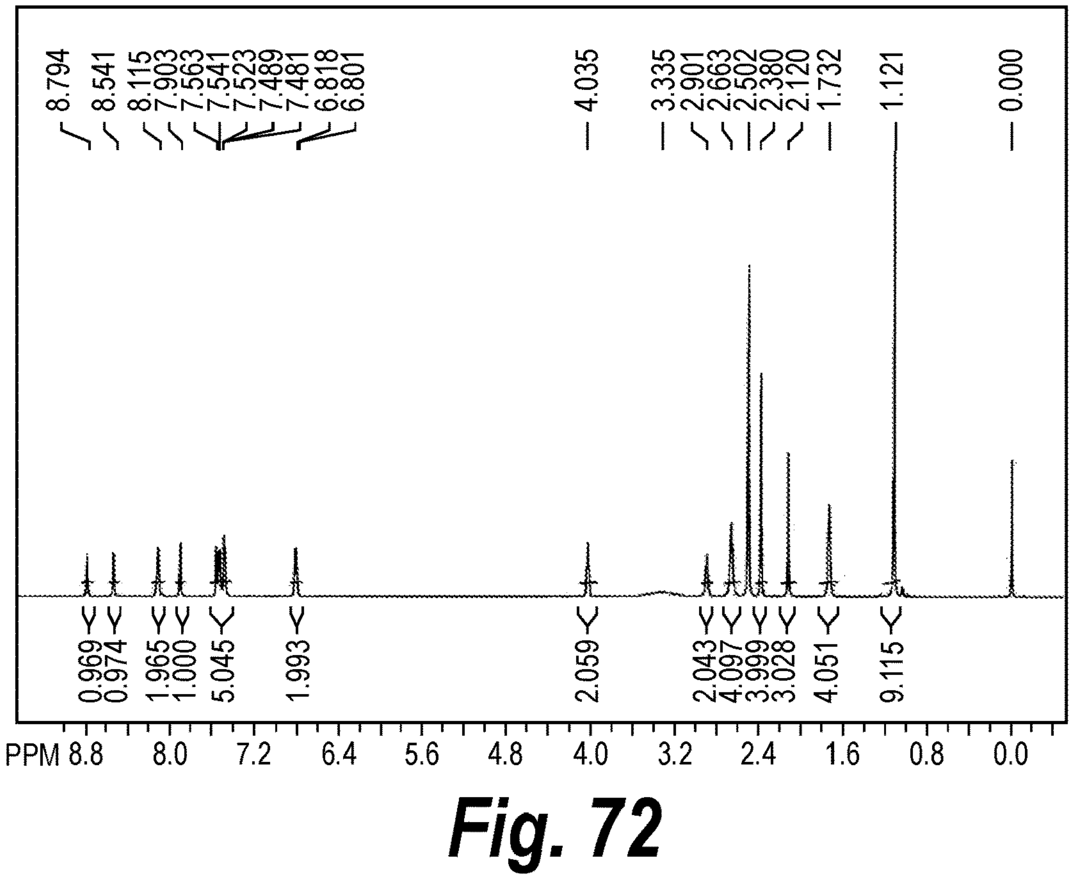
FIG. 72 depicts the $^1$H-NMR spectrum of Form B succinate salt of Compound 1.

In some embodiments, Form B succinate salt is characterized by the $^{1}$H NMR depicted in FIG. 72.

In some embodiments of a complex form of Compound 1, X is gentisic acid. In some such embodiments, a complex form of Compound 1 is a gentisate salt. In some embodiments, a complex form of Compound 1 comprises one equivalent of gentisic acid. In some embodiments, a gentisate salt of Compound 1 is a crystalline gentisate salt. In some embodiments, a crystalline gentisate salt of Compound 1 is characterized by one or more peaks in its X-ray powder diffraction pattern selected from 3.9, 7.9, 11.9, 15.8, and 17.0±0.2 degrees 2θ. In some such embodiments, a complex form of Compound 1 is Form A gentisate salt.

In some embodiments, Form A gentisate salt is characterized by the following peaks in its X-ray powder diffraction pattern:

| Position ° 2θ ± 0.2 degrees | d-spacing [Å] | Height [cts] |
|---|---|---|
| 3.9 | 22.426 | 223 |
| 7.9 | 11.187 | 1891 |
| 9.0 | 9.790 | 169 |
| 11.9 | 7.460 | 5083 |
| 13.6 | 6.520 | 199 |
| 14.4 | 6.169 | 161 |
| 14.8 | 6.006 | 350 |
| 15.8 | 5.593 | 1922 |
| 16.3 | 5.424 | 326 |
| 17.0 | 5.215 | 451 |
| 17.5 | 5.066 | 479 |
| 18.1 | 4.902 | 256 |
| 18.8 | 4.714 | 1155 |
| 19.8 | 4.478 | 641 |
| 20.7 | 4.300 | 256 |
| 21.6 | 4.106 | 565 |
| 21.9 | 4.050 | 559 |
| 23.3 | 3.816 | 252 |
| 24.1 | 3.693 | 1008 |
| 25.1 | 3.543 | 1611 |
| 25.7 | 3.462 | 617 |
| 26.3 | 3.384 | 123 |
| 27.3 | 3.266 | 102 |
| 27.9 | 3.202 | 131 |
| 28.7 | 3.113 | 104 |
| 33.1 | 2.705 | 110 |

Figure 73:
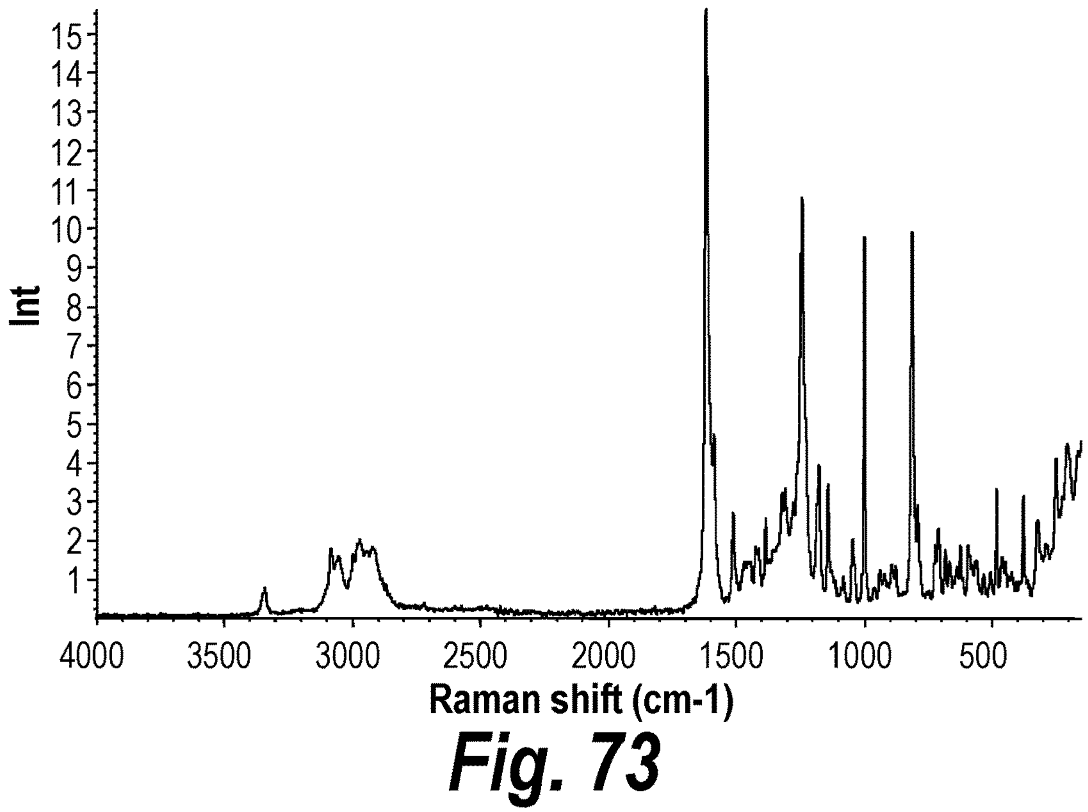
FIG. 73 depicts the FT-Raman spectrum of Form A gentisate salt of Compound 1.

In some embodiments, Form A gentisate salt is characterized by the FT-Raman spectrum depicted in FIG. 73.

Figure 74:
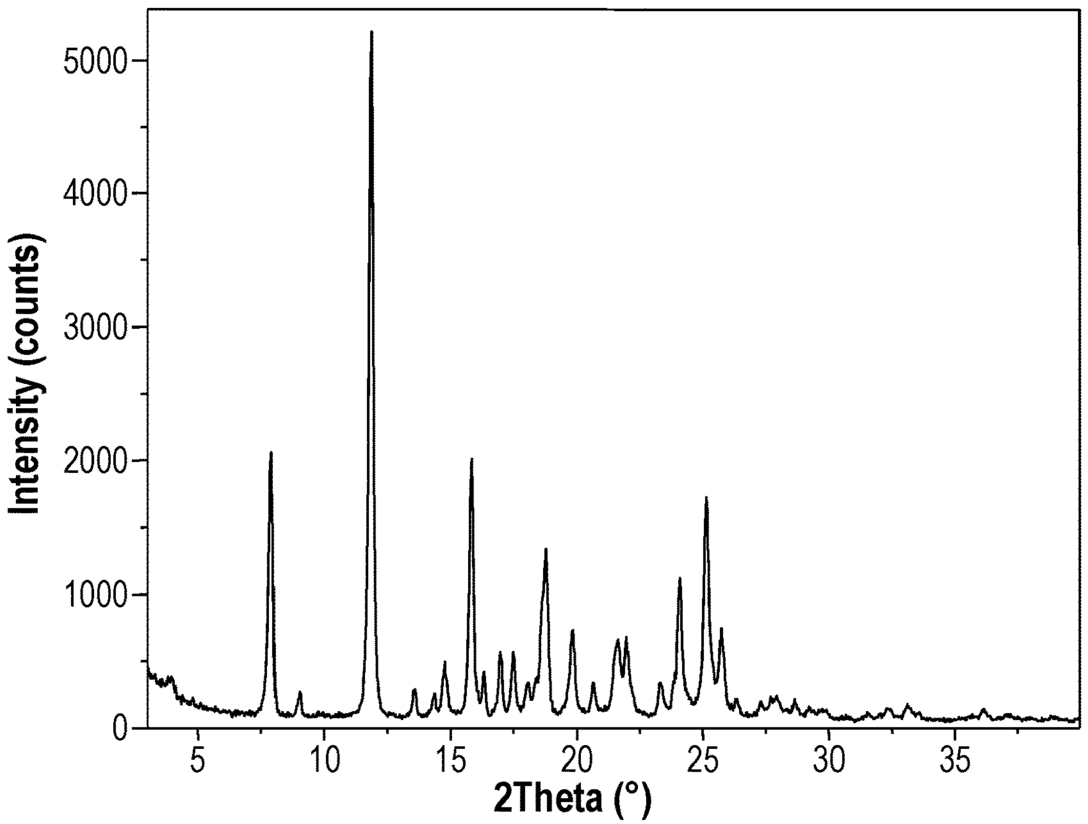
FIG. 74 depicts the XRPD pattern of Form A gentisate salt of Compound 1.

In some embodiments, Form A gentisate salt is characterized by the x-ray powder diffraction (XRPD) pattern depicted in FIG. 74.

Figure 75:
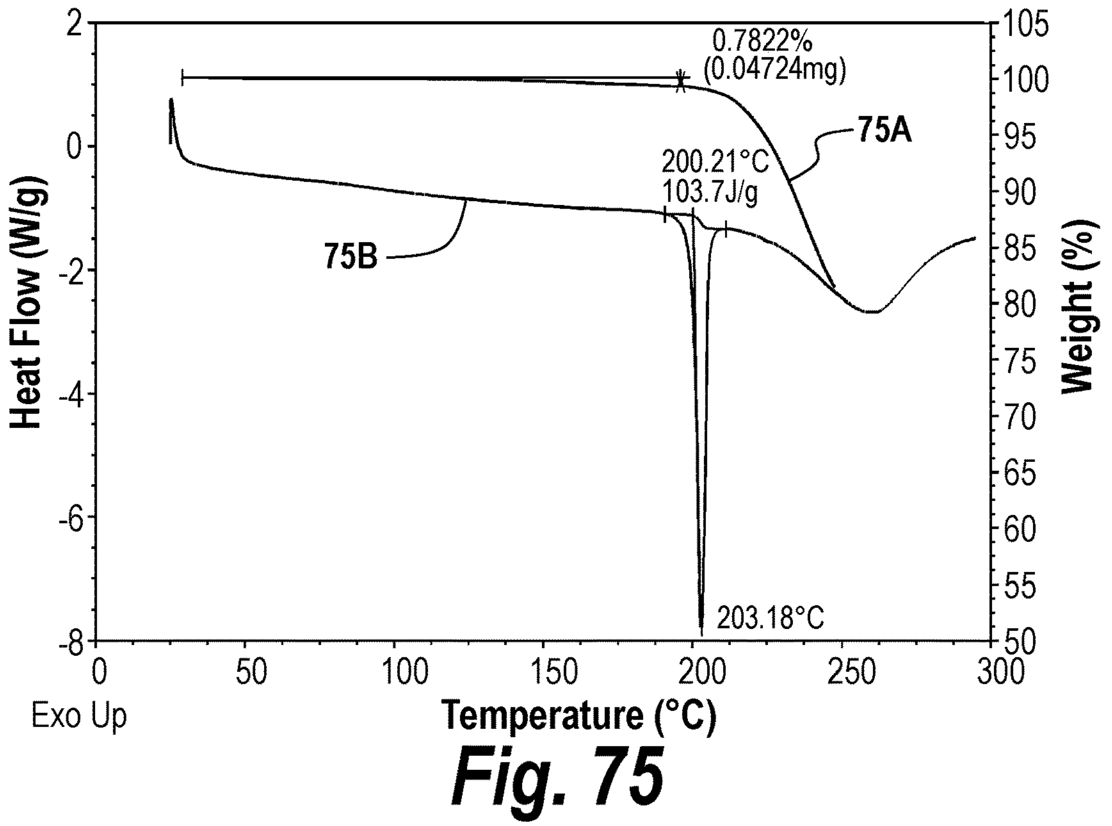
FIG. 75 depicts the TGA pattern of Form A gentisate salt of Compound 1 (75A), and the DSC pattern of Form A gentisate salt of Compound 1 (75B).

In some embodiments, Form A gentisate salt is characterized by the thermogravimetric analysis (TGA) pattern depicted in FIG. 75, trace 75A.

In some embodiments, Form A gentisate salt is characterized by the differential scanning calorimetry (DSC) pattern depicted in FIG. 75, trace 75B.

Figure 76:
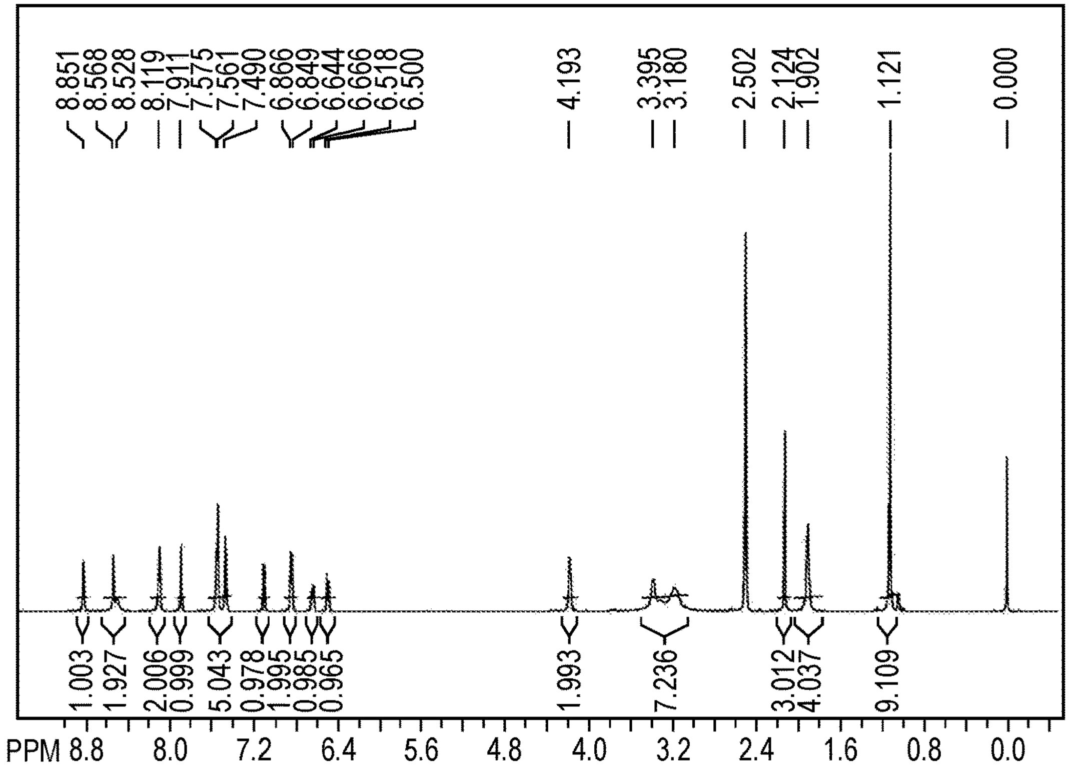
FIG. 76 depicts the $^1$H-NMR spectrum of Form A gentisate salt of Compound 1.

In some embodiments, Form A gentisate salt is characterized by the $^{1}$H NMR depicted in FIG. 76.

In some embodiments of a complex form of Compound 1, X is hippuric acid. In some such embodiments, a complex form of Compound 1 is a hippurate salt. In some embodiments, a complex form of Compound 1 comprises one equivalent of hippuric acid. In some embodiments, a hippurate salt of Compound 1 is a crystalline hippurate salt. In some embodiments, a crystalline hippurate salt of Compound 1 is characterized by one or more peaks in its X-ray powder diffraction pattern selected from 7.6, 9.7, 11.4, 15.2, and 18.6±0.2 degrees 2θ. In some such embodiments, a complex form of Compound 1 is Form A hippurate salt.

In some embodiments, Form A hippurate salt is characterized by the following peaks in its X-ray powder diffraction pattern:

| Position ° 2θ ± 0.2 degrees | d-spacing [Å] | Height [cts] |
|---|---|---|
| 3.8 | 23.433 | 214 |
| 7.6 | 11.687 | 2070 |
| 9.7 | 9.105 | 674 |
| 11.4 | 7.790 | 7720 |
| 13.5 | 6.558 | 428 |
| 14.4 | 6.153 | 524 |
| 14.8 | 5.977 | 261 |
| 15.2 | 5.840 | 5003 |
| 16.1 | 5.496 | 202 |
| 16.9 | 5.239 | 578 |
| 17.3 | 5.115 | 467 |
| 18.0 | 4.933 | 528 |
| 18.6 | 4.775 | 1963 |
| 19.0 | 4.670 | 721 |
| 19.5 | 4.546 | 456 |
| 19.8 | 4.487 | 756 |
| 20.7 | 4.291 | 293 |
| 21.2 | 4.182 | 609 |
| 22.2 | 4.001 | 577 |
| 22.8 | 3.908 | 2086 |
| 23.9 | 3.725 | 845 |
| 24.3 | 3.665 | 199 |
| 24.5 | 3.636 | 219 |
| 24.8 | 3.589 | 742 |
| 25.2 | 3.539 | 388 |
| 26.2 | 3.404 | 287 |
| 27.2 | 3.279 | 1452 |
| 27.7 | 3.224 | 288 |
| 28.1 | 3.174 | 256 |

Figure 77:
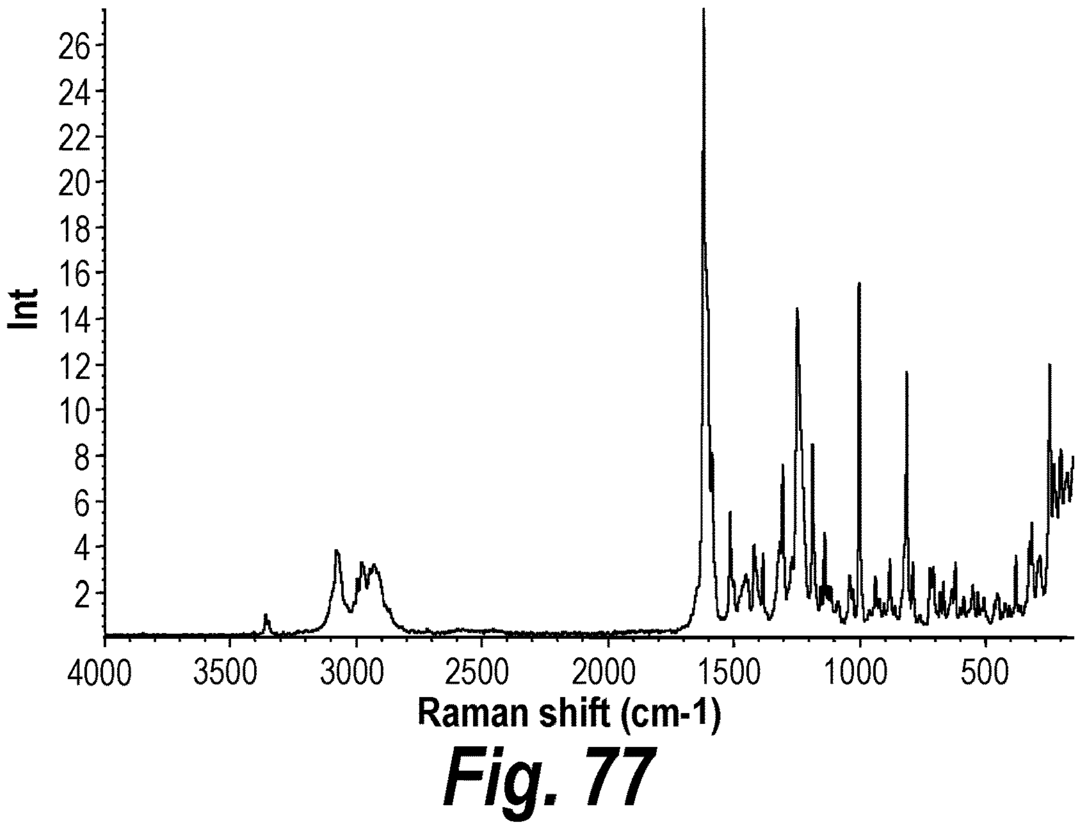
FIG. 77 depicts the FT-Raman spectrum of Form A hippurate salt of Compound 1.

In some embodiments, Form A hippurate salt is characterized by the FT-Raman spectrum depicted in FIG. 77.

Figure 78:
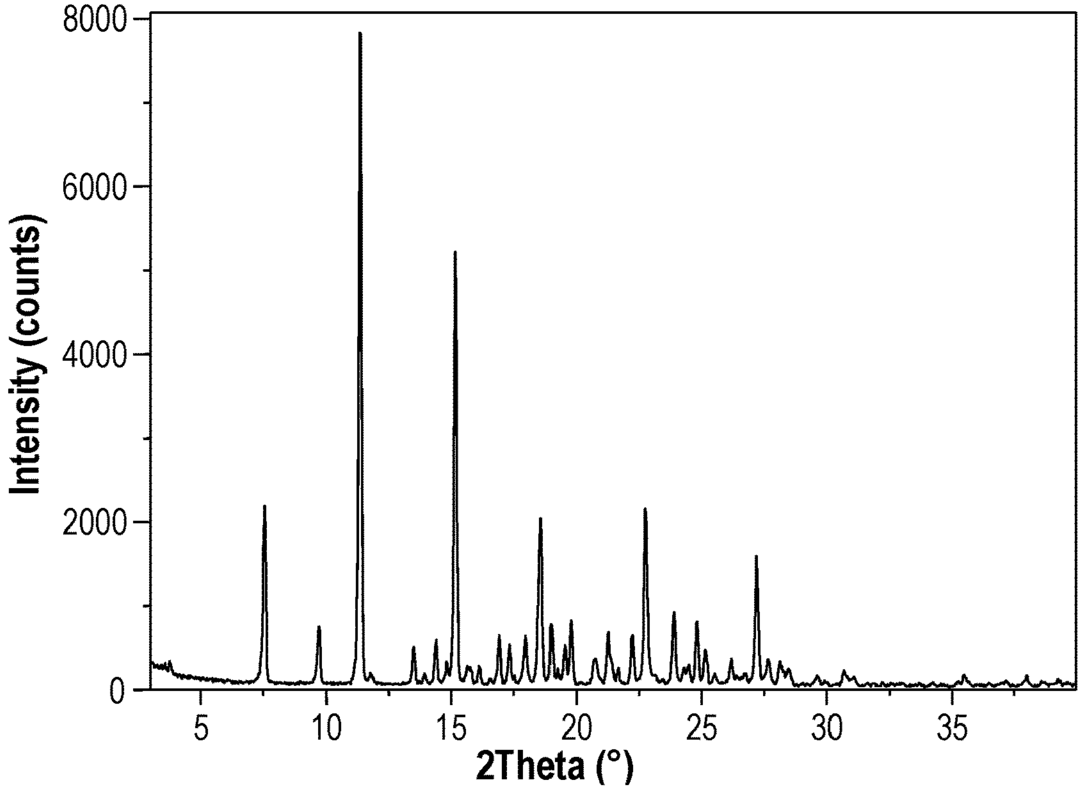
FIG. 78 depicts the XRPD pattern of Form A hippurate salt of Compound 1.

In some embodiments, Form A hippurate salt is characterized by the x-ray powder diffraction (XRPD) pattern depicted in FIG. 78.

Figure 79:
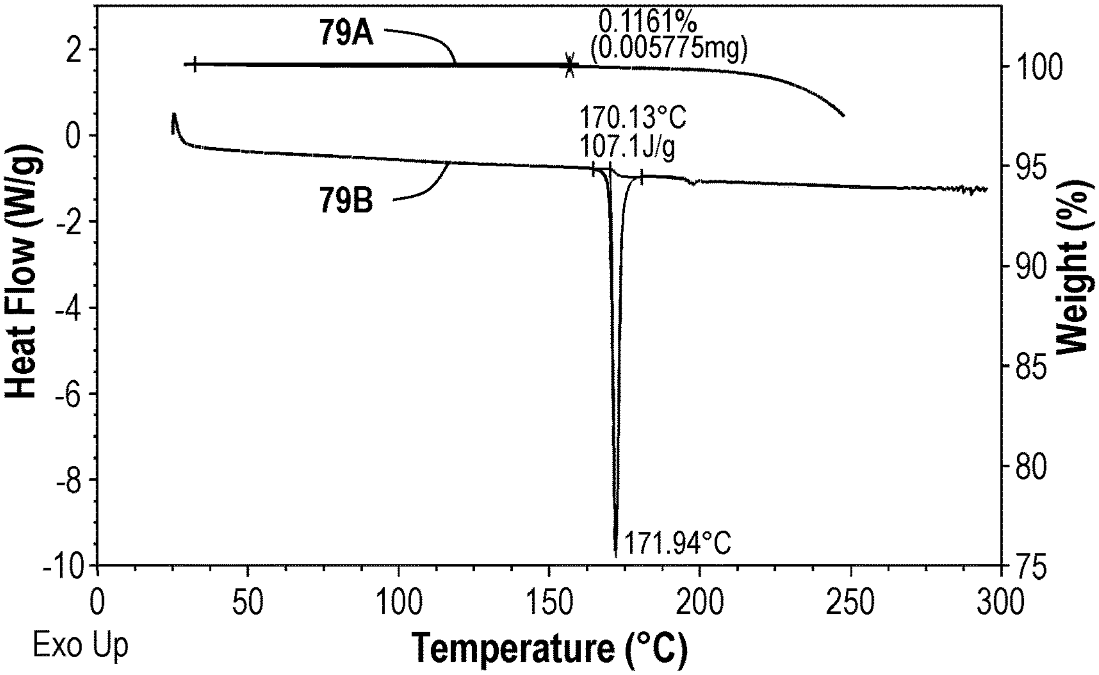
FIG. 79 depicts the TGA pattern of Form A hippurate salt of Compound 1 (79A), and the DSC pattern of Form A hippurate salt of Compound 1 (79B).

In some embodiments, Form A hippurate salt is characterized by the thermogravimetric analysis (TGA) pattern depicted in FIG. 79, trace 79A.

In some embodiments, Form A hippurate salt is characterized by the differential scanning calorimetry (DSC) pattern depicted in FIG. 79, trace 79B.

Figure 80:
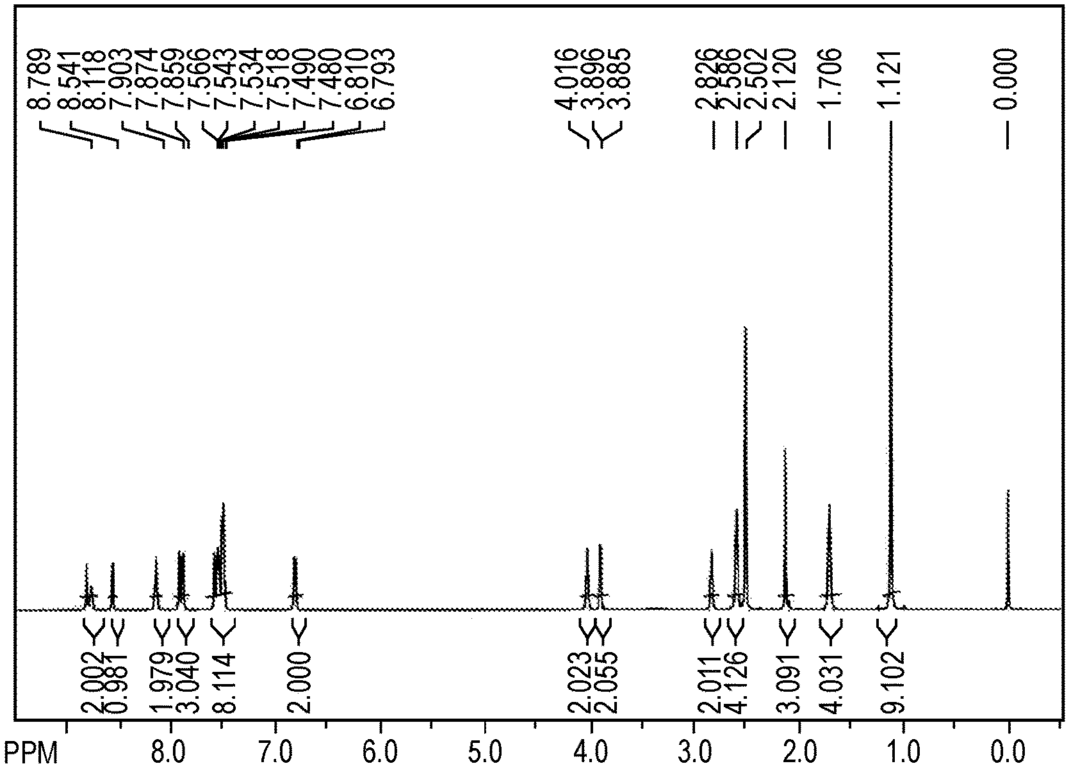
FIG. 80 depicts the $^1$H-NMR spectrum of Form A hippurate salt of Compound 1.

In some embodiments, Form A hippurate salt is characterized by the $^1$H NMR depicted in FIG. 80.

In some embodiments of a complex form of Compound 1, X is adipic acid. In some such embodiments, a complex form of Compound 1 is an adipate salt. In some embodiments, a complex form of Compound 1 comprises 0.9 equivalents of adipic acid. In some embodiments, an adipate salt of Compound 1 is a crystalline adipate salt. In some embodiments, a crystalline adipate salt of Compound 1 is characterized by one or more peaks in its X-ray powder diffraction pattern selected from 8.0, 8.6, 9.5, 12.0, 12.6, 13.0, 15.4, and 16.1±0.2 degrees 2θ. In some such embodiments, a complex form of Compound 1 is Form A adipate salt.

In some embodiments, Form A adipate salt is characterized by the following peaks in its X-ray powder diffraction pattern:

| Position ° 2θ ± 0.2 degrees | d-spacing [Å] | Height [cts] |
|---|---|---|
| 8.0 | 11.061 | 1244 |
| 8.6 | 10.282 | 267 |
| 9.5 | 9.324 | 2272 |
| 11.6 | 7.639 | 929 |
| 12.0 | 7.373 | 3181 |
| 12.6 | 7.025 | 1189 |
| 13.0 | 6.820 | 1297 |
| 13.6 | 6.514 | 245 |
| 15.1 | 5.860 | 1190 |
| 15.4 | 5.738 | 2138 |
| 16.1 | 5.489 | 3619 |
| 16.8 | 5.288 | 294 |
| 17.3 | 5.138 | 881 |
| 17.7 | 5.016 | 1387 |
| 17.9 | 4.942 | 965 |
| 18.4 | 4.825 | 1179 |
| 19.0 | 4.661 | 1221 |
| 19.3 | 4.592 | 800 |
| 20.1 | 4.424 | 1586 |
| 20.5 | 4.341 | 1593 |
| 21.0 | 4.222 | 653 |
| 21.4 | 4.152 | 322 |
| 21.8 | 4.080 | 1138 |
| 22.4 | 3.973 | 246 |
| 22.8 | 3.903 | 1511 |
| 23.3 | 3.821 | 2125 |
| 23.7 | 3.747 | 1462 |
| 24.2 | 3.670 | 323 |
| 24.8 | 3.595 | 821 |
| 25.3 | 3.514 | 2458 |
| 25.9 | 3.439 | 332 |
| 27.3 | 3.272 | 1419 |

Figure 81:
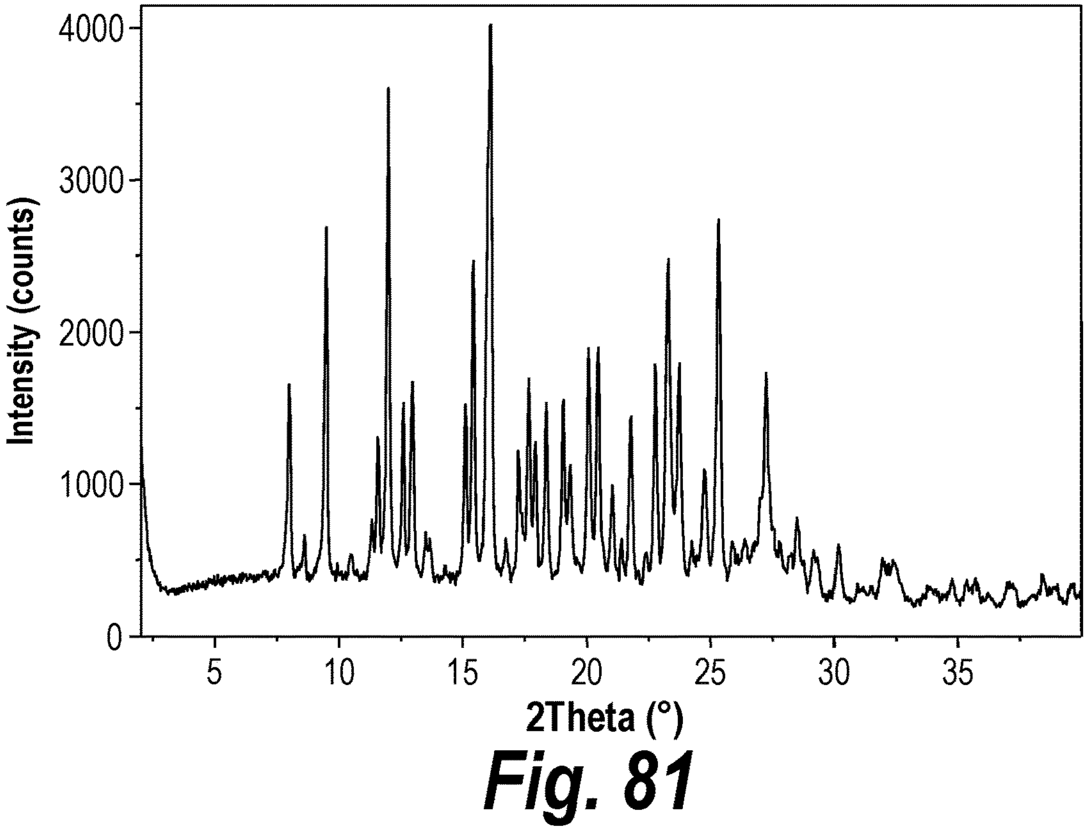
FIG. 81 depicts the XRPD pattern of Form A adipate salt of Compound 1.

In some embodiments, Form A adipate salt is characterized by the x-ray powder diffraction (XRPD) pattern depicted in FIG. 81.

Figure 82:
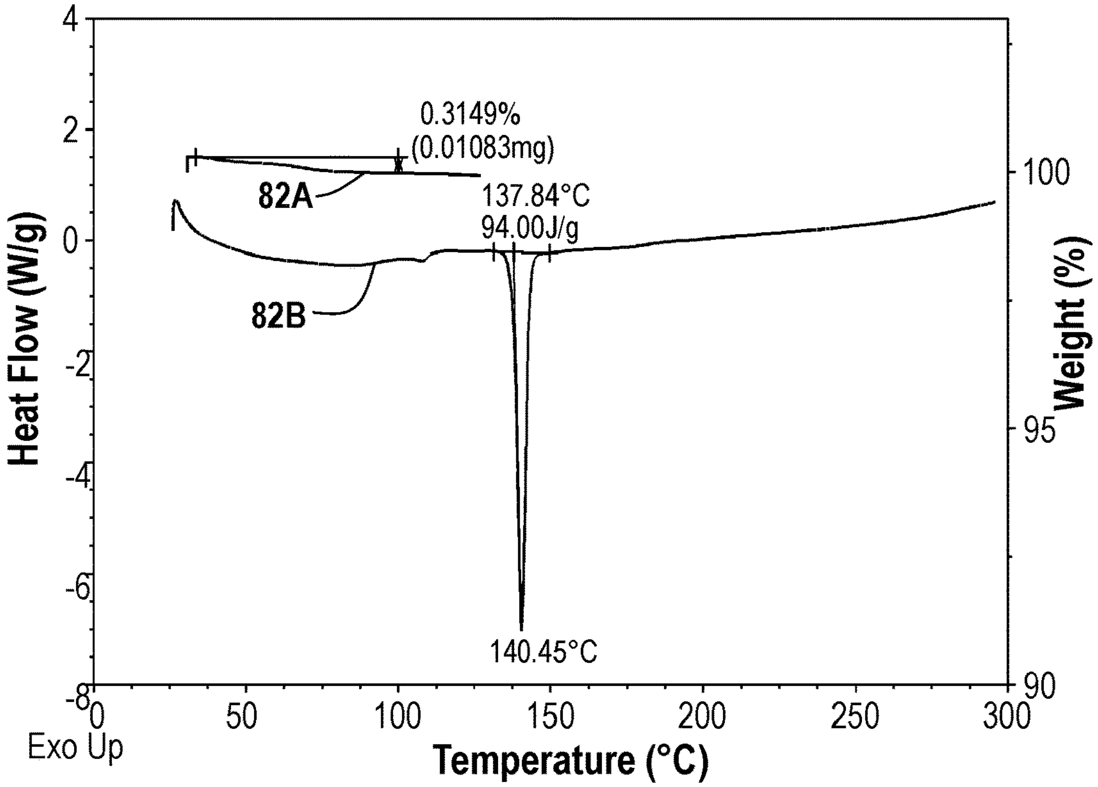
FIG. 82 depicts the TGA pattern of Form A adipate salt of Compound 1 (82A), and the DSC pattern of Form A adipate salt of Compound 1 (82B).

In some embodiments, Form A adipate salt is characterized by the thermogravimetric analysis (TGA) pattern depicted in FIG. 82, trace 82A.

In some embodiments, Form A adipate salt is characterized by the differential scanning calorimetry (DSC) pattern depicted in FIG. 82, trace 82B.

In some embodiments, a crystalline adipate salt of Compound 1 is characterized by one or more peaks in its X-ray powder diffraction pattern selected from 8.1, 9.5, 12.1, 15.7, 16.1, 20.2, and 20.5±0.2 degrees 2θ. In some such embodiments, a complex form of Compound 1 is Form C adipate salt.

In some embodiments, Form C adipate salt is characterized by the following peaks in its X-ray powder diffraction pattern:

| Position ° 2θ ± 0.2 degrees | d-spacing [Å] | Height [cts] |
|---|---|---|
| 4.0 | 21.935 | 262 |
| 8.1 | 10.959 | 3207 |
| 9.5 | 9.270 | 649 |
| 11.6 | 7.607 | 245 |
| 12.1 | 7.328 | 5088 |
| 12.6 | 7.016 | 278 |
| 13.0 | 6.799 | 510 |
| 13.4 | 6.592 | 333 |
| 13.8 | 6.440 | 192 |
| 15.2 | 5.844 | 252 |
| 15.5 | 5.720 | 624 |
| 15.7 | 5.653 | 1097 |
| 16.1 | 5.502 | 2663 |
| 16.9 | 5.239 | 337 |

-continued

| Position ° 2θ ± 0.2 degrees | d-spacing [Å] | Height [cts] |
|---|---|---|
| 17.5 | 5.080 | 321 |
| 17.7 | 5.003 | 619 |
| 18.3 | 4.842 | 652 |
| 19.1 | 4.647 | 353 |
| 20.2 | 4.406 | 1759 |
| 20.5 | 4.325 | 1123 |
| 21.0 | 4.228 | 375 |
| 21.8 | 4.073 | 480 |
| 23.0 | 3.869 | 737 |
| 23.3 | 3.821 | 1130 |
| 23.8 | 3.737 | 894 |
| 24.3 | 3.670 | 453 |
| 24.8 | 3.595 | 350 |
| 25.4 | 3.504 | 1850 |
| 26.5 | 3.363 | 282 |
| 26.8 | 3.323 | 295 |
| 27.1 | 3.293 | 584 |
| 27.3 | 3.263 | 893 |

Figure 83:
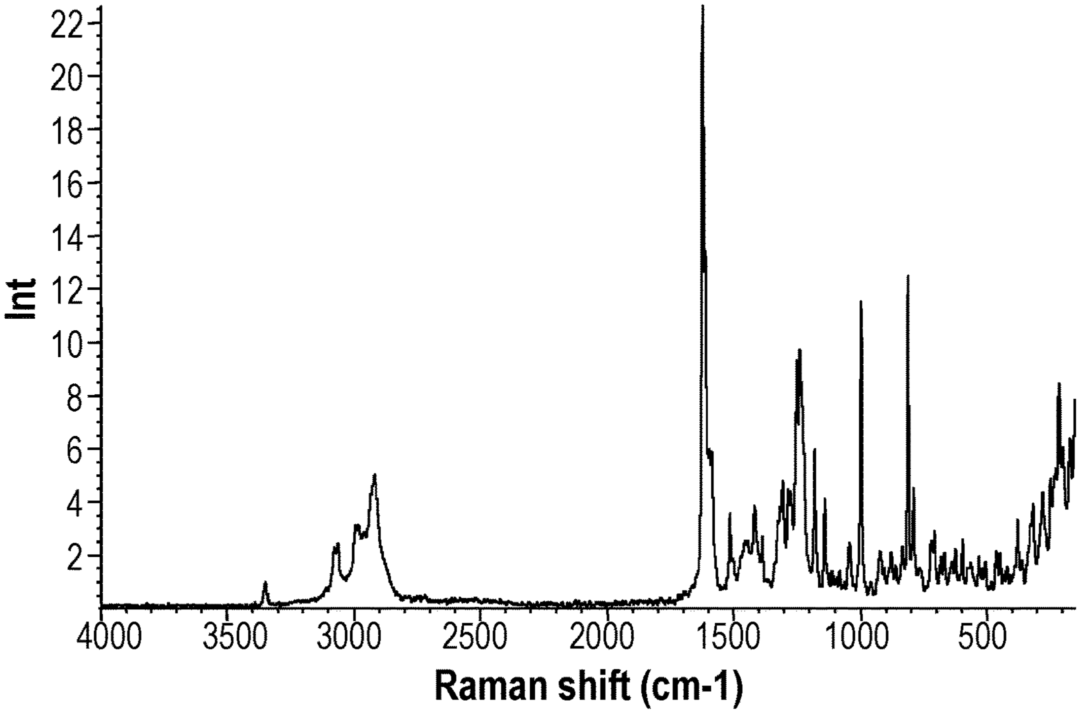
FIG. 83 depicts the FT-Raman spectrum of Form C adipate salt of Compound 1.

In some embodiments, Form C adipate salt is characterized by the FT-Raman spectrum depicted in FIG. 83.

Figure 84:
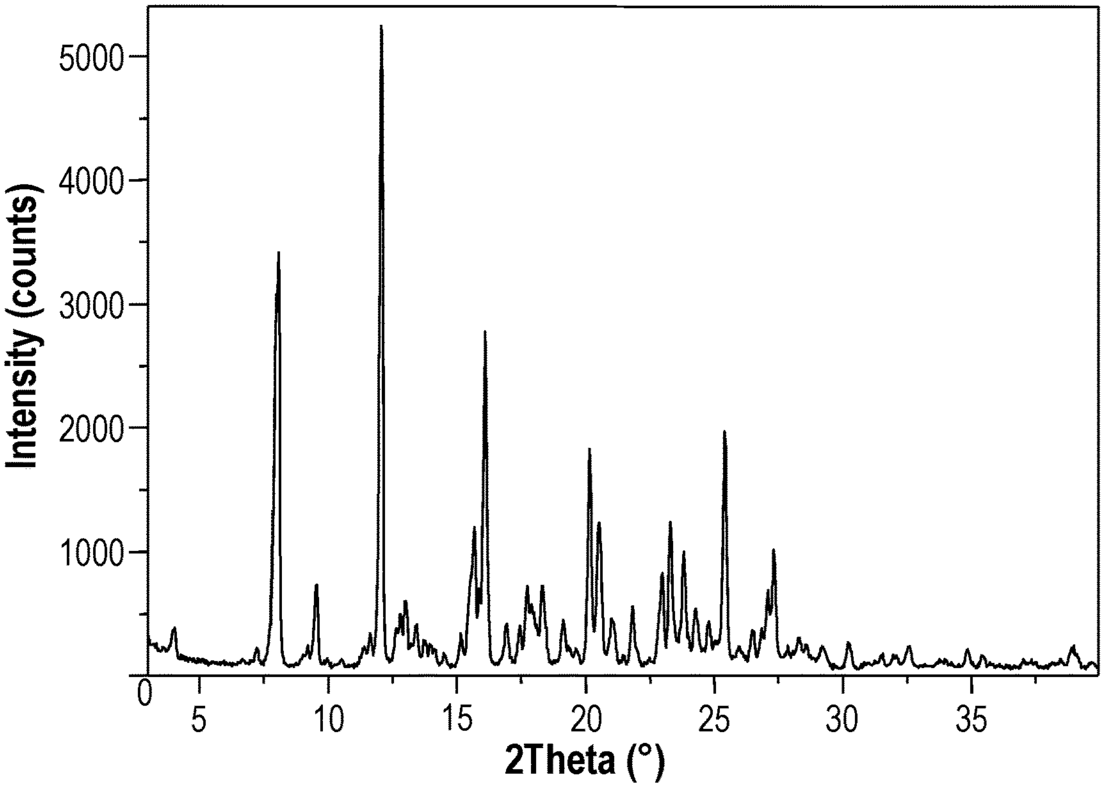
FIG. 84 depicts the XRPD pattern of Form C adipate salt of Compound 1.

In some embodiments, Form C adipate salt is characterized by the x-ray powder diffraction (XRPD) pattern depicted in FIG. 84.

Figure 85:
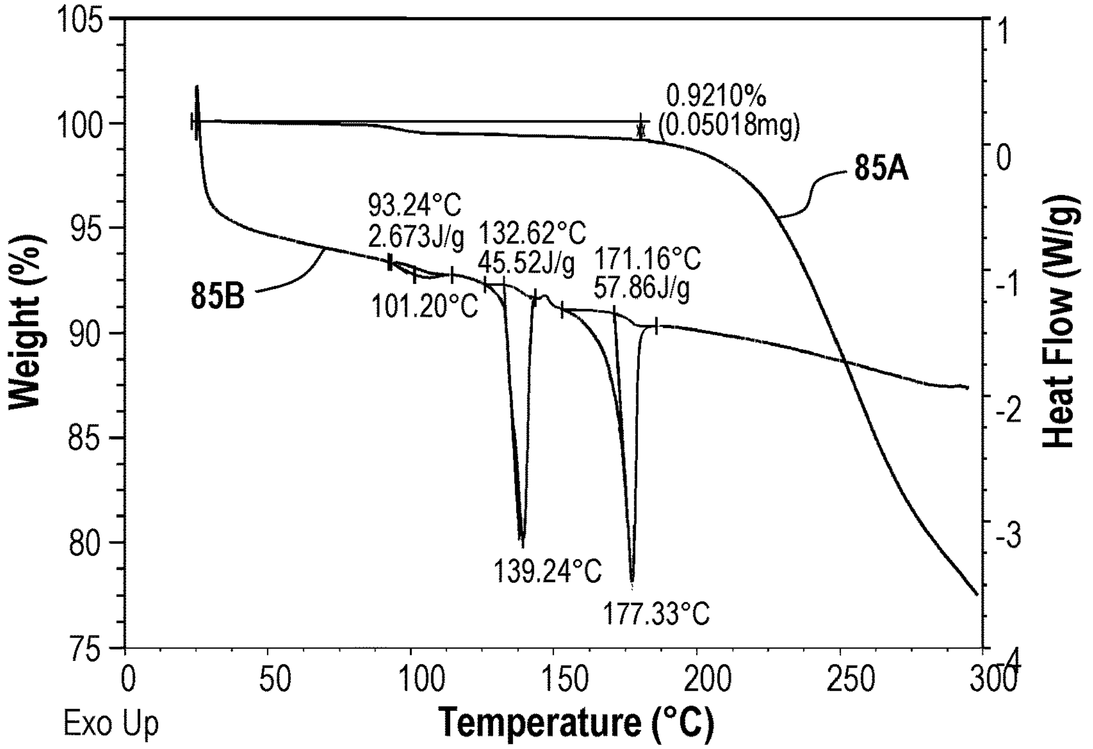
FIG. 85 depicts the TGA pattern of Form C adipate salt of Compound 1 (85A), and the DSC pattern of Form C adipate salt of Compound 1 (85B).

In some embodiments, Form C adipate salt is characterized by the thermogravimetric analysis (TGA) pattern depicted in FIG. 85, trace 85A.

In some embodiments, Form C adipate salt is characterized by the differential scanning calorimetry (DSC) pattern depicted in FIG. 85, trace 85B.

Figure 86:
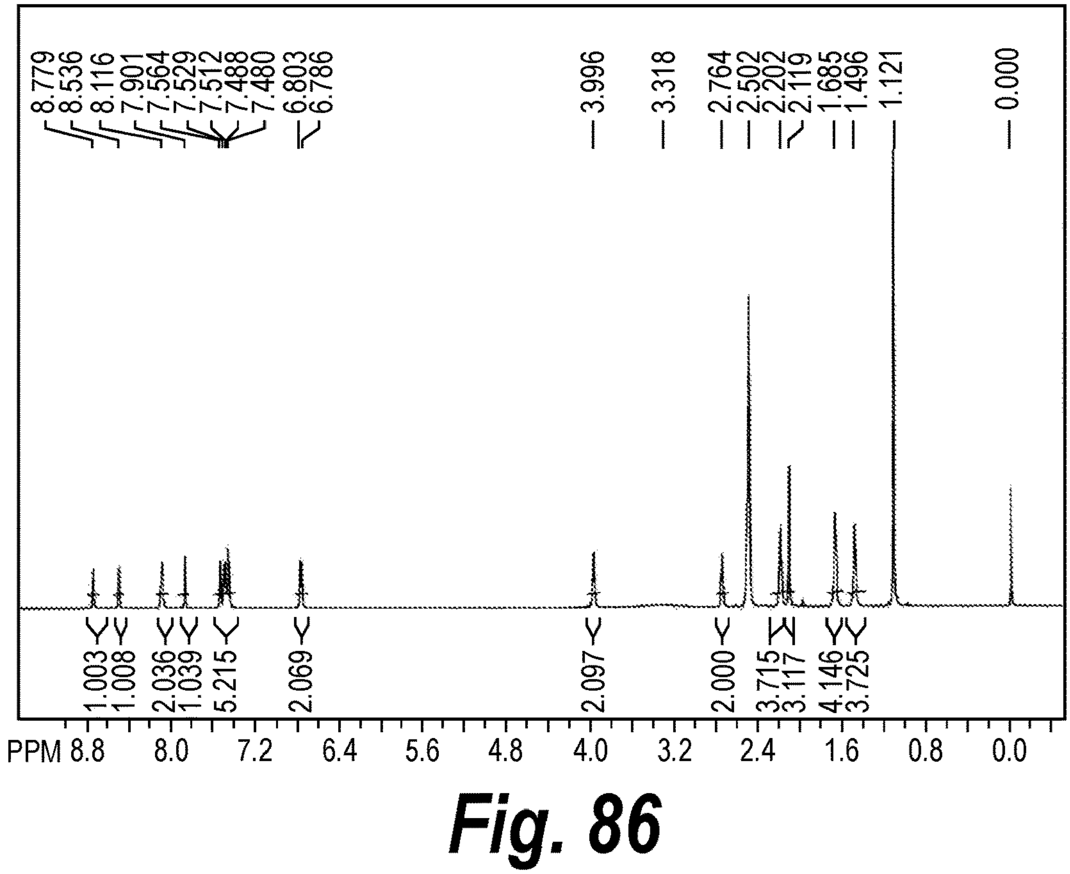
FIG. 86 depicts the $^1$H-NMR spectrum of Form C adipate salt of Compound 1.

In some embodiments, Form C adipate salt is characterized by the $^{1}$H NMR depicted in FIG. 86.

In some embodiments of a complex form of Compound 1, X is galactaric acid. In some such embodiments, a complex form of Compound 1 is a galactarate salt. In some embodiments, a complex form of Compound 1 comprises one equivalent of galactaric acid. In some embodiments, a galactarate salt of Compound 1 is a crystalline galactarate salt. In some embodiments, a crystalline galactarate salt of Compound 1 is characterized by one or more peaks in its X-ray powder diffraction pattern selected from 9.3, 12.1, 12.5, 15.2, 16.6, and 17.0±0.2 degrees 2θ. In some such embodiments, a complex form of Compound 1 is Form A galactarate salt.

In some embodiments, Form A galactarate salt is characterized by the following peaks in its X-ray powder diffraction pattern:

| Position ° 2θ ± 0.2 degrees | d-spacing [Å] | Height [cts] |
|---|---|---|
| 6.7 | 13.178 | 435 |
| 9.3 | 9.519 | 2500 |
| 11.3 | 7.857 | 285 |
| 12.1 | 7.326 | 301 |
| 12.5 | 7.076 | 386 |
| 13.0 | 6.805 | 127 |
| 13.8 | 6.406 | 959 |
| 15.2 | 5.831 | 1012 |
| 16.6 | 5.339 | 1447 |
| 17.0 | 5.226 | 1075 |
| 17.4 | 5.108 | 599 |
| 18.6 | 4.772 | 255 |
| 19.0 | 4.674 | 1133 |
| 19.7 | 4.517 | 1146 |

-continued

| Position ° 2θ ± 0.2 degrees | d-spacing [Å] | Height [cts] |
|---|---|---|
| 20.2 | 4.403 | 634 |
| 21.4 | 4.162 | 2178 |
| 22.4 | 3.965 | 321 |
| 23.0 | 3.875 | 407 |
| 24.3 | 3.659 | 637 |
| 27.0 | 3.299 | 991 |
| 27.8 | 3.215 | 327 |
| 28.3 | 3.155 | 159 |
| 30.8 | 2.907 | 378 |
| 32.7 | 2.740 | 201 |
| 37.2 | 2.419 | 132 |
| 37.7 | 2.387 | 131 |

Figure 87:
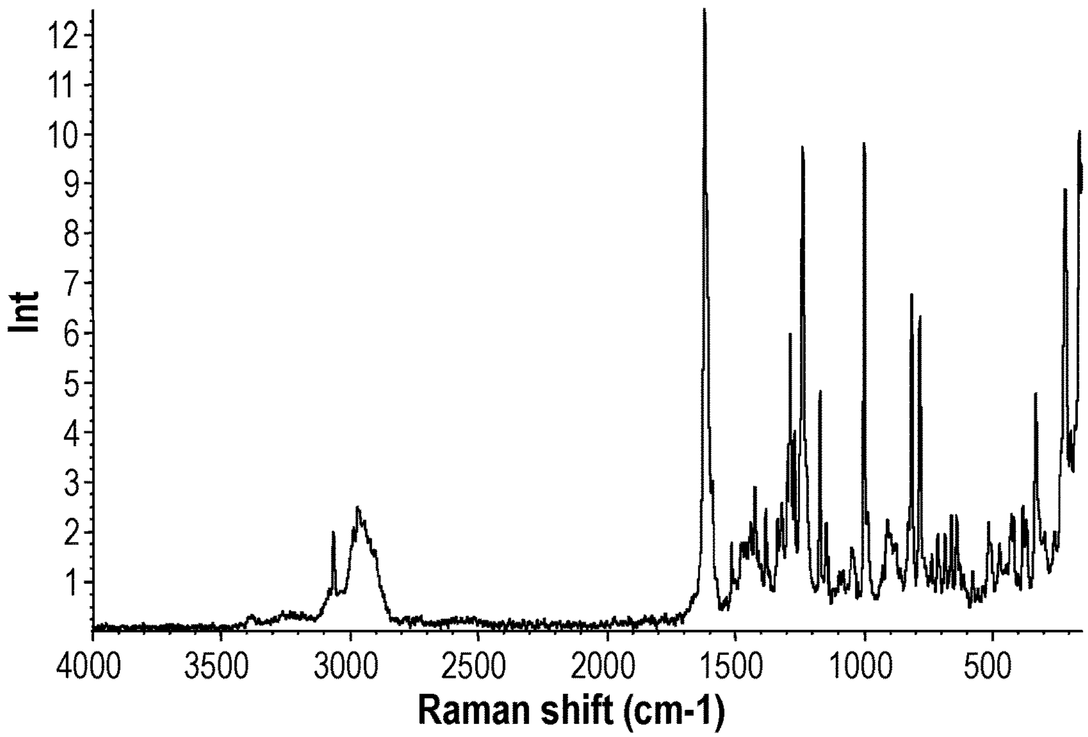
FIG. 87 depicts the FT-Raman spectrum of Form A galactarate salt of Compound 1.

In some embodiments, Form A galactarate salt is characterized by the x-ray powder diffraction (XRPD) pattern depicted in FIG. 87.

Figure 89:
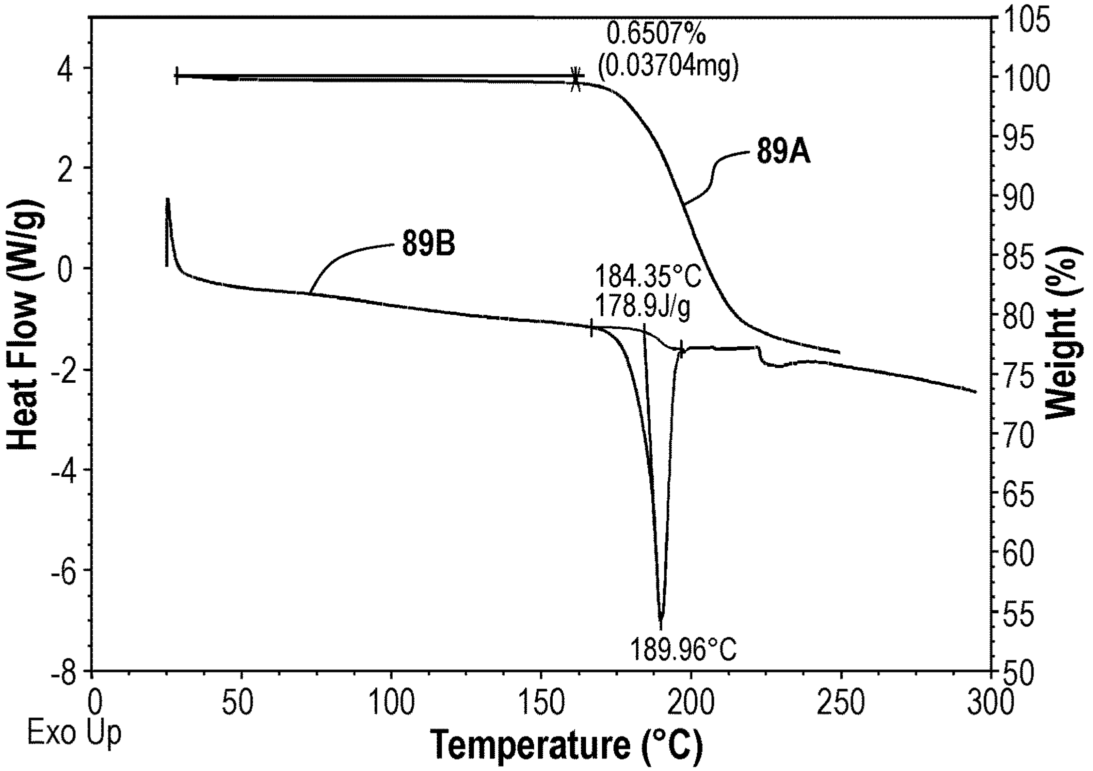
FIG. 89 depicts the TGA pattern of Form A galactarate salt of Compound 1 (89A), and the DSC pattern of Form A galactarate salt of Compound 1 (89B).

In some embodiments, Form A galactarate salt is characterized by the thermogravimetric analysis (TGA) pattern depicted in FIG. 89, trace 89A.

In some embodiments, Form A galactarate salt is characterized by the differential scanning calorimetry (DSC) pattern depicted in FIG. 89, trace 89B.

Figure 90:
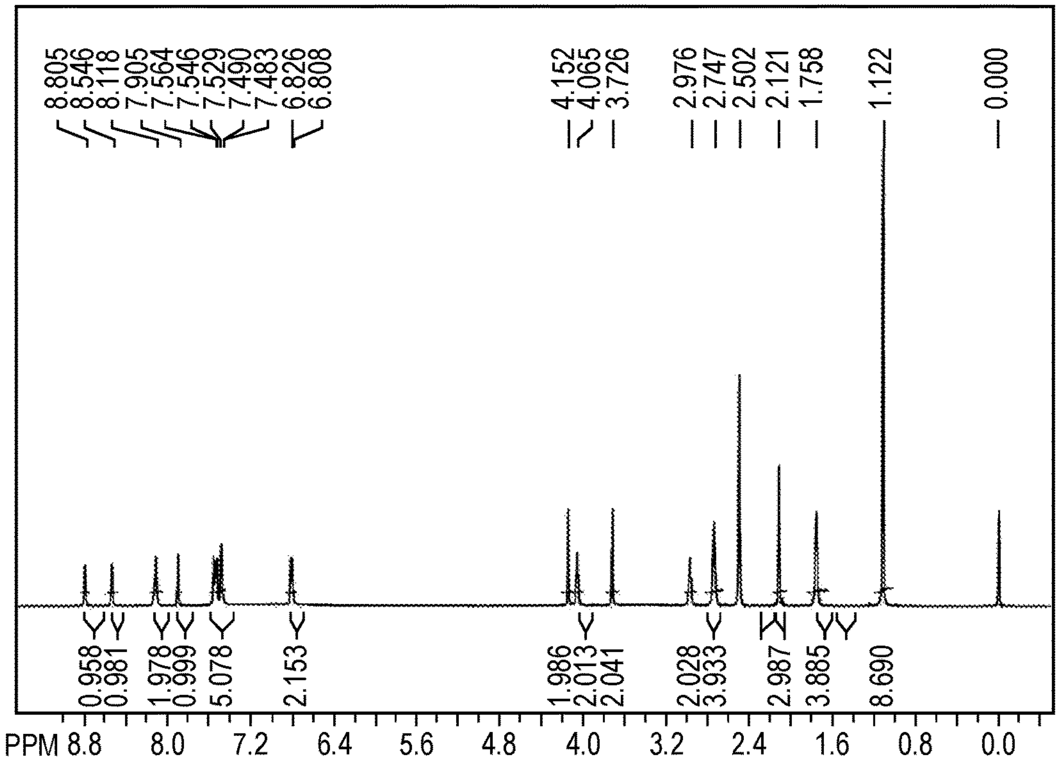
FIG. 90 depicts the $^1$H-NMR spectrum of Form A galactarate salt of Compound 1.

In some embodiments, Form A galactarate salt is characterized by the $^{1}$H NMR depicted in FIG. 90.

In some embodiments of a complex form of Compound 1, X is 1,5-naphthalenedisulfonic acid. In some such embodiments, a complex form of Compound 1 is a 1,5-naphthalenedisulfonate salt (also referred to as a "napadisylate" salt). In some embodiments, a napadisylate salt of Compound 1 is a crystalline napadisylate salt. In some embodiments, a crystalline napadisylate salt of Compound 1 is characterized by one or more peaks in its X-ray powder diffraction pattern selected from 3.8, 6.5, and 7.5±0.2 degrees 2θ. In some such embodiments, a complex form of Compound 1 is Form A napadisylate salt.

In some embodiments, Form A napadisylate salt is characterized by the following peaks in its X-ray powder diffraction pattern:

| Position ° 2θ ± 0.2 degrees | d-spacing [Å] | Height [cts] |
|---|---|---|
| 3.8 | 23.284 | 418 |
| 6.5 | 13.520 | 378 |
| 7.5 | 11.749 | 657 |
| 9.8 | 9.022 | 403 |
| 10.5 | 8.466 | 510 |
| 10.7 | 8.273 | 519 |
| 12.5 | 7.064 | 772 |
| 13.4 | 6.587 | 738 |
| 15.4 | 5.737 | 462 |
| 17.2 | 5.153 | 676 |
| 18.0 | 4.915 | 545 |
| 19.0 | 4.678 | 629 |
| 19.9 | 4.463 | 479 |
| 20.5 | 4.338 | 739 |
| 23.1 | 3.856 | 273 |
| 25.2 | 3.530 | 1908 |
| 27.0 | 3.300 | 386 |
| 29.6 | 3.019 | 107 |

Figure 91:
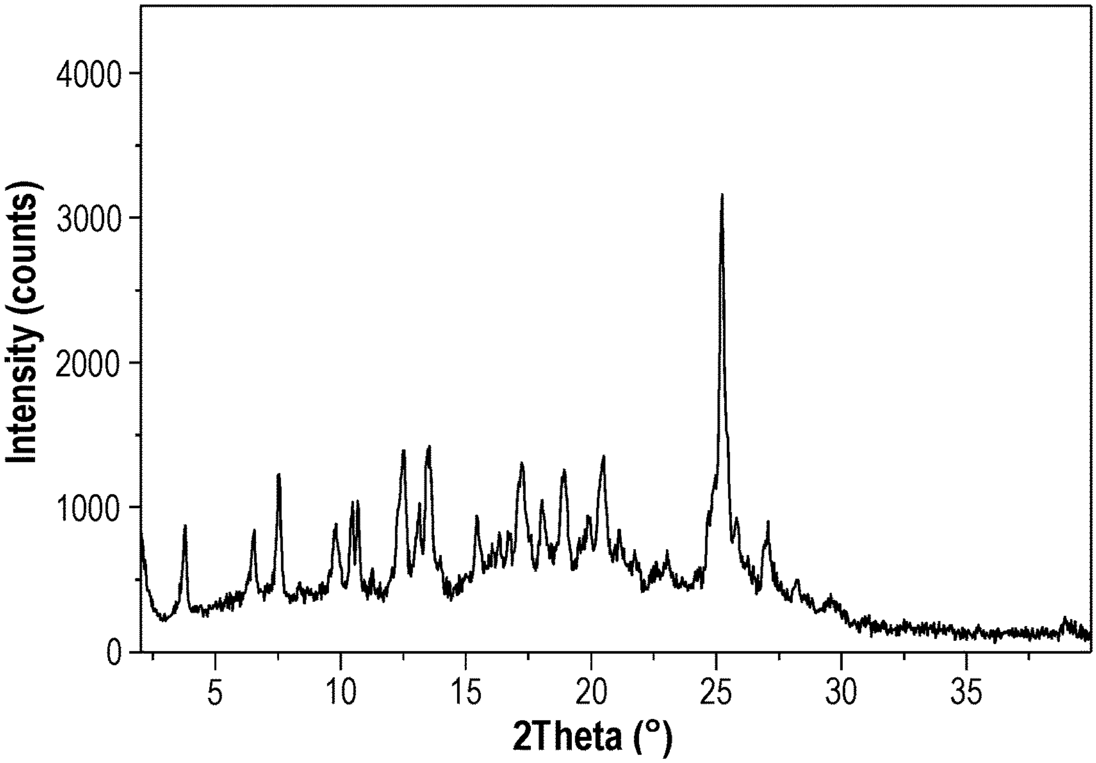
FIG. 91 depicts the XRPD pattern of Form A napadisylate salt of Compound 1.

In some embodiments, Form A napadisylate salt is characterized by the x-ray powder diffraction (XRPD) pattern depicted in FIG. 91.

Figure 94:
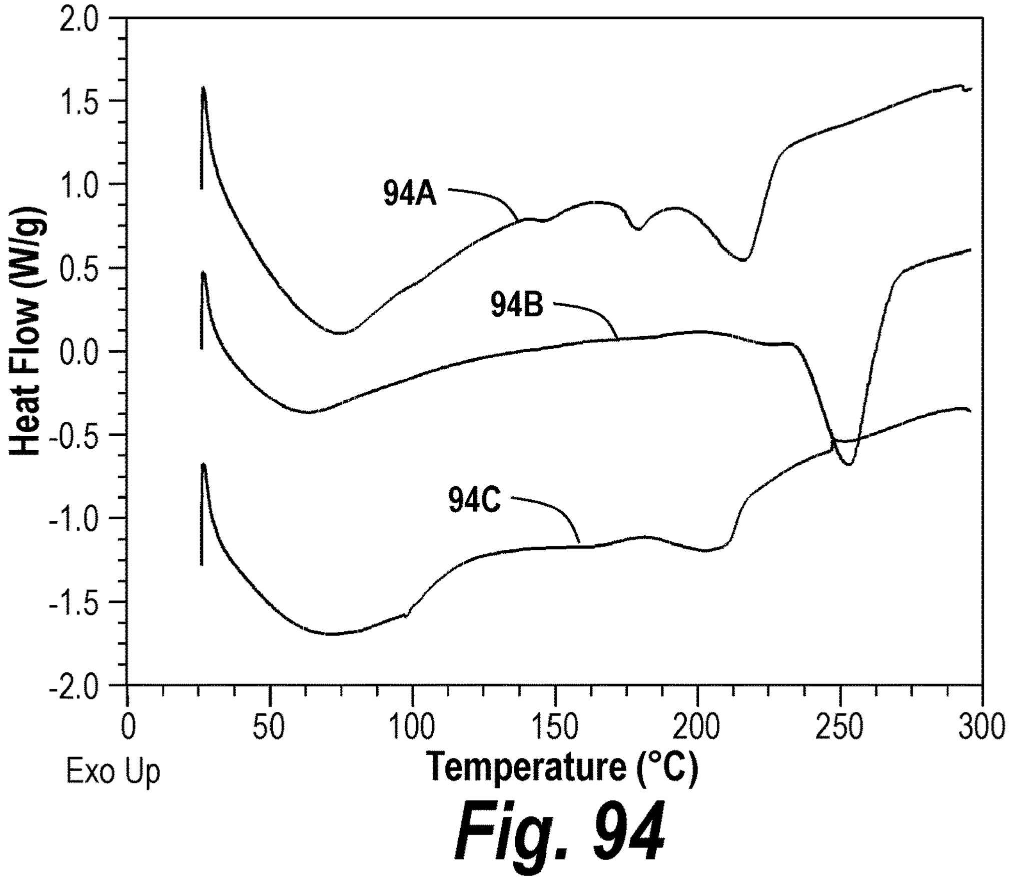
FIG. 94 depicts the DSC pattern of Form A napadisylate salt of Compound 1 (94A), the DSC pattern of Form B napadisylate salt of Compound 1 (94B), and the DSC pattern of Form C napadisylate salt of Compound 1 (94C).

In some embodiments, Form A napadisylate salt is characterized by the differential scanning calorimetry (DSC) pattern depicted in FIG. 94, trace 94A.

In some embodiments, a crystalline napadisylate salt of Compound 1 is characterized by one or more peaks in its X-ray powder diffraction pattern selected from 4.0, 7.9, and 11.8±0.2 degrees 2θ. In some such embodiments, a complex form of Compound 1 is Form B napadisylate salt.

In some embodiments, Form B napadisylate salt is characterized by the following peaks in its X-ray powder diffraction pattern:

| Position ° 2θ ± 0.2 degrees | d-spacing [Å] | Height [cts] |
|---|---|---|
| 4.0 | 22.302 | 443 |
| 7.9 | 11.219 | 2950 |
| 8.1 | 10.870 | 874 |
| 9.9 | 8.937 | 204 |
| 11.1 | 7.949 | 349 |
| 11.8 | 7.489 | 909 |
| 12.2 | 7.253 | 332 |
| 12.6 | 7.015 | 374 |
| 13.9 | 6.383 | 311 |
| 14.4 | 6.169 | 523 |
| 14.7 | 6.032 | 899 |
| 15.8 | 5.620 | 1254 |
| 16.3 | 5.441 | 533 |
| 16.5 | 5.370 | 559 |
| 17.1 | 5.193 | 713 |
| 17.4 | 5.092 | 713 |
| 17.7 | 5.004 | 617 |
| 18.1 | 4.902 | 669 |
| 18.6 | 4.776 | 818 |
| 19.0 | 4.683 | 611 |
| 19.7 | 4.496 | 554 |
| 20.4 | 4.346 | 938 |
| 20.9 | 4.255 | 394 |
| 21.4 | 4.156 | 319 |
| 21.7 | 4.098 | 468 |
| 22.7 | 3.912 | 350 |
| 23.8 | 3.744 | 670 |
| 24.6 | 3.624 | 393 |
| 25.3 | 3.518 | 872 |
| 25.9 | 3.440 | 752 |
| 27.3 | 3.272 | 197 |

Figure 92:
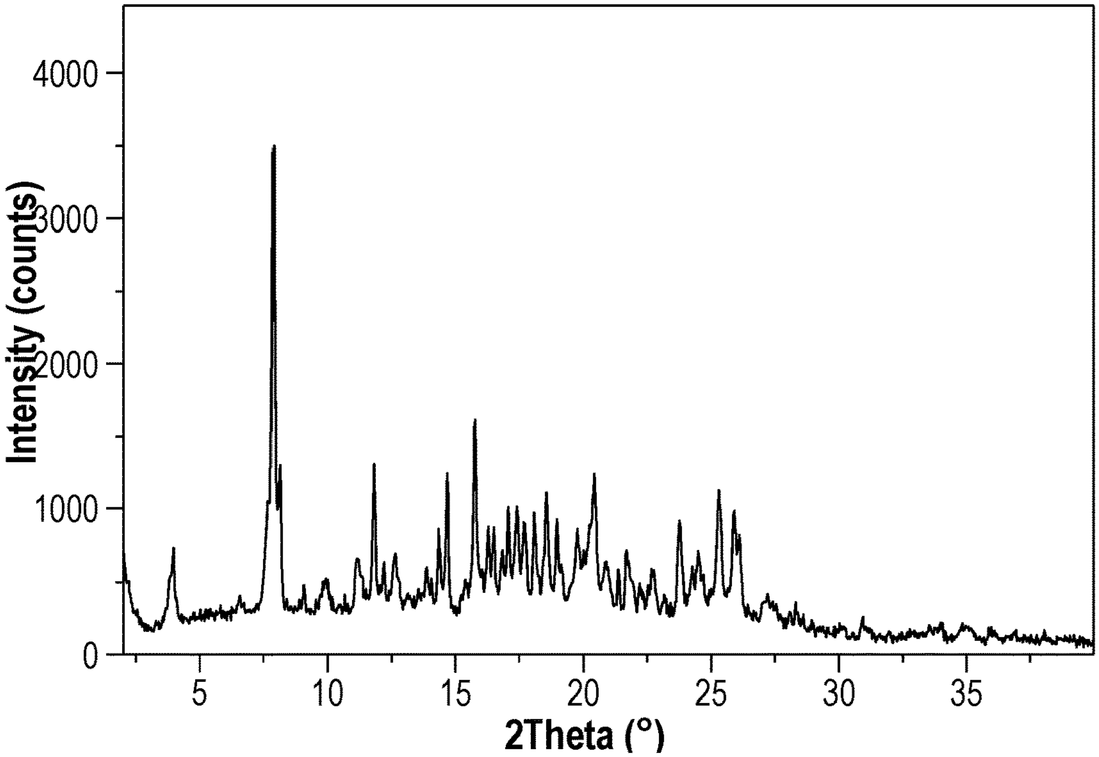
FIG. 92 depicts the XRPD pattern of Form B napadisylate salt of Compound 1.

In some embodiments, Form B napadisylate salt is characterized by the x-ray powder diffraction (XRPD) pattern depicted in FIG. 92.

In some embodiments, Form B napadisylate salt is characterized by the differential scanning calorimetry (DSC) pattern depicted in FIG. 94, trace 94B.

In some embodiments, a crystalline napadisylate salt of Compound 1 is characterized by one or more peaks in its X-ray powder diffraction pattern selected from 5.6, 13.4, and 14.4±0.2 degrees 2θ. In some such embodiments, a complex form of Compound 1 is Form C napadisylate salt.

In some embodiments, Form C napadisylate salt is characterized by the following peaks in its X-ray powder diffraction pattern:

| Position ° 2θ ± 0.2 degrees | d-spacing [Å] | Height [cts] |
|---|---|---|
| 3.6 | 24.308 | 45 |
| 5.6 | 15.871 | 131 |
| 13.4 | 6.614 | 225 |
| 14.4 | 6.169 | 341 |
| 17.8 | 4.988 | 221 |
| 18.6 | 4.766 | 245 |
| 19.7 | 4.515 | 417 |
| 22.0 | 4.049 | 192 |
| 22.9 | 3.876 | 327 |
| 23.6 | 3.768 | 433 |
| 26.4 | 3.381 | 169 |

Figure 93:
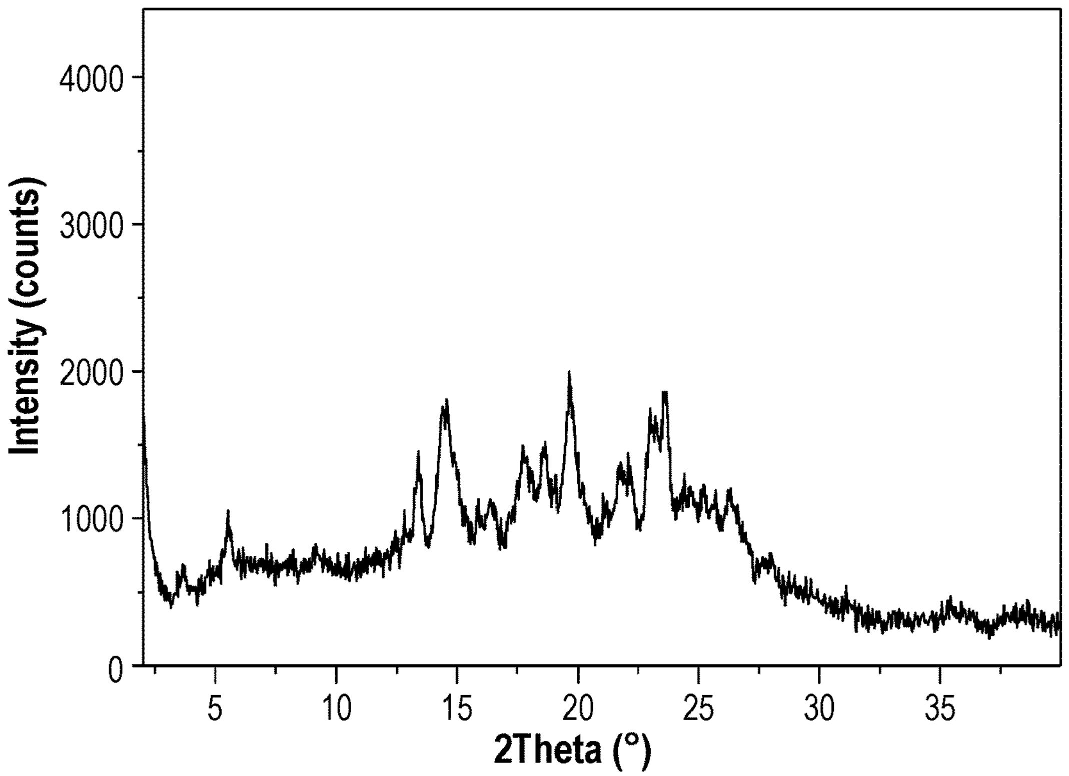
FIG. 93 depicts the XRPD pattern of Form C napadisylate salt of Compound 1.

In some embodiments, Form C napadisylate salt is characterized by the x-ray powder diffraction (XRPD) pattern depicted in FIG. 93.

In some embodiments, Form C napadisylate salt is characterized by the differential scanning calorimetry (DSC) pattern depicted in FIG. 94, trace 94C.

In some embodiments of a complex form of Compound 1, X is (S)-camphorsulfonic acid. In some such embodiments, a complex form of Compound 1 is a (S)-camphorsulfonate salt. In some embodiments, a (S)-camphorsulfonate salt of Compound 1 is a crystalline (S)-camphorsulfonate salt. In some embodiments, a crystalline (S)-camphorsulfonate salt of Compound 1 is characterized by one or more peaks in its X-ray powder diffraction pattern selected from 5.0, 9.9, 10.4, 11.1, and 14.3±0.2 degrees 2θ. In some such embodiments, a complex form of Compound 1 is Form A (S)-camphorsulfonate salt.

In some embodiments, Form A (S)-camphorsulfonate salt is characterized by the following peaks in its X-ray powder diffraction pattern:

| Position ° 2θ ± 0.2 degrees | d-spacing [Å] | Height [cts] |
|---|---|---|
| 5.0 | 17.694 | 6353 |
| 6.3 | 14.118 | 427 |
| 6.7 | 13.123 | 443 |
| 9.9 | 8.896 | 8788 |
| 10.4 | 8.470 | 995 |
| 11.1 | 7.986 | 702 |
| 12.5 | 7.059 | 423 |
| 13.1 | 6.771 | 823 |
| 13.5 | 6.562 | 406 |
| 14.3 | 6.204 | 1168 |
| 14.8 | 5.997 | 584 |
| 15.2 | 5.825 | 2014 |
| 15.8 | 5.603 | 1922 |
| 16.3 | 5.428 | 1031 |
| 16.6 | 5.334 | 1010 |
| 16.9 | 5.257 | 1302 |
| 17.7 | 5.024 | 701 |
| 18.0 | 4.922 | 985 |
| 18.4 | 4.822 | 396 |
| 18.8 | 4.716 | 929 |
| 20.0 | 4.450 | 1448 |
| 20.3 | 4.378 | 550 |
| 20.7 | 4.293 | 539 |
| 21.0 | 4.226 | 950 |
| 21.6 | 4.107 | 711 |
| 22.8 | 3.896 | 890 |
| 23.3 | 3.815 | 564 |
| 23.5 | 3.778 | 943 |
| 24.1 | 3.690 | 989 |
| 25.0 | 3.560 | 786 |
| 25.7 | 3.467 | 555 |
| 26.1 | 3.412 | 690 |
| 27.3 | 3.273 | 407 |
| 28.0 | 3.188 | 835 |

Figure 95:
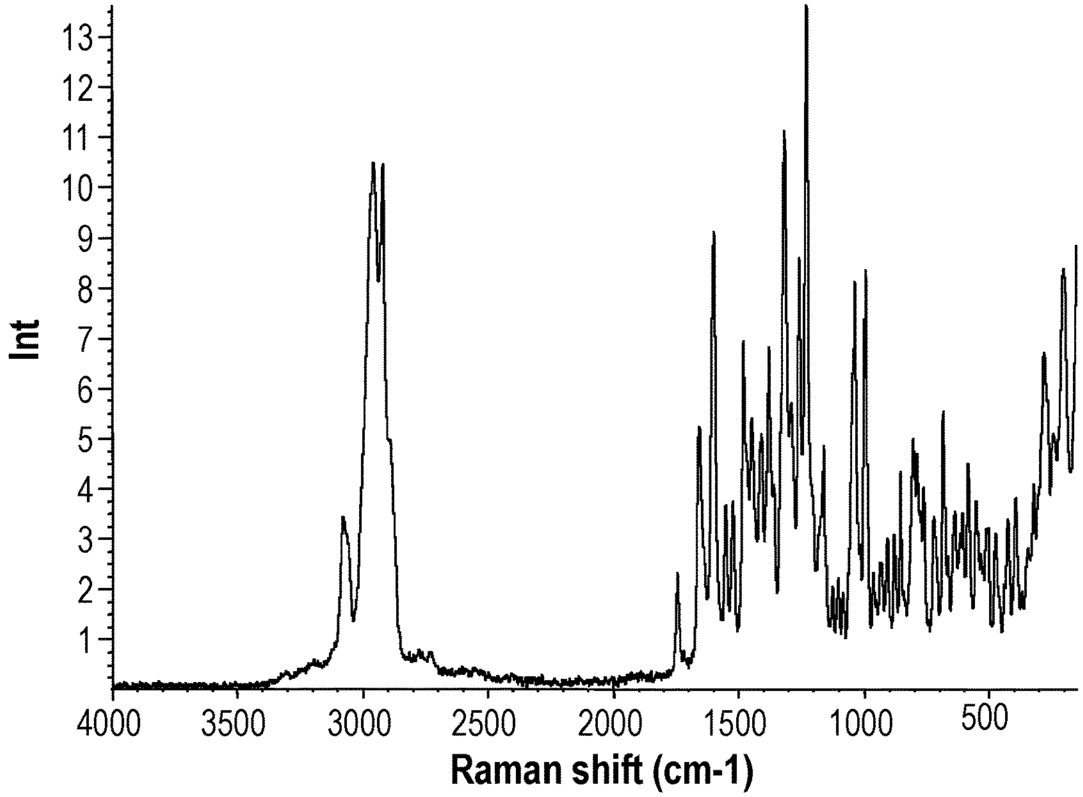
FIG. 95 depicts the FT-Raman spectrum of Form A (S)-camphorsulfonate salt of Compound 1.

In some embodiments, Form A (S')-camphorsulfonate salt is characterized by the FT-Raman spectrum depicted in FIG. 95.

Figure 96:
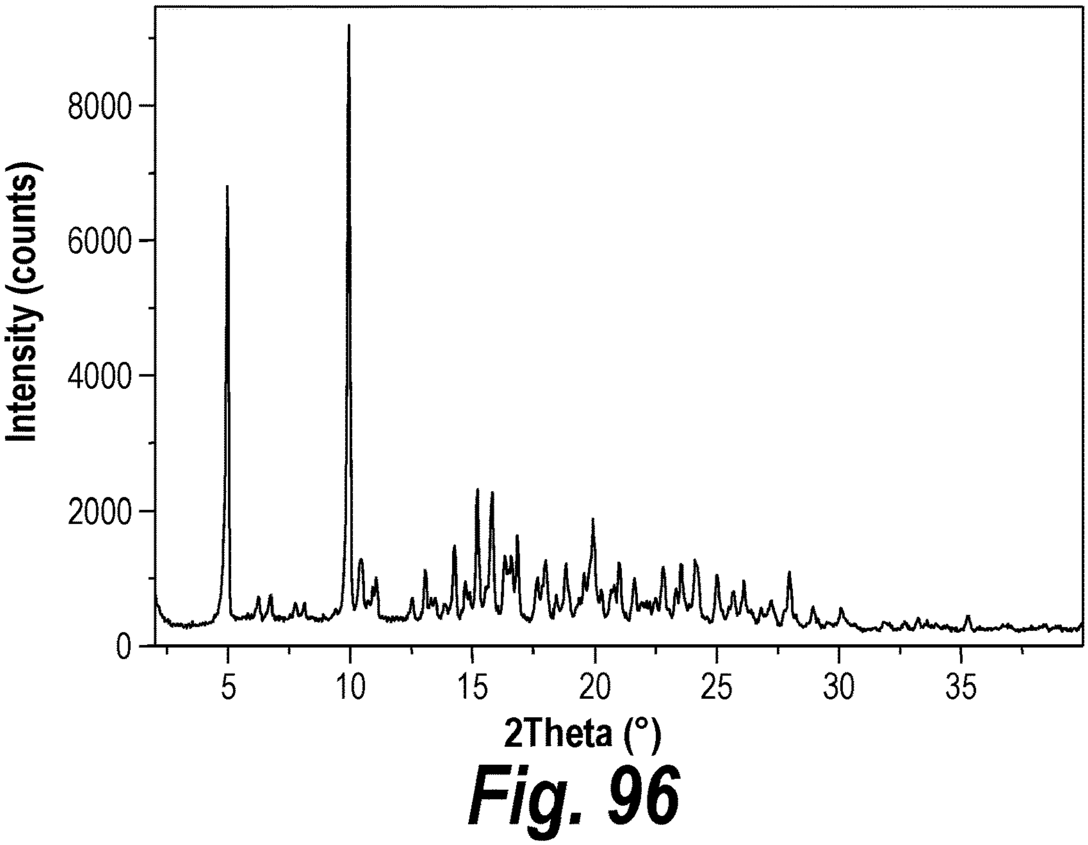
FIG. 96 depicts the XRPD pattern of Form A (S)-camphorsulfonate salt of Compound 1.

In some embodiments, Form A (S)-camphorsulfonate salt is characterized by the x-ray powder diffraction (XRPD) pattern depicted in FIG. 96.

Figure 97:
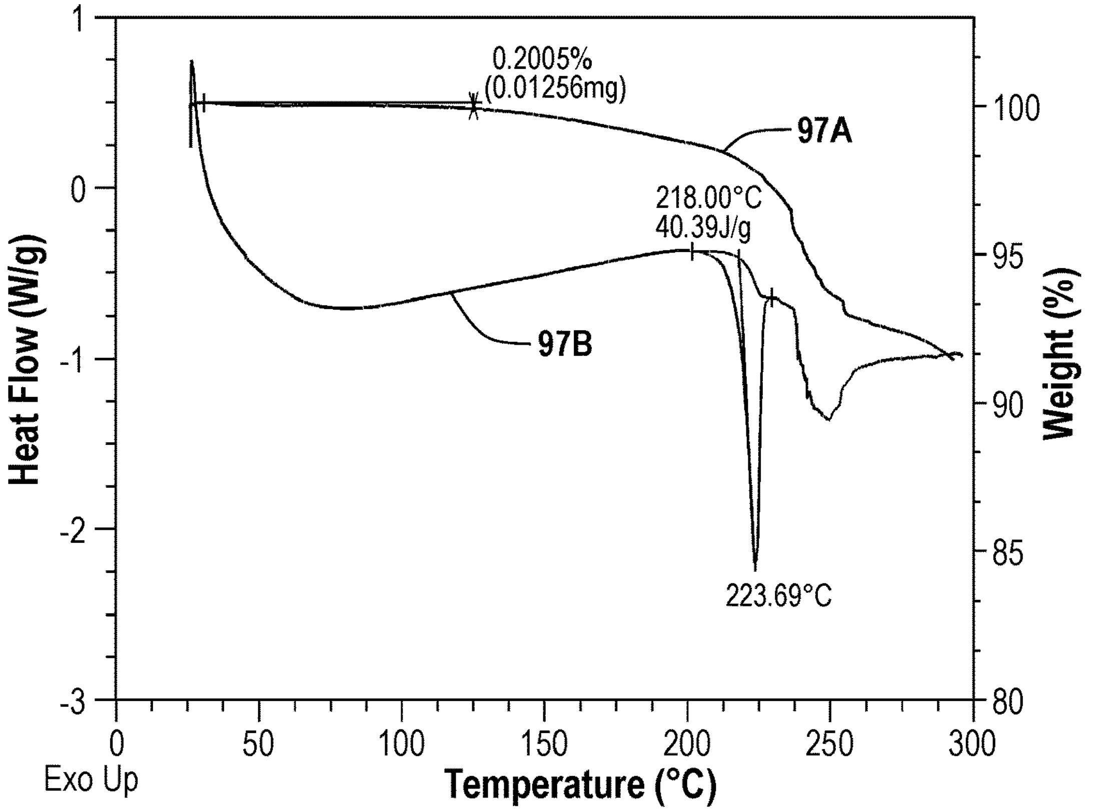
FIG. 97 depicts the TGA pattern of Form A (S)-camphorsulfonate salt of Compound 1 (97A), and the DSC pattern of Form A (S)-camphorsulfonate salt of Compound 1 (97B).

In some embodiments, Form A (S)-camphorsulfonate salt is characterized by the thermogravimetric analysis (TGA) pattern depicted in FIG. 97, trace 97A.

In some embodiments, Form A (S)-camphorsulfonate salt is characterized by the differential scanning calorimetry (DSC) pattern depicted in FIG. 97, trace 97B.

In some embodiments, a crystalline (S)-camphorsulfonate salt of Compound 1 is characterized by one or more peaks in its X-ray powder diffraction pattern selected from 6.9, 10.2, 11.4, and 12.4±0.2 degrees 2θ. In some such embodiments, a complex form of Compound 1 is Form B (S)-camphorsulfonate salt.

In some embodiments, Form B (S)-camphorsulfonate salt is characterized by the following peaks in its X-ray powder diffraction pattern:

| Position ° 2θ ± 0.2 degrees | d-spacing [Å] | Height [cts] |
|---|---|---|
| 6.9 | 12.733 | 754 |
| 7.9 | 11.123 | 270 |
| 10.2 | 8.655 | 1087 |
| 11.4 | 7.742 | 1799 |
| 12.4 | 7.160 | 501 |
| 14.2 | 6.218 | 2102 |
| 14.6 | 6.050 | 356 |
| 15.0 | 5.908 | 3544 |
| 15.3 | 5.805 | 1828 |
| 15.5 | 5.709 | 907 |
| 15.9 | 5.562 | 1801 |
| 16.3 | 5.444 | 417 |
| 16.6 | 5.346 | 2461 |
| 16.9 | 5.244 | 1270 |
| 17.7 | 5.022 | 456 |
| 18.3 | 4.858 | 2270 |
| 18.7 | 4.747 | 644 |
| 19.4 | 4.565 | 615 |
| 19.8 | 4.476 | 1389 |
| 20.4 | 4.353 | 609 |
| 21.0 | 4.236 | 857 |
| 21.3 | 4.178 | 1351 |
| 22.4 | 3.976 | 1462 |
| 22.8 | 3.908 | 1083 |
| 23.2 | 3.830 | 577 |
| 24.0 | 3.714 | 2791 |
| 24.4 | 3.641 | 1067 |
| 24.9 | 3.582 | 351 |
| 25.2 | 3.533 | 401 |
| 25.7 | 3.466 | 870 |
| 26.9 | 3.315 | 534 |
| 27.2 | 3.276 | 668 |

Figure 98:
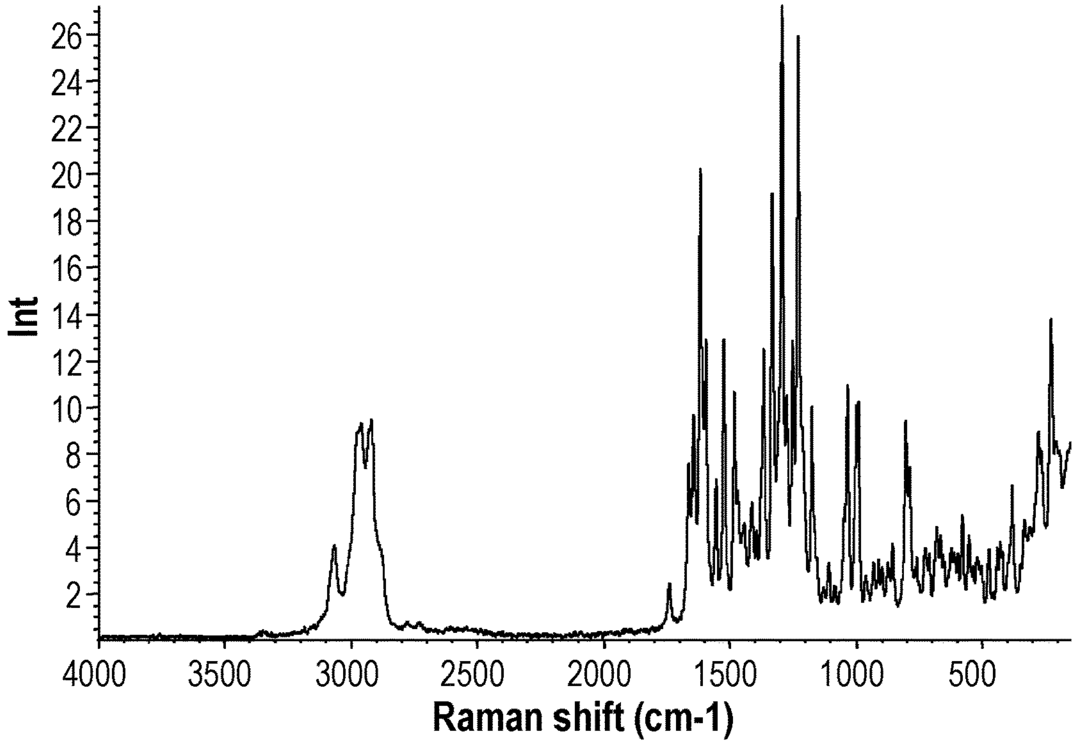
FIG. 98 depicts the FT-Raman spectrum of Form B (S)-camphorsulfonate salt of Compound 1.

In some embodiments, Form B (S)-camphorsulfonate salt is characterized by the FT-Raman spectrum depicted in FIG. 98.

Figure 99:
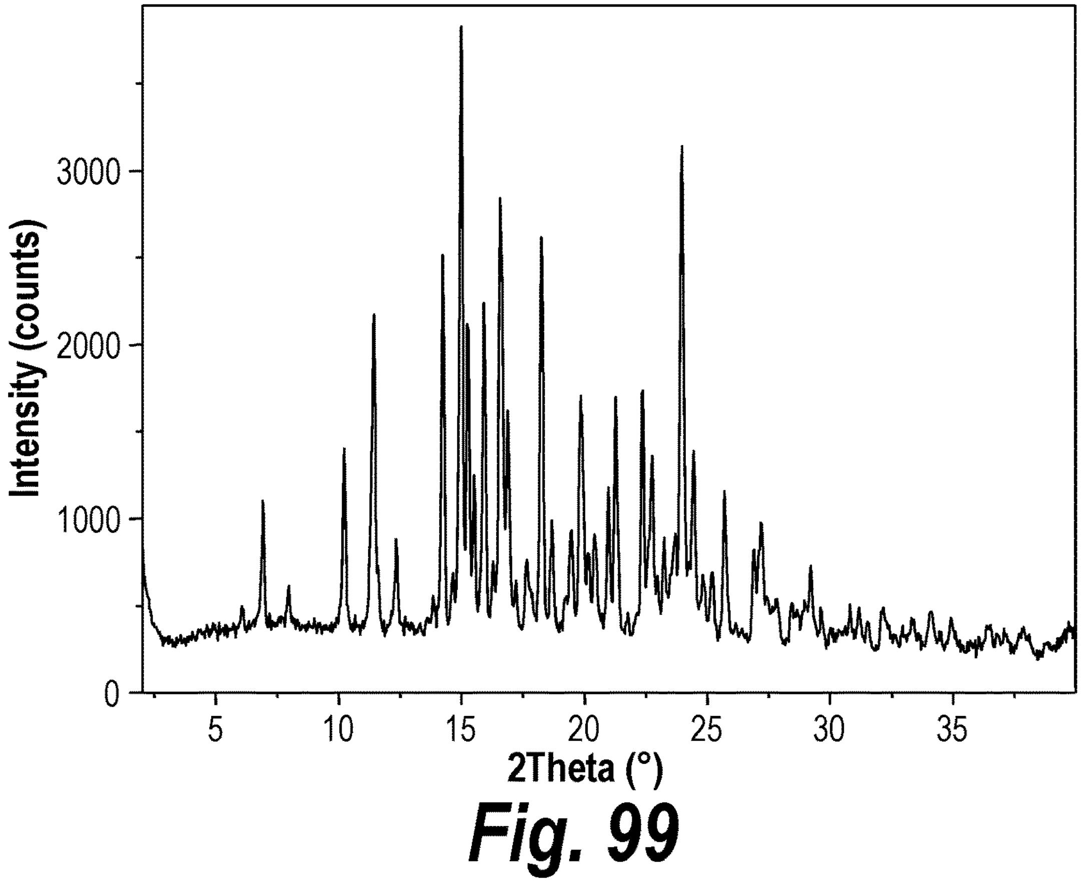
FIG. 99 depicts the XRPD pattern of Form B (S)-camphorsulfonate salt of Compound 1.

In some embodiments, Form B (S)-camphorsulfonate salt is characterized by the x-ray powder diffraction (XRPD) pattern depicted in FIG. 99.

Figure 100:
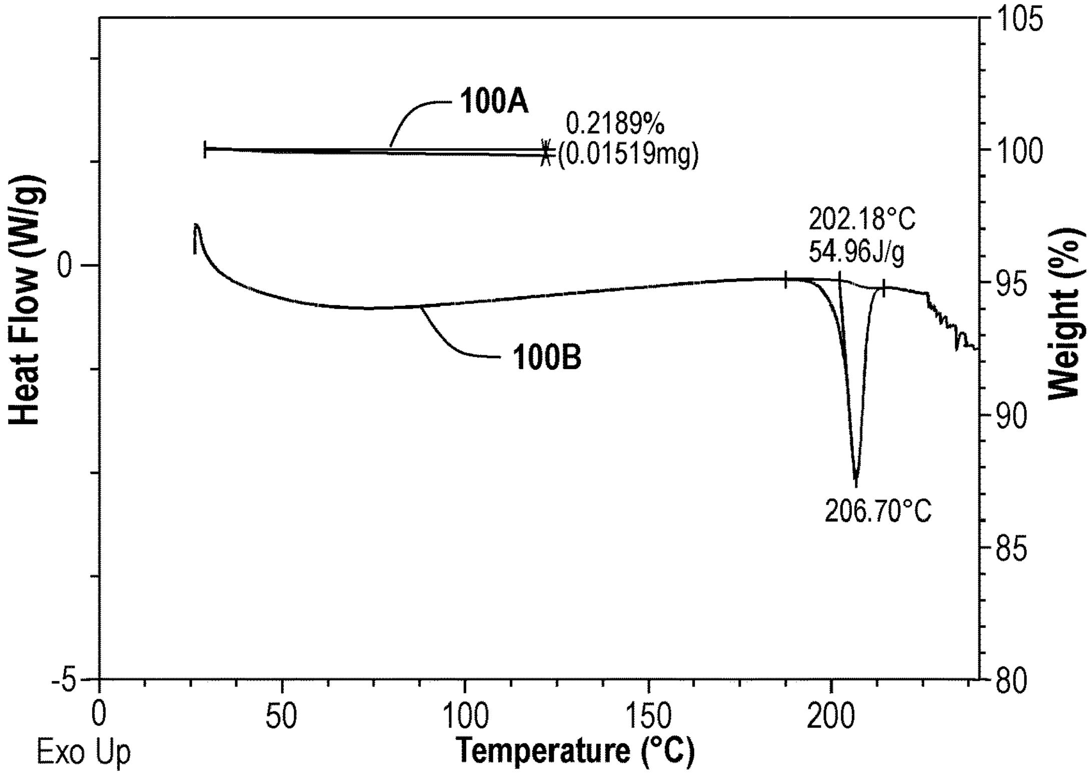
FIG. 100 depicts the TGA pattern of Form B (S)-camphorsulfonate salt of Compound 1 (100A), and the DSC pattern of Form B (S)-camphorsulfonate salt of Compound 1 (100B).

In some embodiments, Form B (S)-camphorsulfonate salt is characterized by the thermogravimetric analysis (TGA) pattern depicted in FIG. 100, trace 100A.

In some embodiments, Form B (S)-camphorsulfonate salt is characterized by the differential scanning calorimetry (DSC) pattern depicted in FIG. 100, trace 100B.

In some embodiments of a complex form of Compound 1, X is 1,2-ethanedisulfonic acid. In some such embodiments, a complex form of Compound 1 is a 1,2-ethanedisulfonate salt (also referred to as an "edisylate" salt). In some embodiments, an edisylate salt of Compound 1 is a crystalline edisylate salt. In some embodiments, an edisylate salt is a hydrate. In some embodiments, a hydrate form of an edisylate salt of Compound 1 is a crystalline hydrate form of an edisylate salt. In some embodiments, a crystalline hydrate form of an edisylate salt of Compound 1 is characterized by one or more peaks in its X-ray powder diffraction pattern selected from 9.1, 10.7, 11.1, 14.0, 14.7, 18.2, and 19.0±0.2 degrees 2θ. In some such embodiments, a complex form of Compound 1 is Form A edisylate salt.

In some embodiments, Form A edisylate salt is characterized by the following peaks

| Position ° 2θ ± 0.2 degrees | d-spacing [Å] | Height [cts] |
|---|---|---|
| 7.2 | 12.282 | 310 |
| 9.1 | 9.731 | 1774 |
| 10.7 | 8.307 | 2111 |
| 11.1 | 7.944 | 1834 |
| 12.0 | 7.359 | 483 |
| 14.0 | 6.338 | 920 |
| 14.4 | 6.163 | 403 |
| 14.7 | 6.022 | 1417 |
| 15.5 | 5.724 | 506 |
| 16.0 | 5.526 | 627 |
| 17.5 | 5.065 | 342 |
| 18.2 | 4.883 | 4716 |
| 19.0 | 4.664 | 3252 |
| 20.0 | 4.441 | 1004 |
| 20.4 | 4.352 | 1013 |
| 20.7 | 4.283 | 629 |
| 21.4 | 4.162 | 1634 |
| 22.0 | 4.037 | 1655 |
| 22.3 | 3.978 | 1387 |
| 22.8 | 3.898 | 3682 |
| 23.9 | 3.718 | 524 |
| 24.3 | 3.660 | 570 |
| 24.8 | 3.590 | 604 |
| 25.4 | 3.509 | 1312 |
| 26.0 | 3.424 | 1296 |
| 26.7 | 3.345 | 630 |
| 27.8 | 3.206 | 578 |
| 29.3 | 3.047 | 325 |
| 31.1 | 2.877 | 327 |
| 32.1 | 2.790 | 498 |

Figure 101:
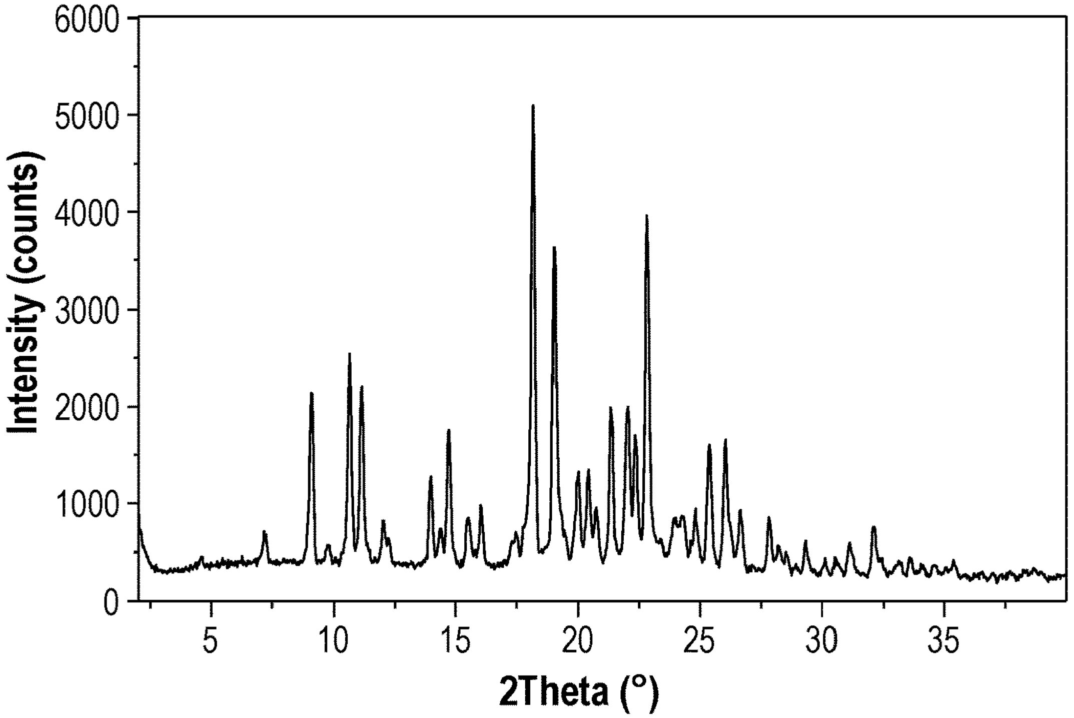
FIG. 101 depicts the XRPD pattern of Form A edisylate salt of Compound 1.

In some embodiments, Form A edisylate salt is characterized by the x-ray powder diffraction (XRPD) pattern depicted in FIG. 101.

Figure 105:
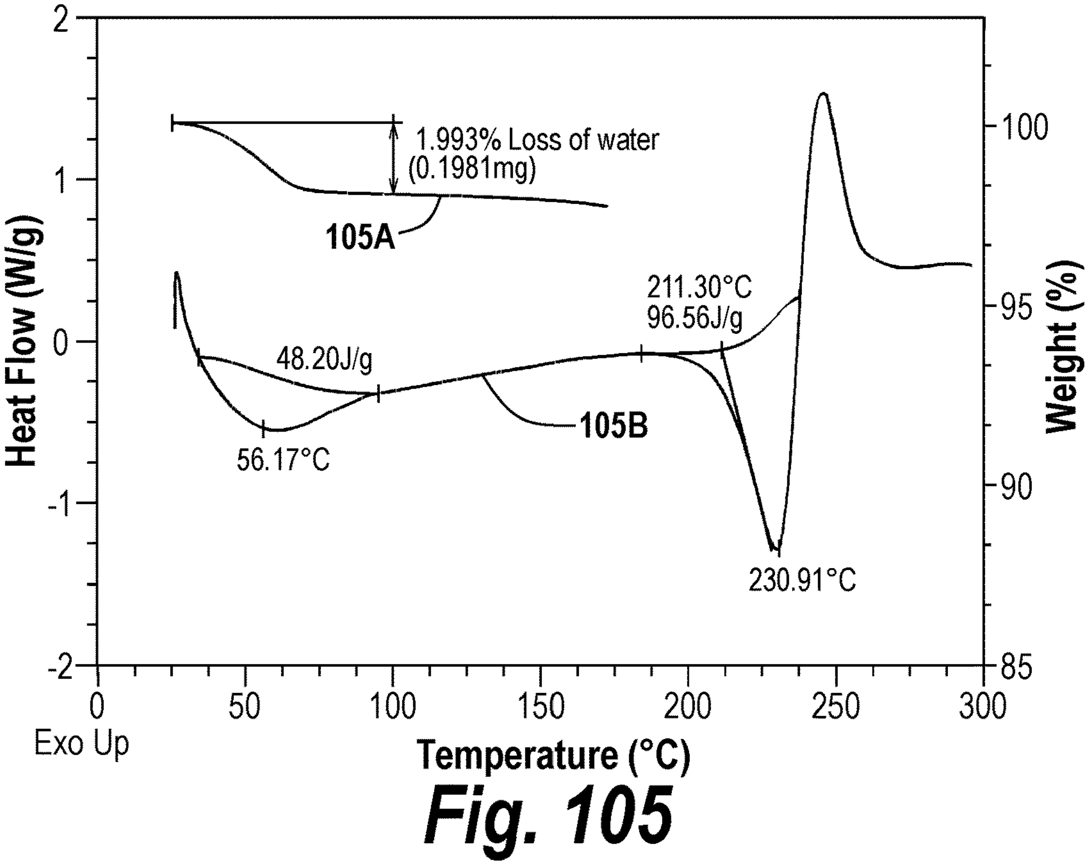
FIG. 105 depicts the TGA pattern of Form A edisylate salt salt of Compound 1 (105A), and the DSC pattern of Form A edisylate salt salt of Compound 1 (105B).

In some embodiments, Form A edisylate salt is characterized by the thermogravimetric analysis (TGA) pattern depicted in FIG. 105, trace 105A.

In some embodiments, Form A edisylate salt is characterized by the differential scanning calorimetry (DSC) pattern depicted in FIG. 105, trace 105B.

In some embodiments, a crystalline edisylate salt of Compound 1 is characterized by one or more peaks in its X-ray powder diffraction pattern selected from 9.8, 10.9, 13.1, 13.6, and 19.5±0.2 degrees 2θ. In some such embodiments, a complex form of Compound 1 is Form B edisylate salt.

In some embodiments, Form B edisylate salt is characterized by the following peaks

| Position ° 2θ ± 0.2 degrees | d-spacing [Å] | Height [cts] |
|---|---|---|
| 9.8 | 9.071 | 1169 |
| 10.9 | 8.127 | 1534 |
| 11.9 | 7.420 | 246 |
| 12.9 | 6.881 | 864 |
| 13.1 | 6.768 | 938 |
| 13.6 | 6.526 | 1272 |
| 15.0 | 5.919 | 392 |
| 15.3 | 5.779 | 228 |
| 16.4 | 5.410 | 202 |
| 17.3 | 5.141 | 576 |
| 18.6 | 4.772 | 984 |
| 19.1 | 4.636 | 1455 |
| 19.5 | 4.545 | 3916 |
| 19.9 | 4.472 | 1106 |
| 20.3 | 4.380 | 625 |
| 20.9 | 4.254 | 1050 |
| 21.3 | 4.181 | 1666 |
| 21.4 | 4.150 | 1957 |
| 21.9 | 4.058 | 232 |
| 22.4 | 3.968 | 1173 |
| 22.8 | 3.905 | 1380 |
| 23.1 | 3.855 | 944 |
| 23.6 | 3.776 | 679 |
| 24.0 | 3.709 | 1478 |
| 24.5 | 3.641 | 876 |
| 25.0 | 3.564 | 334 |
| 25.8 | 3.451 | 225 |
| 26.3 | 3.384 | 948 |
| 26.9 | 3.315 | 633 |

Figure 102:
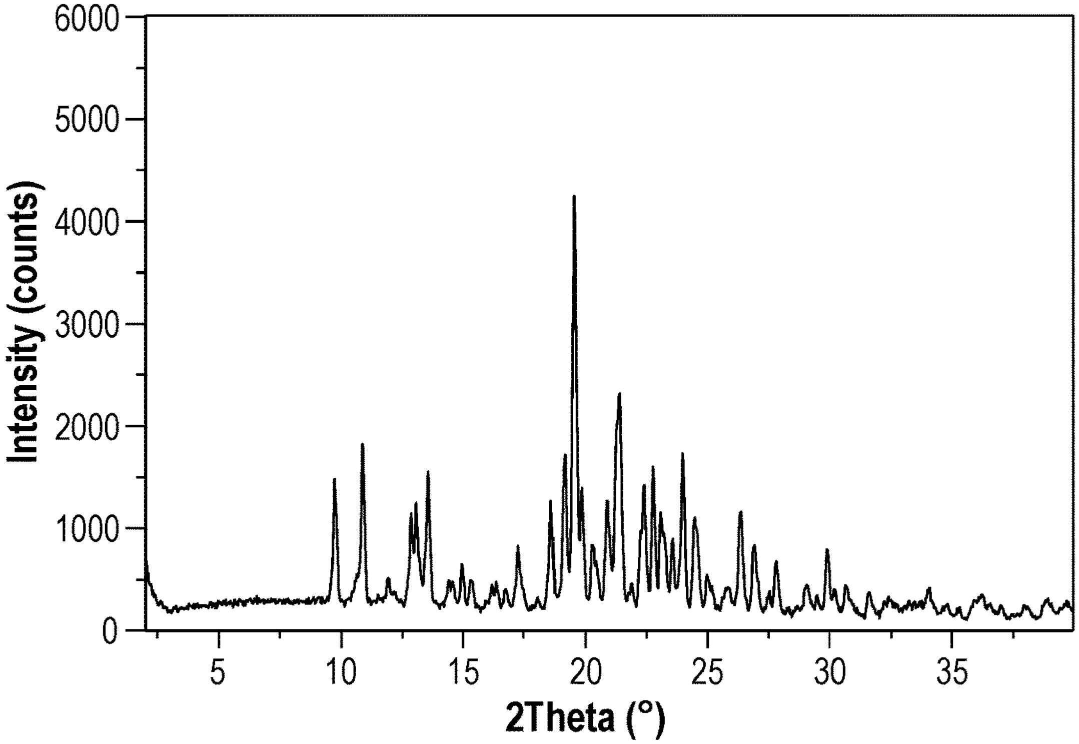
FIG. 102 depicts the XRPD pattern of Form B edisylate salt of Compound 1.

In some embodiments, Form B edisylate salt is characterized by the x-ray powder diffraction (XRPD) pattern depicted in FIG. 102.

Figure 106:
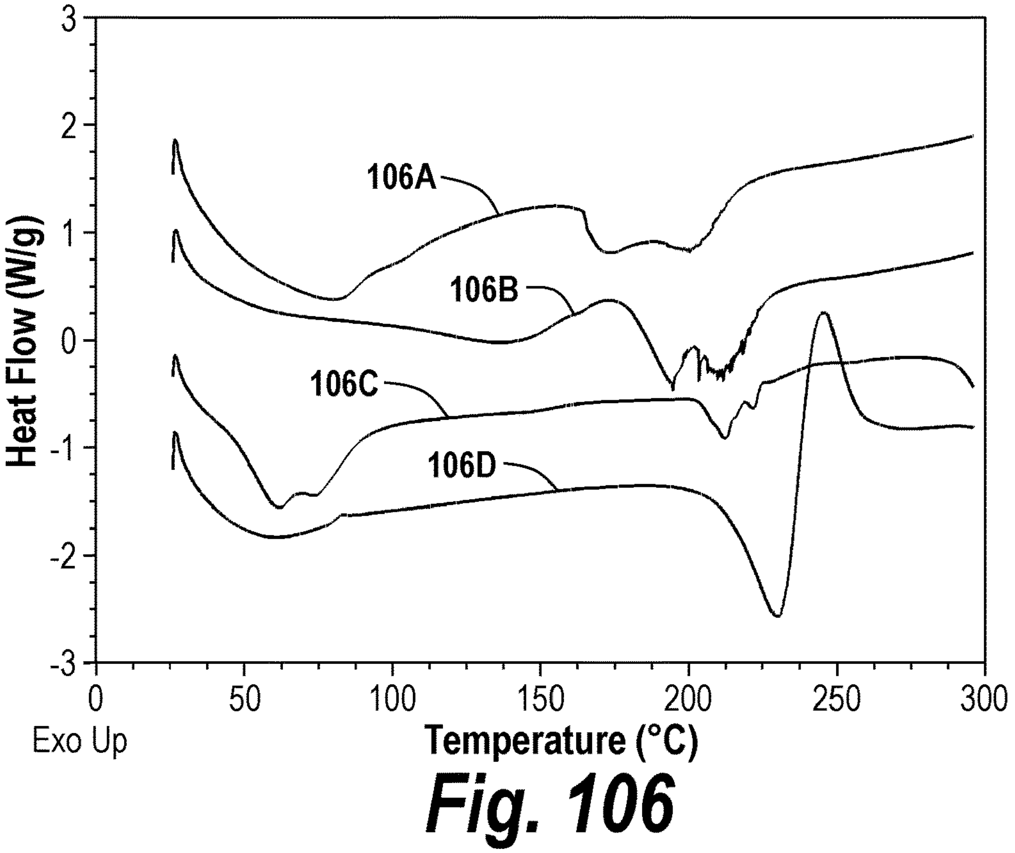
FIG. 106 depicts the DSC pattern of Form C edisylate salt of Compound 1 (106A), the DSC pattern of Form B edisylate salt of Compound 1 (106B), the DSC pattern of Form D edisylate salt of Compound 1 (106C), and the DSC pattern of Form A edisylate salt of Compound 1 (106D).

In some embodiments, Form B edisylate salt is characterized by the differential scanning calorimetry (DSC) pattern depicted in FIG. 106, trace 106B.

In some embodiments, a crystalline edisylate salt of Compound 1 is characterized by one or more peaks in its X-ray powder diffraction pattern selected from 7.0, 12.8, 13.3, 13.7, and 16.7±0.2 degrees 2θ. In some such embodiments, a complex form of Compound 1 is Form C edisylate salt.

In some embodiments, Form C edisylate salt is characterized by the following peaks in its X-ray powder diffraction pattern:

| Position ° 2θ ± 0.2 degrees | d-spacing [Å] | Height [cts] |
|---|---|---|
| 7.0 | 12.609 | 458 |
| 8.8 | 10.105 | 224 |
| 12.8 | 6.917 | 671 |
| 13.3 | 6.648 | 623 |
| 13.7 | 6.458 | 588 |
| 14.7 | 6.025 | 1281 |
| 15.8 | 5.626 | 502 |
| 16.7 | 5.313 | 1133 |
| 17.1 | 5.188 | 888 |
| 17.8 | 4.984 | 542 |
| 18.1 | 4.909 | 672 |
| 18.7 | 4.743 | 1374 |
| 19.2 | 4.619 | 894 |
| 20.5 | 4.334 | 2657 |
| 22.2 | 4.008 | 1010 |
| 22.9 | 3.888 | 1420 |
| 24.0 | 3.713 | 1058 |

-continued

| Position ° 2θ ± 0.2 degrees | d-spacing [Å] | Height [cts] |
|---|---|---|
| 24.5 | 3.640 | 1785 |
| 25.4 | 3.512 | 683 |
| 26.3 | 3.391 | 1044 |
| 26.8 | 3.330 | 660 |
| 27.2 | 3.283 | 648 |
| 28.9 | 3.085 | 258 |
| 30.1 | 2.971 | 169 |
| 32.0 | 2.797 | 185 |

Figure 103:
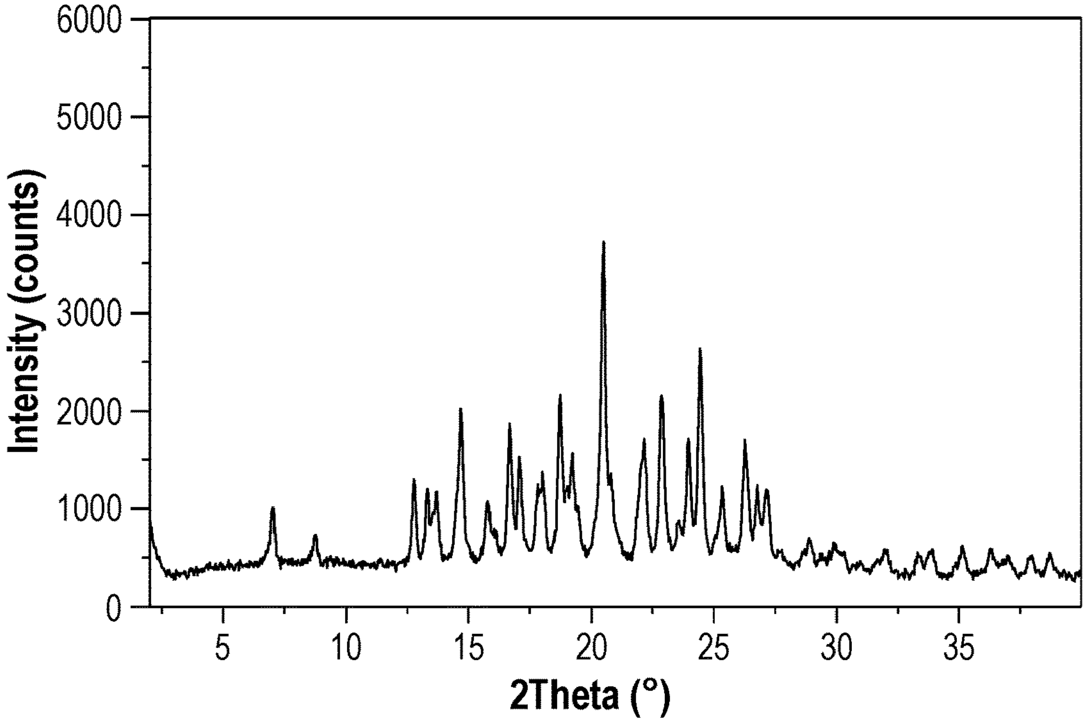
FIG. 103 depicts the XRPD pattern of Form C edisylate salt of Compound 1.

In some embodiments, Form C edisylate salt is characterized by the x-ray powder diffraction (XRPD) pattern depicted in FIG. 103.

In some embodiments, Form C edisylate salt is characterized by the differential scanning calorimetry (DSC) pattern depicted in FIG. 106, trace 106A.

In some embodiments, a crystalline edisylate salt of Compound 1 is characterized by one or more peaks in its X-ray powder diffraction pattern selected from 6.1, 10.2, 10.4, 12.5, 15.8, 16.0, and 17.0±0.2 degrees 2θ. In some such embodiments, a complex form of Compound 1 is Form D edisylate salt.

In some embodiments, Form D edisylate salt is characterized by the following peaks in its X-ray powder diffraction pattern:

| Position ° 2θ ± 0.2 degrees | d-spacing [Å] | Height [cts] |
|---|---|---|
| 6.1 | 14.602 | 531 |
| 10.2 | 8.694 | 952 |
| 10.4 | 8.514 | 882 |
| 11.6 | 7.634 | 728 |
| 11.9 | 7.465 | 295 |
| 12.5 | 7.105 | 2377 |
| 13.0 | 6.805 | 622 |
| 13.3 | 6.633 | 799 |
| 14.1 | 6.301 | 236 |
| 14.9 | 5.938 | 434 |
| 15.3 | 5.805 | 609 |
| 15.8 | 5.611 | 1574 |
| 16.0 | 5.534 | 1894 |
| 17.0 | 5.211 | 1611 |
| 17.8 | 4.974 | 419 |
| 18.2 | 4.878 | 674 |
| 18.7 | 4.746 | 1516 |
| 19.2 | 4.620 | 695 |
| 19.5 | 4.542 | 1849 |
| 20.0 | 4.442 | 4222 |
| 20.8 | 4.274 | 3499 |
| 21.4 | 4.155 | 569 |
| 22.0 | 4.049 | 655 |
| 22.6 | 3.931 | 1039 |
| 23.3 | 3.822 | 1346 |
| 23.9 | 3.728 | 946 |
| 24.3 | 3.670 | 771 |
| 24.5 | 3.637 | 736 |
| 24.9 | 3.578 | 671 |
| 25.5 | 3.493 | 506 |
| 25.8 | 3.450 | 220 |
| 26.2 | 3.406 | 426 |
| 26.5 | 3.363 | 1556 |

Figure 104:
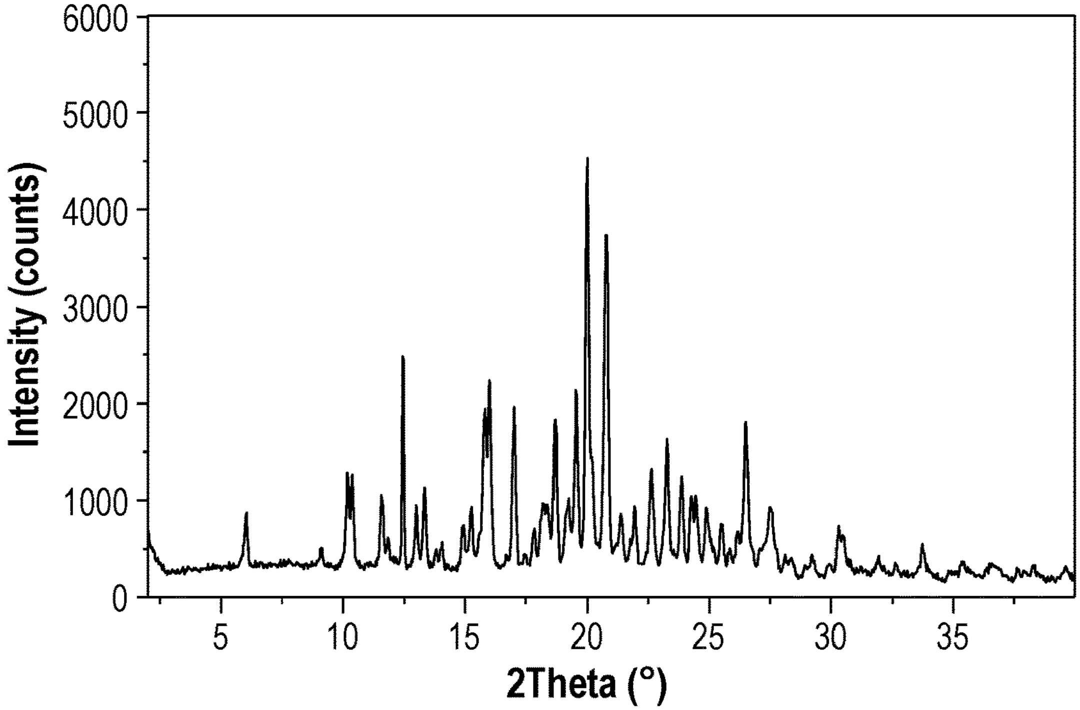
FIG. 104 depicts the XRPD pattern of Form D edisylate salt of Compound 1.

In some embodiments, Form D edisylate salt is characterized by the x-ray powder diffraction (XRPD) pattern depicted in FIG. 104.

In some embodiments, Form D edisylate salt is characterized by the differential scanning calorimetry (DSC) pattern depicted in FIG. 106, trace 106C.

In some embodiments of a complex form of Compound 1, X is ethanesulfonic acid. In some such embodiments, a complex form of Compound 1 is an esylate salt. In some embodiments, an esylate salt of Compound 1 is a crystalline esylate salt. In some embodiments, a crystalline esylate salt of Compound 1 is characterized by one or more peaks in its X-ray powder diffraction pattern selected from 8.4, 17.0, 17.4, 18.2, 18.7, and 25.2±0.2 degrees 2θ. In some such embodiments, a complex form of Compound 1 is Form A esylate salt.

In some embodiments, Form A esylate salt is characterized by the following peaks in its X-ray powder diffraction pattern:

| Position ° 2θ ± 0.2 degrees | d-spacing [Å] | Height [cts] |
|---|---|---|
| 8.4 | 10.570 | 4144 |
| 10.1 | 8.720 | 833 |
| 10.4 | 8.518 | 1651 |
| 13.8 | 6.407 | 1296 |
| 17.0 | 5.228 | 6247 |
| 17.4 | 5.097 | 3323 |
| 18.2 | 4.875 | 2694 |
| 18.7 | 4.753 | 3679 |
| 19.2 | 4.619 | 1741 |
| 20.8 | 4.262 | 860 |
| 21.7 | 4.094 | 2850 |
| 22.2 | 3.999 | 3947 |
| 22.8 | 3.909 | 591 |
| 23.2 | 3.839 | 1037 |
| 23.7 | 3.747 | 641 |
| 24.5 | 3.631 | 782 |
| 25.2 | 3.533 | 18991 |
| 26.1 | 3.419 | 759 |
| 26.4 | 3.382 | 1950 |
| 27.3 | 3.269 | 1084 |
| 27.9 | 3.201 | 804 |
| 28.6 | 3.122 | 641 |
| 28.8 | 3.102 | 758 |
| 33.4 | 2.680 | 1038 |
| 33.8 | 2.650 | 713 |

Figure 107:
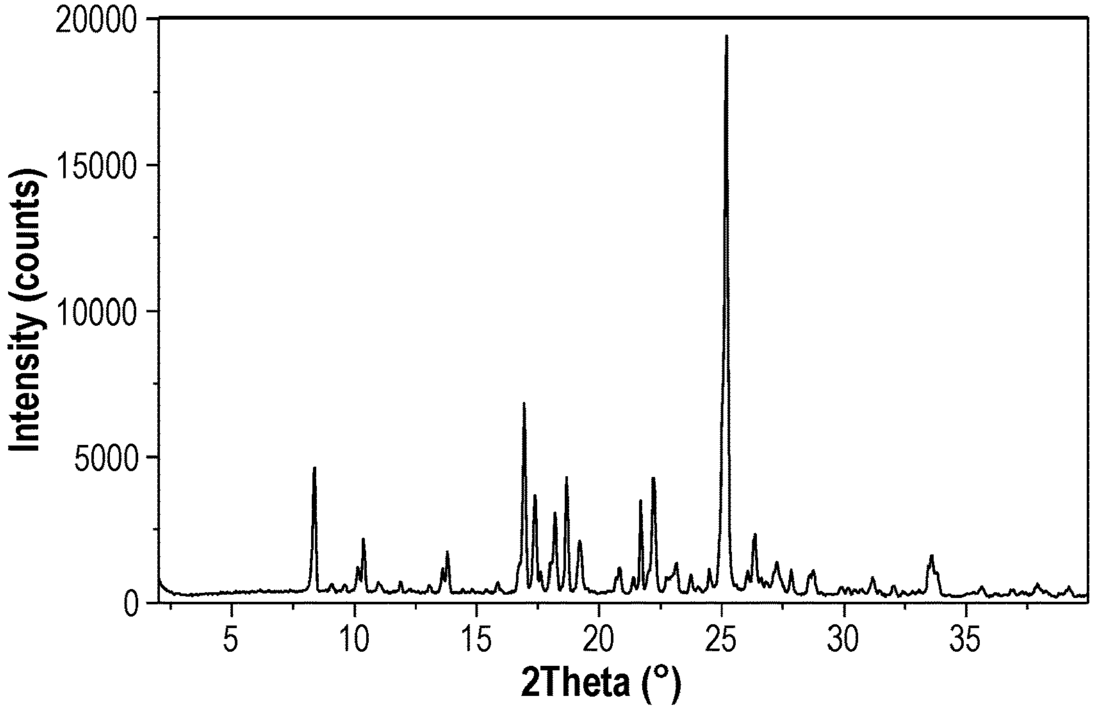
FIG. 107 depicts the XRPD pattern of Form A esylate salt of Compound 1.

In some embodiments, Form A esylate salt is characterized by the x-ray powder diffraction (XRPD) pattern depicted in FIG. 107.

Figure 109:
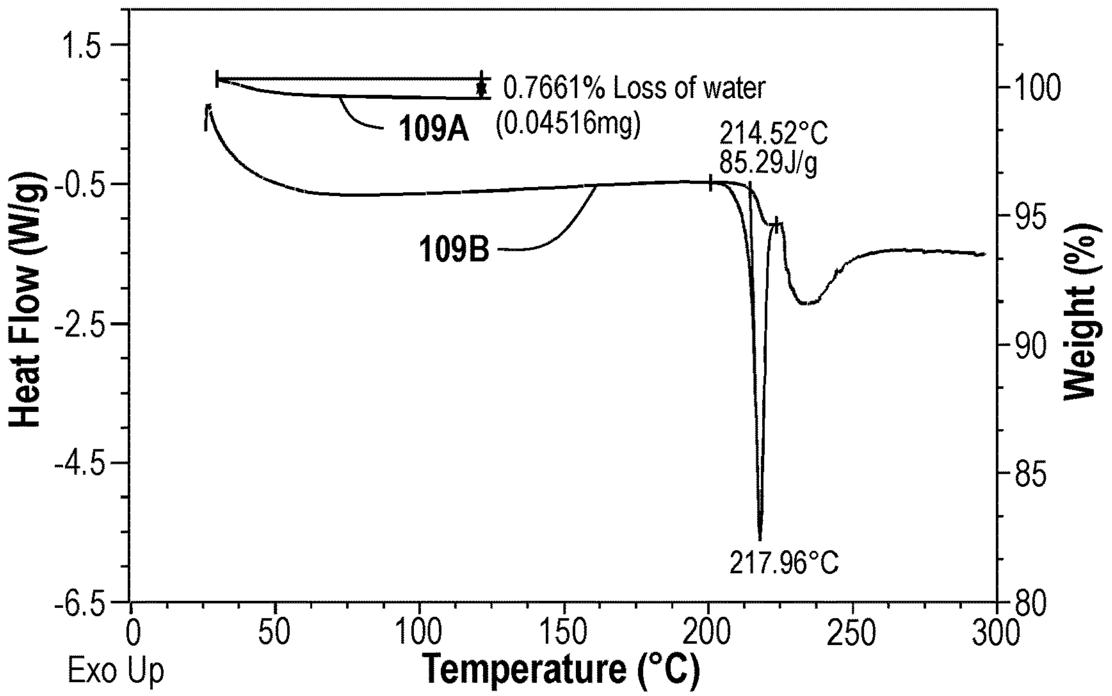
FIG. 109 depicts the TGA pattern of Form A esylate salt of Compound 1 (109A), and the DSC pattern of Form A esylate salt of Compound 1 (109B).

In some embodiments, Form A esylate salt is characterized by the thermogravimetric analysis (TGA) pattern depicted in FIG. 109, trace 109A.

In some embodiments, Form A esylate salt is characterized by the differential scanning calorimetry (DSC) pattern depicted in FIG. 109, trace 109B.

In some embodiments, a crystalline esylate salt of Compound 1 is characterized by one or more peaks in its X-ray powder diffraction pattern selected from 6.5, 9.8, 12.5, 12.9, and 14.8±0.2 degrees 2θ. In some such embodiments, a complex form of Compound 1 is Form B esylate salt.

In some embodiments, Form B esylate salt is characterized by the following peaks in its X-ray powder diffraction pattern:

| Position ° 2θ ± 0.2 degrees | d-spacing [Å] | Height [cts] |
|---|---|---|
| 6.5 | 13.673 | 1941 |
| 9.8 | 8.987 | 1563 |
| 10.7 | 8.261 | 194 |
| 12.5 | 7.103 | 1980 |
| 12.9 | 6.842 | 3137 |

-continued

| Position ° 2θ ± 0.2 degrees | d-spacing [Å] | Height [cts] |
|---|---|---|
| 13.5 | 6.541 | 495 |
| 14.1 | 6.293 | 422 |
| 14.4 | 6.141 | 268 |
| 14.8 | 5.988 | 1487 |
| 15.4 | 5.741 | 297 |
| 16.0 | 5.534 | 616 |
| 16.8 | 5.269 | 1151 |
| 17.1 | 5.184 | 1269 |
| 17.6 | 5.035 | 1064 |
| 18.1 | 4.890 | 2035 |
| 18.5 | 4.793 | 538 |
| 19.2 | 4.617 | 1762 |
| 19.6 | 4.538 | 3087 |
| 19.9 | 4.458 | 904 |
| 20.2 | 4.389 | 2319 |
| 20.6 | 4.320 | 2287 |
| 20.9 | 4.247 | 1623 |
| 21.5 | 4.129 | 467 |
| 22.3 | 3.995 | 570 |
| 22.7 | 3.924 | 387 |
| 22.9 | 3.876 | 1505 |
| 23.3 | 3.818 | 1429 |
| 23.5 | 3.785 | 2645 |
| 23.9 | 3.717 | 3178 |
| 24.2 | 3.677 | 1052 |
| 24.7 | 3.607 | 477 |
| 25.4 | 3.512 | 340 |
| 25.8 | 3.451 | 1895 |
| 26.2 | 3.397 | 417 |
| 27.5 | 3.247 | 1484 |

Figure 108:
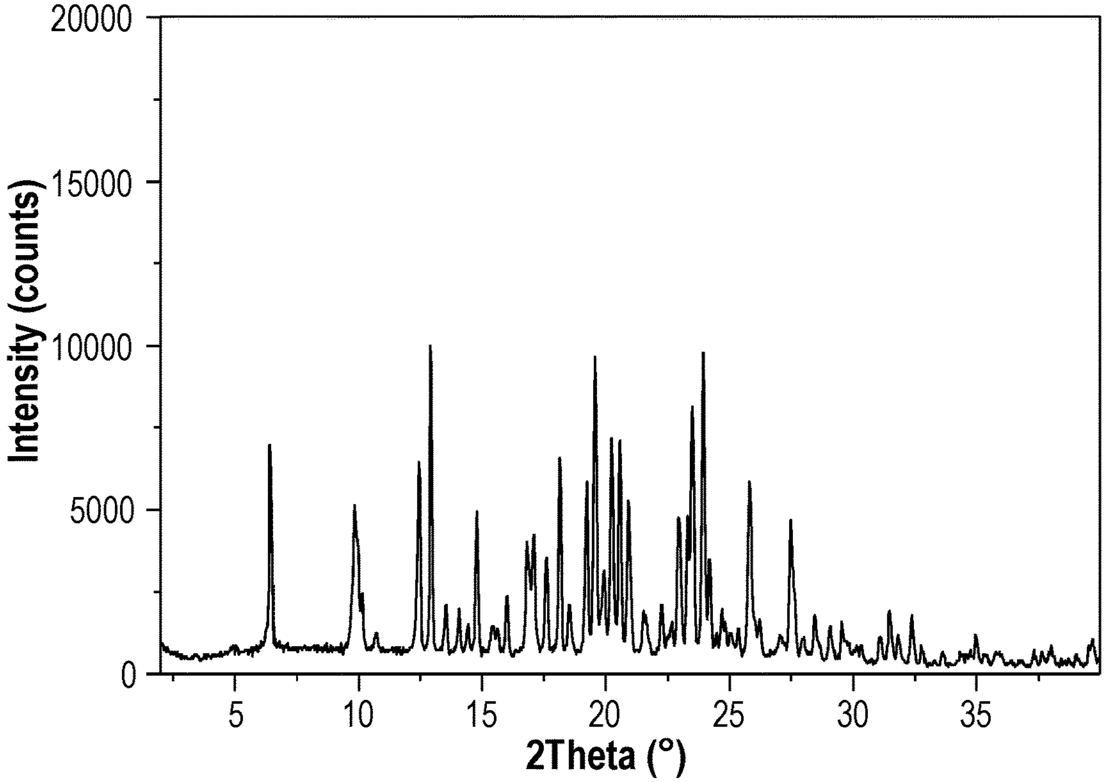
FIG. 108 depicts the XRPD pattern of Form B esylate salt of Compound 1.

In some embodiments, Form B esylate salt is characterized by the x-ray powder diffraction (XRPD) pattern depicted in FIG. 108.

Figure 110:
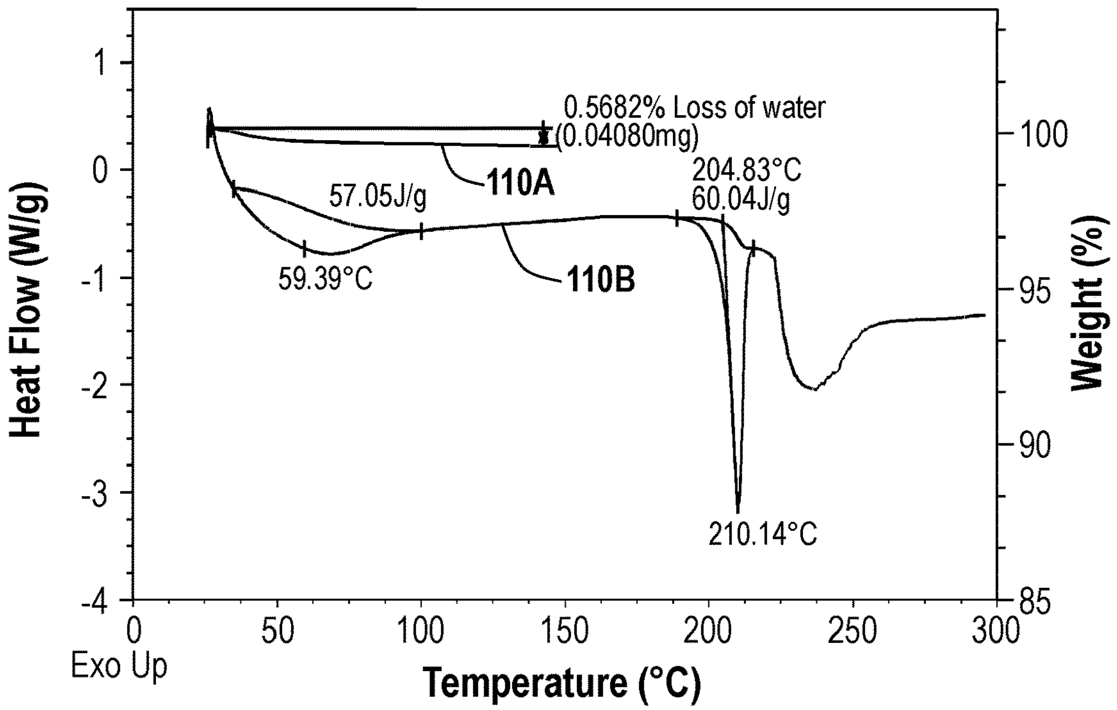
FIG. 110 depicts the TGA pattern of Form B esylate salt of Compound 1 (110A), and the DSC pattern of Form B esylate salt of Compound 1 (110B).

In some embodiments, Form B esylate salt is characterized by the thermogravimetric analysis (TGA) pattern depicted in FIG. 110, trace 110A.

In some embodiments, Form B esylate salt is characterized by the differential scanning calorimetry (DSC) pattern depicted in FIG. 110, trace 110B.

In some embodiments of a complex form of Compound 1, X is benzenesulfonic acid. In some such embodiments, a complex form of Compound 1 is a benzenesulfonate salt (also referred to as a “besylate” salt). In some embodiments, a besylate salt of Compound 1 is a crystalline besylate salt. In some embodiments, a crystalline besylate salt of Compound 1 is characterized by one or more peaks in its X-ray powder diffraction pattern selected from 5.5, 7.5, 10.4, 11.0, 12.8, 14.3, and 14.9±0.2 degrees 2θ. In some such embodiments, a complex form of Compound 1 is Form A besylate salt.

In some embodiments, Form A besylate salt is characterized by the following peaks in its X-ray powder diffraction pattern:

| Position ° 2θ ± 0.2 degrees | d-spacing [Å] | Height [cts] |
|---|---|---|
| 5.5 | 16.019 | 299 |
| 7.5 | 11.749 | 602 |
| 10.4 | 8.488 | 819 |
| 11.0 | 8.025 | 1001 |
| 12.8 | 6.931 | 715 |
| 13.2 | 6.716 | 280 |
| 14.3 | 6.175 | 1709 |
| 14.9 | 5.932 | 1058 |

-continued

| Position ° 2θ ± 0.2 degrees | d-spacing [Å] | Height [cts] |
|---|---|---|
| 15.5 | 5.710 | 395 |
| 16.7 | 5.306 | 1108 |
| 17.0 | 5.202 | 1278 |
| 18.0 | 4.924 | 1316 |
| 18.6 | 4.776 | 567 |
| 19.8 | 4.494 | 462 |
| 20.1 | 4.427 | 525 |
| 20.7 | 4.284 | 735 |
| 21.3 | 4.168 | 550 |
| 22.5 | 3.956 | 1206 |
| 22.9 | 3.878 | 395 |
| 23.2 | 3.830 | 647 |
| 23.6 | 3.769 | 387 |
| 23.9 | 3.718 | 443 |
| 24.6 | 3.620 | 281 |
| 25.4 | 3.502 | 593 |
| 25.7 | 3.466 | 443 |

Figure 111:
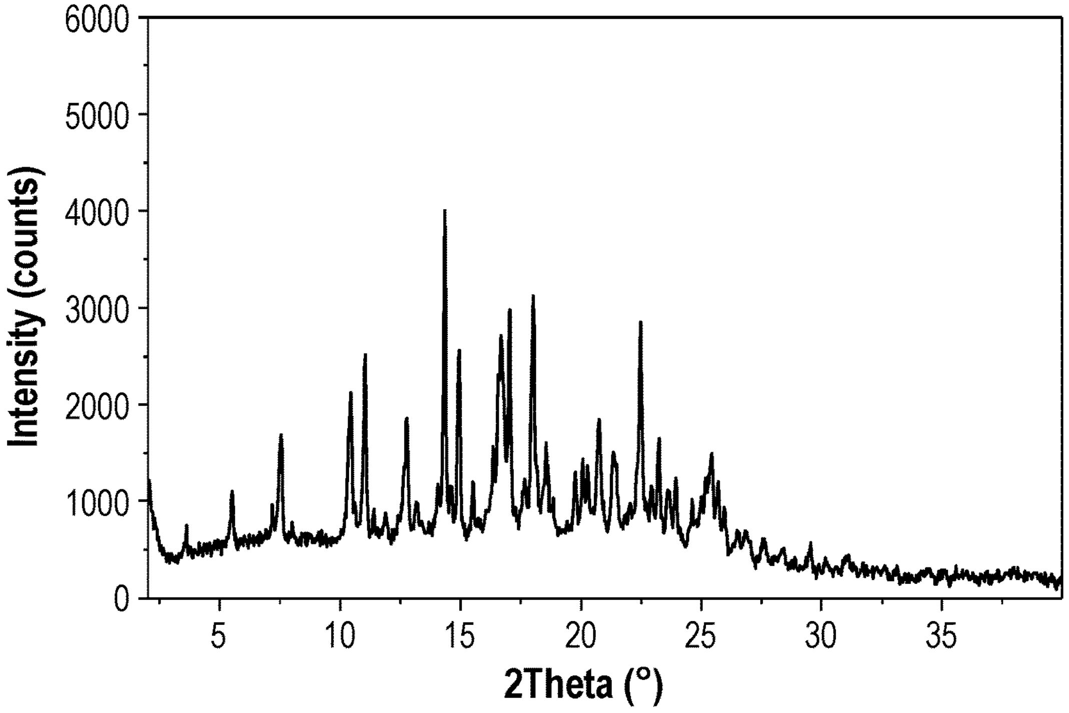
FIG. 111 depicts the XRPD pattern of Form A besylate salt of Compound 1.

In some embodiments, Form A besylate salt is characterized by the x-ray powder diffraction (XRPD) pattern depicted in FIG. 111.

Figure 115:
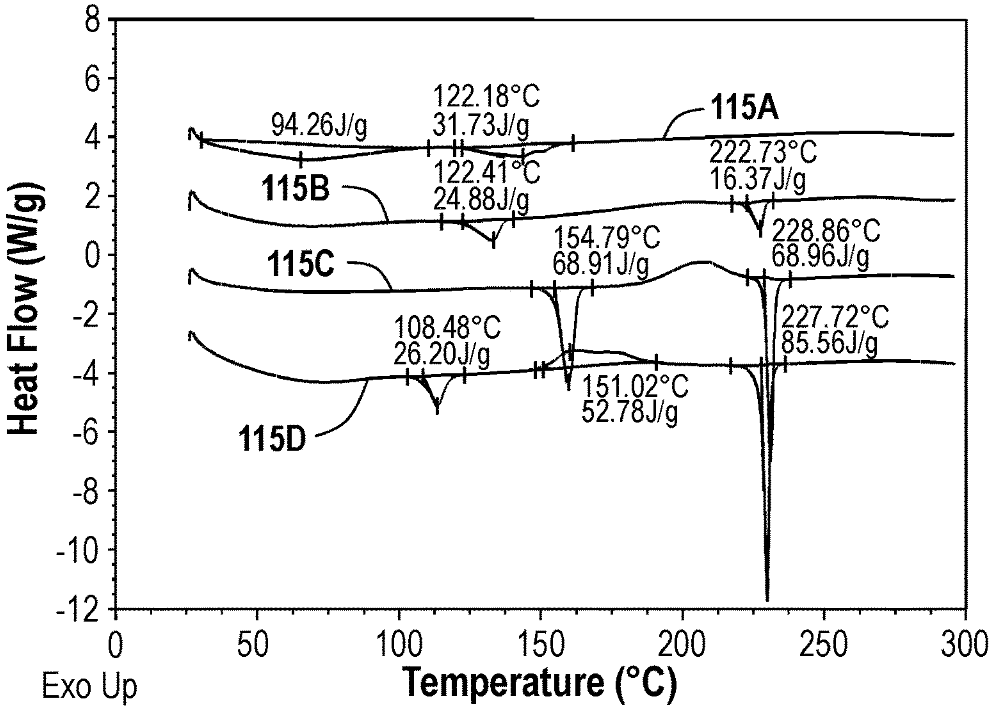
FIG. 115 depicts the DSC pattern of Form A besylate salt of Compound 1 (115A), the DSC pattern of Form B besylate salt of Compound 1 (115B), the DSC pattern of Form C besylate salt of Compound 1 (115C), and the DSC pattern of Form D besylate salt of Compound 1 (115D).

In some embodiments, Form A besylate salt is characterized by the differential scanning calorimetry (DSC) pattern depicted in FIG. 115, trace 115A.

In some embodiments, a crystalline besylate salt of Compound 1 is characterized by one or more peaks in its X-ray powder diffraction pattern selected from 7.5, 9.2, 11.1, 12.1, 14.1, and 15.1±0.2 degrees 2θ. In some such embodiments, a complex form of Compound 1 is Form B besylate salt.

In some embodiments, Form B besylate salt is characterized by the following peaks in its X-ray powder diffraction pattern:

| Position ° 2θ ± 0.2 degrees | d-spacing [Å] | Height [cts] |
|---|---|---|
| 7.5 | 11.860 | 154 |
| 9.2 | 9.588 | 144 |
| 11.1 | 7.962 | 607 |
| 12.1 | 7.308 | 508 |
| 14.1 | 6.284 | 642 |
| 15.1 | 5.871 | 610 |
| 17.5 | 5.075 | 1232 |
| 18.1 | 4.905 | 690 |
| 18.5 | 4.784 | 653 |
| 18.9 | 4.696 | 452 |
| 19.9 | 4.455 | 207 |
| 20.8 | 4.276 | 474 |
| 21.7 | 4.093 | 211 |
| 22.3 | 3.983 | 235 |
| 22.8 | 3.892 | 848 |
| 23.4 | 3.808 | 257 |
| 26.0 | 3.424 | 560 |
| 27.2 | 3.274 | 115 |

Figure 112:
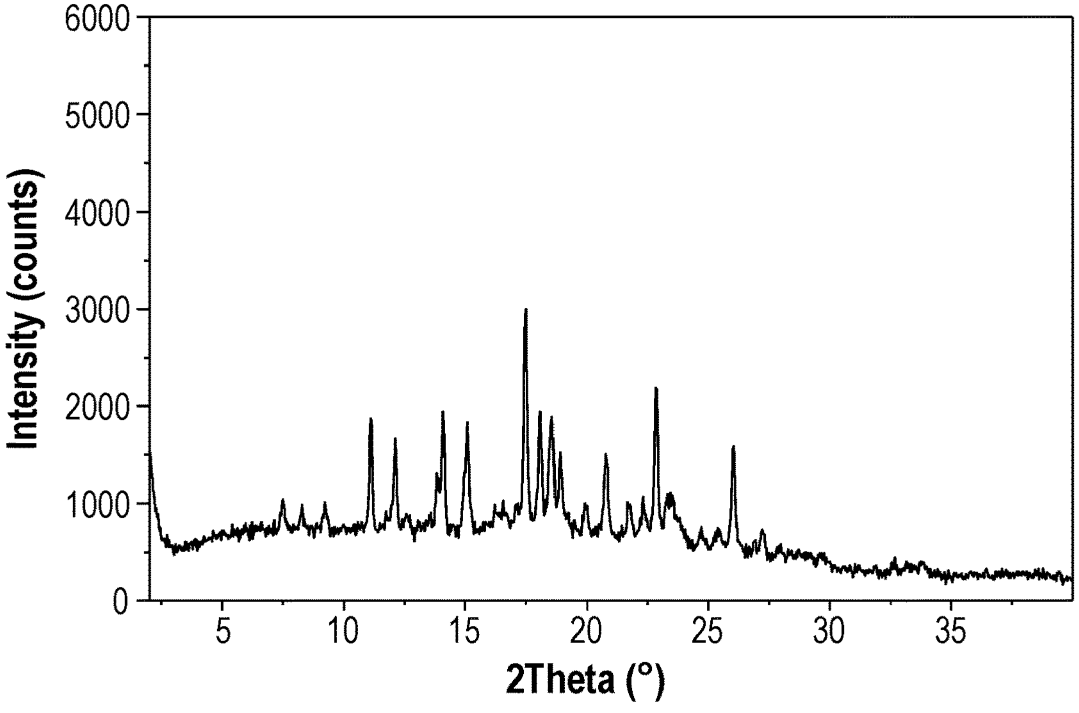
FIG. 112 depicts the XRPD pattern of Form B besylate salt of Compound 1.

In some embodiments, Form B besylate salt is characterized by the x-ray powder diffraction (XRPD) pattern depicted in FIG. 112.

In some embodiments, Form B besylate salt is characterized by the differential scanning calorimetry (DSC) pattern depicted in FIG. 115, trace 115B.

In some embodiments, a crystalline besylate salt of Compound 1 is characterized by one or more peaks in its X-ray powder diffraction pattern selected from 4.1, 8.2, 12.3, 16.4, and 20.5±0.2 degrees 2θ. In some such embodiments, a complex form of Compound 1 is Form C besylate salt.

In some embodiments, Form C besylate salt is characterized by the following peaks in its X-ray powder diffraction pattern:

| Position ° 2θ ± 0.2 degrees | d-spacing [Å] | Height [cts] |
|---|---|---|
| 4.1 | 21.421 | 461 |
| 8.2 | 10.788 | 1502 |
| 12.3 | 7.200 | 12721 |
| 15.2 | 5.826 | 929 |
| 15.4 | 5.736 | 1445 |
| 16.1 | 5.516 | 402 |
| 16.4 | 5.403 | 3281 |
| 16.9 | 5.253 | 788 |
| 18.0 | 4.917 | 1061 |
| 18.4 | 4.820 | 473 |
| 19.4 | 4.577 | 294 |
| 19.7 | 4.498 | 458 |
| 20.2 | 4.402 | 1047 |
| 20.5 | 4.323 | 5107 |
| 21.0 | 4.224 | 980 |
| 21.8 | 4.076 | 1072 |
| 22.4 | 3.962 | 408 |
| 23.6 | 3.770 | 1164 |
| 24.1 | 3.697 | 348 |
| 24.4 | 3.642 | 4747 |
| 25.4 | 3.501 | 532 |
| 26.2 | 3.400 | 3118 |
| 26.8 | 3.324 | 383 |
| 27.3 | 3.263 | 861 |
| 27.8 | 3.211 | 552 |
| 28.9 | 3.088 | 1206 |
| 33.2 | 2.700 | 356 |

Figure 113:
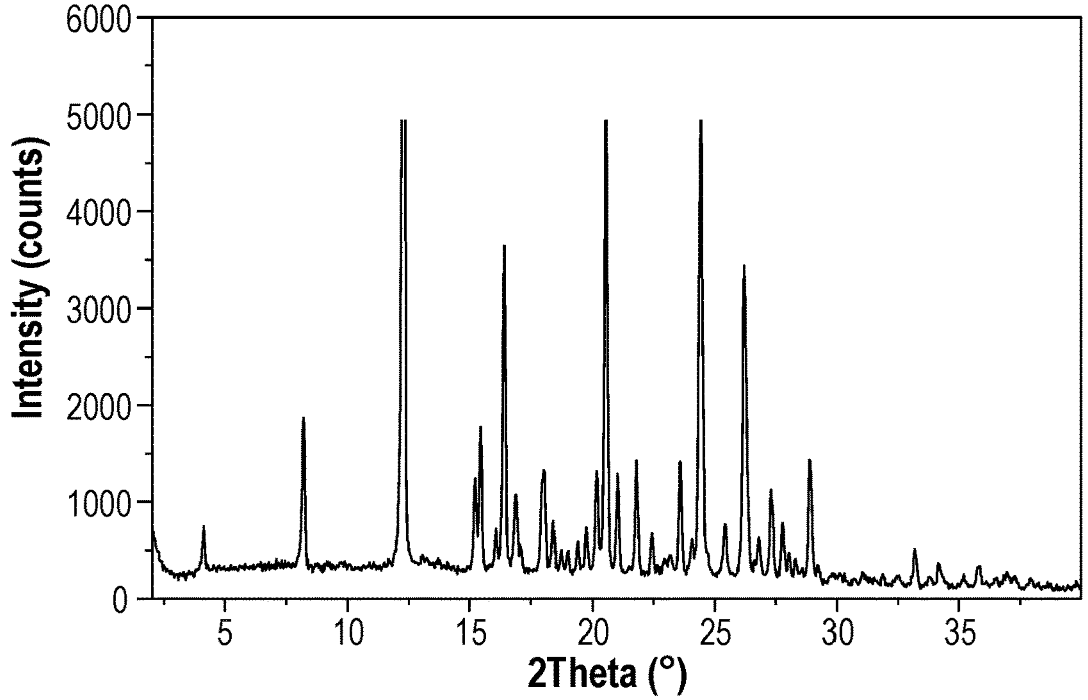
FIG. 113 depicts the XRPD pattern of Form C besylate salt of Compound 1.

In some embodiments, Form C besylate salt is characterized by the x-ray powder diffraction (XRPD) pattern depicted in FIG. 113.

In some embodiments, Form C besylate salt is characterized by the differential scanning calorimetry (DSC) pattern depicted in FIG. 115, trace 115C.

In some embodiments, a besylate salt of Compound 1 is a hydrate. In some embodiments, a hydrate form of a besylate salt of Compound 1 is a crystalline hydrate form of a besylate salt. In some embodiments, a crystalline hydrate form of a besylate salt of Compound 1 is characterized by one or more peaks in its X-ray powder diffraction pattern selected from 6.1, 7.2, 11.5, 12.1, 12.6, and 12.9±0.2 degrees 2θ. In some such embodiments, a complex form of Compound 1 is Form D besylate salt.

In some embodiments, Form D besylate salt is characterized by the following peaks

| Position ° 2θ ± 0.2 degrees | d-spacing [Å] | Height [cts] |
|---|---|---|
| 6.1 | 14.417 | 145 |
| 7.2 | 12.281 | 167 |
| 11.5 | 7.682 | 953 |
| 12.1 | 7.305 | 541 |
| 12.6 | 7.025 | 478 |
| 12.9 | 6.887 | 468 |
| 14.0 | 6.322 | 252 |
| 14.6 | 6.053 | 987 |
| 16.4 | 5.405 | 457 |
| 17.2 | 5.170 | 323 |
| 17.8 | 4.996 | 285 |
| 18.4 | 4.826 | 1021 |
| 18.7 | 4.744 | 528 |
| 19.8 | 4.479 | 405 |
| 21.0 | 4.233 | 560 |

-continued

| Position ° 2θ ± 0.2 degrees | d-spacing [Å] | Height [cts] |
|---|---|---|
| 21.7 | 4.094 | 402 |
| 22.4 | 3.963 | 291 |
| 23.3 | 3.821 | 355 |
| 23.8 | 3.740 | 402 |
| 24.1 | 3.696 | 1363 |
| 25.3 | 3.515 | 804 |
| 26.1 | 3.408 | 197 |
| 26.9 | 3.314 | 209 |

Figure 114:
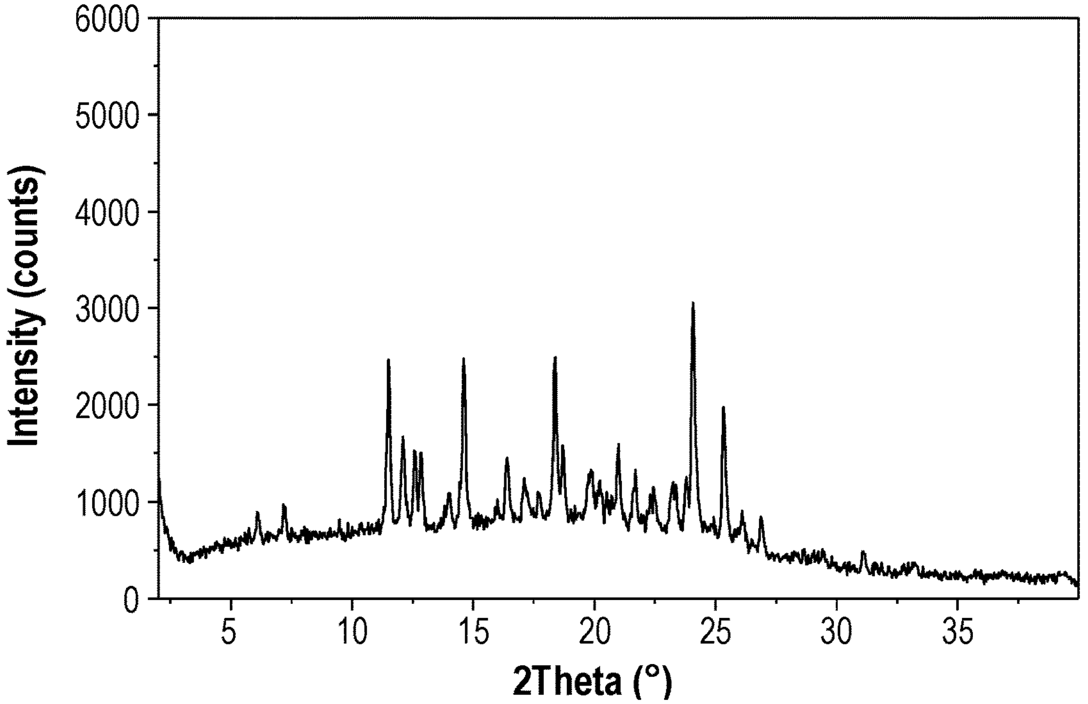
FIG. 114 depicts the XRPD pattern of Form D besylate salt of Compound 1.

In some embodiments, Form D besylate salt is characterized by the x-ray powder diffraction (XRPD) pattern depicted in FIG. 114.

Figure 116:
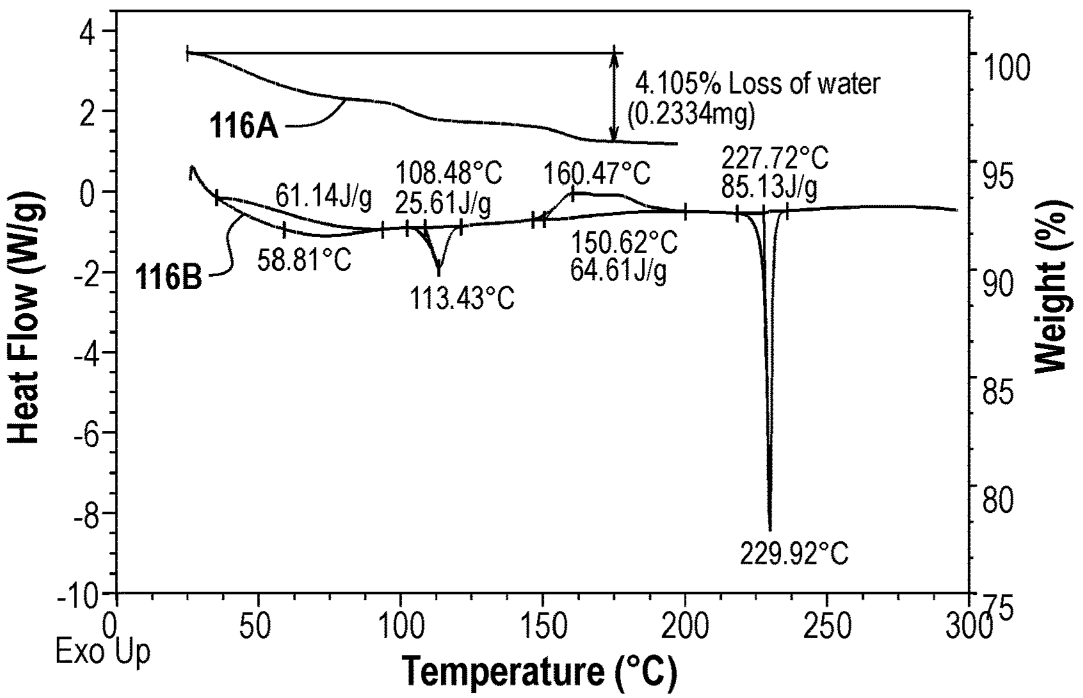
FIG. 116 depicts the TGA pattern of Form D besylate salt of Compound 1 (116A), and the DSC pattern of Form D besylate salt of Compound 1 (116B).

In some embodiments, Form D besylate salt is characterized by the thermogravimetric analysis (TGA) pattern depicted in FIG. 116, trace 116A.

In some embodiments, Form D besylate salt is characterized by the differential scanning calorimetry (DSC) pattern depicted in FIG. 116, trace 116B.

In some embodiments of a complex form of Compound 1, X is oxalic acid. In some such embodiments, a complex form of Compound 1 is an oxalate salt. In some embodiments, an oxalate salt of Compound 1 is a crystalline oxalate salt. In some embodiments, an oxalate salt of Compound 1 is a hydrate. In some embodiments, a hydrate form of an oxalate salt of Compound 1 is a crystalline hydrate form of an oxalate salt. In some embodiments, a crystalline hydrate form of an oxalate salt of Compound 1 is characterized by one or more peaks in its X-ray powder diffraction pattern selected from 4.7, 6.5, 9.4, 11.0, 11.9, and 12.5±0.2 degrees 2θ. In some such embodiments, a complex form of Compound 1 is Form A oxalate salt.

In some embodiments, Form A oxalate salt is characterized by the following peaks in its X-ray powder diffraction pattern:

| Position ° 2θ ± 0.2 degrees | d-spacing [Å] | Height [cts] |
|---|---|---|
| 4.7 | 18.750 | 557 |
| 6.5 | 13.578 | 631 |
| 9.4 | 9.405 | 795 |
| 11.0 | 8.014 | 355 |
| 11.9 | 7.451 | 1031 |
| 12.5 | 7.087 | 1642 |
| 14.2 | 6.257 | 364 |
| 14.8 | 5.969 | 317 |
| 15.4 | 5.760 | 259 |
| 17.2 | 5.162 | 358 |
| 17.7 | 5.016 | 847 |
| 18.9 | 4.688 | 401 |
| 19.6 | 4.525 | 355 |
| 20.4 | 4.347 | 432 |
| 22.3 | 3.984 | 449 |
| 23.2 | 3.830 | 247 |
| 24.2 | 3.679 | 1722 |
| 25.6 | 3.481 | 305 |
| 26.0 | 3.424 | 302 |
| 27.2 | 3.282 | 180 |
| 31.8 | 2.816 | 82 |
| 33.0 | 2.712 | 66 |
| 38.4 | 2.343 | 66 |

Figure 117:
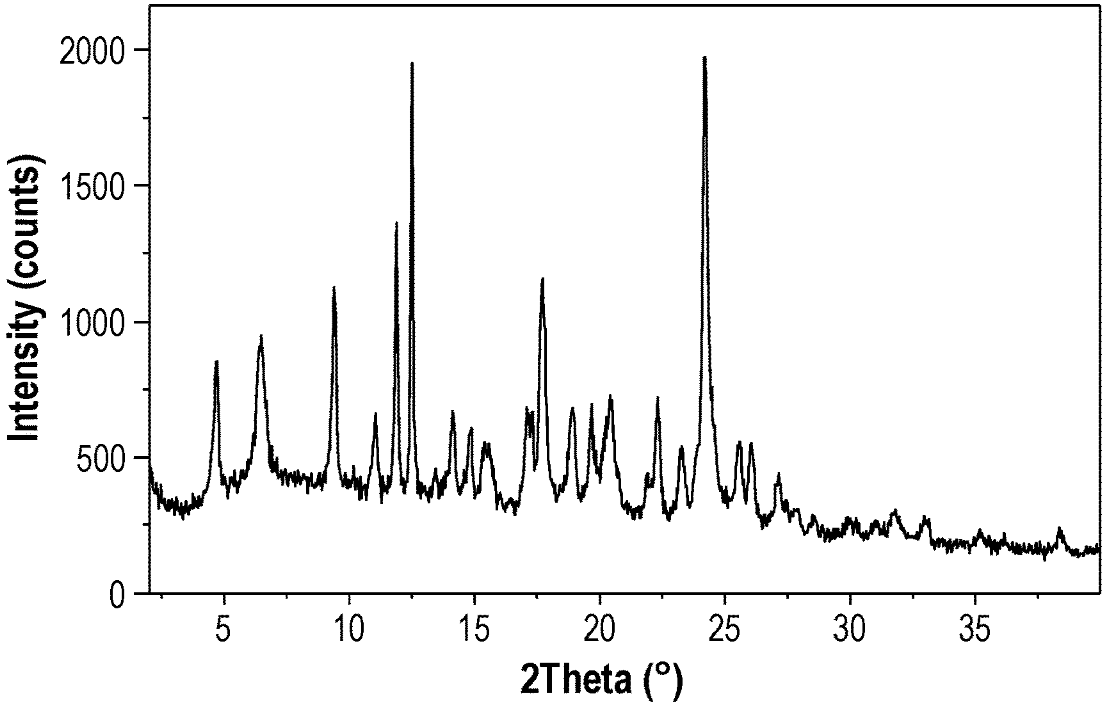
FIG. 117 depicts the XRPD pattern of Form A oxalate salt of Compound 1.

In some embodiments, Form A oxalate salt is characterized by the x-ray powder diffraction (XRPD) pattern depicted in FIG. 117.

Figure 119:
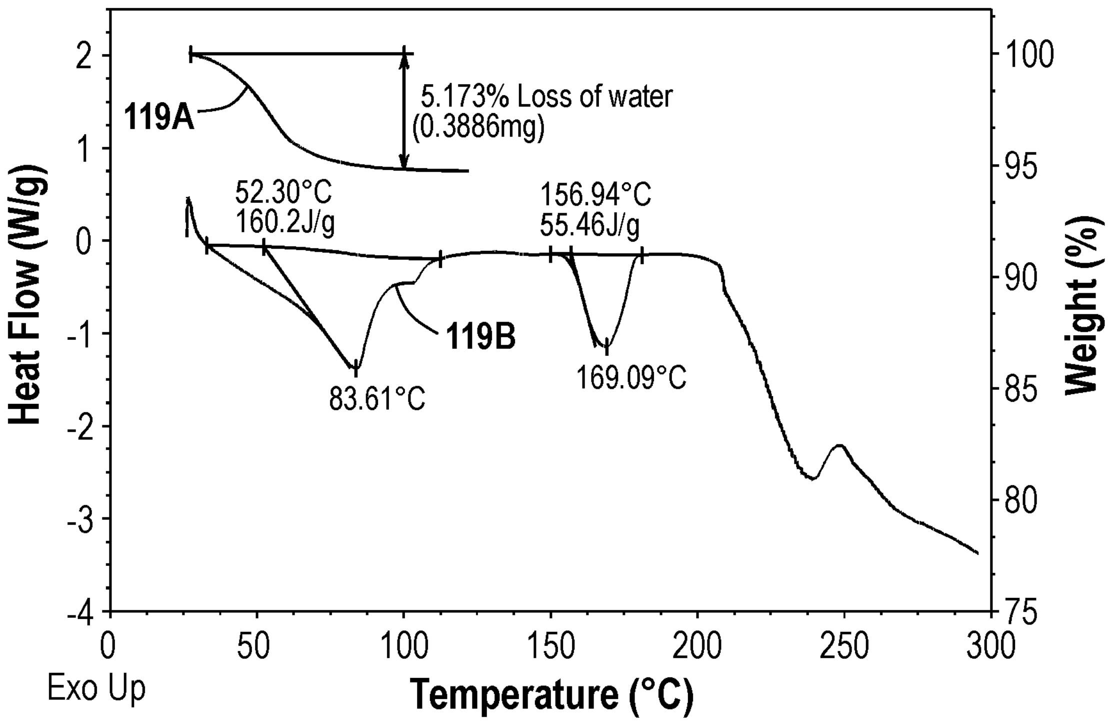

In some embodiments, Form A oxalate salt is characterized by the thermogravimetric analysis (TGA) pattern depicted in FIG. 119, trace 119A.

In some embodiments, Form A oxalate salt is characterized by the differential scanning calorimetry (DSC) pattern depicted in FIG. 119, trace 119B.

In some embodiments, a crystalline oxalate salt of Compound 1 is characterized by one or more peaks in its X-ray powder diffraction pattern selected from 5.3, 8.7, and 12.9±0.2 degrees 2θ. In some such embodiments, a complex form of Compound 1 is Form B oxalate salt.

In some embodiments, Form B oxalate salt is characterized by the following peaks in its X-ray powder diffraction pattern:

| Position ° 2θ ± 0.2 degrees | d-spacing [Å] | Height [cts] |
|---|---|---|
| 5.3 | 16.727 | 1710 |
| 8.1 | 10.931 | 188 |
| 8.7 | 10.151 | 280 |
| 11.1 | 7.961 | 224 |
| 12.5 | 7.109 | 453 |
| 12.9 | 6.884 | 807 |
| 13.1 | 6.752 | 692 |
| 14.1 | 6.300 | 632 |
| 14.4 | 6.140 | 422 |
| 14.9 | 5.942 | 705 |
| 15.4 | 5.757 | 491 |
| 15.8 | 5.619 | 841 |
| 16.8 | 5.267 | 1630 |
| 17.7 | 4.999 | 492 |
| 18.0 | 4.934 | 572 |
| 18.2 | 4.865 | 446 |
| 18.7 | 4.758 | 915 |
| 19.3 | 4.594 | 585 |
| 19.7 | 4.505 | 735 |
| 20.5 | 4.339 | 818 |
| 21.3 | 4.162 | 600 |
| 22.6 | 3.941 | 643 |
| 22.9 | 3.876 | 688 |
| 23.6 | 3.777 | 1144 |
| 24.1 | 3.700 | 1267 |
| 24.9 | 3.570 | 1221 |
| 25.6 | 3.474 | 512 |
| 26.4 | 3.374 | 442 |
| 27.1 | 3.292 | 778 |

Figure 118:
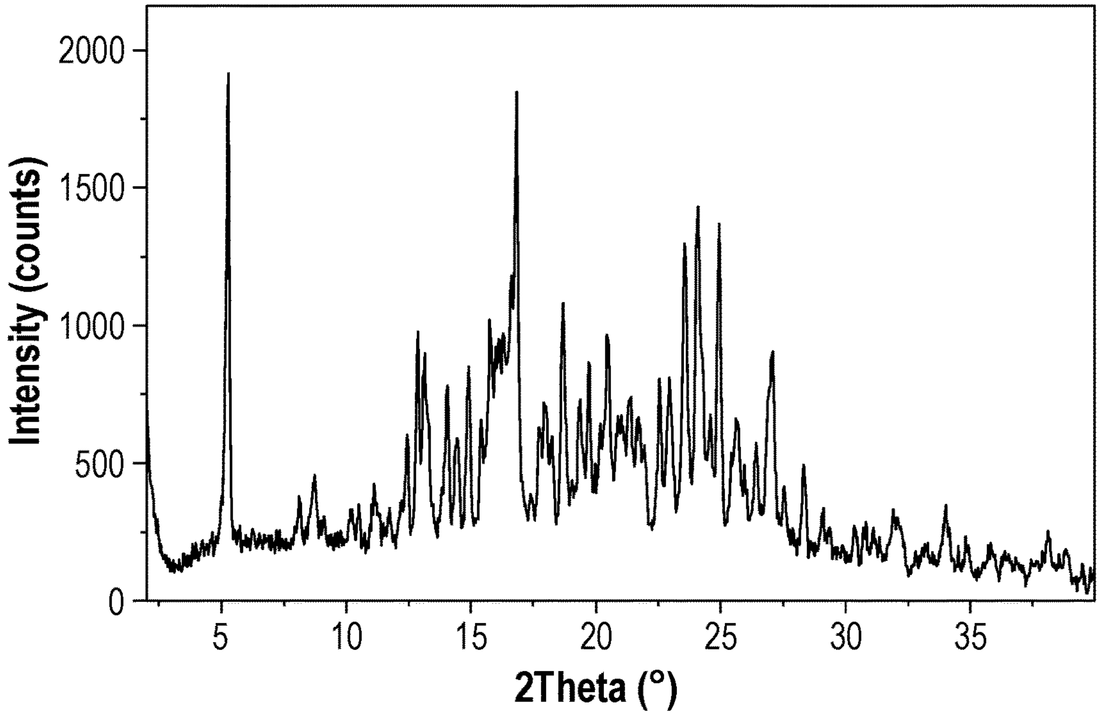
FIG. 118 depicts the XRPD pattern of Form B oxalate salt of Compound 1.

In some embodiments, Form B oxalate salt is characterized by the x-ray powder diffraction (XRPD) pattern depicted in FIG. 118.

Figure 120:
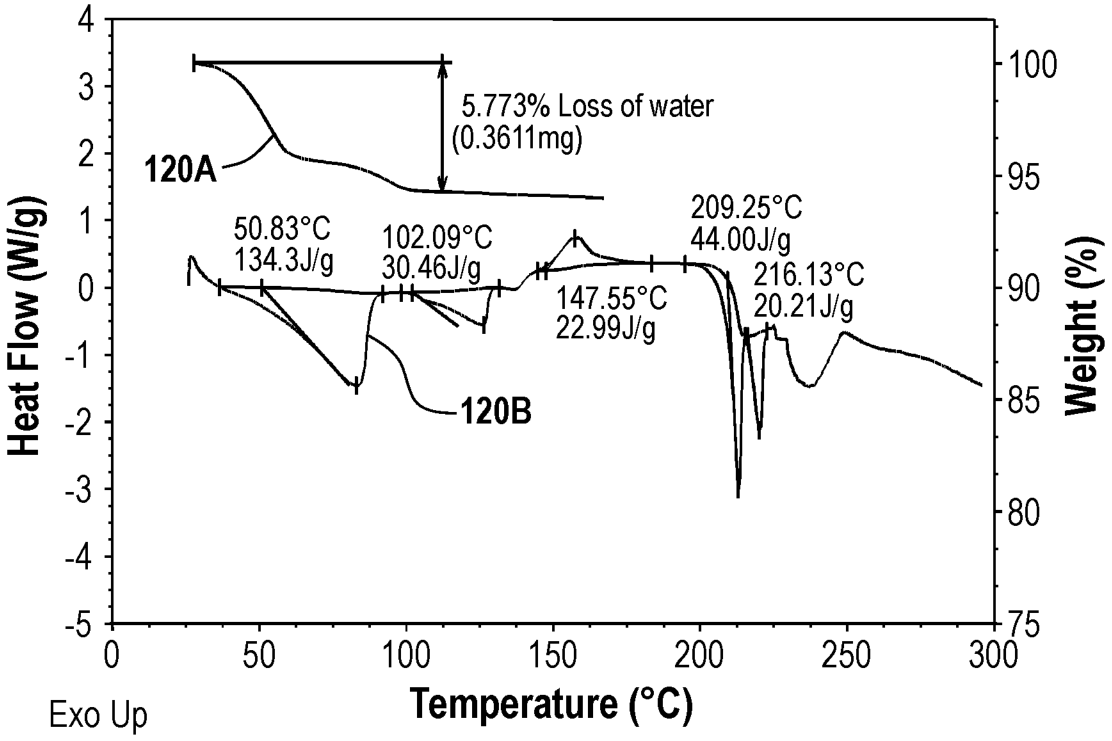

In some embodiments, Form B oxalate salt is characterized by the thermogravimetric analysis (TGA) pattern depicted in FIG. 120, trace 120A.

In some embodiments, Form B oxalate salt is characterized by the differential scanning calorimetry (DSC) pattern depicted in FIG. 120, trace 120B.

In some embodiments of a complex form of Compound 1, X is maleic acid. In some such embodiments, a complex form of Compound 1 is a maleate salt. In some embodiments, a maleate salt of Compound 1 is a crystalline maleate salt. In some embodiments, a maleate salt of Compound 1 is a hydrate. In some embodiments, a hydrate form of a maleate salt of Compound 1 is a crystalline hydrate form of a maleate salt. In some embodiments, a crystalline hydrate form of a maleate salt of Compound 1 is characterized by one or more peaks in its X-ray powder diffraction pattern selected from 7.7, 11.5, 14.1, 15.4, 15.8, and 16.1±0.2 degrees 2θ. In some such embodiments, a complex form of Compound 1 is Form A maleate salt.

In some embodiments, Form A maleate salt is characterized by the following peaks in its X-ray powder diffraction pattern:

| Position ° 2θ ± 0.2 degrees | d-spacing [Å] | Height [cts] |
|---|---|---|
| 3.9 | 22.637 | 252 |
| 7.7 | 11.476 | 3253 |
| 9.8 | 9.056 | 235 |
| 11.5 | 7.669 | 2247 |
| 13.4 | 6.626 | 700 |
| 13.7 | 6.460 | 508 |
| 14.1 | 6.278 | 617 |
| 15.4 | 5.759 | 4592 |
| 15.8 | 5.616 | 967 |
| 16.1 | 5.507 | 2377 |
| 16.9 | 5.253 | 631 |
| 17.2 | 5.159 | 572 |
| 17.6 | 5.040 | 1272 |
| 18.1 | 4.890 | 1144 |
| 18.8 | 4.710 | 1676 |
| 19.3 | 4.611 | 588 |
| 19.6 | 4.536 | 785 |
| 19.9 | 4.469 | 2055 |
| 20.2 | 4.403 | 953 |
| 20.7 | 4.298 | 387 |
| 21.0 | 4.224 | 1239 |
| 22.1 | 4.031 | 1292 |
| 22.9 | 3.885 | 718 |
| 23.1 | 3.843 | 1060 |
| 23.4 | 3.806 | 1147 |
| 24.1 | 3.698 | 1058 |
| 25.0 | 3.565 | 3369 |
| 25.3 | 3.524 | 2734 |
| 26.2 | 3.405 | 3543 |
| 27.1 | 3.294 | 912 |

Figure 121:
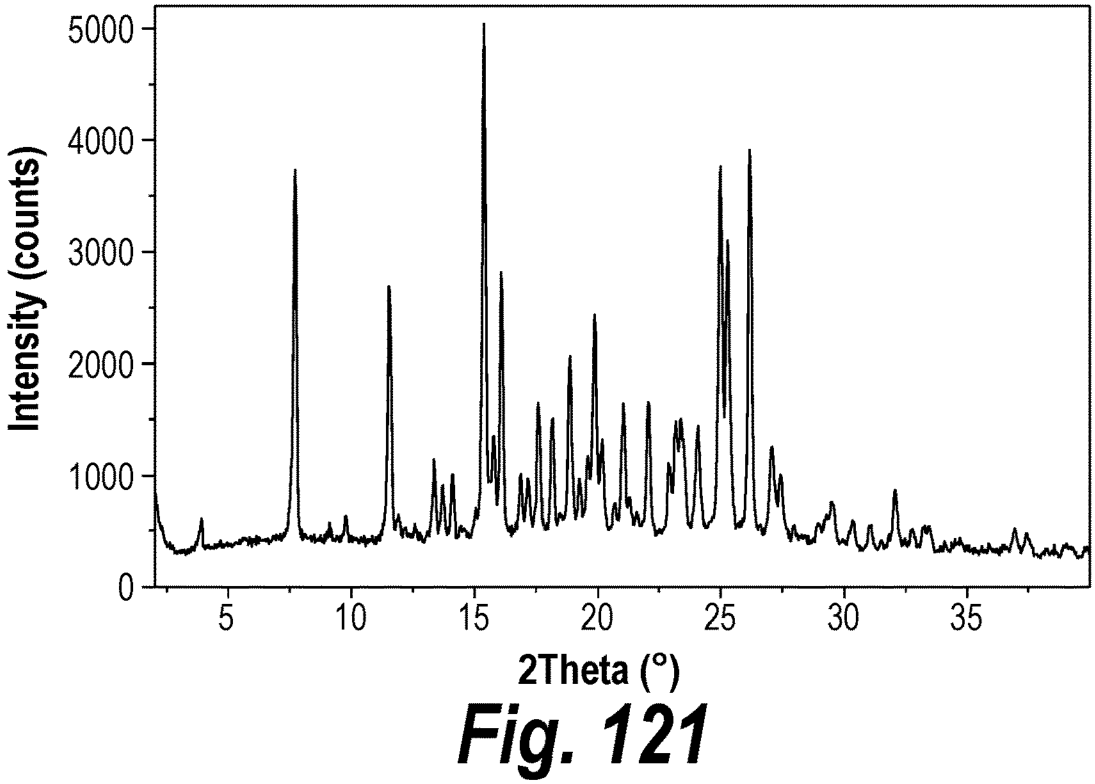

In some embodiments, Form A maleate salt is characterized by the x-ray powder diffraction (XRPD) pattern depicted in FIG. 121.

Figure 122:
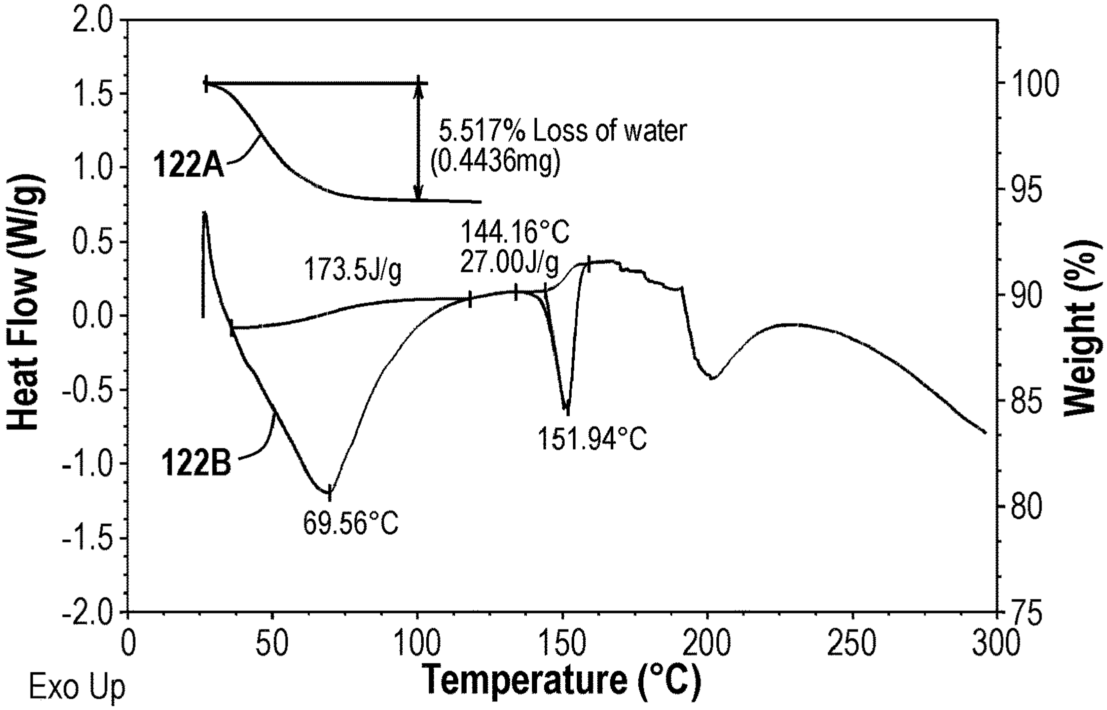

In some embodiments, Form A maleate salt is characterized by the thermogravimetric analysis (TGA) pattern depicted in FIG. 122, trace 122A.

In some embodiments, Form A maleate salt is characterized by the differential scanning calorimetry (DSC) pattern depicted in FIG. 122, trace 122B.

In some embodiments of a complex form of Compound 1, X is pamoic acid. In some such embodiments, a complex form of Compound 1 is a pamoate salt. In some embodiments, a pamoate salt of Compound 1 is a crystalline pamoate salt. In some embodiments, a crystalline pamoate salt of Compound 1 is characterized by one or more peaks in its X-ray powder diffraction pattern selected from 6.1, 10.7, 13.9, 15.4, 20.8, and 21.5±0.2 degrees 2θ. In some such embodiments, a complex form of Compound 1 is Form A pamoate salt.

In some embodiments, Form A pamoate salt is characterized by the following peaks in its X-ray powder diffraction pattern:

| Position ° 2θ ± 0.2 degrees | d-spacing [Å] | Height [cts] |
|---|---|---|
| 6.1 | 14.53 | 3876 |
| 8.2 | 10.73 | 565 |
| 10.2 | 8.67 | 312 |
| 10.7 | 8.26 | 1402 |
| 11.4 | 7.76 | 188 |
| 12.1 | 7.29 | 583 |
| 13.3 | 6.67 | 502 |
| 13.9 | 6.37 | 1477 |
| 15.4 | 5.76 | 1473 |
| 16.0 | 5.55 | 684 |
| 16.8 | 5.28 | 1937 |
| 18.0 | 4.94 | 2406 |
| 19.4 | 4.58 | 2254 |
| 20.8 | 4.26 | 3684 |
| 21.5 | 4.13 | 4769 |
| 22.2 | 4.01 | 568 |
| 22.9 | 3.89 | 514 |
| 23.3 | 3.82 | 605 |
| 24.3 | 3.66 | 491 |
| 25.1 | 3.54 | 5643 |
| 26.5 | 3.36 | 876 |
| 28.3 | 3.15 | 378 |
| 29.3 | 3.05 | 319 |
| 31.2 | 2.87 | 1051 |

-continued

Figure 123:
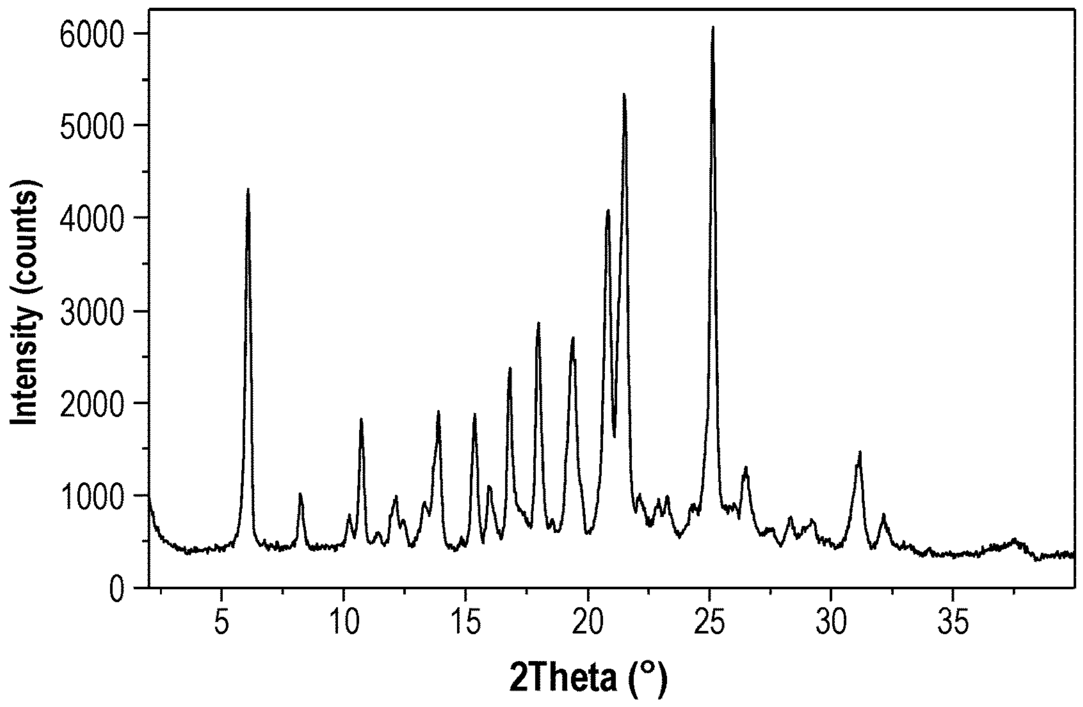

In some embodiments, Form A pamoate salt is characterized by the x-ray powder diffraction (XRPD) pattern depicted in FIG. 123.

Figure 124:
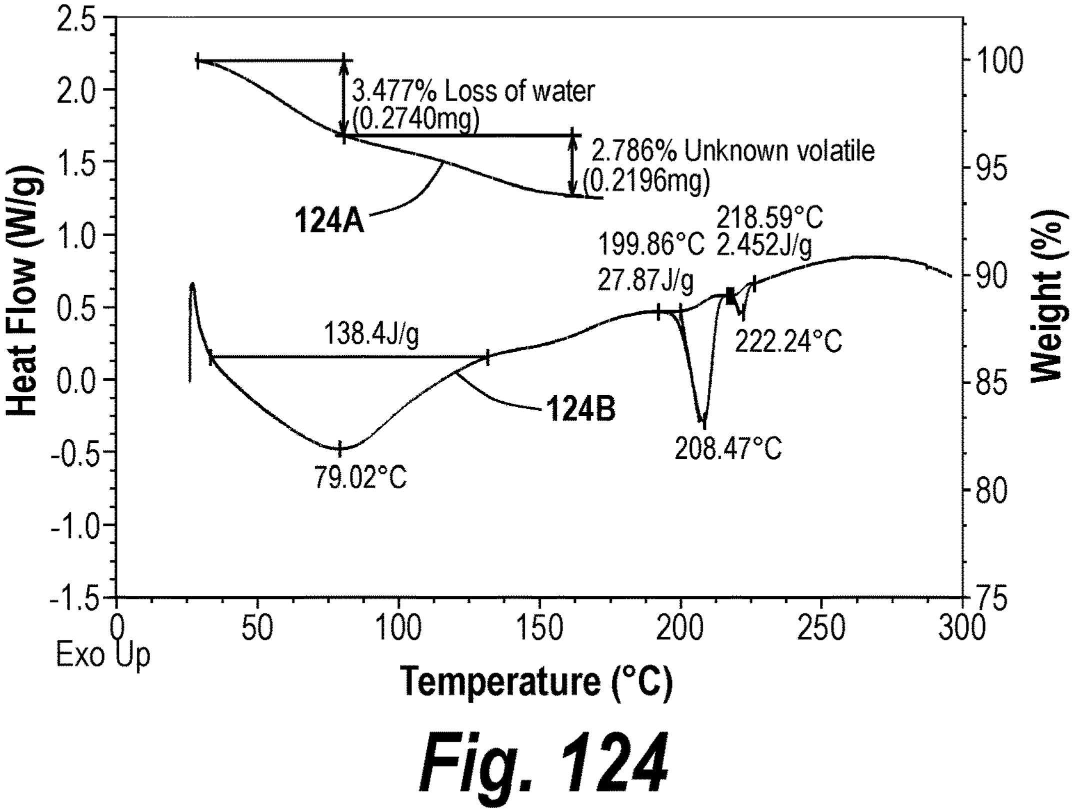

In some embodiments, Form A pamoate salt is characterized by the thermogravimetric analysis (TGA) pattern depicted in FIG. 124, trace 124A.

In some embodiments, Form A pamoate salt is characterized by the differential scanning calorimetry (DSC) pattern depicted in FIG. 124, trace 124B.

In some embodiments of a complex form of Compound 1, X is 1-hydroxy-2-naphthoic acid. In some such embodiments, a complex form of Compound 1 is a 1-hydroxy-2-naphthoate salt. In some embodiments, a 1-hydroxy-2-naphthoate salt of Compound 1 is a crystalline 1-hydroxy-2-naphthoate salt. In some embodiments, a crystalline 1-hydroxy-2-naphthoate salt of Compound 1 is characterized by one or more peaks in its X-ray powder diffraction pattern selected from 6.7, 8.4, 9.7, 10.8, and 16.0±0.2 degrees 2θ. In some such embodiments, a complex form of Compound 1 is Form A 1-hydroxy-2-naphthoate salt.

In some embodiments, Form A 1-hydroxy-2-naphthoate salt is characterized by the following peaks in its X-ray powder diffraction pattern:

| Position ° 2θ ± 0.2 degrees | d-spacing [Å] | Height [cts] |
|---|---|---|
| 4.8 | 18.419 | 175 |
| 6.7 | 13.252 | 527 |
| 7.5 | 11.865 | 271 |
| 8.4 | 10.520 | 554 |
| 9.7 | 9.087 | 1313 |
| 10.8 | 8.208 | 571 |
| 11.9 | 7.415 | 618 |
| 13.5 | 6.568 | 831 |
| 14.4 | 6.166 | 2022 |
| 14.9 | 5.947 | 1065 |
| 15.3 | 5.777 | 817 |
| 16.0 | 5.531 | 1562 |
| 16.4 | 5.402 | 1295 |
| 17.8 | 4.992 | 881 |
| 18.5 | 4.785 | 1405 |
| 19.1 | 4.642 | 923 |
| 19.8 | 4.483 | 964 |
| 21.0 | 4.223 | 875 |
| 22.0 | 4.033 | 749 |
| 22.5 | 3.955 | 874 |

-continued

| Position ° 2θ ± 0.2 degrees | d-spacing [Å] | Height [cts] |
|---|---|---|
| 23.4 | 3.796 | 1148 |
| 23.9 | 3.727 | 2074 |
| 24.3 | 3.663 | 1425 |
| 25.1 | 3.543 | 834 |
| 26.2 | 3.404 | 916 |
| 27.3 | 3.266 | 432 |
| 28.0 | 3.191 | 379 |
| 29.8 | 3.000 | 388 |

Figure 125:
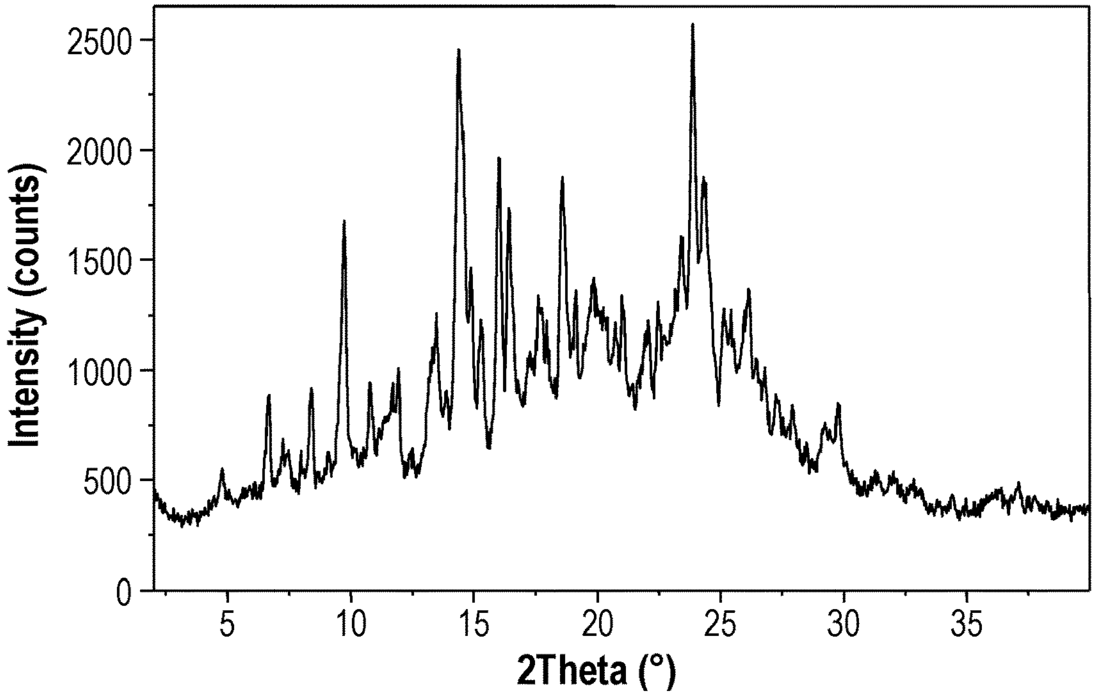

In some embodiments, Form A 1-hydroxy-2-naphthoate salt is characterized by the x-ray powder diffraction (XRPD) pattern depicted in FIG. 125.

Figure 126:
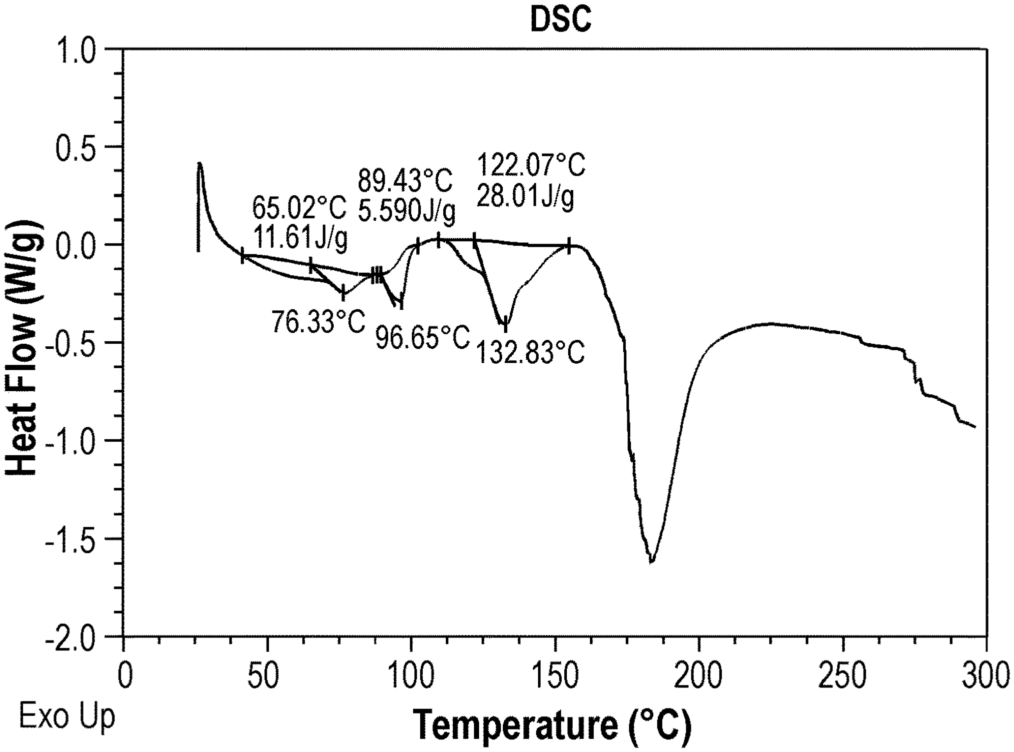

In some embodiments, Form A 1-hydroxy-2-naphthoate salt is characterized by the differential scanning calorimetry (DSC) pattern depicted in FIG. 126.

In some embodiments of a complex form of Compound 1, X is malonic acid. In some such embodiments, a complex form of Compound 1 is a malonate salt. In some embodiments, a malonate salt of Compound 1 is a crystalline malonate salt. In some embodiments, a crystalline malonate salt of Compound 1 is characterized by one or more peaks in its X-ray powder diffraction pattern selected from 7.8, 11.7, 13.2, 13.7, and 15.6±0.2 degrees 2θ. In some such embodiments, a complex form of Compound 1 is Form A malonate salt.

In some embodiments, Form A malonate salt is characterized by the following peaks in its X-ray powder diffraction pattern:

| Position ° 2θ ± 0.2 degrees | d-spacing [Å] | Height [cts] |
|---|---|---|
| 7.8 | 11.328 | 4581 |
| 11.7 | 7.553 | 2996 |
| 12.4 | 7.135 | 164 |
| 13.2 | 6.724 | 402 |
| 13.7 | 6.449 | 660 |
| 15.6 | 5.665 | 4794 |
| 16.1 | 5.495 | 1251 |
| 16.9 | 5.243 | 392 |
| 17.6 | 5.042 | 1225 |
| 17.7 | 5.000 | 1078 |
| 18.9 | 4.699 | 826 |
| 19.4 | 4.585 | 575 |
| 19.6 | 4.530 | 816 |
| 20.0 | 4.430 | 828 |
| 20.4 | 4.345 | 1281 |
| 21.1 | 4.214 | 630 |
| 22.4 | 3.975 | 615 |
| 23.2 | 3.829 | 573 |
| 23.6 | 3.771 | 1883 |
| 24.5 | 3.639 | 335 |
| 25.7 | 3.468 | 2844 |
| 25.9 | 3.442 | 1892 |
| 27.0 | 3.301 | 2136 |
| 27.7 | 3.220 | 262 |
| 32.3 | 2.768 | 380 |

Figure 127:
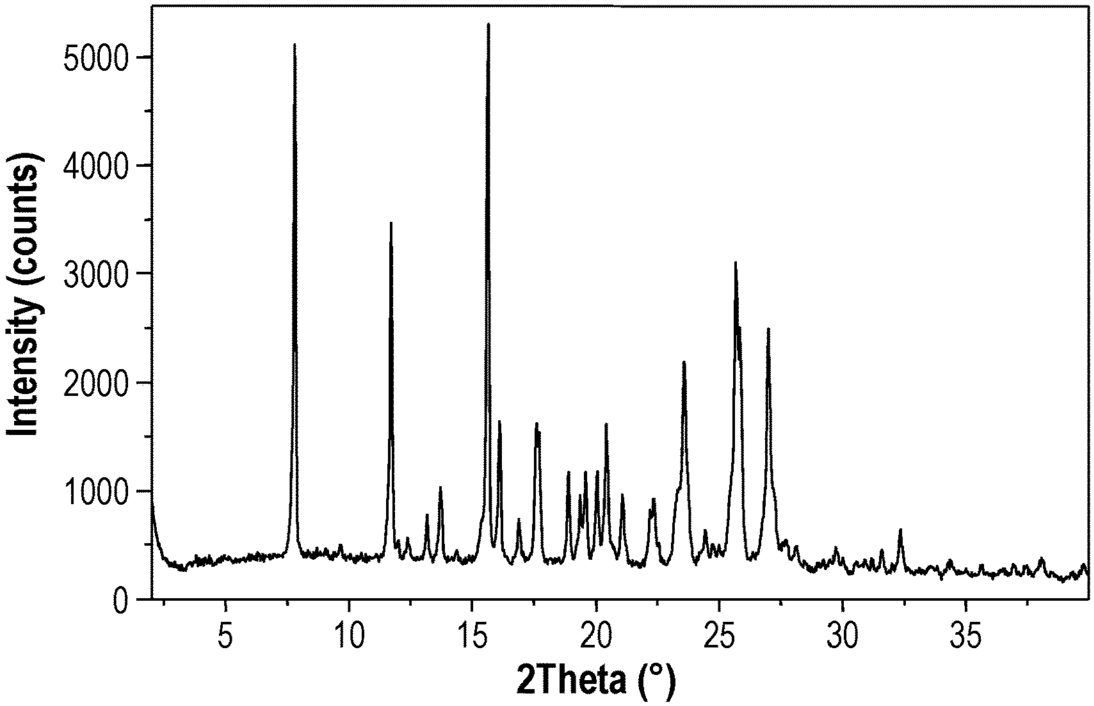

In some embodiments, Form A malonate salt is characterized by the x-ray powder diffraction (XRPD) pattern depicted in FIG. 127.

Figure 128:
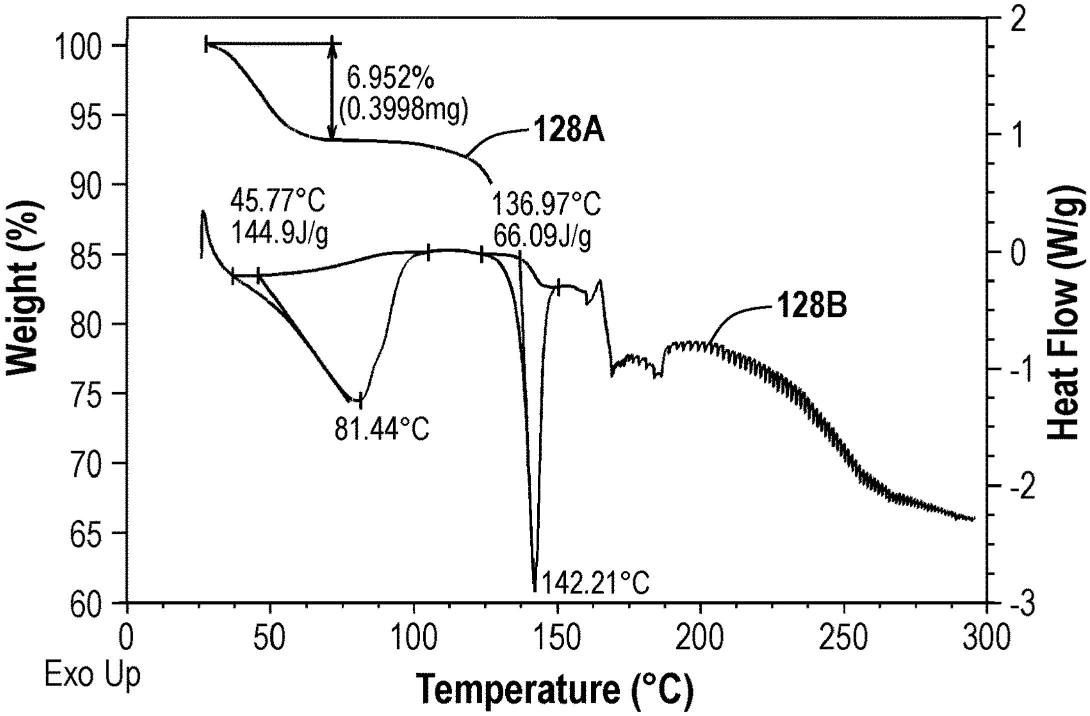

In some embodiments, Form A malonate salt is characterized by the thermogravimetric analysis (TGA) pattern depicted in FIG. 128, trace 128A.

In some embodiments, Form A malonate salt is characterized by the differential scanning calorimetry (DSC) pattern depicted in FIG. 128, trace 128B.

In some embodiments, a crystalline malonate salt of Compound 1 is characterized by one or more peaks in its X-ray powder diffraction pattern selected from 5.6, 7.3, 11.2, 12.3, 14.5, and 16.8±0.2 degrees 2θ. In some such embodiments, a complex form of Compound 1 is Form B malonate salt.

In some embodiments, Form B malonate salt is characterized by the following peaks in its X-ray powder diffraction pattern:

| Position ° 2θ ± 0.2 degrees | d-spacing [Å] | Height [cts] |
|---|---|---|
| 5.6 | 15.89485 | 429 |
| 7.3 | 12.03475 | 262 |
| 10.0 | 8.81941 | 265 |
| 10.9 | 8.13506 | 385 |
| 11.2 | 7.92972 | 1609 |
| 12.3 | 7.17635 | 859 |
| 13.1 | 6.75674 | 231 |
| 13.6 | 6.50525 | 518 |
| 14.1 | 6.27959 | 364 |
| 14.5 | 6.11586 | 1845 |
| 15.9 | 5.57251 | 404 |
| 16.3 | 5.42237 | 622 |
| 16.8 | 5.27905 | 1852 |
| 17.5 | 5.06269 | 516 |
| 17.8 | 4.97879 | 1193 |
| 18.1 | 4.89167 | 686 |
| 18.5 | 4.78865 | 680 |
| 19.0 | 4.66963 | 692 |
| 19.6 | 4.52597 | 653 |
| 20.2 | 4.40622 | 471 |
| 20.7 | 4.30059 | 1610 |
| 21.6 | 4.12176 | 1024 |
| 21.9 | 4.06022 | 1161 |
| 22.5 | 3.95638 | 878 |
| 23.7 | 3.75666 | 1057 |
| 24.7 | 3.60383 | 705 |
| 25.1 | 3.55218 | 354 |
| 26.7 | 3.33519 | 1173 |

Figure 129:
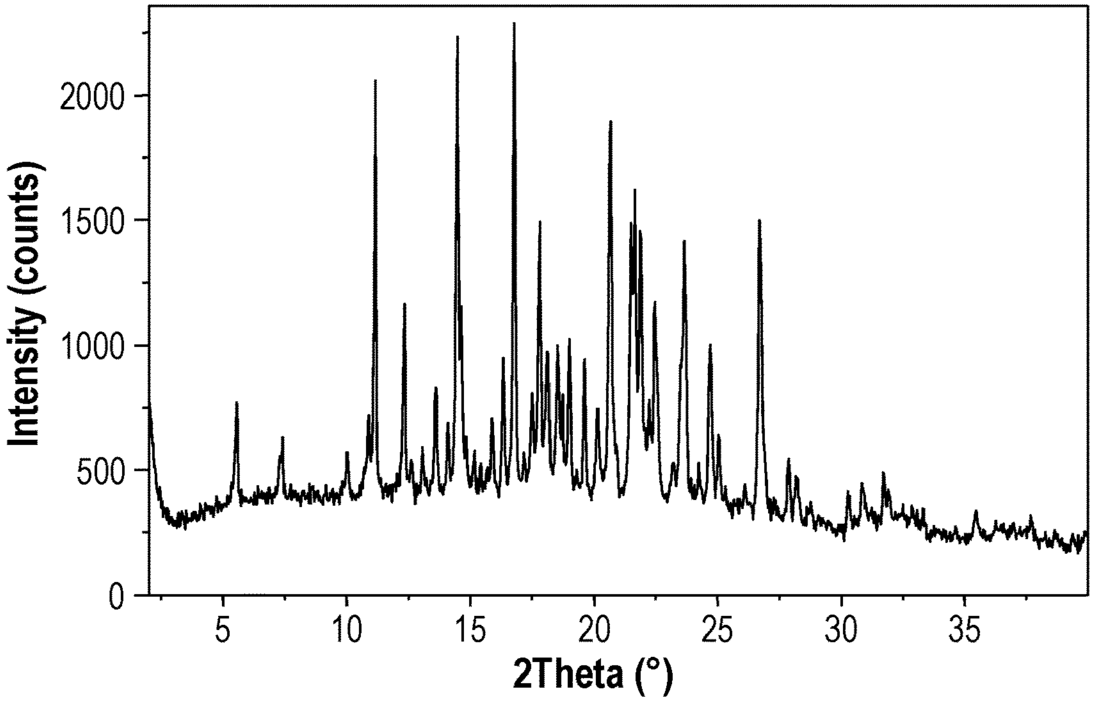

In some embodiments, Form B malonate salt is characterized by the x-ray powder diffraction (XRPD) pattern depicted in FIG. 129.

Figure 130:
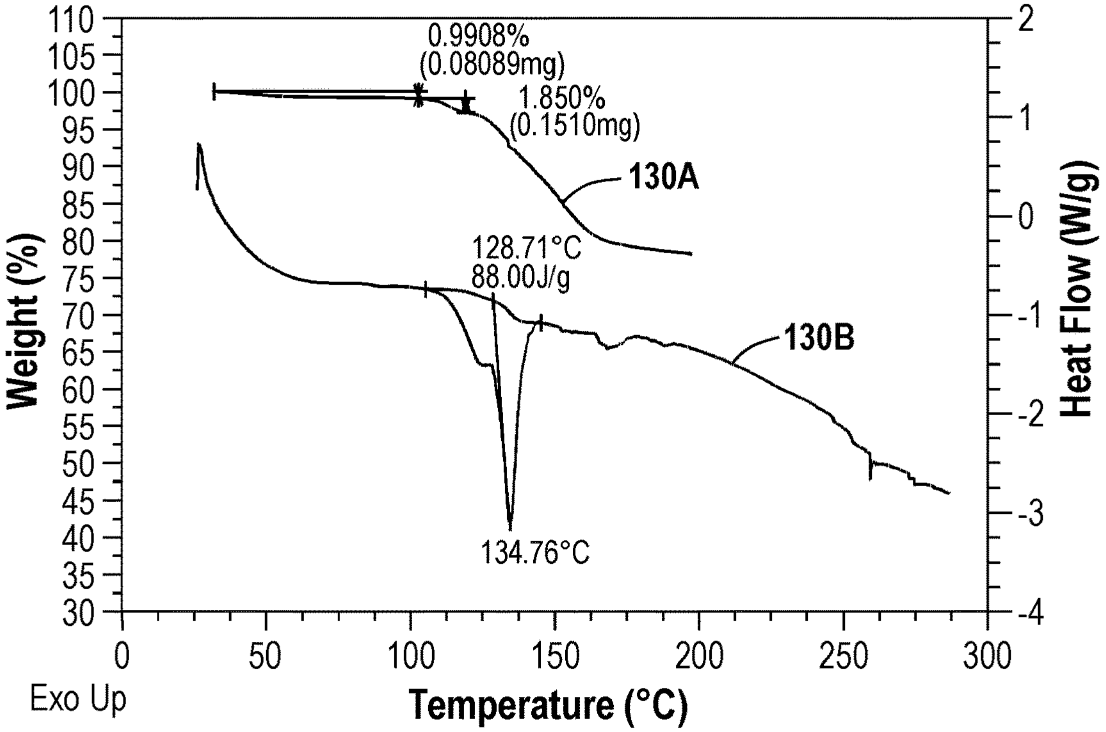

In some embodiments, Form B malonate salt is characterized by the thermogravimetric analysis (TGA) pattern depicted in FIG. 130, trace 130A.

In some embodiments, Form B malonate salt is characterized by the differential scanning calorimetry (DSC) pattern depicted in FIG. 130, trace 130B.

In some embodiments, a crystalline malonate salt of Compound 1 is characterized by one or more peaks in its X-ray powder diffraction pattern selected from 7.8, 11.7, 15.7, and 17.7±0.2 degrees 2θ. In some such embodiments, a complex form of Compound 1 is Form C malonate salt.

In some embodiments, Form C malonate salt is characterized by the following peaks in its X-ray powder diffraction pattern:

| Position ° 2θ ± 0.2 degrees | d-spacing [Å] | Height [cts] |
|---|---|---|
| 7.8 | 11.308 | 391 |
| 11.7 | 7.548 | 188 |
| 15.7 | 5.655 | 303 |
| 17.7 | 5.007 | 582 |
| 25.7 | 3.464 | 80 |

In some embodiments, Form C malonate salt is characterized by the x-ray powder diffraction (XRPD) pattern depicted in FIG. 131.

In some embodiments, Form C malonate salt is characterized by the differential scanning calorimetry (DSC) pattern depicted in FIG. 132.

In some embodiments of a complex form of Compound 1, X is L-tartaric acid. In some such embodiments, a complex form of Compound 1 is an L-tartrate salt. In some embodiments, an L-tartrate salt of Compound 1 is a crystalline L-tartrate salt. In some embodiments, a crystalline L-tartrate salt of Compound 1 is characterized by one or more peaks in its X-ray powder diffraction pattern selected from 9.7, 11.1, 14.9, 16.6, 19.8, and 21.0±0.2 degrees 2θ. In some such embodiments, a complex form of Compound 1 is Form A L-tartrate salt.

In some embodiments, Form A L-tartrate salt is characterized by the following peaks in its X-ray powder diffraction pattern:

| Position ° 2θ ± 0.2 degrees | d-spacing [Å] | Height [cts] |
|---|---|---|
| 7.5 | 11.841 | 61 |
| 9.7 | 9.089 | 88 |
| 11.1 | 7.942 | 137 |
| 14.9 | 5.950 | 334 |
| 15.6 | 5.696 | 77 |
| 16.1 | 5.497 | 54 |
| 16.6 | 5.350 | 115 |
| 18.7 | 4.754 | 78 |
| 19.8 | 4.476 | 154 |
| 21.0 | 4.222 | 129 |
| 22.1 | 4.027 | 47 |
| 23.9 | 3.718 | 58 |
| 25.1 | 3.541 | 214 |
| 25.9 | 3.444 | 310 |
| 27.8 | 3.213 | 124 |
| 32.6 | 2.746 | 50 |

In some embodiments, Form A L-tartrate salt is characterized by the x-ray powder diffraction (XRPD) pattern depicted in FIG. 133.

In some embodiments, Form A L-tartrate salt is characterized by the thermogravimetric analysis (TGA) pattern depicted in FIG. 134, trace 134A.

In some embodiments, Form A L-tartrate salt is characterized by the differential scanning calorimetry (DSC) pattern depicted in FIG. 134, trace 134B.

In some embodiments, a crystalline L-tartrate salt of Compound 1 is characterized by one or more peaks in its X-ray powder diffraction pattern selected from 7.4, 9.7, 11.2, 11.7, and 14.9±0.2 degrees 2θ. In some such embodiments, a complex form of Compound 1 is Form B L-tartrate salt.

In some embodiments, Form B L-tartrate salt is characterized by the following peaks -continued

| Position ° 2θ ± 0.2 degrees | d-spacing [Å] | Height [cts] |
|---|---|---|
| 7.4 | 11.878 | 529 |
| 9.7 | 9.099 | 295 |
| 11.2 | 7.929 | 724 |
| 11.7 | 7.577 | 446 |
| 14.4 | 6.135 | 333 |
| 14.9 | 5.949 | 1770 |
| 15.6 | 5.690 | 676 |
| 16.1 | 5.498 | 557 |
| 16.6 | 5.348 | 504 |
| 17.7 | 5.002 | 240 |
| 18.6 | 4.759 | 409 |
| 19.3 | 4.595 | 483 |
| 19.6 | 4.538 | 722 |
| 21.0 | 4.221 | 418 |
| 22.0 | 4.040 | 214 |
| 24.1 | 3.699 | 392 |
| 25.2 | 3.537 | 523 |
| 25.9 | 3.446 | 684 |
| 27.7 | 3.225 | 241 |
| 29.2 | 3.061 | 153 |

In some embodiments, Form B L-tartrate salt is characterized by the x-ray powder diffraction (XRPD) pattern depicted in FIG. 135.

In some embodiments, Form B L-tartrate salt is characterized by the differential scanning calorimetry (DSC) pattern depicted in FIG. 136.

In some embodiments, a crystalline L-tartrate salt of Compound 1 is characterized by one or more peaks in its X-ray powder diffraction pattern selected from 7.4, 9.7, 11.2, 12.5, and 14.9±0.2 degrees 2θ. In some such embodiments, a complex form of Compound 1 is Form C L-tartrate salt.

In some embodiments, Form C L-tartrate salt is characterized by the following peaks in its X-ray powder diffraction pattern:

| Position ° 2θ ± 0.2 degrees | d-spacing [Å] | Height [cts] |
|---|---|---|
| 7.4 | 11.868 | 717 |
| 9.7 | 9.099 | 447 |
| 11.2 | 7.911 | 889 |
| 12.5 | 7.092 | 152 |
| 13.4 | 6.599 | 232 |
| 14.4 | 6.144 | 445 |
| 14.9 | 5.936 | 1849 |
| 15.5 | 5.702 | 655 |
| 16.1 | 5.496 | 783 |
| 16.6 | 5.348 | 796 |
| 17.7 | 5.004 | 257 |
| 18.2 | 4.864 | 214 |
| 18.7 | 4.737 | 366 |
| 19.3 | 4.599 | 620 |
| 19.6 | 4.539 | 967 |
| 19.8 | 4.485 | 532 |
| 21.0 | 4.226 | 703 |
| 22.1 | 4.022 | 347 |
| 24.0 | 3.703 | 370 |
| 25.1 | 3.542 | 698 |
| 25.8 | 3.447 | 943 |
| 26.7 | 3.333 | 301 |
| 27.4 | 3.255 | 239 |
| 27.8 | 3.211 | 348 |
| 29.1 | 3.064 | 205 |

In some embodiments, Form C L-tartrate salt is characterized by the x-ray powder diffraction (XRPD) pattern depicted in FIG. 137.

In some embodiments, Form C L-tartrate salt is characterized by the thermogravimetric analysis (TGA) pattern depicted in FIG. 138, trace 138A.

In some embodiments, Form C L-tartrate salt is characterized by the differential scanning calorimetry (DSC) pattern depicted in FIG. 138, trace 138B.

In some embodiments, a crystalline L-tartrate salt of Compound 1 is characterized by one or more peaks in its X-ray powder diffraction pattern selected from 4.7, 7.4, 9.5, 11.1, 13.1, 13.5, and 18.3±0.2 degrees 2θ. In some such embodiments, a complex form of Compound 1 is Form D L-tartrate salt.

In some embodiments, Form D L-tartrate salt is characterized by the following peaks in its X-ray powder diffraction pattern:

| Position ° 2θ ± 0.2 degrees | d-spacing [Å] | Height [cts] |
|---|---|---|
| 4.7 | 18.677 | 597 |
| 7.4 | 11.927 | 906 |
| 9.5 | 9.351 | 1215 |
| 11.1 | 8.004 | 2952 |
| 11.7 | 7.580 | 299 |
| 12.4 | 7.149 | 169 |
| 13.1 | 6.736 | 739 |
| 13.5 | 6.577 | 758 |
| 14.2 | 6.232 | 449 |
| 14.9 | 5.963 | 985 |
| 15.3 | 5.776 | 364 |
| 15.9 | 5.567 | 286 |
| 16.5 | 5.378 | 318 |
| 16.8 | 5.287 | 904 |
| 17.6 | 5.047 | 250 |
| 18.3 | 4.853 | 1788 |
| 18.6 | 4.766 | 269 |
| 19.0 | 4.674 | 766 |
| 19.3 | 4.602 | 487 |
| 20.9 | 4.247 | 2066 |
| 21.9 | 4.063 | 252 |
| 22.2 | 4.013 | 671 |
| 22.9 | 3.886 | 166 |
| 24.0 | 3.710 | 798 |
| 25.3 | 3.525 | 302 |
| 25.7 | 3.463 | 799 |
| 26.3 | 3.384 | 422 |
| 27.0 | 3.307 | 559 |

In some embodiments, Form D L-tartrate salt is characterized by the x-ray powder diffraction (XRPD) pattern depicted in FIG. 139.

In some embodiments, Form D L-tartrate salt is characterized by the thermogravimetric analysis (TGA) pattern depicted in FIG. 140, trace 140A.

In some embodiments, Form D L-tartrate salt is characterized by the differential scanning calorimetry (DSC) pattern depicted in FIG. 140, trace 140B.

In some embodiments of a complex form of Compound 1, X is fumaric acid. In some such embodiments, a complex form of Compound 1 is a fumarate salt. In some embodiments, a fumarate salt of Compound 1 is a crystalline fumarate salt. In some embodiments, a crystalline fumarate salt of Compound 1 is characterized by one or more peaks in its X-ray powder diffraction pattern selected from 6.7, 12.3, 13.4, 14.3, and 15.4±0.2 degrees 2θ. In some such embodiments, a complex form of Compound 1 is Form A fumarate salt.

In some embodiments, Form A fumarate salt is characterized by the following peaks in its X-ray powder diffraction pattern:

-continued

| Position ° 2θ ± 0.2 degrees | d-spacing [Å] | Height [cts] |
|---|---|---|
| 6.2 | 14.322 | 288 |
| 6.7 | 13.147 | 922 |
| 11.2 | 7.904 | 494 |
| 12.3 | 7.210 | 2223 |
| 12.7 | 6.948 | 279 |
| 13.4 | 6.597 | 1359 |
| 14.2 | 6.251 | 921 |
| 14.3 | 6.175 | 1080 |
| 14.6 | 6.052 | 213 |
| 15.4 | 5.771 | 5313 |
| 16.0 | 5.542 | 2435 |
| 17.3 | 5.135 | 450 |
| 18.0 | 4.916 | 2002 |
| 18.4 | 4.816 | 368 |
| 18.7 | 4.748 | 1079 |
| 19.0 | 4.660 | 3958 |
| 19.7 | 4.497 | 653 |
| 20.2 | 4.400 | 830 |
| 20.6 | 4.304 | 3817 |
| 22.8 | 3.906 | 2496 |
| 23.5 | 3.778 | 235 |
| 25.0 | 3.566 | 1431 |
| 26.0 | 3.428 | 2806 |
| 26.3 | 3.384 | 435 |
| 26.9 | 3.309 | 335 |
| 27.3 | 3.264 | 331 |
| 30.0 | 2.977 | 647 |

In some embodiments, Form A fumarate salt is characterized by the x-ray powder diffraction (XRPD) pattern depicted in FIG. 141.

In some embodiments, Form A fumarate salt is characterized by the thermogravimetric analysis (TGA) pattern depicted in FIG. 142, trace 142A.

In some embodiments, Form A fumarate salt is characterized by the differential scanning calorimetry (DSC) pattern depicted in FIG. 142, trace 142B.

In some embodiments, a crystalline fumarate salt of Compound 1 is characterized by one or more peaks in its X-ray powder diffraction pattern selected from 7.0, 14.1, 14.6, 15.3, and 19.0±0.2 degrees 2θ. In some such embodiments, a complex form of Compound 1 is Form B fumarate salt.

In some embodiments, Form B fumarate salt is characterized by the following peaks in its X-ray powder diffraction pattern:

| Position °2θ ± 0.2 degrees | d-spacing [Å] | Height [cts] |
|---|---|---|
| 6.1 | 14.387 | 104 |
| 7.0 | 12.585 | 210 |
| 12.3 | 7.224 | 270 |
| 13.4 | 6.609 | 267 |
| 14.1 | 6.283 | 365 |
| 14.6 | 6.060 | 345 |
| 15.3 | 5.779 | 1036 |
| 16.0 | 5.554 | 313 |
| 17.6 | 5.025 | 221 |
| 18.0 | 4.922 | 303 |
| 19.0 | 4.666 | 929 |
| 20.2 | 4.392 | 164 |
| 20.6 | 4.307 | 789 |
| 22.2 | 4.002 | 233 |
| 22.7 | 3.910 | 490 |
| 25.0 | 3.567 | 284 |
| 26.0 | 3.430 | 567 |
| 28.3 | 3.151 | 86 |

In some embodiments, Form B fumarate salt is characterized by the x-ray powder diffraction (XRPD) pattern depicted in FIG. 143.

In some embodiments, Form B fumarate salt is characterized by the differential scanning calorimetry (DSC) pattern depicted in FIG. 144.

In some embodiments, a crystalline fumarate salt of Compound 1 is characterized by one or more peaks in its X-ray powder diffraction pattern selected from 7.6, 11.4, 15.2, and 19.0±0.2 degrees 2θ. In some such embodiments, a complex form of Compound 1 is Form C fumarate salt.

In some embodiments, Form C fumarate salt is characterized by the following peaks in its X-ray powder diffraction pattern:

| Position ° 2θ ± 0.2 degrees | d-spacing [Å] | Height [cts] |
|---|---|---|
| 7.6 | 11.673 | 2345 |
| 11.4 | 7.779 | 2628 |
| 14.5 | 6.091 | 143 |
| 15.2 | 5.834 | 5995 |
| 16.1 | 5.500 | 539 |
| 19.0 | 4.667 | 1865 |
| 21.5 | 4.141 | 543 |
| 22.9 | 3.889 | 437 |
| 24.6 | 3.613 | 919 |
| 26.4 | 3.371 | 494 |
| 29.0 | 3.075 | 112 |
| 30.6 | 2.917 | 456 |

In some embodiments, Form C fumarate salt is characterized by the x-ray powder diffraction (XRPD) pattern depicted in FIG. 145.

In some embodiments, Form C fumarate salt is characterized by the thermogravimetric analysis (TGA) pattern depicted in FIG. 146, trace 146A.

In some embodiments, Form C fumarate salt is characterized by the differential scanning calorimetry (DSC) pattern depicted in FIG. 146, trace 146B.

In some embodiments, a crystalline fumarate salt of Compound 1 is characterized by one or more peaks in its X-ray powder diffraction pattern selected from 14.0, 17.6, 23.3, 23.9, and 25.1±0.2 degrees 2θ. In some such embodiments, a complex form of Compound 1 is Form D fumarate salt.

In some embodiments, Form D fumarate salt is characterized by the following peaks

| Position ° 2θ ± 0.2 degrees | d-spacing [Å] | Height [cts] |
|---|---|---|
| 11.2 | 7.866 | 51 |
| 14.0 | 6.345 | 103 |
| 17.6 | 5.045 | 277 |
| 23.3 | 3.813 | 117 |
| 23.9 | 3.716 | 124 |
| 25.1 | 3.554 | 138 |
| 27.7 | 3.226 | 46 |

In some embodiments, Form D fumarate salt of Compound 1 is characterized by the x-ray powder diffraction (XRPD) pattern depicted in FIG. 147.

In some embodiments, Form D fumarate salt of Compound 1 is characterized by the thermogravimetric analysis (TGA) pattern depicted in FIG. 148, trace 148A.

In some embodiments, Form D fumarate salt of Compound 1 is characterized by the differential scanning calorimetry (DSC) pattern depicted in FIG. 148, trace 148B.

In some embodiments of a complex form of Compound 1, X is citric acid. In some such embodiments, a complex form of Compound 1 is a citrate salt. In some embodiments, a citrate salt of Compound 1 is a crystalline citrate salt. In some embodiments, a crystalline citrate salt of Compound 1 is characterized by one or more peaks in its X-ray powder diffraction pattern selected from 7.5, 11.3, 13.5, 15.1, 18.9, and 19.2±0.2 degrees 2θ. In some such embodiments, a complex form of Compound 1 is Form A citrate salt.

In some embodiments, Form A citrate salt is characterized by the following peaks in its X-ray powder diffraction pattern:

| Position °2θ ± 0.2 degrees | d-spacing [Å] | Height [cts] |
|---|---|---|
| 7.5 | 11.778 | 1525 |
| 11.3 | 7.840 | 1296 |
| 13.5 | 6.578 | 387 |
| 14.7 | 6.026 | 310 |
| 15.1 | 5.879 | 7091 |
| 15.9 | 5.566 | 881 |
| 16.2 | 5.487 | 589 |
| 16.5 | 5.371 | 344 |
| 18.3 | 4.839 | 309 |
| 18.9 | 4.702 | 2152 |
| 19.2 | 4.635 | 1040 |
| 19.4 | 4.585 | 515 |
| 19.8 | 4.488 | 244 |
| 20.1 | 4.424 | 230 |
| 21.0 | 4.237 | 455 |
| 22.4 | 3.974 | 526 |
| 23.0 | 3.871 | 530 |
| 23.7 | 3.752 | 207 |
| 24.3 | 3.659 | 315 |
| 25.2 | 3.536 | 1524 |
| 25.8 | 3.447 | 995 |
| 26.4 | 3.381 | 863 |
| 26.9 | 3.315 | 318 |
| 27.5 | 3.246 | 513 |
| 28.2 | 3.159 | 180 |
| 28.5 | 3.128 | 665 |

In some embodiments, Form A citrate salt is characterized by the x-ray powder diffraction (XRPD) pattern depicted in FIG. 149.

In some embodiments, Form A citrate salt is characterized by the thermogravimetric analysis (TGA) pattern depicted in FIG. 150, trace 150A.

In some embodiments, Form A citrate salt is characterized by the differential scanning calorimetry (DSC) pattern depicted in FIG. 150, trace 150B.

In some embodiments of a complex form of Compound 1, X is L-lactic acid. In some such embodiments, a complex form of Compound 1 is an L-lactate salt. In some embodiments, an L-lactate salt of Compound 1 is a crystalline L-lactate salt. In some embodiments, a crystalline L-lactate salt of Compound 1 is characterized by one or more peaks in its X-ray powder diffraction pattern selected from 7.5, 8.2, 11.2, 12.3, and 16.0±0.2 degrees 2θ. In some such embodiments, a complex form of Compound 1 is Form A L-lactate salt.

In some embodiments, Form A L-lactate salt is characterized by the following peaks in its X-ray powder diffraction pattern:

| Position °2θ ± 0.2 degrees | d-spacing [Å] | Height [cts] |
|---|---|---|
| 7.5 | 11.860 | 463 |
| 8.2 | 10.774 | 1477 |
| 9.9 | 8.924 | 315 |
| 11.2 | 7.913 | 786 |
| 12.3 | 7.170 | 6567 |

-continued

| Position °2θ ± 0.2 degrees | d-spacing [Å] | Height [cts] |
|---|---|---|
| 13.2 | 6.683 | 359 |
| 14.9 | 5.933 | 697 |
| 15.3 | 5.804 | 888 |
| 16.0 | 5.550 | 1525 |
| 16.5 | 5.375 | 819 |
| 16.9 | 5.250 | 555 |
| 17.6 | 5.053 | 997 |
| 18.6 | 4.767 | 1540 |
| 19.5 | 4.546 | 352 |
| 19.9 | 4.460 | 823 |
| 20.7 | 4.299 | 1713 |
| 20.9 | 4.251 | 570 |
| 21.5 | 4.142 | 422 |
| 21.9 | 4.054 | 431 |
| 22.6 | 3.931 | 792 |
| 23.1 | 3.845 | 3717 |
| 23.5 | 3.787 | 427 |
| 24.0 | 3.704 | 1829 |
| 25.2 | 3.530 | 441 |
| 25.7 | 3.466 | 848 |
| 26.5 | 3.360 | 711 |
| 27.6 | 3.228 | 1991 |

In some embodiments, Form A L-lactate salt is characterized by the x-ray powder diffraction (XRPD) pattern depicted in FIG. 151.

In some embodiments, Form A L-lactate salt is characterized by the thermogravimetric analysis (TGA) pattern depicted in FIG. 152, trace 152A.

In some embodiments, Form A L-lactate salt is characterized by the differential scanning calorimetry (DSC) pattern depicted in FIG. 152, trace 152B.

In some embodiments of a complex form of Compound 1, X is acetic acid. In some such embodiments, a complex form of Compound 1 is an acetate salt. In some embodiments, an acetate salt of Compound 1 is a crystalline acetate salt. In some embodiments, a crystalline acetate salt of Compound 1 is characterized by one or more peaks in its X-ray powder diffraction pattern selected from 8.9, 11.6, 11.9, 13.5, 14.1, and 17.9±0.2 degrees 2θ. In some such embodiments, a complex form of Compound 1 is Form A acetate salt.

In some embodiments, Form A acetate salt is characterized by the following peaks in its X-ray powder diffraction pattern:

| Position °2θ ± 0.2 degrees | d-spacing [Å] | Height [cts] |
|---|---|---|
| 8.9 | 9.914 | 286 |
| 10.0 | 8.854 | 137 |
| 11.6 | 7.659 | 501 |
| 11.9 | 7.418 | 1151 |
| 13.5 | 6.550 | 426 |
| 14.1 | 6.260 | 421 |
| 14.8 | 5.978 | 409 |
| 15.1 | 5.886 | 798 |
| 15.4 | 5.761 | 515 |
| 15.9 | 5.587 | 1033 |
| 17.0 | 5.205 | 449 |
| 17.4 | 5.093 | 646 |
| 17.6 | 5.045 | 838 |
| 17.9 | 4.948 | 1616 |
| 18.3 | 4.854 | 387 |
| 19.4 | 4.574 | 206 |
| 20.1 | 4.411 | 366 |
| 20.4 | 4.347 | 526 |
| 21.1 | 4.217 | 145 |
| 21.4 | 4.144 | 223 |
| 21.8 | 4.081 | 314 |

-continued

| Position °2θ ± 0.2 degrees | d-spacing [Å] | Height [cts] |
|---|---|---|
| 22.7 | 3.917 | 512 |
| 23.5 | 3.786 | 1061 |
| 24.3 | 3.667 | 712 |
| 25.2 | 3.539 | 689 |

In some embodiments, Form A acetate salt is characterized by the x-ray powder diffraction (XRPD) pattern depicted in FIG. 153.

In some embodiments, Form A acetate salt is characterized by the thermogravimetric analysis (TGA) pattern depicted in FIG. 154, trace 154A.

In some embodiments, Form A acetate salt is characterized by the differential scanning calorimetry (DSC) pattern depicted in FIG. 154, trace 154B.

In some embodiments, a crystalline acetate salt of Compound 1 is characterized by one or more peaks in its X-ray powder diffraction pattern selected from 10.3, 11.6, 12.8, 15.6, 17.6, and 19.1±0.2 degrees 2θ. In some such embodiments, a complex form of Compound 1 is Form B acetate salt.

In some embodiments, Form B acetate salt is characterized by the following peaks in its X-ray powder diffraction pattern:

| Position °2θ ± 0.2 degrees | d-spacing [Å] | Height [cts] |
|---|---|---|
| 7.0 | 12.563 | 817 |
| 9.3 | 9.525 | 583 |
| 10.3 | 8.582 | 2147 |
| 11.6 | 7.653 | 12433 |
| 11.9 | 7.410 | 684 |
| 12.8 | 6.898 | 1315 |
| 14.9 | 5.930 | 1289 |
| 15.6 | 5.675 | 5401 |
| 16.4 | 5.391 | 2394 |
| 16.8 | 5.293 | 883 |
| 17.1 | 5.175 | 1136 |
| 17.6 | 5.042 | 6016 |
| 18.6 | 4.780 | 868 |
| 19.1 | 4.635 | 6456 |
| 19.8 | 4.478 | 1264 |
| 20.2 | 4.397 | 519 |
| 21.2 | 4.191 | 991 |
| 21.4 | 4.146 | 600 |
| 22.4 | 3.971 | 14373 |
| 23.7 | 3.754 | 3862 |
| 24.2 | 3.678 | 541 |
| 25.0 | 3.557 | 481 |
| 25.5 | 3.499 | 511 |
| 26.3 | 3.386 | 863 |
| 27.1 | 3.293 | 8148 |
| 39.0 | 2.311 | 599 |

In some embodiments, Form B acetate salt is characterized by the x-ray powder diffraction (XRPD) pattern depicted in FIG. 155.

In some embodiments, Form B acetate salt is characterized by the thermogravimetric analysis (TGA) pattern depicted in FIG. 156, trace 156A.

In some embodiments, Form B acetate salt is characterized by the differential scanning calorimetry (DSC) pattern depicted in FIG. 156, trace 156B.

In some embodiments of a complex form of Compound 1, X is propionic acid. In some such embodiments, a complex form of Compound 1 is a propionate salt. In some embodiments, a propionate salt of Compound 1 is a crystalline propionate salt. In some embodiments, a crystalline propionate salt of Compound 1 is characterized by one or more peaks in its X-ray powder diffraction pattern selected from 8.6, 9.7, 12.4, 14.0, 16.4, and 17.7±0.2 degrees 2θ. In some such embodiments, a complex form of Compound 1 is Form A propionate salt.

In some embodiments, Form A propionate salt is characterized by the following peaks in its X-ray powder diffraction pattern:

| Position °2θ ± 0.2 degrees | d-spacing [Å] | Height [cts] |
|---|---|---|
| 8.2 | 10.812 | 249 |
| 8.6 | 10.293 | 405 |
| 8.8 | 10.013 | 177 |
| 9.7 | 9.138 | 608 |
| 10.5 | 8.391 | 381 |
| 11.7 | 7.568 | 228 |
| 12.4 | 7.147 | 544 |
| 14.0 | 6.344 | 1608 |
| 14.3 | 6.197 | 579 |
| 14.5 | 6.088 | 592 |
| 15.3 | 5.809 | 2343 |
| 15.6 | 5.666 | 1062 |
| 16.4 | 5.396 | 6650 |
| 17.2 | 5.143 | 1430 |
| 17.7 | 5.010 | 26155 |
| 18.6 | 4.768 | 330 |
| 19.3 | 4.594 | 670 |
| 19.7 | 4.507 | 787 |
| 20.0 | 4.444 | 1603 |
| 20.5 | 4.334 | 735 |
| 21.3 | 4.163 | 486 |
| 21.6 | 4.111 | 757 |
| 22.0 | 4.036 | 452 |
| 22.3 | 3.987 | 230 |
| 22.8 | 3.906 | 741 |
| 23.2 | 3.830 | 854 |
| 23.5 | 3.782 | 1711 |
| 23.9 | 3.719 | 424 |
| 24.7 | 3.602 | 708 |
| 25.0 | 3.569 | 649 |
| 25.6 | 3.485 | 1538 |
| 25.7 | 3.461 | 1433 |
| 26.5 | 3.362 | 939 |
| 26.7 | 3.339 | 944 |
| 27.5 | 3.238 | 416 |

In some embodiments, Form A propionate salt is characterized by the x-ray powder diffraction (XRPD) pattern depicted in FIG. 157.

In some embodiments, Form A propionate salt is characterized by the thermogravimetric analysis (TGA) pattern depicted in FIG. 158, trace 158A.

In some embodiments, Form A propionate salt is characterized by the differential scanning calorimetry (DSC) pattern depicted in FIG. 158, trace 158B.

In some embodiments of a complex form of Compound 1, X is DL-lactic acid. In some such embodiments, a complex form of Compound 1 is a DL-lactate salt. In some embodiments, a DL-lactate salt of Compound 1 is a crystalline DL-lactate salt. In some embodiments, a crystalline DL-lactate salt of Compound 1 is characterized by one or more peaks in its X-ray powder diffraction pattern selected from 8.3, 12.4, 15.9, 17.6, and 18.8±0.2 degrees 2θ. In some such embodiments, a complex form of Compound 1 is Form A DL-lactate salt.

In some embodiments, Form A DL-lactate salt is characterized by the following peaks in its X-ray powder diffraction pattern:

| Position °2θ ± 0.2 degrees | d-spacing [Å] | Height [cts] |
|---|---|---|
| 8.3 | 10.716 | 1369 |
| 9.9 | 8.927 | 173 |
| 11.3 | 7.856 | 200 |
| 12.4 | 7.142 | 5277 |
| 13.3 | 6.661 | 197 |
| 15.3 | 5.804 | 384 |
| 15.9 | 5.557 | 989 |
| 16.5 | 5.359 | 579 |
| 17.0 | 5.222 | 311 |
| 17.6 | 5.044 | 534 |
| 17.8 | 4.974 | 320 |
| 18.8 | 4.727 | 806 |
| 19.9 | 4.457 | 419 |
| 20.7 | 4.287 | 1046 |
| 21.0 | 4.227 | 369 |
| 21.4 | 4.148 | 267 |
| 21.9 | 4.055 | 254 |
| 22.8 | 3.900 | 589 |
| 23.2 | 3.831 | 3140 |
| 24.2 | 3.675 | 1588 |
| 25.7 | 3.463 | 655 |
| 26.7 | 3.338 | 559 |
| 27.8 | 3.206 | 1626 |
| 28.3 | 3.149 | 257 |
| 28.8 | 3.101 | 236 |
| 29.1 | 3.066 | 826 |

In some embodiments, Form A DL-lactate salt is characterized by the x-ray powder diffraction (XRPD) pattern depicted in FIG. 159.

In some embodiments, Form A DL-lactate salt is characterized by the thermogravimetric analysis (TGA) pattern depicted in FIG. 160, trace 160A.

In some embodiments, Form A DL-lactate salt is characterized by the differential scanning calorimetry (DSC) pattern depicted in FIG. 160, trace 160B.

In some embodiments of a complex form of Compound 1, X is D-gluconic acid. In some such embodiments, a complex form of Compound 1 is a D-gluconate salt. In some embodiments, a D-gluconate salt of Compound 1 is a crystalline D-gluconate salt. In some embodiments, a crystalline D-gluconate salt of Compound 1 is characterized by one or more peaks in its X-ray powder diffraction pattern selected from 7.1, 11.7, 14.7, 16.1, and 16.5±0.2 degrees 2θ. In some such embodiments, a complex form of Compound 1 is Form A D-gluconate salt.

In some embodiments, Form A D-gluconate salt is characterized by the following peaks in its X-ray powder diffraction pattern:

| Position °2θ ± 0.2 degrees | d-spacing [Å] | Height [cts] |
|---|---|---|
| 7.1 | 12.396 | 285 |
| 11.0 | 8.066 | 362 |
| 11.7 | 7.568 | 201 |
| 13.3 | 6.637 | 174 |
| 13.7 | 6.452 | 248 |
| 14.7 | 6.032 | 1555 |
| 15.1 | 5.871 | 353 |
| 16.1 | 5.495 | 615 |
| 16.5 | 5.377 | 314 |
| 17.2 | 5.158 | 184 |
| 18.3 | 4.848 | 227 |
| 19.0 | 4.671 | 222 |
| 19.6 | 4.532 | 384 |
| 22.0 | 4.040 | 229 |
| 23.3 | 3.819 | 517 |
| 24.0 | 3.714 | 309 |
| 25.0 | 3.558 | 305 |

-continued

| Position °2θ ± 0.2 degrees | d-spacing [Å] | Height [cts] |
|---|---|---|
| 25.7 | 3.464 | 307 |
| 26.7 | 3.338 | 183 |
| 27.4 | 3.258 | 187 |
| 32.5 | 2.755 | 110 |

In some embodiments, Form A D-gluconate salt is characterized by the x-ray powder diffraction (XRPD) pattern depicted in FIG. 161.

In some embodiments, Form A D-gluconate salt is characterized by the differential scanning calorimetry (DSC) pattern depicted in FIG. 162.

In some embodiments of a complex form of Compound 1, X is DL-malic acid. In some such embodiments, a complex form of Compound 1 is a DL-malate salt. In some embodiments, a DL-malate salt of Compound 1 is a crystalline DL-malate salt. In some embodiments, a crystalline DL-malate salt of Compound 1 is characterized by one or more peaks in its X-ray powder diffraction pattern selected from 7.5, 9.7, 11.3, 15.1, 16.3, and 21.0±0.2 degrees 2θ. In some such embodiments, a complex form of Compound 1 is Form A DL-malate salt.

In some embodiments, Form A DL-malate salt is characterized by the following peaks in its X-ray powder diffraction pattern:

| Position °2θ ± 0.2 degrees | d-spacing [Å] | Height [cts] |
|---|---|---|
| 7.5 | 11.765 | 441 |
| 9.7 | 9.157 | 335 |
| 11.3 | 7.831 | 540 |
| 12.5 | 7.107 | 196 |
| 13.1 | 6.739 | 100 |
| 13.7 | 6.462 | 197 |
| 14.5 | 6.124 | 198 |
| 15.1 | 5.872 | 1636 |
| 16.3 | 5.423 | 569 |
| 16.8 | 5.291 | 460 |
| 17.4 | 5.100 | 166 |
| 18.1 | 4.898 | 179 |
| 18.9 | 4.696 | 284 |
| 19.2 | 4.615 | 419 |
| 19.4 | 4.574 | 403 |
| 20.0 | 4.431 | 412 |
| 21.0 | 4.231 | 966 |
| 22.2 | 3.997 | 279 |
| 23.1 | 3.854 | 163 |
| 23.6 | 3.773 | 134 |
| 23.9 | 3.725 | 222 |
| 24.3 | 3.656 | 388 |
| 25.1 | 3.542 | 97 |
| 25.8 | 3.459 | 677 |
| 26.3 | 3.388 | 689 |

In some embodiments, Form A DL-malate salt is characterized by the x-ray powder diffraction (XRPD) pattern depicted in FIG. 163.

In some embodiments, Form A DL-malate salt is characterized by the thermogravimetric analysis (TGA) pattern depicted in FIG. 164, trace 164A.

In some embodiments, Form A DL-malate salt is characterized by the differential scanning calorimetry (DSC) pattern depicted in FIG. 164, trace 164B.

In some embodiments, a crystalline DL-malate salt of Compound 1 is characterized by one or more peaks in its X-ray powder diffraction pattern selected from 4.6, 8.3, 11.7, 13.9, and 18.6±0.2 degrees 2θ. In some such embodiments, a complex form of Compound 1 is Form B DL-malate salt.

In some embodiments, Form B DL-malate salt is characterized by the following peaks in its X-ray powder diffraction pattern:

| Position °2θ ± 0.2 degrees | d-spacing [Å] | Height [cts] |
|---|---|---|
| 4.6 | 19.118 | 217 |
| 8.3 | 10.670 | 275 |
| 9.3 | 9.537 | 333 |
| 11.7 | 7.572 | 431 |
| 12.3 | 7.195 | 307 |
| 13.0 | 6.787 | 497 |
| 13.9 | 6.357 | 1996 |
| 16.0 | 5.548 | 302 |
| 16.4 | 5.392 | 960 |
| 16.6 | 5.327 | 725 |
| 17.4 | 5.089 | 369 |
| 17.9 | 4.942 | 419 |
| 18.6 | 4.769 | 804 |
| 19.3 | 4.596 | 311 |
| 20.5 | 4.337 | 309 |
| 22.2 | 4.010 | 500 |
| 24.7 | 3.608 | 609 |
| 25.5 | 3.497 | 383 |
| 25.8 | 3.458 | 495 |
| 26.7 | 3.342 | 544 |
| 28.1 | 3.179 | 466 |
| 29.1 | 3.064 | 129 |
| 30.9 | 2.894 | 221 |
| 33.7 | 2.656 | 215 |
| 34.2 | 2.619 | 352 |
| 37.7 | 2.384 | 268 |

In some embodiments, Form B DL-malate salt is characterized by the x-ray powder diffraction (XRPD) pattern depicted in FIG. 165.

In some embodiments, Form B DL-malate salt is characterized by the thermogravimetric analysis (TGA) pattern depicted in FIG. 166, trace 166A.

In some embodiments, Form B DL-malate salt is characterized by the differential scanning calorimetry (DSC) pattern depicted in FIG. 166, trace 166B.

In some embodiments of a complex form of Compound 1, X is glycolic acid. In some such embodiments, a complex form of Compound 1 is a glycolate salt. In some embodiments, a glycolate salt of Compound 1 is a crystalline glycolate salt. In some embodiments, a crystalline glycolate salt of Compound 1 is characterized by one or more peaks in its X-ray powder diffraction pattern selected from 8.4, 8.6, 10.6, 12.7, and 16.1±0.2 degrees 2θ. In some such embodiments, a complex form of Compound 1 is Form A glycolate salt.

In some embodiments, Form A glycolate salt is characterized by the following peaks in its X-ray powder diffraction pattern:

| Position °2θ ± 0.2 degrees | d-spacing [Å] | Height [cts] |
|---|---|---|
| 8.4 | 10.465 | 1157 |
| 8.6 | 10.263 | 1316 |
| 9.9 | 8.938 | 447 |
| 10.6 | 8.385 | 739 |
| 11.6 | 7.604 | 453 |
| 12.7 | 6.948 | 3441 |
| 13.2 | 6.688 | 493 |
| 14.3 | 6.195 | 724 |
| 15.1 | 5.850 | 1011 |
| 15.4 | 5.758 | 837 |

-continued

| Position °2θ ± 0.2 degrees | d-spacing [Å] | Height [cts] |
|---|---|---|
| 16.1 | 5.504 | 2829 |
| 16.9 | 5.251 | 1447 |
| 17.3 | 5.137 | 2668 |
| 18.0 | 4.940 | 2050 |
| 18.7 | 4.748 | 2165 |
| 19.3 | 4.594 | 631 |
| 19.9 | 4.459 | 1007 |
| 20.2 | 4.397 | 1352 |
| 21.2 | 4.186 | 989 |
| 22.1 | 4.027 | 878 |
| 22.3 | 3.981 | 675 |
| 22.8 | 3.904 | 567 |
| 23.1 | 3.852 | 502 |
| 23.6 | 3.771 | 3089 |
| 24.0 | 3.703 | 482 |
| 24.6 | 3.621 | 1508 |
| 25.1 | 3.548 | 392 |
| 25.5 | 3.494 | 366 |
| 26.0 | 3.424 | 725 |
| 27.4 | 3.258 | 865 |
| 28.1 | 3.179 | 364 |
| 28.4 | 3.148 | 716 |
| 28.7 | 3.109 | 389 |

In some embodiments, Form A glycolate salt is characterized by the x-ray powder diffraction (XRPD) pattern depicted in FIG. 167.

In some embodiments, Form A glycolate salt is characterized by the thermogravimetric analysis (TGA) pattern depicted in FIG. 168, trace 168A.

In some embodiments, Form A glycolate salt is characterized by the differential scanning calorimetry (DSC) pattern depicted in FIG. 168, trace 168B.

In some embodiments of a complex form of Compound 1, X is glutaric acid. In some such embodiments, a complex form of Compound 1 is a glutarate salt. In some embodiments, a glutarate salt of Compound 1 is a crystalline glutarate salt. In some embodiments, a crystalline glutarate salt of Compound 1 is characterized by one or more peaks in its X-ray powder diffraction pattern selected from 7.4, 11.1, 14.9, 16.1, 18.6, and 18.9±0.2 degrees 2θ. In some such embodiments, a complex form of Compound 1 is Form A glutarate salt.

In some embodiments, Form A glutarate salt is characterized by the following peaks in its X-ray powder diffraction pattern:

| Position °2θ ± 0.2 degrees | d-spacing [Å] | Height [cts] |
|---|---|---|
| 7.4 | 11.903 | 2596 |
| 9.5 | 9.277 | 325 |
| 11.1 | 7.939 | 4027 |
| 12.3 | 7.211 | 469 |
| 13.3 | 6.653 | 248 |
| 13.7 | 6.475 | 516 |
| 14.0 | 6.345 | 353 |
| 14.9 | 5.955 | 8673 |
| 16.1 | 5.505 | 2090 |
| 16.8 | 5.292 | 985 |
| 17.2 | 5.142 | 588 |
| 17.7 | 5.012 | 311 |
| 18.6 | 4.765 | 1380 |
| 18.9 | 4.700 | 1339 |
| 19.1 | 4.639 | 816 |
| 19.7 | 4.495 | 376 |
| 20.4 | 4.357 | 434 |
| 20.6 | 4.305 | 377 |
| 22.1 | 4.014 | 857 |

-continued

| Position °2θ ± 0.2 degrees | d-spacing [Å] | Height [cts] |
|---|---|---|
| 22.7 | 3.921 | 501 |
| 23.4 | 3.807 | 627 |
| 23.6 | 3.763 | 511 |
| 24.1 | 3.694 | 331 |
| 24.9 | 3.582 | 1602 |
| 26.6 | 3.354 | 888 |
| 30.0 | 2.977 | 304 |

In some embodiments, Form A glutarate salt is characterized by the x-ray powder diffraction (XRPD) pattern depicted in FIG. 169.

In some embodiments, Form A glutarate salt is characterized by the thermogravimetric analysis (TGA) pattern depicted in FIG. 170, trace 170A.

In some embodiments, Form A glutarate salt is characterized by the differential scanning calorimetry (DSC) pattern depicted in FIG. 170, trace 170B.

In some embodiments, a crystalline glutarate salt of Compound 1 is characterized by one or more peaks in its X-ray powder diffraction pattern selected from 4.8, 5.8, 9.5, 11.3, and 14.8±0.2 degrees 2θ. In some such embodiments, a complex form of Compound 1 is Form B glutarate salt.

In some embodiments, Form B glutarate salt is characterized by the following peaks in its X-ray powder diffraction pattern:

| Position °2θ ± 0.2 degrees | d-spacing [Å] | Height [cts] |
|---|---|---|
| 4.8 | 18.575 | 499 |
| 5.8 | 15.232 | 432 |
| 9.5 | 9.313 | 511 |
| 11.0 | 8.065 | 889 |
| 11.3 | 7.841 | 3148 |
| 12.4 | 7.130 | 261 |
| 14.3 | 6.210 | 896 |
| 14.8 | 5.993 | 2426 |
| 15.2 | 5.815 | 458 |
| 15.6 | 5.693 | 661 |
| 16.5 | 5.364 | 494 |
| 16.8 | 5.268 | 450 |
| 18.4 | 4.813 | 465 |
| 18.7 | 4.744 | 442 |
| 19.0 | 4.663 | 379 |
| 19.7 | 4.496 | 1362 |
| 20.1 | 4.417 | 1908 |
| 21.2 | 4.182 | 375 |
| 22.6 | 3.932 | 725 |
| 23.2 | 3.828 | 577 |
| 24.4 | 3.653 | 380 |
| 25.2 | 3.528 | 1172 |
| 26.1 | 3.413 | 469 |
| 26.7 | 3.337 | 1354 |

In some embodiments, Form B glutarate salt is characterized by the x-ray powder diffraction (XRPD) pattern depicted in FIG. 171.

In some embodiments, Form B glutarate salt is characterized by the thermogravimetric analysis (TGA) pattern depicted in FIG. 172, trace 172A.

In some embodiments, Form B glutarate salt is characterized by the differential scanning calorimetry (DSC) pattern depicted in FIG. 172, trace 172B.

In some embodiments of a complex form of Compound 1, X is L-malic acid. In some such embodiments, a complex form of Compound 1 is an L-malate salt. In some embodiments, an L-malate salt of Compound 1 is a crystalline L-malate salt. In some embodiments, a crystalline L-malate salt of Compound 1 is characterized by one or more peaks in its X-ray powder diffraction pattern selected from 7.5, 9.6, 11.3, 15.1, 16.2, and 16.7±0.2 degrees 2θ. In some such embodiments, a complex form of Compound 1 is Form A L-malate salt.

In some embodiments, Form A L-malate salt is characterized by the following peaks in its X-ray powder diffraction pattern:

| Position °2θ ± 0.2 degrees | d-spacing [Å] | Height [cts] |
|---|---|---|
| 7.5 | 11.773 | 1874 |
| 9.6 | 9.176 | 610 |
| 11.3 | 7.846 | 2689 |
| 12.5 | 7.106 | 565 |
| 13.8 | 6.397 | 509 |
| 14.3 | 6.174 | 678 |
| 15.1 | 5.884 | 7051 |
| 15.3 | 5.780 | 1865 |
| 16.2 | 5.469 | 1734 |
| 16.7 | 5.319 | 1172 |
| 17.5 | 5.069 | 884 |
| 18.2 | 4.861 | 751 |
| 18.9 | 4.706 | 1594 |
| 19.4 | 4.583 | 1767 |
| 20.1 | 4.409 | 1420 |
| 20.8 | 4.265 | 647 |
| 21.2 | 4.191 | 3040 |
| 22.3 | 3.991 | 1373 |
| 23.1 | 3.843 | 760 |
| 23.7 | 3.748 | 447 |
| 24.1 | 3.700 | 355 |
| 24.4 | 3.642 | 1651 |
| 25.6 | 3.480 | 1951 |
| 26.0 | 3.429 | 457 |
| 26.4 | 3.380 | 1872 |
| 27.2 | 3.283 | 860 |
| 33.0 | 2.714 | 394 |

In some embodiments, Form A L-malate salt is characterized by the x-ray powder diffraction (XR-PD) pattern depicted in FIG. 173.

In some embodiments, Form A L-malate salt is characterized by the thermogravimetric analysis (TGA) pattern depicted in FIG. 174, trace 174A.

In some embodiments, Form A L-malate salt is characterized by the differential scanning calorimetry (DSC) pattern depicted in FIG. 174, trace 174B.

In some embodiments of a complex form of Compound 1, X is camphoric acid. In some such embodiments, a complex form of Compound 1 is a camphorate salt. In some embodiments, a camphorate salt of Compound 1 is a crystalline camphorate salt. In some embodiments, a crystalline camphorate salt of Compound 1 is characterized by one or more peaks in its X-ray powder diffraction pattern selected from 6.7, 8.3, 9.9, 15.0, and 15.2±0.2 degrees 2θ. In some such embodiments, a complex form of Compound 1 is Form A camphorate salt.

In some embodiments, Form A camphorate salt is characterized by the following peaks in its X-ray powder diffraction pattern:

| Position °2θ ± 0.2 degrees | d-spacing [Å] | Height [cts] |
|---|---|---|
| 6.7 | 13.201 | 1499 |
| 8.3 | 10.655 | 279 |
| 9.9 | 8.914 | 1772 |
| 10.8 | 8.166 | 694 |
| 12.6 | 7.030 | 1234 |
| 13.4 | 6.618 | 326 |
| 15.0 | 5.903 | 2105 |
| 15.2 | 5.826 | 1936 |
| 15.7 | 5.649 | 1281 |
| 16.0 | 5.541 | 1262 |
| 16.6 | 5.342 | 1003 |
| 17.2 | 5.144 | 302 |
| 18.2 | 4.869 | 1267 |
| 18.4 | 4.823 | 1633 |
| 18.9 | 4.686 | 873 |
| 20.0 | 4.431 | 2624 |
| 20.9 | 4.253 | 832 |
| 21.1 | 4.206 | 620 |
| 22.4 | 3.972 | 444 |
| 24.2 | 3.685 | 394 |
| 24.7 | 3.599 | 1496 |
| 26.3 | 3.395 | 815 |
| 27.2 | 3.276 | 202 |
| 29.1 | 3.070 | 149 |
| 31.4 | 2.853 | 258 |
| 32.2 | 2.780 | 232 |

In some embodiments, Form A camphorate salt is characterized by the x-ray powder diffraction (XRPD) pattern depicted in FIG. 175.

In some embodiments, Form A camphorate salt is characterized by the thermogravimetric analysis (TGA) pattern depicted in FIG. 176, trace 176A.

In some embodiments, Form A camphorate salt is characterized by the differential scanning calorimetry (DSC) pattern depicted in FIG. 176, trace 176B.

In some embodiments, a crystalline camphorate salt of Compound 1 is characterized by one or more peaks in its X-ray powder diffraction pattern selected from 6.9, 9.9, 11.5, 15.3, 16.1, and 16.8±0.2 degrees 2θ. In some such embodiments, a complex form of Compound 1 is Form B camphorate salt.

In some embodiments, Form B camphorate salt is characterized by the following peaks in its X-ray powder diffraction pattern:

| Position ° 2θ ± 0.2 degrees | d-spacing [Å] | Height [cts] |
|---|---|---|
| 6.9 | 12.864 | 1434 |
| 8.4 | 10.555 | 453 |
| 9.9 | 8.945 | 1573 |
| 10.3 | 8.591 | 431 |
| 10.8 | 8.188 | 630 |
| 11.5 | 7.724 | 1177 |
| 12.6 | 7.053 | 620 |
| 13.3 | 6.655 | 678 |
| 15.3 | 5.782 | 3100 |
| 16.1 | 5.492 | 2041 |
| 16.8 | 5.279 | 1982 |
| 17.1 | 5.178 | 678 |
| 18.5 | 4.791 | 1001 |
| 18.9 | 4.695 | 1659 |
| 19.3 | 4.591 | 436 |
| 20.0 | 4.432 | 771 |
| 20.5 | 4.325 | 2213 |
| 20.8 | 4.274 | 1114 |
| 21.5 | 4.138 | 469 |
| 22.1 | 4.025 | 655 |
| 22.5 | 3.945 | 693 |
| 23.3 | 3.823 | 344 |
| 24.0 | 3.703 | 346 |
| 24.3 | 3.664 | 356 |

-continued

| Position ° 2θ ± 0.2 degrees | d-spacing [Å] | Height [cts] |
|---|---|---|
| 25.1 | 3.549 | 886 |
| 25.3 | 3.522 | 736 |
| 26.1 | 3.410 | 785 |

In some embodiments, Form B camphorate salt is characterized by the x-ray powder diffraction (XRPD) pattern depicted in FIG. 177.

In some embodiments, Form B camphorate salt is characterized by the thermogravimetric analysis (TGA) pattern depicted in FIG. 178, trace 178A.

In some embodiments, Form B camphorate salt is characterized by the differential scanning calorimetry (DSC) pattern depicted in FIG. 178, trace 178B.

In some embodiments, a crystalline camphorate salt of Compound 1 is characterized by one or more peaks in its X-ray powder diffraction pattern selected from 4.9, 10.3, 13.6, 15.5, and 16.2±0.2 degrees 2θ. In some such embodiments, a complex form of Compound 1 is Form C camphorate salt.

In some embodiments, Form C camphorate salt is characterized by the following peaks in its X-ray powder diffraction pattern:

| Position ° 2θ ± 0.2 degrees | d-spacing [Å] | Height [cts] |
|---|---|---|
| 4.9 | 18.217 | 1285 |
| 8.7 | 10.197 | 382 |
| 9.7 | 9.092 | 769 |
| 10.3 | 8.620 | 1117 |
| 11.0 | 8.050 | 500 |
| 11.3 | 7.799 | 914 |
| 12.5 | 7.082 | 1555 |
| 13.6 | 6.527 | 6278 |
| 14.0 | 6.324 | 983 |
| 14.2 | 6.256 | 976 |
| 14.4 | 6.165 | 397 |
| 15.5 | 5.720 | 5070 |
| 16.2 | 5.457 | 3226 |
| 16.9 | 5.235 | 915 |
| 17.4 | 5.098 | 439 |
| 17.9 | 4.960 | 2207 |
| 18.2 | 4.862 | 368 |
| 19.2 | 4.614 | 597 |
| 19.5 | 4.546 | 3693 |
| 19.9 | 4.455 | 1177 |
| 20.7 | 4.285 | 916 |
| 21.3 | 4.172 | 1047 |
| 21.8 | 4.079 | 736 |
| 22.1 | 4.023 | 1257 |
| 22.5 | 3.956 | 570 |
| 22.8 | 3.893 | 1137 |
| 25.0 | 3.561 | 422 |
| 25.3 | 3.516 | 1059 |
| 26.7 | 3.335 | 711 |
| 27.4 | 3.260 | 515 |
| 31.3 | 2.860 | 359 |
| 34.5 | 2.598 | 420 |

In some embodiments, Form C camphorate salt is characterized by the x-ray powder diffraction (XRPD) pattern depicted in FIG. 179.

In some embodiments, Form C camphorate salt is characterized by the thermogravimetric analysis (TGA) pattern depicted in FIG. 180, trace 180A.

In some embodiments, Form C camphorate salt is characterized by the differential scanning calorimetry (DSC) pattern depicted in FIG. 180, trace 180B.

In some embodiments, a crystalline camphorate salt of Compound 1 is characterized by one or more peaks in its X-ray powder diffraction pattern selected from 7.7, 8.6, 9.6, 12.1, 13.5, and 15.3±0.2 degrees 2θ. In some such embodiments, a complex form of Compound 1 is Form D camphorate salt.

In some embodiments, Form D camphorate salt is characterized by the following peaks in its X-ray powder diffraction pattern:

| Position ° 2θ ± 0.2 degrees | d-spacing [Å] | Height [cts] |
|---|---|---|
| 7.7 | 11.453 | 285 |
| 8.6 | 10.319 | 285 |
| 9.6 | 9.203 | 2215 |
| 10.2 | 8.682 | 366 |
| 10.9 | 8.138 | 217 |
| 12.1 | 7.344 | 2323 |
| 12.6 | 7.016 | 446 |
| 13.5 | 6.563 | 1055 |
| 13.9 | 6.363 | 527 |
| 14.7 | 6.017 | 414 |
| 15.3 | 5.782 | 3024 |
| 15.8 | 5.605 | 1010 |
| 17.2 | 5.152 | 1002 |
| 17.6 | 5.030 | 958 |
| 18.0 | 4.936 | 534 |
| 19.3 | 4.608 | 1453 |
| 19.9 | 4.468 | 645 |
| 20.2 | 4.401 | 1122 |
| 21.3 | 4.174 | 242 |
| 21.8 | 4.079 | 426 |
| 22.3 | 3.979 | 228 |
| 23.5 | 3.792 | 423 |
| 24.2 | 3.682 | 834 |
| 24.7 | 3.601 | 1476 |
| 29.5 | 3.032 | 238 |

In some embodiments, Form D camphorate salt is characterized by the x-ray powder diffraction (XRPD) pattern depicted in FIG. 181.

In some embodiments, Form D camphorate salt is characterized by the thermogravimetric analysis (TGA) pattern depicted in FIG. 182, trace 182A.

In some embodiments, Form D camphorate salt is characterized by the differential scanning calorimetry (DSC) pattern depicted in FIG. 182, trace 182B.

In some embodiments of a complex form of Compound 1, X is DL-mandelic acid. In some such embodiments, a complex form of Compound 1 is a DL-mandelate salt. In some embodiments, a DL-mandelate salt of Compound 1 is a crystalline DL-mandelate salt. In some embodiments, a crystalline DL-mandelate salt of Compound 1 is characterized by one or more peaks in its X-ray powder diffraction pattern selected from 7.4, 11.1, 13.8, 14.9, and 16.3±0.2 degrees 2θ. In some such embodiments, a complex form of Compound 1 is Form A DL-mandelate salt.

In some embodiments, Form A DL-mandelate salt is characterized by the following peaks in its X-ray powder diffraction pattern:

| Position ° 2θ ± 0.2 degrees | d-spacing [Å] | Height [cts] |
|---|---|---|
| 7.4 | 11.901 | 1119 |
| 9.9 | 8.947 | 326 |
| 11.1 | 7.936 | 2496 |
| 12.2 | 7.277 | 929 |

-continued

| Position ° 2θ ± 0.2 degrees | d-spacing [Å] | Height [cts] |
|---|---|---|
| 13.4 | 6.613 | 698 |
| 13.8 | 6.429 | 1711 |
| 14.4 | 6.139 | 596 |
| 14.9 | 5.951 | 5941 |
| 15.2 | 5.823 | 781 |
| 16.3 | 5.452 | 3008 |
| 16.6 | 5.341 | 1880 |
| 17.4 | 5.108 | 2723 |
| 18.6 | 4.758 | 2375 |
| 19.2 | 4.618 | 2360 |
| 19.8 | 4.489 | 926 |
| 20.0 | 4.437 | 1071 |
| 20.8 | 4.267 | 532 |
| 21.6 | 4.123 | 1109 |
| 22.0 | 4.034 | 1012 |
| 22.5 | 3.948 | 1332 |
| 23.0 | 3.874 | 704 |
| 23.4 | 3.809 | 2454 |
| 23.6 | 3.764 | 1532 |
| 24.3 | 3.665 | 1444 |
| 24.8 | 3.591 | 554 |
| 25.3 | 3.519 | 770 |
| 26.0 | 3.431 | 1175 |
| 26.2 | 3.407 | 875 |
| 27.0 | 3.302 | 355 |
| 27.8 | 3.208 | 1430 |
| 30.0 | 2.975 | 752 |

In some embodiments, Form A DL-mandelate salt is characterized by the x-ray powder diffraction (XRPD) pattern depicted in FIG. 183.

In some embodiments, Form A DL-mandelate salt is characterized by the thermogravimetric analysis (TGA) pattern depicted in FIG. 184, trace 184A.

In some embodiments, Form A DL-mandelate salt is characterized by the differential scanning calorimetry (DSC) pattern depicted in FIG. 184, trace 184B.

In some embodiments, a crystalline DL-mandelate salt of Compound 1 is characterized by one or more peaks in its X-ray powder diffraction pattern selected from 7.5, 9.2, 11.3, 15.1, and 15.9±0.2 degrees 2θ. In some such embodiments, a complex form of Compound 1 is Form B DL-mandelate salt.

In some embodiments, Form B DL-mandelate salt is characterized by the following peaks in its X-ray powder diffraction pattern:

| Position ° 2θ ± 0.2 degrees | d-spacing [Å] | Height [cts] |
|---|---|---|
| 7.5 | 11.762 | 366 |
| 9.2 | 9.640 | 450 |
| 11.3 | 7.826 | 3039 |
| 13.3 | 6.639 | 469 |
| 15.1 | 5.869 | 1722 |
| 15.9 | 5.567 | 1276 |
| 16.8 | 5.278 | 882 |
| 18.4 | 4.815 | 951 |
| 18.6 | 4.764 | 862 |
| 18.9 | 4.695 | 495 |
| 19.3 | 4.607 | 413 |
| 19.5 | 4.541 | 310 |
| 20.5 | 4.335 | 210 |
| 21.3 | 4.179 | 791 |
| 22.7 | 3.913 | 1499 |
| 23.8 | 3.746 | 629 |
| 24.3 | 3.663 | 187 |
| 25.4 | 3.510 | 1661 |
| 26.1 | 3.413 | 533 |
| 26.4 | 3.375 | 372 |
| 27.7 | 3.222 | 334 |
| 27.9 | 3.193 | 312 |

In some embodiments, Form B DL-mandelate salt is characterized by the x-ray powder diffraction (XRPD) pattern depicted in FIG. 185.

In some embodiments, Form B DL-mandelate salt is characterized by the thermogravimetric analysis (TGA) pattern depicted in FIG. 186, trace 186A.

In some embodiments, Form B DL-mandelate salt is characterized by the differential scanning calorimetry (DSC) pattern depicted in FIG. 186, trace 186B.

In some embodiments, a crystalline DL-mandelate salt of Compound 1 is characterized by one or more peaks in its X-ray powder diffraction pattern selected from 8.4, 9.9, 10.9, 14.0, and 14.6±0.2 degrees 2θ. In some such embodiments, a complex form of Compound 1 is Form C DL-mandelate salt.

In some embodiments, Form C DL-mandelate salt is characterized by the following peaks in its X-ray powder diffraction pattern:

| Position ° 2θ ± 0.2 degrees | d-spacing [Å] | Height [cts] |
|---|---|---|
| 8.4 | 10.512 | 517 |
| 9.4 | 9.370 | 493 |
| 9.7 | 9.135 | 935 |
| 9.9 | 8.942 | 1064 |
| 10.9 | 8.084 | 900 |
| 11.9 | 7.408 | 368 |
| 13.5 | 6.579 | 787 |
| 14.0 | 6.311 | 1605 |
| 14.6 | 6.055 | 1509 |
| 15.1 | 5.850 | 524 |
| 15.6 | 5.687 | 427 |
| 15.9 | 5.591 | 708 |
| 16.1 | 5.494 | 705 |
| 17.0 | 5.201 | 1515 |
| 17.4 | 5.100 | 674 |
| 18.5 | 4.788 | 886 |
| 18.9 | 4.699 | 919 |
| 19.2 | 4.634 | 741 |
| 19.5 | 4.556 | 406 |
| 20.4 | 4.358 | 325 |
| 21.7 | 4.100 | 591 |
| 22.2 | 4.009 | 1142 |
| 22.4 | 3.972 | 1460 |
| 22.7 | 3.913 | 438 |
| 23.1 | 3.850 | 555 |
| 23.6 | 3.769 | 2395 |
| 24.8 | 3.586 | 378 |
| 26.1 | 3.411 | 1233 |

In some embodiments, Form C DL-mandelate salt is characterized by the x-ray powder diffraction (XRPD) pattern depicted in FIG. 187.

In some embodiments, Form C DL-mandelate salt is characterized by the thermogravimetric analysis (TGA) pattern depicted in FIG. 188, trace 188A.

In some embodiments, Form C DL-mandelate salt is characterized by the differential scanning calorimetry (DSC) pattern depicted in FIG. 188, trace 188B.

In some embodiments of a complex form of Compound 1, X is saccharin. In some such embodiments, a complex form of Compound 1 is a saccharin co-crystal. In some embodiments, a saccharin co-crystal of Compound 1 is a crystalline saccharin co-crystal. In some embodiments, a complex form of Compound 1 comprises one equivalent of saccharin. In some embodiments, a crystalline saccharin co-crystal of Compound 1 is characterized by one or more peaks in its X-ray powder diffraction pattern selected from 3.9, 7.9, 11.8, 15.0, and 15.8±0.2 degrees 2θ. In some such embodiments, a complex form of Compound 1 is Form A saccharin co-crystal.

In some embodiments, Form A saccharin co-crystal is characterized by the following peaks in its X-ray powder diffraction pattern:

| Position ° 2θ ± 0.2 degrees | d-spacing [Å] | Height [cts] |
|---|---|---|
| 3.9 | 22.496 | 666 |
| 7.9 | 11.241 | 1912 |
| 11.8 | 7.495 | 3968 |
| 12.1 | 7.325 | 285 |
| 13.4 | 6.585 | 454 |
| 15.0 | 5.921 | 1083 |
| 15.8 | 5.623 | 4460 |
| 16.7 | 5.293 | 691 |
| 17.6 | 5.035 | 796 |
| 18.2 | 4.879 | 506 |
| 18.9 | 4.696 | 1354 |
| 19.7 | 4.498 | 1876 |
| 20.0 | 4.441 | 507 |
| 20.8 | 4.268 | 578 |
| 21.3 | 4.180 | 235 |
| 21.8 | 4.073 | 1268 |
| 23.5 | 3.787 | 294 |
| 23.9 | 3.720 | 237 |
| 24.3 | 3.667 | 1453 |
| 25.2 | 3.533 | 1364 |
| 25.5 | 3.496 | 2233 |
| 26.4 | 3.371 | 203 |
| 28.7 | 3.107 | 387 |
| 29.3 | 3.048 | 312 |
| 32.4 | 2.765 | 262 |

In some embodiments, Form A saccharin co-crystal is characterized by the FT-Raman spectrum depicted in FIG. 189.

In some embodiments, Form A saccharin co-crystal is characterized by the x-ray powder diffraction (XRPD) pattern depicted in FIG. 190.

In some embodiments, Form A saccharin co-crystal is characterized by the thermogravimetric analysis (TGA) pattern depicted in FIG. 191, trace 191A.

In some embodiments, Form A saccharin co-crystal is characterized by the differential scanning calorimetry (DSC) pattern depicted in FIG. 191, trace 191B.

In some embodiments, Form A saccharin co-crystal is characterized by the $^{1}$H NMR spectrum depicted in FIG. 192.

In some embodiments of a complex form of Compound 1, X is nicotinic acid. In some such embodiments, a complex form of Compound 1 is a nicotinate salt. In some embodiments, a nicotinate salt of Compound 1 is a crystalline nicotinate salt. In some embodiments, a complex form of Compound 1 comprises one equivalent of nicotinic acid. In some embodiments, a crystalline nicotinate salt of Compound 1 is characterized by one or more peaks in its X-ray powder diffraction pattern selected from 7.8, 8.9, 14.0, 16.8, and 17.9±0.2 degrees 2θ. In some such embodiments, a complex form of Compound 1 is Form A nicotinate salt.

In some embodiments, Form A nicotinate salt is characterized by the following peaks

| Position ° 2θ ± 0.2 degrees | d-spacing [Å] | Height [cts] |
|---|---|---|
| 3.3 | 26.862 | 150 |
| 7.8 | 11.398 | 462 |
| 8.9 | 9.913 | 1721 |
| 10.4 | 8.523 | 344 |
| 11.4 | 7.769 | 213 |
| 11.8 | 7.497 | 121 |
| 12.9 | 6.877 | 260 |
| 13.4 | 6.607 | 238 |
| 14.0 | 6.326 | 1131 |
| 14.4 | 6.146 | 354 |
| 15.6 | 5.696 | 1107 |
| 15.9 | 5.587 | 339 |
| 16.8 | 5.264 | 1541 |
| 17.1 | 5.171 | 1315 |
| 17.9 | 4.955 | 8701 |
| 19.9 | 4.456 | 355 |
| 20.3 | 4.375 | 444 |
| 20.9 | 4.256 | 219 |
| 21.2 | 4.199 | 455 |
| 21.7 | 4.102 | 376 |
| 21.9 | 4.067 | 398 |
| 22.6 | 3.929 | 516 |
| 22.9 | 3.884 | 270 |
| 23.5 | 3.790 | 174 |
| 24.0 | 3.707 | 305 |
| 25.6 | 3.481 | 800 |
| 26.7 | 3.342 | 236 |
| 29.4 | 3.038 | 217 |

In some embodiments, Form A nicotinic acid salt is characterized by the FT-Raman spectrum depicted in FIG. 193.

In some embodiments, Form A nicotinic acid salt is characterized by the x-ray powder diffraction (XRPD) pattern depicted in FIG. 194.

In some embodiments, Form A nicotinic acid salt is characterized by the thermogravimetric analysis (TGA) pattern depicted in FIG. 195, trace 195A.

In some embodiments, Form A nicotinic acid salt is characterized by the differential scanning calorimetry (DSC) pattern depicted in FIG. 195, trace 195B.

In some embodiments, Form A nicotinic acid salt is characterized by the $^{1}$H NMR spectrum depicted in FIG. 196.

In some embodiments, a nicotinate salt of Compound 1 is a hydrate. In some embodiments, a hydrate form of a nicotinate salt of Compound 1 is a crystalline hydrate form of a nicotinate salt. In some embodiments, a crystalline hydrate form of a nicotinate salt of Compound 1 is characterized by one or more peaks in its X-ray powder diffraction pattern selected from 8.2, 12.4, 15.3, 17.9, and 18.2±0.2 degrees 2θ. In some such embodiments, a complex form of Compound 1 is Form B nicotinate salt.

In some embodiments, Form B nicotinate salt is characterized by the following peaks in its X-ray powder diffraction pattern:

| Position<br>° 2θ ± 0.2<br>degrees | d-spacing<br>[Å] | Height<br>[cts] |
|---|---|---|
| 8.2 | 10.726 | 543 |
| 9.9 | 8.927 | 244 |
| 12.0 | 7.358 | 402 |
| 12.4 | 7.158 | 3954 |
| 13.6 | 6.523 | 318 |
| 15.3 | 5.775 | 824 |
| 16.0 | 5.535 | 463 |
| 16.5 | 5.364 | 546 |
| 16.8 | 5.282 | 226 |
| 17.0 | 5.201 | 493 |
| 17.9 | 4.951 | 1106 |
| 18.2 | 4.877 | 1198 |
| 19.4 | 4.572 | 276 |
| 20.2 | 4.402 | 1051 |
| 20.7 | 4.299 | 570 |
| 21.0 | 4.230 | 472 |
| 22.0 | 4.049 | 815 |
| 23.6 | 3.766 | 1242 |
| 24.1 | 3.688 | 431 |
| 24.5 | 3.635 | 1751 |
| 25.5 | 3.495 | 967 |
| 26.3 | 3.394 | 834 |
| 26.5 | 3.363 | 412 |
| 26.9 | 3.316 | 544 |
| 27.4 | 3.257 | 267 |

In some embodiments, Form B nicotinic acid salt is characterized by the x-ray powder diffraction (XRPD) pattern depicted in FIG. 197.

In some embodiments, Form B nicotinic acid salt is characterized by the thermogravimetric analysis (TGA) pattern depicted in FIG. 198, trace 198A.

In some embodiments, Form B nicotinic acid salt is characterized by the differential scanning calorimetry (DSC) pattern depicted in FIG. 198, trace 198B.

In some embodiments, a crystalline nicotinate salt of Compound 1 is characterized by one or more peaks in its X-ray powder diffraction pattern selected from 3.8, 7.5, 11.3, 15.0, and 18.7±0.2 degrees 2θ. In some such embodiments, a complex form of Compound 1 is Form C nicotinate salt.

In some embodiments, Form C nicotinate salt is characterized by the following peaks

| Position<br>° 2θ ± 0.2<br>degrees | d-spacing<br>[Å] | Height<br>[cts] |
|---|---|---|
| 3.8 | 23.326 | 1156 |
| 7.5 | 11.718 | 2429 |
| 9.7 | 9.083 | 270 |
| 11.3 | 7.863 | 1547 |
| 12.0 | 7.362 | 206 |
| 13.4 | 6.617 | 216 |
| 13.9 | 6.370 | 202 |
| 15.0 | 5.902 | 3609 |
| 16.1 | 5.522 | 794 |
| 16.6 | 5.328 | 316 |
| 17.4 | 5.110 | 563 |
| 18.7 | 4.733 | 795 |
| 19.5 | 4.557 | 412 |
| 20.0 | 4.443 | 605 |
| 20.7 | 4.296 | 262 |
| 21.8 | 4.076 | 308 |
| 22.6 | 3.933 | 411 |
| 23.4 | 3.801 | 371 |
| 24.7 | 3.605 | 1015 |
| 25.0 | 3.560 | 1181 |
| 26.1 | 3.411 | 1023 |
| 27.4 | 3.258 | 219 |

In some embodiments, Form C nicotinic acid salt is characterized by the x-ray powder diffraction (XRPD) pattern depicted in FIG. 199.

In some embodiments, Form C nicotinic acid salt is characterized by the thermogravimetric analysis (TGA) pattern depicted in FIG. 200, trace 200A.

In some embodiments, Form C nicotinic acid salt is characterized by the differential scanning calorimetry (DSC) pattern depicted in FIG. 200, trace 200B.

In some embodiments of a complex form of Compound 1, X is ascorbic acid. In some such embodiments, a complex form of Compound 1 is an ascorbate salt. In some embodiments, an ascorbate salt of Compound 1 is a crystalline ascorbate salt. In some embodiments, a complex form of Compound 1 comprises one equivalent of ascorbic acid. In some embodiments, an ascorbate salt of Compound 1 is a hydrate. In some embodiments, a hydrate form of an ascorbate salt of Compound 1 is a crystalline hydrate form of an ascorbate salt. In some embodiments, a crystalline hydrate form of an ascorbate salt of Compound 1 is characterized by one or more peaks in its X-ray powder diffraction pattern selected from 3.7, 7.5, 11.3, 15.0, and 18.8±0.2 degrees 2θ. In some such embodiments, a complex form of Compound 1 is Form A ascorbate salt.

In some embodiments, Form A ascorbate salt is characterized by the following peaks

| Position<br>° 2θ ± 0.2<br>degrees | d-spacing<br>[Å] | Height<br>[cts] |
|---|---|---|
| 3.7 | 23.583 | 2591 |
| 7.5 | 11.791 | 2261 |
| 11.3 | 7.862 | 5996 |
| 14.4 | 6.149 | 445 |
| 15.0 | 5.897 | 8991 |
| 16.5 | 5.360 | 128 |
| 17.7 | 5.025 | 241 |
| 18.8 | 4.718 | 1661 |
| 19.4 | 4.577 | 256 |
| 19.7 | 4.512 | 496 |
| 20.9 | 4.255 | 115 |
| 21.6 | 4.106 | 405 |
| 22.6 | 3.928 | 300 |
| 24.5 | 3.638 | 1127 |
| 24.9 | 3.571 | 1401 |
| 25.8 | 3.448 | 1303 |
| 26.4 | 3.374 | 103 |
| 27.0 | 3.308 | 138 |
| 28.0 | 3.182 | 171 |
| 29.2 | 3.055 | 170 |
| 31.6 | 2.832 | 238 |
| 32.7 | 2.736 | 176 |

In some embodiments, Form A ascorbate salt is characterized by the FT-Raman spectrum depicted in FIG. 201.

In some embodiments, Form A ascorbate salt is characterized by the x-ray powder diffraction (XRPD) pattern depicted in FIG. 202.

In some embodiments, Form A ascorbate salt is characterized by the thermogravimetric analysis (TGA) pattern depicted in FIG. 203, trace 203A.

In some embodiments, Form A ascorbate salt is characterized by the differential scanning calorimetry (DSC) pattern depicted in FIG. 203, trace 203B.

In some embodiments, Form A ascorbate salt is characterized by the $^{1}$H NMR spectrum depicted in FIG. 204.

In some embodiments, a crystalline ascorbate salt of Compound 1 is characterized by one or more peaks in its X-ray powder diffraction pattern selected from 7.4, 9.8, 11.2, 14.9, and 16.1±0.2 degrees 2θ. In some such embodiments, a complex form of Compound 1 is Form B ascorbate salt.

In some embodiments, Form B ascorbate salt is characterized by the following peaks

| Position ° 2θ ± 0.2 degrees | d-spacing [Å] | Height [cts] |
|---|---|---|
| 7.4 | 11.866 | 336 |
| 9.8 | 8.989 | 138 |
| 11.2 | 7.918 | 621 |
| 13.3 | 6.643 | 235 |
| 14.9 | 5.950 | 1565 |
| 15.7 | 5.642 | 381 |
| 16.1 | 5.507 | 689 |
| 16.6 | 5.350 | 380 |
| 17.9 | 4.943 | 233 |
| 18.5 | 4.793 | 306 |
| 19.4 | 4.578 | 714 |
| 21.1 | 4.215 | 343 |
| 22.3 | 3.994 | 137 |
| 23.4 | 3.797 | 250 |
| 24.0 | 3.711 | 387 |
| 24.7 | 3.603 | 446 |
| 25.4 | 3.510 | 567 |

In some embodiments, Form B ascorbate salt is characterized by the x-ray powder diffraction (XRPD) pattern depicted in FIG. 234.

In some embodiments, Form B ascorbate salt is characterized by the thermogravimetric analysis (TGA) pattern depicted in FIG. 235, trace 235A.

In some embodiments, Form B ascorbate salt is characterized by the differential scanning calorimetry (DSC) pattern depicted in FIG. 235, trace 235B.

In some embodiments of a complex form of Compound 1, X is gallic acid. In some such embodiments, a complex form of Compound 1 is a gallate salt. In some embodiments, a gallate salt of Compound 1 is a crystalline gallate salt. In some embodiments, a complex form of Compound 1 comprises one equivalent of gallic acid. In some embodiments, a gallate salt of Compound 1 is a hydrate. In some embodiments, a hydrate form of a gallate salt of Compound 1 is a crystalline hydrate form of a gallate salt. In some embodiments, a crystalline hydrate form of a gallate salt of Compound 1 is characterized by one or more peaks in its X-ray powder diffraction pattern selected from 3.8, 7.6, 11.5, 15.4, and 19.2±0.2 degrees 2θ. In some such embodiments, a complex form of Compound 1 is Form A gallate salt.

In some embodiments, Form A gallate salt is characterized by the following peaks in its X-ray powder diffraction pattern:

| Position ° 2θ ± 0.2 degrees | d-spacing [Å] | Height [cts] |
|---|---|---|
| 3.8 | 23.137 | 642 |
| 7.6 | 11.560 | 2031 |
| 9.6 | 9.178 | 232 |
| 11.5 | 7.699 | 3638 |
| 13.3 | 6.669 | 129 |
| 14.4 | 6.160 | 227 |
| 14.8 | 5.971 | 330 |
| 15.4 | 5.771 | 3518 |
| 15.9 | 5.570 | 319 |
| 16.2 | 5.477 | 250 |
| 17.0 | 5.205 | 119 |
| 17.6 | 5.049 | 227 |
| 18.1 | 4.903 | 195 |
| 18.6 | 4.777 | 430 |
| 19.2 | 4.615 | 801 |
| 19.6 | 4.538 | 325 |
| 21.0 | 4.239 | 193 |
| 21.8 | 4.080 | 504 |
| 23.9 | 3.724 | 224 |
| 24.7 | 3.599 | 905 |
| 25.2 | 3.540 | 750 |
| 25.8 | 3.451 | 1157 |
| 27.1 | 3.294 | 125 |

In some embodiments, Form A gallate salt is characterized by the FT-Raman spectrum depicted in FIG. 205.

In some embodiments, Form A gallate salt is characterized by the x-ray powder diffraction (XRPD) pattern depicted in FIG. 206.

In some embodiments, Form A gallate salt is characterized by the thermogravimetric analysis (TGA) pattern depicted in FIG. 207, trace 207A.

In some embodiments, Form A gallate salt is characterized by the differential scanning calorimetry (DSC) pattern depicted in FIG. 207, trace 207B.

In some embodiments, Form A gallate salt is characterized by the $^{1}H$ NMR spectrum depicted in FIG. 208.

In some embodiments of a complex form of Compound 1, X is salicylic acid. In some such embodiments, a complex form of Compound 1 is a salicylate salt. In some embodiments, a salicylate salt of Compound 1 is a crystalline salicylate salt. In some embodiments, a salicylate salt of Compound 1 is a hydrate. In some embodiments, a hydrate form of a salicylate salt of Compound 1 is a crystalline hydrate form of a salicylate salt. In some embodiments, a crystalline hydrate form of a salicylate salt of Compound 1 is characterized by one or more peaks in its X-ray powder diffraction pattern selected from 3.8, 7.6, 11.5, 15.4, and 19.2±0.2 degrees 2θ. In some such embodiments, a complex form of Compound 1 is Form A salicylate salt.

In some embodiments, Form A salicylate salt is characterized by the following peaks in its X-ray powder diffraction pattern:

| Position ° 2θ ± 0.2 degrees | d-spacing [Å] | Height [cts] |
|---|---|---|
| 3.8 | 23.137 | 642 |
| 7.6 | 11.560 | 2031 |
| 9.6 | 9.178 | 232 |
| 11.5 | 7.699 | 3638 |
| 13.3 | 6.669 | 129 |
| 14.4 | 6.160 | 227 |
| 14.8 | 5.971 | 330 |
| 15.4 | 5.771 | 3518 |
| 15.9 | 5.570 | 319 |
| 16.2 | 5.477 | 250 |
| 17.0 | 5.205 | 119 |
| 17.6 | 5.049 | 227 |
| 18.1 | 4.903 | 195 |
| 18.6 | 4.777 | 430 |
| 19.2 | 4.615 | 801 |
| 19.6 | 4.538 | 325 |
| 21.0 | 4.239 | 193 |
| 21.8 | 4.080 | 504 |
| 23.9 | 3.724 | 224 |
| 24.7 | 3.599 | 905 |
| 25.2 | 3.540 | 750 |

-continued

| Position ° 2θ ± 0.2 degrees | d-spacing [Å] | Height [cts] |
|---|---|---|
| 25.8 | 3.451 | 1157 |
| 27.1 | 3.294 | 125 |

In some embodiments, Form A salicylate salt is characterized by the FT-Raman spectrum depicted in FIG. 209.

In some embodiments, Form A salicylate salt is characterized by the x-ray powder diffraction (XRPD) pattern depicted in FIG. 210.

In some embodiments, Form A salicylate salt is characterized by the thermogravimetric analysis (TGA) pattern depicted in FIG. 211, trace 211A.

In some embodiments, Form A salicylate salt is characterized by the differential scanning calorimetry (DSC) pattern depicted in FIG. 211, trace 2111B.

In some embodiments, Form A salicylate salt is characterized by the $^1$H NMR spectrum depicted in FIG. 212.

In some embodiments, a crystalline salicylate salt of Compound 1 is characterized by one or more peaks in its X-ray powder diffraction pattern selected from 5.1, 7.0, 10.9, 13.9, 15.9, and 16.2±0.2 degrees 2θ. In some such embodiments, a complex form of Compound 1 is Form B salicylate salt.

In some embodiments, Form B salicylate salt is characterized by the following peaks in its X-ray powder diffraction pattern:

| Position ° 2θ ± 0.2 degrees | d-spacing [Å] | Height [cts] |
|---|---|---|
| 5.1 | 17.232 | 1729 |
| 7.0 | 12.673 | 489 |
| 7.6 | 11.569 | 377 |
| 10.2 | 8.689 | 1626 |
| 10.9 | 8.091 | 2879 |
| 11.3 | 7.851 | 853 |
| 11.8 | 7.498 | 803 |
| 12.1 | 7.324 | 1284 |
| 13.5 | 6.582 | 916 |
| 13.9 | 6.362 | 5189 |
| 14.4 | 6.145 | 1726 |
| 14.8 | 5.986 | 1826 |
| 15.2 | 5.814 | 560 |
| 15.9 | 5.581 | 4446 |
| 16.2 | 5.467 | 5887 |
| 16.5 | 5.364 | 3222 |
| 16.9 | 5.236 | 1242 |
| 17.3 | 5.117 | 2339 |
| 17.6 | 5.025 | 1882 |
| 17.9 | 4.957 | 2126 |
| 18.2 | 4.862 | 2224 |
| 18.5 | 4.800 | 1202 |
| 19.5 | 4.563 | 1056 |
| 19.7 | 4.499 | 754 |
| 20.2 | 4.395 | 1701 |
| 20.5 | 4.333 | 599 |
| 21.4 | 4.158 | 573 |
| 22.3 | 3.987 | 659 |
| 22.5 | 3.944 | 933 |
| 23.5 | 3.788 | 1628 |
| 24.2 | 3.682 | 1847 |
| 24.4 | 3.644 | 3120 |
| 24.9 | 3.575 | 2806 |
| 25.5 | 3.497 | 2266 |
| 25.8 | 3.452 | 2388 |
| 26.1 | 3.420 | 1692 |
| 26.5 | 3.365 | 720 |
| 26.9 | 3.311 | 1803 |

-continued

| Position ° 2θ ± 0.2 degrees | d-spacing [Å] | Height [cts] |
|---|---|---|
| 27.5 | 3.249 | 541 |
| 27.8 | 3.209 | 799 |
| 28.8 | 3.099 | 846 |
| 29.4 | 3.043 | 616 |
| 29.6 | 3.018 | 563 |
| 29.9 | 2.985 | 539 |

In some embodiments, Form B salicylate salt is characterized by the x-ray powder diffraction (XRPD) pattern depicted in FIG. 241.

In some embodiments, Form B salicylate salt is characterized by the thermogravimetric analysis (TGA) pattern depicted in FIG. 242, trace 242A.

In some embodiments, Form B salicylate salt is characterized by the differential scanning calorimetry (DSC) pattern depicted in FIG. 242, trace 242B.

In some embodiments of Compound 1, X is orotic acid. In some such embodiments, a complex form of Compound 1 is an orotate salt. In some embodiments, an orotate salt of Compound 1 is a crystalline orotate salt. In some embodiments, a complex form of Compound 1 comprises one equivalent of orotic acid. In some embodiments, a crystalline orotate salt of Compound 1 is characterized by one or more peaks in its X-ray powder diffraction pattern selected from 4.7, 17.6, and 20.9±0.2 degrees 2θ. In some such embodiments, a complex form of Compound 1 is Form A orotate salt.

In some embodiments, Form A orotate salt is characterized by the following peaks in its X-ray powder diffraction pattern:

| Position ° 2θ ± 0.2 degrees | d-spacing [Å] | Height [cts] |
|---|---|---|
| 4.7 | 18.655 | 1952 |
| 8.8 | 10.085 | 4964 |
| 9.4 | 9.393 | 1731 |
| 10.0 | 8.882 | 2251 |
| 11.9 | 7.414 | 550 |
| 12.9 | 6.877 | 1522 |
| 13.4 | 6.608 | 477 |
| 13.8 | 6.398 | 1248 |
| 14.6 | 6.085 | 1052 |
| 15.6 | 5.689 | 2119 |
| 15.8 | 5.619 | 1697 |
| 17.0 | 5.211 | 535 |
| 17.6 | 5.053 | 4692 |
| 17.9 | 4.947 | 2829 |
| 18.2 | 4.875 | 685 |
| 18.7 | 4.752 | 1911 |
| 18.9 | 4.691 | 1119 |
| 20.0 | 4.445 | 1869 |
| 20.9 | 4.259 | 4993 |
| 21.3 | 4.174 | 796 |
| 21.8 | 4.083 | 992 |
| 22.3 | 3.991 | 1178 |
| 22.6 | 3.935 | 2874 |
| 23.3 | 3.814 | 593 |
| 23.6 | 3.765 | 1551 |
| 24.3 | 3.662 | 689 |
| 24.8 | 3.594 | 4698 |
| 25.9 | 3.437 | 973 |
| 26.5 | 3.369 | 697 |
| 26.9 | 3.314 | 628 |
| 27.6 | 3.231 | 849 |
| 29.9 | 2.986 | 896 |

-continued

| Position ° 2θ ± 0.2 degrees | d-spacing [Å] | Height [cts] |
|---|---|---|
| 30.6 | 2.923 | 459 |
| 32.3 | 2.774 | 596 |

In some embodiments, Form A orotate salt is characterized by the x-ray powder diffraction (XRPD) pattern depicted in FIG. 213.

In some embodiments, Form A orotate salt is characterized by the thermogravimetric analysis (TGA) pattern depicted in FIG. 214, trace 214A.

In some embodiments, Form A orotate salt is characterized by the differential scanning calorimetry (DSC) pattern depicted in FIG. 214, trace 214B.

In some embodiments, a crystalline orotate salt of Compound 1 is characterized by one or more peaks in its X-ray powder diffraction pattern selected from 4.8, 8.6, 9.5, 10.0, 15.5, and 21.1±0.2 degrees 2θ. In some such embodiments, a complex form of Compound 1 is Form D orotate salt.

In some embodiments, Form D orotate salt is characterized by the following peaks in its X-ray powder diffraction pattern:

| Position ° 2θ ± 0.2 degrees | d-spacing [Å] | Height [cts] |
|---|---|---|
| 4.8 | 18.504 | 1897 |
| 7.6 | 11.582 | 251 |
| 8.6 | 10.241 | 1674 |
| 9.5 | 9.332 | 1235 |
| 10.0 | 8.842 | 1160 |
| 11.8 | 7.472 | 406 |
| 13.0 | 6.789 | 891 |
| 13.4 | 6.585 | 741 |
| 14.0 | 6.338 | 741 |
| 15.5 | 5.701 | 1496 |
| 16.4 | 5.408 | 629 |
| 17.3 | 5.139 | 2086 |
| 17.9 | 4.960 | 2069 |
| 18.6 | 4.769 | 1355 |
| 19.2 | 4.630 | 1987 |
| 20.0 | 4.441 | 1897 |
| 20.7 | 4.297 | 840 |
| 21.1 | 4.203 | 2559 |
| 22.2 | 4.013 | 1809 |
| 22.8 | 3.898 | 461 |
| 23.8 | 3.740 | 1177 |
| 24.5 | 3.631 | 2398 |
| 26.2 | 3.401 | 920 |
| 27.6 | 3.237 | 406 |
| 28.1 | 3.179 | 345 |
| 28.9 | 3.087 | 422 |
| 30.0 | 2.978 | 325 |
| 31.8 | 2.811 | 273 |
| 35.0 | 2.562 | 86 |

In some embodiments, Form D orotate salt is characterized by the x-ray powder diffraction (XRPD) pattern depicted in FIG. 217.

In some embodiments, Form D orotate salt is characterized by the thermogravimetric analysis (TGA) pattern depicted in FIG. 218, trace 218A.

In some embodiments, Form D orotate salt is characterized by the differential scanning calorimetry (DSC) pattern depicted in FIG. 218, trace 218B.

In some embodiments, a crystalline orotate salt of Compound 1 is characterized by one or more peaks in its X-ray powder diffraction pattern selected from 4.4, 5.0, 6.2, 9.9, 12.4, and 14.9±0.2 degrees 2θ. In some such embodiments, a complex form of Compound 1 is Form F orotate salt.

In some embodiments, Form F orotate salt is characterized by the following peaks in its X-ray powder diffraction pattern:

| Position ° 2θ ± 0.2 degrees | d-spacing [Å] | Height [cts] |
|---|---|---|
| 3.5 | 25.010 | 646 |
| 4.4 | 20.183 | 764 |
| 5.0 | 17.790 | 2831 |
| 6.2 | 14.222 | 553 |
| 7.1 | 12.508 | 172 |
| 7.4 | 11.903 | 285 |
| 7.9 | 11.155 | 195 |
| 8.7 | 10.186 | 569 |
| 9.1 | 9.728 | 159 |
| 9.9 | 8.902 | 779 |
| 10.5 | 8.425 | 312 |
| 12.4 | 7.164 | 1405 |
| 14.4 | 6.151 | 358 |
| 14.9 | 5.945 | 1661 |
| 15.2 | 5.821 | 307 |
| 15.7 | 5.640 | 445 |
| 16.3 | 5.437 | 360 |
| 17.1 | 5.174 | 311 |
| 17.7 | 5.014 | 720 |
| 18.3 | 4.854 | 193 |
| 18.7 | 4.747 | 127 |
| 19.5 | 4.544 | 216 |
| 19.9 | 4.457 | 312 |
| 21.5 | 4.136 | 220 |
| 22.6 | 3.942 | 147 |
| 23.3 | 3.813 | 122 |
| 24.3 | 3.664 | 149 |

In some embodiments, Form F orotate salt is characterized by the FT-Raman spectrum depicted in FIG. 222.

In some embodiments, Form F orotate salt is characterized by the x-ray powder diffraction (XRPD) pattern depicted in FIG. 223.

In some embodiments, Form F orotate salt is characterized by the thermogravimetric analysis (TGA) pattern depicted in FIG. 224, trace 224A.

In some embodiments, Form F orotate salt is characterized by the differential scanning calorimetry (DSC) pattern depicted in FIG. 224, trace 224B.

In some embodiments, Form F orotate salt is characterized by the $^1$H NMR spectrum depicted in FIG. 225.

In some embodiments, a crystalline orotate salt of Compound 1 is characterized by one or more peaks in its X-ray powder diffraction pattern selected from 5.3, 9.0, 11.9, 13.9, 16.8, and 20.3±0.2 degrees 2θ. In some such embodiments, a complex form of Compound 1 is Form H orotate salt.

In some embodiments, Form H orotate salt is characterized by the following peaks in its X-ray powder diffraction pattern:

| Position ° 2θ ± 0.2 degrees | d-spacing [Å] | Height [cts] |
|---|---|---|
| 5.3 | 16.565 | 4288 |
| 7.9 | 11.163 | 394 |
| 9.0 | 9.836 | 2846 |
| 10.7 | 8.303 | 548 |
| 11.4 | 7.768 | 503 |
| 11.9 | 7.440 | 1127 |
| 13.9 | 6.364 | 1616 |

-continued

| Position ° 2θ ± 0.2 degrees | d-spacing [Å] | Height [cts] |
|---|---|---|
| 14.9 | 5.958 | 368 |
| 15.4 | 5.737 | 843 |
| 16.1 | 5.504 | 630 |
| 16.8 | 5.273 | 1243 |
| 17.8 | 4.993 | 326 |
| 18.6 | 4.781 | 441 |
| 19.9 | 4.467 | 281 |
| 20.3 | 4.370 | 1684 |
| 20.9 | 4.256 | 402 |
| 21.3 | 4.171 | 568 |
| 22.4 | 3.970 | 685 |
| 22.9 | 3.891 | 297 |
| 23.9 | 3.723 | 775 |
| 24.7 | 3.611 | 798 |
| 25.1 | 3.547 | 319 |
| 25.9 | 3.437 | 304 |
| 26.8 | 3.324 | 303 |
| 27.8 | 3.209 | 910 |
| 31.2 | 2.871 | 194 |

In some embodiments, Form H orotate salt is characterized by the FT-Raman spectrum depicted in FIG. 226.

In some embodiments, Form H orotate salt is characterized by the x-ray powder diffraction (XRPD) pattern depicted in FIG. 227.

In some embodiments, Form H orotate salt is characterized by the thermogravimetric analysis (TGA) pattern depicted in FIG. 228, trace 228A.

In some embodiments, Form H orotate salt is characterized by the differential scanning calorimetry (DSC) pattern depicted in FIG. 228, trace 228B.

In some embodiments, Form H orotate salt is characterized by the $^{1}$H NMR spectrum depicted in FIG. 229.

In some embodiments of a complex form of Compound 1, X is acetylsalicylic acid. In some such embodiments, a complex form of Compound 1 is an acetylsalicylate salt. In some embodiments, an acetylsalicylate salt of Compound 1 is a crystalline acetylsalicylate salt. In some embodiments, a crystalline acetylsalicylate salt of Compound 1 is characterized by one or more peaks in its X-ray powder diffraction pattern selected from 7.6, 10.3, 11.4, 13.5, and 15.3±0.2 degrees 2θ. In some such embodiments, a complex form of Compound 1 is Form A acetylsalicylate salt.

In some embodiments, Form A acetylsalicylate salt is characterized by the following peaks in its X-ray powder diffraction pattern:

| Position ° 2θ ± 0.2 degrees | d-spacing [Å] | Height [cts] |
|---|---|---|
| 7.6 | 11.603 | 5471 |
| 9.4 | 9.378 | 1061 |
| 10.3 | 8.588 | 1592 |
| 11.4 | 7.736 | 6082 |
| 12.1 | 7.301 | 876 |
| 12.4 | 7.111 | 966 |
| 13.5 | 6.575 | 2288 |
| 13.7 | 6.453 | 908 |
| 14.2 | 6.253 | 2775 |
| 15.3 | 5.806 | 13560 |
| 15.8 | 5.619 | 925 |
| 16.1 | 5.512 | 8968 |
| 16.8 | 5.278 | 1645 |
| 17.3 | 5.124 | 1781 |
| 18.1 | 4.905 | 1155 |
| 18.3 | 4.853 | 862 |

-continued

| Position ° 2θ ± 0.2 degrees | d-spacing [Å] | Height [cts] |
|---|---|---|
| 18.8 | 4.727 | 1013 |
| 19.1 | 4.639 | 6875 |
| 19.7 | 4.509 | 1985 |
| 20.4 | 4.360 | 888 |
| 20.7 | 4.296 | 2084 |
| 20.9 | 4.256 | 4376 |
| 22.0 | 4.048 | 1835 |
| 22.4 | 3.973 | 1088 |
| 22.8 | 3.900 | 5590 |
| 23.4 | 3.805 | 3229 |
| 24.0 | 3.715 | 10155 |
| 25.4 | 3.512 | 7991 |
| 25.8 | 3.449 | 9706 |
| 26.2 | 3.400 | 2772 |
| 27.3 | 3.271 | 5630 |
| 28.3 | 3.154 | 694 |
| 29.5 | 3.024 | 759 |
| 30.0 | 2.978 | 879 |
| 35.1 | 2.559 | 742 |

In some embodiments, a crystalline acetylsalicylate salt of Compound 1 is characterized by one or more peaks in its X-ray powder diffraction pattern selected from 3.6, 5.0, 5.6, 7.0, 7.9, 9.0, 9.9, and 10.5±0.2 degrees 2θ. In some such embodiments, a complex form of Compound 1 is Form B acetylsalicylate salt.

In some embodiments, Form B acetylsalicylate salt is characterized by the following peaks in its X-ray powder diffraction pattern:

| Position ° 2θ ± 0.2 degrees | d-spacing [Å] | Height [cts] |
|---|---|---|
| 3.6 | 24.798 | 1917 |
| 5.0 | 17.698 | 1054 |
| 5.6 | 15.849 | 1538 |
| 7.0 | 12.558 | 1794 |
| 7.9 | 11.234 | 727 |
| 9.0 | 9.870 | 794 |
| 9.9 | 8.901 | 1850 |
| 10.5 | 8.399 | 1925 |
| 12.7 | 6.983 | 703 |
| 12.9 | 6.839 | 605 |
| 13.4 | 6.621 | 2571 |
| 14.1 | 6.290 | 987 |
| 15.1 | 5.863 | 1298 |
| 15.7 | 5.645 | 704 |
| 15.9 | 5.568 | 711 |
| 16.7 | 5.315 | 609 |
| 17.3 | 5.138 | 2598 |
| 17.6 | 5.046 | 447 |
| 18.1 | 4.902 | 1005 |
| 18.9 | 4.683 | 1589 |
| 19.4 | 4.570 | 1256 |
| 19.8 | 4.491 | 1042 |
| 21.5 | 4.143 | 576 |
| 22.6 | 3.942 | 1160 |
| 23.3 | 3.825 | 1164 |
| 23.6 | 3.774 | 1698 |

In some embodiments, Form B acetylsalicylate salt is characterized by the x-ray powder diffraction (XRPD) pattern depicted in FIG. 239.

In some embodiments, Form B acetylsalicylate salt is characterized by the thermogravimetric analysis (TGA) pattern depicted in FIG. 240, trace 240A.

In some embodiments, Form B acetylsalicylate salt is characterized by the differential scanning calorimetry (DSC) pattern depicted in FIG. 240, trace 240B.

Uses, Formulation and Administration

Pharmaceutically Acceptable Compositions

According to another embodiment, the present disclosure provides a composition comprising Compound 1, or a crystalline form or complex thereof, and a pharmaceutically acceptable carrier, adjuvant, or vehicle. In certain embodiments, the amount of Compound 1, or a crystalline form or complex thereof, in compositions of this disclosure is such that it is effective to measurably inhibit JAK2, or a mutant thereof, in a biological sample or in a patient. In certain embodiments, a composition of this disclosure is formulated for administration to a patient in need of such composition. In some embodiments, a composition of this disclosure is formulated for oral administration to a patient.

Compounds and compositions, according to method of the present invention, are administered using any amount and any route of administration effective for treating or lessening the severity of a disorder provided herein (i.e., a JAK2-mediated disease or disorder). The exact amount required will vary from subject to subject, depending on the species, age, and general condition of the subject, the severity of the infection, the particular agent, its mode of administration, and the like. Compound 1, or a crystalline form or complex thereof, is preferably formulated in unit dosage form for ease of administration and uniformity of dosage.

Compositions of the present disclosure may be administered orally, parenterally, by inhalation spray, topically, rectally, nasally, buccally, vaginally, intraperitoneally, intracisternally or via an implanted reservoir. In some embodiments, the compositions are administered orally, intraperitoneally or intravenously.

Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of Compound 1, or a crystalline form or complex thereof, it is often desirable to slow the absorption of the compound from subcutaneous or intramuscular injection. This may be accomplished by the use of a liquid suspension of crystalline or amorphous material with poor water solubility. The rate of absorption of Compound 1, or a crystalline form or complex thereof, then depends upon its rate of dissolution that, in turn, may depend upon crystal size and crystalline form. Alternatively, delayed absorption of a parenterally administered Compound 1, or a crystalline form or complex thereof, is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping Compound 1, or a crystalline form or complex thereof, in liposomes or microemulsions that are compatible with body tissues.

In some embodiments, provided pharmaceutically acceptable compositions are formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

Pharmaceutically acceptable compositions of this disclosure may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Solid dosage forms for oral administration include capsules, tablets, pills, powders, and granules. In such solid dosage forms, Compound 1, or a crystalline form or complex thereof, is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and/or i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

Compound 1, or a crystalline form or complex thereof, can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms Compound 1, or a crystalline form or complex thereof, may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Liquid dosage forms for oral administration include, but are not limited to, pharmaceutically acceptable emulsions, microemulsions, solutions, suspensions, syrups and elixirs. In addition to Compound 1, or a crystalline form or complex thereof, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Alternatively, pharmaceutically acceptable compositions of this disclosure may be administered in the form of suppositories for rectal administration. These can be prepared by mixing Compound 1, or a crystalline form or complex thereof, with a suitable non-irritating excipient that is solid at room temperature but liquid at rectal temperature and therefore will melt in the rectum to release the drug. Such materials include cocoa butter, beeswax and polyethylene glycols.

Compositions for rectal or vaginal administration are preferably suppositories which can be prepared by mixing Compound 1, or a crystalline form or complex thereof, with suitable non-irritating excipients or carriers such as cocoa butter, polyethylene glycol or a suppository wax which are solid at ambient temperature but liquid at body temperature and therefore melt in the rectum or vaginal cavity and release the active compound.

Pharmaceutically acceptable compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing Compound 1, or a crystalline form or complex thereof, suspended or dissolved in one or more carriers. Carriers for topical administration of Compound 1, or a crystalline form or complex thereof, include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing Compound 1, or a crystalline form or complex thereof, suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Dosage forms for topical or transdermal administration of Compound 1, or a crystalline form or complex thereof, include ointments, pastes, creams, lotions, gels, powders, solutions, sprays, inhalants or patches. Compound 1, or a crystalline form or complex thereof, is admixed under sterile conditions with a pharmaceutically acceptable carrier and any needed preservatives or buffers as may be required. Ophthalmic formulation, ear drops, and eye drops are also contemplated as being within the scope of this invention. Additionally, the present disclosure contemplates the use of transdermal patches, which have the added advantage of providing controlled delivery of Compound 1, or a crystalline form or complex thereof, to the body. Such dosage forms can be made by dissolving or dispensing the compound in the proper medium. Absorption enhancers can also be used to increase the flux of Compound 1, or a crystalline form or complex thereof, across the skin. The rate can be controlled by either providing a rate controlling membrane or by dispersing Compound 1, or a crystalline form or complex thereof, in a polymer matrix or gel.

In some embodiments, compositions described herein comprise an amount of Compound 1, or a crystalline form or complex thereof, that is the molar equivalent to free base N-tert-butyl-3-[(5-methyl-2-{[4-(2-pyrrolidin-1-ylethoxy) phenyl]amino}pyrimidin-4-yl)amino]benzenesulfonamide.

For example, a 100 mg formulation of Compound 1 (i.e., unsolvated free base parent N-tert-butyl-3-[(5-methyl-2-{[4-(2-pyrrolidin-1-ylethoxy)phenyl]amino}pyrimidin-4-yl)amino]benzenesulfonamide, MW=524.26) comprises 117.30 mg of a dihydrochloride monohydrate form of Compound 1 (MW=614.22).

In some embodiments, the present disclosure provides a composition comprising Compound 1, or a crystalline form or complex thereof, and one or more pharmaceutically acceptable excipients. In some embodiments, the one or more pharmaceutically acceptable excipients are selected from a binder and a lubricant.

In some embodiments, the binder is a microcrystalline cellulose. In some such embodiments, the microcrystalline cellulose is silicified microcrystalline cellulose.

In some embodiments, the binder is sodium stearyl fumarate.

In some embodiments, the composition comprises:

| Component | Amount |
|---|---|
| Compound 1 (free base) | 100 mg |
| silicified microcrystalline cellulose (high density 90 μm) | 178.45 mg |
| sodium stearyl fumarate | 3.0 mg |
| TOTAL | 281.45 mg |

In certain embodiments, the composition comprises:

| Component | Amount |
|---|---|
| Compound 1 2HCl•$H_2O$ (calculated based on the parent free base) | 117.30 mg (100 mg parent free base) |
| silicified microcrystalline cellulose (high density 90 μm) | 178.45 mg |
| sodium stearyl fumarate | 3.0 mg |
| TOTAL | 298.75 mg |

Uses of Compounds and Pharmaceutically Acceptable Compositions

Compounds and compositions described herein are generally useful for the inhibition of kinase activity of one or more enzymes. Examples of kinases that are inhibited by the compounds and compositions described herein and against which the methods described herein are useful include JAK2, or a mutant thereof.

The activity of Compound 1, or a crystalline form or complex thereof, utilized as an inhibitor of a JAK2 kinase, or a mutant thereof, may be assayed in vitro, in vivo or in a cell line. In vitro assays include assays that determine inhibition of either the phosphorylation activity and/or the subsequent functional consequences, or ATPase activity of activated JAK2 kinase, or a mutant thereof.

According to one embodiment, the invention relates to a method of inhibiting protein kinase activity in a biological sample comprising the step of contacting said biological sample with Compound 1, or a crystalline form or complex thereof, or a composition thereof.

According to another embodiment, the invention relates to a method of inhibiting activity of a JAK2 kinase, or a mutant thereof, in a biological sample comprising the step of contacting said biological sample with Compound 1, or a crystalline form or complex thereof, or a composition thereof.

According to another embodiment, the invention relates to a method of inhibiting activity of a JAK2 kinase, or a mutant thereof, in a patient comprising the step of administering to said patient Compound 1, or a crystalline form or complex thereof, or a composition thereof. In other embodiments, the present disclosure provides a method for treating a JAK2-mediated disease or disorder, in a patient in need thereof, comprising the step of administering to said patient Compound 1, or a crystalline form or complex thereof, or pharmaceutically acceptable composition thereof. Such disorders are described in detail herein.

Compound 1, or a crystalline form or complex thereof, is useful in treating a variety of disorders, including, but not limited to, for example, myeloproliferative disorders, proliferative diabetic retinopathy and other angiogenic-associated disorders including solid tumors and other types of cancer, eye disease, inflammation, psoriasis, and a viral infection. The kinds of cancer that can be treated include, but are not limited to, an alimentary/gastrointestinal tract cancer, colon cancer, liver cancer, skin cancer, breast cancer, ovarian cancer, prostate cancer, lymphoma, leukemia (including acute myelogenous leukemia and chronic myelogenous leukemia), kidney cancer, lung cancer, muscle cancer, bone cancer, bladder cancer or brain cancer.

Some examples of the diseases and disorders that can be treated also include ocular neovasculariaztion, infantile haemangiomas; organ hypoxia, vascular hyperplasia, organ transplant rejection, lupus, multiple sclerosis, rheumatoid arthritis, psoriasis, Type 1 diabetes and complications from diabetes, inflammatory disease, acute pancreatitis, chronic pancreatitis, asthma, allergies, adult respiratory distress syndrome, cardiovascular disease, liver disease, other blood disorders, asthma, rhinitis, atopic, dermatitits, autoimmune thryroid disorders, ulerative colitis, Crohn's disease, metastatic melanoma, Kaposi's sarcoma, multiple myeloma, conditions associated with cytokines, and other autoimmune diseases including glomerulonephritis, scleroderma, chronic thyroiditis, Graves' disease, autoimmune gastritis, autoimmune hemolytic anemia, autoimmune neutropenia, thrombocytopenia, atopy (e.g., allergic asthma, atopic dermatitis, or allergic rhinitis), chronic active hepatitis, myasthenia graivs, multiple scleroiss, inflammatory bowel disease, graft vs host disease, neurodegenerative diseases including motor neuron disease, Alzheimer's disease, Parkinson's disease, amyotrophic lateral scelerosis, Huntington's disease, cerebral ischemia, or neurodegenerative disease caused by traumatic injury, strike, gluatamate neurtoxicity or hypoxia; ischemic/reperfusion injury in stroke, myocardial ischemica, renal ischemia, heart attacks, cardiac hypertrophy, atherosclerosis and arteriosclerosis, organ hyoxia, and platelet aggregation.

Examples of some additional diseases and disorders that can be treated also include cell mediated hypersensitivity (allergic contact dermatitis, hypersensitivity pneumonitis), rheumatic diseases (e.g., systemic lupus erythematosus (SLE), juvenile arthritis, Sjogren's Syndrome, scleroderma, polymyositis, ankylosing spondylitis, psoriatic arthritis), viral diseases (Epstein Barr Virus, Hepatitis B, Hepatitis C, HIV, HTLVI, Vaicella-Zoster Virus, Human Papilloma Virus), food allergy, cutaneous inflammation, and immune suppression induced by solid tumors.

In some embodiments, Compound 1, or a crystalline form or complex thereof, is useful in treating a treating a myeloproliferative disorder. In some embodiments, the myeloproliferative disorder is selected from primary myelofibrosis, polycythemia vera, and essential thrombocythemia. In some embodiments, the myeloproliferative disorder is selected from primary myelofibrosis and secondary myelofibrosis. In some embodiments, the myeloproliferative disorder is secondary myelofibrosis. In some such embodiments, the secondary myelofibrosis is selected from post-polycythemia vera myelofibrosis and post-essential thrombocythemia myelofibrosis.

In some embodiments, a provided method comprises administering Compound 1, or a crystalline form or complex thereof, to a patient previously treated with a JAK2 inhibitor. In some such embodiments, a provided method comprises administering Compound 1, or a crystalline form or complex thereof, to a patient previously treated with ruxolitinib (JAKAFI®).

In some embodiments, a provided method comprises administering Compound 1, or a crystalline form or complex thereof, to a patient suffering from or diagnosed with a myeloproliferative disorder that is unresponsive to ruxolitinib. In some embodiments, the patient is suffering from or has been diagnosed with a myeloproliferative disorder that is refractory or resistant to ruxolitinib.

In some embodiments, the patient has relapsed during or following ruxolitinib therapy.

In some embodiments, the patient is intolerant to ruxolitinib. In some embodiments, patient intolerance to ruxolitinib is evidenced by a hematological toxicity (e.g., anemia, thrombocytopenia, etc.) or a non-hematological toxicity.

In some embodiments, the patient has had an inadequate response to or is intolerant to hydroxyurea.

In some embodiments, the patient is exhibiting or experiencing, or has exhibited or experienced, one or more of the following during treatment with ruxolitinib: lack of response, disease progression, or loss of response at any time during ruxolitinib treatment. In some embodiments, disease progression is evidenced by an increase in spleen size during ruxolitinib treatment.

In some embodiments, a patient previously treated with ruxolitinib has a somatic mutation or clonal marker associated with or indicative of a myeloproliferative disorder. In some embodiments, the somatic mutation is selected from a JAK2 mutation, a CALR mutation or a MPL mutation. In some embodiments, the JAK2 mutation is V617F. In some embodiments, the CALR mutation is a mutation in exon 9. In some embodiments, the MPL mutation is selected from W515K and W515L.

In some embodiments, the present disclosure provides a method of treating a relapsed or refractory myeloproliferative disorder, wherein the myeloproliferative disorder is relapsed or refractory to ruxolitinib.

In some embodiments, a myeloproliferative disorder is selected from intermediate risk myelofibrosis and high risk myelofibrosis.

In some embodiments, the intermediate risk myelofibrosis is selected from primary myelofibrosis, post-polycythemia vera (post-PV) myelofibrosis and post-essential thrombocythemia (post-ET) myelofibrosis. In some embodiments, the myelofibrosis is intermediate risk 1 (also referred to as intermediate-1 risk). In some embodiments, the myelofibrosis is intermediate risk 2 (also referred to as intermediate-2 risk).

In some embodiments, the high risk myelofibrosis is selected from primary myelofibrosis, post-polycythemia vera (post-PV) myelofibrosis and post-essential thrombocythemia (post-ET) myelofibrosis.

In some embodiments, the present disclosure provides an article of manufacture comprising a packaging material and a pharmaceutical composition contained within the packaging material. In some embodiments, the packaging material comprises a label which indicates that the pharmaceutical composition can be used for treatment of one or more disorders identified above.

ADDITIONAL EMBODIMENTS

Embodiment 1. A crystalline form of Compound 1:

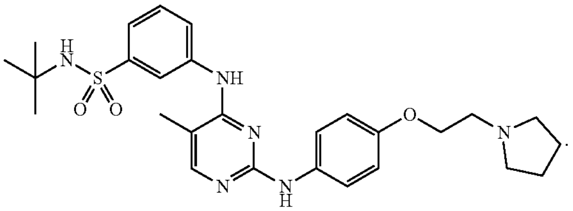 [SMILES: Cc1cnc(Nc2ccc(OCCN3CCCC3)cc2)nc1Nc1cccc(S(=O)(=O)NC(C)(C)C)c1]

Embodiment 2. The crystalline form of embodiment 1, wherein the form is unsolvated.

Embodiment 3. The crystalline form of embodiment 2, wherein the form is characterized by one or more peaks in its X-ray powder diffraction pattern selected from 9.7, 14.6, 19.5, 24.3, and 25.6±0.2 degrees 2θ.

Embodiment 4. The crystalline form of embodiment 2, wherein the form is characterized by the following peaks in its X-ray powder diffraction pattern:

| Position ° 2θ ± 0.2 degrees | d-spacing [Å] | Height [cts] |
|---|---|---|
| 8.8 | 10.102 | 1414 |
| 9.7 | 9.120 | 88376 |
| 10.5 | 8.463 | 2192 |
| 13.6 | 6.516 | 1881 |
| 14.6 | 6.082 | 50409 |
| 16.0 | 5.543 | 3640 |
| 16.4 | 5.413 | 2620 |
| 17.7 | 5.014 | 3311 |
| 18.5 | 4.797 | 5807 |
| 19.1 | 4.637 | 1316 |
| 19.5 | 4.563 | 6885 |
| 19.8 | 4.492 | 1686 |
| 20.1 | 4.415 | 1686 |
| 20.4 | 4.360 | 4156 |
| 21.0 | 4.229 | 4358 |
| 22.7 | 3.914 | 1551 |
| 23.0 | 3.874 | 2648 |
| 23.5 | 3.781 | 1611 |
| 23.9 | 3.730 | 9006 |
| 24.3 | 3.660 | 13329 |
| 24.6 | 3.614 | 1849 |
| 25.6 | 3.479 | 7883 |
| 28.0 | 3.192 | 1510 |
| 28.6 | 3.119 | 1592 |
| 29.4 | 3.043 | 2105 |

Embodiment 5. The crystalline form of embodiment 1, wherein the form is solvated.

Embodiment 6. The crystalline form of embodiment 5, wherein the form is a 2-methyl-tetrahydrofuran solvate.

Embodiment 7. The crystalline form of embodiment 6, wherein the form is characterized by one or more peaks in its X-ray powder diffraction pattern selected from 12.5, 18.3, 18.9, 20.1, and 23.8±0.2 degrees 2θ.

Embodiment 8. The crystalline form of embodiment 6, wherein the form is characterized by the following peaks in its X-ray powder diffraction pattern:

| Position ° 2θ ± 0.2 degrees | d-spacing [Å] | Height [cts] |
|---|---|---|
| 7.6 | 11.633 | 715 |
| 10.2 | 8.690 | 521 |
| 11.9 | 7.430 | 2468 |
| 12.5 | 7.096 | 3531 |
| 12.7 | 6.963 | 2843 |
| 14.1 | 6.265 | 2984 |
| 14.5 | 6.096 | 1620 |
| 16.1 | 5.494 | 2249 |
| 18.3 | 4.836 | 6390 |
| 18.9 | 4.699 | 5752 |
| 20.1 | 4.411 | 6304 |
| 21.4 | 4.147 | 1605 |
| 23.1 | 3.853 | 1981 |
| 23.8 | 3.734 | 25579 |
| 25.5 | 3.498 | 1600 |
| 26.0 | 3.433 | 1425 |
| 27.6 | 3.231 | 1295 |
| 28.3 | 3.149 | 1147 |
| 28.9 | 3.090 | 556 |
| 30.4 | 2.937 | 356 |
| 31.7 | 2.824 | 477 |
| 34.2 | 2.620 | 224 |
| 35.5 | 2.530 | 569 |
| 36.0 | 2.497 | 405 |
| 36.9 | 2.434 | 141 |

Embodiment 9. The crystalline form of embodiment 1, wherein the form is a hydrate.

Embodiment 10. The crystalline form of embodiment 9, wherein the form is a monohydrate.

Embodiment 11. The crystalline form of embodiment 10, wherein the form is characterized by one or more peaks in its X-ray powder diffraction pattern selected from 8.7, 15.2, 17.3, 18.0, and 19.4±0.2 degrees 2θ.

Embodiment 12. The crystalline form of embodiment 10, wherein the form is characterized by the following peaks in its X-ray powder diffraction pattern:

| Position ° 2θ ± 0.2 degrees | d-spacing [Å] | Height [cts] |
|---|---|---|
| 8.7 | 10.184 | 23473 |
| 10.6 | 8.332 | 6912 |
| 14.4 | 6.172 | 8862 |
| 15.2 | 5.825 | 11716 |
| 15.5 | 5.719 | 3493 |
| 16.3 | 5.439 | 5672 |
| 16.6 | 5.329 | 5294 |
| 16.9 | 5.244 | 7167 |
| 17.3 | 5.120 | 51890 |
| 18.0 | 4.917 | 15095 |
| 19.4 | 4.578 | 10908 |
| 20.2 | 4.388 | 8419 |
| 21.8 | 4.078 | 5043 |
| 22.1 | 4.017 | 7400 |
| 22.4 | 3.974 | 6455 |
| 22.8 | 3.894 | 6416 |
| 23.2 | 3.841 | 3537 |
| 23.5 | 3.783 | 7215 |
| 24.4 | 3.647 | 4592 |
| 25.0 | 3.559 | 4787 |
| 25.2 | 3.540 | 4028 |
| 26.1 | 3.414 | 4525 |
| 26.6 | 3.356 | 4349 |
| 27.4 | 3.255 | 5512 |
| 27.6 | 3.231 | 4683 |

Embodiment 13. The crystalline form of embodiment 9, wherein the form is a tetrahydrate.

Embodiment 14. The crystalline form of embodiment 13, wherein the form is characterized by one or more peaks in its X-ray powder diffraction pattern selected from 12.4, 18.5, 19.3, 20.3, and 23.6±0.2 degrees 2θ.

Embodiment 15. The crystalline form of embodiment 13, wherein the form is characterized by the following peaks in its X-ray powder diffraction pattern:

| Position ° 2θ ± 0.2 degrees | d-spacing [Å] | Height [cts] |
|---|---|---|
| 7.7 | 11.475 | 1223 |
| 11.8 | 7.529 | 1943 |
| 12.0 | 7.372 | 2255 |
| 12.4 | 7.142 | 4460 |
| 12.9 | 6.874 | 1805 |
| 13.4 | 6.619 | 1735 |
| 14.1 | 6.282 | 2143 |
| 14.5 | 6.122 | 1529 |
| 15.4 | 5.772 | 1552 |
| 16.4 | 5.397 | 3326 |
| 18.5 | 4.800 | 7100 |
| 19.3 | 4.591 | 4008 |
| 19.7 | 4.497 | 2119 |
| 20.0 | 4.435 | 3039 |
| 20.3 | 4.380 | 4906 |
| 20.8 | 4.267 | 1987 |
| 21.3 | 4.163 | 1495 |
| 21.9 | 4.066 | 999 |
| 22.7 | 3.925 | 836 |
| 23.6 | 3.770 | 22852 |
| 24.8 | 3.585 | 1474 |
| 25.8 | 3.453 | 907 |
| 26.2 | 3.405 | 1278 |
| 27.0 | 3.306 | 1347 |
| 28.5 | 3.133 | 823 |

Embodiment 16. A sample comprising the crystalline form of any one of embodiments 1-15, wherein the sample is substantially free of impurities.

Embodiment 17. The sample of embodiment 16, wherein the sample comprises at least about 90% by weight of Compound 1.

Embodiment 18. The sample of embodiment 16, wherein the sample comprises at least about 95% by weight of Compound 1.

Embodiment 19. The sample of embodiment 16, wherein the sample comprises at least about 99% by weight of Compound 1.

Embodiment 20. The sample of embodiment 16, wherein the sample comprises no more than about 5.0 percent of total organic impurities.

Embodiment 21. The sample of embodiment 16, wherein the sample comprises no more than about 3.0 percent of total organic impurities.

Embodiment 22. The sample of embodiment 16, wherein the sample comprises no more than about 1.5 percent of total organic impurities.

Embodiment 23. The sample of embodiment 16, wherein the sample comprises no more than about 1.0 percent of total organic impurities.

Embodiment 24. The sample of embodiment 16, wherein the sample comprises no more than about 0.5 percent of total organic impurities.

Embodiment 25. A complex comprising Compound 1:

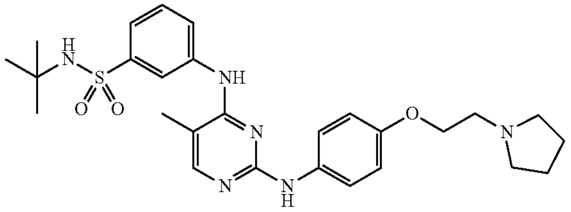

1 and a co-former X;

wherein the complex is crystalline and

X is selected from the group consisting of hydrobromic acid, sulfuric acid, toluenesulfonic acid, methanesulfonic acid, 2-naphthalenesulfonic acid, phosphoric acid, DL-tartaric acid, succinic acid, gentisic acid, hippuric acid, adipic acid, galactaric acid, naphthalene-1,5-disulfonic acid, (S)-camphor-10-sulfonic acid, ethane-1,2-disulfonic acid, ethanesulfonic acid, benzenesulfonic acid, oxalic acid, maleic acid, pamoic acid, 1-hydroxy-2-naphthoic acid, malonic acid, L-tartaric acid, fumaric acid, citric acid, L-lactic acid, acetic acid, propionic acid, DL-lactic acid, D-gluconic acid, DL-malic acid, glutaric acid, camphoric acid, DL-mandelic acid, glutamic acid, glycolic acid, L-mandelic acid, L-malic acid, L-aspartic acid, benzoic acid, saccharin, nicotinic acid, ascorbic acid, gallic acid, salicylic acid, orotic acid, acetylsalicylic acid, choline, potassium hydroxide, and sodium hydroxide.

Embodiment 26. A complex comprising Compound 1:

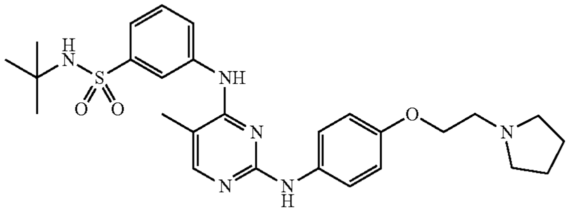

1 and a co-former X;

wherein:

X is selected from the group consisting of 2-naphthalenesulfonic acid, succinic acid, gentisic acid, hippuric acid, adipic acid, galactaric acid, naphthalene-1,5-disulfonic acid, (S)-camphor-10-sulfonic acid, ethane-1,2-disulfonic acid, ethanesulfonic acid, benzenesulfonic acid, maleic acid, pamoic acid, 1-hydroxy-2-naphthoic acid, malonic acid, fumaric acid, L-lactic acid, propionic acid, DL-lactic acid, D-gluconic acid, DL-malic acid, glutaric acid, camphoric acid, glutamic acid, glycolic acid, L-malic acid, L-aspartic acid, benzoic acid, saccharin, nicotinic acid, ascorbic acid, gallic acid, salicylic acid, orotic acid, acetylsalicylic acid, and choline.

Embodiment 27. The complex of embodiment 25, wherein X is hydrobromic acid.

Embodiment 28. The complex of embodiment 25, wherein X is sulfuric acid.

Embodiment 29. The complex of embodiment 25, wherein X is toluenesulfonic acid.

Embodiment 30. The complex of embodiment 25, wherein X is methanesulfonic acid.

Embodiment 31. The complex of embodiment 25 or embodiment 26, wherein X is 2-naphthalenesulfonic acid.

Embodiment 32. The complex of embodiment 25, wherein X is phosphoric acid.

Embodiment 33. The complex of embodiment 25, wherein X is DL-tartaric acid.

Embodiment 34. The complex of embodiment 25 or embodiment 26, wherein X is succinic acid.

Embodiment 35. The complex of embodiment 25 or embodiment 26, wherein X is gentisic acid.

Embodiment 36. The complex of embodiment 25 or embodiment 26, wherein X is hippuric acid.

Embodiment 37. The complex of embodiment 25 or embodiment 26, wherein X is adipic acid.

Embodiment 38. The complex of embodiment 25 or embodiment 26, wherein X is galactaric acid.

Embodiment 39. The complex of embodiment 25 or embodiment 26, wherein X is 1,5-naphthalenedisulfonic acid.

Embodiment 40. The complex of embodiment 25 or embodiment 26, wherein X is (S)-camphorsulfonic acid.

Embodiment 41. The complex of embodiment 25 or embodiment 26, wherein X is 1,2-ethanedisulfonic acid.

Embodiment 42. The complex of embodiment 25 or embodiment 26, wherein X is ethanesulfonic acid.

Embodiment 43. The complex of embodiment 25 or embodiment 26, wherein X is benzenesulfonic acid.

Embodiment 44. The complex of embodiment 25, wherein X is oxalic acid.

Embodiment 45. The complex of embodiment 25 or embodiment 26, wherein X is maleic acid.

Embodiment 46. The complex of embodiment 25 or embodiment 26, wherein X is pamoic acid.

Embodiment 47. The complex of embodiment 25 or embodiment 26, wherein X is 1-hydroxy-2-naphthoic acid.

Embodiment 48. The complex of embodiment 25 or embodiment 26, wherein X is malonic acid.

Embodiment 49. The complex of embodiment 25, wherein X is L-tartaric acid.

Embodiment 50. The complex of embodiment 25 or embodiment 26, wherein X is fumaric acid.

Embodiment 51. The complex of embodiment 25, wherein X is citric acid.

Embodiment 52. The complex of embodiment 25 or embodiment 26, wherein X is L-lactic acid.

Embodiment 53. The complex of embodiment 25, wherein X is acetic acid.

Embodiment 54. The complex of embodiment 25 or embodiment 26, wherein X is propionic acid.

Embodiment 55. The complex of embodiment 25 or embodiment 26, wherein X is DL-lactic acid.

Embodiment 56. The complex of embodiment 25 or embodiment 26, wherein X is D-gluconic acid.

Embodiment 57. The complex of embodiment 25 or embodiment 26, wherein X is DL-malic acid.

Embodiment 58. The complex of embodiment 25 or embodiment 26, wherein X is glycolic acid.

Embodiment 59. The complex of embodiment 25 or embodiment 26, wherein X is glutaric acid.

Embodiment 60. The complex of embodiment 25 or embodiment 26, wherein X is L-malic acid.

Embodiment 61. The complex of embodiment 25 or embodiment 26, wherein X is camphoric acid.

Embodiment 62. The complex of embodiment 25, wherein X is DL-mandelic acid.

Embodiment 63. The complex of embodiment 25 or embodiment 26, wherein X is saccharin.

Embodiment 64. The complex of embodiment 25 or embodiment 26, wherein X is nicotinic acid.

Embodiment 65. The complex of embodiment 25 or embodiment 26, wherein X is ascorbic acid.

Embodiment 66. The complex of embodiment 25 or embodiment 26, wherein X is gallic acid.

Embodiment 67. The complex of embodiment 25 or embodiment 26, wherein X is salicylic acid.

Embodiment 68. The complex of embodiment 25 or embodiment 26, wherein X is orotic acid.

Embodiment 69. The complex of embodiment 25 or embodiment 26, wherein X is acetylsalicylic acid.

Embodiment 70. A sample comprising the complex of any one of embodiments 25-69, wherein the sample is substantially free of impurities.

Embodiment 71. The sample of embodiment 70, wherein the sample comprises at least about 90% by weight of the complex.

Embodiment 72. The sample of embodiment 70, wherein the sample comprises at least about 95% by weight of the complex.

Embodiment 73. The sample of embodiment 70, wherein the sample comprises at least about 99% by weight of the complex.

Embodiment 74. The sample of embodiment 70, wherein the sample comprises no more than about 5.0 percent of total organic impurities.

Embodiment 75. The sample of embodiment 70, wherein the sample comprises no more than about 3.0 percent of total organic impurities.

Embodiment 76. The sample of embodiment 70, wherein the sample comprises no more than about 1.5 percent of total organic impurities.

Embodiment 77. The sample of embodiment 70, wherein the sample comprises no more than about 1.0 percent of total organic impurities.

Embodiment 78. The sample of embodiment 70, wherein the sample comprises no more than about 0.5 percent of total organic impurities.

Embodiment 79. A method of inhibiting activity of a JAK2 kinase, or a mutant thereof, in a biological sample comprising the step of contacting said biological sample with a crystalline form of any one of embodiments 1-15, or a composition thereof.

Embodiment 80. A method of inhibiting activity of a JAK2 kinase, or a mutant thereof, in a patient comprising the step of administering to said patient a crystalline form of any one of embodiments 1-15, or a composition thereof.

Embodiment 81. A method for treating a JAK2-mediated disease or disorder, in a patient in need thereof, comprising the step of administering to the patient a crystalline form of any one of embodiments 1-15, or pharmaceutically acceptable composition thereof.

Embodiment 82. A method of inhibiting activity of a JAK2 kinase, or a mutant thereof, in a biological sample comprising the step of contacting said biological sample with a complex of any one of embodiments 25-69, or a composition thereof.

Embodiment 83. A method of inhibiting activity of a JAK2 kinase, or a mutant thereof, in a patient comprising the step of administering to said patient a complex of any one of embodiments 25-69, or a composition thereof.

Embodiment 84. A method for treating a JAK2-mediated disease or disorder, in a patient in need thereof, comprising the step of administering to the patient a complex of any one of embodiments 25-69, or a pharmaceutically acceptable composition thereof.

Embodiment 85. The complex of embodiment 27, wherein the complex comprises one equivalent of hydrobromic acid.

Embodiment 86. The complex of embodiment 27, wherein the complex comprises two equivalents of hydrobromic acid.

Embodiment 87. The complex of embodiment 28, wherein the complex comprises 0.5 equivalents of sulfuric acid.

Embodiment 88. The complex of embodiment 29, wherein the complex comprises one equivalent of toluenesulfonic acid.

Embodiment 89. The complex of embodiment 30, wherein the complex comprises 1.2 equivalents of methanesulfonic acid.

Embodiment 90. The complex of embodiment 31, wherein the complex comprises 1.5 equivalents of 2-naphthalenesulfonic acid.

Embodiment 91. The complex of embodiment 32, wherein the complex comprises one equivalent of phosphoric acid.

Embodiment 92. The complex of embodiment 33, wherein the complex comprises one equivalent of DL-tartaric acid.

Embodiment 93. The complex of embodiment 34, wherein the complex comprises one equivalent of succinic acid.

Embodiment 94. The complex of embodiment 35, wherein the complex comprises one equivalent of gentisic acid.

Embodiment 95. The complex of embodiment 36, wherein the complex comprises one equivalent of hippuric acid.

Embodiment 96. The complex of embodiment 37, wherein the complex comprises 0.9 equivalents of adipic acid.

Embodiment 97. The complex of embodiment 38, wherein the complex comprises one equivalent of galactaric acid.

Embodiment 98. The complex of embodiment 63, wherein the complex comprises one equivalent of saccharin.

Embodiment 99. The complex of embodiment 64, wherein the complex comprises one equivalent of nicotinic acid.

Embodiment 100. The complex of embodiment 65, wherein the complex comprises one equivalent of ascorbic acid.

Embodiment 101. The complex of embodiment 66, wherein the complex comprises one equivalent of gallic acid.

Embodiment 102. The complex of embodiment 68, wherein the complex comprises one equivalent of orotic acid.

Embodiment 103. The complex of any one of embodiments 27, 33, 41, 43, 44, 45, 64, 65, 66, 67, 86, and 92 wherein the complex is a hydrate.

Embodiment 104. The complex of embodiment 28, wherein the complex is a heterosolvate.

Embodiment 105. The complex of embodiment 104, wherein the heterosolvate is water:tetrahydrofuran.

Embodiment 106. The complex of any one of embodiments 28, 32, and 91, wherein the complex is a solvate.

Embodiment 107. The complex of embodiment 106, wherein the solvate is an acetone solvate.

Embodiment 108. The complex of embodiment 106, wherein the solvate is a methanol solvate.

EXEMPLIFICATION

Instrumentation

FT-Raman Spectroscopy. Raman spectra were collected with a Nicolet NXR9650 or NXR 960 spectrometer (Thermo Electron) equipped with 1064 nm Nd:$YVO_4$ excitation laser, InGaAs and liquid-$N_2$ cooled Ge detectors, and a MicroStage. All spectra were acquired at 4 cm-1 resolution, 64 scans, using Happ-Genzel apodization function and 2-level zero-filling.

Powder X-Ray Diffraction (PXRD or XRPD). PXRD (or XRPD) diffractograms were acquired on PANalytical X'Pert Pro diffractometer using Ni-filtered Cu Kα (45 kV/40 mA) radiation and a step size of 0.02° 2θ and X'celerator' RTMS (Real Time Multi-Strip) detector. Configuration on the incidental beam side: fixed divergence slit (0.25°), 0.04 rad Soller slits, anti-scatter slit (0.25°), and 10 mm beam mask. Configuration on the diffracted beam side: fixed divergence slit (0.25°) and 0.04 rad Soller slit. Samples were mounted flat on zero-background Si wafers.

Differential Scanning Calorimetry (DSC). DSC was conducted with a TA Instruments Q100 differential scanning calorimeter equipped with an autosampler and a refrigerated cooling system under 40 mL/min $N_2$ purge. DSC thermograms were obtained at 15° C./min in crimped Al pans.

Thermogravimetric Analysis (TGA). TGA thermograms were obtained with a TA Instruments Q500 thermogravimetric analyzer under 40 mL/min $N_2$ purge at 15° C./min in Pt or Al pans.

Thermogravimetric Analysis with IR Off-Gas Detection (TGA-IR). TGA-TR was conducted with a TA Instruments Q5000 thermogravimetric analyzer interfaced to a Nicolet 6700 FT-IR spectrometer (Thermo Electron) equipped with an external TGA-IR module with a gas flow cell and DTGS detector. TGA was conducted with 60 mL/min $N_2$ flow and heating rate of 15° C./min in Pt or Al pans. IR spectra were collected at 4 $cm^1$ resolution and 32 scans at each time point.

High-performance Liquid Chromatography (HPLC). HPLC analyses were conducted with an HP1100 system equipped with a G1131 Quad pump, G1367A autosampler, and G1315B diode array detector. Column: Luna C18(2) (50×2.0 mm, 3 μm). Mobile phase: 100% water (0.05% TFA) to 95% ACN (0.05% TFA) over 8 min and 2 min re-equilibration. Flow rate: 1 mL/min. Detection: 254 nm.

Proton Nuclear Magnetic Resonance ($^1H$ NMR). Solution for $^1H$ NMR was prepared by dissolving the solids in DMSO-d6. The spectra were collected using Agilent DD2 500 MHz spectrometer with TMS reference.

Ion Chromatography (IC). Ion chromatography was performed on a Dionex ICS-3000. Column: Dionex IonPac AS12A 4×200 mm; Detection: Suppressed conductivity, ASRS 300 with suppressor current at 22 mA; Eluent (2.7 mM $Na_2CO_3$/0.3 mM $NaHCO_3$) at 1.5 mL/min.

Example 1. Compound 1 Free Base (Form C)

Compound 1 dihydrochloride (44.5 g) was dissolved in water (498 mL). Aqueous sodium hydroxide (2.0 eq; 5N; 28.9 mL) was slowly added, followed by acetonitrile (80 mL) and crystalline seeds of Compound 1 Form C (400 mg). The suspension was stirred at RT for 2 hours. The crystalline solids were isolated via vacuum filtration, washed with water (2×100 mL) and MTBE (2×50 mL), and air-dried under vacuum for 1 hour and dried in a vacuum oven at 40° C. with nitrogen bleed for 24 hours. The yield of crystalline free base was 97.5% (37 g).

Compound 1 Form C is a white crystalline powder and was characterized by XRPD (FIG. 5), TGA (FIG. 6A), DSC (FIG. 6B) and DVS (FIG. 7). Thermal data shows that the free base is a monohydrate form with a weight loss of 3.2% water. HPLC analysis indicated a purity of 99.5%. IC data did not detect the presence of chloride, confirming conversion to the free base.

Solubility of Compound 1 free base (Form C) was estimated by visual assessment of dissolution in various solvents at RT and 40° C. Aliquots of solvents were added to 10 mg of free base at RT until complete dissolution or until a maximum volume of 1.8 mL was added. Suspensions not dissolved at RT were heated to 40° C. and checked for dissolution. Following visual solubility assessment, additional Form C was added to the samples which dissolved to yield thin suspensions. The suspensions were stirred at RT for 18 h, and the solids were isolated by vacuum-filtration. The solids were analyzed by PXRD and compared to the parent groups identified during the concurrent salt screening.

Example 2. Primary Salt Screen of Fedratinib

Fedratinib has two basic sites ($pK_a$=9.3, 6.4) for salt formation. Fifty-three counterions and stoichiometric combinations were selected. Table 1 provides a summary of the additives, $pK_a$ values, method of dosing and equivalents dosed for each additive.

TABLE 1

Additives Utilized in the Screening Studies

| No. | Additive | Dosing Method | pKa | Equivalents Dosed |
|---|---|---|---|---|
| 1 | HBr | 3M solution in water | <−6 | 1, 2 |
| 2 | Naphthalene-1,5-disulfonic acid | 1.5M solution in water | −3.4, −2.6 | 0.5, 1 |
| 3 | Sulfuric acid | 2.5M solution in water | −3, 1.9 | 0.5, 1 |
| 4 | Camphor-10-sulfonic acid | 3M solution in water | −2.2 | 1, 2 |
| 5 | Ethane-1,2-disulfonic acid | 3M solution in water | −2.1,−1.5 | 0.5, 1 |
| 6 | Ethanesulfonic acid | 3M solution in water | −2.1 | 1, 2 |
| 7 | p-Toluenesulfonic acid | 3M solution in water | −1.3 | 1, 2 |
| 8 | Methanesulfonic acid | 3M solution in water | −1.2 | 1, 2 |
| 9 | Naphthalene-2-sulfonic acid | 3M solution in THF | 0.2 | 1, 2 |
| 10 | Benzenesulfonic acid | 3M solution in water | 0.7 | 1, 2 |
| 11 | Oxalic acid | 0.5M solution in water | 1.3 | 1 |
| 12 | Maleic acid | 3M solution in water | 1.9, 6.2 | 1 |

TABLE 1-continued

Additives Utilized in the Screening Studies

| No. | Additive | Dosing Method | pKa | Equivalents Dosed |
|---|---|---|---|---|
| 13 | Phosphoric acid | 3M solution in water | 2, 7.1, 12.3 | 1 |
| 14 | Glutamic acid | Dosed as solid | 2.2, 4.3, 9.7 | 1 |
| 15 | Pamoic acid | Dosed as solid | 2.5, 3.1 | 1 |
| 16 | 1-Hydroxy-2-naphthoic acid | Dosed as solid | 2.7 | 1 |
| 17 | Malonic acid | 3M solution in water | 2.8, 5.7 | 1 |
| 18 | Gentisic acid | Dosed as solid | 2.9 | 1 |
| 19 | L-Tartaric acid | 3M solution in water | 3, 4.4 | 1 |
| 20 | DL-Tartaric acid | 1.5M solution in water | 3, 4.4 | 1 |
| 21 | Fumaric acid | 0.2M solution in EtOH | 3, 4.4 | 1 |
| 22 | Citric acid | 3M solution in water | 3.1, 4.8, 6.4 | 1 |
| 23 | Galactaric (Mucic) acid | Dosed as solid | 3.1, 3.6 | 1 |
| 24 | Glycolic acid | Dosed as solid | 3.3 | 1 |
| 25 | L-Mandelic acid | 1M solution in water | 3.4 | 1 |
| 26 | DL-Mandelic acid | Dosed as solid | 3.4 | 1 |
| 27 | L-Malic acid | Dosed as solid | 3.5, 5.1 | 1 |
| 28 | DL-Malic acid | Dosed as solid | 3.5, 5.1 | 1 |
| 29 | Hippuric acid | Dosed as solid | 3.6 | 1 |
| 30 | D-Gluconic acid | 3.14M solution in water | 3.8 | 1 |
| 31 | L-Aspartic acid | Dosed as solid | 3.9 | 1 |
| 32 | L-Lactic acid | 3M solution in water | 3.9 | 1 |
| 33 | DL-Lactic acid | 12.1M solution in water | 3.9 | 1 |
| 33 | Benzoic acid | Dosed as solid | 4.2 | 1 |
| 34 | Succinic acid | 1M solution in MeOH | 4.2, 5.6 | 1 |
| 35 | Glutaric acid | Dosed as solid | 4.3, 5.3 | 1 |
| 36 | Adipic acid | Dosed as solid | 4.4, 5.4 | 1 |
| 37 | Acetic acid | 3M solution in water | 4.8 | 1 |
| 38 | Camphoric acid | Dosed as solid | 4.7, 5.8 | 1 |
| 39 | Propionic acid | 3M solution in water | 4.9 | 1 |
| 40 | Choline Hydroxide | 4.6M solution in water | >11 | 1 |
| 41 | Potassium Hydroxide | 1M solution in water | ~14 | 1 |
| 42 | Sodium Hydroxide | 5M solution in water | ~14 | 1 |

Multiple modes of crystallization were utilized for the salt screening studies and are as follows:

1. Temperature-cycled ripening of solutions/suspensions between 40° C. and 5° C. for two days.
2. Fast evaporation of solvents under reduced pressure.
3. Cooling of solutions at 5° C. for up to two days.
4. Slow evaporation of solvents at RT for up to seven days.

All samples were examined for crystallinity by polarized light microscopy (PLM) at the end of each crystallization mode. If an experiment yielded a birefringent hit, the solids were isolated by vacuum filtration, air-dried for up to two hours with vacuum pull at room temperature. The solids were analyzed by FT-Raman spectroscopy and/or PXRD.

FT-Raman spectra/PXRD pattern of samples prepared using the same additive were compared to determine whether they were the same crystal form. Representative samples from each unique group were subjected to further characterization using PXRD, DSC, TGA and TGA-IR analyses (as appropriate).

The results from the salt screening study are summarized in Table 2. Salt screening experiments led to crystalline salt hits from 36 of the 42 unique additives. All remaining experiments yielded non-crystalline products (gums/amorphous glassy material) and were not isolated.

TABLE 2

Results from Salt Screening of Fedratinib

| | | Solvents | | | | | | | |
|---|---|---|---|---|---|---|---|---|---|
| No. | Additive (Eq.) | MTBE | MIBK | EtOAc | THF | Acetone | IPA | $CH_3CN$ | MeOH |
| 1 | HBr (1 eq) | A | A | A | A | A | A | A | A |
| 2 | HBr (2 eq) | B | 1 | B | 1 | B | B | B | B |
| 3 | Naphthalenedisulfonic acid (0.5 eq) | A | A | A | G/O | A | A, 2 | B | C, 2 |
| 4 | Naphthalenedisulfonic acid (1 eq) | A | 1 | 1 | G/O | A, 2 | B, 2 | G/O | C |
| 5 | Sulfuric acid (0.5 eq) | FB | FB | FB | B | A | FB | FB | FB |
| 6 | Sulfuric acid (1 eq) | A | A | A | B | B | B | C | B |
| 7 | S-Camphor-10-sulfonic acid (1 eq) | G/O | G/O | G/O | G/O | G/O | G/O | G/O | G/O |
| 8 | S-Camphor-10-sulfonic acid (2 eq) | G/O | A | B | G/O | A | G/O | G/O | G/O |
| 9 | 1, 2-Ethanedisulfonic acid (0.5 eq) | FB | FB | FB | C, 2 | B | FB | FB | A |
| 10 | 1, 2-Ethanedisulfonic acid (1 eq) | G/O | C | G/O | G/O | B | D | A | A |
| 11 | Ethanesulfonic acid (1 eq) | G/O | FB | FB | A | G/O | FB | G/O | G/O |
| 12 | Ethanesulfonic acid (2 eq) | B | FB | B | B | B | A | B | A |
| 13 | Toluenesulfonic acid (1 eq) | A, 2 | A | A | A | A | A | A | A |
| 14 | Toluenesulfonic acid (2 eq) | G/O | G/O | G/O | G/O | G/O | B | G/O | G/O |
| 15 | Methanesulfonic acid (1 eq) | 1 | 1 | 1 | 1 | A | B | G/O | G/O |
| 16 | Methanesulfonic acid (2 eq) | G/O | C | G/O | G/O | C | C | G/O | G/O |

TABLE 2-continued

| Results from Salt Screening of Fedratinib | | | | | | | | | |
|---|---|---|---|---|---|---|---|---|---|
| | | Solvents | | | | | | | |
| No. | Additive (Eq.) | MTBE | MIBK | EtOAc | THF | Acetone | IPA | $CH_3CN$ | MeOH |
| 17 | 2-Naphthalenesulfonic acid (1 eq) | A, 2 | A | A | A | A | A | A | A |
| 18 | 2-Naphthalenesulfonic acid (2 eq) | A | A | A | A | A | A | A | A |
| 19 | Benzenesulfonic acid (1 eq) | G/O | G/O | A | B | G/O | C | D | G/O |
| 20 | Benzenesulfonic acid (2 eq) | G/O | G/O | G/O | G/O | G/O | G/O | G/O | G/O |
| 21 | Oxalic acid (1 eq) | B | B | A | A | A | A | A | A |
| 22 | Maleic acid (1 eq) | A | A | A | A, 2 | G/O | A | G/O | G/O |
| 23 | Phosphoric acid (1 eq) | A | A | A | C | B | B | B | D |
| 24 | Glutamic acid (1 eq) | FB | FB | FB | CI | CI | CI | CI | CI |
| 25 | Pamoic acid (1 eq) | A, 2 | A | A | A | A | A | A | A |
| 26 | 1-Hydroxy-2-napthoic acid (1 eq) | CI | FB | CI | G/O | G/O | A | G/O | G/O |
| 27 | Malonic acid (1 eq) | A | A | A | A | G/O | B | C | G/O |
| 28 | L-Tartaric acid (1 eq) | A | B | C | C | B | C | D | G/O |
| 29 | DL-Tartaric acid (1 eq) | B | A | A | A | A | A | A | A |
| 30 | Fumaric acid (1 eq) | A | B | B | E | A | A, B | C | D |
| 31 | Citric acid (1 eq) | A | A. FB | A, FB | A | A | A, FB | G/O | G/O |
| 32 | L-Mandelic acid (1 eq) | FB | FB | FB | G/O | G/O | FB | FB | FB |
| 33 | L-Lactic acid (1 eq) | A | A | A | G/O | G/O | A | A | G/O |
| 34 | Succinic acid (1 eq) | A | A | A | 1 | 1 | A | 1 | G/O |
| 35 | Acetic acid (1 eq) | B | A | A | B | A | FB | A | G/O |
| 36 | Propionic acid (1 eq) | A | FB | FB | FB | A | FB | FB | A |
| 37 | NaOH (1 eq) | FB | FB | FB | FB | G/O | FB | G/O | FB |
| 38 | KOH (1 eq) | FB | FB | FB | FB | FB | FB | FB | FB |
| 39 | DL-Lactic acid (1 eq) | G/O | A | A | G/O | G/O | G/O | G/O | G/O |
| 40 | D-Gluconic acid (1 eq) | G/O | G/O | 1 | G/O | A, 1 | A, 1 | G/O | G/O |
| 41 | Choline (1 eq) | G/O | G/O | G/O | G/O | G/O | G/O | G/O | FB |
| 42 | DL-Malic acid (1 eq) | FB | FB | A | A | A | B | A | G/O |
| 43 | Glycolic acid (1 eq) | A | A | A | G/O | G/O | A | A | G/O |
| 44 | Gentisic acid (1 eq) | G/O | A | A | G/O | A | A | A | A |
| 45 | Glutaric acid (1 eq) | A | B | A | G/O | G/O | A | A | G/O |
| 46 | L-Malic acid (1 eq) | FE | A, B | A | G/O | A | A | A | G/O |
| 47 | Hippuric acid (1 eq) | A | A | A | G/O | A | A | A | G/O |
| 48 | L-Aspartic acid (1 eq) | G/O | FB, CI | FB, CI | CI | CI | FB | FB | FB |
| 49 | Benzoic acid (1 eq) | FB | G/O | G/O | G/O | G/O | FB, CI | FB | G/O |
| 50 | Adipic acid (1 eq) | A | A | A | G/O | A, B | A | A, FB | G/O |
| 51 | Camphoric acid (1 eq) | A | B | C | G/O | G/O | FB | D | G/O |
| 52 | Galactaric acid (1 eq) | FB | A | A | CI | A | A | A | G/O |
| 53 | DL-Mandelic acid (1 eq) | FB | A | B | G/O | G/O | C | B | G/O |

Legend:

Letters represent Raman/PXRD groupings for each counterion

| New Complex Form(s) Identified (A, B, etc.) | |
|---|---|
| FB | Free base |
| CI | Counterion |
| G/O | Gum/Oil |
| 1 | Discolored/Hygroscopic |
| 2 | Poorly Crystalline |

Example 3. Secondary Salt Screen of Fedratinib

Of the 36 salt hits, the following 13 salts were scaled up to 200 mg scale: HBr (Forms A and B), sulfate (Form A), tosylate (Form A), mesylate (Form A), 2-naphthalenesulfonate (Forms A/B mixture), phosphate (Form D), DL-tartrate (Form A), succinate (Form A), gentisate (Form A), hippurate (Form A), adipate (Form A) and galactarate (Form A).

Example 3.1. Hydrobromide Salt

Two crystalline forms of hydrobromide salt were identified from salt screening experiments and designated Form A and Form B. Form A was identified using one equivalent of HBr, while Form B was identified using two equivalents of HBr. Both Forms A and B had promising thermal properties and were selected for scale up.

Preparation of Form A. THE (6.3 mL) was combined with crystalline free base Form C (315 mg) and aqueous HBr acid (1.0 equivalent; 3M in water; 200 μL). Crystalline seeds of Form A hydrobromide salt (~1 mg) were added. The suspension was stirred at RT (~25° C.) for 16 hours. The crystalline solids were isolated via vacuum filtration, air-dried under vacuum for 1 hour and dried in a vacuum oven at 40° C. for 1 hour. The yield of crystalline Form A was 89.9% (327 mg).

Form A was crystalline by FT-Raman (FIG. 10) and PXRD (FIG. 11), and the material was birefringent with tiny irregular particles by PLM. DSC analysis showed two large endotherms at 215 and 231° C. (FIG. 12, trace 12B), while TGA analysis showed a weight loss of 0.4% up to 100° C. (FIG. 12, trace 12A). Form A was determined to be a 1.1:1.0 (counterion:parent) salt by ion-chromatography. The slight excess of HBr could be due to a trace of Form B (di-HBr salt).

Preparation of Form B. 2-Propanol (6.0 mL) was combined with crystalline free base Form C (300 mg) and aqueous HBr acid (2.0 equivalent; 3M in water; 381 μL).

Crystalline seeds of HBr salt (~1 mg) were added. The suspension was stirred at RT (~25° C.) for 16 hours. The crystalline solids were isolated via vacuum filtration, air-dried under vacuum for 1 hour and dried in a vacuum oven at 40° C. for 1 hour. The yield of crystalline Form B was 83.8% (329 mg).

Figure 17:
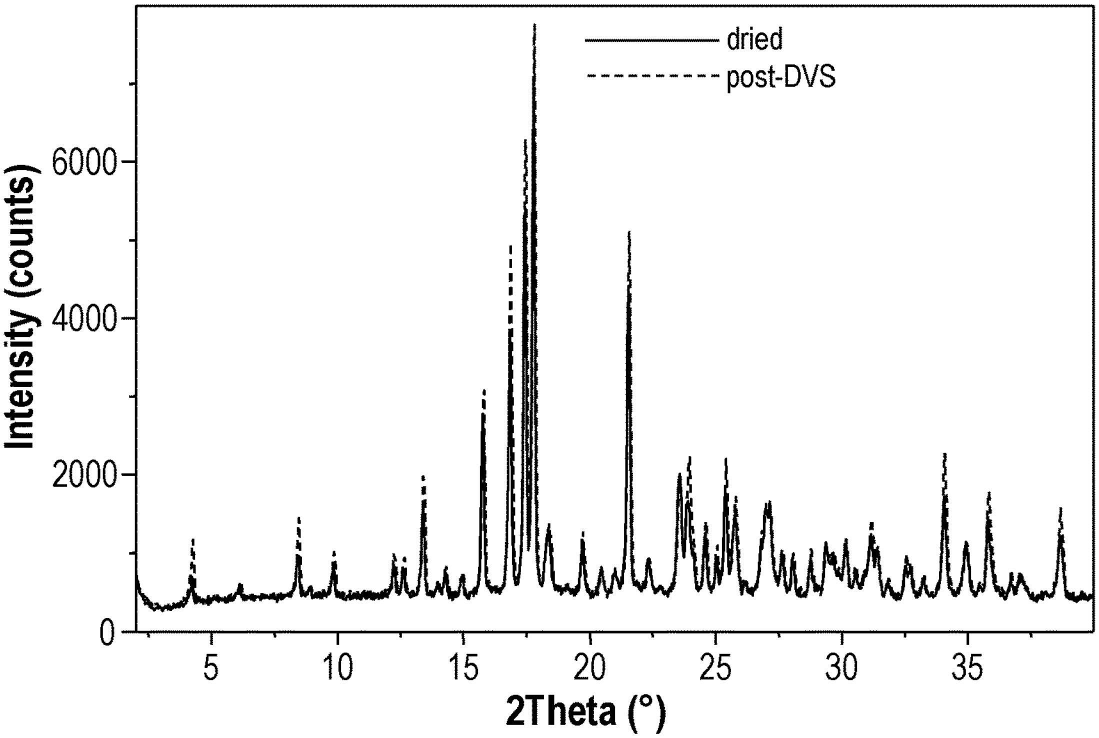
FIG. 17 depicts the XRPD pattern of Form B hydrobromide salt of Compound 1 post-DVS.

Form B was crystalline by FT-Raman (FIG. 13) and PXRD (FIG. 14), and the material was birefringent with tiny needles by PLM. DSC analysis showed a small broad endotherm at 72° C. and large sharp endotherm at 233° C. (FIG. 15, trace 15B), while TGA-IR analysis showed a weight loss of 2.4% water with trace IPA up to 100° C. (FIG. 15, trace 15A). DVS analysis showed 0.9% moisture uptake between 5-95% RH (FIG. 16). PXRD pattern of the post DVS sample did not show any change in crystal form (FIG. 17). Form B was determined to be a 2.0:1.0 (counterion: parent) salt by ion-chromatography.

Example 3.2. Sulfate Salt

At least three crystalline forms of the sulfate salt were identified from salt screening experiments and designated Forms A, B and C. Form A was characterized by FT-Raman (FIG. 18), PXRD (FIG. 19), TGA-IR (FIG. 20, trace 20A), and DSC (FIG. 20, trace 20B). Form B was characterized by FT-Raman (FIG. 21), PXRD (FIG. 22), TGA-IR (FIG. 23, trace 23A), and DSC (FIG. 23, trace 23B). Form C was characterized by FT-Raman (FIG. 24), PXRD (FIG. 25), and DSC (FIG. 26).

Form A had the most promising thermal properties and was selected for scale-up. A new form—Form D—was identified from the scale up experiment.

Preparation of Form D. Acetone (7.4 mL) was combined with crystalline free base Form C (372 mg) and aqueous sulfuric acid (0.5 equivalent; 2.5M; 142 μL). Crystalline seeds of sulfate salt (~1 mg) were added. The suspension was stirred at RT (~25° C.) for 16 hours. The crystalline solids were isolated via vacuum filtration, air-dried under vacuum for 1 hour and dried in a vacuum oven at 40° C. for 4 hours. The yield of crystalline sulfate salt was 77.4% (315 mg).

Form D was crystalline by FT-Raman (FIG. 27) and PXRD (FIG. 28) but did not match Form A. DSC analysis showed multiple complex endotherms (FIG. 29, trace 29B), while TGA-IR analysis showed a weight loss of 1.0% water followed by 6.7% acetone up to 160° C. (FIG. 29, trace 29A). Thermal data suggests that Form D is an acetone solvate. Form D was determined to be a 0.5:1.0 (counterion: parent) sulfate salt by ion-chromatography.

Example 3.3. Tosylate Salt

Two crystalline forms were identified from salt screening experiments and designated Form A and Form B. Form A was identified using one equivalent of p-toluenesulfonic acid, while Form B was identified using two equivalents of p-toluenesulfonic acid. Form A was characterized by PXRD (FIG. 30), TGA-IR (FIG. 31, trace 31A), and DSC (FIG. 31, trace 31B). Form B was characterized by PXRD (FIG. 32), TGA-IR (FIG. 33, trace 33A), and DSC (FIG. 33, trace 33B).

Form A had the most promising thermal properties and was selected for scale up. A new form—Form C—was identified from the scale up experiment.

Preparation of Form C. Acetone (5.3 mL) was combined with crystalline free base Form C (265 mg) and aqueous tosic acid (1.0 equivalent; 3M; 168 μL). Crystalline seeds of tosylate salt (Form A, ~1 mg) were added. The suspension was stirred at RT (~25° C.) for 16 hours. The crystalline solids were isolated via vacuum filtration, air-dried under vacuum for 1 hour and dried in a vacuum oven at 40° C. for 4 hours. The yield of crystalline tosylate salt was 86.7% (305 mg).

The tosylate salt was crystalline by FT-Raman (FIG. 34) and PXRD (FIG. 35) but did not match Form A. DSC analysis (FIG. 36, trace 36B) showed a sharp, higher temperature endotherm at 241° C., while TGA analysis (FIG. 36, trace 36A) showed a 0.1% weight loss up to 100° C. Thermal data suggests that Form C is a nonsolvated and more stable form than Form A. DVS analysis (FIG. 37) showed 1.2% moisture uptake between 5-95% RH. PXRD pattern of the post DVS sample did not show any change in crystal form (FIG. 38). Form C was determined to be a 1.0:1.0 (counterion:parent) tosylate salt by $^1$H NMR (FIG. 39).

Example 3.4. Mesylate Salt

Three crystalline forms were identified from salt screening experiments and designated Forms A, B and C. Forms A and B were identified using one equivalent of methanesulfonic acid, while Form C was identified using two equivalents of methanesulfonic acid. Form B was characterized by PXRD (FIG. 44) and DSC (FIG. 46, trace 46B). Form C was characterized by PXRD (FIG. 45) and DSC (FIG. 46, trace 46C). Form A had the most promising thermal properties and was selected for scale up.

Preparation of Form A. Acetone (6.0 mL) was combined with crystalline free base Form C (298 mg) and aqueous mesic acid (1.0 equivalent; 3M; 189 μL). Crystalline seeds of the mesylate salt (Form A, ~1 mg) were added to the solution, and the solution was concentrated to dryness in vacuo. Acetone (3.0 mL) was added, and the suspension was reseeded with Form A. The suspension was stirred at RT (~25° C.) for 16 hours. The crystalline solids were isolated via vacuum filtration, air-dried under vacuum for 1 hour and dried in a vacuum oven at 40° C. for 4 hours. The yield of crystalline mesylate salt was 91.3% (322 mg).

The mesylate salt was crystalline by FT-Raman (FIG. 40) and PXRD (FIG. 41) and was mostly consistent with Form A. DSC analysis (FIG. 42, trace 42B) showed a sharp endotherm at 207° C., while TGA analysis (FIG. 42, trace 42A) showed a 0.3% weight loss up to 100° C. Form A was determined to be a 1.2:1.0 (counterion:parent) mesylate salt by $^1$H NMR (FIG. 43). The $^1$H NMR data suggests that the trace extra peaks in PXRD for Form A could be due to a di-mesylate salt impurity and that controlling stoichiometry may be difficult.

Example 3.5. 2-Naphthalenesulfonate Salt

One crystalline form (Form A) of 2-naphthalenesulfonate salt was identified from salt screening experiments, using either one or two equivalents of 2-naphthalenesulfonic acid. Form A had promising thermal properties and was selected for scale up.

Preparation of Form A. Acetone (5.0 mL) was combined with crystalline free base Form C (252 mg) and 2-naphthalenesulfonic acid (1.0 equivalent; 3M in THF; 160 μL). Crystalline seeds of 2-naphthalenesulfonate salt (Form A, ~1 mg) were added. The suspension was stirred at RT (~25° C.) for 16 hours. The crystalline solids were isolated via vacuum filtration, air-dried under vacuum for 1 hour and dried in a vacuum oven at 40° C. for 4 hours. The yield of crystalline 2-naphthalenesulfonate salt was 86.8% (349 mg).

Figure 49:
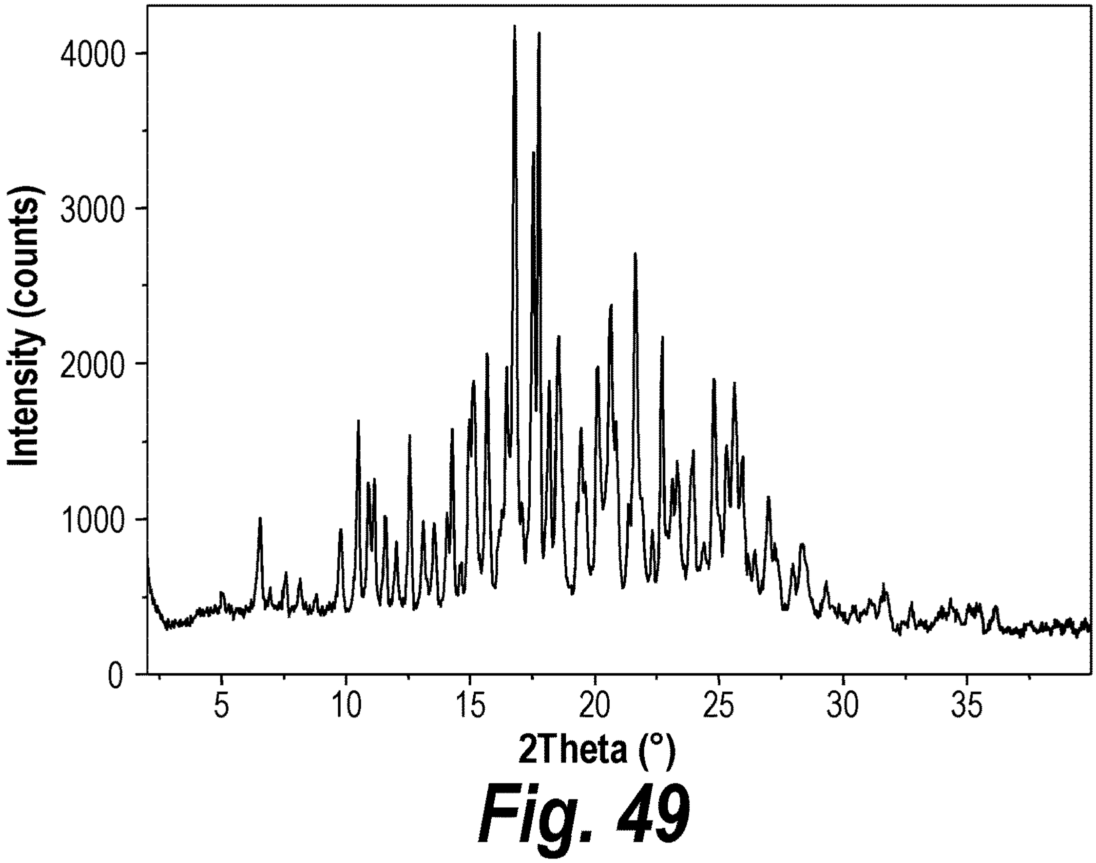
FIG. 49 depicts the XRPD pattern of a mixture of Form A and Form B 2-naphthalene sulfonate salt of Compound 1.
Figure 51:
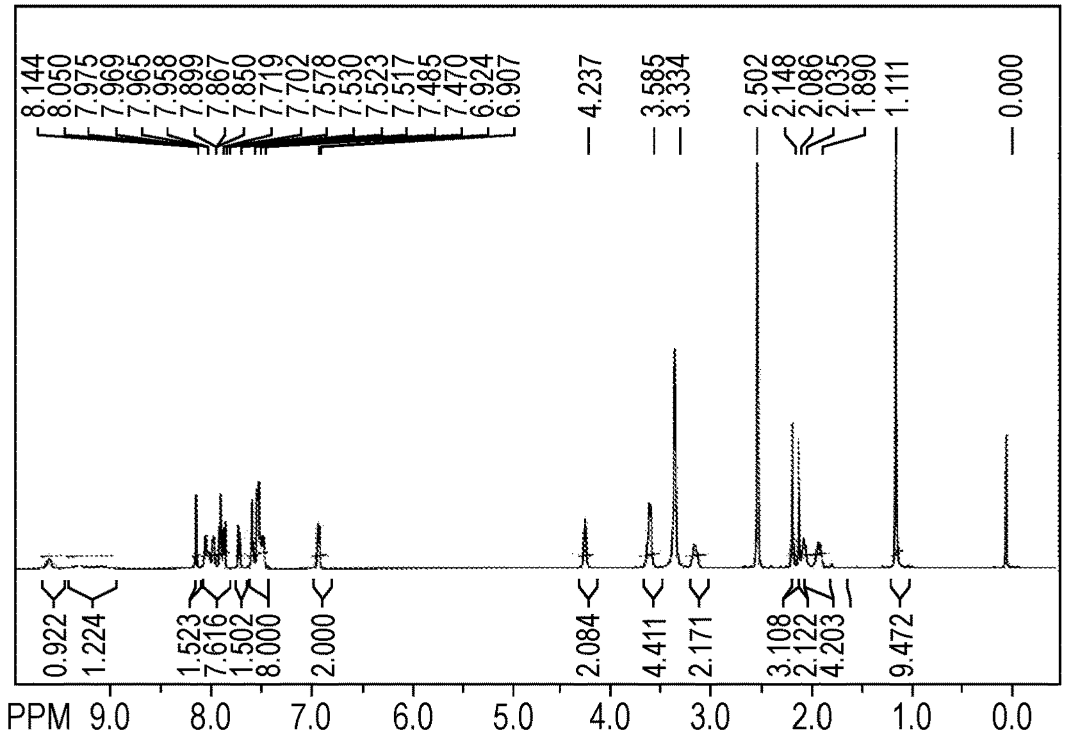
FIG. 51 depicts the $^1$H NMR of a mixture of Form A and Form B 2-naphthalenesulfonate salt of Compound 1.

The 2-naphthalenesulfonate salt was crystalline by FT-Raman (FIG. 47) and PXRD (FIG. 48). Form A was found to be a mixture with Group B (an acetone solvate) (FIG. 49). Thermal data was very complex and showed a step-wise loss of 0.9% water up to 75° C. followed by a loss of 2.6% acetone from 75-175° C. (FIG. 50). Form A was determined to be a 1.5:1.0 (counterion:parent) 2-naphthalenesulfonate salt and has 0.5 equivalents of acetone by $^{1}$H NMR (FIG. 51). The thermal and $^{1}$H NMR data suggests that an acetone solvate impurity (Form B) is present and that controlling stoichiometry may be difficult.

Example 3.6. Phosphate Salt

Four crystalline forms of the phosphate salt were identified from salt screening experiments and designated Forms A, B, C and D. Form A was characterized by PXRD (FIG. 52) and DSC (FIG. 56, trace 56A). Form B was characterized by PXRD (FIG. 53) and DSC (FIG. 56, trace 56B). Form C was characterized by PXRD (FIG. 54) and DSC (FIG. 56, trace 56C). Form D was characterized by PXRD (FIG. 55) and DSC (FIG. 56, trace 56D).

Form D had the most promising thermal properties and was selected for scale up. A new form—Form E—was identified from the scale up experiment.

Preparation of Form E. Methanol (7.0 mL) was combined with crystalline free base Form C (350 mg) and aqueous phosphoric acid (1.0 equivalent; 3M; 222 μL). Crystalline seeds of the phosphate salt (Form D, ~1 mg) were added to the solution, and the solution was concentrated to dryness in vacuo. Methanol (3.0 mL) was added, and the suspension was reseeded. The suspension was stirred at RT (~25° C.) for 16 hours. The crystalline solids were isolated via vacuum filtration, air-dried under vacuum for 1 hour and dried in a vacuum oven at 40° C. for 4 hours. The yield of crystalline phosphate salt was 81.4% (338 mg).

The phosphate salt was crystalline by FT-Raman (FIG. 57) and PXRD (FIG. 58) but did not match the targeted form, Form D. DSC analysis showed multiple complex endotherms (FIG. 59, trace 59B), while TGA-IR analysis showed a weight loss of 3.8% water and methanol up to 125° C. (FIG. 59, trace 59A). Thermal data suggests that Form E is a methanol solvate. Form E was determined to be a 1.0:1.0 (counterion:parent) phosphate salt by ion-chromatography.

Example 3.7. DL-Tartrate Salt

Crystalline DL-tartrate salt hits were isolated from all eight salt formation experiments. These eight hits were sorted into two groups based on FT-Raman spectral match (designated as Form A and Form B). Form A was isolated from seven of the eight experiments and scaled-up on 200 mg scale. Form B was characterized by PXRD (FIG. 65), TGA (FIG. 66, trace 66A) and DSC (FIG. 66, trace 66B).

Preparation of Form A. THE (4.0 mL) was combined with crystalline free base Form C (198.88 mg) and DL-tartaric acid (1.0 equivalent, dosed as solid). Crystalline seeds of DL-tartrate salt (~1 mg) was added. The suspension was heated to 50° C., stirred at 50° C. for 15 minutes, cooled slowly (0.1° C./min) to 25° C. and stirred at 25° C. for 16 hours. The crystalline solids were isolated via vacuum filtration, air-dried under vacuum for 2 hours and dried in a vacuum oven at 40° C. for 4 hours. The yield of crystalline DL-tartrate salt was 66.8% (171 mg).

Form A was crystalline by FT-Raman (FIG. 60) and PXRD (FIG. 61). DSC data showed a small, broad endotherm with onset at 25.4° C. followed by a second sharp endotherm at 194.4° C. (FIG. 62, trace 62B). TGA data showed ~3% wt loss between 30-85° C. (FIG. 62, trace 62A). TGA-TR analysis of evolving gases showed loss of water suggesting that Form A of DL-tartrate salt is a hydrate. DVS analysis (FIG. 63) showed ~2.2% moisture uptake between 5-95% RH. PXRD pattern of the post DVS sample did not show any change in crystal form. The stoichiometry of DL-tartrate salt showed 1.0:1.0 (counterion:parent) by $^{1}$H NMR analysis (FIG. 64).

Example 3.8. Succinate Salt

Crystalline succinate salt hits were isolated from four of the eight salt formation experiments. FT-Raman spectra of all four hits were consistent with each other indicative of a single crystal form (designated as Form A). Form A was characterized by PXRD (FIG. 67), TGA (FIG. 68, trace 68A) and DSC (FIG. 68, trace 68B). An attempt to prepare Form A of succinate salt on a 200 mg scale was unsuccessful and yielded a new crystal form (designated as Form B).

Preparation of Form B. IPA (7.5 mL) was combined with crystalline free base Form C (213.26 mg) and succinic acid (1.0 equivalent, dosed as solid). Crystalline seeds of succinate salt (~1 mg) was added. The suspension was heated to 40° C., stirred at 40° C. for five hours, cooled slowly (0.1° C./min) to 25° C. and stirred at 25° C. for 16 hours. To the suspension MeOH (0.75 mL) was added. The suspension was heated to 50° C., stirred at 50° C. for five hours, cooled slowly (0.1° C./min) to 25° C. and stirred at 25° C. for 16 hours. The crystalline solids were isolated via vacuum filtration, air-dried under vacuum for 2 hours and dried in a vacuum oven at 40° C. for 4 hours. The yield of crystalline succinate salt was 76.2% (199.3 mg).

Form B was crystalline by FT-Raman (FIG. 69) and PXRD (FIG. 70). DSC data (FIG. 71, trace 71B) showed a single endotherm at 153.2° C. TGA data (FIG. 71, trace 71A) showed ~0.8% wt loss between 30-165° C. suggesting that Form B is likely a non-solvated form. The stoichiometry of succinate salt showed 1.0:1.0 (counterion:parent) by $^{1}$H NMR analysis (FIG. 72).

Example 3.9. Gentisate Salt

Crystalline gentisate salt hits were isolated from six of the eight salt formation experiments. The remaining experiments yielded gum/oil. FT-Raman spectra of all six hits were consistent with each other indicative of a single crystal form (designated as Form A). Form A was scaled-up on 200 mg scale.

Preparation of Form A. IPA (7.5 mL) was combined with crystalline free base Form C (230.82 mg) and gentisic acid (1.0 equivalent, dosed as solid). Crystalline seeds of gentisate salt (~1 mg) was added. The suspension was heated to 40° C., stirred at 40° C. for five hours, cooled slowly (0.1° C./min) to 25° C. and stirred at 25° C. for 16 hours. The crystalline solids were isolated via vacuum filtration, air-dried under vacuum for 2 hours and dried in a vacuum oven at 40° C. for 4 hours. The yield of crystalline gentisate salt was 79.3% (237.2 mg).

Form A was crystalline by FT-Raman (FIG. 73) and PXRD (FIG. 74). DSC data showed a single endotherm at 200.2° C. (FIG. 75, trace 75B). TGA data showed ~0.8% wt loss between 30-196° C. suggesting that Form A gentisate salt is likely a non-solvated form (FIG. 75, trace 75A). The stoichiometry of gentisate salt showed 1.0:1.0 (counterion: parent) by $^1$H NMR analysis (FIG. 76).

Example 3.10. Hippurate Salt

Crystalline hippurate salt hits were isolated from six of the eight salt formation experiments. The remaining experiments yielded gum/oil. FT-Raman spectra of all six hits were consistent with each other indicative of a single crystal form (designated as Form A). Form A of hippurate salt was scaled-up on 200 mg scale.

Preparation of Form A. Acetone (7.5 mL) was combined with crystalline free base Form C (218.98 mg) and hippuric acid (1.0 equivalent, dosed as solid). Crystalline seeds of hippurate salt (~1 mg) was added. The suspension was heated to 40° C., stirred at 40° C. for five hours, cooled slowly (0.1° C./min) to 25° C. and stirred at 25° C. for 16 hours. The crystalline solids were isolated via vacuum filtration, air-dried under vacuum for 2 hours and dried in a vacuum oven at 40° C. for 4 hours. The yield of crystalline hippurate salt was 73.7% (217 mg).

Form A was crystalline by FT-Raman (FIG. 77) and PXRD (FIG. 78). DSC data showed a single endotherm at 170.1° C. (FIG. 79, trace 79B). TGA data showed ~0.1% wt. loss between 30-157° C. suggesting that Form A of hippurate salt is a non-solvated form (FIG. 79, trace 79A). The stoichiometry of hippurate salt showed 1.0:1.0 (counterion: parent) by $^1$H NMR analysis (FIG. 80).

Example 3.11. Adipate Salt

Crystalline adipate salt hits were isolated from six of the eight salt formation experiments. FT-Raman spectra of five of the six crystalline hits were consistent with each other indicative of a single crystal form (designated as Form A) while the FT-Raman spectrum of the sample isolated from acetone suggest a mixture of forms. Form A was characterized by PXRD (FIG. 81), TGA (FIG. 82, trace 82A) and DSC (FIG. 82, trace 82B). An attempt to prepare Form A on a 200 mg scale was unsuccessful and yielded a new crystal form (designated as Form C).

Preparation of Group C. EtOAc (7.5 mL) was combined with crystalline free base Form C (210.27 mg) and adipic acid (1.0 equivalent, dosed as solid). Crystalline seeds of adipate salt (~1 mg) was added. The suspension was heated to 40° C., stirred at 40° C. for five hours, cooled slowly (0.1° C./min) to 25° C. and stirred at 25° C. for 16 hours. The suspension was heated to 50° C., stirred at 50° C. for five hours, cooled slowly (0.1° C./min) to 25° C. and stirred at 25° C. for 16 hours. The crystalline solids were isolated via vacuum filtration, air-dried under vacuum for 2 hours and dried in a vacuum oven at 40° C. for 4 hours. The yield of crystalline adipate salt was 76.2% (205.2 mg).

Form C was crystalline by FT-Raman (FIG. 83) and PXRD (FIG. 84). DSC data showed a small endotherm with onset at 93.2° C. followed two sharp endotherms at 132.6° C. and 171.2° C. (FIG. 85, trace 85B). TGA data showed ~0.9% wt loss between 30-180° C. (FIG. 85, trace 85A). The stoichiometry of adipate salt showed 0.9:1.0 (counterion: parent) by $^1$H NMR analysis (FIG. 86).

Example 3.12. Galactarate Salt

Crystalline galactarate salt hits were isolated from five of the eight salt formation experiments. The remaining experiments yielded gum/oil, free-base or counterion. FT-Raman spectra of all five salt hits were consistent with each other indicative of a single crystal form (designated as Form A). Form A of galactarate salt was scaled-up on 200 mg scale.

Preparation of Form A. Acetone (7.5 mL) was combined with crystalline free base Form C (194.89 mg) and galactaric acid (1.0 equivalent, dosed as solid). Crystalline seeds of galactarate salt (~1 mg) was added. The suspension was heated to 40° C., stirred at 40° C. for five hours, cooled slowly (0.1° C./min) to 25° C. and stirred at 25° C. for 16 hours. The crystalline solids were isolated via vacuum filtration, air-dried under vacuum for 2 hours and dried in a vacuum oven at 40° C. for 4 hours. The yield of crystalline galactarate salt was 86.9 (237.5 mg).

Figure 88:
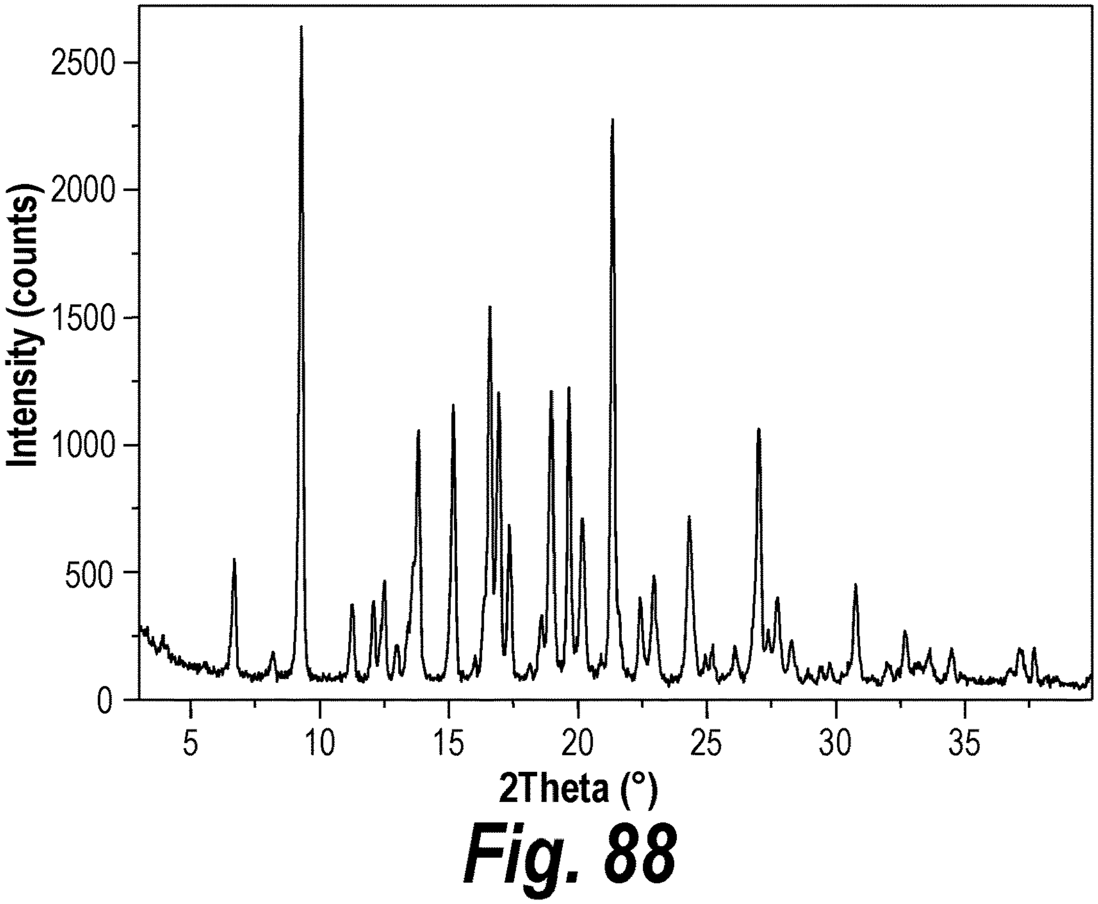
FIG. 88 depicts the XRPD pattern of Form A galactarate salt of Compound 1.

Form A was crystalline by FT-Raman (FIG. 87) and PXRD (FIG. 88). DSC data showed a single endotherm at 184.4° C. (FIG. 89, trace 89B). TGA data showed ~0.7% wt. loss between 30-157° C. suggesting that Form A of galactarate salt is a non-solvated form (FIG. 89, trace 89A). The stoichiometry of galactarate salt showed 1.0:1.0 (counterion: parent) by $^1$H NMR analysis (FIG. 90).

Example 3.13. Crystalline Salt Hits

In addition to the crystalline salts discussed in Examples 3.1-3.12, the salt screening study also yielded salts from a variety of additives. The characterization data of these salt hits are provided in Table 3.

TABLE 3

| Crystalline Hits from Screen | | | | | |
|---|---|---|---|---|---|
| Salt | Form | FT-Raman | PXRD | DSC | TGA |
| Napadisylate | A | — | FIG. 91 | FIG. 94 (94A) | — |
| | B | — | FIG. 92 | FIG. 94 (94B) | — |
| | C | — | FIG. 93 | FIG. 94 (94C) | — |
| (S)-Camphorsulfonate | A | FIG. 95 | FIG. 96 | FIG. 97 (97B) | FIG. 97 (97A) |
| | B | FIG. 98 | FIG. 99 | FIG. 100 (100B) | FIG. 100 (100A) |
| Edisylate | A | — | FIG. 101 | FIG. 105B | FIG. 105 (105A) |
| | B | — | FIG. 102 | FIG. 106 (106B) | — |
| | C | — | FIG. 103 | FIG. 106 (106A) | — |

TABLE 3-continued

| Crystalline Hits from Screen | | | | | |
|---|---|---|---|---|---|
| Salt | Form | FT-Raman | PXRD | DSC | TGA |
| | D | — | FIG. 104 | FIG. 106 (106C) | — |
| Esylate | A | — | FIG. 107 | FIG. 109 (109B) | FIG. 109 (109A) |
| | B | — | FIG. 108 | FIG. 110 (110B) | FIG. 110 (110A) |
| Besylate | A | — | FIG. 111 | FIG. 115 (115A) | — |
| | B | — | FIG. 112 | FIG. 115 (115B) | — |
| | C | — | FIG. 113 | FIG. 115 (115C) | — |
| | D | — | FIG. 114 | FIG. 116 (116B) | FIG. 116 (116A) |
| Oxalate | A | — | FIG. 117 | FIG. 119 (119B) | FIG. 119 (119A) |
| | B | — | FIG. 118 | FIG. 120 (120B) | FIG. 120 (120A) |
| Maleate | A | — | FIG. 121 | FIG. 122 (122B) | FIG. 122 (122A) |
| Pamoate | A | — | FIG. 123 | FIG. 124 (124B) | FIG. 124 (124A) |
| 1-Hydroxy-2-naphthoate | A | — | FIG. 125 | FIG. 126 | — |
| Malonate | A | — | FIG. 127 | FIG. 128 (128B) | FIG. 128 (128A) |
| | B | — | FIG. 129 | FIG. 130 (130B) | FIG. 130 (130A) |
| | C | — | FIG. 131 | FIG. 132 | — |
| L-Tartrate | A | — | FIG. 133 | FIG. 134 (134B) | FIG. 134 (134A) |
| | B | — | FIG. 135 | FIG. 136 | — |
| | C | — | FIG. 137 | FIG. 138 (138B) | FIG. 138 (138A) |
| | D | — | FIG. 139 | FIG. 140 (140B) | FIG. 140 (140A) |
| Fumarate | A | — | FIG. 141 | FIG. 142 (142B) | FIG. 142 (142A) |
| | B | — | FIG. 143 | FIG. 144 | |
| | C | — | FIG. 145 | FIG. 146 (146B) | FIG. 146 (146A) |
| | D | — | FIG. 147 | FIG. 148 (148B) | FIG. 148 (148A) |
| Citrate | A | — | FIG. 149 | FIG. 150 (150B) | FIG. 150 (150A) |
| L-Lactate | A | — | FIG. 151 | FIG. 152 (152B) | FIG. 152 (152A) |
| Acetate | A | — | FIG. 153 | FIG. 154 (154B) | FIG. 154 (154A) |
| | B | — | FIG. 155 | FIG. 156 (156B) | FIG. 156 (156A) |
| Propionate | A | — | FIG. 157 | FIG. 158 (158B) | FIG. 158 (158A) |
| DL-Lactate | A | — | FIG. 159 | FIG. 160 (160B) | FIG. 160 (160A) |
| D-Gluconate | A | — | FIG. 161 | FIG. 162 | |
| DL-Malate | A | — | FIG. 163 | FIG. 164 (164B) | FIG. 164 (164A) |
| | B | — | FIG. 165 | FIG. 166 (166B) | FIG. 166 (166A) |
| Glycolate | A | — | FIG. 167 | FIG. 168 (168B) | FIG. 168 (168A) |
| Glutarate | A | — | FIG. 169 | FIG. 170 (170B) | FIG. 170 (170A) |
| | B | — | FIG. 171 | FIG. 172 (172B) | FIG. 172 (172A) |
| L-Malate | A | — | FIG. 173 | FIG. 174 (174B) | FIG. 174 (174A) |
| Camphorate | A | — | FIG. 175 | FIG. 176 (176B) | FIG. 176 (176A) |
| | B | — | FIG. 177 | FIG. 178 (178B) | FIG. 178 (178A) |
| | C | — | FIG. 179 | FIG. 180 (180B) | FIG. 180 (180A) |
| | D | — | FIG. 181 | FIG. 182 (182B) | FIG. 182 (182A) |

TABLE 3-continued

| Crystalline Hits from Screen | | | | | |
|---|---|---|---|---|---|
| Salt | Form | FT-Raman | PXRD | DSC | TGA |
| DL-Mandelate | A | — | FIG. 183 | FIG. 184 (184B) | FIG. 184 (184A) |
| | B | — | FIG. 185 | FIG. 186 (186B) | FIG. 186 (186A) |
| | C | — | FIG. 187 | FIG. 188 (188B) | FIG. 188 (188A) |

Example 4. Primary Co-Crystal Screen of Fedratinib

A total of 24 co-crystal formers (CCF) were selected based on hydrogen-bonding propensities, molecular diversity, and pharmaceutical acceptability. One equivalent of CCF was dosed in all screening experiments. Table 4 presents the set of CCFs utilized.

TABLE 4

| Co-crystal Formers Utilized in the Screen | | |
|---|---|---|
| # | CCFs | Molar Equivalent |
| 1 | Urea | 1 |
| 2 | Caffeine | 1 |
| 3 | Nicotinamide | 1 |
| 4 | Isonicotinamide | 1 |
| 5 | L-Prolinamide | 1 |
| 6 | Vanillin | 1 |
| 7 | Methyl paraben | 1 |
| 8 | Propyl paraben | 1 |
| 9 | Butylated hydroxyanisole | 1 |
| 10 | Pyrogallol | 1 |
| 11 | Chrysin | 1 |
| 12 | Resveratrol | 1 |
| 13 | Quercetin dihydrate | 1 |
| 14 | Saccharin | 1 |
| 15 | Aspartame | 1 |
| 16 | Xylitol | 1 |
| 17 | Sucralose | 1 |
| 18 | D-Mannitol | 1 |
| 19 | L-Ascorbic acid | 1 |
| 20 | Nicotinic acid | 1 |
| 21 | Gallic acid | 1 |
| 22 | Orotic acid | 1 |
| 23 | Salicylic acid | 1 |
| 24 | Acetylsalicylic acid | 1 |

A total of five neat solvents and two binary mixtures were utilized in the presented cocrystal screening experiments: THF, EtOAc, DCM, MIBK, MeOH, THF/cyclohexane (2:8 v/v), and IPA:water (9:1 v/v). The selection was based on diversity of molecular structure and properties of the solvent (e.g., polarity, chemical diversity), and solubility of free base Form C ("API") from visual solubility assessment.

A total of ~240 co-crystal-screening experiments were conducted using 24 CCFs and a combination of i) solvent-drop grinding (SDG)—with four solvents, ii) slurry-ripening (SR) in six solvents, and iii) evaporation of solutions obtained in step ii.

Solvent-Drop Grinding (SDG). Several preliminary experiments were conducted to determine appropriate milling parameters for the SDG experiments. The results of these experiments are summarized in Table 5 (15 minutes of grinding at 15 Hz with one milling ball). The data indicated that 15 minutes of grinding at 15 Hz with one milling ball was appropriate for 100 mg API with 2-15 µL solvent. The specific (initial) solvent volumes selected for the four solvents were: THF—5 µL; EtOAc, DCM, and MIBK—15 µL.

TABLE 5

| Determination of Appropriate Solvent-Drop Grinding (SDG) Parameters | | | | | | |
|---|---|---|---|---|---|---|
| No. | Free Base (mg) | Solvent (µL) | Yield (mg) | Product Properties | PLM | Free Base Form by PXRD |
| 1 | 98.8 | none | 41.6 | much static; stuck to jar walls | bire-fringent | Form A |
| 2 | 98.7 | THF (2) | 39.3 | much static; stuck to jar walls | bire-fringent | Form A |
| 3 | 98.8 | EtOAc (5) | 26.1 | much static; stuck to jar walls | bire-fringent | Form A |
| 4 | 99 | DCM (5) | 29.6 | much static; stuck to jar walls | bire-fringent | Form A |
| 5 | 101.2 | MIBK (10) | 65.2 | less static; less stuck to jar walls; partial dissolution | bire-fringent | Form A |
| 6 | 99.3 | THF (5) | 37.1 | some static; stuck to jar walls; partial dissolution | bire-fringent | Form A |
| 7 | 99.3 | EtOAc (10) | 48.3 | some static; stuck to jar walls; maybe partial dissolution | bire-fringent | Form A |
| 8 | 98.1 | DCM (10) | 43.7 | much static; stuck to jar walls | bire-fringent | Form A |
| 9 | 100.4 | EtOAc (15) | 56.3 | less static; less stuck to jar walls; partial dissolution | bire-fringent | Form A |
| 10 | 98.8 | DCM (15) | 52.5 | less static; less stuck to jar walls; partial dissolution | bire-fringent | Form A |

For the SDG experiments, the API (~100 mg), a stoichiometric amount of CCF (1 eq), and solvent THE, EtOAc, DCM, or MIBK were combined in a stainless steel milling jar (10 mL). Grinding was conducted on a Retsch Mill (Model MM301) at room temperature (~23° C.) with one milling ball (7 mm) at 15 Hz for 15 minutes. In cases where these parameters were observed or expected (based on properties of the CCF) to result in low yield or gumming, the milling time was reduced to 10 minutes or manual grinding via a mortar and pestle was used.

Slurry-Ripening (SR). Products from the SDG experiments were utilized and combined with the same four neat solvents used in the SDG experiments to conduct SR studies, except that THF:cyclohexane (2:8 v/v) was substituted for THF. For CCFs that yielded potential cocrystals (or salts) from SDG, saturated solutions of the CCFs were prepared in the specific solvents that yielded potential co-crystals or salts and used for SR experiments.

For two additional solvents (MeOH and IPA:water (9:1 v/v)), 1:1 (API:CCF) equivalent mixtures were prepared and combined with the two solvent systems.

The saturated solutions of CCFs were prepared by combining the CCF (estimated amount to achieve suspension) with 2 mL of solvent, then mixing at 23° C. for 16 hours. Suspensions were filtered through a 0.20 μm PTFE filter membrane to yield saturated solutions.

SR experiments were conducted in 2 mL vial s containing a tumble-stir disc and employed up to 1.9 mL solvent [THF:cyclohexane (2:8 v/v), EtOAc, DCM, MIBK, MeOH, or IPA:water (9:1 v/v)]. The samples were mixed and temperature-cycled between 40° C. and 5° C. for seven days, followed by mixing at 25° C. for five days. During this processing time, additional solvent was added to yield mixable suspensions with sufficient solids for isolation and analysis. Suspended solids were isolated by filtration and air-dried for 18 hours.

Evaporation (EV). Solutions that were obtained in slurry-ripening experiments were slowly evaporated (by loosening the vial cap) in a fume hood until dry. Products were examined first by PLM for birefringence, and further analyzed by PXRD if birefringent.

All solid outputs of the screen were analyzed by PXRD to assess co-crystal formation. Likely co-crystals were analyzed by additional techniques as appropriate and as sample quantity permitted (FT-Raman, DSC, TGA-IR, PLM, etc.).

The conducted experiments yielded potential co-crystals (pure or in mixture with parent and/or CCF) of Form C free base with isonicotinamide, pyrogallol, saccharin, and xylitol, and potential salts with L-ascorbic acid, nicotinic acid, gallic acid, orotic acid, salicylic acid, and acetylsalicylic acid. Most potential co-crystals (or salts) were obtained from SR/EV experiments. The PXRD patterns of salicylic acid Form A and acetylsalicylic acid Form A were observed to be identical. Proton NMR analysis confirmed that the acetylsalicylic acid salt Form A was consistent with salicylic acid salt Form A, as no acetyl group was observed. This may be due to hydrolysis of acetylsalicylic acid to salicylic acid during slurry-ripening.

Co-crystal formers that did not yield potential co-crystals included urea, caffeine, nicotinamide, L-prolinamide, vanillin, methyl paraben, propyl paraben, butylated hydroxyanisole, chrysin, resveratrol, quercetin, aspartame, sucralose, and D-mannitol. These co-crystal formers yielded amorphous materials, parent forms, CCF, or a combination thereof. The products obtained in the SDG and SR/EV experiments are shown in Table 6 and Table 7, respectively.

TABLE 6

Co-crystal or Salt Screening Products Obtained from SDG Approach

| # | CCF | THF | EtOAc | DCM | MIBK |
|---|---|---|---|---|---|
| 1 | Urea | C CI | C CI | C CI | C CI |
| 2 | Caffeine | C CI | C CI | C CI | C CI |
| 3 | Nicotinamide | C CI | C CI | C CI | C CI |
| 4 | Isonicotinamide | C CI | C CI | C CI | C CI |
| 5 | L-Prolinamide | C CI | C CI | C CI | C CI |
| 6 | Vanillin | C CI | C CI | C CI | C CI |
| 7 | Methyl paraben | C CI | C CI | C CI | C CI |
| 8 | Propyl paraben | C CI | C CI | C CI | C CI |
| 9 | Butylated hydroxyanisole | C CI | C CI | C CI | C CI |
| 10 | Pyrogallol | C | C | C CI | C |
| 11 | Chrysin | C CI | C CI | C CI | C CI |
| 12 | Resveratrol | C CI | C CI | C CI | C CI |
| 13 | Quercetin dihydrate | C CI | C CI | C CI | C CI |
| 14 | Saccharin | C CI | C CI | C CI | C CI |
| 15 | Aspartame | C CI | C CI | C CI | C CI |
| 16 | Xylitol | C CI | C CI | C CI | C CI |
| 17 | Sucralose | C CI | C CI | C CI | C CI |
| 18 | D-Mannitol | C CI | C CI | C CI | C CI |
| 19 | L-Ascorbic acid | C CI | C CI | C CI | C CI |
| 20 | Nicotinic acid | C CI | C CI | C CI | C CI |
| 21 | Gallic acid | C CI | C CI | C CI | C CI |
| 22 | Orotic acid | C CI | C CI | C CI | C CI |
| 23 | Salicylic acid | C CI | C CI NC | C CI | C CI |
| 24 | Acetylsalicylic acid | C CI | C CI | C CI | C CI NC |

| LEGEND: | |
|---|---|
| NC | New Complex Form Identified |
| FB | Parent Free Base Form |
| CI | Counterion |

Notes:
A, B - crystal forms identified

TABLE 7

Co-crystal or Salt Screening Products Obtained from Slurry-Ripening or Evaporation Approach

| # | CCF | THF/cyclohexane (2:8) | EtOAc | DCM | MIBK | MeOH | IPA/water (9:1) |
|---|---|---|---|---|---|---|---|
| 1 | Urea | C CI | C CI | C CI | C CI | A | C CI |
| 2 | Caffeine | C CI | C CI | C CI | C CI | A CI | C CI |
| 3 | Nicotinamide | C CI | C CI | C,+* CI | C CI | A | C CI |
| 4 | Isonicotinamide | C CI | C CI | C CI NC | C CI | A | C CI |
| 5 | L-Prolinamide | C | C CI | C CI | C CI | C | C |
| 6 | Vanillin | C | C | C CI | C | A | C |
| 7 | Methyl paraben | C | C | ND | C | A | C |
| 8 | Propyl paraben | C | C CI | C,+ | C CI | A | C CI |
| 9 | Butylated hydroxyanisole | C | C | C | C | A | C |
| 10 | Pyrogallol | A, C NC | A, C NC | A, C NC | C NC | A, C (ev) NC | C |
| 11 | Chrysin | C CI | C CI | C CI | C CI | A CI | C CI |
| 12 | Resveratrol | C CI | C CI | C CI | C CI | A | C CI |
| 13 | Quercetin dihydrate | C CI | C CI | C,+ CI | C CI | A CI | C CI |

TABLE 7-continued

| Co-crystal or Salt Screening Products Obtained from Slurry-Ripening or Evaporation Approach | | | | | | | |
|---|---|---|---|---|---|---|---|
| # | CCF | THF/cyclohexane (2:8) | EtOAc | DCM | MIBK | MeOH | IPA/water (9:1) |
| 14 | Saccharin | NC(A) | NC(A) | NC(A) | NC(A) | NC(A) | NC(A) |
| 15 | Aspartame | C CI | C CI | ND CI | C CI | AM(ev) | C CI |
| 16 | Xylitol | C CI | C CI | C,[+] CI NC | C CI | A | C |
| 17 | Sucralose | C CI | C CI | C CI | C CI | A | C |
| 18 | D-Mannitol | C CI | C CI | C CI | C CI | A CI | C CI |
| 19 | L-Ascorbic acid | NC(A, B) | NC(B) | NC(A, B) | NC(B) | NC(A, B (ev)) | NC(A) |
| 20 | Nicotinic acid | NC(A) | NC(B) | AM | NC(A) | NC(C (ev)) | C |
| 21 | Gallic acid | NC(A) | C | NC(A, B) | C | NC(A) | NC(A, B) |
| 22 | Orotic acid | NC(A) | NC(B, E) * | NC(C, E) | NC(D) | NC€ | NC(F) |
| 23 | Salicylic acid | NC(A) | NC(B) [1] | NC(A) | NC(A) | NC(A) | NC(A) |
| 24 | Acetylsalicylic acid | NC(A, B) | C NC(A, B) | AM(ev) | NC(B) [1] | NC(A) | NC(A) |

Notes:
A, B, etc.-crystal forms
[+]-mixture, likely with unidentified forms of parent free base
*-poorly crystalline
(ev)-from solution evaporation
[1] presaturated with CCF (saturated)
ND-form undetermined

| LEGEND: | |
|---|---|
| NC(X) | New Complex Form(s) Identified (X = A, B, etc.) |
| FB | Parent Free Base Form |
| CI | Counterion |
| AM | Amorphous Form |

TABLE 8

| Attributes of Scaled-Up Co-Crystals or Salts | | | | | |
|---|---|---|---|---|---|
| Complex Form Scaled Up | Equivalents of CCF ($^1$H NMR) | DSC Endotherms (Onset, ° C.) | TGA % Wt Loss | Nature | Complex Forms Observed During Scale-Up |
| Saccharin Form A | 1 | 183.8 | 0.1 (26-174° C.) | non-solvated | A |
| Nicotinic acid Form A | 1 | 179.9 | 0.2 (29-168°) | non-solvated | A-C |
| Ascorbic acid Form A | 1 | 46.0<br>116.8<br>157.0<br>(maybe 2 merged) | 5.4 (29-140° C.) | hydrate | A, B |
| Gallic acid Form A | 1 | 48.0<br>193.5 | 2.4 (22-89° C.) | hydrate | A, B |
| Salicylic acid Form A | 1 | 34.9<br>159.8 | 2.5 (26-96° C.) | hydrate | A, B |
| Orotic acid Form F | 1 | 56.5<br>104.7<br>135.2 | 10.8 (24-129° C.) | hydrate | A-H |
| Orotic acid Form H | 1 | 34.3<br>134.5<br>144.4<br>165.8<br>203.4 | 3.2 (23-95° C.) | hydrate | |

Example 5. Scale Up of Co-Crystals

Of the potential co-crystal (or salt) hits, the following seven exhibited desirable physiochemical properties and were scaled up on a 250 mg scale: saccharin Form A, nicotinic acid Form A, ascorbic acid Form A, gallic acid Form A, salicylic acid Form A, and orotic acid Forms F and H. Results are described in detail below.

Example 5.1. Saccharin Co-Crystal

Saccharin co-crystal hits were obtained from six SR experiments. PXRD analysis of the samples indicated one form, designated Form A. Form A (non-solvated) was scaled up (250 mg scale) and subjected to detailed characterization.

Preparation of Form A (Non-solvated). Form C free base (244.5 mg) was combined with saccharin (83.1 mg; 1 eq) and solvent (DCM, 3.5 mL), and mixed at 40° C. for 30 minutes yielding a suspension. Seeds (~5 mg) were added, and the suspension was mixed at 40° C. for two hours, slow-cooled to 20° C., and mixed at 20° C. for 60 hours yielding a moderately thick slurry. The solids were isolated by vacuum-filtration for two hours and dried at 40° C. in a vacuum oven for 18 hours. The product weight was 287 mg of Form A (87% yield relative to the cocrystal).

Form A was determined to be a crystalline powder by FT-Raman (FIG. 189) and PXRD (FIG. 190). DSC analysis showed a melting endotherm with onset at 183.8° C. ($\Delta H$=104.2 J/g) (FIG. 191, trace 191B). TGA analysis showed 0.1% weight loss between 26-174° C., indicating a non-solvated form (FIG. 191, trace 191A). Proton NMR analysis of Form A indicated that Form A comprises 1 equivalent of saccharin (FIG. 192).

Example 5.2. Nicotinic Acid Salt

Nicotinic acid salt hits were obtained from three SR and one EV experiments. PXRD analysis of the samples indicated three forms, designated as Form A, Form B and Form C. Form A (non-solvated) was scaled up (250 mg scale) and subjected to detailed characterization. Form B was characterized by PXRD (FIG. 197), TGA (FIG. 198, trace 198A), and DSC (FIG. 198, trace 198B). Form C was characterized by PXRD (FIG. 199), TGA (FIG. 200, trace 200A), and DSC (FIG. 200, trace 200B).

Preparation of Form A (Non-solvated). Form C free base (252.8 mg) was combined with nicotinic acid (57.9 mg; 1 eq) and solvent (THF/cyclohexane (2:8), 3.0 mL), and mixed at 40° C. for 30 minutes yielding a suspension. Seeds (~5 mg) were added, and the suspension was mixed at 40° C. for two hours, slow-cooled to 20° C., and mixed at 20° C. for 60 hours yielding a moderately thick slurry. The solids were isolated by vacuum-filtration for two hours and dried at 40° C. in a vacuum oven for 18 hours. The product weight was 247 mg of nicotinic acid salt Form A (79% yield relative to the salt).

Form A was determined to be a crystalline powder by FT-Raman (FIG. 193) and PXRD (FIG. 194). DSC analysis showed a melting endotherm with onset at 179.9° C. (ΔH=120.4 J/g) (FIG. 195, trace 195B). TGA analysis showed 0.2% weight loss between 29-168° C., indicating a non-solvated form (FIG. 195, trace 195A). Proton NMR analysis of Form A indicated that Form A comprises 1 equivalent of nicotinic acid (FIG. 196).

Example 5.3. L-Ascorbic Acid Salt

Ascorbic acid salt hits were obtained from six SR experiments. PXRD analysis of the samples indicated two forms, designated as Form A and Form B. Form A (hydrate) was scaled up (250 mg scale) and subjected to detailed characterization.

Preparation of Form A (Hydrate). Form C free base (249.7 mg) was combined with L-ascorbic acid (81.6 mg; 1 eq) and solvent (IPA/water (9:1) v/v, 6.0 mL), and mixed at 40° C. for 30 minutes yielding a suspension. Seeds (~5 mg) were added, and the suspension was mixed at 40° C. for two hours, slow-cooled to 20° C., and mixed at 20° C. for 60 hours yielding a moderately thick slurry. The solids were isolated by vacuum-filtration for four hours and left open in a fume hood for 18 hours. The product weight was 294 mg of ascorbic acid salt Form A (83% yield relative to the salt).

Form A was determined to be a crystalline powder by FT-Raman (FIG. 201) and PXRD (FIG. 202). DSC analysis showed a dehydration endotherm with onset at 46.0° C. (ΔH=168.5 J/g) followed by a small endotherm at 116.8° C. (ΔH=7.5 J/g) and a melting endotherm (possibly two merged) with onset at 157.0° C. (ΔH=71.4 J/g) (FIG. 203, trace 203B). TGA analysis showed 5.4% weight (2.2 eq) loss of water between 29-140° C., indicating a hydrated form (FIG. 203, trace 203A). Proton NMR analysis of Form A indicated that Form A comprises 1 equivalent of L-ascorbic acid (FIG. 204).

Example 5.4. Gallic Acid Salt

Gallic acid salt hits were obtained from four SR experiments. PXRD analysis of the samples indicated two forms, designated as Form A and Form B. Form A was obtained in pure form while Form B was obtained only in mixture with Form A. Form A (hydrate) of the gallic acid salt was scaled up (250 mg scale) and subjected to detailed characterization.

Preparation of Form A (Hydrate). Form C free base (245.0 mg) was combined with gallic acid (77.0 mg; 1 eq) and solvent (MeOH, 4.0 mL), and mixed at 40° C. for 30 minutes yielding a suspension. Seeds (~5 mg) were added, and the suspension was mixed at 40° C. for two hours, slow-cooled to 20° C., and mixed at 20° C. for 60 hours yielding a moderately thick slurry. The solids were isolated by vacuum-filtration for four hours and left open in a fume hood for 18 hours. The product weight was 256 mg of gallic acid salt Form A (77% yield relative to the salt).

Form A was determined to be a crystalline powder by FT-Raman (FIG. 205) and PXRD (FIG. 206). DSC analysis showed a dehydration endotherm with onset at 48.5° C. (ΔH=79.8 J/g) followed by a melting endotherm with onset at 193.5° C. (ΔH=176.1 J/g) (FIG. 207, trace 207B). TGA analysis showed 2.4% weight (1.0 eq) loss of water between 22-89° C., indicating a hydrated form (FIG. 207, trace 207A). Proton NMR analysis of Form A indicated that Form B comprises 1 equivalent of gallic acid (FIG. 208).

Example 5.5. Salicylic Acid Salt

Salicylic acid salt hits were obtained from one SDG experiment and six SR experiments; however, the hit from SDG was a mixture of a potential salt, parent, and CCF. PXRD analysis of the six SR hits indicated two forms, designated as Form A and Form B. Most hits (5/6) were consistent with Form A. Form A (hydrate) of the salicylic acid salt was scaled up (250 mg scale) and subjected to detailed characterization.

Preparation of Form A (Hydrate). Form C free base (253.8 mg) was combined with salicylic acid (64.7 mg; 1 eq) and solvent (IPA/water 9:1, 4.5 mL), and mixed at 40° C. for 30 minutes yielding a suspension. Seeds (~5 mg) were added, and the suspension was mixed at 40° C. for two hours, slow-cooled to 20° C., and mixed at 20° C. for 60 hours yielding a moderately thick slurry. The solids were isolated by vacuum-filtration for 18 hours. The product weight was 272 mg of salicylic acid salt Form A (83% yield relative to the salt).

Form A was determined to be a crystalline powder by FT-Raman (FIG. 209) and PXRD (FIG. 210). DSC analysis showed a dehydration endotherm with onset at 34.9° C. (ΔH=71.0 J/g) followed by a melting endotherm with onset at 159.8° C. (ΔH=83.8 J/g) (FIG. 211, trace 211B). TGA analysis showed 2.5% weight (1.0 eq) loss of water between 26-96° C., indicating a hydrated form (FIG. 211, trace 211A). Proton NMR analysis of Form A indicated that Form A comprises 1 equivalent of salicylic acid (FIG. 212).

Example 5.6. Orotic Acid Salt

Orotic acid salt hits were obtained from six SR experiments. PXRD analysis of the hits indicated six forms, designated as Form A, Form B, Form C, Form D, Form E and Form F. Scale-up experiments (250 mg) were conducted for Forms E and F (hydrates), and the other groups were deprioritized due to solvation or because they were mixtures of two groups as shown in Table 7. The Form E scale-up experiment was unsuccessful and produced two new groups: Form G and Form H. Form G is a MeOH/water solvate that desolvates under ambient conditions to Form H, a hydrate. Form A was characterized by PXRD (FIG. 213), TGA (FIG. 214, trace 214A) and DSC (FIG. 214, trace 214B). The mixture of Form B and Form E was characterized by PXRD (FIG. 215). The mixture of Form C and Form E was characterized by PXRD (FIG. 216). Form D was characterized by PXRD (FIG. 217), TGA (FIG. 218, trace 218A) and DSC (FIG. 218, trace 218B). Form E was characterized by PXRD (FIG. 219), TGA (FIG. 220, trace 220A) and DSC (FIG. 220, trace 220B). Form G was characterized by PXRD (FIG. 221). Form F and Form H (hydrates) of the orotic acid salt were scaled up (250 mg) and subjected to detailed characterization.

Preparation of Form F (Hydrate). Form C free base (250.0 mg) was combined with orotic acid (77.0 mg; 1 eq) and solvent (IPA/water 9:1, 10.0 mL), and mixed at 40° C. for 30 minutes yielding a suspension. Seeds (~5 mg) were added, and the suspension was mixed at 40° C. for two hours, slow-cooled to 20° C., and mixed at 20° C. for 60 hours yielding a moderately thick slurry. The solids were isolated by vacuum-filtration for 22 hours. The product weight was 297 mg of orotic acid salt Form F (82% yield relative to the co-crystal).

Form F was determined to be a crystalline powder by FT-Raman (FIG. 222) and PXRD (FIG. 223). DSC analysis showed two dehydration endotherms with onsets at 56.5° C. (ΔH=86.1 J/g) and 104.7° C. (ΔH=15.4 J/g), respectively, immediately followed by a melting endotherm with onset at 135.2° C. (ΔH=12.3 J/g) (FIG. 224, trace 224B). TGA analysis showed 10.8% weight (4.5 eq) loss of water between 24°-129° C., indicating a hydrated form (FIG. 224, trace 224A). Proton NMR analysis of Form F indicated that Form F comprises 1 equivalent of orotic acid (FIG. 225).

PXRD analysis of the sample post heating indicated significant loss of crystallinity but no change in form.

Preparation of Form H (Hydrate). Form C free base (251.7 mg) was combined with orotic acid (72.7 mg; 1 eq) and solvent (MeOH, 1.0 mL), and mixed at 40° C. for 10 minutes yielding a near clear solution. Seeds (Group E, ~5 mg) were added, and the suspension became very thick, so additional solvent was added (MeOH, 1.5 mL). The suspension was mixed at 40° C. for two hours, slow-cooled to 20° C., and mixed at 20° C. for 18 hours yielding a moderately thick slurry. PXRD indicated a new form, and DSC/TGA-IR indicated a MeOH/water solvate, which was designated Form G. The batch solids were isolated by vacuum-filtration for 18 hours. The product weight was 178 mg. PXRD indicated yet a new form, and DSC/TGA-IR indicated a hydrate, which was designated Form H (53% yield relative to the salt).

Form H was determined to be a crystalline powder by FT-Raman (FIG. 226) and PXRD (FIG. 227). DSC analysis showed a broad dehydration endotherm with onset at 34.3° C. (ΔH=23.4 J/g), followed by two small endotherms at 134.5° C. and 144.4° C., respectively, a large endotherm with onset at 165.8° C. (ΔH=44.6 J/g), and a broad endotherm with onset at 203.4° C. (ΔH=11.1 J/g) (FIG. 228, trace 228B). TGA analysis showed 3.2% weight (1.2 eq) loss of water between 23-95° C., indicating a hydrated form (FIG. 228, trace 228A). Proton NMR analysis of Form H indicated that Form H comprises 1 equivalent of orotic acid (FIG. 229).

PXRD analysis of the post-heated sample indicated some loss of crystallinity and a loss of several major peaks.

Example 5.7. Other Co-Crystal or Salt Hits

Acetylsalicylic acid salt Form A was scaled up, however the PXRD pattern was observed to be identical to that of salicylic acid salt Form A. Proton NMR analysis confirmed that the acetylsalicylic acid salt Form A was consistent with salicylic acid salt Form A, as no acetyl group was observed. This may be due to hydrolysis of acetylsalicylic acid to salicylic acid during slurry-ripening.

In addition to the scaled up co-crystals (or salts), several other potential co-crystals were obtained from screening. These hits were not completely characterized and/or scaled up due to:

- limited sample amounts,
- undesirable physiochemical properties (poor crystallinity/poor thermal properties)
- being identified as a mixture with parent and/or CCF.

Representative samples of these co-crystal (or salt) hits are summarized in Table 9.

TABLE 9

Attributes of Other Co-Crystal or Salt Hits Identified in Screening

| Crystal Form | Potential Co-crystal or Salt | DSC Endotherms (Onset, ° C.) | Comments | PXRD | DSC | TGA |
|---|---|---|---|---|---|---|
| Form A | Isonicotinamide | Not obtained | Mixture with Free Base Form C and CCF | FIG. 230 | — | — |
| Form A | Pyrogallol | 33.8 (broad)<br>134.7 (broad) | Mixture with Free Base Forms A + C; DCM/water solvate | FIG. 231 | FIG. 232B | FIG. 232A |
| Form A | Xylitol | Not obtained | Mixture with Free Base Form C and other forms, CCF | FIG. 233 | — | — |
| Form B | Ascorbic acid | 40.9 (broad)<br>132.0 (broad) | Moderately crystalline; Hydrate | FIG. 234 | FIG. 235B | FIG. 235A |
| Form B | Gallic acid | Not obtained | Mixture with Gallate Form A | FIG. 236 | — | — |
| Form A | Orotic acid | 61.1 (broad)<br>158.0 (broad)<br>178.9 (sharp) | THF/cyclo-hexane/water solvate | FIG. 213 | FIG. 214B | FIG. 214A |
| Form B | | Not obtained | Mixture with Orotate Form E | FIG. 215 | — | — |
| Form C | | Not obtained | Mixture with Orotate Form E | FIG. 216 | — | — |
| Form D | | 166.6 (broad)<br>182.3 (small) | MIBK/water solvate | FIG. 217 | FIG. 218B | FIG. 218A |

TABLE 9-continued

| Attributes of Other Co-Crystal or Salt Hits Identified in Screening | | | | | | |
|---|---|---|---|---|---|---|
| Crystal Form | Potential Co-crystal or Salt | DSC Endotherms (Onset, ° C.) | Comments | PXRD | DSC | TGA |
| Form E | | 41.3 (broad)<br>78.0 (broad)<br>163.9 (broad) | Hydrate; may be difficult to reproduce | FIG. 219 | FIG. 220B | FIG. 220A |
| Form G | | 38.1 (broad)<br>143.5 (small)<br>167.2 (broad)<br>203.3 (broad) | MeOH/water solvate | FIG. 221 | — | — |
| Form B | Salicylic acid | 116.9 (broad)<br>140.2 (broad) | EtOAc solvate | FIG. 237 | FIG. 238B | FIG. 238A |
| Form B | Acetylsalicylic acid | 101.2 (broad) | MIBK solvate | FIG. 239 | FIG. 240B | FIG. 240A |

Example 6. Aqueous Solubility of Certain Complexes

The solid/salt forms (~20-30 mg) were transferred to clear glass vials (4 ml). To each vial containing solid forms, the water (~0.2-2 ml) was separately added. The volume of water added and the weight of the solid/salt form was appropriately adjusted to yield excess undissolved solid/salt form. The vials containing the solid/salt form/water mixture were transferred on to the rack that were kept at rotation and the samples were equilibrated with agitation at ambient temperature for 24 hr. At the end of the equilibration process, visual observations of the suspensions were made and the samples were withdrawn and centrifuged (14,000 rpm for 3 min) in a Costar SPIN-X polypropylene centrifuge tube (2.0 ml) filter (0.22 mm Nylon filter) to separate any un-dissolved drug. The clear filtrate was assayed for drug content to determine solubility of the active in the solution following appropriate dilution where necessary in acetonitrile/water (50:50). A standard curve in the concentration range of 0.126 mg/ml to 0.001 mg/ml was prepared using the free base. The samples and standards were assayed for drug content using the HPLC. Results are set forth in Table 10:

TABLE 10

| Solubility of Certain Forms of Compound 1 | |
|---|---|
| Solid Form | Solubility (mg/mL) |
| Free base Form A | 0.003 |
| HBr Form A | 2.3 |
| HBr Form B | 14.6 |
| Sulfate Form D | 2.9 |
| Tosylate Form C | 0.1 |
| Mesylate Form A | 11.0 |
| 2-Naphthalenesulfonate A | 0.1 |
| Phosphate Form E | 5.0 |
| Gentisate Form A | 0.1 |
| Hippurate Form A | 1.4 |
| Adipate Form A | 9.7 |
| Succinate Form B | 10.6 |
| DL-Tartrate Form A | 0.6 |
| Galactarate Form A | 15.3 |
| Nicotinic Acid Form A | 4.0 |
| Saccharin Form A | 0.1 |
| Ascorbic Acid Form A | 5.4 |
| Gallic Acid Form A | 0.2 |
| Orotic Acid Form F | 0.9 |
| Orotic Acid Form H | 0.6 |
| Salicylic Acid Form A | 0.05 |

The invention claimed is:

1. A crystalline form of Compound 1:

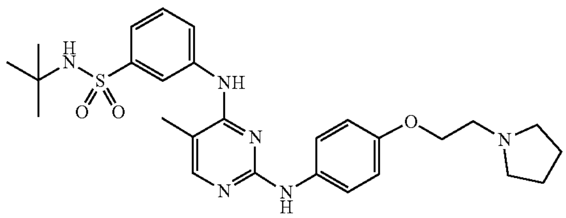 [SMILES: Cc1cnc(Nc2ccc(OCCN3CCCC3)cc2)nc1Nc1cccc(S(=O)(=O)NC(C)(C)C)c1]

wherein the form is a.) unsolvated; and b.) characterized by one or more peaks in its X-ray powder diffraction pattern selected from 9.7, 14.6, 19.5, 24.3, and 25.6±0.2 degrees 2θ.

2. The crystalline form of claim 1, wherein the form is characterized by the following peaks in its X-ray powder diffraction pattern:

| Position ° 2θ ± 0.2 degrees | d-spacing [Å] | Height [cts] |
|---|---|---|
| 8.8 | 10.102 | 1414 |
| 9.7 | 9.120 | 88376 |
| 10.5 | 8.463 | 2192 |
| 13.6 | 6.516 | 1881 |
| 14.6 | 6.082 | 50409 |
| 16.0 | 5.543 | 3640 |
| 16.4 | 5.413 | 2620 |
| 17.7 | 5.014 | 3311 |
| 18.5 | 4.797 | 5807 |
| 19.1 | 4.637 | 1316 |
| 19.5 | 4.563 | 6885 |
| 19.8 | 4.492 | 1686 |
| 20.1 | 4.415 | 1686 |
| 20.4 | 4.360 | 4156 |
| 21.0 | 4.229 | 4358 |
| 22.7 | 3.914 | 1551 |
| 23.0 | 3.874 | 2648 |
| 23.5 | 3.781 | 1611 |
| 23.9 | 3.730 | 9006 |
| 24.3 | 3.660 | 13329 |
| 24.6 | 3.614 | 1849 |

-continued

| Position ° 2θ ± 0.2 degrees | d-spacing [Å] | Height [cts] |
|---|---|---|
| 25.6 | 3.479 | 7883 |
| 28.0 | 3.192 | 1510 |
| 28.6 | 3.119 | 1592 |
| 29.4 | 3.043 | 2105. |

3. A crystalline form of Compound 1:

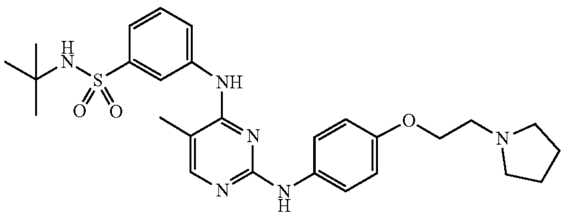 [SMILES: Cc1cnc(Nc2ccc(OCCN3CCCC3)cc2)nc1Nc1cccc(S(=O)(=O)NC(C)(C)C)c1]

wherein the form is a.) a 2-methyl-tetrahydrofuran solvate; and b.) characterized by one or more peaks in its X-ray powder diffraction pattern selected from 12.5, 18.3, 18.9, 20.1, and 23.8±0.2 degrees 2θ.

4. The crystalline form of claim 3, wherein the form is characterized by the following peaks in its X-ray powder diffraction pattern:

| Position ° 2θ ± 0.2 degrees | d-spacing [Å] | Height [cts] |
|---|---|---|
| 7.6 | 11.633 | 715 |
| 10.2 | 8.690 | 521 |
| 11.9 | 7.430 | 2468 |
| 12.5 | 7.096 | 3531 |
| 12.7 | 6.963 | 2843 |
| 14.1 | 6.265 | 2984 |
| 14.5 | 6.096 | 1620 |
| 16.1 | 5.494 | 2249 |
| 18.3 | 4.836 | 6390 |
| 18.9 | 4.699 | 5752 |
| 20.1 | 4.411 | 6304 |
| 21.4 | 4.147 | 1605 |
| 23.1 | 3.853 | 1981 |
| 23.8 | 3.734 | 25579 |
| 25.5 | 3.498 | 1600 |
| 26.0 | 3.433 | 1425 |
| 27.6 | 3.231 | 1295 |
| 28.3 | 3.149 | 1147 |
| 28.9 | 3.090 | 556 |
| 30.4 | 2.937 | 356 |
| 31.7 | 2.824 | 477 |
| 34.2 | 2.620 | 224 |
| 35.5 | 2.530 | 569 |
| 36.0 | 2.497 | 405 |
| 36.9 | 2.434 | 141. |

5. A crystalline form of Compound 1:

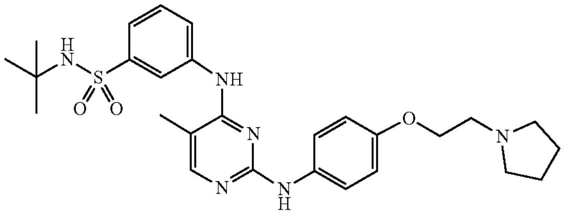 [SMILES: Cc1cnc(Nc2ccc(OCCN3CCCC3)cc2)nc1Nc1cccc(S(=O)(=O)NC(C)(C)C)c1]

wherein the form is a.) a monohydrate; and b.) characterized by one or more peaks in its X-ray powder diffraction pattern selected from 8.7, 15.2, 17.3, 18.0, and 19.4±0.2 degrees 2θ.

6. The crystalline form of claim 5, wherein the form is characterized by the following peaks in its X-ray powder diffraction pattern:

| Position ° 2θ ± 0.2 degrees | d-spacing [Å] | Height [cts] |
|---|---|---|
| 8.7 | 10.184 | 23473 |
| 10.6 | 8.332 | 6912 |
| 14.4 | 6.172 | 8862 |
| 15.2 | 5.825 | 11716 |
| 15.5 | 5.719 | 3493 |
| 16.3 | 5.439 | 5672 |
| 16.6 | 5.329 | 5294 |
| 16.9 | 5.244 | 7167 |
| 17.3 | 5.120 | 51890 |
| 18.0 | 4.917 | 15095 |
| 19.4 | 4.578 | 10908 |
| 20.2 | 4.388 | 8419 |
| 21.8 | 4.078 | 5043 |
| 22.1 | 4.017 | 7400 |
| 22.4 | 3.974 | 6455 |
| 22.8 | 3.894 | 6416 |
| 23.2 | 3.841 | 3537 |
| 23.5 | 3.783 | 7215 |
| 24.4 | 3.647 | 4592 |
| 25.0 | 3.559 | 4787 |
| 25.2 | 3.540 | 4028 |
| 26.1 | 3.414 | 4525 |
| 26.6 | 3.356 | 4349 |
| 27.4 | 3.255 | 5512 |
| 27.6 | 3.231 | 4683. |

7. A crystalline form of Compound 1:

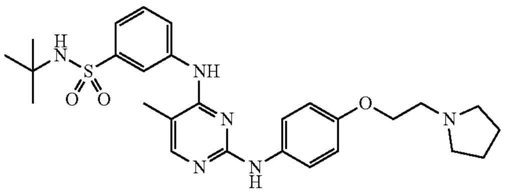 •2HCl.

wherein the form is a.) a tetrahydrate; and b.) characterized by one or more peaks in its X-ray powder diffraction pattern selected from 12.4, 18.5, 19.3, 20.3, and 23.6±0.2 degrees 2θ.

8. The crystalline form of claim 7, wherein the form is characterized by the following peaks in its X-ray powder diffraction pattern:

| Position ° 2θ ± 0.2 degrees | d-spacing [Å] | Height [cts] |
|---|---|---|
| 7.7 | 11.475 | 1223 |
| 11.8 | 7.529 | 1943 |
| 12.0 | 7.372 | 2255 |
| 12.4 | 7.142 | 4460 |
| 12.9 | 6.874 | 1805 |
| 13.4 | 6.619 | 1735 |
| 14.1 | 6.282 | 2143 |
| 14.5 | 6.122 | 1529 |
| 15.4 | 5.772 | 1552 |
| 16.4 | 5.397 | 3326 |
| 18.5 | 4.800 | 7100 |
| 19.3 | 4.591 | 4008 |
| 19.7 | 4.497 | 2119 |
| 20.0 | 4.435 | 3039 |
| 20.3 | 4.380 | 4906 |
| 20.8 | 4.267 | 1987 |
| 21.3 | 4.163 | 1495 |
| 21.9 | 4.066 | 999 |
| 22.7 | 3.925 | 836 |
| 23.6 | 3.770 | 22852 |
| 24.8 | 3.585 | 1474 |
| 25.8 | 3.453 | 907 |
| 26.2 | 3.405 | 1278 |
| 27.0 | 3.306 | 1347 |
| 28.5 | 3.133 | 823. |

9. A sample comprising the crystalline form of claim 5, wherein the sample is substantially free of impurities.

10. A complex comprising Compound 1:

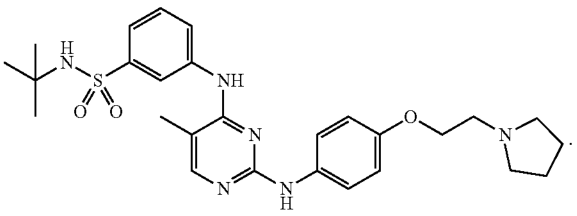 [SMILES: Cc1cnc(Nc2ccc(OCCN3CCCC3)cc2)nc1Nc1cccc(S(=O)(=O)NC(C)(C)C)c1]

and a co-former X;

wherein the complex is crystalline—characterized by one or more peaks in its X-ray powder diffraction pattern selected from 9.7, 14.6, 24.3, and 25.6±0.2 degrees 2θ.

11. A complex comprising Compound 1:

1

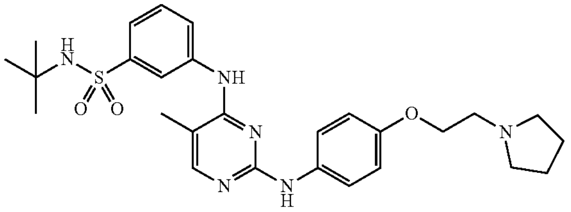

wherein the complex is characterized by one or more peaks in its X-ray powder diffraction pattern selected from 9.7, 14.6, 24.3, and 25.6±0.2 degrees 2θ—and a co former.

12. A sample comprising the complex of claim 10, wherein the sample is substantially free of impurities.

13. A method of inhibiting activity of a JAK2 kinase, or a mutant thereof, in a biological sample comprising the step of contacting said biological sample with a crystalline form of claim 5, or a composition thereof.

14. A method of inhibiting activity of a JAK2 kinase, or a mutant thereof, in a patient comprising the step of administering to said patient a crystalline form of claim 5, or a composition thereof.

15. A method for treating a JAK2-mediated disease or disorder, in a patient in need thereof, comprising the step of administering to the patient a crystalline form of claim 5, or pharmaceutically acceptable composition thereof.

16. A method of inhibiting activity of a JAK2 kinase, or a mutant thereof, in a biological sample comprising the step of contacting said biological sample with a complex of claim 10, or a composition thereof.

17. A method of inhibiting activity of a JAK2 kinase, or a mutant thereof, in a patient comprising the step of administering to said patient a complex of claim 10, or a composition thereof.

18. A method for treating a JAK2-mediated disease or disorder, in a patient in need thereof, comprising the step of administering to the patient a complex of claim 10, or a pharmaceutically acceptable composition thereof.

19. A sample comprising the complex of claim 11, wherein the sample is substantially free of impurities.

20. A method of inhibiting activity of a JAK2 kinase, or a mutant thereof, in a biological sample comprising the step of contacting said biological sample with a complex of claim 11, or a composition thereof.

21. A method of inhibiting activity of a JAK2 kinase, or a mutant thereof, in a patient comprising the step of administering to said patient a complex of claim 11, or a composition thereof.

22. A method for treating a JAK2-mediated disease or disorder, in a patient in need thereof, comprising the step of administering to the patient a complex of claim 11, or a pharmaceutically acceptable composition thereof.

* * * * *